US008084418B2

(12) United States Patent
Hey et al.

(10) Patent No.: US 8,084,418 B2
(45) Date of Patent: Dec. 27, 2011

(54) **METHODS OF INHIBITING INSECTS BY TREATMENT WITH A COMPLEX COMPRISING A *PHOTORHABDUS* INSECTICIDAL PROTEIN AND ONE OR TWO *XENORHABDUS* ENHANCER PROTEINS**

(75) Inventors: Timothy D. Hey, Zionsville, IN (US); Amanda D. Schleper, Westfield, IN (US); Scott A. Bevan, Indianapolis, IN (US); Scott B. Bintrim, Westfield, IN (US); Jon C. Michell, West Lafayette, IN (US); Ze Sheng Li, Westfield, IN (US); Weiting Ni, Carmel, IN (US); Baolong Zhu, San Diego, CA (US); Donald J. Merlo, Carmel, IN (US); Patricia C. Apel-Birkhold, Zionsville, IN (US); Thomas Meade, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 194 days.

(21) Appl. No.: 12/371,825

(22) Filed: Feb. 16, 2009

(65) Prior Publication Data

US 2009/0221501 A1 Sep. 3, 2009

Related U.S. Application Data

(62) Division of application No. 10/754,115, filed on Jan. 7, 2004, now Pat. No. 7,491,698.

(60) Provisional application No. 60/441,723, filed on Jan. 21, 2003.

(51) Int. Cl.
*A01N 33/04* (2006.01)
*A01N 25/00* (2006.01)
*A61K 38/16* (2006.01)
*C07K 14/195* (2006.01)

(52) U.S. Cl. ......... 514/4.5; 424/405; 514/21.2; 530/350

(58) Field of Classification Search .................. 514/4.5, 514/21.2; 424/405; 530/350

See application file for complete search history.

(56) References Cited

U.S. PATENT DOCUMENTS 6,048,838 A 4/2000 Ensign et al.

(Continued)

FOREIGN PATENT DOCUMENTS

WO WO 95/00647 AI 1/1995

(Continued)

OTHER PUBLICATIONS

Bowen, et al., "Insecticidal toxins from the bacterium *Photorhabdus luminescens*," Science 280 (5372), 2129-2132 (1998).

(Continued)

*Primary Examiner* — Rosanne Kosson

(74) *Attorney, Agent, or Firm* — Ronald S. Maciak; Baker & Daniels LLP

(57) ABSTRACT

The subject invention relates to the surprising discovery that toxin complex (TC) proteins, obtainable from *Xenorhabdus*, *Photorhabdus*, and *Paenibacillus*, can be used interchangeably with each other. In particularly preferred embodiments of the subject invention, the toxicity of a "stand-alone" TC protein (from *Photorhabdus, Xenorhabdus*, or *Paenibacillus*, for example) is enhanced by one or more TC protein "potentiators" derived from a source organism of a different genus from which the toxin was derived. As one skilled in the art will recognize with the benefit of this disclosure, this has broad implications and expands the range of utility that individual types of TC proteins will now be recognized to have. Among the most important advantages is that one skilled in the art will now be able to use a single set of potentiators to enhance the activity of a stand-alone *Xenorhabdus* protein toxin as well as a stand-alone *Photorhabdus* protein toxin. (As one skilled in the art knows, *Xenorhabdus* toxin proteins tend to be more desirable for controlling lepidopterans while *Photorhabdus* toxin proteins tend to be more desirable for controlling coleopterans.) This reduces the number of genes, and transformation events, needed to be expressed by a transgenic plant to achieve effective control of a wider spectrum of target pests. Certain preferred combinations of heterologous TC proteins are also disclosed herein. Other objects, advantages, and features of the subject invention will be apparent to one skilled in the art having the benefit of the subject disclosure.

3 Claims, 7 Drawing Sheets

Schematic Diagram of pBT Constructions

U.S. PATENT DOCUMENTS 6,174,860 B1 1/2001 Kramer et al.
6,277,823 B1 8/2001 Kramer et al.
6,281,413 B1 8/2001 Kramer et al.
6,590,142 B1 7/2003 Petell et al.
2002/0078478 A1 6/2002 Ffrench-Constant

FOREIGN PATENT DOCUMENTS

WO WO 97/17432 AI 5/1997
WO WO 98/08388 AI 3/1998
WO WO 98/08932 AI 3/1998
WO WO 98/50427 AI 11/1998
WO WO 99/03328 AI 1/1999
WO WO 99/42589 A2 8/1999
WO WO 99/54472 AI 10/1999
WO WO 00/30453 A2 6/2000
WO WO 00/42855 AI 7/2000
WO WO 01/11029 AI 2/2001
WO WO 02/94867 A2 11/2002
WO WO 2004102223 A2 1/2004

OTHER PUBLICATIONS

Ffrench-Constant et al., "*Photorhabdus* toxins: novel biological insecticides," Current Opinion in Microbiology (1999), p. 284-288, vol. 12.

Ffrench-Constant et al., "Novel insecticidal toxins from nematode-symbiotic bacteria," Cellular and Md. Life Sciences (5100), p. 828-833, vol. 57, No. 5.

Ffrench-Constant, et al., "A Genomic Sample Sequence of the Entomopathogenic Bacterium *Photorhabdus* . . . ," Appl. Environ. Microbial. (8100), p. 3310.3329, vol. 66, No. 8.

Forst et al., "Molecular Biology of the Symbiotic-Pathogenic Bacteria *Xenorhabdus* spp. and *Photorhabdus* spp," Microbiological Reviews (3196), p. 21-43, vol. 60, No. 1.

Hurst et al., "Plasmid-Located Pathogenicity Determinants of *Serratia entomophila* . . . ," Journal of Bacteriology (09100), p. 5127-5138, vol. 182, No. 18.

Hurst et al., "SepA (*Serratia entomophila*)," GENBANK Accession No. AAG09642 (gi:9963678), Nov. 5, 2003.

Hurst et al., "SepB (*Serratia entomophilia*)," GENBANK Accession No. AAG09643 (gi:9963679), Nov. 5, 2003.

Hurst et al., "SepC (*Serratia entomophila*)," GENBANK Accession No. AAG09644 (gi:9963680), Nov. 5, 2003.

Merlo et al., "Toxin A (*Photorhabdus luminescens*)," GENBANK Accession No. AAF05542 (gi:6176340), Nov. 2, 1999.

Morgan et al., "Sequence Analysis of Insecticidal Genes from *Xenorhabdus nematophilus* PMF1296," Appl. Environ. Microbio. (May 2001), p. 2062-2069, vol. 67, No. 5.

Morgan et al., "Putative chitinase (*Xenorhabdus nematophila*)," GENBANK Accession No. CAC38398 (gi:14041727), May 11, 2001.

Morgan et al., "XptA1 protein (*Xenorhabdus nematophilia*)," GENBANK Accession No. CAC38401 (gi:14041730), May 11, 2001.

Morgan et al., "XptB1 protein (*Xenorhabdus nematophilia*)," GENBANK Accession No. CAC38402 (gi:14041731), May 11, 2001.

Morgan et al., "XptCl protein (*Xenorhabdus nematophilia*)," GENBANK Accession No. CAC38403 (gi:14041732), May 11, 2001.

Morgan et al., "XptA2 protein (*Xenorhabdus nematophilia*)," GENBANK Accession No. CAC38404 (gi:14041733), May 11, 2001.

NCBI Microbial Genomes Annotation Project, COG3209: Rhs family protein (*Pseudomanas* . . . ), GENBANK Accession No. ZP_00083266 (gi:23058175) Apr. 9, 2004.

NCBI Microbial Genomes Annotation Project, COG3209: Rha family protein (*Pseudomonas* . . . ), GENBANK Accession No. ZP_00083267 (gi:23058176) Apr. 9, 2004.

NCBI Microbial Genomes Annotation Project, Hypothetical protein (*Pseudomonas fluoresens* . . . ), GENBANK Accession No. ZP_00084399) (gi:23059431) Apr. 9, 2004.

NCBI Microbial Genomes Annotation Project, COG3209: Rhs family protein (*Pseudomonas* . . . ), GENBANK Accession No. ZP_00084400 (gi;23059432) Apr. 9, 2004.

NCBI Microbial Genomes Annotation Project, COG3209: Rhs family protein (*Pseudomonas* . . . ), GENBANK Accession No. ZP_00084401 (gi:23059433) Apr. 9, 2004.

NCBI Microbial Genomes Annotation Project, COG3209: Rhs family protein (*Pseudomonas* . . . ), GENBANK Accession No. ZP_00084403 (gi:23059435) Apr. 9, 2004.

NCBI Microbial Genomes Annotation Project, COG3209: Rhs family protein (*Pseudomonas* . . . ), GENBANK Accession No. ZP_00125560 (gi:23470227) Sep. 23, 2003.

NCBI Microbial Genomes Annotation Project, Hypothetical protein (*Pseudomonas syringae* . . . ), GENBANK Acccession No. ZP_00126265 (gi:23470933) Sep. 23, 2003.

NCBI Microbial Genomes Annotation Project, COG3209: Rhs family protein (*Pseudomonas* . . . ), GENBANK Accession No. ZP_00127864 (gi:23472540) Apr. 9, 2004.

NCBI Microbial Genomes Annotation Project, COG3209: Rhs family protein (*Pseudomonas* . . . ), GENBANK Accession No. ZP_00127865 (gi:23472541) Apr. 9, 2004.

NCBI Microbial Genomes Annotation Project, COG3209: Rhs family protein (*Pseudomonas* . . . ), GENBANK Accession No. ZP_00127867 (gi:23472543) Apr. 9, 2004.

NCBI Microbial Genomes Annotation Project, Hypothetical protein (*Pseudomonas syringae* . . . ), GENBANK Accession No. ZP_00127868 (gi:23472544) Apr. 9, 2004.

NCBI Microbial Genomes Annotation Project, COG3209: Rhs family protein (*Pseudomonas* . . . ), Genbank Accession No. ZPw00127869 (gi:23472545) Apr. 9, 2004.

NCBI Microbial Genomes Annotation Project, COG3209: Rhs family protein (*Pseudomonas* . . . ), Genbank Accession No. ZP_00127870 (gi:23472546) Apr. 9, 2004.

Pettersson et al., "Transfer of *Bacillus lentimorbus* and *Bacillus popillae* to the genus *Paenibacillus* . . . ," int. J. Syst. Bacteriol. (1997) p. 531-540, vol. 49, No, 2 (abstract).

Shida et al., "Emended description of *Paenibacillus amylolyticus* and description of *Paenibacillus* . . . ," int. J. Syst. Bacteriol. (1997) p. 299-306, vol. 47, No. 2 (abstract).

Waterfield et al., "Oral Toxicity of Photorhabdus luminescens W14 Toxin Complexes in *Escherichia coli*," Appl. Environ. Microbio. (11101)m p. 5017-5024, vol. 67, No. 11.

Waterford et al., "The toxin complex genes of *Photohabdus*: a growing gene family," Trends in Microbiolgy (04101), p. 185-191, vol. 9, No. 4.

Waterford et al., "Genomic islands in *Photorhabdus*," Trends Microbio. 10 (12), 541-545 (2002).

Waterford et al., Toxin complex protein (*Photorhabdus luminescens*), GENBANK Accession No. AAL18473 (gi:16416915) Oct. 25, 2001.

Waterfield et al, TcdAI; toxin complex protein (*Photorhabdus luminescens*), GENBANK Accession No. AAL18486 (gi:16416929) Jul. 17, 2003.

Waterfield et al., TcdB1; toxin complex protein (*Photorhabdus luminescens*), GENBANK Accession No. AAL18487 (gi:16416930) Jul. 17, 2003.

Waterfield et al., TccC2; (*Photorhabdus luminescens*), GENBANK Accession No. AAL18492 (gi:27479639) Jul. 17, 2003.

Waterfield et al., TccC4; (*Photorhabdus luminescens*), GENBANK Accession No. AA017196 (gi:27479669) Jul. 17, 2003.

Waterfield et al., TcdA2; (*Photorhabdus luminescens*), GENBANK Accession No, AA017201 (gi:27479674) Jul. 17, 2003.

Waterfield et al., TccC3; (*Photorhabdus luminescens*), GENBANK Accession No. AAO17204 (gi:27479677) Jul. 17, 2003.

Waterfield et al., TcdA4; (*Photorhabdus luminescens*), GENBANK Accession No. AAO17209 (gi:27479682) Jul. 17, 2003.

Waterfield et al., TccC5; (*Photorhabdus luminescens*), GENBANK Accession No. AA017210 (gi:27479683) Jul. 17, 2003.

Waterfield et al., TcdB2; (*Photorhabdus luminescens*), GENBANK Accession No. AA017202 (gi:27479675) Jul. 17, 2003.

H. Guo, et al., "Protein Tolerance to Random Amino Acid Change", PNAS 101(25):9205-9210, 2004.

Figure 1. Orientation of ORFs identified in pDAB2097

Figure 2. Expression Plasmid pBT-TcdA.

Figure 3. Expression Vector Plasmid pET280 Vector

Figure 4. Expression Plasmid pCot-3

Figure 5. Schematic Diagram of pBT Constructions

Figure 6. Schematic Diagram of pET/pCot Constructions

METHODS OF INHIBITING INSECTS BY TREATMENT WITH A COMPLEX COMPRISING A *PHOTORHABDUS* INSECTICIDAL PROTEIN AND ONE OR TWO *XENORHABDUS* ENHANCER PROTEINS

CROSS-REFERENCE TO A RELATED APPLICATION

This application is a divisional of U.S. application Ser. No. 10/754,115, filed Jan. 7, 2004, now U.S. Pat. No. 7,491,698, which claims the benefit of U.S. Provisional Application Ser. No. 60/441,723, filed Jan. 21, 2003 the disclosures of which are expressly incorporated by reference herein.

BACKGROUND OF THE INVENTION

Insects and other pests cost farmers billions of dollars annually in crop losses and in the expense of keeping these pests under control. The losses caused by insect pests in agricultural production environments include decreases in crop yield, reduced crop quality, and increased harvesting costs. Insect pests are also a burden to vegetable and fruit growers, to producers of ornamental flowers, and to home gardeners and homeowners.

Cultivation methods, such as crop rotation and the application of high levels of nitrogen fertilizers, have partially addressed problems caused by agricultural pests. However, various demands on the utilization of farmland restrict the use of crop rotation. In addition, overwintering traits of some insects are disrupting crop rotations in some areas.

Thus, synthetic chemical insecticides are relied upon most heavily to achieve a sufficient level of control. However, the use of synthetic chemical insecticides has several drawbacks. For example, the use of these chemicals can adversely affect many beneficial insects. Target insects have also developed resistance to some chemical pesticides. Furthermore, rain and improper calibration of insecticide application equipment can result in poor control. The use of insecticides often raises environmental concerns such as contamination of soil and water supplies when not used properly, and residues can also remain on treated fruits and vegetables. Working with some insecticides can also pose hazards to the persons applying them. Stringent new restrictions on the use of pesticides and the elimination of some effective pesticides could limit effective options for controlling damaging and costly pests.

The replacement of synthetic chemical pesticides, or combination of these agents with biological pesticides, could reduce the levels of toxic chemicals in the environment. Some biological pesticidal agents that are now being used with some success are derived from the soil microbe *Bacillus thuringiensis* (B.t.). While most B.t. strains do not exhibit pesticidal activity, some B.t. strains produce proteins that are highly toxic to pests, such as insects, and are specific in their toxic activity. Genes that encode δ-endotoxin proteins have been isolated. Other species of *Bacillus* also produce pesticidal proteins.

Recombinant DNA-based B.t. products have been produced and approved for use. In addition, with the use of genetic engineering techniques, various approaches for delivering these toxins to agricultural environments are being perfected. These include the use of plants genetically engineered with toxin genes for insect resistance and the use of stabilized intact microbial cells as toxin delivery vehicles. Thus, isolated *Bacillus* toxin genes are becoming commercially valuable.

B.t. protein toxins were initially formulated as sprayable insect control agents. A relatively more recent application of B.t. technology has been to isolate and transform plants with genes that encode these toxins. Transgenic plants subsequently produce the toxins, thereby providing insect control. See U.S. Pat. Nos. 5,380,831; 5,567,600; and 5,567,862 to Mycogen Corporation. Transgenic B.t. plants are quite efficacious, and usage is predicted to be high in some crops and areas.

There are some obstacles to the successful agricultural use of *Bacillus* (and other biological) pesticidal proteins. Certain insects can be refractory to the effects of *Bacillus* toxins. Insects such as boll weevils, black cutworm, and *Helicoverpa zea*, as well as adult insects of most species, heretofore have demonstrated no significant sensitivity to many B.t. δ-endotoxins.

Another potential obstacle is the development of resistance to B.t. toxins by insects. The potential for wide-spread use of B.t. plants has caused some concern that resistance management issues may arise more quickly than with traditional sprayable applications. While a number of insects have been selected for resistance to B.t. toxins in the laboratory, only the diamondback moth (*Plutella xylostella*) has demonstrated resistance in a field setting (Ferre, J. and Van Rie, J., *Annu. Rev. Entomol.* 47:501-533, 2002).

Resistance management strategies in B.t. transgene plant technology have become of great interest. Several strategies have been suggested for preserving the ability to effectively use *B. thuringiensis* toxins. These strategies include high dose with refuge, and alternation with, or co-deployment of, different toxins (McGaughey et al. (1998), "B.t. Resistance Management," *Nature Biotechnol* 16:144-146), as in a natural bacterium, for example.

Thus, there remains a great need for developing additional genes that can be expressed in plants in order to effectively control various insects. In addition to continually trying to discover new B.t. toxins (which is becoming increasingly difficult due to the numerous B.t. toxins that have already been discovered), it would be quite desirable to discover other bacterial sources (distinct from B.t.) that produce toxins that could be used in transgenic plant strategies.

The relatively more recent efforts to clone insecticidal toxin genes from the *Photorhabdus/Xenorhabdus* group of bacteria present potential alternatives to toxins derived from *B. thuringiensis*. The genus *Xenorhabdus* is taxonomically defined as a member of the Family Enterobacteriaceae, although it has certain traits atypical of this family. For example, strains of this genus are typically nitrate reduction negative and catalase negative. *Xenorhabdus* has only recently been subdivided to create a second genus, *Photorhabdus*, which is comprised of three species, *Photorhabdus asymbiotica, Photorhabdus temperata*, and *P. luminescens. P. luminescens* has three recognized subspecies, *Photorhabdus luminescens* subsp. *akhurstii, Photorhabdus luminescens* subsp. *laumondii*, and *Photorhabdus luminescens* subsp. *luminescens* (Type species). (Fischer-Le Saux, M., Viallard, V., Brunel, B., Normand, P., Boemare, N. E. Title Polyphasic classification of the genus *Photorhabdus* and proposal of new taxa: *P. luminescens* subsp. *luminescens* subsp. *nov., P. luminescens* subsp. *akhurstii* subsp. *nov., P. luminescens* subsp. *laumondii* subsp. *nov., P. temperata* sp. *nov., P. temperata* subsp. *temperata* subsp. *nov.* and *P. asymbiotica* sp. *nov.* Int. J. Syst. Bacteriol. 49; 1645-1656, (1999)). This differentiation is based on several distinguishing characteristics easily identifiable by the skilled artisan. These differences include the following: DNA-DNA characterization studies; phenotypic presence (*Photorhabdus*) or absence (*Xenorhabdus*) of catalase activity; presence (*Photorhabdus*) or absence (*Xenorhabdus*) of bioluminescence; the Family of the nematode host in that *Xenorhabdus* is found in Steinernematidae and *Photorhabdus* is found in Heterorhabditidae); as well as comparative, cellular fatty-acid analyses (Janse et al. 1990, *Lett. Appl. Microbiol.* 10, 131-135; Suzuki et al. 1990, *J. Gen. Appl. Microbiol.,* 36, 393-401). In addition, recent molecular studies focused on sequence (Rainey et al. 1995, *Int. J. Syst. Bacteriol.,* 45, 379-381) and restriction analysis (Brunel et al., 1997, *App. Environ. Micro.,* 63, 574-580) of 16S rRNA genes also support the separation of these two genera.

The expected traits for *Xenorhabdus* are the following: Gram stain negative rods, white to yellow/brown colony pigmentation, presence of inclusion bodies, absence of catalase, inability to reduce nitrate, absence of bioluminescence, ability to uptake dye from medium, positive gelatin hydrolysis, growth on Enterobacteriaceae selective media, growth temperature below 37° C., survival under anaerobic conditions, and motility.

Currently, the bacterial genus *Xenorhabdus* is comprised of four recognized species, *Xenorhabdus nematophilus, Xenorhabdus poinarii, Xenorhabdus bovienii* and *Xenorhabdus beddingii* (Brunel et al., 1997, *App. Environ. Micro.,* 63, 574-580). A variety of related strains have been described in the literature (e.g., Akhurst and Boemare 1988 *J. Gen. Microbiol.,* 134, 1835-1845; Boemare et al. 1993 Int. J. Syst. Bacteriol. 43, pp. 249-255; Putz et al. 1990, *Appl. Environ. Microbiol.,* 56, 181-186, Brunel et al., 1997, *App. Environ. Micro.,* 63, 574-580, Rainey et al. 1995, *Int. J. Syst. Bacteriol.,* 45, 379-381). *Photorhabdus* and *Xenorhabdus* spp. are Gram-negative bacteria that entomopathogenically and symbiotically associate with soil nematodes. These bacteria are found in the gut of entomopathogenic nematodes that invade and kill insects. When the nematode invades an insect host, the bacteria are released into the insect haemocoel (the open circulatory system), and both the bacteria and the nematode undergo multiple rounds of replication; the insect host typically dies. These bacteria can be cultured away from their nematode hosts. For a more detailed discussion of these bacteria, see Forst and Nealson, 60 *Microbiol. Rev.* 1 (1996), pp. 21-43. Unfortunately, as reported in a number of articles, the bacteria only had pesticidal activity when injected into insect larvae and did not exhibit biological activity when delivered orally.

*Xenorhabdus* and *Photorhabus* bacteria secrete a wide variety of substances into the culture medium. See R. H. ffrench-Constant et al. 66 *AEM* No. 8, pp. 3310-3329 (August 2000), for a review of various factors involved in *Photorhabdus* virulence of insects.

It has been difficult to effectively exploit the insecticidal properties of the nematode or its bacterial symbiont. Thus, proteinaceous agents from *Photorhabdus/Xenorhabdus* bacteria that have oral activity are desirable so that the products produced therefrom could be formulated as a sprayable insecticide, or the genes encoding said proteinaceous agents could be isolated and used in the production of transgenic plants.

There has been substantial progress in the cloning of genes encoding insecticidal toxins from both *Photorhabdus luminescens* and *Xenorhabdus nematophilus*. Toxin-complex encoding genes from *P. luminescens* were examined first. See WO 98/08932. Parallel genes were more recently cloned from *X. nematophilus*. See, e.g., Morgan et al., *Applied and Environmental Microbiology* 2001, 67:2062-69. The degree of "parallelism" is discussed in more detail below.

WO 95/00647 relates to the use of *Xenorhabdus* protein toxin to control insects, but it does not recognize orally active toxins. WO 98/08388 relates to orally administered pesticidal agents from *Xenorhabdus*. U.S. Pat. No. 6,048,838 relates to protein toxins/toxin complexes, having oral activity, obtainable from *Xenorhabdus* species and strains.

Four different toxin complexes (TCs)—Tca, Tcb, Tcc and Tcd—have been identified in *Photorhabdus* spp. Each of these toxin complexes resolves as either a single or dimeric species on a native agarose gel but resolution on a denaturing gel reveals that each complex consists of a range of species between 25-280 kDa. The ORFs that encode the typical TCs from *Photorhabdus*, together with protease cleavage sites (vertical arrows), are illustrated in FIG. 7. See also R. H. ffrench-Constant and Bowen, 57 *Cell. Mol Life Sci.* 828-833 (2000).

Genomic libraries of *P. luminescens* were screened with DNA probes and with monoclonal and/or polyclonal antibodies raised against the toxins. Four tc loci were cloned: tca, tcb, tce and tcd. The tca locus is a putative operon of three open reading frames (ORFs), tcaA, tcaB, and tcaC, transcribed from the same DNA strand, with a smaller terminal ORF (tcaZ) transcribed in the opposite direction. The tce locus also is comprised of three ORFs putatively transcribed in the same direction (tccA, tccB, and tccC. The tcb locus is a single large ORF (tcbA), and the tcd locus is composed of two ORFs (tcdA and tcdB); tcbA and tcdA, each about 7.5 kb, encode large insect toxins. It was determined that many of these gene products were cleaved by proteases. For example, both TcbA and TcdA are cleaved into three fragments termed i, ii and iii (e.g. TcbAi, TcbAii and TcbAiii). Products of the tca and tce ORFs are also cleaved. See FIG. 7. See also R. H. ffrench-Constant and D. J. Bowen, *Current Opinions in Microbiology,* 1999, 12:284-288.

As reported in WO 98/08932, protein toxins from the genus *Photorhabdus* have been shown to have oral toxicity against insects. The toxin complex produced by *Photorhabdus luminescens* (W-14), for example, has been shown to contain ten to fourteen proteins, and it is known that these are produced by expression of genes from four distinct genomic regions: tca, tcb, tcc, and tcd. WO 98/08932 discloses nucleotide sequences for many of the native toxin genes.

Bioassays of the Tca toxin complexes revealed them to be highly toxic to first instar tomato hornworms (*Manduca sexta*) when given orally ($LD_{50}$ of 875 ng per square centimeter of artificial diet). R. H. ffrench-Constant and Bowen 1999. Feeding was inhibited at Tca doses as low as 40 ng/$cm^2$. Given the high predicted molecular weight of Tca, on a molar basis, *P. luminescens* toxins are highly active and relatively few molecules appear to be necessary to exert a toxic effect. R. H. ffrench-Constant and Bowen, *Current Opinions in Microbiology,* 1999, 12:284-288.

None of the four loci showed overall similarity to any sequences of known function in GenBank. Regions of sequence similarity raised some suggestion that these proteins (TcaC and TccA) may overcome insect immunity by attacking insect hemocytes. R. H. ffrench-Constant and Bowen, *Current Opinions in Microbiology,* 1999, 12:284-288.

TcaB, TcbA, and TcdA all show amino acid conservation (~50% identity), compared with each other, immediately around their predicted protease cleavage sites. This conservation between three different Tc proteins suggests that they may all be processed by the same or similar proteases. TcbA and TcdA also share ~50% identity overall, as well as a similar predicted pattern of both carboxy- and amino-terminal cleavage. It was postulated that these proteins might thus be homologs (to some degree) of one another. Furthermore, the similar, large size of TcbA and TcdA, and also the fact that both toxins appear to act on the gut of the insect, may suggest similar modes of action. R. H. ffrench-Constant and Bowen, *Current Opinions in Microbiology,* 1999, 12:284-288.

Deletion/knock-out studies suggest that products of the tca and tcd loci account for the majority of oral toxicity to lepidopterans. Deletion of either of the tca or tcd genes greatly reduced oral activity against *Manduca sexta*. That is, products of the tca and tcd loci are oral lepidopteran toxins on their own; their combined effect contributed most of the secreted oral activity. R. H. ffrench-Constant and D. J. Bowen, 57 *Cell. Mol. Life. Sci.* 831 (2000). Interestingly, deletion of either of the tcb or tce loci alone also reduces mortality, suggesting that there may be complex interactions among the different gene products. Thus, products of the tca locus may enhance the toxicity of tcd products. Alternatively, tcd products may modulate the toxicity of tca products and possibly other complexes. Noting that the above relates to oral activity against a single insect species, tcb or tce loci may produce toxins that are more active against other groups of insects (or active via injection directly into the insect haemocoel—the normal route of delivery when secreted by the bacteria in vivo). R. H. ffrench-Constant and Bowen, *Current Opinions in Microbiology,* 1999, 12:284-288.

The insect midgut epithelium contains both columnar (structural) and goblet (secretory) cells. Ingestion of tca products by *M. sexta* leads to apical swelling and blebbing of large cytoplasmic vesicles by the columnar cells, leading to the eventual extrusion of cell nuclei in vesicles into the gut lumen. Goblet cells are also apparently affected in the same fashion. Products of tca act on the insect midgut following either oral delivery or injection. R. H. ffrench-Constant and D. J. Bowen, *Current Opinions in Microbiology,* 1999, 12:284-288. Purified tca products have shown oral toxicity against *Manduca sexta* ($LD_{50}$ of 875 ng/$cm^2$). R. H. ffrench-Constant and D. J. Bowen, 57 *Cell. Mol. Life. Sci.* 828-833 (2000).

WO 99/42589 and U.S. Pat. No. 6,281,413 disclose TC-like ORFs from *Photorhabdus luminescens*. WO 00/30453 and WO 00/42855 disclose TC-like proteins from *Xenorhabdus*. WO 99/03328 and WO 99/54472 (and U.S. Pat. Nos. 6,174,860 and 6,277,823) relate to other toxins from *Xenorhabdus* and *Photorhabdus.*

WO 01/11029 and U.S. Pat. No. 6,590,142 B1 disclose nucleotide sequences that encode TcdA and TcbA and have base compositions that have been altered from that of the native genes to make them more similar to plant genes. Also disclosed are transgenic plants that express Toxin A and Toxin B. These references also disclose *Photorhabdus luminescens* strain W-14 (ATCC 55397; deposited Mar. 5, 1993) and many other strains.

Of the separate toxins isolated from *Photorhabdus luminescens* (W-14), those designated Toxin A and Toxin B have been the subject of focused investigation for their activity against target insect species of interest (e.g., corn rootworm). Toxin A is comprised of two different subunits. The native gene tcdA encodes protoxin TcdA. As determined by mass spectrometry, TcdA is processed by one or more proteases to provide Toxin A. More specifically, TcdA is an approximately 282.9 kDa protein (2516 aa) that is processed to provide TcdAi (the first 88 amino acids), TcdAii (the next 1849 aa; an approximately 208.2 kDa protein encoded by nucleotides 265-5811 of tcdA), and TcdAiii, an approximately 63.5 kDa (579 aa) protein (encoded by nucleotides 5812-7551 of tcdA). TcdAii and TcdAiii appear to assemble into a dimer (perhaps aided by TcdAi), and the dimers assemble into a tetramer of four dimers. Toxin B is similarly derived from TcbA.

While the exact molecular interactions of the TC proteins with each other, and their mechanism(s) of action, are not currently understood, it is known, for example, that the Tca toxin complex of *Photorhabdus* is toxic to *Manduca sexta*. In addition, some TC proteins are known to have "stand alone" insecticidal activity, while other TC proteins are known to potentiate or enhance the activity of the stand-alone toxins. It is known that the TcdA protein is active, alone, against *Manduca sexta*, but that TcdB and TccC, together, can be used to enhance the activity of TcdA. Waterfield, N. et al., *Appl. Environ. Microbiol.* 2001, 67:5017-5024. TcbA (there is only one Tcb protein) is another stand-alone toxin from *Photorhabdus*. The activity of this toxin (TcbA) can also be enhanced by TcdB together with TccC-like proteins.

U.S. Patent Application 20020078478 provides nucleotide sequences for two potentiator genes, tcdB2 and tccC2, from the tcd genomic region of *Photorhabdus luminescens* W-14. It is shown therein that coexpression of tcdB and tccC1 with tcdA in heterologous hosts results in enhanced levels of oral insect toxicity compared to that obtained when tcdA is expressed alone in such heterologous hosts. Coexpression of tcdB and tccC1 with tcdA or tcbA provide enhanced oral insect activity.

As indicated in the chart below, TccA has some level of homology with the N terminus of TcdA, and TccB has some level of homology with the C terminus of TcdA. TccA and TccB are much less active on certain test insects than is TcdA. TccA and TccB from *Photorhabdus* strain W-14 are called "Toxin D." "Toxin A" (TcdA), "Toxin B" (TcbA), and "Toxin C" (TcaA and TcaB) are also indicated below.

Furthermore, TcaA has some level of homology with TccA and likewise with the N terminus of TcdA. Still further, TcaB has some level of homology with TccB and likewise with the N terminus of TcdA.

TccA and TcaA are of a similar size, as are TccB and TcaB. TcdB has a significant level of similarity (both in sequence and size) to TcaC.

| *Photorhabdus* | *Photorhabdus* strain W-14 nomenclature | Some homology to: |
|---|---|---|
| TcaA | Toxin C | TccA |
| TcaB | | TccB |
| TcaC | | TcdB |
| TcbA | Toxin B | |
| TccA | Toxin D | TcdA N terminus |
| TccB | | TcdA C terminus |
| TccC | | |
| TcdA | Toxin A | TccA + TccB |
| TcdB | | TcaC |

Relatively more recent cloning efforts in *Xenorhabdus nematophilus* also appear to have identified novel insecticidal toxin genes with homology to the *P. luminescens* tc loci. See, e.g., WO 98/08388 and Morgan et al., *Applied and Environmental Microbiology* 2001, 67:2062-69. In R. H. ffrench-Constant and D. J. Bowen, *Current Opinions in Microbiology,* 1999, 12:284-288, cosmid clones were screened directly for oral toxicity to another lepidopteran, *Pieris brassicae*. One orally toxic cosmid clone was sequenced. Analysis of the sequence in that cosmid suggested that there are five different ORF's with similarity to *Photorhabdus* tc genes; orf2 and orf5 both have some level of sequence relatedness to both tcbA and tcdA, whereas orf1 is similar to tccB, orf3 is similar to tccC and orf4 is similar to tcaC. A number of these predicted ORFs also share the putative cleavage site documented in *P. luminescens*, suggesting that active toxins might also be proteolytically processed.

The finding of somewhat similar, toxin-encoding loci in these two different bacteria is interesting in terms of the possible origins of these virulence genes. The *X. nematophilus* cosmid also appears to contain transposase-like sequences, the presence of which might suggest the potential that these loci can be transferred horizontally between different strains or species of bacteria. A range of such transfer events may also explain the apparently different genomic organization of the tc operons in the two different bacteria. Further, only a subset of *X. nematophilus* and *P. luminescens* strains appear to be toxic to *M. sexta*, suggesting either that different strains lack the tc genes or that they carry a different tc gene compliment. Detailed analysis of the phylogeny of strains and toxins within, and between, these bacterial species should help clarify the likely origin of the toxin genes and how they are maintained in different bacterial populations. R. H. ffrench-Constant and Bowen, *Current Opinions in Microbiology,* 1999, 12:284-288.

There are five typical *Xenorhabdus* TC proteins: XptA1, XptA2, XptB1, XptC1, and XptD1. XptA1 is a "stand-alone" toxin. XptA2 is another TC protein from *Xenorhabdus* that has stand-alone toxin activity. XptB1 and XptC1 are potentiators that can enhance the activity of either (or both) of the XptA toxins. XptD1 has some level of homology with TccB. XptC1 has some level of similarity to *Photorhabdus* TcaC. The XptA2 protein of *Xenorhabdus* has some degree of similarity to the *Photorhabdus* TcdA protein. XptB1 has some level of similarity to *Photorhabdus* TccC.

TC proteins and genes have more recently been described from other insect-associated bacteria such as *Serratia entomophila*, an insect pathogen. *Pseudomonas* species were found to have potentiators. Waterfield et al., *TRENDS in Microbiology, Vol.* 9, No. 4, April 2001.

Bacteria of the genus *Paenibacillus* are distinguishable from other bacteria by distinctive rRNA and phenotypic characteristics (C. Ash et al. (1993), "Molecular identification of rRNA group 3 bacilli (Ash, Farrow, Wallbanks and Collins) using a PCR probe test: Proposal for the creation of a new genus *Paenibacillus,*" *Antonie Van Leeuwenhoek* 64:253-260). Some species in this genus are known to be pathogenic to honeybees (*Paenibacillus larvae*) and to scarab beetle grubs (*P. popilliae* and *P. lentimorbus*). *P. larvae, P. popilliae*, and *P. lentimorbus* are considered obligate insect pathogens involved with milky disease of scarab beetles (D. P. Stahly et al. (1992), "The genus *Bacillus*: insect pathogens," pp. 1697-1745, In A. Balows et al., ed., *The Procaryotes,* 2nd Ed., Vol. 2, Springer-Verlag, New York, N.Y.).

A crystal protein, Cry18, has been identified in strains of *Paenibacillus popilliae* and *Paenibacillus lentimorbus*. Cry 18 has scarab and grub toxicity, and has about 40% identity to Cry2 proteins (Zhang et al., 1997; Harrison et al., 2000). TC proteins and lepidopteran-toxic Cry proteins have very recently been discovered in *Paenibacillus*. See U.S. Ser. No. 60/392,633 (Bintrim et al.), filed Jun. 28, 2002. Six TC protein ORFs were found in that strain of *Paenibacillus*. ORF3 and ORF1 are shown there to each have some level of homology with TcaA. ORF4 and ORF2 are shown there to have some level of homology with TcaB. ORF5 appears to be a TcaC-like potentiator, and ORF6 has homology with the TccC potentiator.

Although some *Xenorhabdus* TC proteins were found to "correspond" (have a similar function and some level of sequence homology) to some of the *Photorhabdus* TC proteins, a given *Photorhabdus* protein shares only about 40% sequence identity with the "corresponding" *Xenorhabdus* protein. This is illustrated below for four "stand-alone" toxins:

| | Identity to P.1. W-14 TcbA | Identity to P.1. W-14 TcdA |
|---|---|---|
| Xwi XptA1 | 44% | 46% |
| Xwi XptA2 | 41% | 41% |

(For a more complete review, see, e.g., Morgan et al., "Sequence Analysis of Insecticidal Genes from *Xenorhabdus nematophiles* PMFI296," Vol. 67, *Applied and Environmental Microbiology*, May 2001, pp. 2062-2069.) This approximate degree of sequence relatedness is also observed when comparing the more recently discovered TC proteins from *Paenibacillus* (those proteins and that discovery are the subject of co-pending U.S. Ser. No. 60/392,633) to their *Xenorhabdus* and *Photorhabdus* "counterparts."

While *Photorhabdus* toxins have been used successfully, and *Xenorhabdus* toxins have been used successfully (apart from *Photorhabdus* toxins), enhancing the activity of a TC protein toxin from one of these source organisms (such as a *Photorhabdus*) with one or more TC protein potentiators from the other (a *Xenorhabdus*, for example) has not heretofore been proposed or demonstrated.

BRIEF SUMMARY OF THE INVENTION

The subject invention relates to the surprising discovery that toxin complex (TC) proteins, obtainable from organisms such as *Xenorhabdus, Photorhabdus*, and *Paenibacillus*, can be used interchangeably with each other. As one skilled in the art will recognize with the benefit of this disclosure, this has broad implications and expands the range of utility that individual types of TC proteins will now be recognized to have. This was not previously contemplated, and it would not have been thought possible, especially given the high level of divergence at the sequence level of the TC proteins from *Photorhabdus* compared to "corresponding" TC proteins of *Xenorhabdus* and *Paenibacillus*, for example.

In particularly preferred embodiments of the subject invention, the toxicity of a "stand-alone" TC protein (from *Photorhabdus, Xenorhabdus*, or *Paenibacillus*, for example) is enhanced by one or more TC protein "potentiators" derived from a different source organism. The subject invention provides one skilled in the art with many surprising advantages. One of the most important advantages is that one skilled in the art will now be able to use a single pair of potentiators to enhance the activity of a stand-alone *Xenorhabdus* protein toxin and a stand-alone *Photorhabdus* protein toxin. (As one skilled in the art knows, *Xenorhabdus* toxin proteins tend to be more desirable for controlling lepidopterans while *Photorhabdus* toxin proteins tend to be more desirable for controlling coleopterans.) This reduces the number of genes (and transformation events) needed to be co-expressed by individual transgenic plants and/or plant cells to achieve effective control of a wider spectrum of target pests.

Stated another way, the subject invention relates to the discovery that *Xenorhabdus* TC proteins could be used to enhance the activity of *Photorhabdus* TC proteins and vice versa. Similarly, and also surprisingly, it was discovered that TC proteins from *Paenibacillus* could be used in place of *Xenorhabdus/Photorhabdus* TC proteins, and vice versa. Again, there was no expectation that proteins from these divergent organisms would be compatible with each other; this was not previously proposed or demonstrated. The subject invention was surprising especially in light of the notable differences between *Xenorhabdus, Photorhabdus*, and

*Paenibacillus* TC proteins (as well as those from other genera) notwithstanding some characteristics they have in common.

Certain preferred combinations of heterologous TC proteins are also disclosed herein.

Many objects, advantages, and features of the subject invention will be apparent to one skilled in the art having the benefit of the subject disclosure.

BRIEF DESCRIPTION OF THE SEQUENCES

Figure 1:
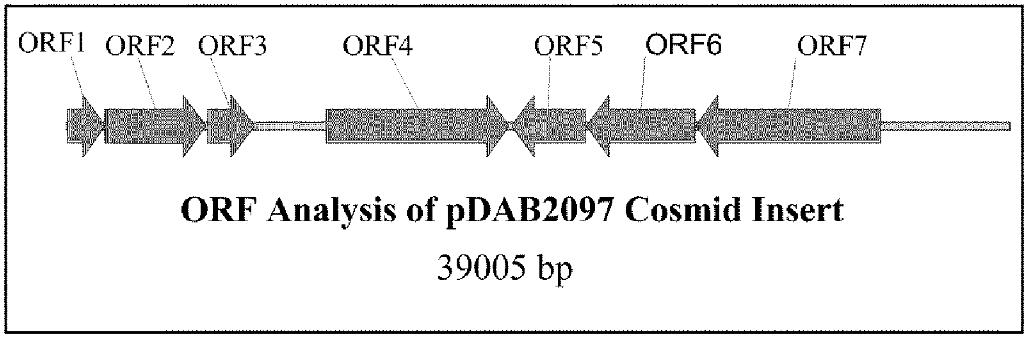
FIG. 1 shows the orientation of ORFs identified in pDAB2097.

SEQ ID NO:1 is the N-terminus of $Toxin_{XwiA}$ 220 kDa protein ($XptA2_{Wi}$).

SEQ ID NO:2 is an internal peptide of $Toxin_{XwiA}$ purified toxin ($XptA2_{Wi}$).

SEQ ID NO:3 is an internal peptide of $Toxin_{XwiA}$ purified toxin ($XptA2_{Wi}$).

SEQ ID NO:4 is an internal peptide of $Toxin_{XwiA}$ purified toxin ($XptA2_{Wi}$).

SEQ ID NO:5 is an internal peptide of $Toxin_{XwiA}$ purified toxin ($XptA2_{Wi}$).

SEQ ID NO:6 is the pDAB2097 cosmid insert: 39,005 bp.

SEQ ID NO:7 is the pDAB2097 cosmid ORF1: nucleotides 1-1,533 of SEQ ID NO:6.

SEQ ID NO:8 is the pDAB2097 cosmid ORF1 deduced protein: 511 aa.

SEQ ID NO:9 is the pDAB2097 cosmid ORF2 ($xptD1_{Wi}$): nucleotides 1,543-5,715 of SEQ ID NO:6.

SEQ ID NO:10 is the pDAB2097 cosmid ORF2 deduced protein: 1,391 aa.

SEQ ID NO: 11 is the pDAB2097 cosmid ORF3: nucleotides 5,764-7,707 of SEQ ID NO:6.

SEQ ID NO:12 is the pDAB2097 cosmid ORF3 deduced protein: 648 aa.

SEQ ID NO:13 is the pDAB2097 cosmid ORF4 ($xptA1_{Wi}$): nucleotides 10,709-18,277 of SEQ ID NO:6.

SEQ ID NO:14 is the pDAB2097 cosmid ORF4 deduced protein: 2,523 aa.

SEQ ID NO:15 is the pDAB2097 cosmid ORF5 ($xptB1_{Wi}$): nucleotides 18,383-21,430 (C) of SEQ ID NO:6.

SEQ ID NO:16 is the pDAB2097 cosmid ORF5 deduced protein: 1,016 aa.

SEQ ID NO:17 is the pDAB2097 cosmid ORF6 ($xptC1_{Wi}$): nucleotides 21,487-25,965 (C) of SEQ ID NO:6.

SEQ ID NO:18 is the pDAB2097 cosmid ORF6 deduced protein: 1,493 aa.

SEQ ID NO:19 is the pDAB2097 cosmid ORF7 ($xptA2_{Wi}$): nucleotides 26,021-33,634 (C) of SEQ ID NO:6.

SEQ ID NO:20 is the pDAB2097 cosmid ORF7 deduced protein: 2,538 aa.

SEQ ID NO:21 is the TcdA nucleic acid sequence from GENBANK Accession No. AF188483.

SEQ ID NO:22 is the TcdB1 nucleic acid sequence from GENBANK Accession No. AF346500.

SEQ ID NO:23 is the forward primer used to amplify the TcdB1 sequence from plasmid pBC-AS4.

SEQ ID NO:24 is the reverse primer used to amplify the TcdB1 sequence from plasmid pBC-AS4.

SEQ ID NO:25 is the nucleic acid sequence for TccC1 from GENBANK Accession No. AAC38630.1.

SEQ ID NO:26 is the forward primer used to amplify TccC1 from the pBC KS+ vector.

SEQ ID NO:27 is the reverse primer used to amplify TccC1 from the pBC KS+ vector.

SEQ ID NO:28 is the forward primer used to amplify $xptA2_{Wi}$.

SEQ ID NO:29 is the reverse primer used to amplify $xptA2_{Wi}$.

SEQ ID NO:30 is the forward primer used to amplify $xptC1_{Wi}$.

SEQ ID NO:31 is the reverse primer used to amplify $xptC1_{Wi}$.

SEQ ID NO:32 is the forward primer used to amplify $xptB1_{Wi}$.

SEQ ID NO:33 is the reverse primer used to amplify $xptB1_{Wi}$.

SEQ ID NO:34 is the amino acid sequence of the $XptA2_{Wi}$ protein from *Xenorhabdus nematophilus* Xwi.

SEQ ID NO:35 is the nucleic acid sequence of ORF3, of *Paenibacillus* strain DAS1529, which encodes a tcaA-like protein.

SEQ ID NO:36 is the amino acid sequence encoded by *Paenibacillus* ORF3.

SEQ ID NO:37 is the nucleic acid sequence of ORF4, of *Paenibacillus* strain DAS1529, which encodes a tcaB-like protein.

SEQ ID NO:38 is the amino acid sequence encoded by *Paenibacillus* ORF4.

SEQ ID NO:39 is the nucleic acid sequence of ORF5, of *Paenibacillus* strain DAS1529, which encodes a tcaC-like protein ($pptB1_{1529}$).

SEQ ID NO:40 is the amino acid sequence encoded by *Paenibacillus* ORF5 ($PptB1_{1529}$).

SEQ ID NO:41 is the nucleic acid sequence of ORF6 (short), of *Paenibacillus* strain DAS1529, which encodes a tccC-like protein ($PptC1_{1529S}$).

SEQ ID NO:42 is a protein sequence encoded by *Paenibacillus* (short) ORF6 ($PptC1_{1529S}$).

SEQ ID NO:43 is an alternate (long) protein sequence ($PptC1_{1529L}$) encoded by *Paenibacillus* ORF6 (long) of SEQ ID NO:55.

SEQ ID NO:44 is the nucleotide sequence for TcdB2.

SEQ ID NO:45 is the amino acid sequence of the TcdB2 protein.

SEQ ID NO:46 is the nucleotide sequence of TccC3.

SEQ ID NO:47 is the amino acid sequence of the TccC3 protein.

SEQ ID NO:48 is the native $xptB1_{xb}$ coding region (4521 bases).

SEQ ID NO:49 is the native $XptB1_{xb}$ protein encoded by SEQ ID NO:48 (1506 amino acids).

SEQ ID NO:50 is the native $XPtC1_{xb}$ coding region (2889 bases).

SEQ ID NO:51 is the native $XptC1_{xb}$ protein encoded by SEQ ID NO:50 (962 amino acids).

SEQ ID NO:52 is the Xba I to Xho I fragment of expression plasmid pDAB6031 comprising the native $xptB1_{xb}$ coding region, where bases 40 to 4557 encode the protein of SEQ ID NO:49 (4595 bases).

SEQ ID NO:53 is the Xba I to Xho I fragment of expression plasmid pDAB6032 comprising the native $XPtC1_{xb}$ coding region, where bases 40 to 2925 encode the protein of SEQ ID NO:51 (2947 bases).

SEQ ID NO:54 is the Xba I to Xho I fragment of expression plasmid pDAB6033 comprising the native xptB1$_{xb}$ and native xptC1$_{xb}$ coding regions, where bases 40 to 4557 encode the protein of SEQ ID NO:49, and bases 4601 to 7486 encode the protein of SEQ ID NO:51 (7508 bases).

SEQ ID NO:55 is the nucleic acid sequence of ORF6 (long; pptC1$_{1529L}$), of *Paenibacillus* strain DAS1529, which encodes a tccC-like protein (PPtC1$_{1529L}$) disclosed in SEQ ID NO:43.

SEQ ID NO:56 is the nucleic acid sequence for TcaC from GENBANK Accession No. AF346497.1.

SEQ ID NO:57 is the nucleic acid sequence for TccC5 from GENBANK Accession No. AF346500.1.

SEQ ID NO:58 is the protein sequence for TccC2 from GENBANK Accession No. AAL18492.

SEQ ID NO:59 shows the amino acid sequence for the TcbA$_{W-14}$ protein.

SEQ ID NO:60 shows the amino acid sequence for the SepB protein.

SEQ ID NO:61 shows the amino acid sequence for the SepC protein.

SEQ ID NO:62 shows the amino acid sequence for the TcdA2$_{W-14}$ protein.

SEQ ID NO:63 shows the amino acid sequence for the TcdA4$_{W-14}$ protein.

SEQ ID NO:64 shows the amino acid sequence for the TccC4$_{W-14}$ protein.

SEQ ID NO:65 shows the TcdA amino acid sequence.

SEQ ID NO:66 shows the TccC5 amino acid sequence.

SEQ ID NO:67 shows the TcdB1 amino acid sequence.

SEQ ID NO:68 shows the TccC1 amino acid sequence.

SEQ ID NO:69 shows the TcaC amino acid sequence.

DETAILED DESCRIPTION OF THE INVENTION

The subject invention relates to the novel use of toxin complex (TC) proteins, obtainable from organisms such as *Xenorhabdus, Photorhabdus*, and *Paenibacillus*. As discussed below, one or more TC potentiators were used to enhance the activity of a TC toxin protein that is different from the TC toxin which one or both of the potentiators enhance in nature. As one skilled in the art will recognize with the benefit of this disclosure, this has broad implications and expands the range of utility that individual types of TC proteins will now be recognized to have.

It was known that some TC proteins have "stand alone" insecticidal activity, and other TC proteins were known to enhance the activity of the stand-alone toxins produced by the same given organism. In particularly preferred embodiments of the subject invention, the toxicity of a "stand-alone" TC protein (from *Photorhabdus, Xenorhabdus*, or *Paenibacillus*, for example) is enhanced by one or more TC protein "potentiators" derived from a source organism of a different genus.

There are three main types of TC proteins. As referred to herein, Class A proteins ("Protein A") are stand alone toxins. Native Class A proteins are approximately 280 kDa.

Class B proteins ("Protein B") and Class C proteins ("Protein C") enhance the toxicity of Class A proteins. As used referred to herein, native Class B proteins are approximately 170 kDa, and native Class C proteins are approximately 112 kDa.

Examples of Class A proteins are TcbA, TcdA, XptA1, and XptA2. Examples of Class B proteins are TcaC, TcdB, XptB1$_{Xb}$, and XptC1$_{Wi}$. Examples of Class C proteins are TccC, XptC1$_{Xb}$, and XptB1$_{Wi}$.

The exact mechanism of action for the toxicity and enhancement activities are not currently known, but the exact mechanism of action is not important. What is important is that the target insect eats or otherwise ingests the A, B, and C proteins.

It was known that the TcdA protein is active, alone, against *Manduca sexta*. It was also known that TcdB1 and TccC, together, can be used to enhance the activity of TcdA. TcbA is another stand-alone *Photorhabdus* toxin. One combination of TC proteins currently contemplated in the art is TcaC (or TcdB) and TccC (as potentiators) together with TcdA or TcbA. Similarly in *Xenorhabdus*, it was known that XptB1 and XptC1 enhanced the activity of XptA1 or XptA2, the latter of which are each "stand alone" toxins.

Although the complex of (TcbA or TcdA)+(TcaC+TccC) might appear to be a similar arrangement as the complex of (XptA1 or XptA2)+(XptC2+XptB1), each *Photorhabdus* component shares only about 40% (approximately) sequence identity with the "corresponding" *Xenorhabdus* component. The unique TC proteins from *Paenibacillus* also share only about 40% sequence identity with "corresponding" *Photorhabdus* and *Xenorhabdus* TC proteins (those proteins and that discovery are the subject of co-pending U.S. application Ser. No. 60/392,633, Bintrim et al., filed Jun. 28, 2002).

It is in this context that it was discovered, as described herein, that *Xenorhabdus* TC proteins could be used to enhance the activity of *Photorhabdus* TC proteins and vice versa. *Paenibacillus* TC proteins are also surprisingly demonstrated herein to potentiate the activity of *Xenorhabdus* (and *Photorhabdus*) TC toxins. This was not previously proposed or demonstrated, and was very surprising especially in light of the notable differences between *Xenorhabdus, Photorhabdus*, and *Paenibacillus* TC proteins. There was certainly no expectation that divergent proteins from these divergent organisms would be compatible with each other.

The subject invention can be performed in many different ways. A plant can be engineered to produce two types of Class A proteins and a single pair of potentiators (B and C proteins). Every cell of the plant, or every cell in a given type of tissue (such as roots or leaves) can have genes to encode the two A proteins and the B and C pair.

Alternatively, different cells of the plant can produce only one (or more) of each of these proteins. In this situation, when an insect bites and eats tissues of the plant, it could eat a cell that produces the first Protein A, another cell that produces the second Protein A, another cell that produces the B protein, and yet another cell that produces the C protein. Thus, what would be important is that the plant (not necessarily each plant cell) produces two A proteins, the B protein, and the C protein of the subject invention so that insect pests eat all four of these proteins when they eat tissue of the plant.

Aside from transgenic plants, there are many other ways of administering the proteins, in a combination of the subject invention, to the target pest. Spray-on applications are known in the art. Some or all of the A, B, and C proteins can be sprayed (the plant could produce one or more of the proteins and the others could be sprayed). Various types of bait granules for soil applications, for example, are also known in the art and can be used according to the subject invention.

Many combinations of various TC proteins are shown herein to function in surprising, new ways. One example set forth herein shows the use of TcdB1 and TccC1 to enhance the activity of XptA2 against corn earworm, for example. Another example set forth herein is the use of XptB1 together with TcdB1 to enhance the activity of TcdA against corn rootworm, for example. Similarly, and also surprisingly, it was further discovered that TC proteins from *Paenibacillus* could be used to enhance the activity of TcdA-like and $XptA2_{Xwi}$-like proteins. Some of the examples included herein are as follows:

| Protein A (Toxin) | Protein B (Potentiator 1) | Protein C (Potentiator 2) |
|---|---|---|
| XptA2 | *Paenibacillus* ORF5 (TcaC-like) | *Paenibacillus* ORF 6 |
| XptA2 | *Photorhabdus* TcdB1 | *Photorhabdus* TccC1 |
| *Photorhabdus* TcdA | *Photorhabdus* TcdB1 | XptB1 |

The use of these and other combinations will now be apparent to those skilled in the art having the benefit of the subject disclosure.

Stand-alone toxins such as TcbA, TcdA, XptA1, and XptA2 are each in the approximate size range of 280 kDa. TcaC, TcdB1, TcdB2, and XptC1 are each approximately 170 kDa. TccC1, TccC3, and XptB1 are each approximately 112 kDa. Thus, preferred embodiments of the subject invention include the use of a 280-kDa type TC protein toxin (as described herein) with a 170-kDa class TC protein (as described herein) together with a 112-kDa class TC protein (as described herein), wherein at least one of said three proteins is derived from a source organism (such as *Photorhabdus, Xenorhabdus*, or *Paenibacillus*) that is of a different genus than the source organism from which one or more of the other TC proteins is/are derived.

The subject invention provides one skilled in the art with many surprising advantages. Among the most important advantages is that one skilled in the art will now be able to use a single pair of potentiators to enhance the activity of a stand-alone *Xenorhabdus* protein toxin, for example, as well as a stand-alone *Photorhabdus* protein toxin, for example. (As one skilled in the art knows, *Xenorhabdus* toxin proteins tend to be more desirable for controlling lepidopterans while *Photorhabdus* toxin proteins tend to be more desirable for controlling coleopterans.) This reduces the number of genes (and transformation events) needed to be expressed by a transgenic plant to achieve effective control of a wider spectrum of target pests. That is, rather than having to express six genes—two toxins and two pairs of potentiators—the subject invention allows for the expression of only four genes—two toxins and one pair of potentiator proteins.

Thus, the subject invention includes a transgenic plant and/or a transgenic plant cell that co-expresses a polynucleotide or polynucleotides encoding two (or more) different stand-alone TC protein toxins, and a polynucleotide or polynucleotides encoding a single pair of TC protein potentiators—a Class B protein and a Class C protein—wherein one or both of said potentiators is/are derived from a bacterium of a genus that is different from the genus from which one of the stand-alone TC protein toxins is derived. Accordingly, one can now obtain a cell having two (or more) TC protein toxins (Class A proteins) that are enhanced by a single pair of protein potentiators (a Class B and a Class C protein). There was no previous suggestion to produce such cells, and certainly no expectation that both (or all) such toxins produced by said cell would be active to adequate levels (due to the surprising enhancement as reported herein). TC proteins, as the term is used herein, are known in the art. Such proteins include stand-alone toxins and potentiators. Bacteria known to produce TC proteins include those of the following genera: *Photorhabdus, Xenorhabdus, Paenibacillus, Serratia*, and *Pseudomonas*. See, e.g., *Pseudomonas syringae* pv. *syringae* B728a (GenBank Accession Numbers gi:23470933 and gi:23472543). Any of such TC proteins can be used according to the subject invention.

Examples of stand-alone (Class A) toxins, as the term is used herein, include TcbA and TcdA from *Photorhabus*, and XptA1 and XptA2 from *Xenorhabdus*. Toxins in this class are about 280 kDa. Further examples of stand-alone toxins include SepA from *Serratia entomophila* (GenBank Accession No. AAG09642.1). Class A proteins can be ~230 kDa (especially if truncated), ~250-290 kDa, ~260-285 kDa, and ~270 kDa, for example.

There are two main types or classes of potentiators, as the term is used herein. Examples of the "Class B" of potentiators (sometimes referred to herein as Potentiator 1) include TcaC, TcdB1, and TcdB2 from *Photorhabus*, XptC1 from *Xenorhabdus*, and the protein product of ORF5 of *Paenibacillus* strain DAS1529. Potentiators in this class are typically in the size range of about 170 kDa. Further examples of ~170 kDa class potentiators are SepB from *Serratia entomophila* (GenBank Accession No. AAG09643.1; reproduced here as SEQ ID NO:60), TcaC homologs from *Pseudomonas syringae* pv. *syringae* B728a (GenBank Accession Numbers gi23472544 and gi23059431), and *X. nematophilus* PO ORF268 (encoded by bases 258-1991 of FIG. 2 of WO 20/004855). A preferred ~170 kDa potentiator is TcdB2 (SEQ ID NOs:44-45). Class B proteins can be ~130-180 kDa, ~140-170 kDa, ~150-165 kDa, and ~155 kDa, for example.

Examples of the "Class C" potentiators (sometimes referred to herein as Potentiator 2) include TccC1 and TccC3 from *Photorhabus*, XptB1 from *Xenorhabdus*, and the protein product of ORF6 of *Paenibacillus* strain DAS1529. Potentiators in this class are typically in the size range of about 112 kDa. Further examples of ~112 kDa class potentiators are SepC from *Serratia* entomophila (GenBank Accession No. AAG09644.1; reproduced here as SEQ ID NO:61), and TccC homologs from *Pseudomonas syringae* pv. *syringae* B728a (GenBank Accession Numbers gi:23470227, gi:23472546, gi:23472540, gi:23472541, gi:23468542, gi:23472545, gi:23058175, gi:23058176, gi:23059433, gi:23059435, and gi:23059432). A preferred ~112 kDa potentiator is TccC3 (SEQ ID NOs:46-47). Class C proteins can be ~90-120 kDa, ~95-115 kDa, ~100-110 kDa, and ~105-107 kDa, for example.

WO 02/94867, U.S. Patent Application 20020078478, and Waterfield et al. (*TRENDS in Microbiology* Vol. 10, No. 12, December 2002, pp. 541-545) disclose TC proteins that can be used according to the subject invention. For example, Waterfield et al. disclose tcdB2, tccC3, tccC5, tcdA2, tcdA3, and tcdA4 genes and proteins. Any of the relevant TC proteins disclosed by relevant references discussed above in the Background section (and any other references relating to TC proteins) can also be used according to the subject invention.

Thus, one embodiment of the subject invention includes a transgenic plant or plant cell that produces one, two, or more types of stand-alone TC protein toxins, and a single pair of potentiators: Potentiator 1 and Potentiator 2 (examples of each of these three components are given above and elsewhere herein) wherein at least one of said TC proteins is derived from an organism of a genus that is different from the genes from which one or more of the other TC proteins is derived.

It should be clear that examples of the subject invention include a transgenic plant or plant cell that produces/co-expresses one type of a *Photorhabdus* toxin (e.g., TcbA or TcdA), one type of a *Xenorhabdus* toxin (e.g., XptA1 or XptA2), and a single (one and only one) pair of potentiator proteins (e.g., TcaC and TccC, without XptC1 or XptB1; or XptC1 and XptB1, without TcaC or TccC; or TcaC and *Paenibacillus* ORF6 without any other potentiators; or TcdB and XptB1 without any other potentiators; these combinations are only exemplary; many other combinations would be clear to one skilled in the art having the benefit of the subject disclosure). Additional potentiators could be used according to the subject invention to enhance heterologous toxins, but multiple types of potentiator pairs are not essential. This is one very surprising aspect of the subject invention.

It should also be clear that the subject invention can be defined in many ways—other than in terms of what is co-expressed by a transgenic plant or plant cell. For example, the subject invention includes methods of potentiating the activity of one or more stand-alone TC protein toxin(s) by coexpressing/coproducing it (or them) with a single pair of potentiators, wherein one or both of the potentiators is/are derived from an organism of a genus that is different from the genus of the organism from which the TC protein toxin is derived. The subject invention also includes methods of controlling insect (and like) pests by feeding them one or more types of TC protein toxins together with one or more pairs of potentiators (e.g., TcbA and XptA1 and XptC1 and XptB1, possibly without TcaC and TccC), including cells that produced this combination of proteins, wherein one or both of the potentiators is/are derived from an organism of a genus that differs from one or both of the stand-alone toxins.

Such arrangements were not heretofore contemplated or expected to have activity. One way of understanding why the subject results were surprising is to consider the sequence relatedness of some of the protein components exemplified herein. For example, XptA2, a stand-alone toxin from *Xenorhabdus*, has about 43% sequence identity with TcdA and about 41% identity with TcbA. TcdA and TcbA are each stand-alone toxins from *Photorhabdus*. XptA1 (another stand-alone toxin from *Xenorhabdus*) has about 45% identity with TcdA and TcbA. TcaC (a *Photorhabdus* 170 kDa potentiator) has about 49% sequence identity with XptC1 (a 170 kDa *Xenorhabdus* potentiator). TccC (a 112 kDa *Photorhabdus* potentiator) has about 48% sequence identity with XptB1 (a ~112 kDa *Xenorhabdus* potentiator). Heretofore, TcaC+TccC, for example, would not have been expected to enhance the activity of a protein (XptA1 or XptA2) that has only 40-45% sequence identity with the native "target" of the TcaC+TccC association. (The scores reported above were obtained by using the program FASTA 6.0 and are from Morgan et al., "Sequence Analysis of Insecticidal Genes from *Xenorhabdus nematophiles* PMFI296," Vol. 67, *Applied and Environmental Microbiology, May* 2001, pp. 2062-2069).

Some examples of components for use according to the subject invention, and their relatedness to each other, include:

| Class A Proteins | | |
|---|---|---|
| *Photorhabdus* TcdA toxin homologs | | |
| Name | Reference | Sequence identity to W-14 TcdA (GenBank Accession NO. AAF05542.1) |
| P.1. Hph2 | SEQ ID NO: 13 of U.S. 6,281,413B1 | ~93% |
| P.1. Hph3 | Encoded by bases 2416 to 9909 of SEQ ID NO: 11 of U.S. 6,281,413B1 | ~57% |
| *Photorhabdus* TcbA toxin homologs | | |
| Name | Reference | Sequence identity to W-14 TcdA (GenBank Accession NO. AAF05542.1) |
| P.1. W-14 TcbA | GenBank Accession No. AAC38627.1 (reproduced here as SEQ ID NO: 59) | (~50% sequence identity to W-14 TcdA) |

-continued

| Class A Proteins | | |
|---|---|---|
| *Xenorhabdus* XptA1 toxin homologs | | |
| Name | Reference | Sequence identity to Xwi XptA1 (disclosed herein as SEQ ID NO: 14) |
| X.n XptA1 | GenBank Accession No. CAC38401.1 (AJ308438) | ~96% |
| *Xenorhabdus* XptA2 toxin homologs | | |
| Name | Reference | Sequence identity to Xwi XptA2 (disclosed herein as SEQ ID NO: 20) |
| X.n. XptA2 | GenBank Accession No. CAC38404.1 (AJ308438) | ~95% |

| Class B Proteins | | |
|---|---|---|
| *Photorhabdus* ~170 kDa Potentiators | | |
| Name | Identifier | Sequence identity to P.1. W-14 TcdB (GenBank Accession No. AAL18487.1) |
| P.1. ORF2 | SEQ ID NO: 14 of U.S. 6,281,413B1 | ~93% |
| P.1. ORF4 | Encoded by bases 9966 to 14633 of SEQ ID NO: 11 of U.S. 6,281,413B1 | ~71% |
| P.1. W-14 TcaC | GenBank Accession No. AF046867 | ~58% |
| *Xenorhabdus* ~170 kDa Potentiators | | |
| Name | Identifier | Sequence identity to Xwi XptC1 (disclosed herein SEQ ID NO: 18) |
| X.n. XptC1 | GenBank Accession No. CAC38403.1 | ~90% |

| Class C Proteins | | |
|---|---|---|
| *Photorhabdus* ~112 kDa Potentiators | | |
| Name | Identifier | Sequence identity to P.1. W-14 TccC1 (GenBank Accession No. AAC38630.1) |
| P.1. ORF5 | SEQ ID NO: 12 of U.S. 6,281,413B1 | ~51% |
| P.1. TccC2 | GenBank Accession No. AAL18492 | ~48% |
| P.1. W-14 TccC3 | SEQ ID NO: 45 | ~53% |

-continued

| Class C Proteins | | |
|---|---|---|
| *Xenorhabdus* ~112 kDa Potentiators | | |
| Name | Identifer | Sequence identity to Xwi XptB1 (disclosed herein as SEQ ID NO: 16) |
| X.n. XptB1 | GenBank Accession No. CAC38402 | ~96% |
| X.nem. P2-ORF 2071 | Encoded by bases 2071 to 4929 of FIG. 2 of WO 20/004855 | ~48% |

Thus, referring to the genus of a bacterium from which a TC protein was derived is not simply a matter of arbitrary nomenclature. As illustrated above, doing so helps define a class of TC proteins that are relatively conserved amongst themselves (such as a given type of TC protein produced by *Photorhabdus* species and strains) but which are relatively quite divergent from other "corresponding" TC proteins derived from a different microbial genus (such as those produced by various *Xenorhabdus* species and strains).

Another way to define each TC protein component of the subject invention is by a given protein's degree of sequence identity to a given toxin or potentiator. Means for calculating identity scores are provided herein. Thus, one specific embodiment of the subject invention includes a transgenic plant or plant cell co-producing a toxin having at least 75% sequence identity with XptA2, a toxin having at least 75% identity with TcdA or TcbA, a potentiator having at least 75% sequence identity with TcdB1 or TcdB2, and a potentiator having at least 75% sequence identity with TccC1 or TccC3. Other TC proteins can be substituted into the above formula, in accordance with the teachings of the subject invention. Other, more specific ranges of identity scores are provided elsewhere herein.

Yet another way of defining a given type of TC protein component of the subject invention is by the hybridization characteristics of the polynucleotide that encodes it. Much more detailed information regarding such "tests" and hybridization (and wash) conditions is provided throughout the subject specification. Thus, TC proteins for use according to the subject invention can be defined by the ability of a polynucleotide that encodes the TC protein to hybridize with a given "tc" gene.

Applying that guidance to a particular example, an XptA2-type toxin of the subject invention could be defined as being encoded by a polynucleotide, wherein a nucleic acid sequence that codes for said XptA2-type toxin hybridizes with the xptA2 gene of SEQ ID NO:19, wherein hybridization is maintained after hybridization and wash under any such conditions described or suggested herein (such as the examples of low, moderate, and high stringency hybridization/wash conditions mentioned herein). Any of the other exemplified or suggested TC proteins (including potentiators or other toxins) could be substituted for XptA2 in this definition, such as TcdB2, TccC3, TcdA, and TcbA.

Thus, the subject invention includes a transgenic plant, a transgenic plant cell, or a bacterial cell that co-expresses certain combinations of polynucleotides that encode TC proteins of the subject invention. It should be clear that the subject invention includes a transgenic plant or plant cell that co-expresses two toxin genes and only one pair of potentiators. Thus, the subject invention includes a transgenic plant or plant cell comprising one or more polynucleotides encoding a toxin in a class of a toxin indicated below as Toxin Pair 1, 2, 3, or 4 as follows, and wherein said plant or cell consists of DNA encoding one pair of potentiators selected from the group consisting of proteins in the class of potentiators shown in Potentiator Pair 1, 2, 3, 4, 5, or 6, as indicated below. Stated another way, said plant or cell consists of a polynucleotide segment encoding one potentiator of Potentiator Pair 1, 2, 3, 4, 5, or 6, and said plant or cell consists of another polynucleotide segment encoding the other potentiator of the selected Potentiator Pair.

| Toxin Pair # | |
|---|---|
| 1 | TcbA & XptA1 |
| 2 | TcbA & XptA2 |
| 3 | TcdA & XptA1 |
| 4 | TcdA & XptA2 |

| Potentiator Pair # | |
|---|---|
| 1 | TcdB1 & TccC |
| 2 | TcaC & TccC |
| 3 | XptC1 & TccC |
| 4 | TcdB1 & XptB1 |
| 5 | TcaC & XptB1 |
| 6 | XptC1 & XptB1 |

The plant or cell can comprise genes encoding additional TC protein toxins (e.g., so that the cell produces TcbA as well as TcdA, and/or XptA1 and XptA2), but only one pair of potentiators is used according to preferred embodiments of the subject invention. (Of course, the cell or plant will produce multiple copies of the potentiators; the key is that additional transformation events can be avoided.)

Further embodiments of the subject invention include a transgenic cell or plant that co-expresses a stand-alone protein toxin and a single (no more than one) potentiator pair comprising at least one "heterologous" (derived from a bacterium of a genus that is other than the genus of the organism from which the toxin is derived) TC protein. The subject invention also includes potentiating the insecticidal activity of a TC protein toxin with a pair of TC proteins that are potentiators, wherein at least one (one or both) of said TC protein potentiators is a heterologous TC protein, with respect to the TC protein toxin it helps to potentiate. Sets of toxins and the potentiators used to enhance the toxin include the following combinations:

| | | |
|---|---|---|
| TcbA | XptC1 | XptB1 |
| TcbA | TcdB1 | XptB1 |
| TcbA | TcaC | XptB1 |
| TcbA | XptC1 | TccC1 |
| TcdA | XptC1 | XptB1 |
| TcdA | TcdB1 | XptB1 |
| TcdA | TcaC | XptB1 |
| TcdA | XptC1 | TccC1 |
| XptA1 | TcdB1 | TccC1 |
| XptA1 | TcdB1 | XptB1 |
| XptA1 | TcaC | TccC1 |
| XptA1 | TcaC | XptB1 |
| XptA1 | XptC1 | TccC1 |
| XptA2 | TcdB1 | TccC1 |
| XptA2 | TcdB1 | XptB1 |
| XptA2 | TcaC | TccC1 |
| XptA2 | TcaC | XptB1 |
| XptA2 | XptC1 | TccC1 |

It should be clear that the above matrices are intended to include, for example, TcdB2+TccC3 (a preferred pair of potentiators) with any of the toxins such as XptA1 and/or XptA2 (together with TcbA and/or TcdA).

Other embodiments and combinations will be apparent to one skilled in the art having the benefit of this disclosure.

The subject invention also provides "mixed pairs" of potentiators such as Potentiator Pairs 3, 4, and 5 as illustrated above. Such combinations were not heretofore expected (or suggested) to be active as TC protein toxin enhancers. Thus, such "heterologous" combinations of potentiators can now be selected to maximize their ability to enhance two (for example) insecticidal toxins. That is, one might now find that, for a given use, TcdB1 and XptB1 is a more desirable pair of potentiators than is XptC1 and XptB1, for example. Again, this is surprising given the relative degree of sequence divergence between a given *Photorhabdus* potentiator and a *Xenorhabdus* potentiator for which it is substituted, as well as the degree of difference between the natural "target" toxins which the potentiators would naturally enhance. Therefore, it should be clear that the subject invention also provides heterologous potentiator pairs (i.e., where the Class B (~170 kDa) potentiator is derived from a bacterial genus that is different from the bacterial genus from which the Class C (~112 kDa) potentiator is derived).

The subject invention is not limited to 280 kDa TC protein toxins and a heterologous 112 kDa and/or 170 kDa TC protein potentiator. As this is the first observation of the ability to "mix and match" *Xenorhabdus* and *Photorhabdus*, for example, TC proteins, the subject invention includes any substitution of a *Xenorhabdus* TC protein with a "corresponding" *Photorhabdus* TC protein, and vice versa. For example, one skilled in the art will also now seek to use various heterlogous combinations involving "Toxin C" components (as discussed above in the Background section) and "Toxin D" components (e.g., TccA+XptD1).

The subject invention also includes the use of a transgenic plant producing a subject TC protein combination together with one or more *Bacillus thuringiensis* Cry proteins, for example.

Proteins and toxins. The present invention provides easily administered, functional proteins. The present invention also provides a method for delivering insecticidal toxins that are functionally active and effective against many orders of insects, preferably lepidopteran insects. By "functional activity" (or "active against") it is meant herein that the protein toxins function as orally active insect control agents (alone or in combination with other proteins), that the proteins have a toxic effect (alone or in combination with other proteins), or are able to disrupt or deter insect growth and/or feeding which may or may not cause death of the insect. When an insect comes into contact with an effective amount of a "toxin" of the subject invention delivered via transgenic plant expression, formulated protein composition(s), sprayable protein composition(s), a bait matrix or other delivery system, the results are typically death of the insect, inhibition of the growth and/or proliferation of the insect, and/or prevention of the insects from feeding upon the source (preferably a transgenic plant) that makes the toxins available to the insects. Functional proteins of the subject invention can also work together or alone to enhance or improve the activity of one or more other toxin proteins. The terms "toxic," "toxicity," or "toxin" as used herein are meant to convey that the subject "toxins" have "functional activity" as defined herein.

Complete lethality to feeding insects is preferred, but is not required to achieve functional activity. If an insect avoids the toxin or ceases feeding, that avoidance will be useful in some applications, even if the effects are sublethal or lethality is delayed or indirect. For example, if insect resistant transgenic plants are desired, the reluctance of insects to feed on the plants is as useful as lethal toxicity to the insects because the ultimate objective is avoiding insect-induced plant damage.

There are many other ways in which toxins can be incorporated into an insect's diet. For example, it is possible to adulterate the larval food source with the toxic protein by spraying the food with a protein solution, as disclosed herein. Alternatively, the purified protein could be genetically engineered into an otherwise harmless bacterium, which could then be grown in culture, and either applied to the food source or allowed to reside in the soil in an area in which insect eradication was desirable. Also, the protein could be genetically engineered directly into an insect food source. For instance, the major food source for many insect larvae is plant material. Therefore the genes encoding toxins can be transferred to plant material so that said plant material expresses the toxin of interest.

Transfer of the functional activity to plant or bacterial systems typically requires nucleic acid sequences, encoding the amino acid sequences for the toxins, integrated into a protein expression vector appropriate to the host in which the vector will reside. One way to obtain a nucleic acid sequence encoding a protein with functional activity is to isolate the native genetic material from the bacterial species which produce the toxins, using information deduced from the toxin's amino acid sequence, as disclosed herein. The native sequences can be optimized for expression in plants, for example, as discussed in more detail below. Optimized polynucleotide can also be designed based on the protein sequence.

The subject invention provides classes of TC proteins having toxin activities. One way to characterize these classes of toxins and the polynucleotides that encode them is by defining a polynucleotide by its ability to hybridize, under a range of specified conditions, with an exemplified nucleotide sequence (the complement thereof and/or a probe or probes derived from either strand) and/or by their ability to be amplified by PCR using primers derived from the exemplified sequences.

There are a number of methods for obtaining the pesticidal toxins for use according to the subject invention. For example, antibodies to the pesticidal toxins disclosed herein can be used to identify and isolate other toxins from a mixture of proteins. Specifically, antibodies may be raised to the portions of the toxins which are most constant and most distinct from other toxins. These antibodies can then be used to specifically identify equivalent toxins with the characteristic activity by immunoprecipitation, enzyme linked immunosorbent assay (ELISA), or immuno-blotting. Antibodies to the toxins disclosed herein, or to equivalent toxins, or to fragments of these toxins, can be readily prepared using standard procedures. Such antibodies are an aspect of the subject invention. Toxins of the subject invention can be obtained from a variety of sources/source microorganisms.

One skilled in the art would readily recognize that toxins (and genes) of the subject invention can be obtained from a variety of sources. A toxin "from" or "obtainable from" any of the subject isolates referred to or suggested herein means that the toxin (or a similar toxin) can be obtained from the isolate or some other source, such as another bacterial strain or a plant. "Derived from" also has this connotation, and includes proteins obtainable from a given type of bacterium that are modified for expression in a plant, for example. One skilled in the art will readily recognize that, given the disclosure of a bacterial gene and toxin, a plant can be engineered to produce the toxin. Antibody preparations, nucleic acid probes (DNA and RNA), and the like may be prepared using the polynucleotide and/or amino acid sequences disclosed herein and used to screen and recover other toxin genes from other (natural) sources.

Polynucleotides and probes. The subject invention further provides nucleotide sequences that encode the TC proteins for use according to the subject invention. The subject invention further provides methods of identifying and characterizing genes that encode proteins having toxin activity. In one embodiment, the subject invention provides unique nucleotide sequences that are useful as hybridization probes and/or primers for PCR techniques. The primers produce characteristic gene fragments that can be used in the identification, characterization, and/or isolation of specific toxin genes. The nucleotide sequences of the subject invention encode toxins that are distinct from previously described toxins.

The polynucleotides of the subject invention can be used to form complete "genes" to encode proteins or peptides in a desired host cell. For example, as the skilled artisan would readily recognize, the subject polynucleotides can be appropriately placed under the control of a promoter in a host of interest, as is readily known in the art.

As the skilled artisan knows, DNA typically exists in a double-stranded form. In this arrangement, one strand is complementary to the other strand and vice versa. As DNA is replicated in a plant (for example), additional complementary strands of DNA are produced. The "coding strand" is often used in the art to refer to the strand that binds with the anti-sense strand. The mRNA is transcribed from the "anti-sense" strand of DNA. The "sense" or "coding" strand has a series of codons (a codon is three nucleotides that can be read as a three-residue unit to specify a particular amino acid) that can be read as an open reading frame (ORF) to form a protein or peptide of interest. In order to produce a protein in vivo, a strand of DNA is typically transcribed into a complementary strand of mRNA which is used as the template for the protein. Thus, the subject invention includes the use of the exemplified polynucleotides shown in the attached sequence listing and/or equivalents including the complementary strands. RNA and PNA (peptide nucleic acids) that are functionally equivalent to the exemplified DNA are included in the subject invention.

In one embodiment of the subject invention, bacterial isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of toxin-encoding genes will be amplified by the procedure, thus identifying the presence of the toxin-encoding gene(s).

Further aspects of the subject invention include genes and isolates identified using the methods and nucleotide sequences disclosed herein. The genes thus identified encode toxins active against pests.

Proteins and genes for use according to the subject invention can be identified and obtained by using oligonucleotide probes, for example. These probes are detectable nucleotide sequences which may be detectable by virtue of an appropriate label or may be made inherently fluorescent as described in International Application No. WO 93/16094. The probes (and the polynucleotides of the subject invention) may be DNA, RNA, or PNA. In addition to adenine (A), cytosine (C), guanine (G), thymine (T), and uracil (U; for RNA molecules), synthetic probes (and polynucleotides) of the subject invention can also have inosine (a neutral base capable of pairing with all four bases; sometimes used in place of a mixture of all four bases in synthetic probes). Thus, where a synthetic, degenerate oligonucleotide is referred to herein, and "N" or "n" is used generically, "N" or "n" can be G, A, T, C, or inosine. Ambiguity codes as used herein are in accordance with standard IUPAC naming conventions as of the filing of the subject application (for example, R means A or G, Y means C or T, etc.).

As is well known in the art, if a probe molecule hybridizes with a nucleic acid sample, it can be reasonably assumed that the probe and sample have substantial homology/similarity/identity. Preferably, hybridization of the polynucleotide is first conducted followed by washes under conditions of low, moderate, or high stringency by techniques well-known in the art, as described in, for example, Keller, G. H., M. M. Manak (1987) *DNA Probes*, Stockton Press, New York, N.Y., pp. 169-170. For example, as stated therein, low stringency conditions can be achieved by first washing with 2×SSC (Standard Saline Citrate)/0.1% SDS (Sodium Dodecyl Sulfate) for 15 minutes at room temperature. Two washes are typically performed. Higher stringency can then be achieved by lowering the salt concentration and/or by raising the temperature. For example, the wash described above can be followed by two washings with 0.1×SSC/0.1% SDS for 15 minutes each at room temperature followed by subsequent washes with 0.1×SSC/0.1% SDS for 30 minutes each at 55E C. These temperatures can be used with other hybridization and wash protocols set forth herein and as would be known to one skilled in the art (SSPE can be used as the salt instead of SSC, for example). The 2×SSC/0.1% SDS can be prepared by adding 50 ml of 20×SSC and 5 ml of 10% SDS to 445 ml of water. 20×SSC can be prepared by combining NaCl (175.3 g/0.150 M), sodium citrate (88.2 g/0.015 M), and water, adjusting pH to 7.0 with 10 N NaOH, then adjusting the volume to 1 liter 10% SDS can be prepared by dissolving 10 g of SDS in 50 ml of autoclaved water, then diluting to 100 ml.

Detection of the probe provides a means for determining in a known manner whether hybridization has been maintained. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Hybridization characteristics of a molecule can be used to define polynucleotides of the subject invention. Thus the subject invention includes polynucleotides (and/or their complements, preferably their full complements) that hybridize with a polynucleotide exemplified herein. That is, one way to define a tcdA-like gene (and the protein it encodes), for example, is by its ability to hybridize (under any of the conditions specifically disclosed herein) with a previously known, including a specifically exemplified, tcdA gene. The same is true for xptA2-, tcaC-, tcaA-, tcaB-, tcdB-, tccC-, and xptB1-like genes and related proteins, for example. This also includes the tcdB2 and tccC3 genes.

As used herein, "stringent" conditions for hybridization refers to conditions which achieve the same, or about the same, degree of specificity of hybridization as the conditions employed by the current applicants. Specifically, hybridization of immobilized DNA on Southern blots with $^{32}P$-labeled gene-specific probes was performed by standard methods (see, e.g., Maniatis, T., E. F. Fritsch, J. Sambrook [1982] *Molecular Cloning: A Laboratory Manual*, Cold Spring Harbor Laboratory, Cold Spring Harbor, N.Y.). In general, hybridization and subsequent washes were carried out under conditions that allowed for detection of target sequences. For double-stranded DNA gene probes, hybridization was carried out overnight at 20-25E C below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Lickbush, P. T. Cherbas, and F. C. Kafatos [1983] *Methods of Enzymology*, R. Wu, L. Grossman and K. Moldave [eds.] Academic Press, New York 100:266-285):

$$Tm=81.5C+16.6\ \mathrm{Log}\ [Na^+]+0.41(\%\ G+C)-0.61(\%\ \mathrm{formamide})-600/\mathrm{length\ of\ duplex\ in\ base\ pairs}.$$

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10-20EC below the melting temperature (Tm) of the hybrid in 6×SSPE, 5×Denhardt's solution, 0.1% SDS, 0.1 mg/ml denatured DNA. Tm for oligonucleotide probes was determined by the following formula:

$$Tm(°\ C.)=2(\mathrm{number}\ T/A\ \mathrm{base\ pairs})+4(\mathrm{number}\ G/C\ \mathrm{base\ pairs})$$

(Suggs, S. V., T. Miyake, E. H. Kawashime, M. J. Johnson, K. Itakura, and R. B. Wallace [1981] *ICN-UCLA Symp. Dev. Biol. Using Purified Genes*, D. D. Brown [ed.], Academic Press, New York, 23:683-693).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

Low: 1 or 2×SSPE, room temperature

Low: 1 or 2×SSPE, 42° C.

Moderate: 0.2× or 1×SSPE, 65° C.

High: 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

PCR technology. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of β-Globin Genomic Sequences and Restriction Site Analysis for Diagnosis of Sickle Cell Anemia," *Science* 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. The extension product of each primer can serve as a template for the other primer, so each cycle essentially doubles the amount of DNA fragment produced in the previous cycle. This results in the exponential accumulation of the specific target fragment, up to several million-fold in a few hours. By using a thermostable DNA polymerase such as Taq polymerase, isolated from the thermophilic bacterium *Thermus aquaticus*, the amplification process can be completely automated. Other enzymes which can be used are known to those skilled in the art.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions, and deletions can be produced in a given primer by methods known to an ordinarily skilled artisan.

Modification of genes and toxins. The genes and toxins useful according to the subject invention include not only the specifically exemplified full-length sequences, but also portions, segments and/or fragments (including internal and/or terminal deletions compared to the full-length molecules) of these sequences, variants, mutants, chimerics, and fusions thereof. Proteins of the subject invention can have substituted amino acids so long as they retain the characteristic pesticidal/functional activity of the proteins specifically exemplified herein. "Variant" genes have nucleotide sequences that encode the same toxins or equivalent toxins having pesticidal activity equivalent to an exemplified protein. The terms "variant proteins" and "equivalent toxins" refer to toxins having the same or essentially the same biological/functional activity against the target pests and equivalent sequences as the exemplified toxins. As used herein, reference to an "equivalent" sequence refers to sequences having amino acid substitutions, deletions, additions, or insertions which improve or do not adversely affect pesticidal activity. Fragments retaining pesticidal activity are also included in this definition. Fragments and other equivalents that retain the same or similar function, or "toxin activity," as a corresponding fragment of an exemplified toxin are within the scope of the subject invention. Changes, such as amino acid substitutions or additions, can be made for a variety of purposes, such as increasing (or decreasing) protease stability of the protein (without materially/substantially decreasing the functional activity of the toxin).

Equivalent toxins and/or genes encoding these equivalent toxins can be obtained/derived from wild-type or recombinant bacteria and/or from other wild-type or recombinant organisms using the teachings provided herein. Other *Bacillus, Serratia, Paenibacillus, Photorhabdus*, and *Xenorhabdus* species, for example, can be used as source isolates.

Variations of genes may be readily constructed using standard techniques for making point mutations, for example. In addition, U.S. Pat. No. 5,605,793, for example, describes methods for generating additional molecular diversity by using DNA reassembly after random fragmentation. Variant genes can be used to produce variant proteins; recombinant hosts can be used to produce the variant proteins. Using these "gene shuffling" techniques, equivalent genes and proteins can be constructed that comprise any 5, 10, or 20 contiguous residues (amino acid or nucleotide) of any sequence exemplified herein. As one skilled in the art knows, the gene shuffling techniques can be adjusted to obtain equivalents having, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 contiguous residues (amino acid or nucleotide), corresponding to a segment (of the same size) in any of the exemplified or suggested sequences (or the complements (full complements) thereof). Similarly sized segments, especially those for conserved regions, can also be used as probes and/or primers.

Fragments of full-length genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

It is within the scope of the invention as disclosed herein that toxins (and TC proteins) may be truncated and still retain functional activity. By "truncated toxin" is meant that a portion of a toxin protein may be cleaved and yet still exhibit activity after cleavage. Cleavage can be achieved by proteases inside or outside of the insect gut. Furthermore, effectively cleaved proteins can be produced using molecular biology techniques wherein the DNA bases encoding said toxin are removed either through digestion with restriction endonucleases or other techniques available to the skilled artisan. After truncation, said proteins can be expressed in heterologous systems such as *E. coli*, baculoviruses, plant-based viral systems, yeast and the like and then placed in insect assays as disclosed herein to determine activity. It is well-known in the art that truncated toxins can be successfully produced so that they retain functional activity while having less than the entire, full-length sequence. It is well known in the art that B.t. toxins can be used in a truncated (core toxin) form. See, e.g., Adang et al., *Gene* 36:289-300 (1985), "Characterized full-length and truncated plasmid clones of the crystal protein of *Bacillus thuringiensis* subsp *kurstaki* HD-73 and their toxicity to *Manduca sexta*." There are other examples of truncated proteins that retain insecticidal activity, including the insect juvenile hormone esterase (U.S. Pat. No. 5,674,485 to the Regents of the University of California). As used herein, the term "toxin" is also meant to include functionally active truncations.

In some cases, especially for expression in plants, it can be advantageous to use truncated genes that express truncated proteins. Höfte et al. 1989, for example, discussed in the Background Section above, discussed protoxin and core toxin segments of B.t. toxins. Preferred truncated genes will typically encode 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the full-length protein. The Background section also discusses protease processing and reassembly of the segments of TcdA and TcbA, for example.

Certain toxins/TC proteins of the subject invention have been specifically exemplified herein. As these toxins/TC proteins are merely exemplary of the proteins of the subject invention, it should be readily apparent that the subject invention comprises variant or equivalent proteins (and nucleotide sequences coding for equivalents thereof) having the same or similar toxin activity of the exemplified proteins. Equivalent proteins will have amino acid similarity (and/or homology) with an exemplified toxin/TC protein. The amino acid identity will typically be greater than 60%, preferably greater than 75%, more preferably greater than 80%, even more preferably greater than 90%, and can be greater than 95%. Preferred polynucleotides and proteins of the subject invention can also be defined in terms of more particular identity and/or similarity ranges. For example, the identity and/or similarity can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified or suggested herein. Any number listed above can be used to define the upper and lower limits. For example, a Class A protein can be defined as having 50-90% identity with a given TcdA protein. Thus, a TcdA-like protein (and/or a tcdA-like gene) can be defined by any numerical identity score provided or suggested herein, as compared to any previously known TcdA protein, including any TcdA protein (and likewise with XptA2 proteins) specifically exemplified herein. The same is true for any other protein or gene, to be used according to the subject invention, such as TcaC-, TcaA-, TcaB-, TcdB-, TccC-, and XptB2-like proteins and genes. Thus, this applies to potentiators (such as TcdB2 and TccC3) and stand-alone toxins.

Unless otherwise specified, as used herein, percent sequence identity and/or similarity of two nucleic acids is determined using the algorithm of Karlin and Altschul (1990), *Proc. Natl. Acad. Sci. USA* 87:2264-2268, modified as in Karlin and Altschul (1993), *Proc. Natl. Acad. Sci. USA* 90:5873-5877. Such an algorithm is incorporated into the NBLAST and XBLAST programs of Altschul et al. (1990), *J. Mol. Biol.* 215:402-410. BLAST nucleotide searches are performed with the NBLAST program, score=100, wordlength=12. Gapped BLAST can be used as described in Altschul et al. (1997), *Nucl. Acids Res.* 25:3389-3402. When utilizing BLAST and Gapped BLAST programs, the default parameters of the respective programs (NBLAST and XBLAST) are used. See NCBI/NIH website. The scores can also be calculated using the methods and algorithms of Crickmore et al. as described in the Background section, above. To obtain gapped alignments for comparison purposes, the AlignX function of Vector NTI Suite 8 (InforMax, Inc., North Bethesda, Md., U.S.A.), was used employing the default parameters. These were: a Gap opening penalty of 15, a Gap extension penalty of 6.66, and a Gap separation penalty range of 8.

The amino acid homology/similarity/identity will be highest in critical regions of the protein that account for its toxin activity or that are involved in the determination of three-dimensional configurations that are ultimately responsible for the toxin activity. In this regard, certain amino acid substitutions are acceptable and can be expected to be tolerated. For example, these substitutions can be in regions of the protein that are not critical to activity. Analyzing the crystal structure of a protein, and software-based protein structure modeling, can be used to identify regions of a protein that can be modified (using site-directed mutagenesis, shuffling, etc.) to actually change the properties and/or increase the functionality of the protein.

Various properties and three-dimensional features of the protein can also be changed without adversely affecting the toxin activity/functionality of the protein. Conservative amino acid substitutions can be expected to be tolerated/to not adversely affect the three-dimensional configuration of the molecule. Amino acids can be placed in the following classes: non-polar, uncharged polar, basic, and acidic. Conservative substitutions whereby an amino acid of one class is replaced with another amino acid of the same type fall within the scope of the subject invention so long as the substitution is not adverse to the biological activity of the compound. Table 1 provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the functional/biological/toxin activity of the protein.

As used herein, reference to "isolated" polynucleotides and/or "purified" toxins refers to these molecules when they are not associated with the other molecules with which they would be found in nature. Thus, reference to "isolated" and/or "purified" signifies the involvement of the "hand of man" as described herein. For example, a bacterial toxin "gene" of the subject invention put into a plant for expression is an "isolated polynucleotide." Likewise, a *Paenibacillus* protein, exemplified herein, produced by a plant is an "isolated protein."

Because of the degeneracy/redundancy of the genetic code, a variety of different DNA sequences can encode the amino acid sequences disclosed herein. It is well within the skill of a person trained in the art to create alternative DNA sequences that encode the same, or essentially the same, toxins. These variant DNA sequences are within the scope of the subject invention.

Optimization of sequence for expression in plants. To obtain high expression of heterologous genes in plants it may be preferred to reengineer said genes so that they are more efficiently expressed in (the cytoplasm of) plant cells. Maize is one such plant where it may be preferred to re-design the heterologous gene(s) prior to transformation to increase the expression level thereof in said plant. Therefore, an additional step in the design of genes encoding a bacterial toxin is reengineering of a heterologous gene for optimal expression.

One reason for the reengineering of a bacterial toxin for expression in maize is due to the non-optimal G+C content of the native gene. For example, the very low G+C content of many native bacterial gene(s) (and consequent skewing towards high A+T content) results in the generation of sequences mimicking or duplicating plant gene control sequences that are known to be highly A+T rich. The presence of some A+T-rich sequences within the DNA of gene(s) introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Therefore, one goal in the design of genes encoding a bacterial toxin for maize expression, more preferably referred to as plant optimized gene(s), is to generate a DNA sequence having a higher G+C content, and preferably one close to that of maize genes coding for metabolic enzymes. Another goal in the design of the plant optimized gene(s) encoding a bacterial toxin is to generate a DNA sequence in which the sequence modifications do not hinder translation.

The table below (Table 2) illustrates how high the G+C content is in maize. For the data in Table 2, coding regions of the genes were extracted from GenBank (Release 71) entries, and base compositions were calculated using the MacVector™ program (Accelerys, San Diego, Calif.). Intron sequences were ignored in the calculations.

Due to the plasticity afforded by the redundancy/degeneracy of the genetic code (i.e., some amino acids are specified by more than one codon), evolution of the genomes in different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. It is thought that the presence of "minor" codons within an mRNA may reduce the absolute translation rate of that mRNA, especially when the relative abundance of the charged tRNA corresponding to the minor codon is low. An extension of this is that the diminution of translation rate by individual minor codons would be at least additive for multiple minor codons. Therefore, mRNAs having high relative contents of minor codons would have correspondingly low translation rates. This rate would be reflected by subsequent low levels of the encoded protein.

In engineering genes encoding a bacterial toxin for maize (or other plant, such as cotton or soybean) expression, the codon bias of the plant has been determined. The codon bias for maize is the statistical codon distribution that the plant uses for coding its proteins and the preferred codon usage is shown in Table 3. After determining the bias, the percent frequency of the codons in the gene(s) of interest is determined. The primary codons preferred by the plant should be determined, as well as the second, third, and fourth choices of preferred codons when multiple choices exist. A new DNA sequence can then be designed which encodes the amino sequence of the bacterial toxin, but the new DNA sequence differs from the native bacterial DNA sequence (encoding the toxin) by the substitution of the plant (first preferred, second preferred, third preferred, or fourth preferred) codons to specify the amino acid at each position within the toxin amino acid sequence. The new sequence is then analyzed for restriction enzyme sites that might have been created by the modification. The identified sites are further modified by replacing the codons with first, second, third, or fourth choice preferred codons. Other sites in the sequence which could affect transcription or translation of the gene of interest are the exon: intron junctions (5' or 3'), poly A addition signals, or RNA polymerase termination signals. The sequence is further analyzed and modified to reduce the frequency of TA or GC doublets. In addition to the doublets, G or C sequence blocks that have more than about four residues that are the same can affect transcription of the sequence. Therefore, these blocks are also modified by replacing the codons of first or second choice, etc. with the next preferred codon of choice.

TABLE 2

Compilation of G + C contents of protein coding regions of maize genes

| Protein Class.sup.a | Range % G + C | Mean % G + C.sup.b |
|---|---|---|
| Metabolic Enzymes (76) | 44.4-75.3 | 59.0 (.+-.8.0) |
| Structural Proteins (18) | 48.6-70.5 | 63.6 (.+-.6.7) |
| Regulatory Proteins (5) | 57.2-68.8 | 62.0 (.+-.4.9) |
| Uncharacterized Proteins (9) | 41.5-70.3 | 64.3 (.+-.7.2) |
| All Proteins (108) | 44.4-75.3 | 60.8 (.+-.5.2) |

[a]Number of genes in class given in parentheses.

[b]Standard deviations given in parentheses.

[c]Combined groups mean ignored in mean calculation

It is preferred that the plant optimized gene(s) encoding a bacterial toxin contain about 63% of first choice codons, between about 22% to about 37% second choice codons, and between about 15% to about 0% third or fourth choice codons, wherein the total percentage is 100%. Most preferred the plant optimized gene(s) contains about 63% of first choice codons, at least about 22% second choice codons, about 7.5% third choice codons, and about 7.5% fourth choice codons, wherein the total percentage is 100%. The preferred codon usage for engineering genes for maize expression are shown in Table 3. The method described above enables one skilled in the art to modify gene(s) that are foreign to a particular plant so that the genes are optimally expressed in plants. The method is further illustrated in PCT application WO 97/13402.

In order to design plant optimized genes encoding a bacterial toxin, a DNA sequence is designed to encode the amino acid sequence of said protein toxin utilizing a redundant genetic code established from a codon bias table compiled for the gene sequences for the particular plant, as shown in Table 2. The resulting DNA sequence has a higher degree of codon diversity, a desirable base composition, can contain strategically placed restriction enzyme recognition sites, and lacks sequences that might interfere with transcription of the gene, or translation of the product mRNA.

TABLE 3

Preferred amino acid codons for proteins expressed in maize

| Amino Acid | Codon* |
|---|---|
| Alanine | GCC/GCG |
| Cysteine | TGC/TGT |
| Aspartic Acid | GAC/GAT |
| Glutamic Acid | GAG/GAA |
| Phenylalanine | TTC/TTT |
| Glycine | GGC/GGG |
| Histidine | CAC/CAT |
| Isoleucine | ATC/ATT |
| Lysine | AAG/AAA |
| Leucine | CTG/CTC |
| Methionine | ATG |
| Asparagine | AAC/AAT |
| Proline | CCG/CCA |
| Glutamine | CAG/CAA |
| Arginine | AGG/CGC |
| Serine | AGC/TCC |
| Threonine | ACC/ACG |
| Valine | GTG/GTC |
| Tryptophan | TGG |
| Tryrosine | TAC/TAT |
| Stop | TGA/TAG |

*The first and second preferred codons for maize.

Thus, synthetic genes that are functionally equivalent to the toxins/genes of the subject invention can be used to transform hosts, including plants. Additional guidance regarding the production of synthetic genes can be found in, for example, U.S. Pat. No. 5,380,831.

Transgenic hosts. The toxin-encoding genes of the subject invention can be introduced into a wide variety of microbial or plant hosts. In preferred embodiments, transgenic plant cells and plants are used. Preferred plants (and plant cells) are corn, maize, and cotton.

In preferred embodiments, expression of the toxin gene results, directly or indirectly, in the intracellular production (and maintenance) of the pesticide proteins. Plants can be rendered insect-resistant in this manner. When transgenic/recombinant/transformed/transfected host cells (or contents thereof) are ingested by the pests, the pests will ingest the toxin. This is the preferred manner in which to cause contact of the pest with the toxin. The result is control (killing or making sick) of the pest. Sucking pests can also be controlled in a similar manner. Alternatively, suitable microbial hosts, e.g., *Pseudomonas* such as *P. fluorescens*, can be applied where target pests are present; the microbes can proliferate there, and are ingested by the target pests. The microbe hosting the toxin gene can be treated under conditions that prolong the activity of the toxin and stabilize the cell. The treated cell, which retains the toxic activity, can then be applied to the environment of the target pest.

Where the toxin gene is introduced via a suitable vector into a microbial host, and said host is applied to the environment in a living state, certain host microbes should be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Also of interest are pigmented microorganisms.

Insertion of genes to form transgenic hosts. One aspect of the subject invention is the transformation/transfection of plants, plant cells, and other host cells with polynucleotides of the subject invention that express proteins of the subject invention. Plants transformed in this manner can be rendered resistant to attack by the target pest(s).

A wide variety of methods are available for introducing a gene encoding a pesticidal protein into the target host under conditions that allow for stable maintenance and expression of the gene. These methods are well known to those skilled in the art and are described, for example, in U.S. Pat. No. 5,135,867.

For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1-46; and An et al. (1985) *EMBO J.* 4:277-287.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If *Agrobacteria* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacteria*. The intermediate vector can be transferred into *Agrobacterium tumefaciens* by means of a helper plasmid (conjugation). Binary vectors can replicate themselves both in *E. coli* and in *Agrobacteria*. They comprise a selection marker gene and a linker or polylinker which are framed by the right and left T-DNA border regions. They can be transformed directly into *Agrobacteria* (Holsters et al. [1978] *Mol. Gen. Genet.* 163:181-187). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In some preferred embodiments of the invention, genes encoding the bacterial toxin are expressed from transcriptional units inserted into the plant genome. Preferably, said transcriptional units are recombinant vectors capable of stable integration into the plant genome and enable selection of transformed plant lines expressing mRNA encoding the proteins.

Once the inserted DNA has been integrated in the genome, it is relatively stable there (and does not come out again). It normally contains a selection marker that confers on the transformed plant cells resistance to a biocide or an antibiotic, such as kanamycin, G418, bleomycin, hygromycin, or chloramphenicol, inter alia. The individually employed marker should accordingly permit the selection of transformed cells rather than cells that do not contain the inserted DNA. The gene(s) of interest are preferably expressed either by constitutive or inducible promoters in the plant cell. Once expressed, the mRNA is translated into proteins, thereby incorporating amino acids of interest into protein. The genes encoding a toxin expressed in the plant cells can be under the control of a constitutive promoter, a tissue-specific promoter, or an inducible promoter.

Several techniques exist for introducing foreign recombinant vectors into plant cells, and for obtaining plants that stably maintain and express the introduced gene. Such techniques include the introduction of genetic material coated onto microparticles directly into cells (U.S. Pat. Nos. 4,945,050 to Cornell and 5,141,131 to DowElanco, now Dow AgroSciences, LLC). In addition, plants may be transformed using *Agrobacterium* technology, see U.S. Pat. Nos. 5,177,010 to University of Toledo; 5,104,310 to Texas A&M; European Patent Application 0131624B1; European Patent Applications 120516, 159418B1 and 176,112 to Schilperoot; U.S. Pat. Nos. 5,149,645, 5,469,976, 5,464,763 and 4,940,838 and 4,693,976 to Schilperoot; European Patent Applications 116718, 290799, 320500 all to Max Planck; European Patent Applications 604662 and 627752, and U.S. Pat. No. 5,591, 616, to Japan Tobacco; European Patent Applications 0267159 and 0292435, and U.S. Pat. No. 5,231,019, all to Ciba Geigy, now Novartis; U.S. Pat. Nos. 5,463,174 and 4,762,785, both to Calgene; and U.S. Pat. Nos. 5,004,863 and 5,159,135, both to Agracetus. Other transformation technology includes whiskers technology. See U.S. Pat. Nos. 5,302, 523 and 5,464,765, both to Zeneca. Electroporation technology has also been used to transform plants. See WO 87/06614 to Boyce Thompson Institute; U.S. Pat. Nos. 5,472,869 and 5,384,253, both to Dekalb; and WO 92/09696 and WO 93/21335, both to Plant Genetic Systems. Furthermore, viral vectors can also be used to produce transgenic plants expressing the protein of interest. For example, monocotyledonous plant can be transformed with a viral vector using the methods described in U.S. Pat. No. 5,569,597 to Mycogen Plant Science and Ciba-Giegy, now Novartis, as well as U.S. Pat. Nos. 5,589,367 and 5,316,931, both to Biosource.

As mentioned previously, the manner in which the DNA construct is introduced into the plant host is not critical to this invention. Any method which provides for efficient transformation may be employed. For example, various methods for plant cell transformation are described herein and include the use of Ti or Ri-plasmids and the like to perform *Agrobacterium* mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation. Where *Agrobacterium* is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria which are known to those skilled in the art. The manner of vector transformation into the *Agrobacterium* host is not critical to this invention. The Ti or Ri plasmid containing the T-DNA for recombination may be capable or incapable of causing gall formation, and is not critical to said invention so long as the vir genes are present in said host.

In some cases where *Agrobacterium* is used for transformation, the expression construct being within the T-DNA borders will be inserted into a broad spectrum vector such as pRK2 or derivatives thereof as described in Ditta et al., (PNAS USA (1980) 77:7347-7351 and EPO 0 120 515, which are incorporated herein by reference. Included within the expression construct and the T-DNA will be one or more markers as described herein which allow for selection of transformed *Agrobacterium* and transformed plant cells. The particular marker employed is not essential to this invention, with the preferred marker depending on the host and construction used.

For transformation of plant cells using *Agrobacterium*, explants may be combined and incubated with the transformed *Agrobacterium* for sufficient time to allow transformation thereof. After transformation, the *Agrobacteria* are killed by selection with the appropriate antibiotic and plant cells are cultured with the appropriate selective medium. Once calli are formed, shoot formation can be encouraged by employing the appropriate plant hormones according to methods well known in the art of plant tissue culturing and plant regeneration. However, a callus intermediate stage is not always necessary. After shoot formation, said plant cells can be transferred to medium which encourages root formation thereby completing plant regeneration. The plants may then be grown to seed and said seed can be used to establish future generations. Regardless of transformation technique, the gene encoding a bacterial toxin is preferably incorporated into a gene transfer vector adapted to express said gene in a plant cell by including in the vector a plant promoter regulatory element, as well as 3' non-translated transcriptional termination regions such as Nos and the like.

In addition to numerous technologies for transforming plants, the type of tissue which is contacted with the foreign genes may vary as well. Such tissue would include but would not be limited to embryogenic tissue, callus tissue types I, II, and III, hypocotyl, meristem, root tissue, tissues for expression in phloem, and the like. Almost all plant tissues may be transformed during dedifferentiation using appropriate techniques described herein.

As mentioned above, a variety of selectable markers can be used, if desired. Preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialaphos); imidazolinones, sulfonylureas and triazolopyrimidine herbicides, such as chlorsulfuron; bromoxynil, dalapon and the like.

In addition to a selectable marker, it may be desirous to use a reporter gene. In some instances a reporter gene may be used with or without a selectable marker. Reporter genes are genes which are typically not present in the recipient organism or tissue and typically encode for proteins resulting in some phenotypic change or enzymatic property. Examples of such genes are provided in K. Wising et al. Ann. Rev. Genetics, 22, 421 (1988). Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (1987 Biochem. Soc. Trans. 15, 17-19) to identify transformed cells.

In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see U.S. Pat. No. 6,166,302, especially Example 7E) and the like may be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters, and tissue specific promoters. Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA by affecting transcription, mRNA stability, and the like. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, the maize streak virus coat protein leader sequence, as well as others available to a skilled artisan. Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and these may also be used.

Promoter regulatory elements may also be active during a certain stage of the plant's development as well as active in plant tissues and organs. Examples of such include but are not limited to pollen-specific, embryo-specific, corn-silk-specific, cotton-fiber-specific, root-specific, seed-endosperm-specific promoter regulatory elements and the like. Under certain circumstances it may be desirable to use an inducible promoter regulatory element, which is responsible for expression of genes in response to a specific signal, such as: physical stimulus (heat shock genes), light (RUBP carboxylase), hormone (Em), metabolites, chemical, and stress. Other desirable transcription and translation elements that function in plants may be used. Numerous plant-specific gene transfer vectors are known in the art.

Standard molecular biology techniques may be used to clone and sequence the toxins described herein. Additional information may be found in Sambrook, J., Fritsch, E. F., and Maniatis, T. (1989), Molecular Cloning, A Laboratory Manual, Cold Spring Harbor Press, which is incorporated herein by reference.

Resistance Management. With increasing commercial use of insecticidal proteins in transgenic plants, one consideration is resistance management. That is, there are numerous companies using *Bacillus thuringiensis* toxins in their products, and there is concern about insects developing resistance to B.t. toxins. One strategy for insect resistance management would be to combine the TC toxins produced by *Xenorhabdus, Photorhabdus*, and the like with toxins such as B.t. crystal toxins, soluble insecticidal proteins from *Bacillus* stains (see, e.g., WO 98/18932 and WO 99/57282), or other insect toxins. The combinations could be formulated for a sprayable application or could be molecular combinations. Plants could be transformed with bacterial genes that produce two or more different insect toxins (see, e.g., Gould, 38 *Bioscience* 26-33 (1988) and U.S. Pat. No. 5,500,365; likewise, European Patent Application 0 400 246 A1 and U.S. Pat. Nos. 5,866,784; 5,908,970; and 6,172,281 also describe transformation of a plant with two B.t. crystal toxins). Another method of producing a transgenic plant that contains more than one insect resistant gene would be to first produce two plants, with each plant containing an insect resistance gene. These plants could then be crossed using traditional plant breeding techniques to produce a plant containing more than one insect resistance gene. Thus, it should be apparent that the phrase "comprising a polynucleotide" as used herein means at least one polynucleotide (and possibly more, contiguous or not) unless specifically indicated otherwise.

Formulations and Other Delivery Systems. Formulated bait granules containing cells and/or proteins of the subject invention (including recombinant microbes comprising the genes described herein) can be applied to the soil. Formulated product can also be applied as a seed-coating or root treatment or total plant treatment at later stages of the crop cycle. Plant and soil treatments of cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include Theological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Another delivery scheme is the incorporation of the genetic material of toxins into a baculovirus vector. Baculoviruses infect particular insect hosts, including those desirably targeted with the toxins. Infectious baculovirus harboring an expression construct for the toxins could be introduced into areas of insect infestation to thereby intoxicate or poison infected insects.

Insect viruses, or baculoviruses, are known to infect and adversely affect certain insects. The effect of the viruses on insects is slow, and viruses do not immediately stop the feeding of insects. Thus, viruses are not viewed as being optimal as insect pest control agents. However, combining the toxin genes into a baculovirus vector could provide an efficient way of transmitting the toxins. In addition, since different baculoviruses are specific to different insects, it may be possible to use a particular toxin to selectively target particularly damaging insect pests. A particularly useful vector for the toxins genes is the nuclear polyhedrosis virus. Transfer vectors using this virus have been described and are now the vectors of choice for transferring foreign genes into insects. The virus-toxin gene recombinant may be constructed in an orally transmissible form. Baculoviruses normally infect insect victims through the mid-gut intestinal mucosa. The toxin gene inserted behind a strong viral coat protein promoter would be expressed and should rapidly kill the infected insect.

In addition to an insect virus or baculovirus or transgenic plant delivery system for the protein toxins of the present invention, the proteins may be encapsulated using *Bacillus thuringiensis* encapsulation technology such as but not limited to U.S. Pat. Nos. 4,695,455; 4,695,462; 4,861,595 which are all incorporated herein by reference. Another delivery system for the protein toxins of the present invention is formulation of the protein into a bait matrix, which could then be used in above and below ground insect bait stations. Examples of such technology include but are not limited to PCT Patent Application WO 93/23998, which is incorporated herein by reference.

Plant RNA viral based systems can also be used to express bacterial toxin. In so doing, the gene encoding a toxin can be inserted into the coat promoter region of a suitable plant virus which will infect the host plant of interest. The toxin can then be expressed thus providing protection of the plant from insect damage. Plant RNA viral based systems are described in U.S. Pat. No. 5,500,360 to Mycogen Plant Sciences, Inc. and U.S. Pat. Nos. 5,316,931 and 5,589,367 to Biosource Genetics Corp.

In addition to producing a transformed plant, there are other delivery systems where it may be desirable to engineer the bacterial gene(s). For example, a protein toxin can be constructed by fusing together a molecule attractive to insects as a food source with a toxin. After purification in the laboratory such a toxic agent with "built-in" bait could be packaged inside standard insect trap housings.

Mutants. Mutants of bacterial isolates can be made by procedures that are well known in the art. For example, asporogenous mutants can be obtained through ethylmethane sulfonate (EMS) mutagenesis of an isolate. The mutants can be made using ultraviolet light and nitrosoguanidine by procedures well known in the art.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

TC Proteins and Genes Obtainable from *Xenorhabdus* Strain Xwi

It was shown previously (U.S. Pat. No. 6,048,838) that *Xenorhabdus nematophilus* strain Xwi (NRRL B-21733, deposited on Apr. 29, 1997) produced extracellular proteins with oral insecticidal activity against members of the insect orders Coleoptera, Lepidoptera, Diptera, and Acarina. Full-length gene and TC protein sequence from strain Xwi are disclosed below. The methods used to obtain them are more fully discussed in concurrently filed U.S. provisional application by Bintrim et al. (Ser. No. 60/441,717), entitled "*Xenorhabdus* TC Proteins and Genes for Pest Control." These sequences, including N-terminal and internal peptide sequences (SEQ ID NOs: 1-5) are also summarized above in the Brief Description of the Sequences section.

In summary, a 39,005 bp fragment of genomic DNA was obtained from strain Xwi and was cloned as cosmid pDAB2097. The sequence of the cosmid insert (SEQ ID NO. 6) was analyzed using the Vector NTI™ Suite (Informax, Inc. North Bethesda, Md., USA) to identify encoded ORFs (Open Reading Frames). Six full length ORFs and one partial ORF were identified (FIG. 1 and Table 4).

TABLE 4

ORFs identified in the pDAB2097 cosmid insert

| ORF Designation | ORF Position in SEQ ID NO. 13 | SEQ ID NO. (Nucleotide) | No. of Deduced Amino Acids | SEQ ID NO. (Amino Acid) |
|---|---|---|---|---|
| ORF1 | 1-1,533 | 7 | 511 | 8 |
| ORF2 | 1,543-5,715 | 9 | 1,391 | 10 |
| ORF3 | 5,764-7,707 | 11 | 648 | 12 |
| ORF4 | 10,709-18,277 | 13 | 2,523 | 14 |
| ORF5 | 18,383-21,430 (C*) | 15 | 1,016 | 16 |
| ORF6 | 21,487-25,965 (C) | 17 | 1,493 | 18 |
| ORF7 | 26,021-33,634 (C) | 19 | 2,538 | 20 |

*(C) designates complementary strand of SEQ ID NO: 6

The nucleotide sequences of the identified ORFs and the deduced amino acid sequences encoded by these ORFs were used to search the databases at the National Center for Biotechnology Information by using BLASTn, BLASTp, and BLASTx, via the government (".gov") website of ncbi/nih for BLAST. These analyses showed that the ORFs identified in the pDAB2097 insert had significant amino acid sequence identity to genes previously identified in *Photorhabdus luminescens* and *Xenorhabdus nematophilus* (Table 5). It is noteworthy that the xpt gene sequences presented in GenBank accession number AJ308438 were obtained from a recombinant cosmid that expressed oral insecticidal activity.

TABLE 5

Similarity of Deduced Proteins encoded by pDAB2097 ORFs to Known Genes

| pDAB2097 ORF* (deduced amino acids) | Gene/ORF Designation (GenBank Accession) | % Amino Acid Sequence Identity to Database Match |
|---|---|---|
| ORF1 (1-511) | tccA (AF047028) | 21.4% |
| ORF2 (313-1,391) | xptD1 (AJ308438) | 96.6% |
| ORF3 (1-648) | chi (AJ308438) | 100% |
| ORF4 (1-2,523) | xptA1 (AJ308438) | 99.5% |
| ORF5 (1-1,016) | xptB1 (AJ308438) | 95.9% |
| ORF6 (1-1,402) | xptC1 (AJ308438) | 96.4% |
| ORF7 (1-2,538) | xptA2 (AJ308438) | 95.1% |

*Deduced Amino Acid Positions with Identity to Database Sequence

Since ORF2, ORF4, ORF5, ORF6, and ORF7 were shown to have at least 95% amino acid sequence identity to previously identified genes, the same gene nomenclature was adopted for further studies on the ORFs identified in the pDAB2097 insert sequence (Table 6).

As used throughout this application, XptA2, for example, signifies a protein and xptA2, for example, signifies a gene. Furthermore, the source isolate for the gene and protein is indicated with subscript. An illustration of this appears in Table 6.

TABLE 6

Nomenclature of ORFs identified in pDAB2097 insert sequence

| pDAB2097 ORF | Gene Designation |
|---|---|
| ORF2 | $xptD1_{Xwi}$ |
| ORF4 | $xptA1_{Xwi}$ |
| ORF5 | $xptB1_{Xwi}$ |
| ORF6 | $xptC1_{Xwi}$ |
| ORF7 | $xptA2_{Xwi}$ |

EXAMPLE 2

Heterologous Expression of Toxin Complex Genes from *Photorhabdus* and *Xenorhabdus*

A series of experiments was done in which *Photorhabdus* and *Xenorhabdus* genes were expressed in *E. coli*. It is shown that co-expression of either the tcdA or xptA2 genes with specific combinations of the tcdB1, tccC1, xptB1 and xptC1 genes, results in significant activity in bioassay against sensitive insects. It is also demonstrated here that expression of the *Photorhabdus* genes tcdA and tcdB with the *Xenorhabdus* gene xptB1 results in significant activity against Southern corn rootworm (*Diabrotica undecimpunctata howardii*). Likewise, expression of *Xenorhabdus* xptA2 with *Photorhabdus* tcdB1 and tccC1 produces activity against corn earworm (*Helicoverpa zea*).

Figure 2:
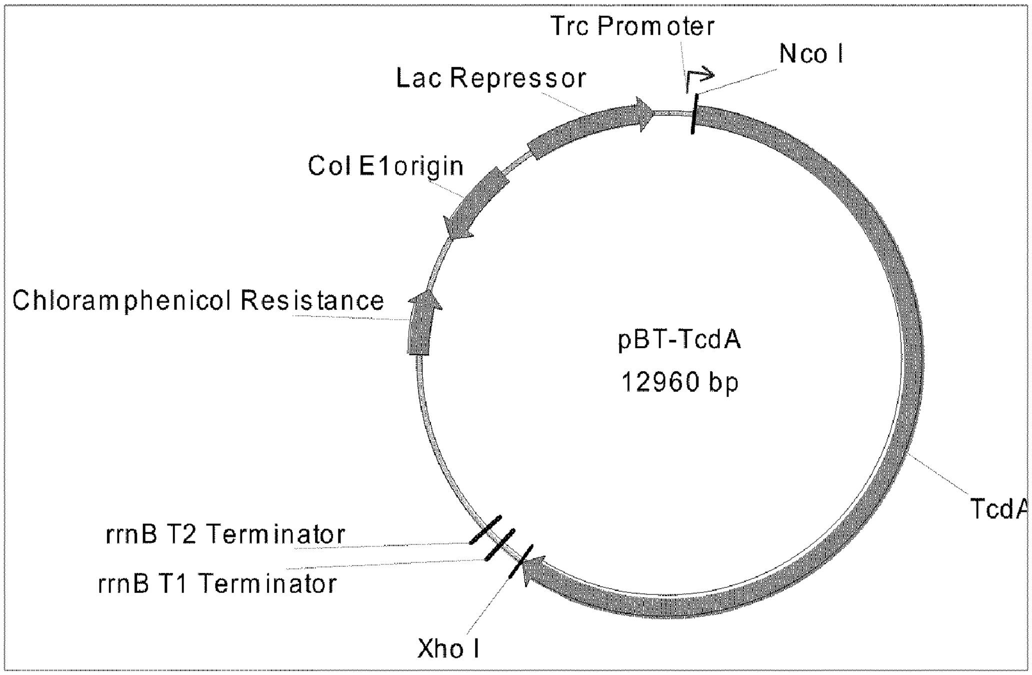
FIG. 2 shows expression vector plasmid pBT-TcdA.
Figure 3:
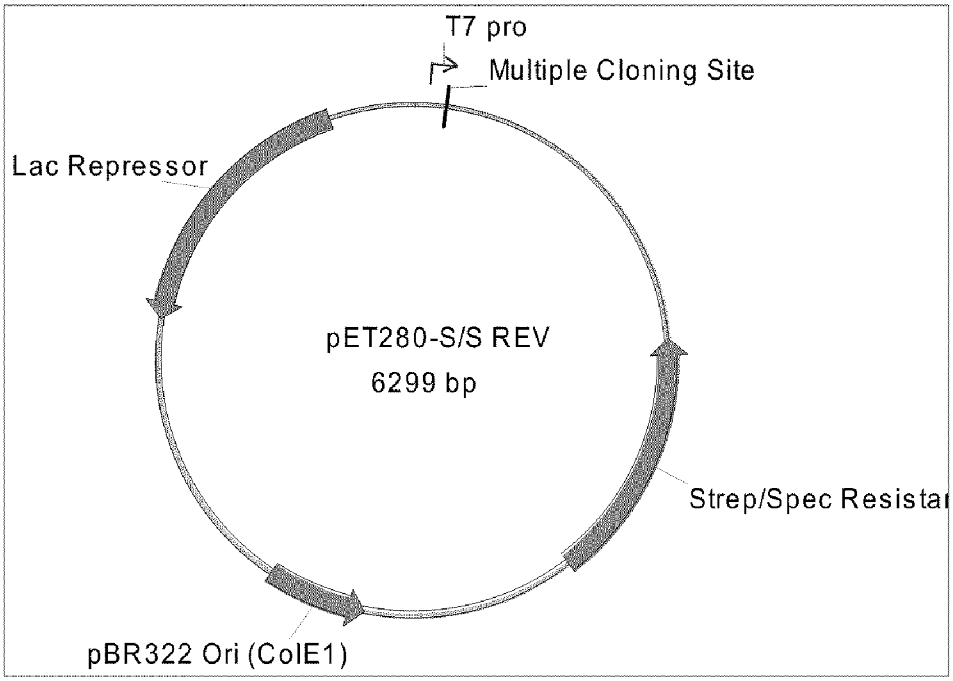
FIG. 3 shows expression vector plasmid pET280 vector.
Figure 4:
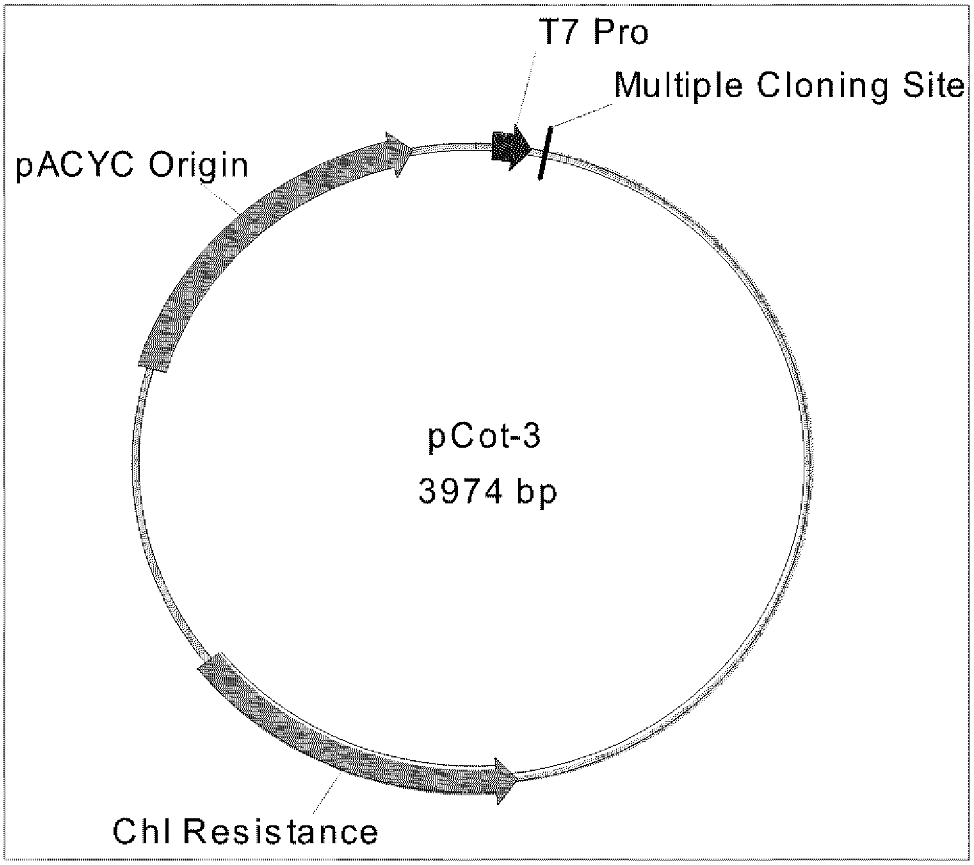
FIG. 4 shows expression vector plasmid pCot-3.
Figure 5:
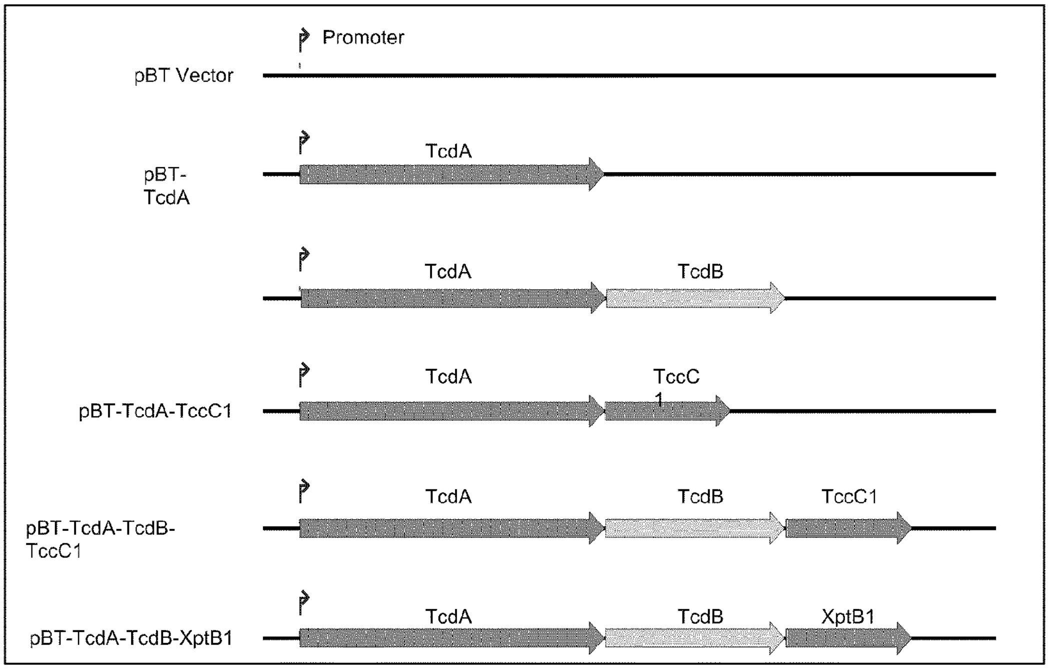
FIG. 5 is a schematic diagram of pBT constructions.
Figure 6:
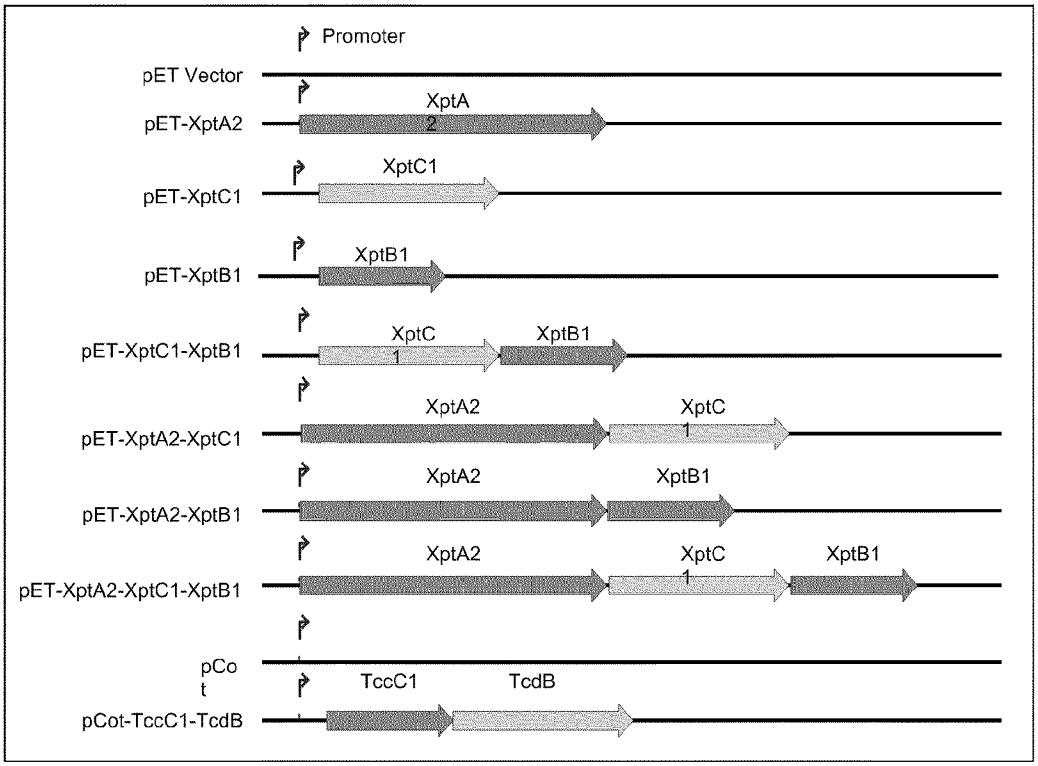
FIG. 6 is a schematic diagram of pET/pCot constructions.
Figure 7:
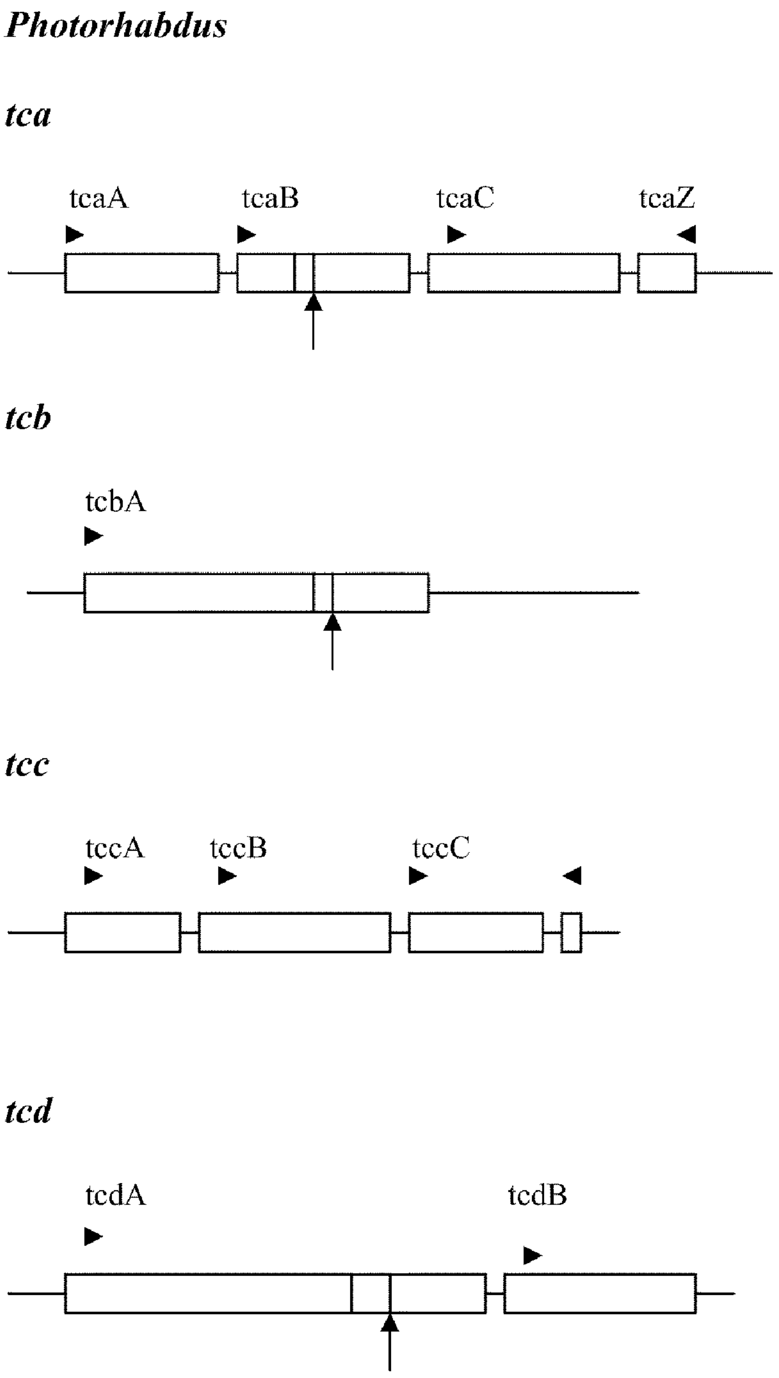
FIG. 7 shows the TC operons from *Photorhabdus* .

Two *E. coli* expression systems were employed for testing *Photorhabdus* and *Xenorhabdus* genes. The first relied on an *E. coli* promoter present in the expression vector pBT-TcdA (FIG. 2). Several plasmids were constructed in which polycistronic arrangements of up to three genes were constructed. Each gene contained a separate ribosome binding site and start codon, a coding sequence and a stop codon. The second system was mediated by the strong T7 phage promoter and T7 RNA polymerase (FIG. 3, pET; FIG. 4, pCot). Similarly, in some constructions polycistronic arrangements of coding sequences were used. In other experiments, compatible plasmids were used for co-expression. Schematic diagrams describing all of the constructions used in the experiments are shown in FIGS. 5 and 6.

Construction of pBT-TcdA. The expression plasmid pBT-TcdA is composed of the replication and antibiotic selection components of plasmid pBC KS+(Stratagene) and the expression components (i.e. a strong *E. Coli* promoter, lac operon repressor and operator, upstream of a multiple cloning site) from plasmid pTrc99a (Amersham Biosciences Corp., Piscataway, N.J.). An Nco I site was removed from the chloramphenicol resistance gene of pBC KS+using in vitro mutagenesis. The modification did not change the amino acid sequence of the chloramphenicaol acetyl transferase protein. As previously described (Example 27 of WO 98/08932, Insecticidal Protein Toxins from *Photorhabdus*), the TcdA coding sequence (GenBank Accession No. AF188483; reproduced here as SEQ ID NO:21 which encodes SEQ ID NO:65) was modified using PCR to engineer both the 5' and 3' ends. This modified coding sequence was subsequently cloned into pTrc99a. Plasmid pBT-TcdA was made by joining the blunted Sph I/Pvu I fragment of pTrc-TcdA with the blunted Asn I/Pvu I fragment of the pBC KS+. The result is plasmid pBT-Tcda (FIGS. 2 and 5).

Construction of pBT-TcdA-TcdB. The TcdB1 coding sequence (GenBank Accession No. AF346500; reproduced here as SEQ ID NO:22) was amplified from plasmid pBC-AS4 (R. ffrench-Constant University of Wisconsin) using the forward primer:

```
                                        (SEQ ID NO: 23)
5' ATATAGTCGACGAATTTTAATCTACTAGTAAAAAGGAGATAACCATG

CAGAATTCACAAACATTCAGTGTTACC 3'.
```

This primer does not change the protein coding sequence and adds Sal I and Spe I sites in the 5' non coding region. The reverse primer used was:

```
                                        (SEQ ID NO: 24)
5' ATAATACGATCGTTTCTCGAGTCATTACACCAGCGCATC

AGCGGCCGTATCATTCTC 3'.
```

Again, no changes were made to the protein coding sequence but an Xho I site was added to the 3' non coding region. The amplified product was cloned into pCR2.1 (Invitrogen) and the DNA sequence was determined. Two changes from the predicted sequence were noted, a single A deletion in the Spe I site of the forward primer (eliminating the site) and an A-to-T substitution at corresponding amino acid position 1041 that resulted in the conservative substitution of Asp-to-Glu. Neither change was corrected. Plasmid pBT-TcdA was digested with Xho I and Pvu I (cutting at the 3' end of the TcdA coding sequence). Plasmid pCR2.1-TcdB1 was cut with Sal I and Pvu I. The fragments were ligated and pBT-TcdA-TcdB1 recombinants (FIG. 5) were isolated. The Xho I and Sal I ends are compatible, but both sites are eliminated upon ligation. The plasmid encodes a polycistronic TcdA-TcdB1 RNA. Each coding region carries separate stop and start codons, and each is preceded by separate ribosome binding sites.

Construction of pDAB3059. The coding sequence for the TccC1 protein (GenBank Accession No. AAC38630.1; reproduced here as SEQ ID NO:25 which encodes SEQ ID NO:68) was amplified from a pBC KS+vector (pTccC ch1; from R. ffrench-Constant, the University of Wisconsin) containing the three gene Tcc operon. The forward primer was:

```
                                        (SEQ ID NO: 26)
5' GTCGACGCACTACTAGTAAAAAGGAGATAACCCCATGAGCCCGTCTG

AGACTACTCTTTATACTCAAACCCCAACAG 3'
```

This primer did not change the coding sequence of the tccC1 gene, but provided 5' non coding Sal I and Spe I sites as well as a ribosome binding site and ATG initiation codon. The reverse primer was:

```
                                        (SEQ ID NO: 27)
5' CGGCCGCAGTCCTCGAGTCAGATTAATTACAAAGAAAAAACTCGTCGT

GCGGCTCCC 3'
```

This primer also did not alter the tccC1 coding sequence, but provided 3' Not I and Xho I cloning sites. Following amplification with components of an EPICENTRE FailSafe PCR kit (EPICENTRE; Madison, Wis.) the engineered TccC1 coding sequence was cloned into pCR2.1-TOPO (Invitrogen). The coding sequence was cut from pCR2.1 and transferred to a modified pET vector (Novagen; Madison Wis.) via the 5' Sal I and 3' Not I sites. The pET vector contains a gene conferring resistance to spectinomycin/streptomycin, and has a modified multiple cloning site. A PCR-induced mutation found via DNA sequencing was corrected using the pTccC ch1 plasmid DNA as template, and the plasmid containing the corrected coding region was named pDAB3059. Double-stranded DNA sequencing confirmed that the mutation had been corrected.

Construction of pBT-TcdA-TccC1. Plasmid pBT-TcdA DNA was cut with Xho I, and ligated to pDAB3059 DNA cut with Sal I and Xho I. The tccC1 gene was subsequently ligated downstream of the tcdA gene to create pBT-TcdA-TccC1 (FIG. 5).

Construction of pBT-TcdA-TcdB1-TccC1. Plasmid pBT-TcdA-TcdB1 DNA was cut with Xho I and ligated to pDAB3059 DNA cut with Sal I and Xho I. Recombinants were screened for insertion of the tccC1 gene behind the tcdB gene to create plasmid pBT-TcdA-TcdB1-TccC1 (FIG. 5).

Construction of pBT-TcdA-TcdB1-XptB1. Plasmid pBT-TcdA-TcdB1 DNA was cut with Xho I and shotgun ligated with pET280-XptB1 DNA which was cut with Sal I and Xho I. Recombinants representing insertion of the xptB1 coding region into the Xho I site of pBT-TcdA-TcdB1 where identified to create plasmid pBT-TcdA-TcdB1-XptB1 (FIG. 5).

Construction of pET28-TcdA. The description of this plasmid can be found elsewhere as Example 27 of WO 98/08932, Insecticidal Protein Toxins from *Photorhabdus.*

Construction of pCot-TcdB1. Plasmid pCR2.1-TcdB1 was cut with Xho I and Sal I and ligated into the Sal I site of the T7 expression plasmid pCot-3 (FIG. 4). Plasmid pCot-3 has a pACYC origin of replication, making it compatible with plasmids bearing a ColE1 origin (pBR322 derivatives). In addition, it carries a chloramphenicol antibiotic resistance marker gene and a T7 RNA polymerase-specific promoter for expression of coding regions inserted into the multiple cloning site.

Construction of pCot-TccC1-TcdB1. The TccC1 coding region was cut from pDAB3059 DNA with Spe I and Not I and ligated into the multiple cloning site of plasmid pET280-K (a modified pET28 which has had the multiple cloning site replaced). This resulted in acquisition of a Swa I site upstream of the Spe I site and an Xho I site downstream of the Not I site. DNA of plasmid pET280-K-TccC1 was cut with Swa I and Xho I to release the TccC1 coding sequence, which was then ligated into the Swa I and Sal I sites of plasmid pCot-3-TcdB1 to create plasmid pCot-3-TccC1-TcdB (FIG. 6).

Construction of pET280-XptA2 pET280-XptC1 and pET280-XptB1. The coding sequences for the XptA2, XptC1, and XptB1 proteins were each PCR amplified from pDAB2097, a recombinant cosmid containing the three genes that encode these proteins. The PCR primer sets used to amplify these coding sequences are listed in Table 7. In all of these primer sets, the forward primer did not change the coding sequence of the gene but provided 5' non coding Sal I and Xba I sites as well as a ribosome binding site. The reverse primers also did not alter the corresponding coding sequences, but provided a 3' Xho I cloning site. Following amplification with components of the EPICENTRE Fail Safe PCR kit, the engineered XptA2, XptC1, and XptB1 coding sequences were each cloned into pCR2.1. The cloned amplified products were sequence confirmed to ensure that PCR-induced mutations did not alter the coding sequences. Recombinant plasmids that contained unaltered coding sequences for XptA2, XptC1, and XptB1 were identified and designated as pDAB3056, pDAB3064, and pDAB3055, respectively. The coding sequences were each cut from the pCR2.1 derivatives and transferred to a modified pET vector (pET280-SS is a pET28 derivative which has had the multiple cloning site replaced, and a streptomycin/spectinomycin resistance gene inserted into the backbone to provide a selectable marker [FIG. 3]), via the 5' Xba 1 and 3' Xho I sites to create plasmids pET280-XptA2, pET280-XptC1, and pET280-XptB1.

TABLE 7

PCR Primers Used to Amplify XptA2, XptC1, and XptB1 Coding Sequences

| Coding Sequence Amplified | Forward Primer Sequence (5'-3') | Reverse Primer Sequence (5'-3') |
|---|---|---|
| XptA2 | GTCTAGACGTGCGTCGACA AGAAGGAGATATACCATGT ATAGCACGGCTGTATTACT CAATAAAATCAGTCCCACT CGCGACGG* (SEQ ID NO: 28) | GCTCGAGATTAATTAAGAAC GAATGGTATAGCGGATATGC AGAATGATATCGCTCAGGCT CTCC (SEQ ID NO: 29) |
| XptC1 | GTCTAGACGTGCGTCGACA AGAAGGAGATATACCATGC AGGGTTCAACACCTTTGAA ACTTGAAATACCGTCATTG CCCTC (SEQ ID NO: 30) | GACTCGAGAGCATTAATTAT GCTGTCATTTCACCGGCAGT GTCATTTTCATCTTCATTCA CCAC (SEQ ID NO: 31) |
| XptB1 | GTCTAGACGTGCGTCGACA AGAAGGAGATATACCATGA AGAATTTCGTTCACAGCAA TACGCCATCCGTCACCGTA CTGGACAACC (SEQ ID NO: 32) | GCTCGAGCAGATTAATTATG CTTCGGATTCATTATGACGT GCAGAGGCGTTAAAGAAGAA GTTATT (SEQ ID NO: 33) |

*Underlined sequences in primers correspond to protein coding sequences

Construction of pET280-XptA2-XptC1. Plasmid pET280-XptA2 DNA was cut with Xho I and ligated into the unique Sal I site in pDAB3064. The resulting ligated product contained both pCR2.1 and pET280-SS vector backbones and could be recovered by antibiotic selection using a combination of streptomycin (25 μg/mL), spectinomycin (25 μg/mL), and ampicillin (100 μg/mL). DNA of the recovered plasmids was digested with Xho I to check fragment orientation. A plasmid with the XptC1 coding region immediately downstream of the XptA2 coding region was obtained and the DNA was digested with Xho I to remove the pCR2.1 vector backbone. The resulting construct, which contains the pET280-SS vector backbone and the coding sequences for XptA2 and XptC1, was self-ligated to produce pET280-XptA2-XptC1.

Construction of pET280-XptC1-XptB1. Plasmid pET280-XptC1 DNA was cut with Xho I and ligated into the unique Sal I site in pDAB3055. The resulting ligated product contained both pCR2.1 and pET280-SS vector backbones and could be recovered by antibiotic selection using a combination of streptomycin (25 μg/mL), spectinomycin (25 μg/mL), and ampicillin (100 μg/mL). DNA of the recovered plasmids was digested with Xho I to check fragment orientation. A plasmid with the XptB1 coding region immediately downstream of the XptC1 coding region was obtained and the DNA was digested with Xho I to remove the pCR2.1 vector backbone. The resulting construct, which contains the pET280-SS vector backbone and the coding sequences for XptC1 and XptB1, was self-ligated to produce pET280-XptC1-XptB1.

Construction of pET280-XptA2-XptB1. Plasmid pET280-XptA2 DNA was cut with Xho I and ligated into the unique Sal I site in pDAB3055. The resulting ligated product contained both pCR2.1 and pET280-SS vector backbones and could be recovered by antibiotic selection using a combination of streptomycin (25 μg/mL), spectinomycin (25 μg/mL), and ampicillin (100 μg/mL). DNA of the recovered plasmids was digested with Xho I to check fragment orientation. A plasmid with the XptB1 coding region immediately downstream of the XptA2 coding region was obtained and the DNA was digested with Xho I to remove the pCR2.1 vector backbone. The resulting construct, which contains the pET280-SS vector backbone and the coding sequences for XptA2 and XptB1, was self-ligated to produce pET280-XptA2-XptB1.

Construction of pET280-XptA2-XptC1-XptB1. Plasmid pET280-XptA2-XptC1 DNA was cut with Xho I and ligated into the unique Sal I site in pDAB3055. The resulting ligated product contained both pCR2.1 and pET280-SS vector backbones and could be recovered by antibiotic selection using a combination of streptomycin (25 μg/mL), spectinomycin (25 μg/mL), and ampicillin (100 μg/mL). The recovered plasmids were digested with Xho I to check fragment orientation. A plasmid with the XptB1 coding region immediately downstream of the XptC1 coding region was obtained and the DNA was digested with Xho I to remove the pCR2.1 vector backbone. The resulting construct, which contains the pET280-SS vector backbone and the XptA2, XptC1, and XptB1 coding sequences, was self-ligated to produce pET280-XptA2-XptC1-XptB1.

Expression of pBT-based constructions. The pBT expression plasmids were transformed into *E. coli* strain BL21 cells and plated on LB agar containing 50 μg/mL chloramphenicol and 50 mM glucose, and transformants were grown at 37° C. overnight. Approximately 10-100 well isolated colonies were used to inoculate 200 mL of sterile LB containing 50 μg/mL chloramphenicol plus 75 μM isopropyl-β-D-thiogalatopyranoside (IPTG) in 500 mL baffled flasks. The cultures were shaken at 200 rpm at 28° C. for 24 hours. Cells were collected by centrifugation (approximately 3000×g) and resuspended in phosphate buffer (30 mM, pH 7.4; NutraMax; Gloucester, Mass.) to a cell density of 30-120 $OD_{600}$ units/mL. Diluted cells were then used for insect bioassay.

Alternatively, the cells were chilled on ice after growth for 24 hours and adjusted to 20-30 $OD_{600}$ units/ml with phosphate buffer. The cells were lysed with a probe sonicator (Soniprep 150, MSE), using 2×45 second bursts at 20 microns amplitude with ⅓ volume 0.1 mm glass beads (Biospec; Bartletsville, Okla.). The lysates were cleared in an Eppendorf microfuge at 14,000 rpm for 10 minutes. Cleared lysates were concentrated in UltraFree 100 kDa units (Millipore; Bedford, Mass.), collected, adjusted to 10 mg/mL in phosphate buffer, and submitted for insect bioassay.

Expression of T7 Based Constructions. The T7 based expression plasmids were handled the same as the pBT expression plasmids described above, with the exception that they were transformed into the T7 expression strain BL21 (DE3) (Novagen, Madison, Wis.), and a combination of streptomycin (25 μg/mL) and spectinomycin (25 μg/mL) was used for the antibiotic selection.

EXAMPLE 3

Insect Bioassay Results of Heterologously Expressed Toxin Complex Genes

A series of expression experiments was performed using the pBT expression system as described above. *E. coli* cells were transformed, induced and grown overnight at 28° C. The cells were collected, washed, normalized to equal concentrations and applied to Southern corn rootworm diet and bioassayed. As shown in Table 8, only when all three *Photorhabdus* genes, tcdA, tcdB1 and tccC1 were expressed in the same cell was significant mortality observed. Other combinations of genes did not result in significant mortality. For example, the specific combination of tcdB1 and tccC1 genes, which showed no insect killing activity, is shown in Table 8. Mortality was observed routinely when the genes on plasmid pBT-TcdA-TcdB1-TccC1 were expressed, and storing the cells at 4° C. for 24 hours before application to insect diet did not decrease or increase mortality significantly in these experiments (Table 8). Southern corn rootworm mortality was also observed if the cells were lysed following co-expression of the genes on plasmid pBT-TcdA-TcdB1-TccC1. Activity did not appear to decrease if the lysate was stored frozen at −70° C. for one week (Table 9).

TABLE 8

Bioassay of pBT-Expressed *Photorhabdus* Toxin Complex Genes on Southern Corn Rootworm Experiment A.

| Plasmid | Day 1 68 units/ml | Day 2 68 units/ml |
|---|---|---|
| pBT | 0 | 0 |
| pBT-TcdA | 0 | 0 |
| pBT-TcdA-TcdB1 | 0 | 0 |
| pBT-TcdA-TccC1 | 0 | 0 |
| pBT-TcdA-TcdB1-TccC1 | ++++ | +++++ |

Experiment B.

| Plasmid | Day 1 85 units/ml | Day 2 85 units/ml |
|---|---|---|
| PBT | 0 | 0 |
| pBT-TcdA | 0 | 0 |
| pBT-TcdA-TcdB1 | 0 | + |
| pBT-TcdA-TccC1 | 0 | 0 |
| pBT-TcdA-TcdB1-TccC1 | ++++ | +++++ |

Whole *E. coli* cells were washed with phosphate buffer, concentrated, adjusted to equal cell concentration, and applied to insect diet. Day 1 samples were assayed immediately. Day 2 samples were the same preparations of cells, but had been stored overnight at 4° C. before application to insect diet.
Grading Scale represents % mortality of Southern corn rootworm (0 = 0-10%;+ = 11-20%; ++ = 21-40%; +++ = 41-60%; ++++ = 61-80%; +++++ = 81-100%).

TABLE 9

Bioassay of pBT-Expressed *Photorhabdus* Toxin Complex Genes on Southern Corn Rootworm

| Plasmid | Cells 74 units/ml | Lysate 10 mg/ml | Frozen Lysate 10 mg/ml |
|---|---|---|---|
| pBT | 0 | 0 | 0 |
| pBT-TcdA-TcdB1-TccC1 | +++++ | +++++ | +++++ |

Whole *E. coli* cells were washed with phosphate buffer, concentrated, adjusted to equal cell concentrations, and applied to insect diet preparations. Alternatively, lysates were prepared by sonication and applied to diet either fresh or after being frozen at −70° C. for 7 days.
Grading Scale represents % mortality of Southern corn rootworm (0 = 0-10%; + = 11-20%; ++ = 21-40%; +++ = 41-60% = ++++, 61-80%; +++++ = 81-100%).

In another series of experiments, the *Xenorhabdus* xptB1 gene was substituted for the *Photorhabdus* tccC1 gene and expressed as part of the polycistronic operon of plasmid pBT-TcdA-TcdB1-XptB1. These experiments demonstrated that the *Xenorhabdus* xptB1 gene was able to substitute for the *Photorhabdus* tccC1 gene, resulting in mortality of Southern corn root worm in bioassay of whole *E. coli* cells (Table 10).

TABLE 10

Bioassay of pBT Expressed *Photorhabdus* and *Xenorhabdus* Toxin Complex Genes on Southern Corn Rootworm

| Plasmid | Trial 1 110 units/ml | Trial 2 55 units/ml | Trial 3 111 units/ml |
|---|---|---|---|
| pBT | 0 | 0 | 0 |
| pBT-TcdA-TcdB1-TccC1 | +++ | +++ | +++ |
| pBT-TcdA-TcdB1-XptB1 | ++ | ++ | +++ |

Whole *E. coli* cells were washed with phosphate buffer, concentrated, adjusted to equal cell concentrations, and applied to insect diet preparations.
Grading Scale represents % mortality of Southern corn rootworm (0 = 0-10%; + = 11-20%; ++ = 21-40%; +++ = 41-60% = ++++, 61-80%; +++++ = 81-100%).

Expression of the various *Photorhabdus* genes from separate plasmids also resulted in Southern corn root worm mortality. When tcdA was present on the pET expression plasmid, and the tccC1 and tcdB1 genes were on the compatible expression vector pCot-3, significant activity was observed as compared to control combinations of these plasmids (Table 11). As noted above, the presence of the tcdB1 and tccC1 genes alone did not result in significant activity (Table 11).

TABLE 11

Bioassay of pCoT/pET (T7 promoter) Expressed *Photorhabdus* Toxin Complex Genes on Southern Corn Rootworm

| Plasmids | Trial 1 40 units/ml | Trial 2 60 units/ml |
|---|---|---|
| pCot/pET | 0 | 0 |
| pCot/pET-TcdA | 0 | 0 |
| pCot-TccC1-TcdB1/pET | 0 | 0 |
| pCot-TccC1-TcdB1/pET-TcdA | +++ | +++ |

Whole *E. coli* cells were washed with phosphate buffer, concentrated, adjusted to equal cell concentrations, and applied to insect diet preparations.
Grading Scale represents % mortality of Southern corn rootworm (0 = 0-10%; + = 11-20%; ++ = 21-40%; +++ = 41-60% = ++++, 61-80%; +++++ = 81-100%).

Bioassay Results of Heterologously Expressed *Xenorhabdus* Toxin Complex Genes. A series of expression experiments was performed using the pET expression system as described above. *E. coli* cells were transformed, induced and grown overnight at 28° C. The cells were collected, washed, normalized to equal concentrations, and tested for insecticidal activity against *Ostrinia nubilalis* European corn borer (ECB), corn earworm (CEW), and tobacco budworm (TBW). As shown in Table 12, the highest levels of insecticidal activity were observed when xptA2, xptC1, and xptB1 were present in the same construct.

TABLE 12

Bioassay of Heterologously Expressed *Xenorhabdus* Toxin Complex Genes on TBW, CEW, and ECB

| Plasmid Tested | TBW Bioassay | CEW Bioassay | ECB Bioassay |
|---|---|---|---|
| pET-280 | 0* | 0 | 0 |
| pET-280-XptA2 | +++ | +++ | ++ |
| pET-280-XptC1 | 0 | 0 | 0 |
| pET-280-XptB1 | 0 | 0 | 0 |
| pET-280-XptA2-XptC1 | + | + | 0 |
| pET-280-XptA2-XptB1 | 0 | 0 | 0 |
| pET-280-XptC1-XptB1 | 0 | 0 | 0 |
| pET-280-XptA2-XptC1-XptB1 | +++++ | +++++ | +++++ |

*Whole *E. coli* cells were washed with phosphate buffer, concentrated, adjusted to equal cell concentrations, and applied to insect diet preparations.
Grading Scale represents % growth inhibition relative to controls (0 = 0-10%; + = 11-20%; ++ = 21-40%; +++ = 41-60% = ++++, 61-80%; +++++ = 81-100%).

Bioassay results of heterologously expressed xptA2 tcdB1 and tccC1. *E. coli* cells were co-transformed with the pET280 and pCoT constructs listed in Table 13. Transformants were induced, processed and bioassayed as described above. In these assays, co-transformants that contained either pCOT/pET280-XptA2-XptC1-XptB1 or pCoT-TcdB1-TccC1/pET280-XptA2 plasmid combinations exhibited the highest levels of insecticidal activity. These experiments show that the *Photorhabdus* tcdB1 and tccC1 genes, even in trans relative to xptA2, were able to substitute for the *Xenorhabdus* xptC1 and xptB1 genes, resulting in qualitatively similar levels of enhanced insecticidal activity.

TABLE 13

Bioassay of Heterologously Expressed xptA2, tcdB1, and tccC1 on CEW

| Plasmids Tested | CEW Bioassay |
|---|---|
| pET280/pCoT | 0* |
| pET280/pCoT-TcdB1-TccC1 | 0 |
| pCoT/pET280-XptA2 | +++ |
| pCoT/pET280-XptA2-XptC1-XptB1 | +++++ |
| pCoT-TcdB-TccC1/pET280-XptA2 | +++++ |

*Whole *E. coli* cells were washed with phosphate buffer, concentrated, adjsuted to equal cell concentrations, and applied to insect diet preparations.
Grading Scale represents % growth inhibition relative to controls (0 = 0-10%; + = 11-20%; ++ = 21-40%; +++ = 41-60% = ++++, 61-80%; +++++ = 81-100%).

EXAMPLE 4

Complementation of *Xenorhabdus* XptA2 Toxin with *Paenibacillus* Strain DAS1529 TC Proteins This example provides additional data relating to co-pending U.S. provisional application Ser. No. 60/392,633, which is discussed in the Background section above. This data is relevant to the present application because it provides experimental evidence of the ability of *Paenibacillus* strain DAS1529 TC proteins (expressed here as a single operon) to complement, for example, the XptA2 toxin from *Xenorhabdus nematophilus* Xwi (see SEQ ID NO:34). Two independent experiments were carried out to express the DAS1529 TC operon and XptA2 independently, or to co-express the XptA2 gene and the TC operon in the same *E. coli* cells. Whole cells expressing different toxins/toxin combinations were tested for activity against two lepidopteran insects: corn earworm (*Heliothis zea*; CEW) and tobacco budworm (*Heliothis virescens*; TBW). The data from both experiments indicate that DAS1529 TC proteins are able to enhance *Xenorhabdus* XptA2 activity against both insect species tested.

A. Co-Expression of DAS1529 TC Proteins and *Xenorhabdus* TC XptA2 Toxin

Expression of the DAS1529 TC operon was regulated by T7 promoter/lac operator in the pET101.D expression vector that carries a ColE1 replication origin and an ampicillin resistance selection marker (Invitrogen). A comprehensive description of cloning and expression of the *Paenibacillus* TC operon can be found in Example 8 of U.S. Ser. No. 60/392,633. The XptA2 gene was cloned in the pCot-3 expression vector, which carries a chloramphenicol resistance selection marker and a replication origin compatible with the ColE1. The pCot-3 vector expression system is also regulated by the T7 promoter/lac operator. Hence, compatible replication origins and different selection markers form the basis for co-expression of the TC operon and XptA2 in the same *E. coli* cells. Plasmid DNAs carrying the TC operon and XptA2 were transformed into *E. coli*, BL21 Star™ (DE3) either independently or in combination. Transformants were selected on LB agar plates containing 50 μg/ml carbenicillin for pET101.D-TC operon, 50 μg/ml chloramphenicol for pCot-3-XptA2, and both antibiotics for pET101.D-TC operon/pCot-3-XptA2. To suppress basal toxin expression, glucose at a final concentration of 50 mM was included in both agar and liquid LB medium.

For toxin production, 5 mL and 50 mL of LB medium containing antibiotics and 50 mM glucose were inoculated with overnight cultures growing on the LB agar plates. Cultures were grown at 30° C. on a shaker at 300 rpm. Once the culture density reached an O.D. of ~0.4 at 600 nm, IPTG at a final concentration of 75 μM was added to the culture medium to induce gene expression. After 24 hours, *E. coli* cells were harvested for protein gel analysis by the NuPAGE system (Invitrogen). Cell pellets from 0.5 mL 1× culture broth was resuspended in 100 μL of 1× NuPAGE LDS sample buffer. Following brief sonication and boiling for 5 min, 5 μL of the sample was loaded onto 4 to 12% NuPAGE bis-tris gradient gel for total protein profile analysis. XptA2 expressed to detectable levels when expressed independently or in the presence of the TC operon. Based on gel scan analysis by a Personal Densitometer SI (Molecular Dynamics), XptA2 expressed nearly 8× as high by itself as when co-expressed with the TC operon. For the 5 mL induction experiment, there is a nearly equal expression of XptA2.

B. Bioassay for Insecticidal Activity

As described in Example 8 of U.S. Ser. No. 60/392,633, DAS1529 TC ORFs, when expressed independently or as an operon, did not appear to be active against TBW and CEW. The following bioassay experiments focused on determining whether *Paenibacillus* (DAS1529) TC proteins (of ORFs 3-6; TcaA-, TcaB-, TcaC-, and TccC-like proteins; see SEQ ID NOs:35-43) could potentiate *Xenorhabdus* TC protein (XptA2 is exemplified) activity. Bioassay samples were prepared as whole *E. coli* cells in 4× cell concentrate for the 5 mL induction experiment, both the XptA2 and XptA2/TC operon cells contained very low but nearly equal amount of XptA2. Data in Table 14 showed that at the 4× cell concentration, the combination of the *Paenibacillus* TC proteins ("TCs" in Table 14)+XptA2 was active against CEW. This demonstrates a complementation effect of *Paenibacillus* DAS1529 TCs on *Xenorhabdus* XptA2.

TABLE 14

Bioassay of DAS1529 TC potentiation of *Xeno*. toxin on *H. zea*

| Insects: | CEW |
|---|---|
| Negative control | – |
| TCs (DAS1529) | – |
| XptA2 | – |
| TCs + XptA2 | ++ |

*–, ++, +++ = no, moderate and high activity, respectively

For the second bioassay experiment, the amount of XptA2 protein in the XptA2 cells and the XptA2+TC operon cells was normalized based on densitometer gel scan analysis. As shown in Table 15, XptA2 per se had moderate activity at 40× on TBW (*H. virescens*), but the activity dropped to a level undetectable at and below 20×. However, when co-expressed with the *Paenibacillus* TC proteins, high levels of activity were very apparent in the presence of 10× and 5× XptA2, and low activity was still noticeable at 1.25× XptA2. These observations indicate there is a significant potentiation effect of these DAS1529 TC proteins on XptA2 against *H. virescens*. At the highest doses tested, neither the negative control nor the TC operon per se had any activity against this pest.

TABLE 15

Bioassay of IDAS1529 TC complementation of XptA2 on *H. virescens*

| | Normalized XptA2 | | | | | |
|---|---|---|---|---|---|---|
| | 40X | 20X | 10X | 5X | 2.5X | 1.25X |
| XptA2 | + | – | – | – | n.d. | n.d. |
| TCs + XptA2 | n.d. | n.d. | ++ | ++ | + | – |

* n.d.—not determined;
–, +, ++, +++ = no, low, moderate, and high activity, respectively

EXAMPLE 5

*Xenorhabdus bovienii* B and C Protein Mixed Complementation

Example 5A

Overview

The identification and isolation of genes encoding factors that potentiate or synergize the activity of the insect active proteins *Photorhabdus* TcdA and *Xenorhabdus* $XptA2_{wi}$ were accomplished using a cosmid complementation screen. Individual *Escherichia coli* clones from a cosmid genomic library of *Xenorhabdus bovienii* (strain ILM104) were used to create crude cell extracts which were mixed with purified toxins and bioassayed. Lysates were assayed with purified *Photorhabdus* toxin TcdA against southern corn rootworm larvae (*Diabrotica undecimpunctata howardi*). Likewise, lysates were also mixed with purified *Xenorhabdus* $XptA2_{wi}$ protein and assayed against tobacco budworm (*Heliothis virescens*) or corn earworm (*Helicoverpa zea*) larvae. Cosmid lysates were scored as positive if the combination of lysate plus purified toxin had activity greater than either component alone.

The primary screen samples (in 96-well format) were tested in duplicate and scored compared to controls for insecticidal activity. Positive samples were re-grown and tested in the secondary screen. Cosmids identified as positive through primary and secondary screens were screened a third time. Larger culture volumes were utilized for tertiary screens (see below), tested for biological activity in a 128-well format bioassay.

DNA from one of the cosmids identified as having potentiating activity in this screen was subcloned. The DNA sequence of a single subclone which retained activity was determined and shown to contain two open reading frames, designated $xptB1_{xb}$ and $XPtC1_{xb}$. These coding regions were subcloned into pET plasmids and expressed in *E. coli*. A dramatic increase in insect activity was seen when either TcdA or $XptA2_{wi}$ protein was mixed with lysates co-expressing both $XptB1_{xb}$ and $XPtC1_{xb}$. Lysates containing only $XptB1_{xb}$ or only $XptC1_{xb}$ had minimal affects when mixed with purified TcdA or $XptA2_{wi}$.

Example 5B

Insect Bioassay Methodology

Insect bioassays were conducted using artificial diets in either 96-well microtiter plates (Becton Dickinson and Company, Franklin Lakes, N.J.) or 128-well trays specifically designed for insect bioassays (C-D International, Pitman, N.J.). Eggs from 2 lepidopteran species were used for bioassays conducted in 96-well microtiter plates: the corn earworm (*Helicoverpa zea* (Boddie)) and the tobacco budworm (*Heliothis virescens* (F.)). Neonate larvae were used for bioassays conducted in 128-well trays. The lepidopteran species tested in this format included the corn earworm, the tobacco budworm, and the beet armyworm (*Spodoptera exigua* (Hübner)). A single coleopteran species, the southern corn rootworm (*Diabrotica undecimpunctata howardii* (Barber)) was also tested in this bioassay format.

The data recorded in these bioassays included the total number of insects in the treatment, number of dead insects, the number of insects whose growth was stunted, and the weight of surviving insects. In cases where growth inhibition is reported, this was calculated as follows:

% Growth Inhibition=[1−(Average Weight of Insects in Treatment/Average Weight of Insects in the Vector-Only Control)]*100

Example 5C

Other Experimental Protocol

This is described in more detail in concurrently filed application by Apel-Birkhold et al., entitled "Toxin Complex Proteins and Genes from *Xenorhabdus bovienii*," under attorney docket no. DAS-114P (Ser. No. 11/020,848)

Example 5D

Plasmid pDAB6026 was shown to encode activities which synergized the insect toxic activities of TcdA and XptA2$_{wi}$. *E. coli* cells containing plasmid pDAB6026 or the pBCKS+ vector control were inoculated into 200 mL of LB containing chloramphenicol (50 μg/mL) and 75 μM IPTG (isopropyl-β-D-thiogalactopyranoside) and grown for two days at 28° C. with shaking at 180 rpm. The cells were then centrifuged for 10 min at 3500×g. The pellets were resuspended in 5 mL of Butterfield's phosphate solution (Fisher Scientific) and transferred to 50 mL conical tubes containing 1.5 mL of 0.1 mm diameter glass beads (Biospec, Bartlesville, Okla., catalog number 1107901). The cell-glass bead mixture was chilled on ice, then the cells were lysed by sonication with two 45 second bursts using a 2 mm probe with a Branson Sonifier 250 (Danbury Conn.) at an output of ~20, chilling completely between bursts. The supernatant was transferred to 2 mL microcentrifuge tubes and centrifuged for 5 min at 16,000×g. The supernatants were then transferred to 15 mL tubes, and the protein concentration was measured. Bio-Rad Protein Dye Assay Reagent was diluted 1:5 with $H_2O$ and 1 mL was added to 10 μL of a 1:10 dilution of each sample and to bovine serum albumin (BSA) at concentrations of 5, 10, 15, 20 and 25 μg/mL. The samples were then read on a spectrophotometer measuring the optical density at the wavelength of 595 in the Shimadzu UV160U spectrophotometer (Kyoto, JP). The amount of protein contained in each sample was then calculated against the BSA standard curve and adjusted to between 3-6 mg/mL with phosphate buffer. Six hundred nanograms of XptA2$_{wi}$ toxin protein were added to 500 μL of the *E. coli* lysate prior to testing in insect feeding bioassays. The combination of pDAB6026 and XptA2 was shown to have potent activity (Table 16).

TABLE 16

Response of 2 lepidopteran species to pDAB6026 lysates alone and with purified XptA2$_{wi}$ protein.

| | tobacco budworm | | | | corn earworm | | | |
|---|---|---|---|---|---|---|---|---|
| Treatment | Dead | Stunted | Total | Weight | Dead | Stunted | Total | Weight |
| 1 pBC | 0 | 0 | 8 | 674 | 0 | 0 | 8 | 352 |
| 2 pBC + XptA2$_{wi}$ | 0 | 0 | 8 | 538 | 0 | 0 | 8 | 423 |
| 3 pDAB6026 | 0 | 0 | 8 | 539 | 0 | 0 | 8 | 519 |
| 4 pDAB6026 + XptA2$_{wi}$ | 0 | 8 | 8 | 18 | 8 | — | 8 | — |

Example 5E

Discovery Engineering and Testing of xptB1$_{xb}$ and xptC1$_{xb}$ Genes

DNA of plasmid pDAB6026 was sent to SeqWright DNA Sequencing (Houston, Tex.) for DNA sequence determination. Two complete open reading frames (ORFs) of substantial size were discovered. The first (disclosed as SEQ ID NO:48) has significant similarity to known toxin complex genes belonging to the "B" class. This ORF was therefore called xptB1$_{xb}$ and encodes the protein disclosed as SEQ ID NO:49. The second ORF (SEQ ID NO:50) encodes a protein (SEQ ID NO:51) with homology to toxin complex "C" proteins and therefore was named XptC1$_{xb}$.

The xptB1$_{xb}$ and XptC1$_{xb}$ genes were engineered (using the polymerase chain reaction; PCR) for high level recombinant expression by addition of restriction sites 5' and 3' to the coding regions, as well as provision of ribosome binding sequences and optimal translational stop signals. In addition, silent mutations (no change in amino acid sequence) were introduced into the 5' end of the coding regions to reduce potential secondary structure of the mRNA and hence increase translation. The strategy was to amplify/engineer segments at the 5' and 3' ends of the genes, join the distal fragments using 'Splice Overlap Extensions' reactions, then add the non-amplified center portion of the open reading frames via restriction sites. This approach minimized the potential of PCR-induced changes in the DNA sequence. The engineered coding regions were cloned into pET expression plasmids (Novagen, Madison, Wis.) as either separate coding regions (SEQ ID NO:52 and SEQ ID NO:53) or a dicistronic operon (SEQ ID NO:54). The names of the expression plasmids are shown in Table 17.

TABLE 17

Expression plasmids containing various coding regions cloned into the pET vector.

| Plasmid Name | Coding Region Engineered for Expression |
|---|---|
| pDAB6031 | $xptB1_{xb}$ as in SEQ ID NO: 52 |
| pDAB6032 | $xptC1_{xb}$ as in SEQ ID NO: 53 |
| pDAB6033 | $xptB1_{xb}$ + $xptC1_{xb}$ as in SEQ ID NO: 54 |

Competent cells of the *E. coli* T7 expression strain BL21 Star™ (DE3) (Stratagene, La Jolla, Calif.) were freshly transformed with DNA of either the pET (control) vector or plasmids pDAB6031, pDAB6032 or pDAB6033, and inoculated into 250 mL of LB containing 50 µg/mL chloramphenicol and 75 µM IPTG. After growth for 24 hrs at 28° C. with shaking at 180 rpm, the cells were centrifuged for 10 min at 5500×g. The pellets were resuspended in 5 mL of phosphate solution and transferred to 50 mL conical tubes containing 1.5 mL of 0.1 mm diameter glass beads, then were sonicated for two 45 sec bursts at "constant" and a setting of 30 as described above. The samples were centrifuged at 3000×g for 15 min, the supernatant was transferred to 2 mL microcentrifuge tubes, centrifuged for 5 min at 14,000 rpm, and the supernatants were then transferred to 15 mL tubes. The protein concentrations were measured as described above and the lysates were adjusted to 5 mg/mL with phosphate buffer. A set of three samples per lysate was submitted for insect bioassay. To the first sample, phosphate buffer was added in place of purified toxin; to the second sample, sufficient TcdA protein was added to provide a dose of 50 ng/cm$^2$ in the insect bioassay well, and to the third sample, sufficient $XptA2_{wi}$ protein was added to provide a dose of 250 ng/cm$^2$ in the insect bioassay well.

The results of the bioassay are shown in Table 18. Control samples, which were not supplemented with low levels of added TcdA or $XptA2_{wi}$ protein, (e.g. samples from vector, pDAB6031, pDAB6032 and pDAB6033), had little impact on the insects. Likewise, samples which contained low levels of TcdA or $XptA2_{wi}$, with either pDAB6031 or pDAB6032 lysates, had minimal effects. In contrast, significant activity was observed in the samples which included low levels of TcdA or $XptA2_{wi}$ with pDAB6033 lysates.

TABLE 18

Response of coleopteran and lepidopteran species to *E. coli* lysates and purified proteins. Responses are presented as percent mortality/percent growth inhibition.

| | | Insect Species | | | |
|---|---|---|---|---|---|
| Sample | Lysates Tested | southern corn rootworm | corn earworm | tobacco budworm | beet armyworm |
| vector | | 0/0 | 8/0 | 0/0 | 31/0 |
| pDAB6031 | $XptB1_{xb}$ | 0/0 | 0/0 | 0/0 | 31/33 |
| pDAB6032 | $XptC1_{xb}$ | 0/0 | 4/11 | 0/2 | 13/15 |
| pDAB6033 | $XptB1_{xb}$ + $XptC1_{xb}$ | 0/0 | 0/0 | 0/6 | 13/38 |
| Vector + TcdA | | 4/0 | 4/3 | 0/6 | 25/22 |
| pDAB6031 + TcdA | $XptB1_{xb}$ + TcdA | 0/0 | 0/0 | 0/5 | 13/34 |
| pDAB6032 + TcdA | $XptC1_{xb}$ + TcdA | 0/0 | 0/2 | 0/14 | 6/25 |
| pDAB6033 + TcdA | $XptB1_{xb}$ + $XptC1_{xb}$ + TcdA | 25/68 | 4/14 | 4/0 | 31/48 |
| Vector + $XptA2_{wi}$ | | 0/0 | 0/79 | 0/9 | 31/0 |
| pDAB6031 + $XptA2_{wi}$ | $XptB1_{xb}$ + $XptA2_{wi}$ | 0/0 | 4/75 | 8/22 | 25/36 |
| pDAB6032 + $XptA2_{wi}$ | $XptC1_{xb}$ + $XptA2_{wi}$ | 0/0 | 0/71 | 0/22 | 6/14 |
| pDAB6033 + $XptA2_{wi}$ | $XptB1_{xb}$ + $XptC1_{xb}$ + $XptA2_{wi}$ | 0/0 | 83/100 | 29/98 | 81/100 |

Example 5F

Identification, Purification, and Characterization of XptB1 and $XptC1_{xb}$ Proteins of *Xenorhabdus bovienii* Strain ILM104

Bioassay driven fractionation of a pDAB6033-containing *E. coli* lysate resulted in the identification by MALDI-TOF of two co-purifying proteins; $XptB1_{xb}$ and $XptC1_{xb}$. Peaks containing these 2 proteins effectively potentiated the activity of TcdA and XptA2wi.

Active fractions were identified based on their ability to synergize or potentiate the activity of TcdA against southern corn rootworm or $XptA2_{wi}$ against corn earworm. All bioassays were conducted in the 128-well format described above in Example 5A.

Two peaks of activity were detected from protein fractions eluting between 22-24 mS/cm conductance (Peak 1 and Peak 2). An example of the potentiating activity of Peaks 1 and 2 is shown in Table 19. Subsequent purification and analysis were performed on both Peak 1 and Peak 2

Gels from both Peak 1 and Peak 2 contained two predominant bands, one migrating at ~170 kDa and the other migrating at ~80 kDa. The gel from Peak 1 contained three additional proteins that migrated at approximately 18, 33 and 50 kDa. Retrospective analysis revealed that the ~170 kDa and ~80 kDa bands were abundant at the initial stages of purification and became progressively enriched at each step Extracted peptides were analyzed using MALDI-TOF mass spectrometry to produce peptide mass fingerprints (PMF) on a Voyager DE-STR MALDI-TOF mass spectrometer (PerSeptive Biosystems, Framingham, Mass.). Analysis of the samples extracted from the ~170 kDa band confirmed the identity as XptB1$_{xb}$. Analysis of the samples extracted from the ~80 kDa band confirmed the identity as XptC1$_{xb}$. Although the predicted molecular weight of the XptC1$_{xb}$ protein as calculated from the gene sequence (SEQ ID NO:50) is 108 kDa, the extracted protein ran significantly faster than expected in the SDS/PAGE. The presence of peptide fragments representing the entire peptide sequence indicated that the protein as extracted is full length.

TABLE 19

Biological activity of purified Peak 1 and Peak 2 from pDAB6033.

| | corn earworm | | southern corn rootworm | |
|---|---|---|---|---|
| Sample | Dead | Stunted | Dead | Stunted |
| Peak 1 | | | | |
| 0 | 0 | 0 | 0 | 0 |
| 125 | 2 | 6 | 4 | 2 |
| Peak 2 | | | | |
| 0 | 1 | 0 | 0 | 0 |
| 125 | 0 | 8 | 5 | 3 |

Values in column labeled Sample represent the concentration of Peak 1 or Peak 2 XptB1$_{xb}$/XptC1$_{xb}$ proteins applied to the diet (in ng/cm$^2$). For bioassays against corn earworm, 250 ng/cm$^2$ of XptA2$_{xi}$ was included in the bioassay. For bioassays against southern corn rootworm, 100 ng/cm$^2$ of TcdA was included in the bioassay. A total of eight larvae were used per sample.

EXAMPLE 6

Additional Mix and Match Example

In this example, it is demonstrated that potent insect suppression is obtained with a combination of three toxin complex (TC) proteins. Compelling insect activity is observed when a Class A protein is mixed with a Class B and Class C protein. The present invention is surprising in that many combinations of a Class A, Class B and Class C protein result in powerful insect repression. The Toxin Complex proteins may be from widely divergent sources and may only share a limited amount of amino acid identity with other functional members of its class.

Example 6A

Introduction

The insecticidal and growth inhibition activities encoded by fifteen different toxin complex genes were tested separately and in combination with one another. Several examples from each of the described classes, A, B or C, were tested. The genes were derived from three genera (Photorhabdus, *Xenorhabdus* and *Paenibacillus*; both gram negative and gram positive bacteria) and four different species. The results within this example are consistent with the observation that Toxin Complex Class A proteins (e.g. TcdA and XptA2$_{wi}$) have significant activity alone. This was recently shown in transgenic plants by Liu et al. (Liu, D., Burton, S., Glancy, T., Li, Z-S., Hampton, R., Meade, T. and Merlo, D. J. "Insect resistance conferred by 283-kDa *Photorhabdus luminescens* protein TcdA in *Arabidopsis thaliana*." Nature Biotechnology October 2003. Volume 21, number 10 pages 1222-1228). The results also agree with the observation that co-expression of three toxin complex genes (Class A, Class B and Class C) from within the same operon, strain, or genus result in greater insect activity than the Class A gene alone, or any single or double combination of the three classes (Hurst, M., Glare, T., Jackson, T. and Ronson, C. "Plasmid-Located Pathogenicity Determinants of *Serratia entomophila*, the Causal Agent of Amber Disease of Grass Grub, Show Similarity to the Insecticidal Toxins of *Photorhabdus luminescens*". Journal of Bacteriology, September 2000, Volume 182, Number 18, pages 5127-5138; Morgan, J. A., Sergeant, M., Ellis, D., Ousley, M. and Jarrett, P. "Sequence Analysis of Insecticidal Genes from *Xenorhabdus nematophilus* PMFI296". Applied and Environmental Microbiology, May 2001, p. 2062-2069, Vol. 67, No. 5; Waterfield, N., Dowling, A., Sharma, S., Daborn, P., Potter, U. and Ffrench-Constant, R. "Oral Toxicity of *Photorhabdus luminescens* W-14 Toxin Complexes in *Escherichia coli*," Applied and Environmental Microbiology, Nov. 2001, Volume 67, Number 11, pages 5017-5024).

Surprisingly, the data below document the discovery that toxin complex Class A proteins may be mixed and matched with, for example, lysates prepared from *E. coli* cells programmed to express Class B and Class C genes from widely divergent sources to produce stunning insecticidal and insect growth inhibition activity. For example, a Class A protein from *Xenorhabdus* may be mixed with a lysate programmed to express a Class B gene from *Photorhabdus* and a Class C gene from *Paenibacillus* to provide an insect active combination. Likewise, a Class A protein from *Photorhabdus* may be mixed with a lysate programmed to express a Class B and Class C gene from *Xenorhabdus*, and vice versa. Many combinations are possible; many are shown below to result in potent insect activity. It was an unexpected revelation that toxin complex Class A, B, and C components from strains noted for either coleopteran (Photorhabdus luminescens strain W-14) or lepidopteran activity (Xenorhabdus nematophilus strain Xwi) may be functionally mixed and matched. Additionally surprising was the discovery of the degree of divergence possible for individual A, B or C proteins. For example, individual Class A's (e.g. TcdA and XptA2$_{wi}$) which function with a Class B/Class C combination may only share 41% amino acid identity with each other. Likewise any individual Class B may only share 41% identity with another functional Class B protein. Similarly, any given Class C may share only 35% identity with another Class C protein.

Example 6B

Protein Sources and Constructions

The Class A proteins TcdA and XptA2$_{wi}$ were utilized in a purified form prepared from cultures of *Pseudomonas fluorescens* heterologously expressing the proteins. Preparations of the TcdA and XptA2$_{wi}$ from other heterologous sources (plant; bacterial) were functionally equivalent in the assays. The Class B and Class C proteins were tested as components of *E. coli* lysates. The use of lysates was validated by comparison to purified preparations of several Class B and Class C combinations. Reading frames encoding Class B and Class C proteins were engineered for expression in *E. coli* by cloning into pET plasmids (Novagen, Madison Wis.). Each coding region contained an appropriately spaced ribosome binding site (relative to the start codon) and termination signal. The DNA sequences at the 5' end of some of the genes were modified to reduce predicted secondary structure of the RNA and hence increase translation. These base changes were silent and did not result in amino acid changes in the protein. In cases where a Class B gene was tested with a Class C gene, an operon was constructed in the pET expression plasmid with the Class B coding sequence being transcribed first, followed by the Class C coding sequence. The two coding regions were separated by a linker sequence which contained a ribosome binding site appropriately spaced relative to the start codon of the Class C protein coding region. The DNA sequence between the coding regions in the dicistronic constructions is shown in the 5' to 3'orientation. Tables 20-27 contain lists of the proteins encoded by the various expression plasmids, the source of the coding regions and the plasmid reference number. Tables 22B, 23B, and 28-31 show linker sequences used in expression plasmids.

TABLE 20

| Class B Proteins | Source | Plasmid Number |
|---|---|---|
| TcdB1 | *Photorhabdus luminescens* str W-14 | pDAB8907 |
| TcdB2 | *Photorhabdus luminescens* str W-14 | pDAB3089 |
| TcaC | *Photorhabdus luminescens* str W-14 | pDAB8905 |
| XptC1$_{wi}$ | *Xenorhabdus nematophilus* str Xwi | pDAB8908 |
| XptB1$_{xb}$ | *Xenorhabdus bovienii* str ILM104 | pDAB6031 |
| PptB1$_{1529}$ | *Paenibacillus* spp str 1529 | pDAB8722 |

TABLE 21

| Class C Proteins | Source | Plasmid Number |
|---|---|---|
| TccC1 | *Photorhabdus luminescens* str W-14 | pDAB8913 |
| TccC2 | *Photorhabdus luminescens* str W-14 | pDAB3118 |
| TccC3 | *Photorhabdus luminescens* str W-14 | pDAB3090 |
| TccC5 | *Photorhabdus luminescens* str W-14 | pDAB3119 |
| XptB1$_{wi}$ | *Xenorhabdus nematophilus* str Xwi | pDAB8909 |
| XptC1$_{xb}$ | *Xenorhabdus bovienii* str ILM104 | pDAB6032 |
| PptC1$_{1529}$ | *Paenibacillus* spp str 1529 | pDAB8723 |

TABLE 22A

| Protein Combination | Source | Plasmid Number |
|---|---|---|
| TcdB1 + TccC1 | *Photorhabdus luminescens* str W-14 | pDAB8912 |
| TcdB1 + TccC2 | *Photorhabdus luminescens* str W-14 | pDAB8712 |
| TcdB1 + TccC3 | *Photorhabdus luminescens* str W-14 | pDAB3104 |
| TcdB1 + TccC5 | *Photorhabdus luminescens* str W-14 | pDAB8718 |
| TcdB1 + XptB1$_{wi}$ | *Photorhabdus luminescens* str W-14 *Xenorhabdus nematophilus* str Xwi | pDAB8713 |

TABLE 22B

| Plasmid Number | Protein Combination | Linker Sequence |
|---|---|---|
| pDAB8912 | TcdB1 + TccC1 | tgactcgacgcactactagtaaaaag gagataacccc |
| pDAB8712 | TcdB1 + TccC2 | tgactcgaatttaaattatatatata tatatactcgacgaattttaatctac tagtaaaaaggagataacc |
| pDAB3104 | TcdB1 + TccC3 | tgactcgacgcactactagtaaacaa gaaggagatatacc |
| pDAB8718 | TcdB1 + TccC5 | tgactcgaatttaaattatatatata tatatactcgacgaattttaatctac tagatttatttaaatttttttactag ttttgtcgacaaaaaggagataaccc c |
| pDAB8713 | TcdB1 + XptB1$_{wi}$ | tgactcgaatttaaattatatatata tatatactcgacaagaaggagatata cc |

TABLE 23A

| Protein Combination | Source | Plasmid Number |
|---|---|---|
| TcdB2 + TccC1 | *Photorhabdus luminescens* str W-14 | pDAB3114 |
| TcdB2 + TccC2 | *Photorhabdus luminescens* str W-14 | pDAB3115 |
| TcdB2 + TccC3 | *Photorhabdus luminescens* str W-14 | pDAB3093 |
| TcdB2 + TccC5 | *Photorhabdus luminescens* str W-14 | pDAB3106 |
| TcdB2 + XptB1$_{wi}$ | *Photorhabdus luminescens* str W-14 *Xenorhabdus nematophilus* str Xwi | pDAB3097 |
| TcdB2 + XptC1$_{xb}$ | *Photorhabdus luminescens* str W-14 *Xenorhabdus bovienii* str ILM104 | pDAB8910 |
| TcdB2 + PptC1$_{1529}$ | *Photorhabdus luminescens* str W-14 *Paenibacillus* spp str1529 | pDAB8725 |

TABLE 23B

| Plasmid Number | Protein Combination | Linker Sequence |
|---|---|---|
| pDAB3114 | TcdB2 + TccC1 | ttaatctgactcgacgcactacta gtaaaaaggagataacccc |
| pDAB3115 | TcdB2 + TccC2 | ttaatctgactcgacgaattttaa tctactagtaaaaaggagataacc |
| pDAB3093 | TcdB2 + TccC3 | ttaatctgactcgacgcactacta gtaaacaagaaggagatatacc |
| pDAB3106 | TcdB2 + TccC5 | ttaatctgactcgacaaaaaggag ataacccc |
| pDAB3097 | TcdB2 + XptB1$_{wi}$ | ttaatctgactcgacaagaaggag atatacc |
| pDAB8910 | TcdB2 + XptC1$_{xb}$ | ttaatctgactcgacaaaaaggag ataccccatgccttaaagaagag agagatatacc |
| pDAB8725 | TcdB2 + PptC1$_{1529}$ | ttaatctgactcgactttactagt aaggagatatacc |

TABLE 24

| Protein Combination | Source | Plasmid Number |
|---|---|---|
| TcaC + TccC1 | *Photorhabdus luminescens* str W-14 | pDAB8901 |
| TcaC + TccC2 | *Photorhabdus luminescens* str W-14 | pDAB8902 |
| TcaC + TccC3 | *Photorhabdus luminescens* str W-14 | pDAB8903 |
| TcaC + TccC5 | *Photorhabdus luminescens* str W-14 | pDAB8904 |
| TcaC + XptB1$_{wi}$ | *Photorhabdus luminescens* str W-14 *Xenorhabdus nematophilus* str Xwi | pDAB8900 |
| TcaC + XptC1$_{xb}$ | *Photorhabdus luminescens* str W-14 *Xenorhabdus bovienii* str ILM104 | pDAB8906 |

TABLE 25

| Protein Combination | Source | Plasmid Number |
|---|---|---|
| XptC1$_{wi}$ + TccC1 | *Xenorhabdus nematophilus* str Xwi *Photorhabdus luminescens* str W-14 | pDAB8914 |
| XptC1$_{wi}$ + TccC2 | *Xenorhabdus nematophilus* str Xwi *Photorhabdus luminescens* str W-14 | pDAB8915 |
| XptC1$_{wi}$ + TccC3 | *Xenorhabdus nematophilus* str Xwi *Photorhabdus luminescens* str W-14 | pDAB3103 |
| XptC1$_{wi}$ + TccC5 | *Xenorhabdus nematophilus* str Xwi *Photorhabdus luminescens* str W-14 | pDAB3105 |
| XptC1$_{wi}$ + XptB1$_{wi}$ | *Xenorhabdus nematophilus* str Xwi | pDAB8916 |

TABLE 26

| Protein Combination | Source | Plasmid Number |
|---|---|---|
| $XptB1_{xb}$ + TccC1 | *Xenorhabdus bovienii* str ILM104<br>*Photorhabdus luminescens* str W-14 | pDAB8918 |
| $XptB1_{xb}$ + TccC3 | *Xenorhabdus bovienii* str ILM104<br>*Photorhabdus luminescens* str W-14 | pDAB6039 |
| $XptB1_{xb}$ + $XptC1_{xb}$ | *Xenorhabdus bovienii* str ILM104 | pDAB6033 |
| $XptB1_{xb}$ + $PptC1_{1529}$ | *Xenorhabdus bovienii* str ILM104<br>*Paenibacillus* spp str1529 | pDAB8732 |

TABLE 27

| Protein Combination | Source | Plasmid Number |
|---|---|---|
| $PptB1_{1529}$ + $PptC1_{1529}$ | *Paenibacillus* spp str1529 | pDAB8724 |
| $PptB1_{1529}$ + TccC3 | *Paenibacillus* spp str1529<br>*Photorhabdus luminescens* str W-14 | pDAB8726 |
| $PptB1_{1529}$ + TccC1 | *Paenibacillus* spp str1529<br>*Photorhabdus luminescens* str W-14 | pDAB8733 |

TABLE 28

| Plasmid Number | Protein Combination | Linker Sequence |
|---|---|---|
| pDAB8901 | TcaC + TccC1 | taactcgatatggctagcatgactggtggacagcaaatgggtcgcggatcgatccgaattcgcccttgtcgacgcactactagtaaaaaggagataacccc |
| pDAB8902 | TcaC + TccC2 | taactcgatatggctagcatgactggtggacagcaaatgggtcgcggatcaaattatatatatatatactcgacgaatttaatctactagtaaaaaggagataacc |
| pDAB8903 | TcaC + TccC3 | taactcgatatggctagcatgactggtggacagcaaatgggtcgcggatccgaattcgagctccgtcgacgcactactagtaaacaagaaggagatatacc |
| pDAB8904 | TcaC + TccC5 | taactcgatatggctagcatgactggtggacagcaaatgggtcgcggatcaaattttttactagttttgtcgacaaaaaggagataacccc |
| pDAB8900 | TcaC + $XptB1_{wi}$ | taactcgatatggctagcatgactggtggacagcaaatgggtcgcggatctcgatcccgcgaaattaatacgactcactataggggaattgtgagcggataacaattccccctctagacgtgcgtcgacaagaaggagatatacc |
| pDAB8906 | TcaC + $XptC1_{xb}$ | taactcgatatggctagcatgactggtggacagcaaatgggtcgcggatcccttaaagaagagagagatatacc |

TABLE 29

| Plasmid Number | Protein Combination | Linker Sequence |
|---|---|---|
| pDAB8914 | $XptC1_{wi}$ + TccC1 | ttaatgctctcgaatttgactagaaataattttgtttaactttaagaaggagatataccatgggcagcagccatcatcatcatcatcacagcagcggcctggtgccgcgcggcagccatatggctagcatgactggtggacagcaaatgggtcgcggatccgaattcgcccttgtcgacgcactactagtaaaaaggagataacccc |
| pDAB8915 | $XptC1_{wi}$ + TccC2 | ttaatgctctcgaatttgactagagtcgacgaattttaatctactagtaaaaaggagataacc |
| pDAB3103 | $XptC1_{wi}$ + TccC3 | ttaatgctctcgaatttgactagtcaaattatatatatatatactcgacgcactactagtaaacaagaaggagatatacc |
| pDAB3105 | $XptC1_{wi}$ + TccC5 | ttaatgctctcgaatttgactagatttatttaaatttttttactagttttgtcgacaaaaaggagataacccc |
| pDAB8916 | $XptC1_{wi}$ + $XptB1_{wi}$ | ttaatgctctcgaatttgactagacgtgcgtcgacaagaaggagatatacc |

TABLE 30

| Plasmid Number | Protein Combination | Linker Sequence |
|---|---|---|
| pDAB8918 | $XptB1_{xb}$ + TccC1 | ttaatgcggccgcaggaaatttttttgtcgactttactagtaaaaaggagataacccc |
| pDAB6039 | $XptB1_{xb}$ + TccC3 | ttaatgcggccgcaggctagtaaacaagaaggagatatacc |
| pDAB6033 | $XptB1_{xb}$ + $XPtC1_{xb}$ | ttaatgcggccgcaggccttaaagaagagagagatatacc |
| pDAB8732 | $XptB1_{xb}$ + $PptC1_{1529}$ | ttaatgcggccgcaggcctctgtaagactctcgactttactagtaaggagatatacc |

TABLE 31

| Plasmid Number | Protein Combination | Linker Sequence |
|---|---|---|
| pDAB8724 | $PptB1_{1529}$ + $PptC1_{1529}$ | taatgtcgactttactagtaaggagatatacc |
| pDAB8726 | $PptB1_{1529}$ + TccC3 | taatgtcgactttactagtaaacaagaaggagatatacc |
| pDAB8733 | $PptB1_{1529}$ + TccC1 | taatgtcgactttactagtaaaaaggagataacccc |

Example 6C

Expression Conditions and Lysate Preparations

The pET expression plasmids listed in Tables 20-27 were transformed into the *E. coli* T7 expression strains BL21 (DE3) (Novagen, Madison Wis.) or BL21 Star™ (DE3) (Stratagene, La Jolla, Calif.) using standard methods. Expression cultures were initiated with 10-200 freshly transformed colonies into 250 mL LB 50 μg/ml antibiotic and 75 μM IPTG. The cultures were grown at 28° C. for 24 hours at 180-200 rpm. The cells were collected by centrifugation in 250 ml Nalgene bottles at 3,400×g for 10 minutes at 4° C. The pellets were suspended in 4-4.5 mL Butterfield's Phosphate solution (Hardy Diagnostics, Santa Maria, Calif.; 0.3 mM potassium phosphate pH 7.2). The suspended cells were transferred to 50 mL polypropylene screw cap centrifuge tubes with 1 mL of 0.1 mm diameter glass beads (Biospec, Bartlesville, Okla., catalog number 1107901). The cell-glass bead mixture was chilled on ice, then the cells were lysed by sonication with two 45 second bursts using a 2 mm probe with a Branson Sonifier 250 (Danbury Conn.) at an output of 20, chilling completely between bursts. The lysates were transferred to 2 mL Eppendorf tubes and centrifuged 5 minutes at 16,000×g. The supernatants were collected and the protein concentration measured. Bio-Rad Protein Dye Assay Reagent was diluted 1:5 with $H_2O$ and 1 mL was added to 10 μL of a 1:10 dilution of each sample and to bovine serum albumin (BSA) at concentrations of 5, 10, 15, 20 and 25 μg/mL. The samples were then read on a spectrophotometer measuring the optical density at the wavelength of 595 nm in the Shimadzu UV160U spectrophotometer (Kyoto, JP). The amount of protein contained in each sample was then calculated against the BSA standard curve and adjusted to between 3-6 mg/mL with phosphate buffer. The lysates were typically assayed fresh, however no loss in activity was observed when stored at −70° C.

Example 6D

Bioassay Conditions

Insect bioassays were conducted with neonate larvae on artificial diets in 128-well trays specifically designed for insect bioassays (C-D International, Pitman, N.J.). The species assayed were the southern corn rootworm, *Diabrotica undecimpunctata howardii* (Barber), the corn earworm, *Helicoverpa zea* (Boddie), the tobacco budworm, *Heliothis virescens* (F.), and the beet armyworm, *Spodoptera exigua* (Hübner).

Bioassays were incubated under controlled environmental conditions (28° C., ~40% r.h., 16:8 [L:D]) for 5 days at which point the total number of insects in the treatment, the number of dead insects, and the weight of surviving insects were recorded. Percent mortality and percent growth inhibition were calculated for each treatment. Growth inhibition was calculated as follows:

% Growth Inhibition=[1−(Average Weight of Insects in Treatment/Average Weight of Insects in the Vector-Only Control)]*100

In cases where the average weight of insects in treatment was greater that of insects in the vector only control, growth inhibition was scored as 0%.

The biological activity of the crude lysates alone or with added TcdA or $XptA2_{wi}$ toxin proteins was assayed as follows. Crude *E. coli* lysates (40 μL) of either control cultures or those expressing potentiator proteins were applied to the surface of artificial diet in 8 wells of a bioassay tray. The average surface area of treated diet in each well was ~1.5 $cm^2$. The lysates were adjusted to between 2-5 mg/mL total protein and were applied with and without TcdA or $XptA2_{wi}$. The TcdA or $XptA2_{wi}$ added were highly purified fractions from bacterial cultures heterologously expressing the proteins. The final concentrations of $XptA2_{wi}$ and TcdA on the diet were 250 ng/$cm^2$ and 50 ng/$cm^2$, respectively.

The results of bioassays are summarized in Tables 32-39. Little to no effect on the survival or growth of the insect species tested was observed when larvae were fed lysates from *E. coli* clones engineered to express a Class B or Class C protein alone (Tables 32 and 33). Similarly, little to no effect was observed when larvae were fed combinations of Class B and Class C proteins in the absence of a purified toxin (Tables 34-39, "none" column). Significant effects on survival and/or growth were commonly observed when larvae were fed lysates from *E. coli* clones engineered to express a combination of a Class B and Class C protein with a purified toxin (Tables 2C-2H, "TcdA" and "$XptA2_{wi}$" columns). Class B and Class C combinations tested with purified TcdA most typically exerted an effect on southern corn rootworm while combinations tested with purified $XptA2_{wi}$ typically exerted an effect on one of the 3 lepidopteran species with corn earworm being the most consistently sensitive species. It is notable that many Class B and Class C combinations produced an observable effect of $XptA2_{wi}$ on southern corn rootworm. The converse, that these combinations would produce an observable effect of TcdA on lepidopteran species, did not hold true.

Tables 32-39 show biological activity of *E. coli* lysates fed to insect larvae alone and combined with *Photorhabdus* or *Xenorhabdus* toxin proteins. The gene contained in each *E. coli* clone corresponds to those contained in Tables 20-27. Biological activity is classified using the following scale: 0=average mortality <50% AND average weight >50% of the average weight of empty vector/no toxin treatment, +=average weight ≦50% of the average weight of empty vector/no toxin treatment, ++=average mortality ≧50% OR average weight ≦20% of the average weight of empty vector/no toxin treatment, and +++=average mortality ≧95% OR average weight ≦5% of the average weight of empty vector/no toxin treatment.

TABLE 32

Biological activity of *E. coli* clones engineered to express Class B protein genes. Lysates were tested alone and with purified TcdA or $XptA2_{wi}$.

| Toxin Protein | Insect Species: southern corn rootworm | | | tobacco budworm | | | corn earworm | | | beet armyworm | | |
|---|---|---|---|---|---|---|---|---|---|---|---|---|
| Class B Genes | none | TcdA | $XptA2_{wi}$ | none | TcdA | $XptA2_{wi}$ | none | TcdA | $XptA2_{wi}$ | none | TcdA | $XptA2_{wi}$ |
| tcdB1 | 0 | + | + | 0 | 0 | 0 | 0 | 0 | 0 | 0 | 0 | 0 |
| tcdB2 | 0 | + | 0 | 0 | 0 | 0 | 0 | 0 | ++ | 0 | 0 | 0 |
| tcaC | 0 | 0 | 0 | 0 | 0 | 0 | 0 | 0 | 0 | 0 | 0 | 0 |
| $xptC1_{wi}$ | 0 | 0 | 0 | 0 | 0 | 0 | 0 | 0 | 0 | 0 | 0 | 0 |
| $xptB1_{xb}$ | 0 | 0 | 0 | 0 | 0 | 0 | 0 | 0 | + | 0 | 0 | 0 |
| $pptB1_{1529}$ | 0 | + | 0 | 0 | 0 | 0 | 0 | 0 | 0 | 0 | 0 | 0 |

TABLE 33

Biological activity of *E. coli* clones engineered to express Class C protein genes. Lysates were tested alone and with purified TcdA or $XptA2_{wi}$.

| | Insect Species | | | | | | | | | | | |
|---|---|---|---|---|---|---|---|---|---|---|---|---|
| Toxin Protein | southern corn rootworm | | | tobacco budworm | | | corn earworm | | | beet armyworm | | |
| Class C Genes | none | TcdA | $XptA2_{wi}$ | none | TcdA | $XptA2_{wi}$ | none | TcdA | $XptA2_{wi}$ | none | TcdA | $XptA2_{wi}$ |
| tccC1 | 0 | 0 | 0 | 0 | 0 | 0 | 0 | 0 | 0 | 0 | 0 | 0 |
| tccC2 | 0 | 0 | 0 | 0 | 0 | 0 | 0 | 0 | 0 | 0 | 0 | 0 |
| tccC3 | 0 | 0 | 0 | 0 | 0 | 0 | 0 | 0 | + | 0 | 0 | 0 |
| tccC5 | 0 | 0 | 0 | 0 | 0 | 0 | 0 | 0 | 0 | 0 | 0 | 0 |
| $xptB1_{wi}$ | 0 | 0 | + | 0 | 0 | 0 | 0 | 0 | + | 0 | 0 | 0 |
| $xptC1_{xb}$ | 0 | 0 | 0 | 0 | 0 | 0 | 0 | 0 | + | 0 | 0 | 0 |
| $pptC1_{1529}$ | 0 | + | 0 | 0 | 0 | 0 | 0 | 0 | 0 | 0 | 0 | 0 |

TABLE 34

Biological activity of *E.* coli clones engineered to express the Class B protein gene tcdB1 in combination with various Class C protein genes. Lysates were tested alone and with purified TcdA or $XptA2_{wi}$.

| | Insect Species | | | | | | | | | | | |
|---|---|---|---|---|---|---|---|---|---|---|---|---|
| Toxin Protein tcdB1 | southern corn rootworm | | | tobacco budworm | | | corn earworm | | | beet armyworm | | |
| Combinations | none | TcdA | $XptA2_{wi}$ | none | TcdA | $XptA2_{wi}$ | none | TcdA | $XptA2_{wi}$ | none | TcdA | $XptA2_{wi}$ |
| tcdB1 + tccC1 | 0 | + | + | 0 | 0 | ++ | 0 | + | +++ | 0 | 0 | 0 |
| tcdB1 + tccC2 | 0 | 0 | 0 | 0 | 0 | 0 | 0 | 0 | + | 0 | 0 | 0 |
| tcdB1 + tccC3 | 0 | ++ | + | 0 | 0 | ++ | 0 | 0 | +++ | 0 | 0 | +++ |
| tcdB1 + tccC5 | 0 | + | + | 0 | 0 | ++ | 0 | 0 | +++ | 0 | 0 | ++ |
| tcdB1 + $xptB1_{wi}$ | 0 | 0 | 0 | 0 | 0 | ++ | 0 | 0 | ++ | 0 | 0 | ++ |

TABLE 35

Biological activity of *E. coli* clones engineered to express the Class B protein gene tcdB2 in combination with various Class C protein genes. Lysates were tested alone and with purified TcdA or $XptA2_{wi}$.

| | Insect Species | | | | | | | | | | | |
|---|---|---|---|---|---|---|---|---|---|---|---|---|
| Toxin Protein tcdB2 | southern corn rootworm | | | tobacco budworm | | | corn earworm | | | beet armyworm | | |
| Combinations | none | TcdA | $XptA2_{wi}$ | none | TcdA | $XptA2_{wi}$ | none | TcdA | $XptA2_{wi}$ | none | TcdA | $XptA2_{wi}$ |
| tcdB2 + tccC3 | 0 | +++ | + | 0 | 0 | +++ | 0 | 0 | +++ | 0 | 0 | +++ |
| tcdB2 + tccC5 | 0 | +++ | + | 0 | 0 | +++ | 0 | 0 | +++ | 0 | 0 | +++ |
| tcdB2 + $xptB1_{wi}$ | 0 | + | + | 0 | 0 | ++ | 0 | + | +++ | 0 | 0 | + |
| tcdB2 + $xptC1_{xb}$ | nt | nt | nt | 0 | 0 | + | 0 | 0 | +++ | 0 | 0 | + |
| tcdB2 + $pptC1_{1529}$ | 0 | +++ | + | 0 | 0 | + | 0 | 0 | ++ | 0 | 0 | + |

TABLE 36

Biological activity of *E. coli* clones engineered to express the Class B protein gene tcaC in combination with various Class C protein genes. Lysates were tested alone and with purified TcdA or $XptA2_{wi}$.

| | Insect Species | | | | | | | | | | | |
|---|---|---|---|---|---|---|---|---|---|---|---|---|
| Toxin Protein tcaC | southern corn rootworm | | | tobacco budworm | | | corn earworm | | | beet armyworm | | |
| Combinations | none | TcdA | $XptA2_{wi}$ | none | TcdA | $XptA2_{wi}$ | none | TcdA | $XptA2_{wi}$ | none | TcdA | $XptA2_{wi}$ |
| tcaC + tccC1 | 0 | ++ | + | 0 | 0 | ++ | 0 | 0 | +++ | 0 | 0 | +++ |
| tcaC + tccC2 | 0 | 0 | 0 | 0 | 0 | 0 | 0 | 0 | + | 0 | 0 | 0 |
| tcaC + tccC3 | 0 | + | + | 0 | 0 | ++ | 0 | 0 | +++ | 0 | 0 | ++ |
| tcaC + tccC5 | 0 | +++ | + | 0 | 0 | ++ | 0 | 0 | ++ | 0 | 0 | +++ |
| tcaC + $xptB1_{wi}$ | 0 | ++ | 0 | + | + | ++ | 0 | 0 | +++ | 0 | 0 | +++ |

TABLE 37

Biological activity of *E. coli* clones engineered to express the Class B protein gene $xptC1_{wi}$ in combination with various Class C protein genes. Lysates were tested alone and with purified TcdA or $XptA2_{wi}$.

| Toxin Protein $xptC1_{wi}$ | Insect Species: southern corn rootworm | | | tobacco budworm | | | corn earworm | | | beet armyworm | | |
|---|---|---|---|---|---|---|---|---|---|---|---|---|
| Combinations | none | TcdA | $XptA2_{wi}$ | none | TcdA | $XptA2_{wi}$ | none | TcdA | $XptA2_{wi}$ | none | TcdA | $XptA2_{wi}$ |
| $xptC1_{wi}$ + tccC1 | 0 | 0 | 0 | 0 | 0 | + | 0 | 0 | +++ | 0 | 0 | 0 |
| $xptC1_{wi}$ + tccC2 | 0 | 0 | 0 | 0 | 0 | 0 | 0 | 0 | + | 0 | 0 | 0 |
| $xptC1_{wi}$ + tccC3 | 0 | ++ | + | 0 | 0 | ++ | 0 | 0 | +++ | 0 | 0 | ++ |
| $xptC1_{wi}$ + tccC5 | 0 | ++ | + | 0 | 0 | + | 0 | 0 | +++ | 0 | 0 | ++ |
| $xptC1_{wi}$ + $xptB1_{wi}$ | 0 | 0 | 0 | 0 | 0 | + | 0 | 0 | ++ | 0 | 0 | 0 |

TABLE 38

Biological activity of *E. coli* clones engineered to express the Class B protein gene $xptB1_{xb}$ in combination with various Class C protein genes. Lysates were tested alone and with purified TcdA or $XptA2_{wi}$.

| Toxin Protein $xptB1_{xb}$ | Insect Species: southern corn rootworm | | | tobacco budworm | | | corn earworm | | | beet armyworm | | |
|---|---|---|---|---|---|---|---|---|---|---|---|---|
| Combinations | none | TcdA | $XptA2_{wi}$ | none | TcdA | $XptA2_{wi}$ | none | TcdA | $XptA2_{wi}$ | none | TcdA | $XptA2_{wi}$ |
| $xptB1_{xb}$ + tccC3 | nt | nt | nt | 0 | 0 | + | 0 | 0 | +++ | 0 | 0 | + |
| $xptB1_{xb}$ + $xptC1_{xb}$ | 0 | + | 0 | 0 | 0 | +++ | 0 | 0 | +++ | 0 | 0 | +++ |

TABLE 39

Biological activity of *E. coli* clones engineered to express the Class B protein gene $pptB1_{1529}$ in combination with various Class C protein genes. Lysates were tested alone and with purified TcdA or $XptA2_{wi}$.

| Toxin Protein $pptB1_{1529}$ | Insect Species: southern corn rootworm | | | tobacco budworm | | | corn earworm | | | beet armyworm | | |
|---|---|---|---|---|---|---|---|---|---|---|---|---|
| Combinations | none | TcdA | $XptA2_{wi}$ | none | TcdA | $XptA2_{wi}$ | none | TcdA | $XptA2_{wi}$ | none | TcdA | $XptA2_{wi}$ |
| $pptB1_{1529}$ + $pptC1_{1529}$ | 0 | +++ | 0 | 0 | 0 | ++ | 0 | 0 | +++ | 0 | 0 | + |
| $pptB1_{1529}$ + tccC3 | 0 | +++ | + | 0 | 0 | ++ | 0 | 0 | +++ | 0 | 0 | +++ |

EXAMPLE 7

Additional Mixing and Matching of TC Proteins

To demonstrate the presently discovered versatility of TC proteins, additional *E. coli* expression experiments were done employing double plasmid expression systems. A T7 promoter based system utilized a pACYC derivative (called pCot-3 or 4, chloramphenicol resistant) to express either the TcdA or XptA2 proteins while a compatible T7 promoter pET280 plasmid (kanamycin resistant) expressed various combinations of the TcdB1 (SEQ ID NO:67), TcdB2 (SEQ ID NO:45), XptC1 (SEQ ID NO:18), TccC1 (SEQ ID NO:68), TccC3 (SEQ ID NO:47) and XptB1 (SEQ ID NO:16) proteins, all within the same cell. Likewise, in another series of experiments, an *E. coli* promoter system was used that utilized a different pACYC derivative (called pCTS, spectinomycin/streptomycin resistant) to express either TcdA (SEQ ID NO:65) or XptA2 (SEQ ID NO:34) proteins while a compatible pBT280 plasmid (chloramphenicol resistant) expressed various combinations of TedB1, TedB2, XptC1, TccC1, TccC3 and XptB1. Both systems produced proteins of similar activities when bioassayed.

The T7 promoter based experiments were done by first preparing stocks of competent BL21(DE3) cells containing either pCot-3, pCot-TcdA or pCot-XptA2. These cells were then transformed with either control pET280 plasmid or any of the combinations of TC genes noted above in the pET280 vector. Cells containing both plasmids were selected on media containing chloramphenicol and kanamycin. Similarly, for the *E. coli* promoted system, competent BL21 cells containing either pCTS, pCTS-TcdA or pCTS-XptA2 were prepared. The competent cells were then transformed with either pBT280 control plasmid or any of TC combinations noted above in the pBT280 vector. When more than one TC gene was present on a particular plasmid, they were arranged as a two gene operon with a single promoter at the 5' end. The first coding region was followed by translational termination signals; a separate ribosome binding site (Shine-Dalgarno sequence) and translational start signal were used to initiation translation of the second coding region. The methods described in Examples 2 and 3 were used to grow expression cultures, prepare lysates and assess insect activity. Some experiments utilized a modified assay method where enriched preparations of proteins TcdA and XptA2 were added to lysates containing either singly or in combination TcdB1, TcdB2, XptC1, TccC1, TccC3 and XptB1 (Tables 40 and 41).

TABLE 40

Bioassay Results of Heterologously Expressed Toxin Complex Genes on TBW, SCR, ECB and BAW

| Sample Tested | TBW Bioassay | SCR Bioassay | ECB Bioassay | BAW Bioassay |
|---|---|---|---|---|
| XptA2 | ++ | 0 | ++ | ++ |
| TcdB1 | 0 | 0 | + | +++ |
| XptC1 | 0 | 0 | 0 | +++ |
| TccC1 | + | 0 | + | +++ |
| XptB1 | 0 | 0 | 0 | +++ |
| TcdB1 + TccC1 | 0 | 0 | | |
| TcdB1 + XptB1 | 0 | 0 | | |
| XptC1 + TccC1 | 0 | 0 | | |
| XptC1 + XptB1 | + | 0 | | |
| XptA2 + TcdB1 | +++ | + | | ++ |
| XptA2 + XptC1 | ++ | 0 | 0 | ++ |
| XptA2 + TccC1 | +++ | + | + | +++ |
| XptA2 + XptB1 | +++ | + | 0 | ++++ |
| XptA2 + TcdB1 + TccC1 | +++++ | +++ | | +++++ |
| XptA2 + TcdB1 + XptB1 | +++++ | +++ | +++++ | ++++ |
| XptA2 + XptC1 + TccC1 | ++++ | 0 | ++++ | ++++ |
| XptA2 + XptC1 + XptB1 | ++++ | + | +++++ | ++++ |
| TcdA | 0 | +++ | ++ | 0 |
| TcdA + TcdB1 | 0 | +++ | ++ | 0 |
| TcdA + XptC1 | 0 | +++ | ++++ | 0 |
| TcdA + TccC1 | 0 | ++ | 0 | 0 |
| TcdA + XptB1 | 0 | +++ | ++ | 0 |
| TcdA + TcdB1 + TccC1 | 0 | ++++ | ++++ | 0 |
| TcdA + TcdB1 + XptB1 | 0 | ++++ | ++++ | 0 |
| TcdA + XptC1 + TccC1 | 0 | ++++ | ++ | 0 |
| TcdA + XptC1 + XptB1 | 0 | +++ | ++++ | 0 |

Whole *E. coli* cells were lysed and the soluble protein generally normalized within an experiment to between 5-10 mg/ml. The lysates were bioassayed as described by top loading onto insect diets.
Grading Scale represents % growth inhibition relative to controls (0 = 0-25%; + = 26-50%; ++ = 51-65%; +++ = 66-80% = ++++, 81-95%; +++++ = 96-100%).

TABLE 41

Bioassay of Heterologously Expressed Toxin Complex Genes on SCR, TBW, CEW, and FAW with the addition of purified TcdA Toxin Protein*

| Plasmid Tested | SCR Bioassay | TBW Bioassay | CEW Bioassay | FAW Bioassay |
|---|---|---|---|---|
| pET-280 | 0 | 0 | 0 | 0 |
| pET-280-TcdB1-XptB1 | ++++ | + | ++ | 0 |
| pET-280-TcdB2-TccC3 | +++++ | + | 0 | ++ |

Whole *E. coli* cells were lysed and the soluble protein was adjusted to equal sample concentrations of between 8-15 mg/ml.
*TcdA protein was added to the samples for a final concentration of 50 $ng/cm^2$ when applied on top of the insect diet preparations.

TABLE 41-continued

Bioassay of Heterologously Expressed Toxin Complex Genes on SCR, TBW, CEW, and FAW with the addition of purified TcdA Toxin Protein*

| Plasmid Tested | SCR Bioassay | TBW Bioassay | CEW Bioassay | FAW Bioassay |
|---|---|---|---|---|

Grading Scale represents % growth inhibition of surviving insects fed the treatment plus TcdA Toxin Protein relative to surviving insects fed the treatment in the absence of TcdA Toxin Protein (0 = 0-10%; + = 11-20%; ++ = 21-40%; +++ = 41-60% = ++++, 61-80%; +++++ >80%).

TABLE 42

Bioassay of Heterologously Expressed Toxin Complex Genes on SCR, TBW, CEW, and FAW with the addition of purified XptA2 Toxin Protein*

| Plasmid Tested | SCR Bioassay | TBW Bioassay | CEW Bioassay | FAW Bioassay |
|---|---|---|---|---|
| pET-280 | 0 | + | +++ | 0 |
| pET-280-TcdB1-XptB1 | ++++ | +++++ | +++++ | +++ |
| pET-280-TcdB2-TccC3 | ++++ | +++++ | +++++ | ++++ |

Whole *E. coli* cells were lysed and the soluble protein was adjusted to equal sample concentrations of between 8-15 mg/ml.
*XptA2 protein was added to the samples for a final concentration of 250 $ng/cm^2$ when applied on top of the insect diet preparations.
Grading Scale represents % growth inhibition of surviving insects fed the treatment plus XptA2 Toxin Protein relative to surviving insects fed the treatment in the absence of XptA2 Toxin Protein (0 = 0-10%; + = 11-20%; ++ = 21-40%; +++ = 41-60% = ++++, 61-80%; +++++ >80%).

EXAMPLE 8

Summary of Mix & Match Assays and Sequence Relatedness

The following Tables summarize and compare proteins used in the assays described above. Tables 43-45 compare A, B, and C class proteins. Tables 46-48 compare A, B, and C class genes (bacterial). Any of the numbers in these tables can be used as upper and/or lower limits for defining proteins and polynucleotides for use according to the subject invention. Table 49 compares the sizes of various TC proteins. Again, any of the numbers in this table can be used to define the upper and/or lower size limits of proteins (and polynucleotides) for use according to the subject invention.

These tables help to show that even highly divergent proteins (in the ~40-75% identity range) can surprisingly be used and substituted for each other according to the subject invention. $TcdA2_{W-14}$ is reproduced here as SEQ ID NO:62, $TcdA4_{W-14}$ as SEQ ID NO:63, and $TccC_{W-14}$ as SEQ ID NO:64.

TABLE 43

| | TcdA | | TcdA2 | | TcdA4 | | TcbA | |
|---|---|---|---|---|---|---|---|---|
| | % Similarity | % Identity | % Similarity | % Identity | % Similarity | % Identity | % Similarity | % Identity |
| *Photorhabdus luminescens* A Class | | | | | | | | |
| TcdA | 100.0 | 100.0 | 61.3 | 55.0 | 74.3 | 68.0 | 61.4 | 50.1 |
| TcdA2 | | | 100.0 | 100.0 | 63.7 | 55.9 | 52.7 | 42.4 |
| TcdA4 | | | | | 100.0 | 100.0 | 59.0 | 49.4 |
| TcbA | | | | | | | 100.0 | 100.0 |

TABLE 43-continued

| | | | | | | | | |
|---|---|---|---|---|---|---|---|---|
| *Xenorhabdus nematophilus* xwi A Class | | | | | | | | |
| XptA1$_{xwi}$ | | | | | | | | |
| XptA2$_{xwi}$ | | | | | | | | |
| *Serratia entomophila* A Class | | | | | | | | |
| SepA | | | | | | | | |
| Tested in Mix & Match Assays? | yes | | no | | no | | yes | |
| Does it work? | yes | | NA | | NA | | yes | |

| | XptA1$_{xwi}$ | | XptA2$_{xwi}$ | | SepA | |
|---|---|---|---|---|---|---|
| | % Similarity | % Identity | % Similarity | % Identity | % Similarity | % Identity |
| *Photorhabdus luminescens* A Class | | | | | | |
| TcdA | 57.3 | 46.3 | 53.8 | 40.6 | 52.6 | 40.7 |
| TcdA2 | 52.3 | 41.3 | 48.3 | 36.8 | 45.5 | 34.7 |
| TcdA4 | 54.8 | 44.4 | 51.7 | 38.7 | 50.6 | 38.7 |
| TcbA | 54.7 | 43.7 | 54.0 | 40.8 | 52.8 | 40.2 |
| *Xenorhabdus nematophilus* xwi A Class | | | | | | |
| XptA1$_{xwi}$ | 100.0 | 100.0 | 57.6 | 44.2 | 57.7 | 46.6 |
| XptA2$_{xwi}$ | | | 100.0 | 100.0 | 50.7 | 38.2 |
| *Serratia entomophila* A Class | | | | | | |
| SepA | | | | | 100.0 | 100.0 |
| Tested in Mix & Match Assays? | no | | yes | | no | |
| Does it work? | NA | | yes | | NA | |

NOTE:
tcdA3 is a pseudo gene (does not encode a full-length protein) so is left out of this analysis

TABLE 44

| | TcdB1 | | TcdB2 | | TcaC | | XptC1$_{xwi}$ | |
|---|---|---|---|---|---|---|---|---|
| | % Similarity | % Identity | % Similarity | % Identity | % Similarity | % Identity | % Similarity | % Identity |
| *Photorhabdus luminescens* B Class | | | | | | | | |
| TcdB1 | 100.0 | 100.0 | 79.9 | 75.6 | 69.5 | 58.2 | 61.3 | 50.2 |
| TcdB2 | | | 100.0 | 100.0 | 68.1 | 57.2 | 60.7 | 49.8 |
| TcaC | | | | | 100.0 | 100.0 | 63.9 | 51.6 |
| *Xenorhabdus nematophilus* xwi B Class | | | | | | | | |
| XptC1$_{xwi}$ | | | | | | | 100.0 | 100.0 |
| *Xenorhabdus bovienii* B Class | | | | | | | | |
| XptB1$_{xb}$ | | | | | | | | |
| *Paenibacillus* spp str 1529 B Class | | | | | | | | |
| PptB1 (Orf5) | | | | | | | | |
| *Serratia entomophila* B Class | | | | | | | | |
| SepB | | | | | | | | |
| Tested in Mix & Match assays? | yes | | yes | | yes | | yes | |
| Does it work? | yes | | yes | | yes | | yes | |

| | XptB1$_{xb}$ | | PptB1 (Orf5) | | SepB | |
|---|---|---|---|---|---|---|
| | % Similarity | % Identity | % Similarity | % Identity | % Similarity | % Identity |
| *Photorhabdus luminescens* B Class | | | | | | |
| TcdB1 | 65.6 | 54.6 | 55.3 | 42.3 | 63.7 | 52.6 |
| TcdB2 | 65.6 | 53.3 | 54.2 | 42.0 | 61.7 | 51.4 |
| TcaC | 70.6 | 59.8 | 56.9 | 42.6 | 61.4 | 50.1 |

TABLE 44-continued

| | | | | | | |
|---|---|---|---|---|---|---|
| *Xenorhabdus nematophilus* xwi B Class | | | | | | |
| XptC1$_{xwi}$ | 65.2 | 53.2 | 53.9 | 40.7 | 58.1 | 47.8 |
| *Xenorhabdus bovienii* B Class | | | | | | |
| XptB1$_{xb}$ | 100.0 | 100.0 | 54.2 | 40.6 | 57.4 | 46.0 |
| *Paenibacillus* spp str 1529 B Class | | | | | | |
| PptB1 (Orf5) | | | 100.0 | 100.0 | 51.5 | 38.7 |
| *Serratia entomophila* B Class | | | | | | |
| SepB | | | | | 100.0 | 100.0 |
| Tested in Mix & Match assays? | yes | | yes | | no | |
| Does it work? | yes | | yes | | NA | |

TABLE 45

| | TccC1 | | TccC2 | | TccC3 | | TccC4 | | TccC5 | |
|---|---|---|---|---|---|---|---|---|---|---|
| | % Sim. | % Id | % Sim. | % Id | % Sim. | % Id | % Sim. | % Id | % Sim. | % Id |
| *Photorhabdus luminescens* C Class | | | | | | | | | | |
| TccC1 | 100.0 | 100.0 | 57.8 | 48.1 | 62.0 | 52.8 | 62.5 | 52.9 | 59.7 | 51.3 |
| TccC2 | | | 100.0 | 100.0 | 60.3 | 52.5 | 62.2 | 53.7 | 67.9 | 61.4 |
| TccC3 | | | | | 100.0 | 100.0 | 65.4 | 59.5 | 66.0 | 58.4 |
| TccC4 | | | | | | | 100.0 | 100.0 | 64.8 | 57.2 |
| TccC5 | | | | | | | | | 100.0 | 100.0 |
| *Xenorhabdus nematophilus* xwi C Class | | | | | | | | | | |
| XptB1$_{xwi}$ | | | | | | | | | | |
| *Xenorhabdus bovienii* C Class | | | | | | | | | | |
| XptC1$_{xb}$ | | | | | | | | | | |
| *Paenibacillus* spp str 1529 C Class | | | | | | | | | | |
| PptC1 (Orf6 long) | | | | | | | | | | |
| PptC1 (Orf6 short) | | | | | | | | | | |
| *Serratia entomophila* C Class | | | | | | | | | | |
| SepC | | | | | | | | | | |
| Tested in Mix & Match assays? | yes | | yes | | yes | | no | | yes | |
| Does it work? | yes | | no | | yes | | NA | | yes | |

| | XptB1$_{xwi}$ | | XptC1$_{xb}$ | | PptC1 (Orf6 long) | | PptC1 (Orf6 short) | | SepC | |
|---|---|---|---|---|---|---|---|---|---|---|
| | % Sim. | % Id | % Sim. | % Id | % Sim. | % Id | % Sim. | % Id | % Sim. | % Id |
| *Photorhabdus luminescens* C Class | | | | | | | | | | |
| TccC1 | 59.0 | 45.5 | 55.8 | 46.5 | 45.0 | 35.0 | 45.9 | 35.7 | 56.0 | 44.1 |
| TccC2 | 54.0 | 44.1 | 56.4 | 47.2 | 46.5 | 35.3 | 45.7 | 36.1 | 55.8 | 46.1 |
| TccC3 | 54.8 | 46.0 | 56.5 | 48.1 | 45.1 | 35.4 | 46.1 | 36.1 | 56.4 | 46.6 |
| TccC4 | 53.6 | 44.8 | 58.8 | 49.1 | 46.3 | 36.9 | 47.3 | 37.7 | 56.6 | 45.3 |
| TccC5 | 55.1 | 45.6 | 57.6 | 48.7 | 45.3 | 35.2 | 46.3 | 36.0 | 54.8 | 44.9 |
| *Xenorhabdus nematophilus* xwi C Class | | | | | | | | | | |
| XptB1$_{xwi}$ | 100.0 | 100.0 | 52.6 | 41.4 | 43.3 | 32.7 | 44.3 | 33.5 | 55.2 | 46.3 |
| *Xenorhabdus bovienii* C Class | | | | | | | | | | |
| XptC1$_{xb}$ | | | 100.0 | 100.0 | 46.4 | 35.4 | 47.4 | 36.2 | 53.0 | 43.5 |
| *Paenibacillus* spp str 1529 C Class | | | | | | | | | | |
| PptC1 (Orf6 long) | | | | | 100.0 | 100.0 | 97.6 | 97.6 | 45.1 | 34.9 |
| PptC1 (Orf6 short) | | | | | | | 100.0 | 100.0 | 46.2 | 35.7 |
| *Serratia entomophila* C Class | | | | | | | | | | |
| SepC | | | | | | | | | 100.0 | 100.0 |
| Tested in Mix & | yes | | yes | | yes | | current | | no | |

TABLE 45-continued

| | | | | | |
|---|---|---|---|---|---|
| Match assays? | | | | testing | |
| Does it work? | yes | yes | yes | ? | NA |

TABLE 46

| | tcdA % Identity | tcdA2 % Identity | tcdA4 % Identity | tcbA % Identity | $xptA1_{xwi}$ % Identity | $xptA2_{xwi}$ % Identity | sepA % Identity |
|---|---|---|---|---|---|---|---|
| | | | *Photorhabdus luminescens* A Class | | | | |
| tcdA | 100.0 | 65.3 | 70.6 | 58.2 | 56.8 | 54.4 | 53.1 |
| tcdA2 | | 100.0 | 64.5 | 56.2 | 55.9 | 53.3 | 51.9 |
| tcdA4 | | | 100.0 | 57.8 | 55.6 | 52.5 | 51.7 |
| tcbA | | | | 100.0 | 56.3 | 54.0 | 52.7 |
| | | | *Xenorhabdus nematophilus* xwi A Class | | | | |
| $xptA1_{xwi}$ | | | | | 100.0 | 55.8 | 55.4 |
| $xptA2_{xwi}$ | | | | | | 100.0 | 53.8 |
| | | | *Serratia entomophila* A Class | | | | |
| sepA | | | | | | | 100.0 |
| Tested in Mix & Match Assays? | yes | no | no | yes | no | yes | no |
| Does it work? | yes | NA | NA | yes | NA | yes | NA |

NOTE:
tcdA3 is a pseudo gene (does not encode a full-length protein) so is left out of this analysis

TABLE 47

| | tcdB1 % Identity | tcdB2 % Identity | tcaC % Identity | $xptC1_{xwi}$ % Identity | $xptB1_{xb}$ % Identity | pptB1 (Orf5) % Identity | sepB % Identity |
|---|---|---|---|---|---|---|---|
| | | | *Photorhabdus luminescens* B Class | | | | |
| tcdB1 | 100.0 | 74.1 | 62.3 | 44.7 | 59.7 | 52.3 | 57.6 |
| tcdB2 | | 100.0 | 61.5 | 44.7 | 59.6 | 52.6 | 57.1 |
| TcaC | | | 100.0 | 46.0 | 62.0 | 52.5 | 55.3 |
| | | | *Xenorhabdus nematophilus* xwi B Class | | | | |
| $xptC1_{xwi}$ | | | | 100.0 | 44.9 | 44.9 | 44.5 |
| | | | *Xenorhabdus bovienii* B Class | | | | |
| $xptB1_{xb}$ | | | | | 100.0 | 52.3 | 54.7 |
| | | | *Paenibacillus* spp str 1529 B Class | | | | |
| pptB1 (Orf5) | | | | | | 100.0 | 52.5 |
| | | | *Serratia entomophila* B Class | | | | |
| sepB | | | | | | | 100.0 |
| Tested in Mix & Match assays? | yes | yes | yes | yes | yes | yes | no |
| Does it work? | yes | yes | yes | yes | yes | yes | NA |

TABLE 48

| | TccC1 % Identity | TccC2 % Identity | TccC3 % Identity | TccC4 % Identity | TccC5 % Identity | $XptB1_{xwi}$ % Identity | $XptC1_{xb}$ % Identity | PptC1 (Orf6 long) % Identity | PptC1 (Orf6 short) % Identity | SepC % Identity |
|---|---|---|---|---|---|---|---|---|---|---|
| | | | | | *Photorhabdus luminescens* C Class | | | | | |
| TccC1 | 100.0 | 55.7 | 58.8 | 60.0 | 59.4 | 45.0 | 55.7 | 47.5 | 48.4 | 54.3 |
| TccC2 | | 100.0 | 62.6 | 62.2 | 69.9 | 43.5 | 58.1 | 51.6 | 52.4 | 55.4 |
| TccC3 | | | 100.0 | 65.7 | 66.4 | 44.9 | 58.4 | 51.5 | 52.4 | 56.8 |
| TccC4 | | | | 100.0 | 65.8 | 43.0 | 59.4 | 52.2 | 53.2 | 54.9 |
| TccC5 | | | | | 100.0 | 43.0 | 58.5 | 50.8 | 51.7 | 56.2 |
| | | | | | *Xenorhabdus nematophilus* xwi C Class | | | | | |
| $XptB1_{xwi}$ | | | | | | 100.0 | 44.6 | 43.6 | 43.2 | 44.0 |
| | | | | | *Xenorhabdus bovienii* C Class | | | | | |
| $XptC1_{xb}$ | | | | | | | 100.0 | 49.7 | 50.6 | 54.5 |

TABLE 48-continued

| | TccC1 % Identity | TccC2 % Identity | TccC3 % Identity | TccC4 % Identity | TccC5 % Identity | $XptB1_{xwi}$ % Identity | $XptC1_{xb}$ % Identity | PptC1 (Orf6 long) % Identity | PptC1 (Orf6 short) % Identity | SepC % Identity |
|---|---|---|---|---|---|---|---|---|---|---|
| *Paenibacillus* spp str 1529 C Class | | | | | | | | | | |
| PptC1 (Orf6 long) | | | | | | | | 100.0 | 97.6 | 50.6 |
| PptC1 (Orf6 short) | | | | | | | | | 100.0 | 51.8 |
| *Serratia entomophila* C Class | | | | | | | | | | |
| SepC | | | | | | | | | | 100.0 |
| Tested in Mix & Match assays? | yes | yes | yes | no | yes | yes | yes | yes | in progress | no |
| Does it work? | yes | no | yes | NA | yes | yes | yes | yes | ? | NA |

TABLE 49

| | DNA Bases | Protein Amino Acids | Protein Daltons | Functional? |
|---|---|---|---|---|
| *Photorhabdus luminescens* A Class | | | | |
| tcdA | 7548 | 2516 | 282,932 | yes |
| tcdA2 | 7497 | 2499 | 283,725 | ? |
| tcdA4 | 7143 | 2381 | 270,397 | ? |
| tcbA | 7512 | 2504 | 280,632 | yes |
| *Xenorhabdus nematophilus* xwi A Class | | | | |
| $xptA1_{xwi}$ | 7569 | 2523 | 286,799 | ? |
| $xptA2_{xwi}$ | 7614 | 2538 | 284,108 | yes |
| *Serratia entomophila* A Class | | | | |
| SepA | 7128 | 2376 | 262,631 | ? |
| Range | 7128-7614 | 2376-2538 | 262,631-286,799 | |
| *Photorhabdus luminescens* B Class | | | | |
| tcdB1 | 4428 | 1476 | 165,127 | yes |
| tcdB2 | 4422 | 1474 | 166,326 | yes |
| TcaC | 4455 | 1485 | 166,153 | yes |
| *Xenorhabdus nematophilus* xwi B Class | | | | |
| $xptC1_{xwi}$ | 4479 | 1493 | 168,076 | yes |
| *Xenorhabdus bovienii* B Class | | | | |
| $xptB1_{xb}$ | 4518 | 1506 | 168,635 | yes |
| *Paenibacillus* spp str 1529 B Class | | | | |
| pptB1 (Orf5) | 4332 | 1444 | 161,708 | yes |
| *Serratia entomophila* B Class | | | | |
| SepB | 4284 | 1428 | 156,539 | ? |
| Range | 4284-4518 | 1428-1506 | 156,539-168,635 | |
| *Photorhabdus luminescens* C Class | | | | |
| TccC1 | 3129 | 1043 | 111,686 | yes |
| TccC2 | 2745 | 915 | 103,398 | no |
| TccC3 | 2880 | 960 | 107,054 | yes |
| TccC4 | 2847 | 949 | 106,563 | ? |
| TccC5 | 2814 | 938 | 105,106 | yes |
| *Xenorhabdus nematophilus* xwi C Class | | | | |
| $XptB1_{xwi}$ | 3048 | 1016 | 111,037 | yes |
| *Xenorhabdus bovienii* C Class | | | | |
| $XptC1_{xb}$ | 2886 | 962 | 107,960 | yes |
| *Paenibacillus* spp str 1529 C Class | | | | |
| PptC1 (Orf6 long) | 2859 | 953 | 109,130 | yes |
| PptC1 (Orf6 short) | 2790 | 930 | 106,244 | ? |
| *Serratia entomophila* C Class | | | | |
| SepC | 2919 | 973 | 107,020 | ? |
| Range | 2745-3129 | 915-1043 | 103,398-111,686 | |

The invention claimed is:

1. A method of inhibiting an insect wherein said method comprises contacting said insect with effective amounts of a Protein A, a Protein B, and a Protein C, wherein said Protein A is an approximately 230-290 kDa complex-forming protein comprising SEQ ID NO:65 (TcdA);

said Protein B is an approximately 130-180 kDa complex-forming protein comprising SEQ ID NO:18 (XptC1xwi), said Protein C is an approximately 90-120 kDa complex-forming protein comprising SEQ ID NO:16 (XptB1xwi);

said Protein A has activity against an insect and said activity is potentiated by said Protein B and said Protein C; and said Protein B and said Protein C potentiate the activity of said Protein A.

2. A method of inhibiting an insect wherein said method comprises contacting said insect with an A component and a B component, wherein said components form an insecticidal toxin complex, wherein said A component is a 230-290 kDa complex-forming protein comprising SEQ ID NO:65 (TcdA);

said B component is a 130-180 kDa complex-forming protein comprising SEQ ID NO:18 (XptC1xwi);

wherein said A component has activity against an insect, and wherein said B component is a potentiator of said A component.

3. A method of inhibiting an insect wherein said method comprises contacting said insect with an A component and a C component, wherein said components form an insecticidal toxin complex, wherein said A component is a 230-290 kDa complex forming protein comprising SEQ ID NO:65 (TcdA);

said Protein C is an approximately 90-120 kDa complex-forming protein comprising SEQ ID NO:16 (XptB1xwi);

wherein said A component has activity against an insect, and wherein said C component is a potentiator of said A component.

* * * * *

SEQUENCE LISTING

<160> NUMBER OF SEQ ID NOS: 69

<210> SEQ ID NO 1
<211> LENGTH: 20
<212> TYPE: PRT
<213> ORGANISM: Xenorhabdus nematophilus

<400> SEQUENCE: 1

Met Tyr Ser Thr Ala Val Leu Leu Asn Lys Ile Ser Pro Thr Arg Asp
1               5                   10                  15

Gly Gln Thr Met
            20

<210> SEQ ID NO 2
<211> LENGTH: 5
<212> TYPE: PRT
<213> ORGANISM: Xenorhabdus nematophilus

<400> SEQUENCE: 2

Met Trp Tyr Val Arg
1               5

<210> SEQ ID NO 3
<211> LENGTH: 6
<212> TYPE: PRT
<213> ORGANISM: Xenorhabdus nematophilus

<400> SEQUENCE: 3

Leu Thr Gln Phe Leu Arg
1               5

<210> SEQ ID NO 4
<211> LENGTH: 10
<212> TYPE: PRT
<213> ORGANISM: Xenorhabdus nematophilus

<400> SEQUENCE: 4

Ala Asn Pro Gln Leu Ser Gly Ala Ile Arg
1               5                   10

<210> SEQ ID NO 5
<211> LENGTH: 8
<212> TYPE: PRT
<213> ORGANISM: Xenorhabdus nematophilus

<400> SEQUENCE: 5

Leu Leu Asp Gln Leu Ile Leu Arg
1               5

<210> SEQ ID NO 6
<211> LENGTH: 39005
<212> TYPE: DNA
<213> ORGANISM: Xenorhabdus nematophilus

<400> SEQUENCE: 6
gatcaggtat tcaatcaacc caaactgttt gatgaacctt tctttgttga taatcgtact 60
tttgattaca acgccattcg tggtaatgat gcacgaacaa ttaagcaact gtgcgccgga 120
ttgaaaatca ccgtagccac cttccaattg ttagctgagc aggtaaacac cgcctttcat 180
ctgccatccg gcaaattaac ctgttcactg cctgttattt cagcgcttta tcgtctggtg 240
actgttcctc ggttatttaa tttaaccgct gaacagggca tgatgctgat taacgcatta 300

-continued

```
aatgccagcg agaaattctc acctcatatt ctggctggtg agcctcgatt aagcctgtta    360
acaacagagg gttcagatac cacagaggtc gatttattgg atgttattct gatgttggaa    420
gaagttgctg tctggctgca acagagcaaa ctgaaaccgg aagaattctg cctgatgctg    480
caaagtgtta tgttgccggt ggttgccacg gacagcagtg tgacattctt cgacaacctg    540
ctgcaaggca ttcccaaaac cttactcaca gaagataact tcaacgcagg ggatatcccc    600
agactccctg aaggagaaac ctggtttgac aaactttcga tgctgataac cagcgatgga    660
ctcgtcaacg tttaccctct cagttggggc cagagtgatg aagattatct gaaatcagta    720
ttgacacctg tcgtcgaaaa aatcattagc gatccaaaca gtgtgattat cactgtttcc    780
gcattaacac aggtcattac tcaggcgaaa actgcgcagg aagatctggt ttccgccagc    840
gtgacacggg aatacggtac tggacgtgat atcgttcctt ggttattacg ctggattggc    900
agcagtgttc ccgatttcct tggcaaaatt tatatacaag gcgcaaccag aggcggacac    960
ttgcgcactc cgccggatat cagcgctgaa ttactgcata tcacctatca tctggcgatg   1020
aataacatgc tgattaagca gttacgactc aaagctcaaa tcatttcatt acgtatcatc   1080
atgcctgaat ggctcggatt accaacgata gatggcagtc cgctatccgt gcatgaaatt   1140
tgggcactga gccggttccg taactgggcg accagctcat tgttcagtga agacgagtta   1200
atcgagtatt ttgcttttgc caatcagccg gagcaggacg ttcgtaacga tgaagatttt   1260
aatcgggact gtgctgaaaa gcttgccgac atactggaat gggatgccga tgaaattgag   1320
ctggcaaccc gacattttga tcctgcccca gcacgtgcca gaaatatggg acaaattgac   1380
tggctgcgtc gtgtcatggc gttgtcgcgt cagactggcc tgtcagtgac accgttaatg   1440
acagccgcaa cgttaccgcc tttcccgccc tatgaccaga taacccatgt cggtgaagcg   1500
gtgattgcgg caacccagta cccatcagag gagtaaggaa cgatgagttc agttacccaa   1560
cctattgaag agcgtttact ggaatcacag cgcgacgcac tgctggattt ctatctcgga   1620
caggtcgttg cctattcacc tgacatgaca agtcagcgcg acaaaattaa ggatattgac   1680
gatgcctgcg actacctcct gctggatctg ctgacttccg ccaaagtcaa agcgacacga   1740
ctttcacttg cgaccaattc attgcagcaa tttgtgaacc gcgtgtcact gaatattgaa   1800
cccggtttgt ttatgaccgc ggaagagagc gaaaattggc aggaatttgc gaatcgttat   1860
aattactggt ctgcggatcg cttattacgg acttatccgg aaagctatct ggaacccctg   1920
ttacgcctga ataaaacaga attcttcttc caactggaaa gtgcccttaa tcagggaaaa   1980
attaccgaag attccgtaca acaagcggtg ctcggttatc tgaataattt tgaagatgtc   2040
agtaacctga aagttatcgc aggttatgaa gatggtgtta acatcaaacg cgataagttc   2100
ttctttgtcg gacgtacccg tacacagcca taccaatatt actggcgttc actgaatctt   2160
tcgatacgcc atcctgatac cgatgcgtta tctcccaatg cctggagcga gtggaaacct   2220
attgacctgc cattgggcag cgtagacccc aatttgatac gccccatttt cctgaataat   2280
cgcctgtata ttgcctggac ggaagttgaa gaacagtctg aaactaaaga tacaactgcg   2340
ttatcactgc ataaccaaaa cgttgagcct agtgcgggtg attgggttcc tcccacaccg   2400
ttcctgaccc ggatcaaaat cgcttatgcc aaatatgatg gcagctggag tacacccacc   2460
attctgcgcg aagacaatct gcaataccgg atggcccaga tggttgctgt gatggatata   2520
cagcaagacc cgcataaccc gtttctggct ctggttccgt ttgtccgtct tcaggggaca   2580
gataagaaag gtaaggatta tgattatgac gaagccttcg gttatgtctg cgatacactg   2640
ctggtagaaa ttactgattt gccggatgac gaatatgctg atggacgaaa aggaaaatat   2700
```

-continued gtcggcaacc tggtctggta ttactcacgt gaacacaagg atgcagaagg caatcctatc 2760
gattaccgta ctatggtgct ctatccggca acccgggaag aacgctttcc tattgccgga 2820
gaagccaaac cggaaggaag ccctgatttt ggcaaagaca gtatcaaact gattgtcaat 2880
tttgttcatg gcactgatga cacactggag attgtcgctc aatctgactt taagtttggt 2940
gcgatagaag atcatcaata ttacaacggt tctttccggc tgatgcacga taatactgtc 3000
ttggatgaac aaccactggt actgaacgaa aaagttcctg atttaaccta tccatcaatc 3060
aagctggggt cggataatcg aatcaccctg aaagccgaac ttctctttaa gcccaaaggt 3120
ggtgttggca atgaaagtgc cagctgtact caagagttca gaatcggtat gcacattcgc 3180
gaactgatta aactcaatga acaggatcag gtgcaattcc tttccttccc cgcagatgaa 3240
actggtaacg cgccacaaaa cattcgcctt aatacactgt ttgcaaaaaa actgatcgcc 3300
attgccagtc agggtatccc gcaggtactg agctggaata cacagcttat tactgaacaa 3360
cccatacccg gttcattccc tacgccgatt gatttaaatg gcgcaaatgg gatctatttc 3420
tgggaactgt tttccatat gccatttctg gtcgcgtggc gactgaatat cgaacaacga 3480
ttaaaagagg ccaccgaatg gctgcactat atttttaatc cgctggaaga tgaacttgtt 3540
caggccagca accaaggtaa accgcgttac tggaattcac ggccaattat tgatcctcca 3600
cccaccgtgt accggatgtt aattgaacca accgatccgg atgccattgc agccagtgaa 3660
cccattcact accggaaagc aatattccgt ttctatgtca agaatctgtt agatcaggga 3720
gacatggaat accgtaagct gacatccagt gcacgtactg tcgccaagca gatctatgac 3780
tccgtcaata tgttactggg taccagccct gatattctgc tcgcggcaaa ctggcaaccc 3840
cgtacgctgc aagatgtggc tctgtatgaa aacagtgaag cacgggcaca ggagttaatg 3900
cttactgtca gcagcgtgcc acttctgcct gtgacatatg atacatccgt ctctgccgca 3960
ccgtctgatt tatttgtcaa acctgttgat acggaatatc tcaaactgtg gcaaatgttg 4020
gatcagcgtc tatataactt acgtcataac ctgaccttgg atggtaaaga gtttccggcc 4080
ggattatacg atgaacccat cagcccgcaa gatctgctca ggcagcgtta ccagcgtgtt 4140
gtggctaatc gtatggcggg catgaaacgc cgggcaatcc cgaattatcg tttcaccccg 4200
atcatgagcc gggcaaaaga ggccgcagaa acgctgattc agtacggcag cacgttactg 4260
agtttgctgg agaaaaaaga caataccgat tttgaacact tccgtatgca gcagcaactg 4320
gggctgtaca gctttacccg caatctgcaa cagcaagcga ttgacatgca acaggcttca 4380
ttggatgcac tgaccatcag ccgacgggcc gctcaggagc gccagcaaca ctataaatcg 4440
ctctatgatg aaaacatctc catcaccgag caggaagtta tcgcattaca atcaagagcg 4500
gctgaaggtg tgatcgctgc ccagtcagcc gccactgcgg ccgctgtggc ggatatggtt 4560
cccaatattt tcggtctggc cgtcgggggg atggtctttg gcggtatgct tcgggcaatc 4620
ggtgaaggaa tacgcattga cgttgaaagt aaaaatgcca aagccaccag cctgagcgtg 4680
tcagaaaatt accgtcgccg tcagcaagaa tgggagctgc aatacaaaca ggcggatatc 4740
aacattgagg agatcgacgc acagattggt atccagcaac gccaactgaa tatcagcaca 4800
acccaactgg cacaattgga agcccagcat gagcaggatc aagtcctgct ggagtactat 4860
tcaaaccgtt ttaccaatga tgcgttatac atgtggatga tcagccaaat ctccgggctt 4920
tacctgcaag cctatgatgc ggttaattcc ctctgtttac tggccgaagc ctcctggcag 4980
tacgaaacag gtcagtatga tatgaatttc gtccaaagtg gtctctggaa tgatctttat 5040
caggggctgc tggtcggaga acatctgaaa ttagccttac aacggatgga tcaggcgtat 5100

-continued ttgcaacata acaccagacg tctggagatc ataaaaacca tatcggtaaa atcattactg 5160
acatcatcac agtgggaaat tggcaagagt acgggttcat tcactttctt actgagcgcc 5220
gaaatgttct tgcgcgatta tccgacccac gctgatcggc gtataaaaac cgtagcgctg 5280
tcattgcccg cattgctggg gccttatgaa gatgtacggg cttcactggt acaactcagc 5340
aatacgcttt acagtactgc tgacttaaaa actatcgatt atttgcttaa ccccttggaa 5400
tacaccaaac ccgaaaacgt tttgctgaac gtacaggcta atcaaggtgt ggtgatttca 5460
acggccatgg aagacagcgg catgttcagg ctcaattttg atgatgaact tttcctgcct 5520
tttgaaggga caggcgccat ttcacagtgg aagttggaat tcggttccga tcaggatcag 5580
ctgctggagt cgctgagcga tattatcctc catctgcgtt ataccgcgcg tgatgtgagt 5640
ggcggaagta atgagttcag ccagcaggtt cgtagccgtc tgaataaaca tcaattaaaa 5700
caagacaatt ctaactgata tcaggagccg gccccggaat ataacggggc cggaagtgaa 5760
attatgtctc aaaatgttta tcgataccct tcaattaaag cgatgtctga cgccagcagc 5820
gaagtaggcg catctctggt tgcctggcag aatcaatctg gtggtcaaac ctggtatgtc 5880
atttatgata gcgcggtttt taaaaacatc ggctgggttg aacgctggca tattcccgac 5940
cgcaatattt cacctgattt accggtttat gagaatgcct ggcaatatgt ccgtgaggcg 6000
acaccggaag aaattgccga tcacggtaac cccaatacgc ctgatgtacc gccgggagaa 6060
aaaaccgagg tattgcaata tgatgcactc acagaagaaa cctatcagaa ggtgggatat 6120
aaacctgacg gcagcggaac tcctttgagt tattcttcag cacgtgttgc caagtccctg 6180
tacaacgaat atgaagttga tccggaaaat acagaaccgc tgcctaaagt ctctgcctat 6240
attactgact ggtgccagta tgatgcgcgt ttgtcgccag aaacccagga taacactgcg 6300
ctgaccagcg acgatgcccc cggccgtggt tttgatctgg aaaaaatccc gcctaccgcc 6360
tacgaccgcc tgattttcag ttttatggcc gtcaacggtg ataaaggcaa gttatccgaa 6420
cggattaatg aggttgttga cgggtggaac cggcaagcag aagccagcag tggccagatt 6480
gcccctatta cattaggcca tattgtaccc gttgatcctt atggtgattt aggcaccaca 6540
cgcaatgtcg gtctggacgc ggatcagcgc cgtgatgcca gcccgaagaa tttcttgcaa 6600
tattacaatc aggatgcagc ctccggttta ctgggggggat tgcgtaatct gaaagcgcga 6660
gcaaaacagg cagggcacaa gctggaactc gcattcagta tcggcggctg gagtatgtca 6720
gggtatttct ctgtgatggc caaagatcct gagcaacgtg ctacatttgt gagtagcatc 6780
gtcgacttct tccggcgttt tcccatgttt actgcggtgg atatcgactg ggaataccccc 6840 ggcgccacag gtgaagaagg taatgaattc gacccggaac atgatggccc aaactatgtt 6900
ttgttagtga aagagctgcg tgaagcactg aacatcgcct ttggaacccg ggcccgtaaa 6960
gaaatcacga tagcctgtag cgccgtcgtt gccaaaatgg agaagtccag cttcaaagaa 7020
atcgcacctt atttagacaa tatctttgtg atgacctacg acttctttgg taccggttgg 7080
gcagaataca tcggtcacca tactaacctg tatcccccca gatatgaata tgacggcgat 7140
aaccctcctc cgcccaatcc tgatcgggac atggattact cggctgatga ggcgatccgc 7200
tttttactgt cacaaggtgt acaaccggag aaaattcacc tcggatttgc taactatgga 7260
cgttcatgtc tgggtgctga tctgacaact cgccgctata acagaacagg agagccactg 7320
ggcacgatgg aaaaaggtgc tccggaattc ttctgtctgc tgaataacca atacgatgcg 7380
gaatatgaaa ttgcacgcgg gaaaaatcag tttgaactgg tgacagacac ggaaaccgac 7440
gctgacgcac tctttaatgc tgacggtggt cactggattt cactggatac gccccgcact 7500

-continued

```
gtgctgcata agggaattta tgcaaccaaa atgaaattgg gcgggatctt ctcttggtca   7560
ggcgatcagg atgatggcct gttggcaaat gctgctcacg aaggtttggg ttacttacct   7620
gtacgcggaa aagagaagat tgatatggga ccgttatata acaaaggacg tctcattcag   7680
cttcctaaag taacccgtcg taaatcgtag taaataaaat tttccggtgg cctcacaggg   7740
gtcaccatat cctgctgtga aaaagcgtat ccatttaatg ctttaacgct tcaattttct   7800
cccggctcag gccggtactg gtgacaatga tgtccagact gacaccatgc cgtaataatg   7860
cgcgcgccgt ttccagcttg ccttcttccc gtccttcagc tctgccttct gttctgcctt   7920
cagccctgcc ttctgtccgg ccttgctcac gcccttttg ttcaagctgt tctgcaatag    7980
tcatcaacat ggtttcatgc tccggagatt gttcagtcag ttgatggaca aactgggcga   8040
gatccagcgt atgtccattc agtaaaatat agcttaacac aacatggcgc tgttcggcgc   8100
tattataacc ggcattcaac aacgccacta attggggaac ccactccagc atatcccggc   8160
aacggatatg tttttgtacc agctccatca aggcaatgct tttatgtgtc aggatctctt   8220
catcactgag cgcactgata tccaccaacg gcaggggctg attatacagg tgagccgcgt   8280
gttcagagag tgtaaaacaa tccagccatc gatttgagta agggtaaggc ctcacctcac   8340
catgataaaa cagcaggggg acgaccaaag ggagttcagt atgtcctttt ttcagatgcg   8400
cagccatggc tgacagcgaa taatacatca gccgccaggc cattaacgga tcaggcgtgg   8460
actggtgttc aatcaggcaa taaatgtaac cgtccccgtg ggttgtctcg acagaataca   8520
gcacatcact gtgcaactga cgtaattgcc tgtccacaaa gctgccgggt tccagtttta   8580
gtgtggttaa atcacacact gaccggatcg cttccggcag ataaagggat aaaaattccc   8640
gggcggtttc tggttgggtt aaaaaatgtt tgaataacgc gtcatggtga ggcttttttg   8700
ctttcctggc cacaatccgt ctctctgttt tatcggttat taatcgcctt tactgccaaa   8760
gctatcatct cgctgaaaaa tccacagcca atatacaaca tattatctgc tgacccaaca   8820
ctcgtccggc taatcaatcc agtatcaatg cgagttctac agtaaataca gctcttcatg   8880
gtcaggaaac cggacaaaag ttgattgaat ttcctaacca tgaattttct gttatgttaa   8940
ttattaccgt ctcacaataa taatcacatc caacagaatt tatttactat ataaataaac   9000
tatcaattat tataagaaaa ataatatgat tggcattaaa tataaaacca taaaaaagta   9060
gaattaattt ttaaaactta attgcagaaa ccagatgaaa tataaactta atttcttatc   9120
cataaataat aatgaatcaa tatttattca ataccatcag tggaaggttc ccgtttgttt   9180
taatttcaag cttataatcc cctttgcctt tagctgaatc accagacata atttgcttat   9240
tgctaaattg tttactactg tctgtaaaat aaacataact gccatgttga aacatgtagt   9300
tcacaatatc agcagcgtcc tttttactga aagtaacttt gatataatgg ccagagttaa   9360
tatctttctg actatcgcac caaggaatcc acataccacc ggtagatgaa tcatttcccg   9420
gagaaacaac cacatggtca ggtattatgg ggaataactc atttgctgac tcctgattaa   9480
ataaatccgc tttatattca caaccaaaat tgttatcaac attaataata ttacgaacat   9540
ctgacataat aatttccccc gaatatagtt taaaggtttt ttcaatttaa taacatatca   9600
aaggaactat aatactgtat atttacatcc gtcaacatta ttcacctaca gggtgacatt   9660
cctctattaa ataaaaaata agttttgatt tttaactttt gataacttat gcaccaaatc   9720
agtgaccact gccgttaact tagttttgat cctcgtcact acggttaaac ttccgactcc   9780
cagaaagcaa aaaaccccgc gagtgcgggg ctatattcaa agtgcttgag ttatttcact   9840
atgcggatag ttttgacatc aatttcaaca ctgttccagt ctttgtccac ttcaccttcg   9900
```

-continued

```
atacgaactt tgtcagttgg agtggccgtc agacccatcc agcgcttatc atcaatgtca   9960
acataaacag aaccactgtt atccctgaat tcatagagtt cgtgaccaac ctgtttaaca  10020
atgtttcctt ccagaacaac ccacgcatca tcacgaaaag attttgcttg agcaacgctg  10080
gtcaggttgg gagttggacc tttaaatcca ccctgagtat agtctgtgct gtctggggaa  10140
acgaagccac cctgctgtgc caaagcacca aaagaaaggg tactgagaat aagagtaatc  10200
agtgtttttt tcatagcttt ctctttgatt atgcgaagaa aaaccccgca tttgcgaggt  10260
tcgggtattc aataaattat gtgacattac tatcactctt gtcacgatat atcaactttt  10320
gtaattacgc aactttatta aggatttctt tttgcacaca tttatctgac tccaacgtag  10380
cccccctgaaa ccagcaagac atcctcaata aataatcttt catagataaa tattagttat  10440
tcatttttca aacagcacaa acacaattaa aaatatttaa acaattgttg agttgaattt  10500
tttcatgaaa gtttgttaaa atttaatttt taacatacgg tattcattat ttaaatccat  10560
gtattatagg gaagttcttt atttttttatt gaaagaatag agcgataaat cagtatcaat  10620
ttaattaacc ataatattcc tatcagatta taataatctc cacctaaaaa ccattaatca  10680
ttaaattgac aataacttaa ggatttatat gataaaagtt aatgaactgt tagataagat  10740
aaatagaaaa aggtctggtg atactttatt attgacaaac atttcgttta tgtctttcag  10800
cgaatttcgt cataggacaa gtggaactct gacgtggcga gaaacagact ttttatatca  10860
acaggctcat caggaatcaa aacagaataa acttgaagaa ctgcgcattt tgtcccgtgc  10920
taatccacaa ctggctaata ccactaacct taatattaca ccgtcaaccc taaacaatag  10980
ttacaacagt tggttttatg gccgtgccca ccgttttgta aaaccgggat caattgcttc  11040
catattttca ccagcggctt atttaacaga attatatcgg gaagcgaaag attttcatcc  11100
tgacaattct caatatcacc tgaataaacg acgccccgac attgcttcac tggcactgac  11160
acagaataat atggatgaag aaatttccac attatcctta tctaatgaat tactgctgca  11220
taatattcag acgttagaga aaactgacta taacggtgta atgaaaaatgt tgtccactta  11280
ccggcaaacc ggcatgacac cctatcatct gccgtatgag tcagcccgtc aggcaatttt  11340
attgcaagat aaaaacctca ccgcatttag ccgtaataca gacgtagcgg aattaatgga  11400
cccaacatcg ctactggcta ttaagactga tatatcgcct gaattgtatc aaatccttgt  11460
agaagaaatt acaccggaaa attcaacaga actgatgaag aaaaatttcg gtacagatga  11520
tgtactgatt tttaagagtt atgcttcttt ggctcgctac tacgatttgt cttatgatga  11580
actcagttta tttgtcaatc tctccttcgg taagaaaaat acaaatcaac agtataagaa  11640
tgagcaactg ataacattgg tcaatgacgg gaatgatacg gcaacggcaa gattgattaa  11700
gcgaacccgc aaagatttct acgattcaca tttaaactat gcagaactaa ttccaatcaa  11760
agaaaatgaa tacaaatata atttcagtgt aaaaaaaaca gaacctgacc acttggattt  11820
tcgtctccag aatggagata aagaatatat ataccaagat aaaaatttcg tccccattgc  11880
taatacccat tacagtattc ccattaaatt gacgacagag caaatcacca acggtataac  11940
actccgctta tggcgagtta aaccaaatcc gtcggatgct atcaatgcca atgcatactt  12000
taaaatgatg gagttccccg gtgatatatt cctgttaaag ctgaataaag cgattcgttt  12060
gtataaagcc acaggcatat ctccagaaga tatctggcaa gtaatagaaa gtatttatga  12120
tgacttaacc attgacagca atgtgttggg taagctgttt tatgttcaat attatatgca  12180
gcactataat attagcgtca gcgatgcgct ggtattgtgt cattcagata tcagccaata  12240
ttccactaaa caacaaccca gtcattttac aatactgttc aatacaccgc tattaaatgg  12300
```

-continued

```
ccaagagttt tctgctgata ataccaaact ggatttaacc cccggtgaat caaaaaacca  12360
tttttatttg ggaataatga aacgtgcttt cagagtgaat gatactgaac tgtatacatt  12420
atggaagctg gctaatggcg gaacaaatcc agaatttatg tgttccatcg agaacctgtc  12480
tctgctttat cgcgttcgtc tgctggcaga cattcatcat ctgacagtga atgaattatc  12540
catgttgttg tcggtttctc cctatgtgaa cacgaaaatt gcccttttt ctgatacagc  12600
attaacgcaa ttaatcagct ttctgttcca atgcacccag tggctgacaa cacagaaatg  12660
gtctgtcagt gatgtgtttc tgatgaccac ggataattac agcactgtcc ttacgccgga  12720
tattgaaaac cttatcacga cactaagtaa tggattatca acactttcac tcggtgatga  12780
cgaactgatc cgtgcagctg ccccgctgat tgctgccagc attcaaatgg attcagccaa  12840
gacagcagaa actattttgc tgtggattaa tcagataaaa ccacaaggac tgacattcga  12900
tgatttcatg attattgcgg ctaaccgtga tcgctcagag aatgaaacca gcaacatggt  12960
ggctttttgt caggtactgg ggcaactttc tctgattgtg cgcaatattg gactcagcga  13020
aaacgaactg accctgttgg tgacaaaacc ggagaaattc caatcagaaa ccacagcact  13080
gcaacatgat ctccccactt tgcaagcgct gacccgcttc catgctgtga tcatgcgttg  13140
tggaagctac gcgacagaaa tcttaacagc attggaacta ggagcgctga ctgccgaaca  13200
attggcggtg gcgttaaaat ttgatgctca ggttgtgaca caagcattgc aacagaccgg  13260
tttgggagtg aataccttta ccaactggag aactatagat gtcactctgc aatggctgga  13320
tgtcgctgct acattgggta ttaccccgga tggtgttgct gcactcataa aattaaaata  13380
tatcggtgaa ccagaaaccc cgatgccaac atttgatgat tggcaagccg ccagtacttt  13440
gttgcaggcg ggactgaaca gtcaacaatc cgaccagctt caggcatggc tggatgaagc  13500
cacgacgaca gcggccagtg cttactacat caaaaatagt gcacctcaac agattaagag  13560
ccgggatgag ttgtacagct atctgctgat tgataaccaa gtttctgccc aagtgaaaac  13620
cacccgtgtg gcagaagcca ttgccagcat tcagttatat gtcaaccggg cgttgaataa  13680
tgttgaagga aaagtatcaa agccagtgaa aacccgtcag ttcttctgcg actgggaaac  13740
ctacaatcga cggtatagca cctgggccgg cgtatctgaa ctggcctatt atccggaaaa  13800
ctatatcgac cccacgattc gtattggtca gacaggtatg atgaacaacc tgttacagca  13860
actttcccaa agtcagttaa atatcgatac cgttgaagat agctttaaaa attatctgac  13920
cgcatttgaa gatgtcgcta acttgcaggt gattagcgga tatcatgaca gtatcaatgt  13980
caatgaggga ctcacttatt taattggtta tagccagaca gaacccagaa tatattattg  14040
gcgcaatgtc gatcaccaaa agtgccagca cggtcaattt gctgccaatg cctggggaga  14100
atggaaaaaa attgaaatac ccatcaatgt atggcaggaa aatatcagac ctgttattta  14160
caagtctcgt ttgtatttac tgtggctgga acaaaaagag ctgaaaaatg aaagtgaaga  14220
tggcaagata gatatcactg attatatatt aaaactgtca catattcgtt atgatggcag  14280
ctggagctca ccgtttaatt ttaatgtgac tgataaaata gaaaacctga tcaataaaaa  14340
agccagcatt ggtatgtatt gttcttctga ttatgaaaaa gacgtcatta ttgtttattt  14400
ccatgagaaa aaagacaatt attcttttaa tagtcttcct gcaagagaag ggatgaccat  14460
taaccctgat atgacattat ccattctcac agaaaatgat ttagacgcca ttgttaagag  14520
cacattatca gaacttgata ccaggacaga atacaaagtc aacaatcaat ttgctacaga  14580
ttatttggcc gaatataagg aatctataac cacaaaaaat aaattagcca gttttaccgg  14640
aaatattttt gatctctcgt atatatcacc aggaaatggt catattaatt taacgttcaa  14700
```

-continued

```
tccttcaatg gaaattaatt tttcaaaagg caatatatat aatgatgagg ttaaatacct  14760
gttatcgatg gtagaagatg aaacggttat tttatttgat tatgatagac atgatgaaat  14820
gcttggaaaa gaagaagaag tttttcatta tggaactttg gattttatta tttccatcga  14880
tcttaaaaat gccgaatatt ttagagtgtt aatgcatcta agaaccaagg aaaaaattcc  14940
tagaaaatca gaaattggag ttggtataaa ttatgattat gaatcaaatg atgctgaatt  15000
caaacttgat actaacatag tattagattg gaaagataac acaggagtat ggcatactat  15060
atgtgaatca tttactaatg atgtttcaat cattaataac atgggaaata ttgcggcact  15120
gttccttcgc gaggatccat gtgtgtattt atgttcaata gccacagata taaaaattgc  15180
ttcatctatg atcgaacaga tccaagataa aaacattagt tttttattaa aaaatggctc  15240
tgatattcta gtggagttaa atgctgaaga ccatgtggca tctaaacctt cacacgaatc  15300
tgaccctatg gtatatgatt ttaatcaagt aaaagttgat attgaaggct atgatattcc  15360
tctggtgagc gagtttatta ttaagcaacc cgacggcggt tataacgata ttgttattga  15420
atcgccaatt catataaaac taaaatccaa agatacaagt aacgttatat cactgcataa  15480
aatgccatca ggcacacaat atatgcagat tggcccttac agaacccggt taaatacttt  15540
attttccaga aaattagctg aaagagccaa tattggtatt gataatgttt taagtatgga  15600
aacgcaaaat ttaccagagc cgcaattagg tgaagggttt tatgcgacat ttaagttgcc  15660
cccctacaat aaagaggagc atggtgatga acgttggttt aagatccata ttgggaatat  15720
tgatggcaat tctgccagac aaccttatta cgaaggaatg ttatctgata ttgaaaccac  15780
agtaacgctc tttgttccct atgctaaagg atattacata cgtgaaggtg tcagattagg  15840
ggttgggtac aaaaaaatta tctatgacaa atcctgggaa tctgctttct tttattttga  15900
tgagacgaaa aatcaattta tattcattaa tgatgccgat catgattcgg gaatgacaca  15960
acaggggata gtaaaaaata tcaaaaaata taaagggttt attcatgtcg ttgtcatgaa  16020
aaataacact gaacccatgg atttcaacgg cgccaatgca atctatttct gggaattgtt  16080
ctattacacg cccatgatgg tattccagcg cttattgcaa gagcagaatt ttaccgaatc  16140
gacacgctgg ctgcgctata tctggaaccc ggccggatat tcggttcagg gtgaaatgca  16200
ggattattac tggaacgtcc gcccattgga ggaagatacg tcctggaatg ccaatccgct  16260
ggattcggtc gatcctgacg ccgttgccca gcatgatccg atgcactata aagtggctac  16320
ctttatgaaa atgctggatt tgttgattac ccgcggagat agcgcctatc gccagcttga  16380
acgtgatacc ttaaacgaag ctaaaatgtg gtatgtacag gcgctcactt tattgggtga  16440
tgagccttat ttttcattgg ataacgattg gtcagagcca cggctggaag aagctgccag  16500
ccaaacaatg cggcatcatt atcaacataa aatgctgcaa ctgcgtcagc gcgctgcatt  16560
acccacgaaa cgtacggcaa attcgttaac cgcattgttc ctccctcaaa ttaataaaaa  16620
actgcaaggt tactggcaga cattgacgca acgcctctat aacttacgcc ataacctgac  16680
aatcgacggt cagccactgt cattatctct ctatgccacg cccgcagatc cgtccatgtt  16740
actcagtgct gccatcactg cttcacaagg cggcggcgat ttacctcatg cagtgatgcc  16800
gatgtaccgt tttccggtga ttctggaaaa tgccaagtgg ggggtaagcc agttgataca  16860
atttggcaat accctgctca gcattactga acggcaggat gcagaagcct tggctgaaat  16920
actgcaaact caaggcagtg agttagccct gcaaagtatt aaaatgcagg ataaggtcat  16980
ggctgaaatt gatgctgata aattggcgct tcaagaaagc cgtcatggtg cacagtctcg  17040
ttttgacagt ttcaatacgc tgtacgacga agatgttaac gctggtgaaa aacaagcgat  17100
```

-continued

```
ggatctttac ctctcttcat cggtcttgag caccagcggc acagccctgc atatggccgc  17160

cgccgcggca gatctcgtcc ccaatattta cggttttgct gtgggaggtt cccgttttgg  17220

ggcgcttttc aatgccagtg cgattggtat cgaaatttct gcgtcagcaa cacgtattgc  17280

cgcagacaaa atcagccaat cagaaatata ccgtcgccgt cggcaagagt gggaaattca  17340

gcgcaataat gcggaagctg agataaaaca aattgatgct caattagcga cgctggctgt  17400

acgtcgtgaa gcggcagtat tacaaaaaaa ctatctggaa actcagcagg cacaaactca  17460

ggcgcagtta gcctttctgc aaagtaaatt cagtaatgca gcgctataca actggctccg  17520

tggaaggttg tccgctattt attatcagtt ttatgatttg gcggtctcac tctgtttaat  17580

ggcagagcaa acttatcagt atgaattgaa taatgcggca gcacacttta ttaaaccagg  17640

tgcctggcat gggacttatg cgggtttatt agcgggtgaa accctgatgc tgaatttagc  17700

acagatggaa aaaagctatt tggaaaaaga tgaacgggca ctggaggtca ccagaaccgt  17760

ttctctggct gaagtgtatg ctggtctgac agaaaatagt ttcattttaa aagataaagt  17820

gactgagtta gtcaatgcag gtgaaggcag tgcaggcaca acgcttaacg gtttgaacgt  17880

cgaagggaca caactgcaag ccagcctcaa attatcggat ctgaatattg ctaccgatta  17940

tcctgacggt ttaggtaata cacgccgtat caaacaaatc agtgtgacat tacctgccct  18000

tttagggcct tatcaggatg ttcgggcaat actaagttat ggcggcagca caatgatgcc  18060

acgtggctgc aaagcgattg cgatctcaca tggcatgaat gacagtggtc aattccagat  18120

ggatttcaat gatgccaagt acctgccatt tgaagggctt cctgtggccg atacaggcac  18180

attaaccctc agttttcccg gtatcagtgg taaacagaaa agcttattgc tcagcctgag  18240

cgatatcatt ctgcatatcc gttacaccat tcgttcttga tccaaaaatt aactggacag  18300

agaccctgta cgggtctctg tccacacatc cgaaaaaccc accttgtcat ccatgacaaa  18360

gtgggaatga acatgattgt tatgcttcgg attcattatg acgtgcagag gcgttaaaga  18420

agaagttatt aaaagcccgc ttaaagccgc tccaggtaac ccggctagcg gcattggcaa  18480

cttcccctcc aacggcatga tgagcggccg cggctgtccc gccaatggct gcaccaaccc  18540

attcaccggg tgtacggcta taaggtaata atacttcaga aatatttctc ccgacacttt  18600

ctcctatcat tcggccaaac cagctcctgg aactgacagc gtgggaaatg gcagagctaa  18660

tgcctcttct gagcagtaac ctgccgataa accgataagg gccatcccat agattaccaa  18720

tgatccttcc ccatcgagca ccatacatag caccaatcgc tgcccgttca cccagctcag  18780

aacttccctg atggcggcca agtaatatgc cgccaataat tgcgcctgat agtgccccta  18840

accgctctgg cgcgctgaca ttaccgggcc tgagcgtatc cagcgtacct tgtccggcgg  18900

gtgtggcaat actgatagcc atgcccgtgt tatgctctcc ggctaaagcc attaatcctc  18960

caacggtgac cgctgttgct gcggaaatgg cggtacctgt cgaagagctg ttaaatagtg  19020

cagacgtcac aagcgatgtg acaacaaaag cgccaacctg aacaggaaca gaacgtttac  19080

gcgtcagata acttaaaact tccccaattt tttctgagat gttgttcgcg aaaaacccca  19140

tcaccgcccc ggagacaaaa ccaccaatgg cagccccgac aatcccccaa ggcgacgctc  19200

ctgcaatcgt ggccgccttc acccccagac ttgctacccc cacacccaaa acaaacgttc  19260

gcaatcctcg gtttaatttc aagaacgtat caaaggaagc gccttgttca agcaggtgtt  19320

ctgtcgtgat gttgactgcc tttcgatacg ctttttttccc tatccaggca aggacaccct  19380

gaccggggaa acgaccatca gaatcagaaa aaacgatggg gttattcctg cacattcgga  19440

acaaattgag accatcgacc tcaccggcag gatctacact caaccatcgc cctgtccacg  19500
```

-continued

```
attgataata acgataaccg tagtaataca accctgttgc atcccgctct ttgccagaat  19560
aacgcacggt tttgtaatca gcttctgact gacttcgggc tgcccacacg gcggttcccc  19620
cataggggta atattcttcc tgactaatga tctgcccgtc actgtccaat tccagcccgc  19680
tactgccaat caggttgcca taactgtagc gcagctgatc attgctgata tccgccggtt  19740
tgcctgtttc ccaatgcagc acccgcactt gtgcctgacc cgattcaccg acagtgatga  19800
cctgcaaaaa ctcttttaat gtattgccgc tatatgtcgt gcgccattcc agctctggca  19860
aatataatgt tcgctgtatt tgctcactgt tacctgtctt ctgaatatga gtcttaatga  19920
cacgctgact gtctgcatca taacggtaga attcctgatc aggcgtcgta ttttccctat  19980
tgaccaatat cacttgttgc aattcgtcac ggggtgtcca gaaaagatcc tgaccgggaa  20040
caagccgggt ctgatgcccg ccgggggtga acaacatatc cacctgagtg ggatcttgcg  20100
ccagctcttc cagtacagcc cggttgctgt gatctgaaac ggtcatgttc gttgtatagt  20160
tattaccggt gatcggtgaa ttatggcgaa ttctggtcag atttccccca cgatcatagt  20220
cgtaagtgcg agagtaattc gtataagtat tgttatcaat cagagcgggg atgggtaact  20280
ggtttttttg tcggccaata ttcgccattt cacgcccagt gacggaaacc agctggtaca  20340
ggctgtcata ggtgtaagta ttttccggta caattttctg gttgcgccaa aagcgggtaa  20400
tttcagcatc attagttgat ttcagcacat ttccgacagg atcatattca taacgcaggt  20460
tttgtaaaat tttctcccca gcggcatgac cggaaggacg ttctgttttt atgccaataa  20520
ctcgttgcgt ctcgggttca taggtatatg tagtcactat cccgttacca tgttcctccc  20580
gtagcttctg gctggcagcc gaataggtca gggatttcac gataacttgt tcttgtttcc  20640
ccttcagcgc caaccaactg ccttgaagca gaccggccac atcataggcg atacgttgct  20700
tgtttccggc agcatctgta ctcgttaata ccgtgccggt agcatccgtt gtgctgacag  20760
aagtgaagct ttccggcgcc agcgcgtttt tccagccaga ttcatccata ccgtgccaat  20820
cggcttcgct gtcatctttc agtaattgct gtgtgatgga caagggtatg ctggttaacg  20880
atatgctgtt ggtttgattc attccggtgg gatcataatg gaccacgcac tggccggcca  20940
gattattgcc tttttctgcc ggcgtatttc ctgaccagat caatcgctcc gtgatacagg  21000
cgttctctcc ttttacctgc tcggtaatcg ttagcaatcg tcccggaagg ttatcacttt  21060
catactgaaa cgttcggcta acgccattgg cgctgacagc taaaacggga cgcccggcaa  21120
catcatgcag ggcgacacgg gttccggcat ccacactttg cgtacgcaat gccttcttac  21180
tgagtgatga caagagaata agattgggtg taatggcgtt cttgtcactc gctgtctgct  21240
ggcgttcata aaatcgcgga tcaatactct gagtcagaga tccttgagca tcatattgat  21300
aaccggtgat gcgttcatcg gttacctgag gtgtatcggg gtgccgatac caggctattt  21360
cgcgtactgt ctgaccacgg ttgtccagta cggtgacgga tggcgtattg ctgtgaacga  21420
aattcttcat gattcattcc taaatggagt gatgtctgtt cagtgaacag gcatcactga  21480
gctttatgct gtcatttcac cggcagtgtc attttcatct tcattcacca caaaccaggg  21540
agtgaataag gatcgacgaa acccgccttt ggccgtgata acctgatatt cacgccccaa  21600
cggatcatag taatgggtat cggcatatat atcctgccgg gcactgtcat cactgacgta  21660
ctgccaacta ttcaggaaat acggttgata cttacgcagg gcttggcctt ttccgtcata  21720
ttctgtacgt ccggaaactg cccaacggaa atctgtcatc gccgtttcag gcgcgccatg  21780
attttcagcc acaatggctc catactcatc acgtacccag gcttcaccac tttcatggcg  21840
tacggctgtt tgtaaggttc gcccaaaacc atcactaaac gtaaacgttt gacgtaattg  21900
```

```
ttgttccgga tcggcatcat agcggtcggt gatcacactc agtacatggg gtgggttctg  21960
tgaattgact tgctttggca tggcagcggc agggttattt tgttgccagc ggcgaaaagc  22020
aagcgacagg agataaccat cttcagtgat gatcccagcc ggtttcagct ctccataaag  22080
ctccccatca ttagaaaagc tggcctgaac catccagctc agaggggcat aaaccatcag  22140
ccctgcaaca ggtataccgg gtttcaatgc cagagcatca tccaccgttg tggggacaat  22200
aaaggggaca gtttcatttt ccgcaggggt atatccttgt ttttcaccgt tttcagtccc  22260
ccagaaacgg aagctggtta ccctccccag tgcatcaaac gtcacggtgt gatagttatc  22320
attgacatct gtggtgttat ccgcaaccat aaatcgataa tcgtaatgcg cttgcatacg  22380
caggccagcc gcatcctctg ttgcggtgat aacacagtaa tggctatccc acgtgactgt  22440
cgttttacct gtaagcttgg tttcccgttg caccaatggc cgatagaatc cgtctgcacc  22500
ggcatattct gtaaattcct tttgtcccac ccagacatgg aaatctgtct tttcactgaa  22560
cggcactttt gccgtattcc agcccgcatc attcagctgt tttgtcagct cctgctcatc  22620
catcacctcc tcaaaagccg ccaacgatcg ttcatcaaac tctgcggttt caatgtatgc  22680
caccagcgga ggaatagcgg gttgttcttc tggaccggta tatgctacac gctgatgtcc  22740
cagataatcg gctgcggcat caggcaacaa caatgctcct gcacctgtgg cagaaaacca  22800
ttcaagggaa aatccaccgt ccggcacttt atcggcttga taaatacgtg cgtcactgcg  22860
tgaggtatcc ataagccctg tgatccacgt attatcatca tgattcagat gatgataaga  22920
agaacgctgg cgtgtcagac gaaggaacat ctgctgttcg tcgaaactgc tggtgaaaag  22980
tgtttcgggc agggtatccg gataaggcga gaactcaggc tgtggacgtc tcgaataggc  23040
aatctcaaga ttgtcctgcg gaaatcctaa cgcatcagat ttaaggacga tcttttggct  23100
gcactgtgga tcggtagcaa cccgttcata tcggtattgg cgggattcgg ccaccgaaac  23160
cagtaccgca ggcacgtccg ataccatcac cggtaacaaa cgtacttggg tgcgggattc  23220
atccactgaa taaggcgtac cggccagtat agaatcatca tccccataca gctcactgcg  23280
taaacgttgt ccttttaagg ctcgatgtaa ccagtattct tcctgttcgc tcggcgtgac  23340
cgtcatatca ccaccggatt tttcgtcata acgggtaaag cgtggggtaa aatggggaaa  23400
tgcctgttga tccccctgcc aatattccgt gggcagaaga atatcgactt cccgtacgcc  23460
agtgccgtac caattaaccg tgcgcgaagg tgccggtggt tcagcatgtg tcccctgtgt  23520
cgcactcgcc cgtgaatcaa tatcagtttg tgtcacccgc ccaaaaccac gaaactcccg  23580
ttccagacca tcccaggcac catgtgagta atgataatgg ctggtcaatc ggttaccgga  23640
aatttcatcc agcacttccg tgcgccacaa cacatgcacc gggaacggta agtagctgac  23700
caccgtcatc ccggattcag aagcctgtaa tttctcatcc agccagaact gggcagagct  23760
gcgataatac agcgtggttt ctgttcccat attgttattg acggcattca gcagccaagg  23820
cttgaatatg gtcatatcca atcgccagtg ctgcaccttc atatgggggga tcgtcaaaat  23880
aatgctggca gtccctaatc cttgtgtatc cgctatttgt aaccgacaag tatcatcaaa  23940
acgtacccca tccggcagat caatacgctg aggttcagca aaatgattgc cgctttcatt  24000
ggcatagagt tcaaggtaag tattgcgggc ataaataaaa tcggtggtgc ctgagccatc  24060
tatgtctacc atatacagtc tgtcggggtt aaacgtttcc ccgctaatct ggaagcctgt  24120
catcatcaga ggctcaccaa attttccatg ccccaggttc ggccagtagc gcacgctatc  24180
tgccgttact tccaccagat gtgattgccc ggagcctgtc atatcactga atgcgacaag  24240
atgacgctca tttctgccgg gaaccggcag tggcatatct gacaaatgaa tcacatcctg  24300
```

-continued

```
agcgcgatcc catcctgccc gattatttga ccagacacgt acactatttg gcccgataag  24360
cgctaagtca ggcagcccag ccccatcaat atcagccagt tttgcctgcg gatggaaata  24420
ttccattggc acagcggata atggaataaa gggtgtccat tcaccttccg gtgacatggt  24480
gtggtagccc cgtaaccctg atgccgtaat cacccaatcc agacgcccgt caccattgat  24540
gtccaacaac atcgcgcttt cctgttgtgc cggaatatgt ggcagtggtt tggcctcctc  24600
ataggtaacc gcattcgttc cttcggcagt gatatcccgt accggagcac ggtaccacca  24660
ggctttctga gtatcctgat aaagtacgcc ggaaattcct tctccatata aatcaaccaa  24720
ttggtatggc tgcaacgtgt tcattttttc taactgcggc atggactgcc agttcagatt  24780
cacgccatga ttaacacgtt gataatccat ttccagcggg gacatcatca ctggcgtacc  24840
gtccgtttca tgggccagtc tgcgggccgt ttgcagcaag gaaaccttgt tgttcaggtc  24900
ataatccaga ataagacggg aaaccagcgc cggtgtttct tctgcaacct tttcccctgc  24960
cagcgctttc agctgatgaa acatcagaac ttggcgacac aagcgacggg ttcgaatttc  25020
aaacccatat tcatagcggg agaaactgtc cggacgacaa cgccattttt caggcacatt  25080
gttttcagac acattgtttt ctgacacatt gaattcgggt acagagttca gcgaagatga  25140
gcgctcaccg taatcaaata ccagatgaaa cagccagtca ttatcagcag gaatacctga  25200
ttttaccgcg aaaaaagcgg tttccggctg agtattgcca tagctgactt ttgccagata  25260
acgctgggcc gtaacacctg aatgctgagc aagttcatgc tcatcacagt caagatcgtc  25320
ttctgcccga tagtgatagt aaatatgttc cccggtatgc gtgacggttt cctccatcag  25380
ccagcgggca attctggttt catcctgcgg gtcagcaata cgtgcatggt gatgcttacc  25440
gaataggtgc actaaaccat ccgcagtaaa aagtacccaa aaagacgtct cttcctcacg  25500
tctctgctgt ggctgccagt gttctaaacg aacgattttt tctgccacgc gggactgata  25560
gcgggtaaca gtatgcggct gtgtcagaac cgtccccaac agtgaggttg cggtgcgttg  25620
ctctggttgc ccttggctgt ccggcacaat actcaacact tccccatccg gcccgagata  25680
ctcatcttgt cccgtatagt gcggaacgcc cttggcggta cgcaggctga taaaaccaac  25740
cccacattgc caccccatcc cgaatgaccc attgccggca gtactgctgt aattcagtga  25800
tagcaccggc accagaccac gcccgacaga gatcggcaag ggcagtgaaa atgacgctcc  25860
cccttccgct ccgacggcat tgagtgcttc tcccattcct tttagtgatc cgcccccaga  25920
gggcaatgac ggtatttcaa gtttcaaagg tgttgaaccc tgcataaaaa ctccttaaac  25980
aggctccctc aggagcctgc ctatcacaat gttttaatta agaacgaatg gtatagcgga  26040
tatgcagaat gatatcgctc aggctctcca gcagcgcttt ctgccgatca gtcgcatccg  26100
ggaaactcaa cgtcaggctg ccgctgtcat tcacggaaat accttcaaac ggcagataac  26160
gggaatcgtt gaaatccagc ataaattgac cactgtcatt cacgccgtgg gagagagcaa  26220
tagcactgca accgcgtggc atgacgatgc tgcccccgta attcagcacc gcccgaatat  26280
cttcatacgg cccaaccagc gccggcaagg tgacactcac ctgtttcaac tgacgggtat  26340
tgccaaggct ttcggggtag tcgctgaaaa ttttcaaatc agacaatcgc actgaggctt  26400
ctatctgacg gttactgagt tttaattcat tgccggaagc tcctacgttg cctttccctt  26460
cacgcaggaa ttgcgtgagt ttttcggtca gattaaagtt gtctgatgat aaggcctgat  26520
agaactgtgc caacgagacg gtacgggtca cttccagtgc ccgctcatca cgctccagcc  26580
agactttttc catttctgcc agattcagca gcaacgtttc acccgccatc aaacccgcag  26640
tcgtaccgtt ccaggcccca ccccggataa aggtaacacc gttgtcggtc agctcgcggc  26700
```

```
gcagcgcttc ctgtgccatc aggcagaagg actgggtcag gtcaaagaac tggtaataga  26760
tagcactcag cttgccgcgc atccaactgt aaagcgcttt gtttgtgaat ttacgctgta  26820
acagctctaa ctgagcctga gtatgggcct gctgggtctc ctgatattcc acctgcatct  26880
gtgctgcttc gcggcggatt ttcaggcttt ccaactgggc atccatttgt ttgacttcac  26940
cgtcagcatt atcacgctga atttcccact cctgacggcg gcggcggtag gcttccgaac  27000
ggctgatttt gtctgcggaa tattgggaag ctgtggcaga aagcgacatc acggaggcgg  27060
aagcacgcag tgctgccccc caacgactgc cgccacaagc taaaccgaac acgtttggca  27120
ctaaatcggc cacccccttcc gctattgaaa gcacctgccc ggccagagac tgacctgccg  27180
ctgcatcaag cagtgacatt gcccgctgtt ctccgtggtt gatatcctcg tcatacagct  27240
gctggtattt ttccagacga ttttgtgcac tgcggcggct ctctgccaat acagcaatat  27300
cagcatccac ttcatcgaca gttcgttgct gaatacggat gctctgtgtc gccagttcca  27360
taccctgctg tagtagcagc gtggtgagtt catcggcatc atcatgctct gccatactga  27420
gcagagaggt gccgaactgg gttaattgcg ctaccagatt gcgggtccgc tccagcatca  27480
ccgggaagcg gtataacgac aatgtgccgg gcagcactgc actaccgccc tgagaggcct  27540
gtaccatact ggtgagcagc gctttcggat cggtaggctc ggcgtaaatc gccagcgata  27600
acggctgtcc gtcaatggaa agattatggc gcaggttaaa caggcgcaaa cgcagggttt  27660
gccagtaatc ggtgagcgcc gggttatatt ccggcaggaa caaacccacc aacgagttag  27720
cggtacggag attcttggaa accccaccac ggcccagcat cgtaagatcc tgctgataag  27780
ccgcctgcac ggtttgactc gccgccccgg aaagggacgg tgctgcccac tgttggctac  27840
cgtaatcctc cggctcatca ccgagcaatt ctaaagtacg cacataccac attttggctt  27900
cattcaacgc atcgcgggtc agttctcgat aggccatatc gccgcgcaga ataagttgat  27960
ccaacaggcg cataaaggtg gcaatcttgt agtgcattgg gtcattttgg gcgacggcat  28020
ccggatcgat ggcatccagc ggattggcat tccaggaggt ggtctcttcc agcggccggc  28080
agttccagat ccagggggcg atttctccgt taacgatata gccggcggga ttgtagacgt  28140
agtttatcca ttgtgtggct tcgtcgaatt gtttttcctg tagcaaacgc tggaagcaca  28200
tcatcggggt gtaatagaac aattcccagt aatagagggc gctggcacta ttgaaatcca  28260
tcggggcgga atagcccgtt gcgatagaaa cattcaaaaa tcctttgtat ttcttgatat  28320
ttttcacgat cccctgttgc gtcattcctg aatcatgatc agcatcgtta attaatacaa  28380
attgctgttt tgtctcatca aaataaaaga aagcagattc ccaagtgttg tcataggtaa  28440
ttttctggta tccaaccccc aatctgacac cttcatgcat gtaataccct tcggcataag  28500
ggacaaacag tgtcatactg gtttccgacg tatcggataa cattccgctg taataaggct  28560
gccttcccgt gttaccgcca acattcccaa tatggatttt aaaccaccgc tcatcgccat  28620
gttcagcagg gtcatattta ggcagaacaa agttggcaaa gaagccttct cccaacggag  28680
gttccggtaa ccgctgggtt tccattgtca ggatagtatc aatgcccgtg tttgctctgg  28740
ataccagttg agaagccagc agggtattaa gacgaatacg atacaccccg agctgcatat  28800
attgggcacc cgaatgagtt tcacgcagaa acagaatatc ttccggatta taatttaccc  28860
gtttcaccga taatgtttgc ttgatcttac ccagcactcg cccgtctttg gctttggtct  28920
caaaaacgat atccagagga gcaatattat tggtaaaggc caacgatgaa gcatcgattt  28980
ccagtggctt aaaggtgtac ggcatagcat caaaactgtt tgccggcaag gaagcaatat  29040
ggtcactggc cgtaaaggtg tgggttttac tgccagccat caccgtaatt ttgatatcgg  29100
```

-continued

```
tattgttaat gcctgtatca atatccagcc agccggatga ttgataggaa ctaaatatct  29160
ggaagccctg agaattatta ccatcaacag cataactgca ctttttaaaa tcactggttt  29220
tattgctacc aaccgtgaaa acggtgttta aaattgtgtt tggagaaaat ggaaactcga  29280
acaatctggc ataataatta ttttcaactg gtgttagaat caaacgccta gtgtaatctg  29340
cgttcatcaa gtggccttga actgatgcaa tatagttttt cgttttatta taaacggtga  29400
tcggcccccc cagatcagag taaccgccat aatgtttaac ggtatttgcg atgataaatg  29460
cattgccgta ctgggacttt ccatccaccc ccgtcagttt catggcgctg atttgtttgt  29520
ttctgatgac attgccactg ccatcatatc tgacagtgaa agcggcgtta tgtagcgtaa  29580
tagcaaggtt atcgctggag tatttactgg ttatctgcgg aatattcccg ttctccatca  29640
ccgtcagact atcatcaccg atggcagaac ccatattcaa cgaggcaggc acttcaaaat  29700
cctgcgcgaa acgatagctg gcctttctta ccaagtcgtt gccttgagta tgaatgatat  29760
caaaggtatt tttcagttgg ctgtaacggc tgagtgctgt gttctccatc tttttgaagg  29820
agccatcgcc gtaaatggtc atgcctgcca catttttatt gctgccgcca aaatccgagt  29880
aactcttccc ggttttgtag acaaacacca gcagagtgtc ctcgccctga aagcctgatg  29940
cggccagcgc cagccgttca gtgtcaggtt ttttgtcagt gaccgcctcc acctgcgttg  30000
tgatatcgta agaccagggg gcactccaac tgccatcatg acgcagaaac gccagtttca  30060
gagtaaaacg gtcataggtt tccaccggat cagtaccatt tttcgccact tcctcttttt  30120
ctacccagat aaggtgcaaa cgttccctga atatgaccgg acgtattgca tccttgtagg  30180
ggttgaccgc tgtatcaatc ttcgtccact ctttccaggc attggcggcc agttcacccg  30240
cctgcatccg tgatatatcc acgttacgcc agtagtattc cggcaggttc tcccgcgttt  30300
ggccgacaaa ccaggtcagt ccggtgttgc tgttgacgtt gtcgtgatag gcgctgacaa  30360
ctttcagatc cgccacggtt tcaaagcggg tcaggtaagt tttaaaggca tcctccactg  30420
tgtcccggct aagtttactc tggctgatat tttccagcag ttcatccatc atccgggtct  30480
gcccgatacg ctgggttggg tcaatgtaat tttccggata ataaaccagc cgcgacaccc  30540
cgccccaggt gctgtaacgg ttattcaccg tccagtcggt aaaaaactgg cgggttgaca  30600
catcggcacg ggcattaggc tctatccgat tcagcgcccg gttgatgtag agctgaatac  30660
cggcaatggc ctctgccagt cgggtggttt ttatggcaga agagacctga ttatcaatca  30720
ggaaatagct gtacaggtca tcccggctgt gcagggacac cccttctggc tggatattcg  30780
ccagaaacca attgcacagc acgctactca ggcgctccgc ggtataatcc gccagcgtct  30840
gagcctgttg tgtactgagt ccggcttcca tattttctgc cagtgtctgc cactcatccc  30900
aggaaggcag attcgactcg gctttgttta atgcagtcac gtaacggata ttcaccagcg  30960
tacggataac cgacggcatc gtgtgcagtg ctgatgccac atctatccac tgcaacacgg  31020
tgttgatatc ctgccaacac tgaagctggt tcacgccggc ggaaaccatg gcctgcgtta  31080
ccatactgat gtccagcccc atcacggagg ccagtctgtc ggccgtgagt gtctgctggc  31140
gcagcatatc cagcgtgtca gagccgggat tgcccagccc attaatccac tggtggaatc  31200
ggtagagtga gaatagcgta tcaatattgt gctgtccggc aggttgattt tttgccccca  31260
gcacggcgaa tccggagatg accagcacgg atagctccgc ttcactgagg cgcagtgtct  31320
gtacggaaag cgataactgt gccatcacat ggcagaattg taccaattgg gtggtttcat  31380
tggcatttaa cgactctttc aataccagtg tcataaaccc ggcaatatct aagccacccg  31440
gccgcaggtt atcggtccac aacaggatat accgtgccat atccggtgac gccagatgca  31500
```

-continued

```
gcgttgcagc aataaacggc gcgagaattt cagcctgcag ctcccgattg tgactctgtg  31560
ccatatcttc actaatactc ggtcggaggt tattgagcag attactgatt tccggtgaaa  31620
tattcccgct aaactctggc gtacataata accagatcgc ttcagtggtg atttccgcct  31680
cagtcagcca ctgcgtcacc tgatacagcc agataaccag ccgtggcaac tccccggaag  31740
acaaagaagc cgttgttttg ccattgaacg gcgaaagacc ataaagcata cacagttcat  31800
tgaccgtcag ctgatggaca cgggccagta acgtgaggcg atacagtgaa gagataacga  31860
agacagaaag tgtgatggta ttttgggcgt ccagcacacc cgccagtttg cctaactgat  31920
acagttcacc actgttgacc cccagaccac gcatcagggc tgaacgggca aaggtagatt  31980
gctcttcatc cggatcaatg ctgaccgtgt tgccgtcggc ttcaaagatt ttccctttca  32040
gcggcggtgt attaaagaga cggttaaaat gactgacact gtcatcgtcg gcatattgat  32100
taatgaccga tccgttcagt acctgtgcat catcaaagct cagtgcataa cggtgactgt  32160
agaacagagt atagaaaact ttggtcagaa cggagtcgtt gatgatgcct tgtgcattgt  32220
cactgcgtac gatagtttgc agttcattcg gtgaaagccc gctagtcagg cacaagcgaa  32280
tggctttatt cagtttgagc gcaaatatag tcaggggata agactcaaaa gtgaatattc  32340
cgccgccctg atttgtggcg ctggtggaag acgtatagcg ataggcgtat atctttacac  32400
cgtttttgta ttcagaatca gatatgttac ttagataatt acttttaaaa ttcgtattgg  32460
ctattagagg accggaaagg ctgccgacaa tgccacttgg ccctgcgttt tttctaagag  32520
tagccccaaa ttctcttgat accttaaaat tagcacgtat aaagaactga ttatttcctt  32580
catacatcaa atcaaagtaa tttatatttt tatcataatc atctgttttt acacgtgtta  32640
ttttgtaagc ttcgagttta ctttcattat tgaccactaa acccgttgag atattatcca  32700
cataagcaga ggtgctgtca gaatagccat tctgcaacat cccgaggtat ttttgcacct  32760
cagaaagttc aagaccataa tacttggcta tccatgattg tgacgcgaaa ttttcgggcg  32820
tgatattttc actgaagttt tgcgcaaata aagcatcagc gttcttttcc gtaatctctt  32880
cggtcaaaat gttataaagc tccggagaaa tattggccag aatcgccagt aatgaagccc  32940
cttccgcctg ccccatcacc tcaggattac gggacagcgc tgacagtgta ctgtcatggg  33000
tcataatgac ctgacggata gtctcgtaag gctgatggta aggggtatca atggcctgac  33060
ggtaagttga caggctctcc atcaatgcgt ccgaatcacc tccggtcttg cgggtaatat  33120
gctccagcaa cagttcgtta gacagtgtca gggtggaaat ttctgtatcc atattactct  33180
ggctcagagt cagatcagcc agatccggac ggcgattatc aagatgataa gcagagcttg  33240
aaaaatgtaa gtccttcgct tcacgataca attcggtgag atagccagcc ggtgaaaaca  33300
tggaagccac tgaacccggt ttcacaaagg aagaagaacg ggcaccaaac atttcatcat  33360
aactgcgtga aacgctgtct cgttcaatac cgagtcggat agcaccggat aattgtgggt  33420
tggcacgggt aaaaatacgc gcttccagca agcgattatt ttttttctgc tctatagttt  33480
catgatagag atggcgagcc tctccccaac tgagctggtc atcaaagatt tttctcagtt  33540
cactgaagga taaatattgc agatccgcaa gagtcatcgt ctgaccgtcg cgagtgggac  33600
tgattttatt gagtaataca gccgtgctat acataataac ctcaattatt ttataaaata  33660
gtgttgtcag ttaagagttc atctgaagat ttagtgctta ttttgtaagt cattattcta  33720
ttcacattgt aattatttgt tttatctgag attaatgata ttaaagagga tgctattgta  33780
aatggcggaa tagaatacga ttttctactg aaatttcatt ttaatcataa aatttataac  33840
tgactttaat gttacagtcg taatcgatat tgtgtcatgt tggcatcctc ttcatctgcc  33900
```

-continued

```
ttaaaataaa gtagggtacc aaaaggaata catacttgaa tccaagattg agcacaaatc  33960
cacatattca gcttattaaa gataattaaa ttttatttat cataaataaa taggataacg  34020
gccctggatt ctgaccaggc gaggccaaaa gtcgatgaag ctaagttacg gttgaacaaa  34080
tttgtttact ggttaaatgg gcacaaactc tttatataaa taaatagcat attgtaacga  34140
gtaattaaaa aatgaaaatc cagcttacct ggttattcat tcattaacaa aacacaaaat  34200
atttatgcca acggcactta gaattaaata attttcttta tcaactttta cgttaacttc  34260
atttgataaa agtaagatcc catgattttt caagatcctt attcggttat aactgaccag  34320
attgggaaaa tcaaccttaa tgtctcatgt gaaataaaat attgtccaag tgatttattg  34380
ttttgtatta taattcagtc tcttttatca acatctaact taagtcctca agagaaatta  34440
attgcaaatc ggtcaccata accggctaat aatgtattga tctcatattc cattgtttcc  34500
tgagtccagg tgataaaacg tcgccagtgg tatttagcct ccctccagac gatttcaatc  34560
aaattcagtt ctgggctgta ggcgggaagg taaagtaaaa gcaggttgtg ctctcgtaac  34620
cagcgatttt taagtttttc atcgatccca tgatggatag gcgcattatc taacacgaca  34680
aatgtcaggc gatgctcgcc ttgttgggcg acctgctcta aaaaatcaat gacattactt  34740
cgcgtgacac tgcttgatat tatctgataa aacagcctgt tatcagtgta atttagcgca  34800
cctagcactg accgtctgac agagctttgc ggctctgctt catggggctt acctcgtgga  34860
ctccatccat attggaccgg tgggcaggcg gaaaaacccg cctcatcaag atagagcagc  34920
cgataatgac ctgcccgtgc gcccgcctta attttattca gtaaggcggc tttttcagca  34980
aattccgttt tattgcgttt tttttaagcg acaggcgggg gcgtttatag gggagtccct  35040
gtttttcag ggtattcgcc agcgtttcaa gcgtacaggg cagggaaccc tgcctggctt  35100
cgacgcacgt cagggactct gcgctggcgg cttcgagcgc agtggcaatc atgtcaggcg  35160
tcatggcgag ataccggcct ccggcatgac cccctaataa tcccgctatc cctgaatggt  35220
gccacatgtg aacccaatta tagataaccc ggagactgca tccgatttca gcggtgatct  35280
gggacggctt gatccctctg gcaagcatga gcaaacccgt tcctcgcgta cgaatgtccc  35340
ggtgtgggtg attcaaagcg agtggttgca atgtgattcg ttcaggctca gaaaggatta  35400
tcttcgagtt cataagaaca ggcagaaagt caggttatcg tgttatcgat tataacagta  35460
atgcagataa tttatctgat taacttaatt tatttttgca ataaacgttt ttagcaccat  35520
gaaaaataat aagaaagaat cctgattatg ttgagagagt atacaaaagt ataaaaatgg  35580
cgaattaaat caccattctg atagtgacaa ttattccctt acttttatag tataattttt  35640
attgaactct ttccctgcgt acattgtacc caaagtaaat cctaccactt caatttttat  35700
caattctgtc ttctttgggg tacctgttat atttatatga tgataatctt ttcttatttc  35760
ttttttcca ccctatagga aagaactatc ttttggattc catgttagtc ctgagccagt  35820
aggatgaatt tttacccaaa cgcttttttc attcaatgca cctcctgtga tggtaattga  35880
tgcctgatat ggttcattta tcactgcatc aggaagaaac tctgattttg gtaaaacttt  35940
tggcgttgga ttaccacaac cataaagtaa aaaaataaaa ataattaata ttttttcat  36000
gttatttcat tggtttaaaa accaaccctc aaaaaatatg gttgagtaca taatctagtg  36060
atttgttttt tttaatttga tgttccactt taccccatga aaacagattt aaatttacat  36120
attgattcag atctgaatta tttgtgatat tttctttctc atagttttct actactcctt  36180
cccaaactat ccaatgattt tttcctgatg tttctatgtc accaaaatct gataacattc  36240
ctgctgaaat caaagtaaca acatgatatc ctttgttata gtaatcacta agagttacta  36300
```

-continued

```
tgtcatttat attagaatgg gataagccga cattactaaa tactttttca taccctgatt  36360
tttcaaacca ttctgtcaat tttccccaca ttgtaatacc agctacttca tcatcaacct  36420
catcataact catcatcata ttttctgaat ctcttaggct tgccaatgtc agccaatcta  36480
acccagatat tctttcacca tattgattat aaaaagtacc tttaggatgt cggcaaccct  36540
cacccagctt aatttccagt tgaccaattt tagttcggcc atattgccat aattctcgtg  36600
cagcttgctc ataaatatct ggtctatcta ttggcaggca ataaaaaaaa gcggcagggc  36660
cacataaact tgctccattt tgatccggat aagttctttt cgataccctg tcctgtattt  36720
atgattcaat tttacttttt tcaaatggat cgtgtgggtg accaatggga tattctttgg  36780
caataaaagt ccgttcagga atggtgattt ttaattcgac ggtattatcc ccgtcgctga  36840
caggttttgt ttcaactgta ctttcaaaat aacaggcatt ttcccgtttt ttctccgaac  36900
aggctttacc ggaagttaat tcaccgaggg tatacatttt cttaaaatgg gtttgcagtg  36960
ccggaaatat atttgagcca tgtttgcggt gaagcataat ttgcataata taaatcacag  37020
aaagatcgtc gtctatttcc tgcgtgatat gctgttgtgt ttcataatta ctctgtagtt  37080
tctcctgaaa aacatcaagc aagatatgga aatttccttt tgcattctga cgataaatgg  37140
ttaagtcata aagcaggttt tcaacaggta cgttggattc tatttttgtc tgaacggtat  37200
aggctggcat ggtattaatc ctttaaaata tgaaattcaa gtttattttt gtcatccgta  37260
agatgccatt gggtgtaacc ttgtttatca gtctttcctt cttttatctg accatccggc  37320
aggcaaaccc gatacttgcg ttcggttaaa agattgccgt catcatccac acaacgataa  37380
cgggcatgat gtttagcggg ttttaccggg gtttcttcaa ccagcggctt cttaagtggc  37440
ttaacattcg agaccccaga taaaagcggc ttgccttctt cacttccggc taattgcgta  37500
atgctgtagc ccgaagtccc tgcggcgatg tggttgcatg aaatggactt ataatcgagc  37560
atcaccactt catggggtat cgcaccatta tcattgattg aatgcggata attataggaa  37620
atatccacaa tcgtggcact ggtcagcttg atttcataaa agaactccag ttgtcccatc  37680
tggcttgtcc tgtaatgcac aaaactggca tccagcaaac aggggagagg atttatcaat  37740
gggtttcaca aaactgacgg gttgatgatt aacattctgg tcacggctca tcgaatgatt  37800
caggctcaat acctgtattt gatcacacag gccagctggt ttgcccgttc gttaagctgg  37860
cggtaggtca gtgttgcgcc ttcaaacacc agtgccccgt tatccggtgt cctttccacc  37920
tgagcttcaa acagttgtgg cagggttttg tcctgtggat aaggcgcatc ggtctggttc  37980
caggtatgca gcagggtatg gcgctcctgt gcggacagaa tatccagcgc ggacagcggt  38040
tgtttctggt ctgccacaaa ggcttccagt acccgttgat agctctctgt cagcctgacg  38100
atggtggttt cattaaacag gctgactgcg taattcaggc aaccggtaat ctcggtttgt  38160
ccgtcggaca taaacaggct gaggtcaaac ttggcggggc tgtatagcgg ctcatccaga  38220
gtcaccggcc tgaatggcag gcggttgtct gacggatttt ctccaaagct ctgtaaacca  38280
aacatgatct gaaaaatcgg gtggcgggcg gtatcacgtt caatattcag ggcatcaagg  38340
agctgttcaa acggcatatc ctgataggcc ttggcttcgg caacctgttt atgggtctgc  38400
tcaatcaggg cttccacgct gacagtctgt tgcaactgtg cccttaagac cagtgaattg  38460
acaaacatcc caatcagggg ctgagtctgg gcatggtggc ggttatcggt tggcgtcccc  38520
agtacgatat cgttttgccc ggataatttt gccagcgtga cataaaaggc actgagcaac  38580
acggtataca gggtggtttc ctgtgttttt gccagactcc ttaactgttc agatagccgg  38640
gtattcagcc caaaactgaa attacatccc tgataattca cctgagccgg tctggggtaa  38700
```

-continued tcggttggca aggccagtga ttcatagttg gctaaagcct gttgccagta agcgagttgg 38760
cgttcgcgcc ggtccccttg taaatagttg cgttgccatg cggcataatc gccataggtg 38820
atatccagcg ctgcaagctg gctgtcgcgg ttttcccgca aggactggta aatttccgcc 38880
agttcagcca taaagatatc aattgaccag ccatcaatgg cgatatggtg ccataacaat 38940
aataaatagt ggctgtcaga aaccggatag tgacacaggc gcagactggg ttctgtggtc 39000
agatc 39005

<210> SEQ ID NO 7
<211> LENGTH: 1533
<212> TYPE: DNA
<213> ORGANISM: Xenorhabdus nematophilus

<400> SEQUENCE: 7
gatcaggtat tcaatcaacc caaactgttt gatgaacctt tctttgttga taatcgtact 60
tttgattaca acgccattcg tggtaatgat gcacgaacaa ttaagcaact gtgcgccgga 120
ttgaaaatca ccgtagccac cttccaattg ttagctgagc aggtaaacac cgcctttcat 180
ctgccatccg gcaaattaac ctgttcactg cctgttattt cagcgcttta tcgtctggtg 240
actgttcctc ggttatttaa tttaaccgct gaacagggca tgatgctgat taacgcatta 300
aatgccagcg agaaattctc acctcatatt ctggctggtg agcctcgatt aagcctgtta 360
acaacagagg gttcagatac cacagaggtc gatttattgg atgttattct gatgttggaa 420
gaagttgctg tctggctgca acagagcaaa ctgaaaccgg aagaattctg cctgatgctg 480
caaagtgtta tgttgccggt ggttgccacg gacagcagtg tgacattctt cgacaacctg 540
ctgcaaggca ttcccaaaac cttactcaca gaagataact tcaacgcagg ggatatcccc 600
agactccctg aaggagaaac ctggtttgac aaactttcga tgctgataac cagcgatgga 660
ctcgtcaacg tttaccctct cagttggggc cagagtgatg aagattatct gaaatcagta 720
ttgacacctg tcgtcgaaaa aatcattagc gatccaaaca gtgtgattat cactgtttcc 780
gcattaacac aggtcattac tcaggcgaaa actgcgcagg aagatctggt ttccgccagc 840
gtgacacggg aatacggtac tggacgtgat atcgttcctt ggttattacg ctggattggc 900
agcagtgttc ccgatttcct tggcaaaatt tatatacaag gcgcaaccag aggcggacac 960
ttgcgcactc cgccggatat cagcgctgaa ttactgcata tcacctatca tctggcgatg 1020
aataacatgc tgattaagca gttacgactc aaagctcaaa tcatttcatt acgtatcatc 1080
atgcctgaat ggctcggatt accaacgata gatggcagtc cgctatccgt gcatgaaatt 1140
tgggcactga gccggttccg taactgggcg accagctcat tgttcagtga agacgagtta 1200
atcgagtatt ttgcttttgc caatcagccg gagcaggacg ttcgtaacga tgaagatttt 1260
aatcgggact gtgctgaaaa gcttgccgac atactggaat gggatgccga tgaaattgag 1320
ctggcaaccc gacattttga tcctgcccca gcacgtgcca gaaatatggg acaaattgac 1380
tggctgcgtc gtgtcatggc gttgtcgcgt cagactggcc tgtcagtgac accgttaatg 1440
acagccgcaa cgttaccgcc tttcccgccc tatgaccaga taacccatgt cggtgaagcg 1500
gtgattgcgg caacccagta cccatcagag gag 1533

<210> SEQ ID NO 8
<211> LENGTH: 511
<212> TYPE: PRT
<213> ORGANISM: Xenorhabdus nematophilus

<400> SEQUENCE: 8

-continued

```
Asp Gln Val Phe Asn Gln Pro Lys Leu Phe Asp Glu Pro Phe Phe Val
1               5                   10                  15

Asp Asn Arg Thr Phe Asp Tyr Asn Ala Ile Arg Gly Asn Asp Ala Arg
            20                  25                  30

Thr Ile Lys Gln Leu Cys Ala Gly Leu Lys Ile Thr Val Ala Thr Phe
        35                  40                  45

Gln Leu Leu Ala Glu Gln Val Asn Thr Ala Phe His Leu Pro Ser Gly
    50                  55                  60

Lys Leu Thr Cys Ser Leu Pro Val Ile Ser Ala Leu Tyr Arg Leu Val
65                  70                  75                  80

Thr Val Pro Arg Leu Phe Asn Leu Thr Ala Glu Gln Gly Met Met Leu
                85                  90                  95

Ile Asn Ala Leu Asn Ala Ser Glu Lys Phe Ser Pro His Ile Leu Ala
            100                 105                 110

Gly Glu Pro Arg Leu Ser Leu Leu Thr Thr Glu Gly Ser Asp Thr Thr
        115                 120                 125

Glu Val Asp Leu Leu Asp Val Ile Leu Met Leu Glu Glu Val Ala Val
    130                 135                 140

Trp Leu Gln Gln Ser Lys Leu Lys Pro Glu Glu Phe Cys Leu Met Leu
145                 150                 155                 160

Gln Ser Val Met Leu Pro Val Val Ala Thr Asp Ser Ser Val Thr Phe
                165                 170                 175

Phe Asp Asn Leu Leu Gln Gly Ile Pro Lys Thr Leu Leu Thr Glu Asp
            180                 185                 190

Asn Phe Asn Ala Gly Asp Ile Pro Arg Leu Pro Glu Gly Glu Thr Trp
        195                 200                 205

Phe Asp Lys Leu Ser Met Leu Ile Thr Ser Asp Gly Leu Val Asn Val
    210                 215                 220

Tyr Pro Leu Ser Trp Gly Gln Ser Asp Glu Asp Tyr Leu Lys Ser Val
225                 230                 235                 240

Leu Thr Pro Val Val Glu Lys Ile Ile Ser Asp Pro Asn Ser Val Ile
                245                 250                 255

Ile Thr Val Ser Ala Leu Thr Gln Val Ile Thr Gln Ala Lys Thr Ala
            260                 265                 270

Gln Glu Asp Leu Val Ser Ala Ser Val Thr Arg Glu Tyr Gly Thr Gly
        275                 280                 285

Arg Asp Ile Val Pro Trp Leu Leu Arg Trp Ile Gly Ser Ser Val Pro
    290                 295                 300

Asp Phe Leu Gly Lys Ile Tyr Ile Gln Gly Ala Thr Arg Gly Gly His
305                 310                 315                 320

Leu Arg Thr Pro Pro Asp Ile Ser Ala Glu Leu Leu His Ile Thr Tyr
                325                 330                 335

His Leu Ala Met Asn Asn Met Leu Ile Lys Gln Leu Arg Leu Lys Ala
            340                 345                 350

Gln Ile Ile Ser Leu Arg Ile Ile Met Pro Glu Trp Leu Gly Leu Pro
        355                 360                 365

Thr Ile Asp Gly Ser Pro Leu Ser Val His Glu Ile Trp Ala Leu Ser
    370                 375                 380

Arg Phe Arg Asn Trp Ala Thr Ser Ser Leu Phe Ser Glu Asp Glu Leu
385                 390                 395                 400

Ile Glu Tyr Phe Ala Phe Ala Asn Gln Pro Glu Gln Asp Val Arg Asn
                405                 410                 415

Asp Glu Asp Phe Asn Arg Asp Cys Ala Glu Lys Leu Ala Asp Ile Leu
            420                 425                 430
```

-continued

```
Glu Trp Asp Ala Asp Glu Ile Glu Leu Ala Thr Arg His Phe Asp Pro
        435                 440                 445

Ala Pro Ala Arg Ala Arg Asn Met Gly Gln Ile Asp Trp Leu Arg Arg
    450                 455                 460

Val Met Ala Leu Ser Arg Gln Thr Gly Leu Ser Val Thr Pro Leu Met
465                 470                 475                 480

Thr Ala Ala Thr Leu Pro Pro Phe Pro Pro Tyr Asp Gln Ile Thr His
                485                 490                 495

Val Gly Glu Ala Val Ile Ala Ala Thr Gln Tyr Pro Ser Glu Glu
            500                 505                 510


<210> SEQ ID NO 9
<211> LENGTH: 4173
<212> TYPE: DNA
<213> ORGANISM: Xenorhabdus nematophilus

<400> SEQUENCE: 9

atgagttcag ttacccaacc tattgaagag cgtttactgg aatcacagcg cgacgcactg     60

ctggatttct atctcggaca ggtcgttgcc tattcacctg acatgacaag tcagcgcgac    120

aaaattaagg atattgacga tgcctgcgac tacctcctgc tggatctgct gacttccgcc    180

aaagtcaaag cgacacgact ttcacttgcg accaattcat tgcagcaatt tgtgaaccgc    240

gtgtcactga atattgaacc cggtttgttt atgaccgcgg aagagagcga aaattggcag    300

gaatttgcga atcgttataa ttactggtct gcggatcgct tattacggac ttatccggaa    360

agctatctgg aacccctgtt acgcctgaat aaaacagaat tcttcttcca actggaaagt    420

gcccttaatc agggaaaaat taccgaagat tccgtacaac aagcggtgct cggttatctg    480

aataattttg aagatgtcag taacctgaaa gttatcgcag gttatgaaga tggtgttaac    540

atcaaacgcg ataagttctt ctttgtcgga cgtacccgta cacagccata ccaatattac    600

tggcgttcac tgaatctttc gatacgccat cctgataccg atgcgttatc tcccaatgcc    660

tggagcgagt ggaaacctat tgacctgcca ttgggcagcg tagaccccaa tttgatacgc    720

cccattttcc tgaataatcg cctgtatatt gcctggacgg aagttgaaga acagtctgaa    780

actaaagata caactgcgtt atcactgcat aaccaaaacg ttgagcctag tgcgggtgat    840

tgggttcctc ccacaccgtt cctgacccgg atcaaaatcg cttatgccaa atatgatggc    900

agctggagta cacccaccat tctgcgcgaa gacaatctgc aataccggat ggcccagatg    960

gttgctgtga tggatataca gcaagacccg cataacccgt ttctggctct ggttccgttt   1020

gtccgtcttc aggggacaga taagaaaggt aaggattatg attatgacga agccttcggt   1080

tatgtctgcg atacactgct ggtagaaatt actgatttgc cggatgacga atatgctgat   1140

ggacgaaaag gaaaatatgt cggcaacctg gtctggtatt actcacgtga acacaaggat   1200

gcagaaggca atcctatcga ttaccgtact atggtgctct atccggcaac ccgggaagaa   1260

cgctttccta ttgccggaga agccaaaccg gaaggaagcc ctgattttgg caaagacagt   1320

atcaaactga ttgtcaattt tgttcatggc actgatgaca cactggagat tgtcgctcaa   1380

tctgacttta agtttggtgc gatagaagat catcaatatt acaacggttc tttccggctg   1440

atgcacgata atactgtctt ggatgaacaa ccactggtac tgaacgaaaa agttcctgat   1500

ttaacctatc catcaatcaa gctggggtcg gataatcgaa tcaccctgaa agccgaactt   1560

ctctttaagc ccaaaggtgg tgttggcaat gaaagtgcca gctgtactca agagttcaga   1620

atcggtatgc acattcgcga actgattaaa ctcaatgaac aggatcaggt gcaattcctt   1680
```

-continued

```
tccttccccg cagatgaaac tggtaacgcg ccacaaaaca ttcgccttaa tacactgttt   1740
gcaaaaaaac tgatcgccat tgccagtcag ggtatcccgc aggtactgag ctggaataca   1800
cagcttatta ctgaacaacc catacccggt tcattcccta cgccgattga tttaaatggc   1860
gcaaatggga tctatttctg ggaactgttt ttccatatgc catttctggt cgcgtggcga   1920
ctgaatatcg aacaacgatt aaaagaggcc accgaatggc tgcactatat ttttaatccg   1980
ctggaagatg aacttgttca ggccagcaac caaggtaaac cgcgttactg gaattcacgg   2040
ccaattattg atcctccacc caccgtgtac cggatgttaa ttgaaccaac cgatccggat   2100
gccattgcag ccagtgaacc cattcactac cggaaagcaa tattccgttt ctatgtcaag   2160
aatctgttag atcagggaga catggaatac cgtaagctga catccagtgc acgtactgtc   2220
gccaagcaga tctatgactc cgtcaatatg ttactgggta ccagccctga tattctgctc   2280
gcggcaaact ggcaaccccg tacgctgcaa gatgtggctc tgtatgaaaa cagtgaagca   2340
cgggcacagg agttaatgct tactgtcagc agcgtgccac ttctgcctgt gacatatgat   2400
acatccgtct ctgccgcacc gtctgattta tttgtcaaac ctgttgatac ggaatatctc   2460
aaactgtggc aaatgttgga tcagcgtcta tataacttac gtcataacct gaccttggat   2520
ggtaaagagt ttccggccgg attatacgat gaacccatca gcccgcaaga tctgctcagg   2580
cagcgttacc agcgtgttgt ggctaatcgt atggcgggca tgaaacgccg ggcaatcccg   2640
aattatcgtt tcaccccgat catgagccgg gcaaaagagg ccgcagaaac gctgattcag   2700
tacggcagca cgttactgag tttgctggag aaaaaagaca ataccgattt tgaacacttc   2760
cgtatgcagc agcaactggg gctgtacagc tttacccgca atctgcaaca gcaagcgatt   2820
gacatgcaac aggcttcatt ggatgcactg accatcagcc gacgggccgc tcaggagcgc   2880
cagcaacact ataaatcgct ctatgatgaa aacatctcca tcaccgagca ggaagttatc   2940
gcattacaat caagagcggc tgaaggtgtg atcgctgccc agtcagccgc cactgcggcc   3000
gctgtggcgg atatggttcc caatattttc ggtctggccg tcggggggat ggtctttggc   3060
ggtatgcttc gggcaatcgg tgaaggaata cgcattgacg ttgaaagtaa aaatgccaaa   3120
gccaccagcc tgagcgtgtc agaaaattac cgtcgccgtc agcaagaatg ggagctgcaa   3180
tacaaacagg cggatatcaa cattgaggag atcgacgcac agattggtat ccagcaacgc   3240
caactgaata tcagcacaac ccaactggca caattggaag cccagcatga gcaggatcaa   3300
gtcctgctgg agtactattc aaaccgtttt accaatgatg cgttatacat gtggatgatc   3360
agccaaatct ccgggcttta cctgcaagcc tatgatgcgg ttaattccct ctgtttactg   3420
gccgaagcct cctggcagta cgaaacaggt cagtatgata tgaatttcgt ccaaagtggt   3480
ctctggaatg atctttatca ggggctgctg gtcggagaac atctgaaatt agccttacaa   3540
cggatggatc aggcgtattt gcaacataac accagacgtc tggagatcat aaaaaccata   3600
tcggtaaaat cattactgac atcatcacag tgggaaattg gcaagagtac gggttcattc   3660
actttcttac tgagcgccga aatgttcttg cgcgattatc cgacccacgc tgatcggcgt   3720
ataaaaaccg tagcgctgtc attgcccgca ttgctggggc cttatgaaga tgtacgggct   3780
tcactggtac aactcagcaa tacgctttac agtactgctg acttaaaaac tatcgattat   3840
ttgcttaacc ccttggaata caccaaaccc gaaaacgttt tgctgaacgt acaggctaat   3900
caaggtgtgg tgatttcaac ggccatggaa gacagcggca tgttcaggct caattttgat   3960
gatgaacttt tcctgccttt tgaagggaca ggcgccattt cacagtggaa gttggaattc   4020
ggttccgatc aggatcagct gctggagtcg ctgagcgata ttatcctcca tctgcgttat   4080
```

```
accgcgcgtg atgtgagtgg cggaagtaat gagttcagcc agcaggttcg tagccgtctg   4140

aataaacatc aattaaaaca agacaattct aac                                4173


<210> SEQ ID NO 10
<211> LENGTH: 1391
<212> TYPE: PRT
<213> ORGANISM: Xenorhabdus nematophilus

<400> SEQUENCE: 10

Met Ser Ser Val Thr Gln Pro Ile Glu Glu Arg Leu Leu Glu Ser Gln
1               5                   10                  15

Arg Asp Ala Leu Leu Asp Phe Tyr Leu Gly Gln Val Val Ala Tyr Ser
            20                  25                  30

Pro Asp Met Thr Ser Gln Arg Asp Lys Ile Lys Asp Ile Asp Asp Ala
        35                  40                  45

Cys Asp Tyr Leu Leu Leu Asp Leu Leu Thr Ser Ala Lys Val Lys Ala
    50                  55                  60

Thr Arg Leu Ser Leu Ala Thr Asn Ser Leu Gln Gln Phe Val Asn Arg
65                  70                  75                  80

Val Ser Leu Asn Ile Glu Pro Gly Leu Phe Met Thr Ala Glu Glu Ser
                85                  90                  95

Glu Asn Trp Gln Glu Phe Ala Asn Arg Tyr Asn Tyr Trp Ser Ala Asp
            100                 105                 110

Arg Leu Leu Arg Thr Tyr Pro Glu Ser Tyr Leu Glu Pro Leu Leu Arg
        115                 120                 125

Leu Asn Lys Thr Glu Phe Phe Phe Gln Leu Glu Ser Ala Leu Asn Gln
    130                 135                 140

Gly Lys Ile Thr Glu Asp Ser Val Gln Gln Ala Val Leu Gly Tyr Leu
145                 150                 155                 160

Asn Asn Phe Glu Asp Val Ser Asn Leu Lys Val Ile Ala Gly Tyr Glu
                165                 170                 175

Asp Gly Val Asn Ile Lys Arg Asp Lys Phe Phe Phe Val Gly Arg Thr
            180                 185                 190

Arg Thr Gln Pro Tyr Gln Tyr Tyr Trp Arg Ser Leu Asn Leu Ser Ile
        195                 200                 205

Arg His Pro Asp Thr Asp Ala Leu Ser Pro Asn Ala Trp Ser Glu Trp
    210                 215                 220

Lys Pro Ile Asp Leu Pro Leu Gly Ser Val Asp Pro Asn Leu Ile Arg
225                 230                 235                 240

Pro Ile Phe Leu Asn Asn Arg Leu Tyr Ile Ala Trp Thr Glu Val Glu
                245                 250                 255

Glu Gln Ser Glu Thr Lys Asp Thr Thr Ala Leu Ser Leu His Asn Gln
            260                 265                 270

Asn Val Glu Pro Ser Ala Gly Asp Trp Val Pro Pro Thr Pro Phe Leu
        275                 280                 285

Thr Arg Ile Lys Ile Ala Tyr Ala Lys Tyr Asp Gly Ser Trp Ser Thr
    290                 295                 300

Pro Thr Ile Leu Arg Glu Asp Asn Leu Gln Tyr Arg Met Ala Gln Met
305                 310                 315                 320

Val Ala Val Met Asp Ile Gln Gln Asp Pro His Asn Pro Phe Leu Ala
                325                 330                 335

Leu Val Pro Phe Val Arg Leu Gln Gly Thr Asp Lys Lys Gly Lys Asp
            340                 345                 350

Tyr Asp Tyr Asp Glu Ala Phe Gly Tyr Val Cys Asp Thr Leu Leu Val
        355                 360                 365
```

```
Glu Ile Thr Asp Leu Pro Asp Asp Glu Tyr Ala Asp Gly Arg Lys Gly
    370                 375                 380

Lys Tyr Val Gly Asn Leu Val Trp Tyr Tyr Ser Arg Glu His Lys Asp
385                 390                 395                 400

Ala Glu Gly Asn Pro Ile Asp Tyr Arg Thr Met Val Leu Tyr Pro Ala
                405                 410                 415

Thr Arg Glu Glu Arg Phe Pro Ile Ala Gly Glu Ala Lys Pro Glu Gly
            420                 425                 430

Ser Pro Asp Phe Gly Lys Asp Ser Ile Lys Leu Ile Val Asn Phe Val
        435                 440                 445

His Gly Thr Asp Asp Thr Leu Glu Ile Val Ala Gln Ser Asp Phe Lys
    450                 455                 460

Phe Gly Ala Ile Glu Asp His Gln Tyr Tyr Asn Gly Ser Phe Arg Leu
465                 470                 475                 480

Met His Asp Asn Thr Val Leu Asp Glu Gln Pro Leu Val Leu Asn Glu
                485                 490                 495

Lys Val Pro Asp Leu Thr Tyr Pro Ser Ile Lys Leu Gly Ser Asp Asn
            500                 505                 510

Arg Ile Thr Leu Lys Ala Glu Leu Leu Phe Lys Pro Lys Gly Gly Val
        515                 520                 525

Gly Asn Glu Ser Ala Ser Cys Thr Gln Glu Phe Arg Ile Gly Met His
    530                 535                 540

Ile Arg Glu Leu Ile Lys Leu Asn Glu Gln Asp Gln Val Gln Phe Leu
545                 550                 555                 560

Ser Phe Pro Ala Asp Glu Thr Gly Asn Ala Pro Gln Asn Ile Arg Leu
                565                 570                 575

Asn Thr Leu Phe Ala Lys Lys Leu Ile Ala Ile Ala Ser Gln Gly Ile
            580                 585                 590

Pro Gln Val Leu Ser Trp Asn Thr Gln Leu Ile Thr Glu Gln Pro Ile
        595                 600                 605

Pro Gly Ser Phe Pro Thr Pro Ile Asp Leu Asn Gly Ala Asn Gly Ile
    610                 615                 620

Tyr Phe Trp Glu Leu Phe Phe His Met Pro Phe Leu Val Ala Trp Arg
625                 630                 635                 640

Leu Asn Ile Glu Gln Arg Leu Lys Glu Ala Thr Glu Trp Leu His Tyr
                645                 650                 655

Ile Phe Asn Pro Leu Glu Asp Glu Leu Val Gln Ala Ser Asn Gln Gly
            660                 665                 670

Lys Pro Arg Tyr Trp Asn Ser Arg Pro Ile Ile Asp Pro Pro Pro Thr
        675                 680                 685

Val Tyr Arg Met Leu Ile Glu Pro Thr Asp Pro Asp Ala Ile Ala Ala
    690                 695                 700

Ser Glu Pro Ile His Tyr Arg Lys Ala Ile Phe Arg Phe Tyr Val Lys
705                 710                 715                 720

Asn Leu Leu Asp Gln Gly Asp Met Glu Tyr Arg Lys Leu Thr Ser Ser
                725                 730                 735

Ala Arg Thr Val Ala Lys Gln Ile Tyr Asp Ser Val Asn Met Leu Leu
            740                 745                 750

Gly Thr Ser Pro Asp Ile Leu Leu Ala Ala Asn Trp Gln Pro Arg Thr
        755                 760                 765

Leu Gln Asp Val Ala Leu Tyr Glu Asn Ser Glu Ala Arg Ala Gln Glu
    770                 775                 780

Leu Met Leu Thr Val Ser Ser Val Pro Leu Leu Pro Val Thr Tyr Asp
```

-continued 785 790 795 800

Thr Ser Val Ser Ala Ala Pro Ser Asp Leu Phe Val Lys Pro Val Asp
805 810 815

Thr Glu Tyr Leu Lys Leu Trp Gln Met Leu Asp Gln Arg Leu Tyr Asn
820 825 830

Leu Arg His Asn Leu Thr Leu Asp Gly Lys Glu Phe Pro Ala Gly Leu
835 840 845

Tyr Asp Glu Pro Ile Ser Pro Gln Asp Leu Leu Arg Gln Arg Tyr Gln
850 855 860

Arg Val Val Ala Asn Arg Met Ala Gly Met Lys Arg Arg Ala Ile Pro
865 870 875 880

Asn Tyr Arg Phe Thr Pro Ile Met Ser Arg Ala Lys Glu Ala Ala Glu
885 890 895

Thr Leu Ile Gln Tyr Gly Ser Thr Leu Leu Ser Leu Leu Glu Lys Lys
900 905 910

Asp Asn Thr Asp Phe Glu His Phe Arg Met Gln Gln Gln Leu Gly Leu
915 920 925

Tyr Ser Phe Thr Arg Asn Leu Gln Gln Gln Ala Ile Asp Met Gln Gln
930 935 940

Ala Ser Leu Asp Ala Leu Thr Ile Ser Arg Arg Ala Ala Gln Glu Arg
945 950 955 960

Gln Gln His Tyr Lys Ser Leu Tyr Asp Glu Asn Ile Ser Ile Thr Glu
965 970 975

Gln Glu Val Ile Ala Leu Gln Ser Arg Ala Ala Glu Gly Val Ile Ala
980 985 990

Ala Gln Ser Ala Ala Thr Ala Ala Ala Val Ala Asp Met Val Pro Asn
995 1000 1005

Ile Phe Gly Leu Ala Val Gly Gly Met Val Phe Gly Gly Met Leu
1010 1015 1020

Arg Ala Ile Gly Glu Gly Ile Arg Ile Asp Val Glu Ser Lys Asn
1025 1030 1035

Ala Lys Ala Thr Ser Leu Ser Val Ser Glu Asn Tyr Arg Arg Arg
1040 1045 1050

Gln Gln Glu Trp Glu Leu Gln Tyr Lys Gln Ala Asp Ile Asn Ile
1055 1060 1065

Glu Glu Ile Asp Ala Gln Ile Gly Ile Gln Gln Arg Gln Leu Asn
1070 1075 1080

Ile Ser Thr Thr Gln Leu Ala Gln Leu Glu Ala Gln His Glu Gln
1085 1090 1095

Asp Gln Val Leu Leu Glu Tyr Tyr Ser Asn Arg Phe Thr Asn Asp
1100 1105 1110

Ala Leu Tyr Met Trp Met Ile Ser Gln Ile Ser Gly Leu Tyr Leu
1115 1120 1125

Gln Ala Tyr Asp Ala Val Asn Ser Leu Cys Leu Leu Ala Glu Ala
1130 1135 1140

Ser Trp Gln Tyr Glu Thr Gly Gln Tyr Asp Met Asn Phe Val Gln
1145 1150 1155

Ser Gly Leu Trp Asn Asp Leu Tyr Gln Gly Leu Leu Val Gly Glu
1160 1165 1170

His Leu Lys Leu Ala Leu Gln Arg Met Asp Gln Ala Tyr Leu Gln
1175 1180 1185

His Asn Thr Arg Arg Leu Glu Ile Ile Lys Thr Ile Ser Val Lys
1190 1195 1200

-continued

```
Ser Leu  Leu Thr Ser Ser Gln  Trp Glu Ile Gly Lys  Ser Thr Gly
    1205                 1210                 1215

Ser Phe  Thr Phe Leu Leu Ser  Ala Glu Met Phe Leu  Arg Asp Tyr
    1220                 1225                 1230

Pro Thr  His Ala Asp Arg Arg  Ile Lys Thr Val Ala  Leu Ser Leu
    1235                 1240                 1245

Pro Ala  Leu Leu Gly Pro Tyr  Glu Asp Val Arg Ala  Ser Leu Val
    1250                 1255                 1260

Gln Leu  Ser Asn Thr Leu Tyr  Ser Thr Ala Asp Leu  Lys Thr Ile
    1265                 1270                 1275

Asp Tyr  Leu Leu Asn Pro Leu  Glu Tyr Thr Lys Pro  Glu Asn Val
    1280                 1285                 1290

Leu Leu  Asn Val Gln Ala Asn  Gln Gly Val Val Ile  Ser Thr Ala
    1295                 1300                 1305

Met Glu  Asp Ser Gly Met Phe  Arg Leu Asn Phe Asp  Asp Glu Leu
    1310                 1315                 1320

Phe Leu  Pro Phe Glu Gly Thr  Gly Ala Ile Ser Gln  Trp Lys Leu
    1325                 1330                 1335

Glu Phe  Gly Ser Asp Gln Asp  Gln Leu Leu Glu Ser  Leu Ser Asp
    1340                 1345                 1350

Ile Ile  Leu His Leu Arg Tyr  Thr Ala Arg Asp Val  Ser Gly Gly
    1355                 1360                 1365

Ser Asn  Glu Phe Ser Gln Gln  Val Arg Ser Arg Leu  Asn Lys His
    1370                 1375                 1380

Gln Leu  Lys Gln Asp Asn Ser  Asn
    1385                 1390
```

<210> SEQ ID NO 11
<211> LENGTH: 1944
<212> TYPE: DNA
<213> ORGANISM: Xenorhabdus nematophilus

<400> SEQUENCE: 11

```
atgtctcaaa atgtttatcg atacccttca attaaagcga tgtctgacgc cagcagcgaa      60
gtaggcgcat ctctggttgc ctggcagaat caatctggtg gtcaaacctg gtatgtcatt     120
tatgatagcg cggtttttaa aaacatcggc tgggttgaac gctggcatat tcccgaccgc     180
aatatttcac ctgatttacc ggtttatgag aatgcctggc aatatgtccg tgaggcgaca     240
ccggaagaaa ttgccgatca cggtaacccc aatacgcctg atgtaccgcc gggagaaaaa     300
accgaggtat tgcaatatga tgcactcaca gaagaaacct atcagaaggt gggatataaa     360
cctgacggca gcggaactcc tttgagttat tcttcagcac gtgttgccaa gtccctgtac     420
aacgaatatg aagttgatcc ggaaaataca gaaccgctgc ctaaagtctc tgcctatatt     480
actgactggt gccagtatga tgcgcgtttg tcgccagaaa cccaggataa cactgcgctg     540
accagcgacg atgcccccgg ccgtggtttt gatctggaaa aaatcccgcc taccgcctac     600
gaccgcctga ttttcagttt tatggccgtc aacggtgata aaggcaagtt atccgaacgg     660
attaatgagg ttgttgacgg gtggaaccgg caagcagaag ccagcagtgg ccagattgcc     720
cctattacat taggccatat tgtacccgtt gatccttatg gtgatttagg caccacacgc     780
aatgtcggtc tggacgcgga tcagcgccgt gatgccagcc cgaagaattt cttgcaatat     840
tacaatcagg atgcagcctc cggtttactg gggggattgc gtaatctgaa agcgcgagca     900
aaacaggcag ggcacaagct ggaactcgca ttcagtatcg gcggctggag tatgtcaggg     960
tatttctctg tgatggccaa agatcctgag caacgtgcta catttgtgag tagcatcgtc    1020
```

-continued

```
gacttcttcc ggcgttttcc catgtttact gcggtggata tcgactggga ataccccggc   1080

gccacaggtg aagaaggtaa tgaattcgac ccggaacatg atggcccaaa ctatgttttg   1140

ttagtgaaag agctgcgtga agcactgaac atcgcctttg gaacccgggc ccgtaaagaa   1200

atcacgatag cctgtagcgc cgtcgttgcc aaaatggaga agtccagctt caaagaaatc   1260

gcaccttatt tagacaatat ctttgtgatg acctacgact tctttggtac cggttgggca   1320

gaatacatcg gtcaccatac taacctgtat ccccccagat atgaatatga cggcgataac   1380

cctcctccgc ccaatcctga tcgggacatg gattactcgg ctgatgaggc gatccgcttt   1440

ttactgtcac aaggtgtaca accggagaaa attcacctcg gatttgctaa ctatggacgt   1500

tcatgtctgg gtgctgatct gacaactcgc cgctataaca gaacaggaga gccactgggc   1560

acgatggaaa aaggtgctcc ggaattcttc tgtctgctga ataaccaata cgatgcggaa   1620

tatgaaattg cacgcgggaa aaatcagttt gaactggtga cagacacgga aaccgacgct   1680

gacgcactct ttaatgctga cggtggtcac tggatttcac tggatacgcc ccgcactgtg   1740

ctgcataagg gaatttatgc aaccaaaatg aaattgggcg ggatcttctc ttggtcaggc   1800

gatcaggatg atggcctgtt ggcaaatgct gctcacgaag gtttgggtta cttacctgta   1860

cgcggaaaag agaagattga tatgggaccg ttatataaca aaggacgtct cattcagctt   1920

cctaaagtaa cccgtcgtaa atcg                                          1944


<210> SEQ ID NO 12
<211> LENGTH: 648
<212> TYPE: PRT
<213> ORGANISM: Xenorhabdus nematophilus

<400> SEQUENCE: 12

Met Ser Gln Asn Val Tyr Arg Tyr Pro Ser Ile Lys Ala Met Ser Asp
1               5                   10                  15

Ala Ser Ser Glu Val Gly Ala Ser Leu Val Ala Trp Gln Asn Gln Ser
            20                  25                  30

Gly Gly Gln Thr Trp Tyr Val Ile Tyr Asp Ser Ala Val Phe Lys Asn
        35                  40                  45

Ile Gly Trp Val Glu Arg Trp His Ile Pro Asp Arg Asn Ile Ser Pro
    50                  55                  60

Asp Leu Pro Val Tyr Glu Asn Ala Trp Gln Tyr Val Arg Glu Ala Thr
65                  70                  75                  80

Pro Glu Glu Ile Ala Asp His Gly Asn Pro Asn Thr Pro Asp Val Pro
                85                  90                  95

Pro Gly Glu Lys Thr Glu Val Leu Gln Tyr Asp Ala Leu Thr Glu Glu
            100                 105                 110

Thr Tyr Gln Lys Val Gly Tyr Lys Pro Asp Gly Ser Gly Thr Pro Leu
        115                 120                 125

Ser Tyr Ser Ser Ala Arg Val Ala Lys Ser Leu Tyr Asn Glu Tyr Glu
    130                 135                 140

Val Asp Pro Glu Asn Thr Glu Pro Leu Pro Lys Val Ser Ala Tyr Ile
145                 150                 155                 160

Thr Asp Trp Cys Gln Tyr Asp Ala Arg Leu Ser Pro Glu Thr Gln Asp
                165                 170                 175

Asn Thr Ala Leu Thr Ser Asp Asp Ala Pro Gly Arg Gly Phe Asp Leu
            180                 185                 190

Glu Lys Ile Pro Pro Thr Ala Tyr Asp Arg Leu Ile Phe Ser Phe Met
        195                 200                 205
```

-continued

```
Ala Val Asn Gly Asp Lys Gly Lys Leu Ser Glu Arg Ile Asn Glu Val
    210                 215                 220

Val Asp Gly Trp Asn Arg Gln Ala Glu Ala Ser Ser Gly Gln Ile Ala
225                 230                 235                 240

Pro Ile Thr Leu Gly His Ile Val Pro Val Asp Pro Tyr Gly Asp Leu
                245                 250                 255

Gly Thr Thr Arg Asn Val Gly Leu Asp Ala Asp Gln Arg Arg Asp Ala
            260                 265                 270

Ser Pro Lys Asn Phe Leu Gln Tyr Tyr Asn Gln Asp Ala Ala Ser Gly
        275                 280                 285

Leu Leu Gly Gly Leu Arg Asn Leu Lys Ala Arg Ala Lys Gln Ala Gly
    290                 295                 300

His Lys Leu Glu Leu Ala Phe Ser Ile Gly Gly Trp Ser Met Ser Gly
305                 310                 315                 320

Tyr Phe Ser Val Met Ala Lys Asp Pro Glu Gln Arg Ala Thr Phe Val
                325                 330                 335

Ser Ser Ile Val Asp Phe Phe Arg Arg Phe Pro Met Phe Thr Ala Val
            340                 345                 350

Asp Ile Asp Trp Glu Tyr Pro Gly Ala Thr Gly Glu Glu Gly Asn Glu
        355                 360                 365

Phe Asp Pro Glu His Asp Gly Pro Asn Tyr Val Leu Leu Val Lys Glu
    370                 375                 380

Leu Arg Glu Ala Leu Asn Ile Ala Phe Gly Thr Arg Ala Arg Lys Glu
385                 390                 395                 400

Ile Thr Ile Ala Cys Ser Ala Val Val Ala Lys Met Glu Lys Ser Ser
                405                 410                 415

Phe Lys Glu Ile Ala Pro Tyr Leu Asp Asn Ile Phe Val Met Thr Tyr
            420                 425                 430

Asp Phe Phe Gly Thr Gly Trp Ala Glu Tyr Ile Gly His His Thr Asn
        435                 440                 445

Leu Tyr Pro Pro Arg Tyr Glu Tyr Asp Gly Asp Asn Pro Pro Pro Pro
    450                 455                 460

Asn Pro Asp Arg Asp Met Asp Tyr Ser Ala Asp Glu Ala Ile Arg Phe
465                 470                 475                 480

Leu Leu Ser Gln Gly Val Gln Pro Glu Lys Ile His Leu Gly Phe Ala
                485                 490                 495

Asn Tyr Gly Arg Ser Cys Leu Gly Ala Asp Leu Thr Thr Arg Arg Tyr
            500                 505                 510

Asn Arg Thr Gly Glu Pro Leu Gly Thr Met Glu Lys Gly Ala Pro Glu
        515                 520                 525

Phe Phe Cys Leu Leu Asn Asn Gln Tyr Asp Ala Glu Tyr Glu Ile Ala
    530                 535                 540

Arg Gly Lys Asn Gln Phe Glu Leu Val Thr Asp Thr Glu Thr Asp Ala
545                 550                 555                 560

Asp Ala Leu Phe Asn Ala Asp Gly Gly His Trp Ile Ser Leu Asp Thr
                565                 570                 575

Pro Arg Thr Val Leu His Lys Gly Ile Tyr Ala Thr Lys Met Lys Leu
            580                 585                 590

Gly Gly Ile Phe Ser Trp Ser Gly Asp Gln Asp Asp Gly Leu Leu Ala
        595                 600                 605

Asn Ala Ala His Glu Gly Leu Gly Tyr Leu Pro Val Arg Gly Lys Glu
    610                 615                 620

Lys Ile Asp Met Gly Pro Leu Tyr Asn Lys Gly Arg Leu Ile Gln Leu
625                 630                 635                 640
```

Pro Lys Val Thr Arg Arg Lys Ser
645

<210> SEQ ID NO 13
<211> LENGTH: 7569
<212> TYPE: DNA
<213> ORGANISM: Xenorhabdus nematophilus

<400> SEQUENCE: 13
atgataaaag ttaatgaact gttagataag ataaatagaa aaaggtctgg tgatacttta 60
ttattgacaa acatttcgtt tatgtctttc agcgaatttc gtcataggac aagtggaact 120
ctgacgtggc gagaaacaga ctttttatat caacaggctc atcaggaatc aaaacagaat 180
aaacttgaag aactgcgcat tttgtcccgt gctaatccac aactggctaa taccactaac 240
cttaatatta caccgtcaac cctaaacaat agttacaaca gttggtttta tggccgtgcc 300
caccgttttg taaaaccggg atcaattgct tccatatttt caccagcggc ttatttaaca 360
gaattatatc gggaagcgaa agattttcat cctgacaatt ctcaatatca cctgaataaa 420
cgacgccccg acattgcttc actggcactg acacagaata atatggatga agaaatttcc 480
acattatcct tatctaatga attactgctg cataatattc agacgttaga gaaaactgac 540
tataacggtg taatgaaaat gttgtccact taccggcaaa ccggcatgac accctatcat 600
ctgccgtatg agtcagcccg tcaggcaatt ttattgcaag ataaaaacct caccgcattt 660
agccgtaata cagacgtagc ggaattaatg gacccaacat cgctactggc tattaagact 720
gatatatcgc ctgaattgta tcaaatcctt gtagaagaaa ttacaccgga aaattcaaca 780
gaactgatga agaaaaattt cggtacagat gatgtactga tttttaagag ttatgcttct 840
ttggctcgct actacgattt gtcttatgat gaactcagtt tatttgtcaa tctctccttc 900
ggtaagaaaa atacaaatca acagtataag aatgagcaac tgataacatt ggtcaatgac 960
gggaatgata cggcaacggc aagattgatt aagcgaaccc gcaaagattt ctacgattca 1020
catttaaact atgcagaact aattccaatc aaagaaaatg aatacaaata taatttcagt 1080
gtaaaaaaaa cagaacctga ccacttggat tttcgtctcc agaatggaga taaagaatat 1140
atataccaag ataaaaattt cgtccccatt gctaataccc attacagtat tcccattaaa 1200
ttgacgacag agcaaatcac caacggtata acactccgct tatggcgagt taaaccaaat 1260
ccgtcggatg ctatcaatgc caatgcatac tttaaaatga tggagttccc cggtgatata 1320
ttcctgttaa agctgaataa agcgattcgt ttgtataaag ccacaggcat atctccagaa 1380
gatatctggc aagtaataga aagtatttat gatgacttaa ccattgacag caatgtgttg 1440
ggtaagctgt tttatgttca atattatatg cagcactata atattagcgt cagcgatgcg 1500
ctggtattgt gtcattcaga tatcagccaa tattccacta aacaacaacc cagtcatttt 1560
acaatactgt tcaatacacc gctattaaat ggccaagagt tttctgctga taataccaaa 1620
ctggatttaa cccccggtga atcaaaaaac cattttttatt tgggaataat gaaacgtgct 1680
ttcagagtga atgatactga actgtataca ttatggaagc tggctaatgg cggaacaaat 1740
ccagaattta tgtgttccat cgagaacctg tctctgcttt atcgcgttcg tctgctggca 1800
gacattcatc atctgacagt gaatgaatta tccatgttgt tgtcggtttc tccctatgtg 1860
aacacgaaaa ttgccctttt ttctgataca gcattaacgc aattaatcag ctttctgttc 1920
caatgcaccc agtggctgac aacacagaaa tggtctgtca gtgatgtgtt tctgatgacc 1980
acggataatt acagcactgt ccttacgccg gatattgaaa accttatcac gacactaagt 2040

-continued

```
aatggattat caacactttc actcggtgat gacgaactga tccgtgcagc tgccccgctg   2100
attgctgcca gcattcaaat ggattcagcc aagacagcag aaactatttt gctgtggatt   2160
aatcagataa aaccacaagg actgacattc gatgatttca tgattattgc ggctaaccgt   2220
gatcgctcag agaatgaaac cagcaacatg gtggcttttt gtcaggtact ggggcaactt   2280
tctctgattg tgcgcaatat tggactcagc gaaaacgaac tgaccctgtt ggtgacaaaa   2340
ccggagaaat tccaatcaga aaccacagca ctgcaacatg atctccccac tttgcaagcg   2400
ctgacccgct tccatgctgt gatcatgcgt tgtggaagct acgcgacaga aatcttaaca   2460
gcattggaac taggagcgct gactgccgaa caattggcgg tggcgttaaa atttgatgct   2520
caggttgtga cacaagcatt gcaacagacc ggtttgggag tgaatacctt taccaactgg   2580
agaactatag atgtcactct gcaatggctg gatgtcgctg ctacattggg tattaccccg   2640
gatggtgttg ctgcactcat aaaattaaaa tatatcggtg aaccagaaac cccgatgcca   2700
acatttgatg attggcaagc cgccagtact ttgttgcagg cgggactgaa cagtcaacaa   2760
tccgaccagc ttcaggcatg gctggatgaa gccacgacga cagcggccag tgcttactac   2820
atcaaaaata gtgcacctca acagattaag agccgggatg agttgtacag ctatctgctg   2880
attgataacc aagtttctgc ccaagtgaaa accacccgtg tggcagaagc cattgccagc   2940
attcagttat atgtcaaccg ggcgttgaat aatgttgaag gaaaagtatc aaagccagtg   3000
aaaacccgtc agttcttctg cgactgggaa acctacaatc gacggtatag cacctgggcc   3060
ggcgtatctg aactggccta ttatccggaa aactatatcg accccacgat tcgtattggt   3120
cagacaggta tgatgaacaa cctgttacag caactttccc aaagtcagtt aaatatcgat   3180
accgttgaag atagctttaa aaattatctg accgcatttg aagatgtcgc taacttgcag   3240
gtgattagcg gatatcatga cagtatcaat gtcaatgagg gactcactta tttaattggt   3300
tatagccaga cagaacccag aatatattat tggcgcaatg tcgatcacca aaagtgccag   3360
cacggtcaat ttgctgccaa tgcctgggga gaatggaaaa aaattgaaat acccatcaat   3420
gtatggcagg aaaatatcag acctgttatt tacaagtctc gtttgtattt actgtggctg   3480
gaacaaaaag agctgaaaaa tgaaagtgaa gatggcaaga tagatatcac tgattatata   3540
ttaaaactgt cacatattcg ttatgatggc agctggagct caccgtttaa ttttaatgtg   3600
actgataaaa tagaaaacct gatcaataaa aaagccagca ttggtatgta ttgttcttct   3660
gattatgaaa aagacgtcat tattgtttat ttccatgaga aaaaagacaa ttattctttt   3720
aatagtcttc ctgcaagaga agggatgacc attaaccctg atatgacatt atccattctc   3780
acagaaaatg atttagacgc cattgttaag agcacattat cagaacttga taccaggaca   3840
gaatacaaag tcaacaatca atttgctaca gattatttgg ccgaatataa ggaatctata   3900
accacaaaaa ataaattagc cagttttacc ggaaatattt ttgatctctc gtatatatca   3960
ccaggaaatg gtcatattaa tttaacgttc aatccttcaa tggaaattaa tttttcaaaa   4020
ggcaatatat ataatgatga ggttaaatac ctgttatcga tggtagaaga tgaaacggtt   4080
attttatttg attatgatag acatgatgaa atgcttggaa aagaagaaga agtttttcat   4140
tatggaactt tggattttat tatttccatc gatcttaaaa atgccgaata ttttagagtg   4200
ttaatgcatc taagaaccaa ggaaaaaatt cctagaaaat cagaaattgg agttggtata   4260
aattatgatt atgaatcaaa tgatgctgaa ttcaaacttg atactaacat agtattagat   4320
tggaaagata acacaggagt atggcatact atatgtgaat catttactaa tgatgtttca   4380
atcattaata acatgggaaa tattgcggca ctgttccttc gcgaggatcc atgtgtgtat   4440
```

-continued

```
ttatgttcaa tagccacaga tataaaaatt gcttcatcta tgatcgaaca gatccaagat   4500
aaaaacatta gtttttttatt aaaaaatggc tctgatattc tagtggagtt aaatgctgaa   4560
gaccatgtgg catctaaacc ttcacacgaa tctgacccta tggtatatga ttttaatcaa   4620
gtaaaagttg atattgaagg ctatgatatt cctctggtga gcgagtttat tattaagcaa   4680
cccgacggcg gttataacga tattgttatt gaatcgccaa ttcatataaa actaaaatcc   4740
aaagatacaa gtaacgttat atcactgcat aaaatgccat caggcacaca atatatgcag   4800
attggccctt acagaacccg gttaaatact ttattttcca gaaaattagc tgaaagagcc   4860
aatattggta ttgataatgt tttaagtatg gaaacgcaaa atttaccaga gccgcaatta   4920
ggtgaagggt tttatgcgac atttaagttg ccccccctaca ataaagagga gcatggtgat   4980
gaacgttggt ttaagatcca tattgggaat attgatggca attctgccag acaaccttat   5040
tacgaaggaa tgttatctga tattgaaacc acagtaacgc tctttgttcc ctatgctaaa   5100
ggatattaca tacgtgaagg tgtcagatta ggggttgggt acaaaaaaat tatctatgac   5160
aaatcctggg aatctgcttt cttttatttt gatgagacga aaaatcaatt tatattcatt   5220
aatgatgccg atcatgattc gggaatgaca caacagggga tagtaaaaaa tatcaaaaaa   5280
tataaagggt ttattcatgt cgttgtcatg aaaaataaca ctgaacccat ggatttcaac   5340
ggcgccaatg caatctattt ctgggaattg ttctattaca cgcccatgat ggtattccag   5400
cgcttattgc aagagcagaa ttttaccgaa tcgacacgct ggctgcgcta tatctggaac   5460
ccggccggat attcggttca gggtgaaatg caggattatt actggaacgt ccgcccattg   5520
gaggaagata cgtcctggaa tgccaatccg ctggattcgg tcgatcctga cgccgttgcc   5580
cagcatgatc cgatgcacta taaagtggct acctttatga aaatgctgga tttgttgatt   5640
acccgcggag atagcgccta tcgccagctt gaacgtgata ccttaaacga agctaaaatg   5700
tggtatgtac aggcgctcac tttattgggt gatgagcctt atttttcatt ggataacgat   5760
tggtcagagc cacggctgga agaagctgcc agccaaacaa tgcggcatca ttatcaacat   5820
aaaatgctgc aactgcgtca gcgcgctgca ttacccacga aacgtacggc aaattcgtta   5880
accgcattgt tcctccctca aattaataaa aaactgcaag gttactggca gacattgacg   5940
caacgcctct ataacttacg ccataacctg acaatcgacg gtcagccact gtcattatct   6000
ctctatgcca cgcccgcaga tccgtccatg ttactcagtg ctgccatcac tgcttcacaa   6060
ggcggcggcg atttacctca tgcagtgatg ccgatgtacc gttttccggt gattctggaa   6120
aatgccaagt ggggggtaag ccagttgata caatttggca ataccctgct cagcattact   6180
gaacggcagg atgcagaagc cttggctgaa atactgcaaa ctcaaggcag tgagttagcc   6240
ctgcaaagta ttaaaatgca ggataaggtc atggctgaaa ttgatgctga taaattggcg   6300
cttcaagaaa gccgtcatgg tgcacagtct cgttttgaca gtttcaatac gctgtacgac   6360
gaagatgtta acgctggtga aaaacaagcg atggatcttt acctctcttc atcggtcttg   6420
agcaccagcg gcacagccct gcatatggcc gccgccgcgg cagatctcgt ccccaatatt   6480
tacggttttg ctgtgggagg ttcccgtttt ggggcgcttt tcaatgccag tgcgattggt   6540
atcgaaattt ctgcgtcagc aacacgtatt gccgcagaca aaatcagcca atcagaaata   6600
taccgtcgcc gtcggcaaga gtgggaaatt cagcgcaata atgcggaagc tgagataaaa   6660
caaattgatg ctcaattagc gacgctggct gtacgtcgtg aagcggcagt attacaaaaa   6720
aactatctgg aaactcagca ggcacaaact caggcgcagt tagcctttct gcaaagtaaa   6780
ttcagtaatg cagcgctata caactggctc cgtggaaggt tgtccgctat ttattatcag   6840
```

```
ttttatgatt tggcggtctc actctgttta atggcagagc aaacttatca gtatgaattg   6900

aataatgcgg cagcacactt tattaaacca ggtgcctggc atgggactta tgcgggttta   6960

ttagcgggtg aaaccctgat gctgaattta gcacagatgg aaaaaagcta tttggaaaaa   7020

gatgaacggg cactggaggt caccagaacc gtttctctgg ctgaagtgta tgctggtctg   7080

acagaaaata gtttcatttt aaaagataaa gtgactgagt tagtcaatgc aggtgaaggc   7140

agtgcaggca caacgcttaa cggtttgaac gtcgaaggga cacaactgca agccagcctc   7200

aaattatcgg atctgaatat tgctaccgat tatcctgacg gtttaggtaa tacacgccgt   7260

atcaaacaaa tcagtgtgac attacctgcc cttttagggc cttatcagga tgttcgggca   7320

atactaagtt atggcggcag cacaatgatg ccacgtggct gcaaagcgat tgcgatctca   7380

catggcatga atgacagtgg tcaattccag atggatttca atgatgccaa gtacctgcca   7440

tttgaagggc ttcctgtggc cgatacaggc acattaaccc tcagttttcc cggtatcagt   7500

ggtaaacaga aaagcttatt gctcagcctg agcgatatca ttctgcatat ccgttacacc   7560

attcgttct                                                           7569
```

<210> SEQ ID NO 14
<211> LENGTH: 2523
<212> TYPE: PRT
<213> ORGANISM: Xenorhabdus nematophilus

<400> SEQUENCE: 14

```
Met Ile Lys Val Asn Glu Leu Leu Asp Lys Ile Asn Arg Lys Arg Ser
1               5                   10                  15

Gly Asp Thr Leu Leu Leu Thr Asn Ile Ser Phe Met Ser Phe Ser Glu
            20                  25                  30

Phe Arg His Arg Thr Ser Gly Thr Leu Thr Trp Arg Glu Thr Asp Phe
        35                  40                  45

Leu Tyr Gln Gln Ala His Gln Glu Ser Lys Gln Asn Lys Leu Glu Glu
    50                  55                  60

Leu Arg Ile Leu Ser Arg Ala Asn Pro Gln Leu Ala Asn Thr Thr Asn
65                  70                  75                  80

Leu Asn Ile Thr Pro Ser Thr Leu Asn Asn Ser Tyr Asn Ser Trp Phe
                85                  90                  95

Tyr Gly Arg Ala His Arg Phe Val Lys Pro Gly Ser Ile Ala Ser Ile
            100                 105                 110

Phe Ser Pro Ala Ala Tyr Leu Thr Glu Leu Tyr Arg Glu Ala Lys Asp
        115                 120                 125

Phe His Pro Asp Asn Ser Gln Tyr His Leu Asn Lys Arg Arg Pro Asp
    130                 135                 140

Ile Ala Ser Leu Ala Leu Thr Gln Asn Asn Met Asp Glu Glu Ile Ser
145                 150                 155                 160

Thr Leu Ser Leu Ser Asn Glu Leu Leu Leu His Asn Ile Gln Thr Leu
                165                 170                 175

Glu Lys Thr Asp Tyr Asn Gly Val Met Lys Met Leu Ser Thr Tyr Arg
            180                 185                 190

Gln Thr Gly Met Thr Pro Tyr His Leu Pro Tyr Glu Ser Ala Arg Gln
        195                 200                 205

Ala Ile Leu Leu Gln Asp Lys Asn Leu Thr Ala Phe Ser Arg Asn Thr
    210                 215                 220

Asp Val Ala Glu Leu Met Asp Pro Thr Ser Leu Leu Ala Ile Lys Thr
225                 230                 235                 240

Asp Ile Ser Pro Glu Leu Tyr Gln Ile Leu Val Glu Glu Ile Thr Pro
```

```
                245                 250                 255

Glu Asn Ser Thr Glu Leu Met Lys Lys Asn Phe Gly Thr Asp Asp Val
            260                 265                 270

Leu Ile Phe Lys Ser Tyr Ala Ser Leu Ala Arg Tyr Tyr Asp Leu Ser
        275                 280                 285

Tyr Asp Glu Leu Ser Leu Phe Val Asn Leu Ser Phe Gly Lys Lys Asn
    290                 295                 300

Thr Asn Gln Gln Tyr Lys Asn Glu Gln Leu Ile Thr Leu Val Asn Asp
305                 310                 315                 320

Gly Asn Asp Thr Ala Thr Ala Arg Leu Ile Lys Arg Thr Arg Lys Asp
                325                 330                 335

Phe Tyr Asp Ser His Leu Asn Tyr Ala Glu Leu Ile Pro Ile Lys Glu
            340                 345                 350

Asn Glu Tyr Lys Tyr Asn Phe Ser Val Lys Lys Thr Glu Pro Asp His
        355                 360                 365

Leu Asp Phe Arg Leu Gln Asn Gly Asp Lys Glu Tyr Ile Tyr Gln Asp
    370                 375                 380

Lys Asn Phe Val Pro Ile Ala Asn Thr His Tyr Ser Ile Pro Ile Lys
385                 390                 395                 400

Leu Thr Thr Glu Gln Ile Thr Asn Gly Ile Thr Leu Arg Leu Trp Arg
                405                 410                 415

Val Lys Pro Asn Pro Ser Asp Ala Ile Asn Ala Asn Ala Tyr Phe Lys
            420                 425                 430

Met Met Glu Phe Pro Gly Asp Ile Phe Leu Leu Lys Leu Asn Lys Ala
        435                 440                 445

Ile Arg Leu Tyr Lys Ala Thr Gly Ile Ser Pro Glu Asp Ile Trp Gln
    450                 455                 460

Val Ile Glu Ser Ile Tyr Asp Asp Leu Thr Ile Asp Ser Asn Val Leu
465                 470                 475                 480

Gly Lys Leu Phe Tyr Val Gln Tyr Tyr Met Gln His Tyr Asn Ile Ser
                485                 490                 495

Val Ser Asp Ala Leu Val Leu Cys His Ser Asp Ile Ser Gln Tyr Ser
            500                 505                 510

Thr Lys Gln Gln Pro Ser His Phe Thr Ile Leu Phe Asn Thr Pro Leu
        515                 520                 525

Leu Asn Gly Gln Glu Phe Ser Ala Asp Asn Thr Lys Leu Asp Leu Thr
    530                 535                 540

Pro Gly Glu Ser Lys Asn His Phe Tyr Leu Gly Ile Met Lys Arg Ala
545                 550                 555                 560

Phe Arg Val Asn Asp Thr Glu Leu Tyr Thr Leu Trp Lys Leu Ala Asn
                565                 570                 575

Gly Gly Thr Asn Pro Glu Phe Met Cys Ser Ile Glu Asn Leu Ser Leu
            580                 585                 590

Leu Tyr Arg Val Arg Leu Leu Ala Asp Ile His His Leu Thr Val Asn
        595                 600                 605

Glu Leu Ser Met Leu Leu Ser Val Ser Pro Tyr Val Asn Thr Lys Ile
    610                 615                 620

Ala Leu Phe Ser Asp Thr Ala Leu Thr Gln Leu Ile Ser Phe Leu Phe
625                 630                 635                 640

Gln Cys Thr Gln Trp Leu Thr Thr Gln Lys Trp Ser Val Ser Asp Val
                645                 650                 655

Phe Leu Met Thr Thr Asp Asn Tyr Ser Thr Val Leu Thr Pro Asp Ile
            660                 665                 670
```

```
Glu Asn Leu Ile Thr Thr Leu Ser Asn Gly Leu Ser Thr Leu Ser Leu
        675                 680                 685

Gly Asp Asp Glu Leu Ile Arg Ala Ala Ala Pro Leu Ile Ala Ala Ser
    690                 695                 700

Ile Gln Met Asp Ser Ala Lys Thr Ala Glu Thr Ile Leu Leu Trp Ile
705                 710                 715                 720

Asn Gln Ile Lys Pro Gln Gly Leu Thr Phe Asp Asp Phe Met Ile Ile
                725                 730                 735

Ala Ala Asn Arg Asp Arg Ser Glu Asn Glu Thr Ser Asn Met Val Ala
            740                 745                 750

Phe Cys Gln Val Leu Gly Gln Leu Ser Leu Ile Val Arg Asn Ile Gly
        755                 760                 765

Leu Ser Glu Asn Glu Leu Thr Leu Leu Val Thr Lys Pro Glu Lys Phe
    770                 775                 780

Gln Ser Glu Thr Thr Ala Leu Gln His Asp Leu Pro Thr Leu Gln Ala
785                 790                 795                 800

Leu Thr Arg Phe His Ala Val Ile Met Arg Cys Gly Ser Tyr Ala Thr
                805                 810                 815

Glu Ile Leu Thr Ala Leu Glu Leu Gly Ala Leu Thr Ala Glu Gln Leu
            820                 825                 830

Ala Val Ala Leu Lys Phe Asp Ala Gln Val Val Thr Gln Ala Leu Gln
        835                 840                 845

Gln Thr Gly Leu Gly Val Asn Thr Phe Thr Asn Trp Arg Thr Ile Asp
    850                 855                 860

Val Thr Leu Gln Trp Leu Asp Val Ala Ala Thr Leu Gly Ile Thr Pro
865                 870                 875                 880

Asp Gly Val Ala Ala Leu Ile Lys Leu Lys Tyr Ile Gly Glu Pro Glu
                885                 890                 895

Thr Pro Met Pro Thr Phe Asp Asp Trp Gln Ala Ala Ser Thr Leu Leu
            900                 905                 910

Gln Ala Gly Leu Asn Ser Gln Gln Ser Asp Gln Leu Gln Ala Trp Leu
        915                 920                 925

Asp Glu Ala Thr Thr Thr Ala Ala Ser Ala Tyr Tyr Ile Lys Asn Ser
    930                 935                 940

Ala Pro Gln Gln Ile Lys Ser Arg Asp Glu Leu Tyr Ser Tyr Leu Leu
945                 950                 955                 960

Ile Asp Asn Gln Val Ser Ala Gln Val Lys Thr Thr Arg Val Ala Glu
                965                 970                 975

Ala Ile Ala Ser Ile Gln Leu Tyr Val Asn Arg Ala Leu Asn Asn Val
            980                 985                 990

Glu Gly Lys Val Ser Lys Pro Val  Lys Thr Arg Gln Phe  Phe Cys Asp
        995                 1000                1005

Trp Glu  Thr Tyr Asn Arg Arg  Tyr Ser Thr Trp Ala  Gly Val Ser
    1010                1015                1020

Glu Leu  Ala Tyr Tyr Pro Glu  Asn Tyr Ile Asp Pro  Thr Ile Arg
    1025                1030                1035

Ile Gly  Gln Thr Gly Met Met  Asn Asn Leu Leu Gln  Gln Leu Ser
    1040                1045                1050

Gln Ser  Gln Leu Asn Ile Asp  Thr Val Glu Asp Ser  Phe Lys Asn
    1055                1060                1065

Tyr Leu  Thr Ala Phe Glu Asp  Val Ala Asn Leu Gln  Val Ile Ser
    1070                1075                1080

Gly Tyr  His Asp Ser Ile Asn  Val Asn Glu Gly Leu  Thr Tyr Leu
    1085                1090                1095
```

```
Ile Gly  Tyr Ser Gln Thr Glu  Pro Arg Ile Tyr Tyr  Trp Arg Asn
    1100                 1105                 1110

Val Asp  His Gln Lys Cys Gln  His Gly Gln Phe Ala  Ala Asn Ala
    1115                 1120                 1125

Trp Gly  Glu Trp Lys Lys Ile  Glu Ile Pro Ile Asn  Val Trp Gln
    1130                 1135                 1140

Glu Asn  Ile Arg Pro Val Ile  Tyr Lys Ser Arg Leu  Tyr Leu Leu
    1145                 1150                 1155

Trp Leu  Glu Gln Lys Glu Leu  Lys Asn Glu Ser Glu  Asp Gly Lys
    1160                 1165                 1170

Ile Asp  Ile Thr Asp Tyr Ile  Leu Lys Leu Ser His  Ile Arg Tyr
    1175                 1180                 1185

Asp Gly  Ser Trp Ser Ser Pro  Phe Asn Phe Asn Val  Thr Asp Lys
    1190                 1195                 1200

Ile Glu  Asn Leu Ile Asn Lys  Lys Ala Ser Ile Gly  Met Tyr Cys
    1205                 1210                 1215

Ser Ser  Asp Tyr Glu Lys Asp  Val Ile Ile Val Tyr  Phe His Glu
    1220                 1225                 1230

Lys Lys  Asp Asn Tyr Ser Phe  Asn Ser Leu Pro Ala  Arg Glu Gly
    1235                 1240                 1245

Met Thr  Ile Asn Pro Asp Met  Thr Leu Ser Ile Leu  Thr Glu Asn
    1250                 1255                 1260

Asp Leu  Asp Ala Ile Val Lys  Ser Thr Leu Ser Glu  Leu Asp Thr
    1265                 1270                 1275

Arg Thr  Glu Tyr Lys Val Asn  Asn Gln Phe Ala Thr  Asp Tyr Leu
    1280                 1285                 1290

Ala Glu  Tyr Lys Glu Ser Ile  Thr Thr Lys Asn Lys  Leu Ala Ser
    1295                 1300                 1305

Phe Thr  Gly Asn Ile Phe Asp  Leu Ser Tyr Ile Ser  Pro Gly Asn
    1310                 1315                 1320

Gly His  Ile Asn Leu Thr Phe  Asn Pro Ser Met Glu  Ile Asn Phe
    1325                 1330                 1335

Ser Lys  Gly Asn Ile Tyr Asn  Asp Glu Val Lys Tyr  Leu Leu Ser
    1340                 1345                 1350

Met Val  Glu Asp Glu Thr Val  Ile Leu Phe Asp Tyr  Asp Arg His
    1355                 1360                 1365

Asp Glu  Met Leu Gly Lys Glu  Glu Glu Val Phe His  Tyr Gly Thr
    1370                 1375                 1380

Leu Asp  Phe Ile Ile Ser Ile  Asp Leu Lys Asn Ala  Glu Tyr Phe
    1385                 1390                 1395

Arg Val  Leu Met His Leu Arg  Thr Lys Glu Lys Ile  Pro Arg Lys
    1400                 1405                 1410

Ser Glu  Ile Gly Val Gly Ile  Asn Tyr Asp Tyr Glu  Ser Asn Asp
    1415                 1420                 1425

Ala Glu  Phe Lys Leu Asp Thr  Asn Ile Val Leu Asp  Trp Lys Asp
    1430                 1435                 1440

Asn Thr  Gly Val Trp His Thr  Ile Cys Glu Ser Phe  Thr Asn Asp
    1445                 1450                 1455

Val Ser  Ile Ile Asn Asn Met  Gly Asn Ile Ala Ala  Leu Phe Leu
    1460                 1465                 1470

Arg Glu  Asp Pro Cys Val Tyr  Leu Cys Ser Ile Ala  Thr Asp Ile
    1475                 1480                 1485

Lys Ile  Ala Ser Ser Met Ile  Glu Gln Ile Gln Asp  Lys Asn Ile
```

-continued 1490 1495 1500

Ser Phe Leu Leu Lys Asn Gly Ser Asp Ile Leu Val Glu Leu Asn
1505 1510 1515

Ala Glu Asp His Val Ala Ser Lys Pro Ser His Glu Ser Asp Pro
1520 1525 1530

Met Val Tyr Asp Phe Asn Gln Val Lys Val Asp Ile Glu Gly Tyr
1535 1540 1545

Asp Ile Pro Leu Val Ser Glu Phe Ile Ile Lys Gln Pro Asp Gly
1550 1555 1560

Gly Tyr Asn Asp Ile Val Ile Glu Ser Pro Ile His Ile Lys Leu
1565 1570 1575

Lys Ser Lys Asp Thr Ser Asn Val Ile Ser Leu His Lys Met Pro
1580 1585 1590

Ser Gly Thr Gln Tyr Met Gln Ile Gly Pro Tyr Arg Thr Arg Leu
1595 1600 1605

Asn Thr Leu Phe Ser Arg Lys Leu Ala Glu Arg Ala Asn Ile Gly
1610 1615 1620

Ile Asp Asn Val Leu Ser Met Glu Thr Gln Asn Leu Pro Glu Pro
1625 1630 1635

Gln Leu Gly Glu Gly Phe Tyr Ala Thr Phe Lys Leu Pro Pro Tyr
1640 1645 1650

Asn Lys Glu Glu His Gly Asp Glu Arg Trp Phe Lys Ile His Ile
1655 1660 1665

Gly Asn Ile Asp Gly Asn Ser Ala Arg Gln Pro Tyr Tyr Glu Gly
1670 1675 1680

Met Leu Ser Asp Ile Glu Thr Thr Val Thr Leu Phe Val Pro Tyr
1685 1690 1695

Ala Lys Gly Tyr Tyr Ile Arg Glu Gly Val Arg Leu Gly Val Gly
1700 1705 1710

Tyr Lys Lys Ile Ile Tyr Asp Lys Ser Trp Glu Ser Ala Phe Phe
1715 1720 1725

Tyr Phe Asp Glu Thr Lys Asn Gln Phe Ile Phe Ile Asn Asp Ala
1730 1735 1740

Asp His Asp Ser Gly Met Thr Gln Gln Gly Ile Val Lys Asn Ile
1745 1750 1755

Lys Lys Tyr Lys Gly Phe Ile His Val Val Val Met Lys Asn Asn
1760 1765 1770

Thr Glu Pro Met Asp Phe Asn Gly Ala Asn Ala Ile Tyr Phe Trp
1775 1780 1785

Glu Leu Phe Tyr Tyr Thr Pro Met Met Val Phe Gln Arg Leu Leu
1790 1795 1800

Gln Glu Gln Asn Phe Thr Glu Ser Thr Arg Trp Leu Arg Tyr Ile
1805 1810 1815

Trp Asn Pro Ala Gly Tyr Ser Val Gln Gly Glu Met Gln Asp Tyr
1820 1825 1830

Tyr Trp Asn Val Arg Pro Leu Glu Glu Asp Thr Ser Trp Asn Ala
1835 1840 1845

Asn Pro Leu Asp Ser Val Asp Pro Asp Ala Val Ala Gln His Asp
1850 1855 1860

Pro Met His Tyr Lys Val Ala Thr Phe Met Lys Met Leu Asp Leu
1865 1870 1875

Leu Ile Thr Arg Gly Asp Ser Ala Tyr Arg Gln Leu Glu Arg Asp
1880 1885 1890

```
Thr Leu  Asn Glu Ala Lys Met  Trp Tyr Val Gln Ala  Leu Thr Leu
    1895                 1900                 1905

Leu Gly  Asp Glu Pro Tyr Phe  Ser Leu Asp Asn Asp  Trp Ser Glu
    1910                 1915                 1920

Pro Arg  Leu Glu Glu Ala Ala  Ser Gln Thr Met Arg  His His Tyr
    1925                 1930                 1935

Gln His  Lys Met Leu Gln Leu  Arg Gln Arg Ala Ala  Leu Pro Thr
    1940                 1945                 1950

Lys Arg  Thr Ala Asn Ser Leu  Thr Ala Leu Phe Leu  Pro Gln Ile
    1955                 1960                 1965

Asn Lys  Lys Leu Gln Gly Tyr  Trp Gln Thr Leu Thr  Gln Arg Leu
    1970                 1975                 1980

Tyr Asn  Leu Arg His Asn Leu  Thr Ile Asp Gly Gln  Pro Leu Ser
    1985                 1990                 1995

Leu Ser  Leu Tyr Ala Thr Pro  Ala Asp Pro Ser Met  Leu Leu Ser
    2000                 2005                 2010

Ala Ala  Ile Thr Ala Ser Gln  Gly Gly Gly Asp Leu  Pro His Ala
    2015                 2020                 2025

Val Met  Pro Met Tyr Arg Phe  Pro Val Ile Leu Glu  Asn Ala Lys
    2030                 2035                 2040

Trp Gly  Val Ser Gln Leu Ile  Gln Phe Gly Asn Thr  Leu Leu Ser
    2045                 2050                 2055

Ile Thr  Glu Arg Gln Asp Ala  Glu Ala Leu Ala Glu  Ile Leu Gln
    2060                 2065                 2070

Thr Gln  Gly Ser Glu Leu Ala  Leu Gln Ser Ile Lys  Met Gln Asp
    2075                 2080                 2085

Lys Val  Met Ala Glu Ile Asp  Ala Asp Lys Leu Ala  Leu Gln Glu
    2090                 2095                 2100

Ser Arg  His Gly Ala Gln Ser  Arg Phe Asp Ser Phe  Asn Thr Leu
    2105                 2110                 2115

Tyr Asp  Glu Asp Val Asn Ala  Gly Glu Lys Gln Ala  Met Asp Leu
    2120                 2125                 2130

Tyr Leu  Ser Ser Ser Val Leu  Ser Thr Ser Gly Thr  Ala Leu His
    2135                 2140                 2145

Met Ala  Ala Ala Ala Ala Asp  Leu Val Pro Asn Ile  Tyr Gly Phe
    2150                 2155                 2160

Ala Val  Gly Gly Ser Arg Phe  Gly Ala Leu Phe Asn  Ala Ser Ala
    2165                 2170                 2175

Ile Gly  Ile Glu Ile Ser Ala  Ser Ala Thr Arg Ile  Ala Ala Asp
    2180                 2185                 2190

Lys Ile  Ser Gln Ser Glu Ile  Tyr Arg Arg Arg Arg  Gln Glu Trp
    2195                 2200                 2205

Glu Ile  Gln Arg Asn Asn Ala  Glu Ala Glu Ile Lys  Gln Ile Asp
    2210                 2215                 2220

Ala Gln  Leu Ala Thr Leu Ala  Val Arg Arg Glu Ala  Ala Val Leu
    2225                 2230                 2235

Gln Lys  Asn Tyr Leu Glu Thr  Gln Gln Ala Gln Thr  Gln Ala Gln
    2240                 2245                 2250

Leu Ala  Phe Leu Gln Ser Lys  Phe Ser Asn Ala Ala  Leu Tyr Asn
    2255                 2260                 2265

Trp Leu  Arg Gly Arg Leu Ser  Ala Ile Tyr Tyr Gln  Phe Tyr Asp
    2270                 2275                 2280

Leu Ala  Val Ser Leu Cys Leu  Met Ala Glu Gln Thr  Tyr Gln Tyr
    2285                 2290                 2295
```

```
Glu Leu  Asn Asn Ala Ala Ala  His Phe Ile Lys Pro  Gly Ala Trp
    2300                 2305                 2310

His Gly  Thr Tyr Ala Gly Leu  Leu Ala Gly Glu Thr  Leu Met Leu
    2315                 2320                 2325

Asn Leu  Ala Gln Met Glu Lys  Ser Tyr Leu Glu Lys  Asp Glu Arg
    2330                 2335                 2340

Ala Leu  Glu Val Thr Arg Thr  Val Ser Leu Ala Glu  Val Tyr Ala
    2345                 2350                 2355

Gly Leu  Thr Glu Asn Ser Phe  Ile Leu Lys Asp Lys  Val Thr Glu
    2360                 2365                 2370

Leu Val  Asn Ala Gly Glu Gly  Ser Ala Gly Thr Thr  Leu Asn Gly
    2375                 2380                 2385

Leu Asn  Val Glu Gly Thr Gln  Leu Gln Ala Ser Leu  Lys Leu Ser
    2390                 2395                 2400

Asp Leu  Asn Ile Ala Thr Asp  Tyr Pro Asp Gly Leu  Gly Asn Thr
    2405                 2410                 2415

Arg Arg  Ile Lys Gln Ile Ser  Val Thr Leu Pro Ala  Leu Leu Gly
    2420                 2425                 2430

Pro Tyr  Gln Asp Val Arg Ala  Ile Leu Ser Tyr Gly  Gly Ser Thr
    2435                 2440                 2445

Met Met  Pro Arg Gly Cys Lys  Ala Ile Ala Ile Ser  His Gly Met
    2450                 2455                 2460

Asn Asp  Ser Gly Gln Phe Gln  Met Asp Phe Asn Asp  Ala Lys Tyr
    2465                 2470                 2475

Leu Pro  Phe Glu Gly Leu Pro  Val Ala Asp Thr Gly  Thr Leu Thr
    2480                 2485                 2490

Leu Ser  Phe Pro Gly Ile Ser  Gly Lys Gln Lys Ser  Leu Leu Leu
    2495                 2500                 2505

Ser Leu  Ser Asp Ile Ile Leu  His Ile Arg Tyr Thr  Ile Arg Ser
    2510                 2515                 2520
```

<210> SEQ ID NO 15
<211> LENGTH: 3048
<212> TYPE: DNA
<213> ORGANISM: Xenorhabdus nematophilus

<400> SEQUENCE: 15

```
atgaagaatt tcgttcacag caatacgcca tccgtcaccg tactggacaa ccgtggtcag     60

acagtacgcg aaatagcctg gtatcggcac cccgatacac ctcaggtaac cgatgaacgc    120

atcaccggtt atcaatatga tgctcaagga tctctgactc agagtattga tccgcgattt    180

tatgaacgcc agcagacagc gagtgacaag aacgccatta cacccaatct tattctcttg    240

tcatcactca gtaagaaggc attgcgtacg caaagtgtgg atgccggaac ccgtgtcgcc    300

ctgcatgatg ttgccgggcg tcccgtttta gctgtcagcg ccaatggcgt tagccgaacg    360

tttcagtatg aaagtgataa ccttccggga cgattgctaa cgattaccga gcaggtaaaa    420

ggagagaacg cctgtatcac ggagcgattg atctggtcag gaaatacgcc ggcagaaaaa    480

ggcaataatc tggccggcca gtgcgtggtc cattatgatc ccaccggaat gaatcaaacc    540

aacagcatat cgttaaccag catacccttg tccatcacac agcaattact gaaagatgac    600

agcgaagccg attggcacgg tatggatgaa tctggctgga aaaacgcgct ggcgccggaa    660

agcttcactt ctgtcagcac aacggatgct accggcacgg tattaacgag tacagatgct    720

gccggaaaca agcaacgtat cgcctatgat gtggccggtc tgcttcaagg cagttggttg    780
```

-continued

```
gcgctgaagg ggaaacaaga acaagttatc gtgaaatccc tgacctattc ggctgccagc    840
cagaagctac gggaggaaca tggtaacggg atagtgacta catataccta tgaacccgag    900
acgcaacgag ttattggcat aaaaacagaa cgtccttccg gtcatgccgc tggggagaaa    960
attttacaaa acctgcgtta tgaatatgat cctgtcggaa atgtgctgaa atcaactaat   1020
gatgctgaaa ttacccgctt ttggcgcaac cagaaaattg taccggaaaa tacttacacc   1080
tatgacagcc tgtaccagct ggtttccgtc actgggcgtg aaatggcgaa tattggccga   1140
caaaaaaacc agttacccat ccccgctctg attgataaca atacttatac gaattactct   1200
cgcacttacg actatgatcg tgggggaaat ctgaccagaa ttcgccataa ttcaccgatc   1260
accggtaata actatacaac gaacatgacc gtttcagatc acagcaaccg ggctgtactg   1320
gaagagctgg cgcaagatcc cactcaggtg gatatgttgt tcacccccgg cgggcatcag   1380
acccggcttg ttcccggtca ggatcttttc tggacacccc gtgacgaatt gcaacaagtg   1440
atattggtca atagggaaaa tacgacgcct gatcaggaat tctaccgtta tgatgcagac   1500
agtcagcgtg tcattaagac tcatattcag aagacaggta acagtgagca aatacagcga   1560
acattatatt tgccagagct ggaatggcgc acgacatata gcggcaatac attaaaagag   1620
tttttgcagg tcatcactgt cggtgaatcg ggtcaggcac aagtgcgggt gctgcattgg   1680
gaaacaggca aaccggcgga tatcagcaat gatcagctgc gctacagtta tggcaacctg   1740
attggcagta gcgggctgga attggacagt gacgggcaga tcattagtca ggaagaatat   1800
taccccctatg gggaaccgc cgtgtgggca gcccgaagtc agtcagaagc tgattacaaa   1860
accgtgcgtt attctggcaa agagcgggat gcaacagggt tgtattacta cggttatcgt   1920
tattatcaat cgtggacagg gcgatggttg agtgtagatc ctgccggtga ggtcgatggt   1980
ctcaatttgt tccgaatgtg caggaataac ccccatcgttt tttctgattc tgatggtcgt   2040
ttccccggtc agggtgtcct tgcctggata gggaaaaaag cgtatcgaaa ggcagtcaac   2100
atcacgacag aacacctgct tgaacaaggc gcttcctttg atacgttctt gaaattaaac   2160
cgaggattgc gaacgtttgt tttgggtgtg ggggtagcaa gtctgggggt gaaggcggcc   2220
acgattgcag gagcgtcgcc ttgggggatt gtcggggctg ccattggtgg ttttgtctcc   2280
ggggcggtga tggggttttt cgcgaacaac atctcagaaa aaattgggga agttttaagt   2340
tatctgacgc gtaaacgttc tgttcctgtt caggttggcg cttttgttgt cacatcgctt   2400
gtgacgtctg cactatttaa cagctcttcg acaggtaccg ccatttccgc agcaacagcg   2460
gtcaccgttg gaggattaat ggctttagcc ggagagcata acacgggcat ggctatcagt   2520
attgccacac ccgccggaca aggtacgctg gatacgctca ggcccggtaa tgtcagcgcg   2580
ccagagcggt taggggcact atcaggcgca attattggcg gcatattact tggccgccat   2640
cagggaagtt ctgagctggg tgaacgggca gcgattggtg ctatgtatgg tgctcgatgg   2700
ggaaggatca ttggtaatct atgggatggc ccttatcggt ttatcggcag gttactgctc   2760
agaagaggca ttagctctgc catttcccac gctgtcagtt ccaggagctg gtttggccga   2820
atgataggag aaagtgtcgg gagaaatatt tctgaagtat tattacctta tagccgtaca   2880
cccggtgaat gggttggtgc agccattggc gggacagccg cggccgctca tcatgccgtt   2940
ggaggggaag ttgccaatgc cgctagccgg gttacctgga gcggctttaa gcgggctttt   3000
aataacttct tctttaacgc ctctgcacgt cataatgaat ccgaagca               3048
```

<210> SEQ ID NO 16
<211> LENGTH: 1016
<212> TYPE: PRT

<213> ORGANISM: Xenorhabdus nematophilus

<400> SEQUENCE: 16

```
Met Lys Asn Phe Val His Ser Asn Thr Pro Ser Val Thr Val Leu Asp
1               5                   10                  15

Asn Arg Gly Gln Thr Val Arg Glu Ile Ala Trp Tyr Arg His Pro Asp
            20                  25                  30

Thr Pro Gln Val Thr Asp Glu Arg Ile Thr Gly Tyr Gln Tyr Asp Ala
        35                  40                  45

Gln Gly Ser Leu Thr Gln Ser Ile Asp Pro Arg Phe Tyr Glu Arg Gln
    50                  55                  60

Gln Thr Ala Ser Asp Lys Asn Ala Ile Thr Pro Asn Leu Ile Leu Leu
65                  70                  75                  80

Ser Ser Leu Ser Lys Lys Ala Leu Arg Thr Gln Ser Val Asp Ala Gly
                85                  90                  95

Thr Arg Val Ala Leu His Asp Val Ala Gly Arg Pro Val Leu Ala Val
            100                 105                 110

Ser Ala Asn Gly Val Ser Arg Thr Phe Gln Tyr Glu Ser Asp Asn Leu
        115                 120                 125

Pro Gly Arg Leu Leu Thr Ile Thr Glu Gln Val Lys Gly Glu Asn Ala
    130                 135                 140

Cys Ile Thr Glu Arg Leu Ile Trp Ser Gly Asn Thr Pro Ala Glu Lys
145                 150                 155                 160

Gly Asn Asn Leu Ala Gly Gln Cys Val Val His Tyr Asp Pro Thr Gly
                165                 170                 175

Met Asn Gln Thr Asn Ser Ile Ser Leu Thr Ser Ile Pro Leu Ser Ile
            180                 185                 190

Thr Gln Gln Leu Leu Lys Asp Asp Ser Glu Ala Asp Trp His Gly Met
        195                 200                 205

Asp Glu Ser Gly Trp Lys Asn Ala Leu Ala Pro Glu Ser Phe Thr Ser
    210                 215                 220

Val Ser Thr Thr Asp Ala Thr Gly Thr Val Leu Thr Ser Thr Asp Ala
225                 230                 235                 240

Ala Gly Asn Lys Gln Arg Ile Ala Tyr Asp Val Ala Gly Leu Leu Gln
                245                 250                 255

Gly Ser Trp Leu Ala Leu Lys Gly Lys Gln Glu Gln Val Ile Val Lys
            260                 265                 270

Ser Leu Thr Tyr Ser Ala Ala Ser Gln Lys Leu Arg Glu Glu His Gly
        275                 280                 285

Asn Gly Ile Val Thr Thr Tyr Thr Tyr Glu Pro Glu Thr Gln Arg Val
    290                 295                 300

Ile Gly Ile Lys Thr Glu Arg Pro Ser Gly His Ala Ala Gly Glu Lys
305                 310                 315                 320

Ile Leu Gln Asn Leu Arg Tyr Glu Tyr Asp Pro Val Gly Asn Val Leu
                325                 330                 335

Lys Ser Thr Asn Asp Ala Glu Ile Thr Arg Phe Trp Arg Asn Gln Lys
            340                 345                 350

Ile Val Pro Glu Asn Thr Tyr Thr Tyr Asp Ser Leu Tyr Gln Leu Val
        355                 360                 365

Ser Val Thr Gly Arg Glu Met Ala Asn Ile Gly Arg Gln Lys Asn Gln
    370                 375                 380

Leu Pro Ile Pro Ala Leu Ile Asp Asn Asn Thr Tyr Thr Asn Tyr Ser
385                 390                 395                 400

Arg Thr Tyr Asp Tyr Asp Arg Gly Gly Asn Leu Thr Arg Ile Arg His
```

-continued

```
                405                 410                 415

Asn Ser Pro Ile Thr Gly Asn Asn Tyr Thr Thr Asn Met Thr Val Ser
            420                 425                 430

Asp His Ser Asn Arg Ala Val Leu Glu Glu Leu Ala Gln Asp Pro Thr
        435                 440                 445

Gln Val Asp Met Leu Phe Thr Pro Gly Gly His Gln Thr Arg Leu Val
    450                 455                 460

Pro Gly Gln Asp Leu Phe Trp Thr Pro Arg Asp Glu Leu Gln Gln Val
465                 470                 475                 480

Ile Leu Val Asn Arg Glu Asn Thr Thr Pro Asp Gln Glu Phe Tyr Arg
                485                 490                 495

Tyr Asp Ala Asp Ser Gln Arg Val Ile Lys Thr His Ile Gln Lys Thr
            500                 505                 510

Gly Asn Ser Glu Gln Ile Gln Arg Thr Leu Tyr Leu Pro Glu Leu Glu
        515                 520                 525

Trp Arg Thr Thr Tyr Ser Gly Asn Thr Leu Lys Glu Phe Leu Gln Val
    530                 535                 540

Ile Thr Val Gly Glu Ser Gly Gln Ala Gln Val Arg Val Leu His Trp
545                 550                 555                 560

Glu Thr Gly Lys Pro Ala Asp Ile Ser Asn Asp Gln Leu Arg Tyr Ser
                565                 570                 575

Tyr Gly Asn Leu Ile Gly Ser Ser Gly Leu Glu Leu Asp Ser Asp Gly
            580                 585                 590

Gln Ile Ile Ser Gln Glu Glu Tyr Tyr Pro Tyr Gly Gly Thr Ala Val
        595                 600                 605

Trp Ala Ala Arg Ser Gln Ser Glu Ala Asp Tyr Lys Thr Val Arg Tyr
    610                 615                 620

Ser Gly Lys Glu Arg Asp Ala Thr Gly Leu Tyr Tyr Tyr Gly Tyr Arg
625                 630                 635                 640

Tyr Tyr Gln Ser Trp Thr Gly Arg Trp Leu Ser Val Asp Pro Ala Gly
                645                 650                 655

Glu Val Asp Gly Leu Asn Leu Phe Arg Met Cys Arg Asn Asn Pro Ile
            660                 665                 670

Val Phe Ser Asp Ser Asp Gly Arg Phe Pro Gly Gln Gly Val Leu Ala
        675                 680                 685

Trp Ile Gly Lys Lys Ala Tyr Arg Lys Ala Val Asn Ile Thr Thr Glu
    690                 695                 700

His Leu Leu Glu Gln Gly Ala Ser Phe Asp Thr Phe Leu Lys Leu Asn
705                 710                 715                 720

Arg Gly Leu Arg Thr Phe Val Leu Gly Val Gly Val Ala Ser Leu Gly
                725                 730                 735

Val Lys Ala Ala Thr Ile Ala Gly Ala Ser Pro Trp Gly Ile Val Gly
            740                 745                 750

Ala Ala Ile Gly Gly Phe Val Ser Gly Ala Val Met Gly Phe Phe Ala
        755                 760                 765

Asn Asn Ile Ser Glu Lys Ile Gly Glu Val Leu Ser Tyr Leu Thr Arg
    770                 775                 780

Lys Arg Ser Val Pro Val Gln Val Gly Ala Phe Val Val Thr Ser Leu
785                 790                 795                 800

Val Thr Ser Ala Leu Phe Asn Ser Ser Ser Thr Gly Thr Ala Ile Ser
                805                 810                 815

Ala Ala Thr Ala Val Thr Val Gly Gly Leu Met Ala Leu Ala Gly Glu
            820                 825                 830
```

His Asn Thr Gly Met Ala Ile Ser Ile Ala Thr Pro Ala Gly Gln Gly
835 840 845

Thr Leu Asp Thr Leu Arg Pro Gly Asn Val Ser Ala Pro Glu Arg Leu
850 855 860

Gly Ala Leu Ser Gly Ala Ile Ile Gly Gly Ile Leu Leu Gly Arg His
865 870 875 880

Gln Gly Ser Ser Glu Leu Gly Glu Arg Ala Ala Ile Gly Ala Met Tyr
885 890 895

Gly Ala Arg Trp Gly Arg Ile Ile Gly Asn Leu Trp Asp Gly Pro Tyr
900 905 910

Arg Phe Ile Gly Arg Leu Leu Leu Arg Arg Gly Ile Ser Ser Ala Ile
915 920 925

Ser His Ala Val Ser Ser Arg Ser Trp Phe Gly Arg Met Ile Gly Glu
930 935 940

Ser Val Gly Arg Asn Ile Ser Glu Val Leu Leu Pro Tyr Ser Arg Thr
945 950 955 960

Pro Gly Glu Trp Val Gly Ala Ala Ile Gly Gly Thr Ala Ala Ala Ala
965 970 975

His His Ala Val Gly Gly Glu Val Ala Asn Ala Ala Ser Arg Val Thr
980 985 990

Trp Ser Gly Phe Lys Arg Ala Phe Asn Asn Phe Phe Phe Asn Ala Ser
995 1000 1005

Ala Arg His Asn Glu Ser Glu Ala
1010 1015

<210> SEQ ID NO 17
<211> LENGTH: 4479
<212> TYPE: DNA
<213> ORGANISM: Xenorhabdus nematophilus

<400> SEQUENCE: 17
atgcagggtt caacaccttt gaaacttgaa ataccgtcat tgccctctgg gggcggatca 60
ctaaaaggaa tgggagaagc actcaatgcc gtcggagcgg aagggggagc gtcattttca 120
ctgcccttgc cgatctctgt cgggcgtggt ctggtgccgg tgctatcact gaattacagc 180
agtactgccg gcaatgggtc attcgggatg ggtggcaat gtggggttgg ttttatcagc 240
ctgcgtaccg ccaagggcgt tccgcactat acgggacaag atgagtatct cgggccggat 300
ggggaagtgt tgagtattgt gccggacagc caagggcaac cagagcaacg caccgcaacc 360
tcactgttgg ggacggttct gacacagccg catactgtta cccgctatca gtcccgcgtg 420
gcagaaaaaa tcgttcgttt agaacactgg cagccacagc agagacgtga ggaagagacg 480
tctttttggg tactttttac tgcggatggt ttagtgcacc tattcggtaa gcatcaccat 540
gcacgtattg ctgacccgca ggatgaaacc agaattgccc gctggctgat ggaggaaacc 600
gtcacgcata ccggggaaca tatttactat cactatcggg cagaagacga tcttgactgt 660
gatgagcatg aacttgctca gcattcaggt gttacggccc agcgttatct ggcaaaagtc 720
agctatggca atactcagcc ggaaaccgct tttttcgcgg taaaatcagg tattcctgct 780
gataatgact ggctgtttca tctggtattt gattacggtg agcgctcatc ttcgctgaac 840
tctgtacccg aattcaatgt gtcagaaaac aatgtgtctg aaaacaatgt gcctgaaaaa 900
tggcgttgtc gtccggacag tttctcccgc tatgaatatg ggtttgaaat tcgaacccgt 960
cgcttgtgtc gccaagttct gatgtttcat cagctgaaag cgctggcagg ggaaaaggtt 1020
gcagaagaaa caccggcgct ggtttcccgt cttattctgg attatgacct gaacaacaag 1080

-continued gtttccttgc tgcaaacggc ccgcagactg gcccatgaaa cggacggtac gccagtgatg 1140
atgtccccgc tggaaatgga ttatcaacgt gttaatcatg gcgtgaatct gaactggcag 1200
tccatgccgc agttagaaaa aatgaacacg ttgcagccat accaattggt tgatttatat 1260
ggagaaggaa tttccggcgt actttatcag gatactcaga aagcctggtg gtaccgtgct 1320
ccggtacggg atatcactgc cgaaggaacg aatgcggtta cctatgagga ggccaaacca 1380
ctgccacata ttccggcaca acaggaaagc gcgatgttgt tggacatcaa tggtgacggg 1440
cgtctggatt gggtgattac ggcatcaggg ttacggggct accacaccat gtcaccggaa 1500
ggtgaatgga cacccttat tccattatcc gctgtgccaa tggaatattt ccatccgcag 1560
gcaaaactgg ctgatattga tggggctggg ctgcctgact tagcgcttat cgggccaaat 1620
agtgtacgtg tctggtcaaa taatcgggca ggatgggatc gcgctcagga tgtgattcat 1680
ttgtcagata tgccactgcc ggttcccggc agaaatgagc gtcatcttgt cgcattcagt 1740
gatatgacag gctccgggca atcacatctg gtggaagtaa cggcagatag cgtgcgctac 1800
tggccgaacc tggggcatgg aaaatttggt gagcctctga tgatgacagg cttccagatt 1860
agcggggaaa cgtttaaccc cgacagactg tatatggtag acatagatgg ctcaggcacc 1920
accgatttta tttatgcccg caatacttac cttgaactct atgccaatga aagcggcaat 1980
cattttgctg aacctcagcg tattgatctg ccggatgggg tacgttttga tgatacttgt 2040
cggttacaaa tagcggatac acaaggatta gggactgcca gcattatttt gacgatcccc 2100
catatgaagg tgcagcactg gcgattggat atgaccatat tcaagccttg gctgctgaat 2160
gccgtcaata acaatatggg aacagaaacc acgctgtatt atcgcagctc tgcccagttc 2220
tggctggatg agaaattaca ggcttctgaa tccgggatga cggtggtcag ctacttaccg 2280
ttcccggtgc atgtgttgtg gcgcacggaa gtgctggatg aaatttccgg taaccgattg 2340
accagccatt atcattactc acatggtgcc tgggatggtc tggaacggga gtttcgtggt 2400
tttgggcggg tgacacaaac tgatattgat tcacgggcga gtgcgacaca ggggacacat 2460
gctgaaccac cggcaccttc gcgcacggtt aattggtacg gcactggcgt acgggaagtc 2520
gatattcttc tgcccacgga atattggcag gggggatcaac aggcatttcc ccattttacc 2580
ccacgcttta cccgttatga cgaaaaatcc ggtggtgata tgacggtcac gccgagcgaa 2640
caggaagaat actggttaca tcgagcctta aaaggacaac gtttacgcag tgagctgtat 2700
ggggatgatg attctatact ggccggtacg ccttattcag tggatgaatc ccgcacccaa 2760
gtacgtttgt taccggtgat ggtatcggac gtgcctgcgg tactggtttc ggtggccgaa 2820
tcccgccaat accgatatga acgggttgct accgatccac agtgcagcca aaagatcgtc 2880
cttaaatctg atgcgttagg atttccgcag gacaatcttg agattgccta ttcgagacgt 2940
ccacagcctg agttctcgcc ttatccggat accctgcccg aaacactttt caccagcagt 3000
ttcgacgaac agcagatgtt ccttcgtctg acacgccagc gttcttctta tcatcatctg 3060
aatcatgatg ataatacgtg gatcacaggg cttatggata cctcacgcag tgacgcacgt 3120
atttatcaag ccgataaagt gccggacggt ggattttccc ttgaatggtt ttctgccaca 3180
ggtgcaggag cattgttgtt gcctgatgcc gcagccgatt atctgggaca tcagcgtgta 3240
gcatataccg gtccagaaga acaacccgct attcctccgc tggtggcata cattgaaacc 3300
gcagagtttg atgaacgatc gttggcggct tttgaggagg tgatggatga gcaggagctg 3360
acaaaacagc tgaatgatgc gggctggaat acggcaaaag tgccgttcag tgaaaagaca 3420
gatttccatg tctgggtggg acaaaaggaa tttacagaat atgccggtgc agacggattc 3480

-continued tatcggccat tggtgcaacg ggaaaccaag cttacaggta aaacgacagt cacgtgggat 3540
agccattact gtgttatcac cgcaacagag gatgcggctg gcctgcgtat gcaagcgcat 3600
tacgattatc gatttatggt tgcggataac accacagatg tcaatgataa ctatcacacc 3660
gtgacgtttg atgcactggg gagggtaacc agcttccgtt tctgggggac tgaaaacggt 3720
gaaaaacaag gatataccccc tgcggaaaat gaaactgtcc cctttattgt ccccacaacg 3780
gtggatgatg ctctggcatt gaaacccggt atacctgttg cagggctgat ggtttatgcc 3840
cctctgagct ggatggttca ggccagcttt tctaatgatg gggagcttta tggagagctg 3900
aaaccggctg ggatcatcac tgaagatggt tatctcctgt cgcttgcttt tcgccgctgg 3960
caacaaaata accctgccgc tgccatgcca aagcaagtca attcacagaa cccaccccat 4020
gtactgagtg tgatcaccga ccgctatgat gccgatccgg aacaacaatt acgtcaaacg 4080
tttacgttta gtgatggttt tgggcgaacc ttacaaacag ccgtacgcca tgaaagtggt 4140
gaagcctggg tacgtgatga gtatggagcc attgtggctg aaaatcatgg cgcgcctgaa 4200
acggcgatga cagatttccg ttgggcagtt tccggacgta cagaatatga cggaaaaggc 4260
caagccctgc gtaagtatca accgtatttc ctgaatagtt ggcagtacgt cagtgatgac 4320
agtgcccggc aggatatata tgccgatacc cattactatg atccgttggg gcgtgaatat 4380
caggttatca cggccaaagg cgggtttcgt cgatccttat tcactccctg gtttgtggtg 4440
aatgaagatg aaaatgacac tgccggtgaa atgacagca 4479

<210> SEQ ID NO 18
<211> LENGTH: 1493
<212> TYPE: PRT
<213> ORGANISM: Xenorhabdus nematophilus

<400> SEQUENCE: 18

Met Gln Gly Ser Thr Pro Leu Lys Leu Glu Ile Pro Ser Leu Pro Ser
1 5 10 15

Gly Gly Gly Ser Leu Lys Gly Met Gly Glu Ala Leu Asn Ala Val Gly
20 25 30

Ala Glu Gly Gly Ala Ser Phe Ser Leu Pro Leu Pro Ile Ser Val Gly
35 40 45

Arg Gly Leu Val Pro Val Leu Ser Leu Asn Tyr Ser Ser Thr Ala Gly
50 55 60

Asn Gly Ser Phe Gly Met Gly Trp Gln Cys Gly Val Gly Phe Ile Ser
65 70 75 80

Leu Arg Thr Ala Lys Gly Val Pro His Tyr Thr Gly Gln Asp Glu Tyr
85 90 95

Leu Gly Pro Asp Gly Glu Val Leu Ser Ile Val Pro Asp Ser Gln Gly
100 105 110

Gln Pro Glu Gln Arg Thr Ala Thr Ser Leu Leu Gly Thr Val Leu Thr
115 120 125

Gln Pro His Thr Val Thr Arg Tyr Gln Ser Arg Val Ala Glu Lys Ile
130 135 140

Val Arg Leu Glu His Trp Gln Pro Gln Gln Arg Arg Glu Glu Glu Thr
145 150 155 160

Ser Phe Trp Val Leu Phe Thr Ala Asp Gly Leu Val His Leu Phe Gly
165 170 175

Lys His His His Ala Arg Ile Ala Asp Pro Gln Asp Glu Thr Arg Ile
180 185 190

Ala Arg Trp Leu Met Glu Glu Thr Val Thr His Thr Gly Glu His Ile
195 200 205

-continued

```
Tyr Tyr His Tyr Arg Ala Glu Asp Asp Leu Asp Cys Asp Glu His Glu
    210                 215                 220

Leu Ala Gln His Ser Gly Val Thr Ala Gln Arg Tyr Leu Ala Lys Val
225                 230                 235                 240

Ser Tyr Gly Asn Thr Gln Pro Glu Thr Ala Phe Phe Ala Val Lys Ser
                245                 250                 255

Gly Ile Pro Ala Asp Asn Asp Trp Leu Phe His Leu Val Phe Asp Tyr
            260                 265                 270

Gly Glu Arg Ser Ser Ser Leu Asn Ser Val Pro Glu Phe Asn Val Ser
        275                 280                 285

Glu Asn Asn Val Ser Glu Asn Asn Val Pro Glu Lys Trp Arg Cys Arg
    290                 295                 300

Pro Asp Ser Phe Ser Arg Tyr Glu Tyr Gly Phe Glu Ile Arg Thr Arg
305                 310                 315                 320

Arg Leu Cys Arg Gln Val Leu Met Phe His Gln Leu Lys Ala Leu Ala
                325                 330                 335

Gly Glu Lys Val Ala Glu Glu Thr Pro Ala Leu Val Ser Arg Leu Ile
            340                 345                 350

Leu Asp Tyr Asp Leu Asn Asn Lys Val Ser Leu Leu Gln Thr Ala Arg
        355                 360                 365

Arg Leu Ala His Glu Thr Asp Gly Thr Pro Val Met Met Ser Pro Leu
    370                 375                 380

Glu Met Asp Tyr Gln Arg Val Asn His Gly Val Asn Leu Asn Trp Gln
385                 390                 395                 400

Ser Met Pro Gln Leu Glu Lys Met Asn Thr Leu Gln Pro Tyr Gln Leu
                405                 410                 415

Val Asp Leu Tyr Gly Glu Gly Ile Ser Gly Val Leu Tyr Gln Asp Thr
            420                 425                 430

Gln Lys Ala Trp Trp Tyr Arg Ala Pro Val Arg Asp Ile Thr Ala Glu
        435                 440                 445

Gly Thr Asn Ala Val Thr Tyr Glu Glu Ala Lys Pro Leu Pro His Ile
    450                 455                 460

Pro Ala Gln Gln Glu Ser Ala Met Leu Leu Asp Ile Asn Gly Asp Gly
465                 470                 475                 480

Arg Leu Asp Trp Val Ile Thr Ala Ser Gly Leu Arg Gly Tyr His Thr
                485                 490                 495

Met Ser Pro Glu Gly Glu Trp Thr Pro Phe Ile Pro Leu Ser Ala Val
            500                 505                 510

Pro Met Glu Tyr Phe His Pro Gln Ala Lys Leu Ala Asp Ile Asp Gly
        515                 520                 525

Ala Gly Leu Pro Asp Leu Ala Leu Ile Gly Pro Asn Ser Val Arg Val
    530                 535                 540

Trp Ser Asn Asn Arg Ala Gly Trp Asp Arg Ala Gln Asp Val Ile His
545                 550                 555                 560

Leu Ser Asp Met Pro Leu Pro Val Pro Gly Arg Asn Glu Arg His Leu
                565                 570                 575

Val Ala Phe Ser Asp Met Thr Gly Ser Gly Gln Ser His Leu Val Glu
            580                 585                 590

Val Thr Ala Asp Ser Val Arg Tyr Trp Pro Asn Leu Gly His Gly Lys
        595                 600                 605

Phe Gly Glu Pro Leu Met Met Thr Gly Phe Gln Ile Ser Gly Glu Thr
    610                 615                 620

Phe Asn Pro Asp Arg Leu Tyr Met Val Asp Ile Asp Gly Ser Gly Thr
```

```
625                 630                 635                 640

Thr Asp Phe Ile Tyr Ala Arg Asn Thr Tyr Leu Glu Leu Tyr Ala Asn
                645                 650                 655

Glu Ser Gly Asn His Phe Ala Glu Pro Gln Arg Ile Asp Leu Pro Asp
            660                 665                 670

Gly Val Arg Phe Asp Asp Thr Cys Arg Leu Gln Ile Ala Asp Thr Gln
        675                 680                 685

Gly Leu Gly Thr Ala Ser Ile Ile Leu Thr Ile Pro His Met Lys Val
    690                 695                 700

Gln His Trp Arg Leu Asp Met Thr Ile Phe Lys Pro Trp Leu Leu Asn
705                 710                 715                 720

Ala Val Asn Asn Asn Met Gly Thr Glu Thr Thr Leu Tyr Tyr Arg Ser
                725                 730                 735

Ser Ala Gln Phe Trp Leu Asp Glu Lys Leu Gln Ala Ser Glu Ser Gly
            740                 745                 750

Met Thr Val Val Ser Tyr Leu Pro Phe Pro Val His Val Leu Trp Arg
        755                 760                 765

Thr Glu Val Leu Asp Glu Ile Ser Gly Asn Arg Leu Thr Ser His Tyr
    770                 775                 780

His Tyr Ser His Gly Ala Trp Asp Gly Leu Glu Arg Glu Phe Arg Gly
785                 790                 795                 800

Phe Gly Arg Val Thr Gln Thr Asp Ile Asp Ser Arg Ala Ser Ala Thr
                805                 810                 815

Gln Gly Thr His Ala Glu Pro Pro Ala Pro Ser Arg Thr Val Asn Trp
            820                 825                 830

Tyr Gly Thr Gly Val Arg Glu Val Asp Ile Leu Leu Pro Thr Glu Tyr
        835                 840                 845

Trp Gln Gly Asp Gln Gln Ala Phe Pro His Phe Thr Pro Arg Phe Thr
    850                 855                 860

Arg Tyr Asp Glu Lys Ser Gly Gly Asp Met Thr Val Thr Pro Ser Glu
865                 870                 875                 880

Gln Glu Glu Tyr Trp Leu His Arg Ala Leu Lys Gly Gln Arg Leu Arg
                885                 890                 895

Ser Glu Leu Tyr Gly Asp Asp Asp Ser Ile Leu Ala Gly Thr Pro Tyr
            900                 905                 910

Ser Val Asp Glu Ser Arg Thr Gln Val Arg Leu Leu Pro Val Met Val
        915                 920                 925

Ser Asp Val Pro Ala Val Leu Val Ser Val Ala Glu Ser Arg Gln Tyr
    930                 935                 940

Arg Tyr Glu Arg Val Ala Thr Asp Pro Gln Cys Ser Gln Lys Ile Val
945                 950                 955                 960

Leu Lys Ser Asp Ala Leu Gly Phe Pro Gln Asp Asn Leu Glu Ile Ala
                965                 970                 975

Tyr Ser Arg Arg Pro Gln Pro Glu Phe Ser Pro Tyr Pro Asp Thr Leu
            980                 985                 990

Pro Glu Thr Leu Phe Thr Ser Ser  Phe Asp Glu Gln Gln  Met Phe Leu
        995                 1000                1005

Arg Leu  Thr Arg Gln Arg Ser  Ser Tyr His His Leu  Asn His Asp
    1010                1015                1020

Asp Asn  Thr Trp Ile Thr Gly  Leu Met Asp Thr Ser  Arg Ser Asp
    1025                1030                1035

Ala Arg  Ile Tyr Gln Ala Asp  Lys Val Pro Asp Gly  Gly Phe Ser
    1040                1045                1050
```

Leu Glu Trp Phe Ser Ala Thr Gly Ala Gly Ala Leu Leu Leu Pro
1055 1060 1065

Asp Ala Ala Ala Asp Tyr Leu Gly His Gln Arg Val Ala Tyr Thr
1070 1075 1080

Gly Pro Glu Glu Gln Pro Ala Ile Pro Pro Leu Val Ala Tyr Ile
1085 1090 1095

Glu Thr Ala Glu Phe Asp Glu Arg Ser Leu Ala Ala Phe Glu Glu
1100 1105 1110

Val Met Asp Glu Gln Glu Leu Thr Lys Gln Leu Asn Asp Ala Gly
1115 1120 1125

Trp Asn Thr Ala Lys Val Pro Phe Ser Glu Lys Thr Asp Phe His
1130 1135 1140

Val Trp Val Gly Gln Lys Glu Phe Thr Glu Tyr Ala Gly Ala Asp
1145 1150 1155

Gly Phe Tyr Arg Pro Leu Val Gln Arg Glu Thr Lys Leu Thr Gly
1160 1165 1170

Lys Thr Thr Val Thr Trp Asp Ser His Tyr Cys Val Ile Thr Ala
1175 1180 1185

Thr Glu Asp Ala Ala Gly Leu Arg Met Gln Ala His Tyr Asp Tyr
1190 1195 1200

Arg Phe Met Val Ala Asp Asn Thr Thr Asp Val Asn Asp Asn Tyr
1205 1210 1215

His Thr Val Thr Phe Asp Ala Leu Gly Arg Val Thr Ser Phe Arg
1220 1225 1230

Phe Trp Gly Thr Glu Asn Gly Glu Lys Gln Gly Tyr Thr Pro Ala
1235 1240 1245

Glu Asn Glu Thr Val Pro Phe Ile Val Pro Thr Thr Val Asp Asp
1250 1255 1260

Ala Leu Ala Leu Lys Pro Gly Ile Pro Val Ala Gly Leu Met Val
1265 1270 1275

Tyr Ala Pro Leu Ser Trp Met Val Gln Ala Ser Phe Ser Asn Asp
1280 1285 1290

Gly Glu Leu Tyr Gly Glu Leu Lys Pro Ala Gly Ile Ile Thr Glu
1295 1300 1305

Asp Gly Tyr Leu Leu Ser Leu Ala Phe Arg Arg Trp Gln Gln Asn
1310 1315 1320

Asn Pro Ala Ala Ala Met Pro Lys Gln Val Asn Ser Gln Asn Pro
1325 1330 1335

Pro His Val Leu Ser Val Ile Thr Asp Arg Tyr Asp Ala Asp Pro
1340 1345 1350

Glu Gln Gln Leu Arg Gln Thr Phe Thr Phe Ser Asp Gly Phe Gly
1355 1360 1365

Arg Thr Leu Gln Thr Ala Val Arg His Glu Ser Gly Glu Ala Trp
1370 1375 1380

Val Arg Asp Glu Tyr Gly Ala Ile Val Ala Glu Asn His Gly Ala
1385 1390 1395

Pro Glu Thr Ala Met Thr Asp Phe Arg Trp Ala Val Ser Gly Arg
1400 1405 1410

Thr Glu Tyr Asp Gly Lys Gly Gln Ala Leu Arg Lys Tyr Gln Pro
1415 1420 1425

Tyr Phe Leu Asn Ser Trp Gln Tyr Val Ser Asp Asp Ser Ala Arg
1430 1435 1440

Gln Asp Ile Tyr Ala Asp Thr His Tyr Tyr Asp Pro Leu Gly Arg
1445 1450 1455

-continued

Glu Tyr Gln Val Ile Thr Ala Lys Gly Gly Phe Arg Arg Ser Leu
    1460                1465                1470

Phe Thr Pro Trp Phe Val Val Asn Glu Asp Glu Asn Asp Thr Ala
    1475                1480                1485

Gly Glu Met Thr Ala
    1490

<210> SEQ ID NO 19
<211> LENGTH: 7614
<212> TYPE: DNA
<213> ORGANISM: Xenorhabdus nematophilus

<400> SEQUENCE: 19
atgtatagca cggctgtatt actcaataaa atcagtccca ctcgcgacgg tcagacgatg 60
actcttgcgg atctgcaata tttatccttc agtgaactga gaaaaatctt tgatgaccag 120
ctcagttggg gagaggctcg ccatctctat catgaaacta tagagcagaa aaaaaataat 180
cgcttgctgg aagcgcgtat ttttacccgt gccaacccac aattatccgg tgctatccga 240
ctcggtattg aacgagacag cgtttcacgc agttatgatg aaatgtttgg tgcccgttct 300
tcttcctttg tgaaaccggg ttcagtggct tccatgtttt caccggctgg ctatctcacc 360
gaattgtatc gtgaagcgaa ggacttacat ttttcaagct ctgcttatca tcttgataat 420
cgccgtccgg atctggctga tctgactctg agccagagta atatggatac agaaatttcc 480
accctgacac tgtctaacga actgttgctg gagcatatta cccgcaagac cggaggtgat 540
tcggacgcat tgatggagag cctgtcaact taccgtcagg ccattgatac cccttaccat 600
cagccttacg agactatccg tcaggtcatt atgacccatg acagtacact gtcagcgctg 660
tcccgtaatc ctgaggtgat ggggcaggcg gaaggggctt cattactggc gattctggcc 720
aatatttctc cggagcttta taacattttg accgaagaga ttacggaaaa gaacgctgat 780
gctttatttg cgcaaaactt cagtgaaaat atcacgcccg aaaatttcgc gtcacaatca 840
tggatagcca agtattatgg tcttgaactt tctgaggtgc aaaaatacct cgggatgttg 900
cagaatggct attctgacag cacctctgct tatgtggata atatctcaac gggtttagtg 960
gtcaataatg aaagtaaact cgaagcttac aaaataacac gtgtaaaaac agatgattat 1020
gataaaaata taaattactt tgatttgatg tatgaaggaa ataatcagtt ctttatacgt 1080
gctaatttta aggtatcaag agaatttggg gctactctta gaaaaaacgc agggccaagt 1140
ggcattgtcg gcagcctttc cggtcctcta atagccaata cgaattttaa aagtaattat 1200
ctaagtaaca tatctgattc tgaatacaaa aacggtgtaa agatatacgc ctatcgctat 1260
acgtcttcca ccagcgccac aaatcagggc ggcggaatat tcacttttga gtcttatccc 1320
ctgactatat ttgcgctcaa actgaataaa gccattcgct tgtgcctgac tagcgggctt 1380
tcaccgaatg aactgcaaac tatcgtacgc agtgacaatg cacaaggcat catcaacgac 1440
tccgttctga ccaaagtttt ctatactctg ttctacagtc accgttatgc actgagcttt 1500
gatgatgcac aggtactgaa cggatcggtc attaatcaat atgccgacga tgacagtgtc 1560
agtcatttta accgtctctt taatacaccg ccgctgaaag ggaaaatctt tgaagccgac 1620
ggcaacacgg tcagcattga tccggatgaa gagcaatcta cctttgcccg ttcagccctg 1680
atgcgtggtc tgggggtcaa cagtggtgaa ctgtatcagt taggcaaact ggcgggtgtg 1740
ctggacgccc aaaataccat cacactttct gtcttcgtta tctcttcact gtatcgcctc 1800
acgttactgg cccgtgtcca tcagctgacg gtcaatgaac tgtgtatgct ttatggtctt 1860

-continued

```
tcgccgttca atggcaaaac aacggcttct ttgtcttccg gggagttgcc acggctggtt   1920
atctggctgt atcaggtgac gcagtggctg actgaggcgg aaatcaccac tgaagcgatc   1980
tggttattat gtacgccaga gtttagcggg aatatttcac cggaaatcag taatctgctc   2040
aataacctcc gaccgagtat tagtgaagat atggcacaga gtcacaatcg ggagctgcag   2100
gctgaaattc tcgcgccgtt tattgctgca acgctgcatc tggcgtcacc ggatatggca   2160
cggtatatcc tgttgtggac cgataacctg cggccgggtg gcttagatat tgccgggttt   2220
atgacactgg tattgaaaga gtcgttaaat gccaatgaaa ccacccaatt ggtacaattc   2280
tgccatgtga tggcacagtt atcgctttcc gtacagacac tgcgcctcag tgaagcggag   2340
ctatccgtgc tggtcatctc cggattcgcc gtgctggggg caaaaaatca acctgccgga   2400
cagcacaata ttgatacgct attctcactc taccgattcc accagtggat taatgggctg   2460
ggcaatcccg gctctgacac gctggatatg ctgcgccagc agacactcac ggccgacaga   2520
ctggcctccg tgatggggct ggacatcagt atggtaacgc aggccatggt ttccgccggc   2580
gtgaaccagc ttcagtgttg gcaggatatc aacaccgtgt tgcagtggat agatgtggca   2640
tcagcactgc acacgatgcc gtcggttatc cgtacgctgg tgaatatccg ttacgtgact   2700
gcattaaaca aagccgagtc gaatctgcct tcctgggatg agtggcagac actggcagaa   2760
aatatggaag ccggactcag tacacaacag gctcagacgc tggcggatta taccgcggag   2820
cgcctgagta gcgtgctgtg caattggttt ctggcgaata tccagccaga aggggtgtcc   2880
ctgcacagcc gggatgacct gtacagctat ttcctgattg ataatcaggt ctcttctgcc   2940
ataaaaacca cccgactggc agaggccatt gccggtattc agctctacat caaccgggcg   3000
ctgaatcgga tagagcctaa tgcccgtgcc gatgtgtcaa cccgccagtt ttttaccgac   3060
tggacggtga ataaccgtta cagcacctgg ggcggggtgt cgcggctggt ttattatccg   3120
gaaaattaca ttgacccaac ccagcgtatc gggcagaccc ggatgatgga tgaactgctg   3180
gaaaatatca gccagagtaa acttagccgg gacacagtgg aggatgcctt taaaacttac   3240
ctgacccgct ttgaaaccgt ggcggatctg aaagttgtca gcgcctatca cgacaacgtc   3300
aacagcaaca ccggactgac ctggtttgtc ggccaaacgc gggagaacct gccggaatac   3360
tactggcgta acgtggatat atcacggatg caggcgggtg aactggccgc caatgcctgg   3420
aaagagtgga cgaagattga tacagcggtc aacccctaca aggatgcaat acgtccggtc   3480
atattcaggg aacgtttgca ccttatctgg gtagaaaaag aggaagtggc gaaaaatggt   3540
actgatccgg tggaaaccta tgaccgtttt actctgaaac tggcgtttct gcgtcatgat   3600
ggcagttgga gtgccccctg gtcttacgat atcacaacgc aggtggaggc ggtcactgac   3660
aaaaaacctg acactgaacg gctggcgctg gccgcatcag gctttcaggg cgaggacact   3720
ctgctggtgt ttgtctacaa aaccgggaag agttactcgg attttggcgg cagcaataaa   3780
aatgtggcag gcatgaccat ttacggcgat ggctccttca aaaagatgga gaacacagca   3840
ctcagccgtt acagccaact gaaaaatacc tttgatatca ttcatactca aggcaacgac   3900
ttggtaagaa aggccagcta tcgtttcgcg caggattttg aagtgcctgc ctcgttgaat   3960
atgggttctg ccatcggtga tgatagtctg acggtgatgg agaacgggaa tattccgcag   4020
ataaccagta aatactccag cgataacctt gctattacgc tacataacgc cgctttcact   4080
gtcagatatg atggcagtgg caatgtcatc agaaacaaac aaatcagcgc catgaaactg   4140
acgggggtgg atggaaagtc ccagtacggc aatgcattta tcatcgcaaa taccgttaaa   4200
cattatggcg gttactctga tctggggggg ccgatcaccg tttataataa aacgaaaaac   4260
```

-continued

```
tatattgcat cagttcaagg ccacttgatg aacgcagatt acactaggcg tttgattcta   4320
acaccagttg aaaataatta ttatgccaga ttgttcgagt ttccattttc tccaaacaca   4380
attttaaaca ccgttttcac ggttggtagc aataaaacca gtgattttaa aaagtgcagt   4440
tatgctgttg atggtaataa ttctcagggc ttccagatat ttagttccta tcaatcatcc   4500
ggctggctgg atattgatac aggcattaac aataccgata tcaaaattac ggtgatggct   4560
ggcagtaaaa cccacacctt tacggccagt gaccatattg cttccttgcc ggcaaacagt   4620
tttgatgcta tgccgtacac ctttaagcca ctggaaatcg atgcttcatc gttggccttt   4680
accaataata ttgctcctct ggatatcgtt tttgagacca aagccaaaga cgggcgagtg   4740
ctgggtaaga tcaagcaaac attatcggtg aaacgggtaa attataatcc ggaagatatt   4800
ctgtttctgc gtgaaactca ttcgggtgcc caatatatgc agctcggggt gtatcgtatt   4860
cgtcttaata ccctgctggc ttctcaactg gtatccagag caaacacggg cattgatact   4920
atcctgacaa tggaaaccca gcggttaccg gaacctccgt tgggagaagg cttctttgcc   4980
aactttgttc tgcctaaata tgaccctgct gaacatggcg atgagcggtg gtttaaaatc   5040
catattggga atgttggcgg taacacggga aggcagcctt attacagcgg aatgttatcc   5100
gatacgtcgg aaaccagtat gacactgttt gtcccttatg ccgaagggta ttacatgcat   5160
gaaggtgtca gattgggggt tggataccag aaaattacct atgacaacac ttgggaatct   5220
gctttctttt attttgatga gacaaaacag caatttgtat taattaacga tgctgatcat   5280
gattcaggaa tgacgcaaca ggggatcgtg aaaaatatca agaaatacaa aggattttg   5340
aatgtttcta tcgcaacggg ctattccgcc ccgatggatt tcaatagtgc cagcgccctc   5400
tattactggg aattgttcta ttacaccccg atgatgtgct tccagcgttt gctacaggaa   5460
aaacaattcg acgaagccac acaatggata aactacgtct acaatcccgc cggctatatc   5520
gttaacggag aaatcgcccc ctggatctgg aactgccggc cgctggaaga gaccacctcc   5580
tggaatgcca atccgctgga tgccatcgat ccggatgccg tcgcccaaaa tgacccaatg   5640
cactacaaga ttgccacctt tatgcgcctg ttggatcaac ttattctgcg cggcgatatg   5700
gcctatcgag aactgacccg cgatgcgttg aatgaagcca aaatgtggta tgtgcgtact   5760
ttagaattgc tcggtgatga gccggaggat tacggtagcc aacagtgggc agcaccgtcc   5820
ctttccgggg cggcgagtca aaccgtgcag gcggcttatc agcaggatct tacgatgctg   5880
ggccgtggtg ggtttccaa gaatctccgt accgctaact cgttggtggg tttgttcctg   5940
ccggaatata acccggcgct caccgattac tggcaaaccc tgcgtttgcg cctgtttaac   6000
ctgcgccata atctttccat tgacggacag ccgttatcgc tggcgattta cgccgagcct   6060
accgatccga aagcgctgct caccagtatg gtacaggcct ctcagggcgg tagtgcagtg   6120
ctgcccggca cattgtcgtt ataccgcttc ccggtgatgc tggagcggac ccgcaatctg   6180
gtagcgcaat taacccagtt cggcacctct ctgctcagta tggcagagca tgatgatgcc   6240
gatgaactca ccacgctgct actacagcag ggtatggaac tggcgacaca gagcatccgt   6300
attcagcaac gaactgtcga tgaagtggat gctgatattg ctgtattggc agagagccgc   6360
cgcagtgcac aaaatcgtct ggaaaaatac cagcagctgt atgacgagga tatcaaccac   6420
ggagaacagc gggcaatgtc actgcttgat gcagcggcag gtcagtctct ggccgggcag   6480
gtgctttcaa tagcggaagg ggtggccgat ttagtgccaa acgtgttcgg tttagcttgt   6540
ggcggcagtc gttgggggc agcactgcgt gcttccgcct ccgtgatgtc gctttctgcc   6600
acagcttccc aatattccgc agacaaaatc agccgttcgg aagcctaccg ccgccgccgt   6660
```

-continued

```
caggagtggg aaattcagcg tgataatgct gacggtgaag tcaaacaaat ggatgcccag   6720

ttggaaagcc tgaaaatccg ccgcgaagca gcacagatgc aggtggaata tcaggagacc   6780

cagcaggccc atactcaggc tcagttagag ctgttacagc gtaaattcac aaacaaagcg   6840

ctttacagtt ggatgcgcgg caagctgagt gctatctatt accagttctt tgacctgacc   6900

cagtccttct gcctgatggc acaggaagcg ctgcgccgcg agctgaccga caacggtgtt   6960

acctttatcc ggggtggggc ctggaacggt acgactgcgg gtttgatggc gggtgaaacg   7020

ttgctgctga atctggcaga aatggaaaaa gtctggctgg agcgtgatga gcgggcactg   7080

gaagtgaccc gtaccgtctc gttggcacag ttctatcagg ccttatcatc agacaacttt   7140

aatctgaccg aaaaactcac gcaattcctg cgtgaaggga aaggcaacgt aggagcttcc   7200

ggcaatgaat taaaactcag taaccgtcag atagaagcct cagtgcgatt gtctgatttg   7260

aaaattttca gcgactaccc cgaaagcctt ggcaataccc gtcagttgaa acaggtgagt   7320

gtcaccttgc cggcgctggt tggccgtat gaagatattc gggcggtgct gaattacggg   7380

ggcagcatcg tcatgccacg cggttgcagt gctattgctc tctcccacgg cgtgaatgac   7440

agtggtcaat ttatgctgga tttcaacgat tcccgttatc tgccgtttga aggtatttcc   7500

gtgaatgaca gcggcagcct gacgttgagt ttcccggatg cgactgatcg gcagaaagcg   7560

ctgctggaga gcctgagcga tatcattctg catatccgct ataccattcg ttct         7614
```

<210> SEQ ID NO 20
<211> LENGTH: 2538
<212> TYPE: PRT
<213> ORGANISM: Xenorhabdus nematophilus

<400> SEQUENCE: 20

```
Met Tyr Ser Thr Ala Val Leu Leu Asn Lys Ile Ser Pro Thr Arg Asp
1               5                   10                  15

Gly Gln Thr Met Thr Leu Ala Asp Leu Gln Tyr Leu Ser Phe Ser Glu
            20                  25                  30

Leu Arg Lys Ile Phe Asp Asp Gln Leu Ser Trp Gly Glu Ala Arg His
        35                  40                  45

Leu Tyr His Glu Thr Ile Glu Gln Lys Lys Asn Asn Arg Leu Leu Glu
    50                  55                  60

Ala Arg Ile Phe Thr Arg Ala Asn Pro Gln Leu Ser Gly Ala Ile Arg
65                  70                  75                  80

Leu Gly Ile Glu Arg Asp Ser Val Ser Arg Ser Tyr Asp Glu Met Phe
                85                  90                  95

Gly Ala Arg Ser Ser Ser Phe Val Lys Pro Gly Ser Val Ala Ser Met
            100                 105                 110

Phe Ser Pro Ala Gly Tyr Leu Thr Glu Leu Tyr Arg Glu Ala Lys Asp
        115                 120                 125

Leu His Phe Ser Ser Ser Ala Tyr His Leu Asp Asn Arg Arg Pro Asp
    130                 135                 140

Leu Ala Asp Leu Thr Leu Ser Gln Ser Asn Met Asp Thr Glu Ile Ser
145                 150                 155                 160

Thr Leu Thr Leu Ser Asn Glu Leu Leu Leu Glu His Ile Thr Arg Lys
                165                 170                 175

Thr Gly Gly Asp Ser Asp Ala Leu Met Glu Ser Leu Ser Thr Tyr Arg
            180                 185                 190

Gln Ala Ile Asp Thr Pro Tyr His Gln Pro Tyr Glu Thr Ile Arg Gln
        195                 200                 205

Val Ile Met Thr His Asp Ser Thr Leu Ser Ala Leu Ser Arg Asn Pro
```

```
    210                 215                 220

Glu Val Met Gly Gln Ala Glu Gly Ala Ser Leu Leu Ala Ile Leu Ala
225                 230                 235                 240

Asn Ile Ser Pro Glu Leu Tyr Asn Ile Leu Thr Glu Glu Ile Thr Glu
                245                 250                 255

Lys Asn Ala Asp Ala Leu Phe Ala Gln Asn Phe Ser Glu Asn Ile Thr
            260                 265                 270

Pro Glu Asn Phe Ala Ser Gln Ser Trp Ile Ala Lys Tyr Tyr Gly Leu
        275                 280                 285

Glu Leu Ser Glu Val Gln Lys Tyr Leu Gly Met Leu Gln Asn Gly Tyr
    290                 295                 300

Ser Asp Ser Thr Ser Ala Tyr Val Asp Asn Ile Ser Thr Gly Leu Val
305                 310                 315                 320

Val Asn Asn Glu Ser Lys Leu Glu Ala Tyr Lys Ile Thr Arg Val Lys
                325                 330                 335

Thr Asp Asp Tyr Asp Lys Asn Ile Asn Tyr Phe Asp Leu Met Tyr Glu
            340                 345                 350

Gly Asn Asn Gln Phe Phe Ile Arg Ala Asn Phe Lys Val Ser Arg Glu
        355                 360                 365

Phe Gly Ala Thr Leu Arg Lys Asn Ala Gly Pro Ser Gly Ile Val Gly
    370                 375                 380

Ser Leu Ser Gly Pro Leu Ile Ala Asn Thr Asn Phe Lys Ser Asn Tyr
385                 390                 395                 400

Leu Ser Asn Ile Ser Asp Ser Glu Tyr Lys Asn Gly Val Lys Ile Tyr
                405                 410                 415

Ala Tyr Arg Tyr Thr Ser Ser Thr Ser Ala Thr Asn Gln Gly Gly Gly
            420                 425                 430

Ile Phe Thr Phe Glu Ser Tyr Pro Leu Thr Ile Phe Ala Leu Lys Leu
        435                 440                 445

Asn Lys Ala Ile Arg Leu Cys Leu Thr Ser Gly Leu Ser Pro Asn Glu
    450                 455                 460

Leu Gln Thr Ile Val Arg Ser Asp Asn Ala Gln Gly Ile Ile Asn Asp
465                 470                 475                 480

Ser Val Leu Thr Lys Val Phe Tyr Thr Leu Phe Tyr Ser His Arg Tyr
                485                 490                 495

Ala Leu Ser Phe Asp Asp Ala Gln Val Leu Asn Gly Ser Val Ile Asn
            500                 505                 510

Gln Tyr Ala Asp Asp Asp Ser Val Ser His Phe Asn Arg Leu Phe Asn
        515                 520                 525

Thr Pro Pro Leu Lys Gly Lys Ile Phe Glu Ala Asp Gly Asn Thr Val
    530                 535                 540

Ser Ile Asp Pro Asp Glu Glu Gln Ser Thr Phe Ala Arg Ser Ala Leu
545                 550                 555                 560

Met Arg Gly Leu Gly Val Asn Ser Gly Glu Leu Tyr Gln Leu Gly Lys
                565                 570                 575

Leu Ala Gly Val Leu Asp Ala Gln Asn Thr Ile Thr Leu Ser Val Phe
            580                 585                 590

Val Ile Ser Ser Leu Tyr Arg Leu Thr Leu Leu Ala Arg Val His Gln
        595                 600                 605

Leu Thr Val Asn Glu Leu Cys Met Leu Tyr Gly Leu Ser Pro Phe Asn
    610                 615                 620

Gly Lys Thr Thr Ala Ser Leu Ser Ser Gly Glu Leu Pro Arg Leu Val
625                 630                 635                 640
```

-continued

```
Ile Trp Leu Tyr Gln Val Thr Gln Trp Leu Thr Glu Ala Glu Ile Thr
                645                 650                 655

Thr Glu Ala Ile Trp Leu Leu Cys Thr Pro Glu Phe Ser Gly Asn Ile
            660                 665                 670

Ser Pro Glu Ile Ser Asn Leu Leu Asn Asn Leu Arg Pro Ser Ile Ser
        675                 680                 685

Glu Asp Met Ala Gln Ser His Asn Arg Glu Leu Gln Ala Glu Ile Leu
    690                 695                 700

Ala Pro Phe Ile Ala Ala Thr Leu His Leu Ala Ser Pro Asp Met Ala
705                 710                 715                 720

Arg Tyr Ile Leu Leu Trp Thr Asp Asn Leu Arg Pro Gly Gly Leu Asp
                725                 730                 735

Ile Ala Gly Phe Met Thr Leu Val Leu Lys Glu Ser Leu Asn Ala Asn
            740                 745                 750

Glu Thr Thr Gln Leu Val Gln Phe Cys His Val Met Ala Gln Leu Ser
        755                 760                 765

Leu Ser Val Gln Thr Leu Arg Leu Ser Glu Ala Glu Leu Ser Val Leu
    770                 775                 780

Val Ile Ser Gly Phe Ala Val Leu Gly Ala Lys Asn Gln Pro Ala Gly
785                 790                 795                 800

Gln His Asn Ile Asp Thr Leu Phe Ser Leu Tyr Arg Phe His Gln Trp
                805                 810                 815

Ile Asn Gly Leu Gly Asn Pro Gly Ser Asp Thr Leu Asp Met Leu Arg
            820                 825                 830

Gln Gln Thr Leu Thr Ala Asp Arg Leu Ala Ser Val Met Gly Leu Asp
        835                 840                 845

Ile Ser Met Val Thr Gln Ala Met Val Ser Ala Gly Val Asn Gln Leu
    850                 855                 860

Gln Cys Trp Gln Asp Ile Asn Thr Val Leu Gln Trp Ile Asp Val Ala
865                 870                 875                 880

Ser Ala Leu His Thr Met Pro Ser Val Ile Arg Thr Leu Val Asn Ile
                885                 890                 895

Arg Tyr Val Thr Ala Leu Asn Lys Ala Glu Ser Asn Leu Pro Ser Trp
            900                 905                 910

Asp Glu Trp Gln Thr Leu Ala Glu Asn Met Glu Ala Gly Leu Ser Thr
        915                 920                 925

Gln Gln Ala Gln Thr Leu Ala Asp Tyr Thr Ala Glu Arg Leu Ser Ser
    930                 935                 940

Val Leu Cys Asn Trp Phe Leu Ala Asn Ile Gln Pro Glu Gly Val Ser
945                 950                 955                 960

Leu His Ser Arg Asp Asp Leu Tyr Ser Tyr Phe Leu Ile Asp Asn Gln
                965                 970                 975

Val Ser Ser Ala Ile Lys Thr Thr Arg Leu Ala Glu Ala Ile Ala Gly
            980                 985                 990

Ile Gln Leu Tyr Ile Asn Arg Ala  Leu Asn Arg Ile Glu  Pro Asn Ala
        995                 1000                1005

Arg Ala  Asp Val Ser Thr Arg  Gln Phe Phe Thr Asp  Trp Thr Val
    1010                1015                1020

Asn Asn  Arg Tyr Ser Thr Trp  Gly Gly Val Ser Arg  Leu Val Tyr
    1025                1030                1035

Tyr Pro  Glu Asn Tyr Ile Asp  Pro Thr Gln Arg Ile  Gly Gln Thr
    1040                1045                1050

Arg Met  Met Asp Glu Leu Leu  Glu Asn Ile Ser Gln  Ser Lys Leu
    1055                1060                1065
```

```
Ser Arg  Asp Thr Val Glu Asp  Ala Phe Lys Thr Tyr  Leu Thr Arg
    1070                 1075                 1080

Phe Glu  Thr Val Ala Asp Leu  Lys Val Val Ser Ala  Tyr His Asp
    1085                 1090                 1095

Asn Val  Asn Ser Asn Thr Gly  Leu Thr Trp Phe Val  Gly Gln Thr
    1100                 1105                 1110

Arg Glu  Asn Leu Pro Glu Tyr  Tyr Trp Arg Asn Val  Asp Ile Ser
    1115                 1120                 1125

Arg Met  Gln Ala Gly Glu Leu  Ala Ala Asn Ala Trp  Lys Glu Trp
    1130                 1135                 1140

Thr Lys  Ile Asp Thr Ala Val  Asn Pro Tyr Lys Asp  Ala Ile Arg
    1145                 1150                 1155

Pro Val  Ile Phe Arg Glu Arg  Leu His Leu Ile Trp  Val Glu Lys
    1160                 1165                 1170

Glu Glu  Val Ala Lys Asn Gly  Thr Asp Pro Val Glu  Thr Tyr Asp
    1175                 1180                 1185

Arg Phe  Thr Leu Lys Leu Ala  Phe Leu Arg His Asp  Gly Ser Trp
    1190                 1195                 1200

Ser Ala  Pro Trp Ser Tyr Asp  Ile Thr Thr Gln Val  Glu Ala Val
    1205                 1210                 1215

Thr Asp  Lys Lys Pro Asp Thr  Glu Arg Leu Ala Leu  Ala Ala Ser
    1220                 1225                 1230

Gly Phe  Gln Gly Glu Asp Thr  Leu Leu Val Phe Val  Tyr Lys Thr
    1235                 1240                 1245

Gly Lys  Ser Tyr Ser Asp Phe  Gly Gly Ser Asn Lys  Asn Val Ala
    1250                 1255                 1260

Gly Met  Thr Ile Tyr Gly Asp  Gly Ser Phe Lys Lys  Met Glu Asn
    1265                 1270                 1275

Thr Ala  Leu Ser Arg Tyr Ser  Gln Leu Lys Asn Thr  Phe Asp Ile
    1280                 1285                 1290

Ile His  Thr Gln Gly Asn Asp  Leu Val Arg Lys Ala  Ser Tyr Arg
    1295                 1300                 1305

Phe Ala  Gln Asp Phe Glu Val  Pro Ala Ser Leu Asn  Met Gly Ser
    1310                 1315                 1320

Ala Ile  Gly Asp Asp Ser Leu  Thr Val Met Glu Asn  Gly Asn Ile
    1325                 1330                 1335

Pro Gln  Ile Thr Ser Lys Tyr  Ser Ser Asp Asn Leu  Ala Ile Thr
    1340                 1345                 1350

Leu His  Asn Ala Ala Phe Thr  Val Arg Tyr Asp Gly  Ser Gly Asn
    1355                 1360                 1365

Val Ile  Arg Asn Lys Gln Ile  Ser Ala Met Lys Leu  Thr Gly Val
    1370                 1375                 1380

Asp Gly  Lys Ser Gln Tyr Gly  Asn Ala Phe Ile Ile  Ala Asn Thr
    1385                 1390                 1395

Val Lys  His Tyr Gly Gly Tyr  Ser Asp Leu Gly Gly  Pro Ile Thr
    1400                 1405                 1410

Val Tyr  Asn Lys Thr Lys Asn  Tyr Ile Ala Ser Val  Gln Gly His
    1415                 1420                 1425

Leu Met  Asn Ala Asp Tyr Thr  Arg Arg Leu Ile Leu  Thr Pro Val
    1430                 1435                 1440

Glu Asn  Asn Tyr Tyr Ala Arg  Leu Phe Glu Phe Pro  Phe Ser Pro
    1445                 1450                 1455

Asn Thr  Ile Leu Asn Thr Val  Phe Thr Val Gly Ser  Asn Lys Thr
```

```
    1460                1465                1470

Ser Asp Phe Lys Lys Cys Ser Tyr Ala Val Asp Gly Asn Asn Ser
    1475                1480                1485

Gln Gly Phe Gln Ile Phe Ser Ser Tyr Gln Ser Ser Gly Trp Leu
    1490                1495                1500

Asp Ile Asp Thr Gly Ile Asn Asn Thr Asp Ile Lys Ile Thr Val
    1505                1510                1515

Met Ala Gly Ser Lys Thr His Thr Phe Thr Ala Ser Asp His Ile
    1520                1525                1530

Ala Ser Leu Pro Ala Asn Ser Phe Asp Ala Met Pro Tyr Thr Phe
    1535                1540                1545

Lys Pro Leu Glu Ile Asp Ala Ser Ser Leu Ala Phe Thr Asn Asn
    1550                1555                1560

Ile Ala Pro Leu Asp Ile Val Phe Glu Thr Lys Ala Lys Asp Gly
    1565                1570                1575

Arg Val Leu Gly Lys Ile Lys Gln Thr Leu Ser Val Lys Arg Val
    1580                1585                1590

Asn Tyr Asn Pro Glu Asp Ile Leu Phe Leu Arg Glu Thr His Ser
    1595                1600                1605

Gly Ala Gln Tyr Met Gln Leu Gly Val Tyr Arg Ile Arg Leu Asn
    1610                1615                1620

Thr Leu Leu Ala Ser Gln Leu Val Ser Arg Ala Asn Thr Gly Ile
    1625                1630                1635

Asp Thr Ile Leu Thr Met Glu Thr Gln Arg Leu Pro Glu Pro Pro
    1640                1645                1650

Leu Gly Glu Gly Phe Phe Ala Asn Phe Val Leu Pro Lys Tyr Asp
    1655                1660                1665

Pro Ala Glu His Gly Asp Glu Arg Trp Phe Lys Ile His Ile Gly
    1670                1675                1680

Asn Val Gly Gly Asn Thr Gly Arg Gln Pro Tyr Tyr Ser Gly Met
    1685                1690                1695

Leu Ser Asp Thr Ser Glu Thr Ser Met Thr Leu Phe Val Pro Tyr
    1700                1705                1710

Ala Glu Gly Tyr Tyr Met His Glu Gly Val Arg Leu Gly Val Gly
    1715                1720                1725

Tyr Gln Lys Ile Thr Tyr Asp Asn Thr Trp Glu Ser Ala Phe Phe
    1730                1735                1740

Tyr Phe Asp Glu Thr Lys Gln Gln Phe Val Leu Ile Asn Asp Ala
    1745                1750                1755

Asp His Asp Ser Gly Met Thr Gln Gln Gly Ile Val Lys Asn Ile
    1760                1765                1770

Lys Lys Tyr Lys Gly Phe Leu Asn Val Ser Ile Ala Thr Gly Tyr
    1775                1780                1785

Ser Ala Pro Met Asp Phe Asn Ser Ala Ser Ala Leu Tyr Tyr Trp
    1790                1795                1800

Glu Leu Phe Tyr Tyr Thr Pro Met Met Cys Phe Gln Arg Leu Leu
    1805                1810                1815

Gln Glu Lys Gln Phe Asp Glu Ala Thr Gln Trp Ile Asn Tyr Val
    1820                1825                1830

Tyr Asn Pro Ala Gly Tyr Ile Val Asn Gly Glu Ile Ala Pro Trp
    1835                1840                1845

Ile Trp Asn Cys Arg Pro Leu Glu Glu Thr Thr Ser Trp Asn Ala
    1850                1855                1860
```

```
Asn Pro  Leu Asp Ala Ile Asp  Pro Asp Ala Val Ala  Gln Asn Asp
    1865                 1870                 1875

Pro Met  His Tyr Lys Ile Ala  Thr Phe Met Arg Leu  Leu Asp Gln
    1880                 1885                 1890

Leu Ile  Leu Arg Gly Asp Met  Ala Tyr Arg Glu Leu  Thr Arg Asp
    1895                 1900                 1905

Ala Leu  Asn Glu Ala Lys Met  Trp Tyr Val Arg Thr  Leu Glu Leu
    1910                 1915                 1920

Leu Gly  Asp Glu Pro Glu Asp  Tyr Gly Ser Gln Gln  Trp Ala Ala
    1925                 1930                 1935

Pro Ser  Leu Ser Gly Ala Ala  Ser Gln Thr Val Gln  Ala Ala Tyr
    1940                 1945                 1950

Gln Gln  Asp Leu Thr Met Leu  Gly Arg Gly Gly Val  Ser Lys Asn
    1955                 1960                 1965

Leu Arg  Thr Ala Asn Ser Leu  Val Gly Leu Phe Leu  Pro Glu Tyr
    1970                 1975                 1980

Asn Pro  Ala Leu Thr Asp Tyr  Trp Gln Thr Leu Arg  Leu Arg Leu
    1985                 1990                 1995

Phe Asn  Leu Arg His Asn Leu  Ser Ile Asp Gly Gln  Pro Leu Ser
    2000                 2005                 2010

Leu Ala  Ile Tyr Ala Glu Pro  Thr Asp Pro Lys Ala  Leu Leu Thr
    2015                 2020                 2025

Ser Met  Val Gln Ala Ser Gln  Gly Gly Ser Ala Val  Leu Pro Gly
    2030                 2035                 2040

Thr Leu  Ser Leu Tyr Arg Phe  Pro Val Met Leu Glu  Arg Thr Arg
    2045                 2050                 2055

Asn Leu  Val Ala Gln Leu Thr  Gln Phe Gly Thr Ser  Leu Leu Ser
    2060                 2065                 2070

Met Ala  Glu His Asp Asp Ala  Asp Glu Leu Thr Thr  Leu Leu Leu
    2075                 2080                 2085

Gln Gln  Gly Met Glu Leu Ala  Thr Gln Ser Ile Arg  Ile Gln Gln
    2090                 2095                 2100

Arg Thr  Val Asp Glu Val Asp  Ala Asp Ile Ala Val  Leu Ala Glu
    2105                 2110                 2115

Ser Arg  Arg Ser Ala Gln Asn  Arg Leu Glu Lys Tyr  Gln Gln Leu
    2120                 2125                 2130

Tyr Asp  Glu Asp Ile Asn His  Gly Glu Gln Arg Ala  Met Ser Leu
    2135                 2140                 2145

Leu Asp  Ala Ala Ala Gly Gln  Ser Leu Ala Gly Gln  Val Leu Ser
    2150                 2155                 2160

Ile Ala  Glu Gly Val Ala Asp  Leu Val Pro Asn Val  Phe Gly Leu
    2165                 2170                 2175

Ala Cys  Gly Gly Ser Arg Trp  Gly Ala Ala Leu Arg  Ala Ser Ala
    2180                 2185                 2190

Ser Val  Met Ser Leu Ser Ala  Thr Ala Ser Gln Tyr  Ser Ala Asp
    2195                 2200                 2205

Lys Ile  Ser Arg Ser Glu Ala  Tyr Arg Arg Arg Arg  Gln Glu Trp
    2210                 2215                 2220

Glu Ile  Gln Arg Asp Asn Ala  Asp Gly Glu Val Lys  Gln Met Asp
    2225                 2230                 2235

Ala Gln  Leu Glu Ser Leu Lys  Ile Arg Arg Glu Ala  Ala Gln Met
    2240                 2245                 2250

Gln Val  Glu Tyr Gln Glu Thr  Gln Gln Ala His Thr  Gln Ala Gln
    2255                 2260                 2265
```

Leu Glu Leu Leu Gln Arg Lys Phe Thr Asn Lys Ala Leu Tyr Ser
2270 2275 2280

Trp Met Arg Gly Lys Leu Ser Ala Ile Tyr Tyr Gln Phe Phe Asp
2285 2290 2295

Leu Thr Gln Ser Phe Cys Leu Met Ala Gln Glu Ala Leu Arg Arg
2300 2305 2310

Glu Leu Thr Asp Asn Gly Val Thr Phe Ile Arg Gly Gly Ala Trp
2315 2320 2325

Asn Gly Thr Thr Ala Gly Leu Met Ala Gly Glu Thr Leu Leu Leu
2330 2335 2340

Asn Leu Ala Glu Met Glu Lys Val Trp Leu Glu Arg Asp Glu Arg
2345 2350 2355

Ala Leu Glu Val Thr Arg Thr Val Ser Leu Ala Gln Phe Tyr Gln
2360 2365 2370

Ala Leu Ser Ser Asp Asn Phe Asn Leu Thr Glu Lys Leu Thr Gln
2375 2380 2385

Phe Leu Arg Glu Gly Lys Gly Asn Val Gly Ala Ser Gly Asn Glu
2390 2395 2400

Leu Lys Leu Ser Asn Arg Gln Ile Glu Ala Ser Val Arg Leu Ser
2405 2410 2415

Asp Leu Lys Ile Phe Ser Asp Tyr Pro Glu Ser Leu Gly Asn Thr
2420 2425 2430

Arg Gln Leu Lys Gln Val Ser Val Thr Leu Pro Ala Leu Val Gly
2435 2440 2445

Pro Tyr Glu Asp Ile Arg Ala Val Leu Asn Tyr Gly Gly Ser Ile
2450 2455 2460

Val Met Pro Arg Gly Cys Ser Ala Ile Ala Leu Ser His Gly Val
2465 2470 2475

Asn Asp Ser Gly Gln Phe Met Leu Asp Phe Asn Asp Ser Arg Tyr
2480 2485 2490

Leu Pro Phe Glu Gly Ile Ser Val Asn Asp Ser Gly Ser Leu Thr
2495 2500 2505

Leu Ser Phe Pro Asp Ala Thr Asp Arg Gln Lys Ala Leu Leu Glu
2510 2515 2520

Ser Leu Ser Asp Ile Ile Leu His Ile Arg Tyr Thr Ile Arg Ser
2525 2530 2535

<210> SEQ ID NO 21
<211> LENGTH: 7551
<212> TYPE: DNA
<213> ORGANISM: Photorhabdus luminescens

<400> SEQUENCE: 21
atgaacgagt ctgtaaaaga gatacctgat gtattaaaaa gccagtgtgg ttttaattgt 60
ctgacagata ttagccacag ctcttttaat gaatttcgcc agcaagtatc tgagcacctc 120
tcctggtccg aaacacacga cttatatcat gatgcacaac aggcacaaaa ggataatcgc 180
ctgtatgaag cgcgtattct caaacgcgcc aatccccaat tacaaaatgc ggtgcatctt 240
gccattctcg ctcccaatgc tgaactgata ggctataaca atcaatttag cggtagagcc 300
agtcaatatg ttgcgccggg taccgtttct tccatgttct cccccgccgc ttatttgact 360
gaactttatc gtgaagcacg caatttacac gcaagtgact ccgtttatta tctggatacc 420
cgccgcccag atctcaaatc aatggcgctc agtcagcaaa atatggatat agaattatcc 480
acactctctt tgtccaatga gctgttattg gaaagcatta aaactgaatc taaactggaa 540

-continued

```
aactatacta aagtgatgga aatgctctcc actttccgtc cttccggcgc aacgccttat    600
catgatgctt atgaaaatgt gcgtgaagtt atccagctac aagatcctgg acttgagcaa    660
ctcaatgcat caccggcaat tgccgggttg atgcatcaag cctccctatt gggtattaac    720
gcttcaatct cgcctgagct atttaatatt ctgacggagg agattaccga aggtaatgct    780
gaggaacttt ataagaaaaa ttttggtaat atcgaaccgg cctcattggc tatgccggaa    840
taccttaaac gttattataa tttaagcgat gaagaactta gtcagtttat tggtaaagcc    900
agcaattttg gtcaacagga atatagtaat aaccaactta ttactccggt agtcaacagc    960
agtgatggca cggttaaggt atatcggatc acccgcgaat atacaaccaa tgcttatcaa   1020
atggatgtgg agctatttcc cttcggtggt gagaattatc ggttagatta taaattcaaa   1080
aatttttata atgcctctta tttatccatc aagttaaatg ataaaagaga acttgttcga   1140
actgaaggcg ctcctcaagt caatatagaa tactccgcaa atatcacatt aaataccgct   1200
gatatcagtc aacctttga aattggcctg acacgagtac ttccttccgg ttcttgggca   1260
tatgccgccg caaaatttac cgttgaagag tataaccaat actcttttct gctaaaactt   1320
aacaaggcta ttcgtctatc acgtgcgaca gaattgtcac ccacgattct ggaaggcatt   1380
gtgcgcagtg ttaatctaca actggatatc aacacagacg tattaggtaa agtttttctg   1440
actaaatatt atatgcagcg ttatgctatt catgctgaaa ctgccctgat actatgcaac   1500
gcgcctattt cacaacgttc atatgataat caacctagcc aatttgatcg cctgtttaat   1560
acgccattac tgaacggaca atatttttct accggcgatg aggagattga tttaaattca   1620
ggtagcaccg gcgattggcg aaaaaccata cttaagcgtg catttaatat tgatgatgtc   1680
tcgctcttcc gcctgcttaa aattaccgac catgataata aagatggaaa aattaaaaat   1740
aacctaaaga atctttccaa tttatatatt ggaaaattac tggcagatat tcatcaatta   1800
accattgatg aactggattt attactgatt gccgtaggtg aaggaaaaac taatttatcc   1860
gctatcagtg ataagcaatt ggctaccctg atcagaaaac tcaatactat taccagctgg   1920
ctacatacac agaagtggag tgtattccag ctatttatca tgacctccac cagctataac   1980
aaaacgctaa cgcctgaaat taagaatttg ctggataccg tctaccacgg tttacaaggt   2040
tttgataaag acaaagcaga tttgctacat gtcatggcgc cctatattgc ggccaccttg   2100
caattatcat cggaaaatgt cgcccactcg gtactccttt gggcagataa gttacagccc   2160
ggcgacggcg caatgacagc agaaaaattc tgggactggt tgaatactaa gtatacgccg   2220
ggttcatcgg aagccgtaga aacgcaggaa catatcgttc agtattgtca ggctctggca   2280
caattggaaa tggtttacca ttccaccggc atcaacgaaa acgccttccg tctatttgtg   2340
acaaaaccag agatgtttgg cgctgcaact ggagcagcgc ccgcgcatga tgccctttca   2400
ctgattatgc tgacacgttt tgcggattgg gtgaacgcac taggcgaaaa agcgtcctcg   2460
gtgctagcgg catttgaagc taactcgtta acggcagaac aactggctga tgccatgaat   2520
cttgatgcta atttgctgtt gcaagccagt attcaagcac aaaatcatca acatcttccc   2580
ccagtaactc cagaaaatgc gttctcctgt tggacatcta tcaatactat cctgcaatgg   2640
gttaatgtcg cacaacaatt gaatgtcgcc ccacagggcg tttccgcttt ggtcgggctg   2700
gattatattc aatcaatgaa agagacaccg acctatgccc agtgggaaaa cgcggcaggc   2760
gtattaaccg ccgggttgaa ttcacaacag gctaatacat tacacgcttt tctggatgaa   2820
tctcgcagtg ccgcattaag cacctactat atccgtcaag tcgccaaggc agcggcggct   2880
attaaaagcc gtgatgactt gtatcaatac ttactgattg ataatcaggt ttctgcggca   2940
```

-continued

```
ataaaaacca cccggatcgc cgaagccatt gccagtattc aactgtacgt caaccgggca   3000
ttggaaaatg tggaagaaaa tgccaattcg ggggttatca gccgccaatt ctttatcgac   3060
tgggacaaat acaataaacg ctacagcact tgggcgggtg tttctcaatt agtttactac   3120
ccggaaaact atattgatcc gaccatgcgt atcggacaaa ccaaaatgat ggacgcatta   3180
ctgcaatccg tcagccaaag ccaattaaac gccgataccg tcgaagatgc ctttatgtct   3240
tatctgacat cgtttgaaca agtggctaat cttaaagtta ttagcgcata tcacgataat   3300
attaataacg atcaagggct gacctatttt atcggactca gtgaaactga tgccggtgaa   3360
tattattggc gcagtgtcga tcacagtaaa ttcaacgacg gtaaattcgc ggctaatgcc   3420
tggagtgaat ggcataaaat tgattgtcca attaaccctt ataaaagcac tatccgtcca   3480
gtgatatata aatcccgcct gtatctgctc tggttggaac aaaaggagat caccaaacag   3540
acaggaaata gtaaagatgg ctatcaaact gaaacggatt atcgttatga actaaaattg   3600
gcgcatatcc gctatgatgg cacttggaat acgccaatca cctttgatgt caataaaaaa   3660
atatccgagc taaaactgga aaaaaataga gcgcccggac tctattgtgc cggttatcaa   3720
ggtgaagata cgttgctggt gatgttttat aaccaacaag acacactaga tagttataaa   3780
aacgcttcaa tgcaaggact atatatcttt gctgatatgg catccaaaga tatgacccca   3840
gaacagagca atgtttatcg ggataatagc tatcaacaat ttgataccaa taatgtcaga   3900
agagtgaata accgctatgc agaggattat gagattcctt cctcggtaag tagccgtaaa   3960
gactatggtt ggggagatta ttacctcagc atggtatata acggagatat tccaactatc   4020
aattacaaag ccgcatcaag tgatttaaaa atctatatct caccaaaatt aagaattatt   4080
cataatggat atgaaggaca gaagcgcaat caatgcaatc tgatgaataa atatggcaaa   4140
ctaggtgata aatttattgt ttatactagc ttgggggtca atccaaataa ctcgtcaaat   4200
aagctcatgt tttaccccgt ctatcaatat agcggaaaca ccagtggact caatcaaggg   4260
agactactat tccaccgtga caccacttat ccatctaaag tagaagcttg gattcctgga   4320
gcaaaacgtt ctctaaccaa ccaaaatgcc gccattggtg atgattatgc tacagactct   4380
ctgaataaac cggatgatct taagcaatat atctttatga ctgacagtaa agggactgct   4440
actgatgtct caggcccagt agagattaat actgcaattt ctccagcaaa agttcagata   4500
atagtcaaag cgggtggcaa ggagcaaact tttaccgcag ataaagatgt ctccattcag   4560
ccatcaccta gctttgatga aatgaattat caatttaatg cccttgaaat agacggttct   4620
ggtctgaatt ttattaacaa ctcagccagt attgatgtta cttttaccgc atttgcggag   4680
gatggccgca aactgggtta tgaaagtttc agtattcctg ttaccctcaa ggtaagtacc   4740
gataatgccc tgaccctgca ccataatgaa aatggtgcgc aatatatgca atggcaatcc   4800
tatcgtaccc gcctgaatac tctatttgcc cgccagttgg ttgcacgcgc caccaccgga   4860
atcgatacaa ttctgagtat ggaaactcag aatattcagg aaccgcagtt aggcaaaggt   4920
ttctatgcta cgttcgtgat acctccctat aacctatcaa ctcatggtga tgaacgttgg   4980
tttaagcttt atatcaaaca tgttgttgat aataattcac atattatcta ttcaggccag   5040
ctaacagata caaatataaa catcacatta tttattcctc ttgatgatgt cccattgaat   5100
caagattatc acgccaaggt ttatatgacc ttcaagaaat caccatcaga tggtacctgg   5160
tggggccctc actttgttag agatgataaa ggaatagtaa caataaaccc taaatccatt   5220
ttgacccatt ttgagagcgt caatgtcctg aataatatta gtagcgaacc aatggatttc   5280
agcggcgcta acagcctcta tttctgggaa ctgttctact ataccccgat gctggttgct   5340
```

caacgtttgc tgcatgaaca gaacttcgat gaagccaacc gttggctgaa atatgtctgg 5400
agtccatccg gttatattgt ccacggccag attcagaact accagtggaa cgtccgcccg 5460
ttactggaag acaccagttg gaacagtgat cctttggatt ccgtcgatcc tgacgcggta 5520
gcacagcacg atccaatgca ctacaaagtt tcaactttta tgcgtacctt ggatctattg 5580
atagcacgcg gcgaccatgc ttatcgccaa ctggaacgag atacactcaa cgaagcgaag 5640
atgtggtata tgcaagcgct gcatctatta ggtgacaaac cttatctacc gctgagtacg 5700
acatggagtg atccacgact agacagagcc gcggatatca ctacccaaaa tgctcacgac 5760
agcgcaatag tcgctctgcg gcagaatata cctacaccgg cacctttatc attgcgcagc 5820
gctaataccc tgactgatct cttcctgccg caaatcaatg aagtgatgat gaattactgg 5880
cagacattag ctcagagagt atacaatctg cgtcataacc tctctatcga cggccagccg 5940
ttatatctgc caatctatgc cacaccggcc gatccgaaag cgttactcag cgccgccgtt 6000
gccacttctc aaggtggagg caagctaccg gaatcattta tgtccctgtg gcgtttcccg 6060
cacatgctgg aaaatgcgcg cggcatggtt agccagctca cccagttcgg ctccacgtta 6120
caaaatatta tcgaacgtca ggacgcggaa gcgctcaatg cgttattaca aaatcaggcc 6180
gccgagctga tattgactaa cctgagcatt caggacaaaa ccattgaaga attggatgcc 6240
gagaaaacgg tgttggaaaa atccaaagcg ggagcacaat cgcgctttga tagctacggc 6300
aaactgtacg atgagaatat caacgccggt gaaaaccaag ccatgacgct acgagcgtcc 6360
gccgccgggc ttaccacggc agttcaggca tcccgtctgg ccggtgcggc ggctgatctg 6420
gtgcctaaca tcttcggctt tgccggtggc ggcagccgtt gggggctat cgctgaggcg 6480 acaggttatg tgatggaatt ctccgcgaat gttatgaaca ccgaagcgga taaaattagc 6540
caatctgaaa cctaccgtcg tcgccgtcag gagtgggaga tccagcggaa taatgccgaa 6600
gcggaattga agcaaatcga tgctcagctc aaatcactcg ctgtacgccg cgaagccgcc 6660
gtattgcaga aaaccagtct gaaaacccaa caagaacaga cccaatctca attggccttc 6720
ctgcaacgta agttcagcaa tcaggcgtta tacaactggc tgcgtggtcg actggcggcg 6780
atttacttcc agttctacga tttggccgtc gcgcgttgcc tgatggcaga acaagcttac 6840
cgttgggaac tcaatgatga ctctgcccgc ttcattaaac cgggcgcctg gcagggaacc 6900
tatgccggtc tgcttgcagg tgaaaccttg atgctgagtc tggcacaaat ggaagacgct 6960
catctgaaac gcgataaacg cgcattagag gttgaacgca cagtatcgct ggccgaagtt 7020
tatgcaggat taccaaaaga taacggtcca ttttccctgg ctcaggaaat tgacaagctg 7080
gtgagtcaag gttcaggcag tgccggcagt ggtaataata atttggcgtt cggcgccggc 7140
acggacacta aaacctcttt gcaggcatca gtttcattcg ctgatttgaa aattcgtgaa 7200
gattacccgg catcgcttgg caaaattcga cgtatcaaac agatcagcgt cactttgccc 7260
gcgctactgg gaccgtatca ggatgtacag gcaatattgt cttacggcga taaagccgga 7320
ttagctaacg gctgtgaagc gctggcagtt tctcacggta tgaatgacag cggccaattc 7380
cagctcgatt tcaacgatgg caaattcctg ccattcgaag gcatcgccat tgatcaaggc 7440
acgctgacac tgagcttccc aaatgcatct atgccggaga aaggtaaaca agccactatg 7500
ttaaaaaccc tgaacgatat cattttgcat attcgctaca ccattaaata a 7551

<210> SEQ ID NO 22
<211> LENGTH: 4431
<212> TYPE: DNA
<213> ORGANISM: Photorhabdus luminescens

<400> SEQUENCE: 22
atgcagaatt cacaaacatt cagtgttacc gagctgtcat tacccaaagg cggcggcgct 60
attaccggta tgggtgaagc attaacacca gccgggccgg atggtatggc cgccttatcc 120
ctgccattac ccatttccgc cgggcgtggt tacgcaccct cgctcactct gaattacaac 180
agtggaaccg gtaacagccc atttggtctc ggttgggact gcggcgtcat ggcaattcgt 240
cgtcgcacca gtaccggcgt accgaattac gatgaaaccg atacttttct ggggccggaa 300
ggtgaagtgt tggtcgtagc attaaatgag gcaggtcaag ctgatatccg cagtgaatcc 360
tcattgcagg gcatcaattt gggtgcgacc ttcaccgtta cctgttatcg ctcccgccta 420
gaaagccact ttaaccggtt ggaatactgg caaccccaaa caaccggcgc aaccgatttc 480
tggctgatat acagccccga cggacaggtc catttactgg gcaaaaatcc tcaggcacgt 540
atcagcaatc cactcaatgt taaccaaaca gcgcaatggc tgttggaagc ctcgatatca 600
tcccacagcg aacagattta ttatcaatat cgcgctgaag atgaagcagg ttgtgaaacc 660
gacgagctag cagcccaccc cagcgcaacc gttcagcgct acctgcaaac agtacattac 720
gggaacctga ccgccagcga cgtttttcct acactaaacg gagatgaccc acttaaatct 780
ggctggatgt tctgtttagt atttgactac ggtgagcgca aaaacagctt atctgaaatg 840
ccgctgttta aagccacagg caattggctt tgccgaaaag accgttttc ccgttatgag 900
tacggttttg aattgcgtac tcgccgctta tgccgccaaa tactgatgtt tcaccgtcta 960
caaaccctat ctggtcaggc aaagggggat gatgaacctg cgctagtgtc gcgtctgata 1020
ctggattatg acgaaaacgc gatggtcagt acgctcgttt ctgtccgccg ggtaggccat 1080
gaggacaaca acacggttac cgcgctgcca ccactggaac tggcctatca gccttttgag 1140
ccagaacaaa ccgcactctg gcaatcaatg gatgtactgg caaatttcaa caccattcag 1200
cgctggcaac tgcttgacct gaaaggagaa ggcgtgcccg gcattctcta tcaggataga 1260
aatggctggt ggtatcgatc tgcccaacgt caggccgggg aagagatgaa tgcggtcacc 1320
tgggggaaaa tgcaactcct tcccatcaca ccagctgtgc aggataacgc ctcactgatg 1380
gatattaacg gtgacgggca actggactgg gtgattaccg ggccggggct aaggggctat 1440
cacagccaac acccggatgg cagttggacg cgttttacgc cattacatgc cctgccgata 1500
gaatattctc atcctcgcgc tcaacttgcc gatttaatgg gagccgggct gtccgattta 1560
gtgctaattg gtcccaaaag tgtgcgctta tatgtcaata accgtgatgg ttttaccgaa 1620
gggcgggatg tggtgcaatc cggtgatatc accctgccgc taccgggcgc cgatgcccgt 1680
aagttagtgg catttagtga cgtactgggt tcaggccaag cacatctggt tgaagttagt 1740
gcaactcaag tcacctgctg gccgaatctg ggcatggcc gttttggtca gccaatcgta 1800
ttgccgggat tcagccaatc tgccgccagt tttaatcctg atcgagttca tctggccgat 1860
ttggatggga gcggccctgc cgatttgatt tatgttcatg ctgaccgtct ggatattttc 1920
agcaatgaaa gtggcaacgg ttttgcaaaa ccattcacac tctcttttcc tgacggcctg 1980
cgttttgatg atacctgcca gttgcaagta gccgatgtac aagggttagg cgttgtcagc 2040
ctgatcctaa gcgtaccgca tatggcgcca catcattggc gctgcgatct gaccaacgcg 2100
aaaccgtggt tactcagtga aacgaacaac aatatggggg ccaatcacac cttgcattac 2160
cgtagctctg tccagttctg gctggatgaa aaagctgcgg cattggctac cggacaaaca 2220
ccggtctgtt acctgccctt cccggtccat accctttggc aaacagaaac cgaggatgaa 2280
atcagcggca ataagttagt gaccacgtta cgttatgctc acggcgcttg ggatggacgt 2340

-continued

```
gaacgggaat ttcgtggctt tggttatgtt gagcagacag acagccatca actcgctcaa   2400

ggcaatgcgc cggaacgtac accaccggca ctcaccaaaa gctggtatgc caccggatta   2460

cctgcggtag ataatgcgtt atccgccggg tattggcgtg gcgataagca agctttcgcc   2520

ggttttacgc cacgttttac tctctggaaa gagggcaaag atgttccact gacaccggaa   2580

gatgaccata atctatactg gttaaaccgg gcgctaaaag gtcagccact gcgtagtgaa   2640

ctctacgggc tggatggcag cgcacagcaa cagatcccct atacagtgac tgaatcccgt   2700

ccacaggtgc gccaattaca agatggcgcc accgtttccc cggtgctctg ggcctcagtc   2760

gtggaaagcc gtagttatca ctacgaacgt attatcagtg atccccagtg caatcaggat   2820

atcacgttgt ccagtgacct attcgggcaa ccactgaaac aggtttccgt acaatatccc   2880

cgccgcaaca aaccaacaac caatccgtat cccgataccc taccggatac gctgtttgcc   2940

agcagttatg acgatcaaca acagctattg cgattaacct gccgacaatc cagttggcac   3000

catcttattg gtaatgagct aagagtgttg ggattaccgg atggcacacg cagtgatgcc   3060

tttacttacg atgccaaaca ggtacctgtc gatggcttaa atctggaaac cctgtgtgct   3120

gaaaatagcc tgattgccga tgataaacct cgcgaatacc tcaatcagca acgaacgttc   3180

tataccgacg ggaaaaacca aacaccgctg aaaacaccga cacgacaagc gttaatcgcc   3240

tttaccgaaa cggcggtatt aacggaatct ctgttatccg cgtttgatgg cggtattacg   3300

ccagacgaat taccgggaat actgacacag gccggatacc aacaagagcc ttatctgttt   3360

ccacgcaccg gcgaaaacaa agtttgggta gcgcgtcaag gctataccga ttacgggacg   3420

gaagcacaat tttggcgtcc tgtcgcacaa cgtaacagcc tgttaaccgg gaaaatgacg   3480

ttaaaatggg atactcacta ttgtgtcatc acccaaaccc aagatgctgc cggcctcacc   3540

gtctcagcca attatgactg gcgttttctc acaccaacgc aactgactga catcaacgat   3600

aatgtgcatc tcatcacctt ggatgctctg ggacgccctg tcacgcaacg tttctggggg   3660

atcgaaagcg gtgtggcaac aggttactct tcatcagaag aaaaaccatt ctctccacca   3720

aacgatatcg ataccgctat taatctaacc ggaccactcc ctgtcgcaca gtgtctggtc   3780

tatgcaccgg acagttggat gccactattc agtcaagaaa ccttcaacac attaacgcag   3840

gaagagcagg agacgctgcg tgattcacgt attatcacgg aagattggcg tatttgcgca   3900

ctgactcgcc gccgttggct acaaagtcaa aagatcagta caccattagt taaactgtta   3960

accaacagca ttggtttacc tccccataac cttacgctga ccacagaccg ttatgaccgc   4020

gactctgagc agcaaattcg ccaacaagtc gcatttagtg atggttttgg ccgtctgcta   4080

caagcgtctg tacgacatga ggcaggcgaa gcctggcaac gtaaccaaga cggttctctg   4140

gtgacaaaag tggagaatac caaaacgcgt tgggcggtca cgggacgcac cgaatatgat   4200

aataaagggc aaacgatacg cacttatcag ccctatttcc tcaacgactg gcgatatgtc   4260

agtgatgaca gcgccagaaa agaagcctat gcggatactc atatttatga tccaattggg   4320

cgagaaatcc gggttattac tgcaaaaggc tggctgcgcc aaagccaata tttcccgtgg   4380

tttaccgtga gtgaggatga gaatgatacg gccgctgatg cgctggtgta a            4431
```

<210> SEQ ID NO 23
<211> LENGTH: 74
<212> TYPE: DNA
<213> ORGANISM: Artificial Sequence
<220> FEATURE:
<223> OTHER INFORMATION: Forward primer used to amplify the TcdB1
      sequence from plasmid pBC-AS4.

<400> SEQUENCE: 23
atatagtcga cgaattttaa tctactagta aaaaggagat aaccatgcag aattcacaaa 60
cattcagtgt tacc 74

<210> SEQ ID NO 24
<211> LENGTH: 57
<212> TYPE: DNA
<213> ORGANISM: Artificial Sequence
<220> FEATURE:
<223> OTHER INFORMATION: Reverse primer used to amplify the TcdB1 sequence from plasmid pBC-AS4.

<400> SEQUENCE: 24
ataatacgat cgtttctcga gtcattacac cagcgcatca gcggccgtat cattctc 57

<210> SEQ ID NO 25
<211> LENGTH: 3132
<212> TYPE: DNA
<213> ORGANISM: Photorhabdus luminescens

<400> SEQUENCE: 25
atgagtccgt ctgagactac tctttatact caaaccccaa cagtcagcgt gttagataat 60
cgcggtctgt ccattcgtga tattggtttt caccgtattg taatcggggg ggatactgac 120
acccgcgtca cccgtcacca gtatgatgcc cgtggacacc tgaactacag tattgaccca 180
cgcttgtatg atgcaaagca ggctgataac tcagtaaagc ctaattttgt ctggcagcat 240
gatctggccg gtcatgccct gcggacagag agtgtcgatg ctggtcgtac tgttgcattg 300
aatgatattg aaggtcgttc ggtaatgaca atgaatgcga ccggtgttcg tcagacccgt 360
cgctatgaag gcaacacctt gcccggtcgc ttgttatctg tgagcgagca agttttcaac 420
caagagagtg ctaaagtgac agagcgcttt atctgggctg ggaatacaac ctcggagaaa 480
gagtataacc tctccggtct gtgtatacgc cactacgaca cagcgggagt gacccggttg 540
atgagtcagt cactggcggg cgccatgcta tcccaatctc accaattgct ggcggaaggg 600
caggaggcta actggagcgg tgacgacgaa actgtctggc agggaatgct ggcaagtgag 660
gtctatacga cacaaagtac cactaatgcc atcggggctt tactgaccca aaccgatgcg 720
aaaggcaata ttcagcgtct ggcttatgac attgccggtc agttaaaagg gagttggttg 780
acggtgaaag gccagagtga acaggtgatt gttaagtccc tgagctggtc agccgcaggt 840
cataaattgc gtgaagagca cggtaacggc gtggttacgg agtacagtta tgagccggaa 900
actcaacgtc tgataggtat caccacccgg cgtgccgaag ggagtcaatc aggagccaga 960
gtattgcagg atctacgcta taagtatgat ccggtgggga atgttatcag tatccataat 1020
gatgccgaag ctacccgctt ttggcgtaat cagaaagtgg agccggagaa tcgctatgtt 1080
tatgattctc tgtatcagct tatgagtgcg acagggcgtg aaatggctaa tatcggtcag 1140
caaagcaacc aacttccctc acccgttata cctgttccta ctgacgacag cacttatacc 1200
aattaccttc gtacctatac ttatgaccgt ggcggtaatt tggttcaaat ccgacacagt 1260
tcacccgcga ctcaaaatag ttacaccaca gatatcaccg tttcaagccg cagtaaccgg 1320
gcggtattga gtacattaac gacagatcca acccgagtgg atgcgctatt tgattccggc 1380
ggtcatcaga agatgttaat accggggcaa aatctggatt ggaatattcg gggtgaattg 1440
caacgagtca caccggtgag ccgtgaaaat agcagtgaca gtgaatggta tcgctatagc 1500
agtgatggca tgcggctgct aaaagtgagt gaacagcaga cgggcaacag tactcaagta 1560
caacgggtga cttatctgcc gggattagag ctacggacaa ctggggttgc agataaaaca 1620
accgaagatt tgcaggtgat tacggtaggt gaagcgggtc gcgcacaggt aagggtattg 1680
cactgggaaa gtggtaagcc gacagatatt gacaacaatc aggtgcgcta cagctacgat 1740
aatctgcttg gctccagcca gcttgaactg gatagcgaag ggcagattct cagtcaggaa 1800
gagtattatc cgtatggcgg tacggcgata tgggcggcga gaaatcagac agaagccagc 1860
tacaaattta ttcgttactc cggtaaagag cgggatgcca ctggattgta ttattacggc 1920
taccgttatt atcaaccttg ggtgggtcga tggttgagtg ctgatccggc gggaaccgtg 1980
gatgggctga atttgtaccg aatggtgagg aataacccca tcacattgac tgaccatgac 2040
ggattagcac cgtctccaaa tagaaatcga aatacatttt ggtttgcttc atttttgttt 2100
cgtaaacctg atgagggaat gtccgcgtca atgagacggg gacaaaaaat tggcagagcc 2160
attgccggcg ggattgcgat tggcggtctt gcggctacca ttgccgctac ggctggcgcg 2220
gctatccccg tcattctggg ggttgcggcc gtaggcgcgg ggattggcgc gttgatggga 2280
tataacgtcg gtagcctgct ggaaaaaggc ggggcattac ttgctcgact cgtacagggg 2340
aaatcgacgt tagtacagtc ggcggctggc gcggctgccg gagcgagttc agccgcggct 2400
tatggcgcac gggcacaagg tgtcggtgtt gcatcagccg ccggggcggt aacaggggct 2460
gtgggatcat ggataaataa tgctgatcgg gggattggcg gcgctattgg ggccgggagt 2520
gcggtaggca ccattgatac tatgttaggg actgcctcta cccttaccca tgaagtcggg 2580
gcagcggcgg gtggggcggc gggtgggatg atcaccggta cgcaagggag tactcgggca 2640
ggtatccatg ccggtattgg cacctattat ggctcctgga ttggttttgg tttagatgtc 2700
gctagtaacc ccgccggaca tttagcgaat tacgcagtgg gttatgccgc tggtttgggt 2760
gctgaaatgg ctgtcaacag aataatgggt ggtggatttt tgagtaggct cttaggccgg 2820
gttgtcagcc catatgccgc cggtttagcc agacaattag tacatttcag tgtcgccaga 2880
cctgtctttg agccgatatt tagtgttctc ggcgggcttg tcggtggtat tggaactggc 2940
ctgcacagag tgatgggaag agagagttgg atttccagag cgttaagtgc tgccggtagt 3000
ggtatagatc atgtcgctgg catgattggt aatcagatca gaggcagggt cttgaccaca 3060
accgggatcg ctaatgcgat agactatggc accagtgctg tgggagccgc acgacgagtt 3120
ttttctttgt aa 3132

<210> SEQ ID NO 26
<211> LENGTH: 77
<212> TYPE: DNA
<213> ORGANISM: Artificial Sequence
<220> FEATURE:
<223> OTHER INFORMATION: Forward primer used to amplify TccC1 from the pBC KS+ vector.

<400> SEQUENCE: 26
gtcgacgcac tactagtaaa aaggagataa ccccatgagc ccgtctgaga ctactcttta 60
tactcaaacc ccaacag 77

<210> SEQ ID NO 27
<211> LENGTH: 57
<212> TYPE: DNA
<213> ORGANISM: Artificial Sequence
<220> FEATURE:
<223> OTHER INFORMATION: Reverse primer used to amplify TccC1 from the pBC KS+ vector.

<400> SEQUENCE: 27
cggccgcagt cctcgagtca gattaattac aaagaaaaaa ctcgtcgtgc ggctccc 57

<210> SEQ ID NO 28
<211> LENGTH: 84
<212> TYPE: DNA
<213> ORGANISM: Artificial Sequence
<220> FEATURE:
<223> OTHER INFORMATION: Forward primer used to amplify XptA2.

<400> SEQUENCE: 28
gtctagacgt gcgtcgacaa gaaggagata taccatgtat agcacggctg tattactcaa 60
taaaatcagt cccactcgcg acgg 84

<210> SEQ ID NO 29
<211> LENGTH: 64
<212> TYPE: DNA
<213> ORGANISM: Artificial Sequence
<220> FEATURE:
<223> OTHER INFORMATION: Reverse primer used to amplify XptA2.

<400> SEQUENCE: 29
gctcgagatt aattaagaac gaatggtata gcggatatgc agaatgatat cgctcaggct 60
ctcc 64

<210> SEQ ID NO 30
<211> LENGTH: 81
<212> TYPE: DNA
<213> ORGANISM: Artificial Sequence
<220> FEATURE:
<223> OTHER INFORMATION: Forward primer used to amplify XptC1.

<400> SEQUENCE: 30
gtctagacgt gcgtcgacaa gaaggagata taccatgcag ggttcaacac ctttgaaact 60
tgaaataccg tcattgccct c 81

<210> SEQ ID NO 31
<211> LENGTH: 64
<212> TYPE: DNA
<213> ORGANISM: Artificial Sequence
<220> FEATURE:
<223> OTHER INFORMATION: Reverse primer used to amplify XptC1.

<400> SEQUENCE: 31
gactcgagag cattaattat gctgtcattt caccggcagt gtcattttca tcttcattca 60
ccac 64

<210> SEQ ID NO 32
<211> LENGTH: 86
<212> TYPE: DNA
<213> ORGANISM: Artificial Sequence
<220> FEATURE:
<223> OTHER INFORMATION: Forward primer used to amplify XptB1.

<400> SEQUENCE: 32
gtctagacgt gcgtcgacaa gaaggagata taccatgaag aatttcgttc acagcaatac 60
gccatccgtc accgtactgg acaacc 86

<210> SEQ ID NO 33
<211> LENGTH: 66
<212> TYPE: DNA
<213> ORGANISM: Artificial Sequence
<220> FEATURE:
<223> OTHER INFORMATION: Reverse primer used to amplify XptB1.

<400> SEQUENCE: 33
gctcgagcag attaattatg cttcggattc attatgacgt gcagaggcgt taaagaagaa 60
gttatt 66

<210> SEQ ID NO 34
<211> LENGTH: 2538
<212> TYPE: PRT
<213> ORGANISM: Xenorhabdus nematophilus

<400> SEQUENCE: 34

Met Tyr Ser Thr Ala Val Leu Leu Asn Lys Ile Ser Pro Thr Arg Asp
1 5 10 15

Gly Gln Thr Met Thr Leu Ala Asp Leu Gln Tyr Leu Ser Phe Ser Glu
20 25 30

Leu Arg Lys Ile Phe Asp Asp Gln Leu Ser Trp Gly Glu Ala Arg His
35 40 45

Leu Tyr His Glu Thr Ile Glu Gln Lys Lys Asn Asn Arg Leu Leu Glu
50 55 60

Ala Arg Ile Phe Thr Arg Ala Asn Pro Gln Leu Ser Gly Ala Ile Arg
65 70 75 80

Leu Gly Ile Glu Arg Asp Ser Val Ser Arg Ser Tyr Asp Glu Met Phe
85 90 95

Gly Ala Arg Ser Ser Ser Phe Val Lys Pro Gly Ser Val Ala Ser Met
100 105 110

Phe Ser Pro Ala Gly Tyr Leu Thr Glu Leu Tyr Arg Glu Ala Lys Asp
115 120 125

Leu His Phe Ser Ser Ser Ala Tyr His Leu Asp Asn Arg Arg Pro Asp
130 135 140

Leu Ala Asp Leu Thr Leu Ser Gln Ser Asn Met Asp Thr Glu Ile Ser
145 150 155 160

Thr Leu Thr Leu Ser Asn Glu Leu Leu Leu Glu His Ile Thr Arg Lys
165 170 175

Thr Gly Gly Asp Ser Asp Ala Leu Met Glu Ser Leu Ser Thr Tyr Arg
180 185 190

Gln Ala Ile Asp Thr Pro Tyr His Gln Pro Tyr Glu Thr Ile Arg Gln
195 200 205

Val Ile Met Thr His Asp Ser Thr Leu Ser Ala Leu Ser Arg Asn Pro
210 215 220

Glu Val Met Gly Gln Ala Glu Gly Ala Ser Leu Leu Ala Ile Leu Ala
225 230 235 240

Asn Ile Ser Pro Glu Leu Tyr Asn Ile Leu Thr Glu Glu Ile Thr Glu
245 250 255

Lys Asn Ala Asp Ala Leu Phe Ala Gln Asn Phe Ser Glu Asn Ile Thr
260 265 270

Pro Glu Asn Phe Ala Ser Gln Ser Trp Ile Ala Lys Tyr Tyr Gly Leu
275 280 285

Glu Leu Ser Glu Val Gln Lys Tyr Leu Gly Met Leu Gln Asn Gly Tyr
290 295 300

Ser Asp Ser Thr Ser Ala Tyr Val Asp Asn Ile Ser Thr Gly Leu Val
305 310 315 320

Val Asn Asn Glu Ser Lys Leu Glu Ala Tyr Lys Ile Thr Arg Val Lys
325 330 335

Thr Asp Asp Tyr Asp Lys Asn Ile Asn Tyr Phe Asp Leu Met Tyr Glu
340 345 350

Gly Asn Asn Gln Phe Phe Ile Arg Ala Asn Phe Lys Val Ser Arg Glu

-continued

```
        355                 360                 365

Phe Gly Ala Thr Leu Arg Lys Asn Ala Gly Pro Ser Gly Ile Val Gly
    370                 375                 380

Ser Leu Ser Gly Pro Leu Ile Ala Asn Thr Asn Phe Lys Ser Asn Tyr
385                 390                 395                 400

Leu Ser Asn Ile Ser Asp Ser Glu Tyr Lys Asn Gly Val Lys Ile Tyr
                405                 410                 415

Ala Tyr Arg Tyr Thr Ser Ser Thr Ser Ala Thr Asn Gln Gly Gly Gly
            420                 425                 430

Ile Phe Thr Phe Glu Ser Tyr Pro Leu Thr Ile Phe Ala Leu Lys Leu
        435                 440                 445

Asn Lys Ala Ile Arg Leu Cys Leu Thr Ser Gly Leu Ser Pro Asn Glu
    450                 455                 460

Leu Gln Thr Ile Val Arg Ser Asp Asn Ala Gln Gly Ile Ile Asn Asp
465                 470                 475                 480

Ser Val Leu Thr Lys Val Phe Tyr Thr Leu Phe Tyr Ser His Arg Tyr
                485                 490                 495

Ala Leu Ser Phe Asp Asp Ala Gln Val Leu Asn Gly Ser Val Ile Asn
            500                 505                 510

Gln Tyr Ala Asp Asp Asp Ser Val Ser His Phe Asn Arg Leu Phe Asn
        515                 520                 525

Thr Pro Pro Leu Lys Gly Lys Ile Phe Glu Ala Asp Gly Asn Thr Val
    530                 535                 540

Ser Ile Asp Pro Asp Glu Glu Gln Ser Thr Phe Ala Arg Ser Ala Leu
545                 550                 555                 560

Met Arg Gly Leu Gly Val Asn Ser Gly Glu Leu Tyr Gln Leu Gly Lys
                565                 570                 575

Leu Ala Gly Val Leu Asp Ala Gln Asn Thr Ile Thr Leu Ser Val Phe
            580                 585                 590

Val Ile Ser Ser Leu Tyr Arg Leu Thr Leu Leu Ala Arg Val His Gln
        595                 600                 605

Leu Thr Val Asn Glu Leu Cys Met Leu Tyr Gly Leu Ser Pro Phe Asn
    610                 615                 620

Gly Lys Thr Thr Ala Ser Leu Ser Ser Gly Glu Leu Pro Arg Leu Val
625                 630                 635                 640

Ile Trp Leu Tyr Gln Val Thr Gln Trp Leu Thr Glu Ala Glu Ile Thr
                645                 650                 655

Thr Glu Ala Ile Trp Leu Leu Cys Thr Pro Glu Phe Ser Gly Asn Ile
            660                 665                 670

Ser Pro Glu Ile Ser Asn Leu Leu Asn Asn Leu Arg Pro Ser Ile Ser
        675                 680                 685

Glu Asp Met Ala Gln Ser His Asn Arg Glu Leu Gln Ala Glu Ile Leu
    690                 695                 700

Ala Pro Phe Ile Ala Ala Thr Leu His Leu Ala Ser Pro Asp Met Ala
705                 710                 715                 720

Arg Tyr Ile Leu Leu Trp Thr Asp Asn Leu Arg Pro Gly Gly Leu Asp
                725                 730                 735

Ile Ala Gly Phe Met Thr Leu Val Leu Lys Glu Ser Leu Asn Ala Asn
            740                 745                 750

Glu Thr Thr Gln Leu Val Gln Phe Cys His Val Met Ala Gln Leu Ser
        755                 760                 765

Leu Ser Val Gln Thr Leu Arg Leu Ser Glu Ala Glu Leu Ser Val Leu
    770                 775                 780
```

-continued

```
Val Ile Ser Gly Phe Ala Val Leu Gly Ala Lys Asn Gln Pro Ala Gly
785                 790                 795                 800

Gln His Asn Ile Asp Thr Leu Phe Ser Leu Tyr Arg Phe His Gln Trp
                805                 810                 815

Ile Asn Gly Leu Gly Asn Pro Gly Ser Asp Thr Leu Asp Met Leu Arg
            820                 825                 830

Gln Gln Thr Leu Thr Ala Asp Arg Leu Ala Ser Val Met Gly Leu Asp
        835                 840                 845

Ile Ser Met Val Thr Gln Ala Met Val Ser Ala Gly Val Asn Gln Leu
    850                 855                 860

Gln Cys Trp Gln Asp Ile Asn Thr Val Leu Gln Trp Ile Asp Val Ala
865                 870                 875                 880

Ser Ala Leu His Thr Met Pro Ser Val Ile Arg Thr Leu Val Asn Ile
                885                 890                 895

Arg Tyr Val Thr Ala Leu Asn Lys Ala Glu Ser Asn Leu Pro Ser Trp
            900                 905                 910

Asp Glu Trp Gln Thr Leu Ala Glu Asn Met Glu Ala Gly Leu Ser Thr
        915                 920                 925

Gln Gln Ala Gln Thr Leu Ala Asp Tyr Thr Ala Glu Arg Leu Ser Ser
    930                 935                 940

Val Leu Cys Asn Trp Phe Leu Ala Asn Ile Gln Pro Glu Gly Val Ser
945                 950                 955                 960

Leu His Ser Arg Asp Asp Leu Tyr Ser Tyr Phe Leu Ile Asp Asn Gln
                965                 970                 975

Val Ser Ser Ala Ile Lys Thr Thr Arg Leu Ala Glu Ala Ile Ala Gly
            980                 985                 990

Ile Gln Leu Tyr Ile Asn Arg Ala  Leu Asn Arg Ile Glu  Pro Asn Ala
        995                 1000                1005

Arg Ala  Asp Val Ser Thr Arg  Gln Phe Phe Thr Asp  Trp Thr Val
    1010                1015                1020

Asn Asn  Arg Tyr Ser Thr Trp  Gly Gly Val Ser Arg  Leu Val Tyr
    1025                1030                1035

Tyr Pro  Glu Asn Tyr Ile Asp  Pro Thr Gln Arg Ile  Gly Gln Thr
    1040                1045                1050

Arg Met  Met Asp Glu Leu Leu  Glu Asn Ile Ser Gln  Ser Lys Leu
    1055                1060                1065

Ser Arg  Asp Thr Val Glu Asp  Ala Phe Lys Thr Tyr  Leu Thr Arg
    1070                1075                1080

Phe Glu  Thr Val Ala Asp Leu  Lys Val Val Ser Ala  Tyr His Asp
    1085                1090                1095

Asn Val  Asn Ser Asn Thr Gly  Leu Thr Trp Phe Val  Gly Gln Thr
    1100                1105                1110

Arg Glu  Asn Leu Pro Glu Tyr  Tyr Trp Arg Asn Val  Asp Ile Ser
    1115                1120                1125

Arg Met  Gln Ala Gly Glu Leu  Ala Ala Asn Ala Trp  Lys Glu Trp
    1130                1135                1140

Thr Lys  Ile Asp Thr Ala Val  Asn Pro Tyr Lys Asp  Ala Ile Arg
    1145                1150                1155

Pro Val  Ile Phe Arg Glu Arg  Leu His Leu Ile Trp  Val Glu Lys
    1160                1165                1170

Glu Glu  Val Ala Lys Asn Gly  Thr Asp Pro Val Glu  Thr Tyr Asp
    1175                1180                1185

Arg Phe  Thr Leu Lys Leu Ala  Phe Leu Arg His Asp  Gly Ser Trp
    1190                1195                1200
```

```
Ser Ala  Pro Trp Ser Tyr Asp  Ile Thr Thr Gln Val  Glu Ala Val
    1205                 1210                 1215

Thr Asp  Lys Lys Pro Asp Thr  Glu Arg Leu Ala Leu  Ala Ala Ser
    1220                 1225                 1230

Gly Phe  Gln Gly Glu Asp Thr  Leu Leu Val Phe Val  Tyr Lys Thr
    1235                 1240                 1245

Gly Lys  Ser Tyr Ser Asp Phe  Gly Gly Ser Asn Lys  Asn Val Ala
    1250                 1255                 1260

Gly Met  Thr Ile Tyr Gly Asp  Gly Ser Phe Lys Lys  Met Glu Asn
    1265                 1270                 1275

Thr Ala  Leu Ser Arg Tyr Ser  Gln Leu Lys Asn Thr  Phe Asp Ile
    1280                 1285                 1290

Ile His  Thr Gln Gly Asn Asp  Leu Val Arg Lys Ala  Ser Tyr Arg
    1295                 1300                 1305

Phe Ala  Gln Asp Phe Glu Val  Pro Ala Ser Leu Asn  Met Gly Ser
    1310                 1315                 1320

Ala Ile  Gly Asp Asp Ser Leu  Thr Val Met Glu Asn  Gly Asn Ile
    1325                 1330                 1335

Pro Gln  Ile Thr Ser Lys Tyr  Ser Ser Asp Asn Leu  Ala Ile Thr
    1340                 1345                 1350

Leu His  Asn Ala Ala Phe Thr  Val Arg Tyr Asp Gly  Ser Gly Asn
    1355                 1360                 1365

Val Ile  Arg Asn Lys Gln Ile  Ser Ala Met Lys Leu  Thr Gly Val
    1370                 1375                 1380

Asp Gly  Lys Ser Gln Tyr Gly  Asn Ala Phe Ile Ile  Ala Asn Thr
    1385                 1390                 1395

Val Lys  His Tyr Gly Gly Tyr  Ser Asp Leu Gly Gly  Pro Ile Thr
    1400                 1405                 1410

Val Tyr  Asn Lys Thr Lys Asn  Tyr Ile Ala Ser Val  Gln Gly His
    1415                 1420                 1425

Leu Met  Asn Ala Asp Tyr Thr  Arg Arg Leu Ile Leu  Thr Pro Val
    1430                 1435                 1440

Glu Asn  Asn Tyr Tyr Ala Arg  Leu Phe Glu Phe Pro  Phe Ser Pro
    1445                 1450                 1455

Asn Thr  Ile Leu Asn Thr Val  Phe Thr Val Gly Ser  Asn Lys Thr
    1460                 1465                 1470

Ser Asp  Phe Lys Lys Cys Ser  Tyr Ala Val Asp Gly  Asn Asn Ser
    1475                 1480                 1485

Gln Gly  Phe Gln Ile Phe Ser  Ser Tyr Gln Ser Ser  Gly Trp Leu
    1490                 1495                 1500

Asp Ile  Asp Thr Gly Ile Asn  Asn Thr Asp Ile Lys  Ile Thr Val
    1505                 1510                 1515

Met Ala  Gly Ser Lys Thr His  Thr Phe Thr Ala Ser  Asp His Ile
    1520                 1525                 1530

Ala Ser  Leu Pro Ala Asn Ser  Phe Asp Ala Met Pro  Tyr Thr Phe
    1535                 1540                 1545

Lys Pro  Leu Glu Ile Asp Ala  Ser Ser Leu Ala Phe  Thr Asn Asn
    1550                 1555                 1560

Ile Ala  Pro Leu Asp Ile Val  Phe Glu Thr Lys Ala  Lys Asp Gly
    1565                 1570                 1575

Arg Val  Leu Gly Lys Ile Lys  Gln Thr Leu Ser Val  Lys Arg Val
    1580                 1585                 1590

Asn Tyr  Asn Pro Glu Asp Ile  Leu Phe Leu Arg Glu  Thr His Ser
```

1595 1600 1605

Gly Ala Gln Tyr Met Gln Leu Gly Val Tyr Arg Ile Arg Leu Asn
1610 1615 1620

Thr Leu Leu Ala Ser Gln Leu Val Ser Arg Ala Asn Thr Gly Ile
1625 1630 1635

Asp Thr Ile Leu Thr Met Glu Thr Gln Arg Leu Pro Glu Pro Pro
1640 1645 1650

Leu Gly Glu Gly Phe Phe Ala Asn Phe Val Leu Pro Lys Tyr Asp
1655 1660 1665

Pro Ala Glu His Gly Asp Glu Arg Trp Phe Lys Ile His Ile Gly
1670 1675 1680

Asn Val Gly Gly Asn Thr Gly Arg Gln Pro Tyr Tyr Ser Gly Met
1685 1690 1695

Leu Ser Asp Thr Ser Glu Thr Ser Met Thr Leu Phe Val Pro Tyr
1700 1705 1710

Ala Glu Gly Tyr Tyr Met His Glu Gly Val Arg Leu Gly Val Gly
1715 1720 1725

Tyr Gln Lys Ile Thr Tyr Asp Asn Thr Trp Glu Ser Ala Phe Phe
1730 1735 1740

Tyr Phe Asp Glu Thr Lys Gln Gln Phe Val Leu Ile Asn Asp Ala
1745 1750 1755

Asp His Asp Ser Gly Met Thr Gln Gln Gly Ile Val Lys Asn Ile
1760 1765 1770

Lys Lys Tyr Lys Gly Phe Leu Asn Val Ser Ile Ala Thr Gly Tyr
1775 1780 1785

Ser Ala Pro Met Asp Phe Asn Ser Ala Ser Ala Leu Tyr Tyr Trp
1790 1795 1800

Glu Leu Phe Tyr Tyr Thr Pro Met Met Cys Phe Gln Arg Leu Leu
1805 1810 1815

Gln Glu Lys Gln Phe Asp Glu Ala Thr Gln Trp Ile Asn Tyr Val
1820 1825 1830

Tyr Asn Pro Ala Gly Tyr Ile Val Asn Gly Glu Ile Ala Pro Trp
1835 1840 1845

Ile Trp Asn Cys Arg Pro Leu Glu Glu Thr Thr Ser Trp Asn Ala
1850 1855 1860

Asn Pro Leu Asp Ala Ile Asp Pro Asp Ala Val Ala Gln Asn Asp
1865 1870 1875

Pro Met His Tyr Lys Ile Ala Thr Phe Met Arg Leu Leu Asp Gln
1880 1885 1890

Leu Ile Leu Arg Gly Asp Met Ala Tyr Arg Glu Leu Thr Arg Asp
1895 1900 1905

Ala Leu Asn Glu Ala Lys Met Trp Tyr Val Arg Thr Leu Glu Leu
1910 1915 1920

Leu Gly Asp Glu Pro Glu Asp Tyr Gly Ser Gln Gln Trp Ala Ala
1925 1930 1935

Pro Ser Leu Ser Gly Ala Ala Ser Gln Thr Val Gln Ala Ala Tyr
1940 1945 1950

Gln Gln Asp Leu Thr Met Leu Gly Arg Gly Gly Val Ser Lys Asn
1955 1960 1965

Leu Arg Thr Ala Asn Ser Leu Val Gly Leu Phe Leu Pro Glu Tyr
1970 1975 1980

Asn Pro Ala Leu Thr Asp Tyr Trp Gln Thr Leu Arg Leu Arg Leu
1985 1990 1995

-continued

```
Phe Asn  Leu Arg His Asn Leu  Ser Ile Asp Gly Gln  Pro Leu Ser
    2000                 2005                 2010

Leu Ala  Ile Tyr Ala Glu Pro  Thr Asp Pro Lys Ala  Leu Leu Thr
    2015                 2020                 2025

Ser Met  Val Gln Ala Ser Gln  Gly Gly Ser Ala Val  Leu Pro Gly
    2030                 2035                 2040

Thr Leu  Ser Leu Tyr Arg Phe  Pro Val Met Leu Glu  Arg Thr Arg
    2045                 2050                 2055

Asn Leu  Val Ala Gln Leu Thr  Gln Phe Gly Thr Ser  Leu Leu Ser
    2060                 2065                 2070

Met Ala  Glu His Asp Asp Ala  Asp Glu Leu Thr Thr  Leu Leu Leu
    2075                 2080                 2085

Gln Gln  Gly Met Glu Leu Ala  Thr Gln Ser Ile Arg  Ile Gln Gln
    2090                 2095                 2100

Arg Thr  Val Asp Glu Val Asp  Ala Asp Ile Ala Val  Leu Ala Glu
    2105                 2110                 2115

Ser Arg  Arg Ser Ala Gln Asn  Arg Leu Glu Lys Tyr  Gln Gln Leu
    2120                 2125                 2130

Tyr Asp  Glu Asp Ile Asn His  Gly Glu Gln Arg Ala  Met Ser Leu
    2135                 2140                 2145

Leu Asp  Ala Ala Ala Gly Gln  Ser Leu Ala Gly Gln  Val Leu Ser
    2150                 2155                 2160

Ile Ala  Glu Gly Val Ala Asp  Leu Val Pro Asn Val  Phe Gly Leu
    2165                 2170                 2175

Ala Cys  Gly Gly Ser Arg Trp  Gly Ala Ala Leu Arg  Ala Ser Ala
    2180                 2185                 2190

Ser Val  Met Ser Leu Ser Ala  Thr Ala Ser Gln Tyr  Ser Ala Asp
    2195                 2200                 2205

Lys Ile  Ser Arg Ser Glu Ala  Tyr Arg Arg Arg Arg  Gln Glu Trp
    2210                 2215                 2220

Glu Ile  Gln Arg Asp Asn Ala  Asp Gly Glu Val Lys  Gln Met Asp
    2225                 2230                 2235

Ala Gln  Leu Glu Ser Leu Lys  Ile Arg Arg Glu Ala  Ala Gln Met
    2240                 2245                 2250

Gln Val  Glu Tyr Gln Glu Thr  Gln Gln Ala His Thr  Gln Ala Gln
    2255                 2260                 2265

Leu Glu  Leu Leu Gln Arg Lys  Phe Thr Asn Lys Ala  Leu Tyr Ser
    2270                 2275                 2280

Trp Met  Arg Gly Lys Leu Ser  Ala Ile Tyr Tyr Gln  Phe Phe Asp
    2285                 2290                 2295

Leu Thr  Gln Ser Phe Cys Leu  Met Ala Gln Glu Ala  Leu Arg Arg
    2300                 2305                 2310

Glu Leu  Thr Asp Asn Gly Val  Thr Phe Ile Arg Gly  Gly Ala Trp
    2315                 2320                 2325

Asn Gly  Thr Thr Ala Gly Leu  Met Ala Gly Glu Thr  Leu Leu Leu
    2330                 2335                 2340

Asn Leu  Ala Glu Met Glu Lys  Val Trp Leu Glu Arg  Asp Glu Arg
    2345                 2350                 2355

Ala Leu  Glu Val Thr Arg Thr  Val Ser Leu Ala Gln  Phe Tyr Gln
    2360                 2365                 2370

Ala Leu  Ser Ser Asp Asn Phe  Asn Leu Thr Glu Lys  Leu Thr Gln
    2375                 2380                 2385

Phe Leu  Arg Glu Gly Lys Gly  Asn Val Gly Ala Ser  Gly Asn Glu
    2390                 2395                 2400
```

Leu Lys Leu Ser Asn Arg Gln Ile Glu Ala Ser Val Arg Leu Ser
2405 2410 2415

Asp Leu Lys Ile Phe Ser Asp Tyr Pro Glu Ser Leu Gly Asn Thr
2420 2425 2430

Arg Gln Leu Lys Gln Val Ser Val Thr Leu Pro Ala Leu Val Gly
2435 2440 2445

Pro Tyr Glu Asp Ile Arg Ala Val Leu Asn Tyr Gly Gly Ser Ile
2450 2455 2460

Val Met Pro Arg Gly Cys Ser Ala Ile Ala Leu Ser His Gly Val
2465 2470 2475

Asn Asp Ser Gly Gln Phe Met Leu Asp Phe Asn Asp Ser Arg Tyr
2480 2485 2490

Leu Pro Phe Glu Gly Ile Ser Val Asn Asp Ser Gly Ser Leu Thr
2495 2500 2505

Leu Ser Phe Pro Asp Ala Thr Asp Arg Gln Lys Ala Leu Leu Glu
2510 2515 2520

Ser Leu Ser Asp Ile Ile Leu His Ile Arg Tyr Thr Ile Arg Ser
2525 2530 2535

<210> SEQ ID NO 35
<211> LENGTH: 3300
<212> TYPE: DNA
<213> ORGANISM: Paenibacillus strain DAS1529

<400> SEQUENCE: 35
atggtgtcaa caacagacaa cacggccggc gtattccggc tcggaaccga agaattaaca 60
gaagcgctta agcagtccgg ttatcggacc gtctttgata ttgtatctga caatcttgcg 120
gaatttcaga aaaacaatcc ggagattccc tcttctgacg cgaaggagat tcatcaatta 180
gccgtccaga ggacagaaaa cttatgcatg ctttataagg cctggcagct gcacaatgat 240
ccggttgtcc agagccttcc caaattatcc gcggataccg gcctgcaagg catgcgtgcc 300
gcgttggagc ggagtcttgg aggcggagcc gattttggag acttgttccc ggagcgatcg 360
ccagagggct atgcggaagc ctcctctata cagtcgcttt tctcgccggg acgttacctg 420
acggtgctgt ataaaattgc gcgggatctc cacgacccaa aagataaact gcatattgac 480
aaccgccgtc cagatttgaa gtcgctgatc ctcaataatg acaatatgaa ccgagaggta 540
tcttctctgg atatccttct ggatgtgctg cagcccgaag gctctgacac gctgacatcc 600
ttgaaggata cctaccatcc gatgaccctt ccctatgatg acgaccttgc gcaaatcaat 660
gccgtggcgg aggcgcgttc atctaatttg ctggggattt gggataccct gctggacacg 720
cagcggactt ccatcctgca gaattccgcc gctgcccgcc ggataagcaa ggcgcggcac 780
tcggcatacg ccaatcagaa agcctccaat gatgagccgg tattcatcac gggagaggaa 840
atctacctgg aaaccggagg taaacggctt tttctggcgc ataaactcga gataggttca 900
actattagcg ctaaaatcaa cattggaccg ccgcaagcgg ccgatatcgc gccggcaaag 960
ttgcaactcg tatattacgg cagaggcggc agagggaact acttcctgcg cgtggcagac 1020
gatgtgtccc tcggtggaaa gctgctgacc aattgttatc tgaccagcga tgacggacag 1080
agcaacaata ttagcgggcc atactgccta atgatcaacc gaggcaccgg cagcatgcct 1140
agcgggactc accttccagt tcagattgaa agagtgaccg atacatccat ccgcattttt 1200
gtgccggatc acggctattt ggggctaggc gaaagccttg ccagcaactg gaatgaaccg 1260
ttggcgctga atctgggctt ggatgaagcg ttgaccttta ccttgagaaa gaaggagacg 1320
ggaaatgaca ccatttccat aatcgacatg ctgccgccgg tagcgaacac gactccgtct 1380
ccgccgacga gggaaacgct ttccttgacg ccaaacagct tccgtctgct ggtcaaccct 1440
gagccgacag cggaggacat cgccaagcac tacaacgtca cgacggtaac ccgggctcct 1500
gccgatctgg cctccgcctt aaatgttgtc gatgatttct gcttgaaaac cggtttgagc 1560
tttaacgaat tgctggattt aaccatgcag aaggattatc agtcaaaaag cagtgagtac 1620
aaaagccgat ttgtaaaatt cggcggcggg gagaatgttc cggtatcaag ctatggcgca 1680
gcctttctga caggagcgga agatactcct ttgtgggtga aacagtataa cagcgtgggg 1740
actgcaacaa gcacccctgt tttaaacttt acgccagata atgttgtggc tttggcagga 1800
agggcggaaa agcttgtccg gctgatgcgc agcacgggtc tttcctttga gcagttggat 1860
tggctgattg ccaatgccag ccgtgccgtt atcgaacacg gtggagagct ttttctggat 1920
aagccggtac tggaagctgt ggccgaattc acaaggctca ataagcgtta tggcgtcaca 1980
tcggatatgt tcgccgcgtt tatcggcgaa gtcaatacgt atacagaagc gggcaaggac 2040
agcttttatc aggcgagttt cagcacggcc gaccattcgg ctaccttacc tttgggcgct 2100
tctttgcaac ttgaggtgag caagcaggat cgatatgaag cgatttgctg cggggctatg 2160
ggggtgaccg ccgatgagtt ctcccgtatc ggcaaatact gctttgggga taaagcacag 2220
caaatcacgg ccaatgaaac aaccgttgcc cagctttatc gtttaggccg aattcctcat 2280
atgctaggct tgcgttttac cgaggcagag ctgttgtgga aattgatggc tgggggcgag 2340
gataccttgc tccgcacgat tggcgcgaac cctcgcagtt tagaagcgtt agagattatt 2400
cgccggacgg aggtcctttt ggactggatg gatgcccatc agctggatgt tgtctccctg 2460
caagccatgg ttaccaatcg gtacagcggc acagccacgc cggagctgta caattttttg 2520
gcacaggtgc atcaatccgc aagcagtgcc gcgaacgtgg ccagagcgga tggtcaggat 2580
acgttgcctg cggacaagct gctccgggca ttggcggcgg gcttcaaact gaaagccaac 2640
gtgatggcgc gagtaatcga ctggatggac aaaaccaata aagcgtttac gctgcgggct 2700
ttctgggaca agcttcaagc gtatttcagc gccgatcatg aagaagaact gaccgccctg 2760
gaaggagaag ccgcaatgct gcagtggtgc cagcagatca gccagtatgc gctcattgtc 2820
cgctggtgcg ggttaagcga gcaggatctg gcgctgctga ccgggaatcc ggagcagctt 2880
ctggacggac aacatacggt gcccgtaccc tcgctgcatc tcctgctggt gctgacccgc 2940
ctgaaggaat ggcagcagcg cgtccaggtt tccagcgagg aggctatgcg ctattttgcc 3000
caggccgatt cgccaaccgt cacgcgcgac gatgcggtta atctgcttgc ccgtatccat 3060
ggctggaatg aagcggatac cgtctcgatg aatgactacc tgctgggaga gaacgaatat 3120
cctaagaact ttgatcagat ctttgcactg gaaagctggg tcaacctggg ccgtcaactg 3180
aacgtgggca gcagaacgct gggagagctg gttgacatgg ctgaagagga taaaaccgcg 3240
gaaaacatgg atctgattac ttcggtggcc catagcctga tggctgcagc gaaagcctga 3300

<210> SEQ ID NO 36
<211> LENGTH: 1080
<212> TYPE: PRT
<213> ORGANISM: Paenibacillus strain DAS1529

<400> SEQUENCE: 36

Met Val Ser Thr Thr Asp Asn Thr Ala Gly Val Phe Arg Leu Gly Thr
1               5                   10                  15

Glu Glu Leu Thr Glu Ala Leu Lys Gln Ser Gly Tyr Arg Thr Val Phe
            20                  25                  30

-continued

```
Asp Ile Val Ser Asp Asn Leu Ala Glu Phe Gln Lys Asn Asn Pro Glu
        35                  40                  45

Ile Pro Ser Ser Asp Ala Lys Glu Ile His Gln Leu Ala Val Gln Arg
    50                  55                  60

Thr Glu Asn Leu Cys Met Leu Tyr Lys Ala Trp Gln Leu His Asn Asp
65                  70                  75                  80

Pro Val Val Gln Ser Leu Pro Lys Leu Ser Ala Asp Thr Gly Leu Gln
                85                  90                  95

Gly Met Arg Ala Ala Leu Glu Arg Ser Leu Gly Gly Gly Ala Asp Phe
            100                 105                 110

Gly Asp Leu Phe Pro Glu Arg Ser Pro Glu Gly Tyr Ala Glu Ala Ser
        115                 120                 125

Ser Ile Gln Ser Leu Phe Ser Pro Gly Arg Tyr Leu Thr Val Leu Tyr
    130                 135                 140

Lys Ile Ala Arg Asp Leu His Asp Pro Lys Asp Lys Leu His Ile Asp
145                 150                 155                 160

Asn Arg Arg Pro Asp Leu Lys Ser Leu Ile Leu Asn Asn Asp Asn Met
                165                 170                 175

Asn Arg Glu Val Ser Ser Leu Asp Ile Leu Leu Asp Val Leu Gln Pro
            180                 185                 190

Glu Gly Ser Asp Thr Leu Thr Ser Leu Lys Asp Thr Tyr His Pro Met
        195                 200                 205

Thr Leu Pro Tyr Asp Asp Asp Leu Ala Gln Ile Asn Ala Val Ala Glu
    210                 215                 220

Ala Arg Ser Ser Asn Leu Leu Gly Ile Trp Asp Thr Leu Leu Asp Thr
225                 230                 235                 240

Gln Arg Thr Ser Ile Leu Gln Asn Ser Ala Ala Ala Arg Arg Ile Ser
                245                 250                 255

Lys Ala Arg His Ser Ala Tyr Ala Asn Gln Lys Ala Ser Asn Asp Glu
            260                 265                 270

Pro Val Phe Ile Thr Gly Glu Glu Ile Tyr Leu Glu Thr Gly Gly Lys
        275                 280                 285

Arg Leu Phe Leu Ala His Lys Leu Glu Ile Gly Ser Thr Ile Ser Ala
    290                 295                 300

Lys Ile Asn Ile Gly Pro Pro Gln Ala Ala Asp Ile Ala Pro Ala Lys
305                 310                 315                 320

Leu Gln Leu Val Tyr Tyr Gly Arg Gly Gly Arg Gly Asn Tyr Phe Leu
                325                 330                 335

Arg Val Ala Asp Asp Val Ser Leu Gly Gly Lys Leu Leu Thr Asn Cys
            340                 345                 350

Tyr Leu Thr Ser Asp Asp Gly Gln Ser Asn Asn Ile Ser Gly Pro Tyr
        355                 360                 365

Cys Leu Met Ile Asn Arg Gly Thr Gly Ser Met Pro Ser Gly Thr His
    370                 375                 380

Leu Pro Val Gln Ile Glu Arg Val Thr Asp Thr Ser Ile Arg Ile Phe
385                 390                 395                 400

Val Pro Asp His Gly Tyr Leu Gly Leu Gly Glu Ser Leu Ala Ser Asn
                405                 410                 415

Trp Asn Glu Pro Leu Ala Leu Asn Leu Gly Leu Asp Glu Ala Leu Thr
            420                 425                 430

Phe Thr Leu Arg Lys Lys Glu Thr Gly Asn Asp Thr Ile Ser Ile Ile
        435                 440                 445

Asp Met Leu Pro Pro Val Ala Asn Thr Thr Pro Ser Pro Pro Thr Arg
    450                 455                 460
```

```
Glu Thr Leu Ser Leu Thr Pro Asn Ser Phe Arg Leu Leu Val Asn Pro
465                 470                 475                 480

Glu Pro Thr Ala Glu Asp Ile Ala Lys His Tyr Asn Val Thr Thr Val
                485                 490                 495

Thr Arg Ala Pro Ala Asp Leu Ala Ser Ala Leu Asn Val Val Asp Asp
            500                 505                 510

Phe Cys Leu Lys Thr Gly Leu Ser Phe Asn Glu Leu Leu Asp Leu Thr
        515                 520                 525

Met Gln Lys Asp Tyr Gln Ser Lys Ser Ser Glu Tyr Lys Ser Arg Phe
    530                 535                 540

Val Lys Phe Gly Gly Gly Glu Asn Val Pro Val Ser Ser Tyr Gly Ala
545                 550                 555                 560

Ala Phe Leu Thr Gly Ala Glu Asp Thr Pro Leu Trp Val Lys Gln Tyr
                565                 570                 575

Asn Ser Val Gly Thr Ala Thr Ser Thr Pro Val Leu Asn Phe Thr Pro
            580                 585                 590

Asp Asn Val Val Ala Leu Ala Gly Arg Ala Glu Lys Leu Val Arg Leu
        595                 600                 605

Met Arg Ser Thr Gly Leu Ser Phe Glu Gln Leu Asp Trp Leu Ile Ala
    610                 615                 620

Asn Ala Ser Arg Ala Val Ile Glu His Gly Gly Glu Leu Phe Leu Asp
625                 630                 635                 640

Lys Pro Val Leu Glu Ala Val Ala Glu Phe Thr Arg Leu Asn Lys Arg
                645                 650                 655

Tyr Gly Val Thr Ser Asp Met Phe Ala Ala Phe Ile Gly Glu Val Asn
            660                 665                 670

Thr Tyr Thr Glu Ala Gly Lys Asp Ser Phe Tyr Gln Ala Ser Phe Ser
        675                 680                 685

Thr Ala Asp His Ser Ala Thr Leu Pro Leu Gly Ala Ser Leu Gln Leu
    690                 695                 700

Glu Val Ser Lys Gln Asp Arg Tyr Glu Ala Ile Cys Cys Gly Ala Met
705                 710                 715                 720

Gly Val Thr Ala Asp Glu Phe Ser Arg Ile Gly Lys Tyr Cys Phe Gly
                725                 730                 735

Asp Lys Ala Gln Gln Ile Thr Ala Asn Glu Thr Thr Val Ala Gln Leu
            740                 745                 750

Tyr Arg Leu Gly Arg Ile Pro His Met Leu Gly Leu Arg Phe Thr Glu
        755                 760                 765

Ala Glu Leu Leu Trp Lys Leu Met Ala Gly Gly Glu Asp Thr Leu Leu
    770                 775                 780

Arg Thr Ile Gly Ala Asn Pro Arg Ser Leu Glu Ala Leu Glu Ile Ile
785                 790                 795                 800

Arg Arg Thr Glu Val Leu Leu Asp Trp Met Asp Ala His Gln Leu Asp
                805                 810                 815

Val Val Ser Leu Gln Ala Met Val Thr Asn Arg Tyr Ser Gly Thr Ala
            820                 825                 830

Thr Pro Glu Leu Tyr Asn Phe Leu Ala Gln Val His Gln Ser Ala Ser
        835                 840                 845

Ser Ala Ala Asn Val Ala Arg Ala Asp Gly Gln Asp Thr Leu Pro Ala
    850                 855                 860

Asp Lys Leu Leu Arg Ala Leu Ala Ala Gly Phe Lys Leu Lys Ala Asn
865                 870                 875                 880

Val Met Ala Arg Val Ile Asp Trp Met Asp Lys Thr Asn Lys Ala Phe
```

```
                885                 890                 895

Thr Leu Arg Ala Phe Trp Asp Lys Leu Gln Ala Tyr Phe Ser Ala Asp
            900                 905                 910

His Glu Glu Glu Leu Thr Ala Leu Glu Gly Glu Ala Ala Met Leu Gln
        915                 920                 925

Trp Cys Gln Gln Ile Ser Gln Tyr Ala Leu Ile Val Arg Trp Cys Gly
    930                 935                 940

Leu Ser Glu Gln Asp Leu Ala Leu Leu Thr Gly Asn Pro Glu Gln Leu
945                 950                 955                 960

Leu Asp Gly Gln His Thr Val Pro Val Pro Ser Leu His Leu Leu Leu
                965                 970                 975

Val Leu Thr Arg Leu Lys Glu Trp Gln Gln Arg Val Gln Val Ser Ser
            980                 985                 990

Glu Glu Ala Met Arg Tyr Phe Ala  Gln Ala Asp Ser Pro  Thr Val Thr
        995                 1000                1005

Arg Asp  Asp Ala Val Asn Leu  Leu Ala Arg Ile His  Gly Trp Asn
    1010                1015                1020

Glu Ala  Asp Thr Val Ser Met  Asn Asp Tyr Leu Leu  Gly Glu Asn
    1025                1030                1035

Glu Tyr  Pro Lys Asn Phe Asp  Gln Ile Phe Ala Leu  Glu Ser Trp
    1040                1045                1050

Val Asn  Leu Gly Arg Gln Leu  Asn Val Gly Ser Arg  Thr Leu Gly
    1055                1060                1065

Glu Leu  Val Asp Met Ala Glu  Glu Asp Lys Thr Ala
    1070                1075                1080


<210> SEQ ID NO 37
<211> LENGTH: 3627
<212> TYPE: DNA
<213> ORGANISM: Paenibacillus strain DAS1529

<400> SEQUENCE: 37

atgaccaagg aaggtgataa gcatatgtct acttcaaccc tgttgcaatc gattaaagaa     60

gcccgccggg atgcgctggt caaccattat attgctaatc aggttccgac agcgcttgcg    120

gacaagatta cggacgcgga cagcctgtat gagtacttgc tgctggatac caagatcagt    180

gaactcgtaa aaacatcgcc gatagcggag gccatcagca gcgtgcagtt atacatgaac    240

cgctgcgtcg aaggctatga aggcaagttg actccggaaa gtaatactca ttttggccca    300

ggtaaatttc tatataactg ggatacgtac aacaaacgtt tttccacctg ggcaggaaaa    360

gaacgcttga aatattatgc aggcagctat attgagccgt ccttgcgcta caacaaaacc    420

gatccattcc tgaacctgga acagagcatc agccagggaa gaattactga tgataccgta    480

aagaacgcgc tgcaacacta cctgactgaa tatgaagtgt tggcggatct ggattatatc    540

agcgttaata aaggcggcga cgaaagtgtt ttactctttg ttggacgcac caaaaccgta    600

ccgtatgaat actactggcg ccgtttgctt ttaaaaaggg acaataataa taagctagta    660

ccagcagtct ggtctcagtg gaaaaaaatc agtgccaata tcggtgaagc ggttgatagt    720

tatgtggtgc ctcggtggca taaaaaccgg ctacatgtgc aatggtgttc tatagagaaa    780

agtgaaaatg atgccggtga acccattgag aaacgatatt tgaatgactg gttcatggat    840

agttccggag tctggtcttc atttcgaaag attccggttg tggaaaagag tttcgaatat    900

ttggacggaa gcctcgatcc ccgatttgtc gctcttgtta gaaatcaaat attaattgat    960

gagccagaaa tattcagaat tacagtatca gcccctaatc cgatagatgc aaatggaaga   1020
```

```
gtagaggtac attttgaaga aaactatgca aacagatata atattaccat taaatatggg   1080
acaacgagtc ttgctattcc tgcagggcag gtagggcatc caaatatctc tattaatgaa   1140
acattaaggg ttgaattcgg caccaggccg gattggtatt atactttcag atatttagga   1200
aatacaatcc aaaactcata cggttcaatt gtcaataatc aattttcacc tccatcagga   1260
agcaatatta aaggtcctat cgaccttacc ctgaaaaata acatcgacct gtcggccttg   1320
ttggatgaga gccttgacgc actgttcgac tataccattc agggcgataa ccaattgggc   1380
ggcttagctg cctttaacgg gccttacgga ctttacttgt gggaaatctt cttccatgtt   1440
cctttttttaa tggcggttcg cttccacacc gagcagcggt atgagttggc ggaacgttgg   1500
tttaaattca tcttcaacag cgcaggatac cgtgatgatt acggcagtct gctgacggat   1560
gacaaaggca acgtgcgtta ctggaacgtg ataccgctgc aagaggacac ggagtgggat   1620
gacacgttgt ccctggcaac gaccgacccg gacgagattg cgatggccga cccgatgcaa   1680
tacaagctgg ctatatttat tcacaccatg gacttcctga tcagccgcgg cgatagcttg   1740
taccggatgc tggagcggga taccctggcc gaagccaaga tgtattacat tcaggccagc   1800
caactgcttg ggccccgccc cgacatccgg ctcaatcaca gttggcctaa tccgaccttg   1860
caaagcgaag cggacgcggt aaccgccgtg ccgacgcgaa gcgattcgcc ggcagcgcca   1920
attttggcct tgcgagcgct tctgacaggc gaaaacggtc atttcctgcc gccttataat   1980
gatgaactgt tcgctttctg ggacaaaatc gatctgcgtt tatacaattt gcgccacaat   2040
ttgagtctgg acggtcagcc gcttcatttg ccgctctttg ccgaaccggt caatccgcgt   2100
gaattgcagg ttcagcatgg cccgggcgat ggcttggggg gaagcgcggg ttccgcccaa   2160
agccgtcaga gtgtctatcg ttttcctctg gtcatcgata aggcgcgcaa tgcggccaac   2220
agtgtcatcc aattcggcaa tgccctggaa aacgcactga ccaagcaaga cagcgaagca   2280
atgaccatgc tgttgcagtc ccagcagcag attgtcctgc agcaaacccg cgatattcag   2340
gagaagaacc tggccgcgct gcaagcaagt ctggaagcaa cgatgacagc gaaagcgggg   2400
gcggagtccc ggaagaccca ttttgccggc ttggcggaca actggatgtc ggacaatgaa   2460
accgcctcac tcgcactgcg taccaccgcg ggaatcatca ataccagctc aaccgtgccg   2520
atcgccatca ccggcggctt ggatatggct ccgaacattt ttggtttcgc agttggaggt   2580
tcccgctggg gagcagccag cgcggctgta gcccaaggat tgcaaatcgc cgccggcgta   2640
atggaacaga cggccaatat tatcgatatt agcgaaagct accgccggcg ccgggaggat   2700
tggctgctgc agcgggatgt tgccgaaaat gaagcggcgc agttggattc gcagattgcg   2760
gccctgcggg aacagatgga tatggcgcgc aagcaacttg cgctggcgga gacggaacag   2820
gcgcacgcgc aagcggtcta cgagctgcaa agcacccgct ttacgaatca agctttgtat   2880
aactggatgg ctggacgtct gtcgtctcta tactatcaaa tgtatgacgc cgcattgccg   2940
ctctgcttga tggcgaagca ggctttagag aaagaaatcg gttcggataa aacggtcgga   3000
gtcttgtccc tcccggcctg gaatgatcta tatcagggat tattggcggg cgaggcgctg   3060
ctgctcgagc ttcagaagct ggagaatctg tggctggagg aagacaagcg cggaatggaa   3120
gccgtaaaaa cagtctctct ggatactctt ctccgcaaaa caaatccgaa ctccgggttt   3180
gcggatctcg tcaaggaggc actggacgaa aacggaaaga cgcctgaccc ggtgagcgga   3240
gtcggcgtac agctgcaaaa caatattttc agcgcaaccc ttgacctctc cgttcttggc   3300
ctggatcgct cttacaatca ggcggaaaag tcccgcagga tcaaaaaatat gtcggttacc   3360
ttacctgcgc tattggggcc ttaccaggat atagaggcaa ccttatcgct aggcggcgag   3420
```

```
accgttgcgc tgtcccatgg cgtggatgac agcggcttgt tcatcactga tctcaacgac   3480

agccggttcc tgcctttcga gggcatggat ccgttatccg gcacactcgt cctgtcgata   3540

ttccatgccg ggcaagacgg cgaccagcgc ctcctgctgg aaagtctcaa tgacgtcatc   3600

ttccacattc gatatgttat gaaatag                                       3627


<210> SEQ ID NO 38
<211> LENGTH: 1208
<212> TYPE: PRT
<213> ORGANISM: Paenibacillus strain DAS1529

<400> SEQUENCE: 38

Met Thr Lys Glu Gly Asp Lys His Met Ser Thr Ser Thr Leu Leu Gln
1               5                   10                  15

Ser Ile Lys Glu Ala Arg Arg Asp Ala Leu Val Asn His Tyr Ile Ala
            20                  25                  30

Asn Gln Val Pro Thr Ala Leu Ala Asp Lys Ile Thr Asp Ala Asp Ser
        35                  40                  45

Leu Tyr Glu Tyr Leu Leu Leu Asp Thr Lys Ile Ser Glu Leu Val Lys
    50                  55                  60

Thr Ser Pro Ile Ala Glu Ala Ile Ser Ser Val Gln Leu Tyr Met Asn
65                  70                  75                  80

Arg Cys Val Glu Gly Tyr Glu Gly Lys Leu Thr Pro Glu Ser Asn Thr
                85                  90                  95

His Phe Gly Pro Gly Lys Phe Leu Tyr Asn Trp Asp Thr Tyr Asn Lys
            100                 105                 110

Arg Phe Ser Thr Trp Ala Gly Lys Glu Arg Leu Lys Tyr Tyr Ala Gly
        115                 120                 125

Ser Tyr Ile Glu Pro Ser Leu Arg Tyr Asn Lys Thr Asp Pro Phe Leu
    130                 135                 140

Asn Leu Glu Gln Ser Ile Ser Gln Gly Arg Ile Thr Asp Asp Thr Val
145                 150                 155                 160

Lys Asn Ala Leu Gln His Tyr Leu Thr Glu Tyr Glu Val Leu Ala Asp
                165                 170                 175

Leu Asp Tyr Ile Ser Val Asn Lys Gly Gly Asp Glu Ser Val Leu Leu
            180                 185                 190

Phe Val Gly Arg Thr Lys Thr Val Pro Tyr Glu Tyr Tyr Trp Arg Arg
        195                 200                 205

Leu Leu Leu Lys Arg Asp Asn Asn Asn Lys Leu Val Pro Ala Val Trp
    210                 215                 220

Ser Gln Trp Lys Lys Ile Ser Ala Asn Ile Gly Glu Ala Val Asp Ser
225                 230                 235                 240

Tyr Val Val Pro Arg Trp His Lys Asn Arg Leu His Val Gln Trp Cys
                245                 250                 255

Ser Ile Glu Lys Ser Glu Asn Asp Ala Gly Glu Pro Ile Glu Lys Arg
            260                 265                 270

Tyr Leu Asn Asp Trp Phe Met Asp Ser Ser Gly Val Trp Ser Ser Phe
        275                 280                 285

Arg Lys Ile Pro Val Val Glu Lys Ser Phe Glu Tyr Leu Asp Gly Ser
    290                 295                 300

Leu Asp Pro Arg Phe Val Ala Leu Val Arg Asn Gln Ile Leu Ile Asp
305                 310                 315                 320

Glu Pro Glu Ile Phe Arg Ile Thr Val Ser Ala Pro Asn Pro Ile Asp
                325                 330                 335

Ala Asn Gly Arg Val Glu Val His Phe Glu Glu Asn Tyr Ala Asn Arg
```

-continued

```
            340                 345                 350

Tyr Asn Ile Thr Ile Lys Tyr Gly Thr Thr Ser Leu Ala Ile Pro Ala
        355                 360                 365

Gly Gln Val Gly His Pro Asn Ile Ser Ile Asn Glu Thr Leu Arg Val
    370                 375                 380

Glu Phe Gly Thr Arg Pro Asp Trp Tyr Tyr Thr Phe Arg Tyr Leu Gly
385                 390                 395                 400

Asn Thr Ile Gln Asn Ser Tyr Gly Ser Ile Val Asn Asn Gln Phe Ser
                405                 410                 415

Pro Pro Ser Gly Ser Asn Ile Lys Gly Pro Ile Asp Leu Thr Leu Lys
            420                 425                 430

Asn Asn Ile Asp Leu Ser Ala Leu Leu Asp Glu Ser Leu Asp Ala Leu
        435                 440                 445

Phe Asp Tyr Thr Ile Gln Gly Asp Asn Gln Leu Gly Gly Leu Ala Ala
    450                 455                 460

Phe Asn Gly Pro Tyr Gly Leu Tyr Leu Trp Glu Ile Phe Phe His Val
465                 470                 475                 480

Pro Phe Leu Met Ala Val Arg Phe His Thr Glu Gln Arg Tyr Glu Leu
                485                 490                 495

Ala Glu Arg Trp Phe Lys Phe Ile Phe Asn Ser Ala Gly Tyr Arg Asp
            500                 505                 510

Asp Tyr Gly Ser Leu Leu Thr Asp Asp Lys Gly Asn Val Arg Tyr Trp
        515                 520                 525

Asn Val Ile Pro Leu Gln Glu Asp Thr Glu Trp Asp Asp Thr Leu Ser
    530                 535                 540

Leu Ala Thr Thr Asp Pro Asp Glu Ile Ala Met Ala Asp Pro Met Gln
545                 550                 555                 560

Tyr Lys Leu Ala Ile Phe Ile His Thr Met Asp Phe Leu Ile Ser Arg
                565                 570                 575

Gly Asp Ser Leu Tyr Arg Met Leu Glu Arg Asp Thr Leu Ala Glu Ala
            580                 585                 590

Lys Met Tyr Tyr Ile Gln Ala Ser Gln Leu Leu Gly Pro Arg Pro Asp
        595                 600                 605

Ile Arg Leu Asn His Ser Trp Pro Asn Pro Thr Leu Gln Ser Glu Ala
    610                 615                 620

Asp Ala Val Thr Ala Val Pro Thr Arg Ser Asp Ser Pro Ala Ala Pro
625                 630                 635                 640

Ile Leu Ala Leu Arg Ala Leu Leu Thr Gly Glu Asn Gly His Phe Leu
                645                 650                 655

Pro Pro Tyr Asn Asp Glu Leu Phe Ala Phe Trp Asp Lys Ile Asp Leu
            660                 665                 670

Arg Leu Tyr Asn Leu Arg His Asn Leu Ser Leu Asp Gly Gln Pro Leu
        675                 680                 685

His Leu Pro Leu Phe Ala Glu Pro Val Asn Pro Arg Glu Leu Gln Val
    690                 695                 700

Gln His Gly Pro Gly Asp Gly Leu Gly Gly Ser Ala Gly Ser Ala Gln
705                 710                 715                 720

Ser Arg Gln Ser Val Tyr Arg Phe Pro Leu Val Ile Asp Lys Ala Arg
                725                 730                 735

Asn Ala Ala Asn Ser Val Ile Gln Phe Gly Asn Ala Leu Glu Asn Ala
            740                 745                 750

Leu Thr Lys Gln Asp Ser Glu Ala Met Thr Met Leu Leu Gln Ser Gln
        755                 760                 765
```

```
Gln Gln Ile Val Leu Gln Gln Thr Arg Asp Ile Gln Glu Lys Asn Leu
    770                 775                 780

Ala Ala Leu Gln Ala Ser Leu Glu Ala Thr Met Thr Ala Lys Ala Gly
785                 790                 795                 800

Ala Glu Ser Arg Lys Thr His Phe Ala Gly Leu Ala Asp Asn Trp Met
                805                 810                 815

Ser Asp Asn Glu Thr Ala Ser Leu Ala Leu Arg Thr Thr Ala Gly Ile
            820                 825                 830

Ile Asn Thr Ser Ser Thr Val Pro Ile Ala Ile Thr Gly Gly Leu Asp
        835                 840                 845

Met Ala Pro Asn Ile Phe Gly Phe Ala Val Gly Gly Ser Arg Trp Gly
    850                 855                 860

Ala Ala Ser Ala Ala Val Ala Gln Gly Leu Gln Ile Ala Ala Gly Val
865                 870                 875                 880

Met Glu Gln Thr Ala Asn Ile Ile Asp Ile Ser Glu Ser Tyr Arg Arg
                885                 890                 895

Arg Arg Glu Asp Trp Leu Leu Gln Arg Asp Val Ala Glu Asn Glu Ala
            900                 905                 910

Ala Gln Leu Asp Ser Gln Ile Ala Ala Leu Arg Glu Gln Met Asp Met
        915                 920                 925

Ala Arg Lys Gln Leu Ala Leu Ala Glu Thr Glu Gln Ala His Ala Gln
    930                 935                 940

Ala Val Tyr Glu Leu Gln Ser Thr Arg Phe Thr Asn Gln Ala Leu Tyr
945                 950                 955                 960

Asn Trp Met Ala Gly Arg Leu Ser Ser Leu Tyr Tyr Gln Met Tyr Asp
                965                 970                 975

Ala Ala Leu Pro Leu Cys Leu Met Ala Lys Gln Ala Leu Glu Lys Glu
            980                 985                 990

Ile Gly Ser Asp Lys Thr Val Gly  Val Leu Ser Leu Pro  Ala Trp Asn
        995                 1000                 1005

Asp Leu  Tyr Gln Gly Leu Leu  Ala Gly Glu Ala Leu  Leu Leu Glu
    1010                 1015                 1020

Leu Gln  Lys Leu Glu Asn Leu  Trp Leu Glu Glu Asp  Lys Arg Gly
    1025                 1030                 1035

Met Glu  Ala Val Lys Thr Val  Ser Leu Asp Thr Leu  Leu Arg Lys
    1040                 1045                 1050

Thr Asn  Pro Asn Ser Gly Phe  Ala Asp Leu Val Lys  Glu Ala Leu
    1055                 1060                 1065

Asp Glu  Asn Gly Lys Thr Pro  Asp Pro Val Ser Gly  Val Gly Val
    1070                 1075                 1080

Gln Leu  Gln Asn Asn Ile Phe  Ser Ala Thr Leu Asp  Leu Ser Val
    1085                 1090                 1095

Leu Gly  Leu Asp Arg Ser Tyr  Asn Gln Ala Glu Lys  Ser Arg Arg
    1100                 1105                 1110

Ile Lys  Asn Met Ser Val Thr  Leu Pro Ala Leu Leu  Gly Pro Tyr
    1115                 1120                 1125

Gln Asp  Ile Glu Ala Thr Leu  Ser Leu Gly Gly Glu  Thr Val Ala
    1130                 1135                 1140

Leu Ser  His Gly Val Asp Asp  Ser Gly Leu Phe Ile  Thr Asp Leu
    1145                 1150                 1155

Asn Asp  Ser Arg Phe Leu Pro  Phe Glu Gly Met Asp  Pro Leu Ser
    1160                 1165                 1170

Gly Thr  Leu Val Leu Ser Ile  Phe His Ala Gly Gln  Asp Gly Asp
    1175                 1180                 1185
```

Gln Arg Leu Leu Leu Glu Ser Leu Asn Asp Val Ile Phe His Ile
1190 1195 1200

Arg Tyr Val Met Lys
1205

<210> SEQ ID NO 39
<211> LENGTH: 4335
<212> TYPE: DNA
<213> ORGANISM: Paenibacillus strain DAS1529

<400> SEQUENCE: 39
atgccacaat ctagcaatgc cgatatcaag ctattgtcgc catcgctgcc aaagggcggc 60
ggttccatga agggaatcga agaaaacatc gcggctcccg gctccgacgg catggcacgt 120
tgtaatgtgc cgctgccggt aacctccggc cgctatatta ctcctgatat aagcctgtcc 180
tatgcgagcg gccacggcaa cggcgcttat ggaatgggct ggacgatggg agtgatgagc 240
attagccgga gaacaagccg agggaccccc agttatacat ccgaagacca gttccttggt 300
ccggatgggg aggtgcttgt tccggaaagc aacgaacaag ggagatcat tacccgccac 360 accgatacgg cccaagggat accgttaggc gagacgttta cggttacacg ctattttccc 420
cggatcgaga gcgcttttca tttgctggaa tactgggaag cgcaagcagg aagcgcaaca 480
gcgtcgtttt ggcttattca ctctgccgat ggagtgctgc actgtctggg taaaactgct 540
caggcgagga tagccgcccc tgacgattcc gccaagatcg cagaatggct agtggaggag 600
tccgtctccc ccttcggaga gcatatttat taccaataca aagaagaaga caatcaaggc 660
gtgaatctgg aggaagacaa tcatcaatat ggggcgaacc gctatctgaa atcgattcgc 720
tatggaaata aggttgcctc tccttctctc tatgtctgga agggggaaat tccggcagac 780
ggccaatggc tgtattccgt tatcctggat tatggcgaga acgatacctc agcggatgtt 840
cctcccctat acacgcccca aggggagtgg ctggtgcgcc cggaccgttt ttcccgctat 900
gactacggat ttgaggtccg gacttgccgc ttgtgccgcc aggtcttgat gttccacgtc 960
tttaaggagc ttggcgggga gccggcgctg gtgtggcgga tgcagttgga atacgacgag 1020
aacccggcgg cgtccatgct gagcgcggtc cggcaattgg cttatgaagc agatggggcc 1080
attcgaagct tgccgccgct ggaattcgat tatactccat ttggcatcga gacaacggcc 1140
gattggcagc cttttctgcc tgtgcctgaa tgggcggatg aagaacatta tcagttggtc 1200
gatttgtacg gagaaggcat accgggctta ttatatcaga acaatgacca ctggcattat 1260
cgttcgcccg cccggggcga cacaccggac gggatcgcct ataacagctg gcggccgctt 1320
cctcatatcc ccgtgaactc ccggaacggg atgctgatgg atctgaatgg agacgggtat 1380
ctggaatggt tgcttgcgga acccggggtt gcggggcgct atagcatgaa cccggataag 1440
agctggtccg gttttgtgcc gctccaggca ctgccaacgg aattcttcca tccgcaggca 1500
cagcttgcca atgttaccgg atcgggttta accgacttgg ttatgatcgg tccgaagagc 1560
gtccggtttt atgccggaga agaagcgggc ttcaagcgcg catgtgaagt gtggcagcaa 1620
gtgggcatta ctttgcctgt ggaacgcgtg gataaaaagg aactggtggc attcagcgat 1680
atgctgggat cgggtcagtc tcatctggtg cgcatccggc atgatggcgt tacatgctgg 1740
cctaatctgg ggaacggcgt gttcggggcg ccgttggccc ttcacgggtt tacggcatcg 1800
gagcgggaat tcaatccgga acgtgtatat cttgtggacc ttgatggatc cggcgcttcc 1860
gatatcattt atgcttctcg tgacgctcta ctcatttacc gaaatctttc cggcaatggc 1920
tttgctgatc cggtgcgggt tccgctgcct gacggcgtgc ggtttgataa tctgtgccgg 1980

```
ctgctgcctg ccgatatccg cgggttaggt gtggccagtc tggtgctgca tgtaccttac   2040
atggcccccc gcagttggaa attagatttc tttgcggcga agccgtattt attgcaaacg   2100
gtcagcaaca atcttggagc ttccagctcg ttttggtacc gaagctccac ccagtattgg   2160
ctggatgaga aacaggcggc ctcatcggct gtctccgctt tgcccttccc gataaacgtg   2220
gtatcggata tgcacacggt ggacgaaatc agcggccgca ccaggactca gaagtatact   2280
taccgccatg gcgtgtatga ccggaccgaa aaggaatttg ccggattcgg ccgcattgac   2340
acatgggaag aggagcggga ttccgaagga accctgagcg tcagcactcc gcccgtgctg   2400
acgcggacct ggtatcatac cgggcaaaag caggatgagg agcgtgccgt gcagcaatat   2460
tggcaaggcg accctgcggc ttttcaggtt aaacccgtcc ggcttactcg attcgatgcg   2520
gcagcggccc aggatctgcc gctagattct aataatgggc agcaagaata ctggctgtac   2580
cgatcattac aagggatgcc gctgcggact gagatttttg cgggagatgt tggcgggtcg   2640
cctccttatc aggtagagag cttccgttat caagtgcgct tggtgcagag catcgattcg   2700
gaatgtgttg ccttgcccat gcagttggag cagcttacgt acaactatga gcaaatcgcc   2760
tctgatccgc agtgttcaca gcagatacag caatggttcg acgaatacgg cgtggcggca   2820
cagagtgtaa caatccaata tccgcgccgg gcacagccgg aggacaatcc gtaccctcgc   2880
acgctgccgg ataccagctg gagcagcagt tatgattcgc agcaaatgct gctgcggttg   2940
accaggcaaa ggcaaaaagc gtaccacctt gcagatcctg aaggctggcg cttgaatatt   3000
ccccatcaga cacgcctgga tgccttcatt tattctgctg acagcgtgcc cgccgaagga   3060
ataagcgccg agctgctgga ggtggacggc acgttacgat cttcggcgct ggaacaggct   3120
tatggcggcc agtcagagat catctatgcg ggcgggggcg aaccggattt gcgagccctg   3180
gtccattaca ccagaagcgc ggttcttgat gaagactgtt tacaagccta tgaaggcgta   3240
ctgagcgata gccaattgaa ctcgcttctt gcctcttccg gctatcaacg aagcgcaaga   3300
atattgggtt cgggcgatga agtggatatt tttgtcgcgg aacaaggatt tacccgttat   3360
gcggatgaac cgaatttttt ccgtattctg ggcaacaat cctctctctt gtccggggaa   3420
caagtattaa catgggatga taatttctgt gcggttacat ccatcgaaga cgcgcttggc   3480
aatcaaattc agattgcata tgattaccgc tttgtggagg ccatccagat taccgatacg   3540
aataataatg tgaatcaggt cgccctggat gctctcggcc gggtcgtata cagccggacc   3600
tggggcacgg aggaagggat aaagaccggc ttccgcccgg aggtggaatt cgcgacgccc   3660
gagacaatgg agcaggcgct tgccctggca tctcccttgc cggttgcatc ctgctgtgta   3720
tatgatgcgc atagctggat gggaacgata actcttgcac aactgtcaga gcttgttcca   3780
gatagtgaaa agcaatggtc gttcttgata gacaatcgct tgattatgcc ggacggcaga   3840
atcagatccc gcggtcggga tccatggtcg cttcaccggc tattgccgcc tgctgtgggc   3900
gaattgctga gcgaggcgga ccgtaaaccg ccgcatacgg taattttggc agcagatcgt   3960
tacccggatg acccatccca gcaaattcag gcgagcatcg tgtttagcga tggctttggg   4020
cgtacgatac aaactgctaa aagagaagat acccgatggg cgattgcgga acgggtggac   4080
tatgacggaa ccggagccgt aatccgcagc tttcagcctt tttatcttga cgactggaat   4140
tatgtgggcg aagaggctgt cagcagctct atgtacgcaa cgatctatta ttatgatgct   4200
ctggcacgac aattaaggat ggtcaacgct aaaggatatg agaggagaac tgctttttac   4260
ccatggttta cagtaaacga agatgaaaat gataccatgg actcatcatt atttgcttca   4320
ccgcctgcgc ggtga                                                    4335
```

<210> SEQ ID NO 40
<211> LENGTH: 1444
<212> TYPE: PRT
<213> ORGANISM: Paenibacillus strain DAS1529

<400> SEQUENCE: 40

```
Met Pro Gln Ser Ser Asn Ala Asp Ile Lys Leu Leu Ser Pro Ser Leu
1               5                   10                  15

Pro Lys Gly Gly Gly Ser Met Lys Gly Ile Glu Glu Asn Ile Ala Ala
            20                  25                  30

Pro Gly Ser Asp Gly Met Ala Arg Cys Asn Val Pro Leu Pro Val Thr
        35                  40                  45

Ser Gly Arg Tyr Ile Thr Pro Asp Ile Ser Leu Ser Tyr Ala Ser Gly
    50                  55                  60

His Gly Asn Gly Ala Tyr Gly Met Gly Trp Thr Met Gly Val Met Ser
65                  70                  75                  80

Ile Ser Arg Arg Thr Ser Arg Gly Thr Pro Ser Tyr Thr Ser Glu Asp
                85                  90                  95

Gln Phe Leu Gly Pro Asp Gly Glu Val Leu Val Pro Glu Ser Asn Glu
            100                 105                 110

Gln Gly Glu Ile Ile Thr Arg His Thr Asp Thr Ala Gln Gly Ile Pro
        115                 120                 125

Leu Gly Glu Thr Phe Thr Val Thr Arg Tyr Phe Pro Arg Ile Glu Ser
    130                 135                 140

Ala Phe His Leu Leu Glu Tyr Trp Glu Ala Gln Ala Gly Ser Ala Thr
145                 150                 155                 160

Ala Ser Phe Trp Leu Ile His Ser Ala Asp Gly Val Leu His Cys Leu
                165                 170                 175

Gly Lys Thr Ala Gln Ala Arg Ile Ala Ala Pro Asp Asp Ser Ala Lys
            180                 185                 190

Ile Ala Glu Trp Leu Val Glu Glu Ser Val Ser Pro Phe Gly Glu His
        195                 200                 205

Ile Tyr Tyr Gln Tyr Lys Glu Glu Asp Asn Gln Gly Val Asn Leu Glu
    210                 215                 220

Glu Asp Asn His Gln Tyr Gly Ala Asn Arg Tyr Leu Lys Ser Ile Arg
225                 230                 235                 240

Tyr Gly Asn Lys Val Ala Ser Pro Ser Leu Tyr Val Trp Lys Gly Glu
                245                 250                 255

Ile Pro Ala Asp Gly Gln Trp Leu Tyr Ser Val Ile Leu Asp Tyr Gly
            260                 265                 270

Glu Asn Asp Thr Ser Ala Asp Val Pro Pro Leu Tyr Thr Pro Gln Gly
        275                 280                 285

Glu Trp Leu Val Arg Pro Asp Arg Phe Ser Arg Tyr Asp Tyr Gly Phe
    290                 295                 300

Glu Val Arg Thr Cys Arg Leu Cys Arg Gln Val Leu Met Phe His Val
305                 310                 315                 320

Phe Lys Glu Leu Gly Gly Glu Pro Ala Leu Val Trp Arg Met Gln Leu
                325                 330                 335

Glu Tyr Asp Glu Asn Pro Ala Ala Ser Met Leu Ser Ala Val Arg Gln
            340                 345                 350

Leu Ala Tyr Glu Ala Asp Gly Ala Ile Arg Ser Leu Pro Pro Leu Glu
        355                 360                 365

Phe Asp Tyr Thr Pro Phe Gly Ile Glu Thr Thr Ala Asp Trp Gln Pro
    370                 375                 380
```

```
Phe Leu Pro Val Pro Glu Trp Ala Asp Glu Glu His Tyr Gln Leu Val
385                 390                 395                 400

Asp Leu Tyr Gly Glu Gly Ile Pro Gly Leu Leu Tyr Gln Asn Asn Asp
                405                 410                 415

His Trp His Tyr Arg Ser Pro Ala Arg Gly Asp Thr Pro Asp Gly Ile
            420                 425                 430

Ala Tyr Asn Ser Trp Arg Pro Leu Pro His Ile Pro Val Asn Ser Arg
        435                 440                 445

Asn Gly Met Leu Met Asp Leu Asn Gly Asp Gly Tyr Leu Glu Trp Leu
    450                 455                 460

Leu Ala Glu Pro Gly Val Ala Gly Arg Tyr Ser Met Asn Pro Asp Lys
465                 470                 475                 480

Ser Trp Ser Gly Phe Val Pro Leu Gln Ala Leu Pro Thr Glu Phe Phe
                485                 490                 495

His Pro Gln Ala Gln Leu Ala Asn Val Thr Gly Ser Gly Leu Thr Asp
            500                 505                 510

Leu Val Met Ile Gly Pro Lys Ser Val Arg Phe Tyr Ala Gly Glu Glu
        515                 520                 525

Ala Gly Phe Lys Arg Ala Cys Glu Val Trp Gln Gln Val Gly Ile Thr
    530                 535                 540

Leu Pro Val Glu Arg Val Asp Lys Lys Glu Leu Val Ala Phe Ser Asp
545                 550                 555                 560

Met Leu Gly Ser Gly Gln Ser His Leu Val Arg Ile Arg His Asp Gly
                565                 570                 575

Val Thr Cys Trp Pro Asn Leu Gly Asn Gly Val Phe Gly Ala Pro Leu
            580                 585                 590

Ala Leu His Gly Phe Thr Ala Ser Glu Arg Glu Phe Asn Pro Glu Arg
        595                 600                 605

Val Tyr Leu Val Asp Leu Asp Gly Ser Gly Ala Ser Asp Ile Ile Tyr
    610                 615                 620

Ala Ser Arg Asp Ala Leu Leu Ile Tyr Arg Asn Leu Ser Gly Asn Gly
625                 630                 635                 640

Phe Ala Asp Pro Val Arg Val Pro Leu Pro Asp Gly Val Arg Phe Asp
                645                 650                 655

Asn Leu Cys Arg Leu Leu Pro Ala Asp Ile Arg Gly Leu Gly Val Ala
            660                 665                 670

Ser Leu Val Leu His Val Pro Tyr Met Ala Pro Arg Ser Trp Lys Leu
        675                 680                 685

Asp Phe Phe Ala Ala Lys Pro Tyr Leu Leu Gln Thr Val Ser Asn Asn
    690                 695                 700

Leu Gly Ala Ser Ser Ser Phe Trp Tyr Arg Ser Ser Thr Gln Tyr Trp
705                 710                 715                 720

Leu Asp Glu Lys Gln Ala Ala Ser Ser Ala Val Ser Ala Leu Pro Phe
                725                 730                 735

Pro Ile Asn Val Val Ser Asp Met His Thr Val Asp Glu Ile Ser Gly
            740                 745                 750

Arg Thr Arg Thr Gln Lys Tyr Thr Tyr Arg His Gly Val Tyr Asp Arg
        755                 760                 765

Thr Glu Lys Glu Phe Ala Gly Phe Gly Arg Ile Asp Thr Trp Glu Glu
    770                 775                 780

Glu Arg Asp Ser Glu Gly Thr Leu Ser Val Ser Thr Pro Pro Val Leu
785                 790                 795                 800

Thr Arg Thr Trp Tyr His Thr Gly Gln Lys Gln Asp Glu Glu Arg Ala
```

```
                805                 810                 815

Val Gln Gln Tyr Trp Gln Gly Asp Pro Ala Ala Phe Gln Val Lys Pro
            820                 825                 830

Val Arg Leu Thr Arg Phe Asp Ala Ala Ala Ala Gln Asp Leu Pro Leu
        835                 840                 845

Asp Ser Asn Asn Gly Gln Gln Glu Tyr Trp Leu Tyr Arg Ser Leu Gln
    850                 855                 860

Gly Met Pro Leu Arg Thr Glu Ile Phe Ala Gly Asp Val Gly Gly Ser
865                 870                 875                 880

Pro Pro Tyr Gln Val Glu Ser Phe Arg Tyr Gln Val Arg Leu Val Gln
                885                 890                 895

Ser Ile Asp Ser Glu Cys Val Ala Leu Pro Met Gln Leu Glu Gln Leu
            900                 905                 910

Thr Tyr Asn Tyr Glu Gln Ile Ala Ser Asp Pro Gln Cys Ser Gln Gln
        915                 920                 925

Ile Gln Gln Trp Phe Asp Glu Tyr Gly Val Ala Ala Gln Ser Val Thr
    930                 935                 940

Ile Gln Tyr Pro Arg Arg Ala Gln Pro Glu Asp Asn Pro Tyr Pro Arg
945                 950                 955                 960

Thr Leu Pro Asp Thr Ser Trp Ser Ser Ser Tyr Asp Ser Gln Gln Met
                965                 970                 975

Leu Leu Arg Leu Thr Arg Gln Arg Gln Lys Ala Tyr His Leu Ala Asp
            980                 985                 990

Pro Glu Gly Trp Arg Leu Asn Ile  Pro His Gln Thr Arg  Leu Asp Ala
        995                 1000                1005

Phe Ile  Tyr Ser Ala Asp Ser  Val Pro Ala Glu Gly  Ile Ser Ala
    1010                1015                1020

Glu Leu  Leu Glu Val Asp Gly  Thr Leu Arg Ser Ser  Ala Leu Glu
    1025                1030                1035

Gln Ala  Tyr Gly Gly Gln Ser  Glu Ile Ile Tyr Ala  Gly Gly Gly
    1040                1045                1050

Glu Pro  Asp Leu Arg Ala Leu  Val His Tyr Thr Arg  Ser Ala Val
    1055                1060                1065

Leu Asp  Glu Asp Cys Leu Gln  Ala Tyr Glu Gly Val  Leu Ser Asp
    1070                1075                1080

Ser Gln  Leu Asn Ser Leu Leu  Ala Ser Ser Gly Tyr  Gln Arg Ser
    1085                1090                1095

Ala Arg  Ile Leu Gly Ser Gly  Asp Glu Val Asp Ile  Phe Val Ala
    1100                1105                1110

Glu Gln  Gly Phe Thr Arg Tyr  Ala Asp Glu Pro Asn  Phe Phe Arg
    1115                1120                1125

Ile Leu  Gly Gln Gln Ser Ser  Leu Leu Ser Gly Glu  Gln Val Leu
    1130                1135                1140

Thr Trp  Asp Asp Asn Phe Cys  Ala Val Thr Ser Ile  Glu Asp Ala
    1145                1150                1155

Leu Gly  Asn Gln Ile Gln Ile  Ala Tyr Asp Tyr Arg  Phe Val Glu
    1160                1165                1170

Ala Ile  Gln Ile Thr Asp Thr  Asn Asn Asn Val Asn  Gln Val Ala
    1175                1180                1185

Leu Asp  Ala Leu Gly Arg Val  Val Tyr Ser Arg Thr  Trp Gly Thr
    1190                1195                1200

Glu Glu  Gly Ile Lys Thr Gly  Phe Arg Pro Glu Val  Glu Phe Ala
    1205                1210                1215
```

```
Thr Pro  Glu Thr Met Glu Gln  Ala Leu Ala Leu Ala  Ser Pro Leu
    1220                 1225                 1230

Pro Val  Ala Ser Cys Cys Val  Tyr Asp Ala His Ser  Trp Met Gly
    1235                 1240                 1245

Thr Ile  Thr Leu Ala Gln Leu  Ser Glu Leu Val Pro  Asp Ser Glu
    1250                 1255                 1260

Lys Gln  Trp Ser Phe Leu Ile  Asp Asn Arg Leu Ile  Met Pro Asp
    1265                 1270                 1275

Gly Arg  Ile Arg Ser Arg Gly  Arg Asp Pro Trp Ser  Leu His Arg
    1280                 1285                 1290

Leu Leu  Pro Pro Ala Val Gly  Glu Leu Leu Ser Glu  Ala Asp Arg
    1295                 1300                 1305

Lys Pro  Pro His Thr Val Ile  Leu Ala Ala Asp Arg  Tyr Pro Asp
    1310                 1315                 1320

Asp Pro  Ser Gln Gln Ile Gln  Ala Ser Ile Val Phe  Ser Asp Gly
    1325                 1330                 1335

Phe Gly  Arg Thr Ile Gln Thr  Ala Lys Arg Glu Asp  Thr Arg Trp
    1340                 1345                 1350

Ala Ile  Ala Glu Arg Val Asp  Tyr Asp Gly Thr Gly  Ala Val Ile
    1355                 1360                 1365

Arg Ser  Phe Gln Pro Phe Tyr  Leu Asp Asp Trp Asn  Tyr Val Gly
    1370                 1375                 1380

Glu Glu  Ala Val Ser Ser Ser  Met Tyr Ala Thr Ile  Tyr Tyr Tyr
    1385                 1390                 1395

Asp Ala  Leu Ala Arg Gln Leu  Arg Met Val Asn Ala  Lys Gly Tyr
    1400                 1405                 1410

Glu Arg  Arg Thr Ala Phe Tyr  Pro Trp Phe Thr Val  Asn Glu Asp
    1415                 1420                 1425

Glu Asn  Asp Thr Met Asp Ser  Ser Leu Phe Ala Ser  Pro Pro Ala
    1430                 1435                 1440

Arg


<210> SEQ ID NO 41
<211> LENGTH: 2793
<212> TYPE: DNA
<213> ORGANISM: Paenibacillus strain DAS1529

<400> SEQUENCE: 41

atgaacacaa cgtccatata taggggcacg cctacgattt cagttgtgga taaccggaac      60

ttggagattc gcattcttca gtataaccgt atcgcggctg aagatccggc agatgagtgt    120

atcctgcgga acacgtatac gccgttaagc tatcttggca gcagcatgga tccccgtttg    180

ttctcgcaat atcaggatga tcgcggaaca ccgccgaata tacgaaccat ggcttccctg    240

agaggcgaag cgctgtgttc ggaaagtgtg gatgccggcc gcaaggcgga gctttttgat    300

atcgaggggc ggcccgtctg gcttatcgat gccaacggca cagagacgac tctcgaatat    360

gatgtcttag gcaggccaac agccgtattc gagcaacagg aaggtacgga ctccccccag    420

tgcagggagc ggtttattta tggtgagaag gaggcggatg cccaggccaa caatttgcgc    480

ggacaactgg ttcgccacta cgataccgcg ggccggatac agaccgacag catctccttg    540

gctggactgc cgttgcgcca aagccgtcaa ctgctgaaaa attgggatga acctggcgac    600

tggagtatgg atgaggaaag cgcctgggcc tcgttgctgg ctgccgaagc ttatgatacg    660

agctggcggt atgacgcgca ggacagggtg ctcgcccaaa ccgacgccaa agggaatctc    720

cagcaactga cttacaatga cgccggccag ccgcaggcgg tcagcctcaa gctgcaaggc    780
```

```
caagcggagc aacggatttg gaaccggatc gagtacaacg cggcgggtca agtggatctc    840
gccgaagccg ggaatggaat cgtaacggaa tatacttacg aggaaagcac gcagcggtta    900
atccgaaaaa aagattcccg cggactgtcc tccggggaaa gagaagtgct gcaggattat    960
cgttatgaat atgatccggt aggcaatatc ctttctattt acaatgaagc ggagccggtt   1020
cgttatttcc gcaatcaggc cgttgctccg aaaaggcaat atgcctacga tgccttgtat   1080
cagcttgtat ctagttcggg gcgggaatcc gacgcgcttc ggcagcagac gtcgcttcct   1140
cccttgatca cgcctatccc tctggacgat agccaatacg tcaattacgc tgaaaaatac   1200
agctatgatc aggcgggcaa tttaatcaag cttagccata acggggcaag tcaatataca   1260
acgaatgtgt atgtggacaa aagctcaaac cgggggattt ggcggcaagg ggaagacatc   1320
ccggatatcg cggcttcctt tgacagagca ggcaatcaac aagctttatt cccggggaga   1380
ccgttggaat gggatacacg caatcaatta agccgtgtcc atatggtcgt gcgcgaaggc   1440
ggagacaacg actgggaagg ctatctctat gacagctcgg gaatgcgtat cgtaaaacga   1500
tctacccgca aaacacagac aacgacgcaa acggatacga ccctctattt gccgggcctg   1560
gagctgcgaa tccgccagac cggggaccgg gtcacggaag cattgcaggt cattaccgtg   1620
gatgagggag cgggacaagt gagggtgctg cactgggagg atggaaccga gccgggcggc   1680
atcgccaatg atcagtaccg gtacagcctg aacgatcatc ttacctcctc tttattggaa   1740
gttgacgggc aaggtcagat cattagtaag gaagaatttt atccctatgg cggcacagcc   1800
ctgtggacag cccggtcaga ggtagaggca agctacaaga ccatccgcta ttcaggcaaa   1860
gagcgggatg ccacaggcct gtattattac ggacaccgct actatatgcc atggttgggt   1920
cgctggctga atccggaccc ggccggaatg gtagatggac taaacctgta ccgtatggtc   1980
aggaacaatc ctataggact gatggatccg aatgggaatg cgccaatcaa cgtggcggat   2040
tatagcttcg tgcatggtga tttagtttat ggtcttagta aggaaagagg aagatatcta   2100
aagctattta atccaaactt taatatggaa aaatcagact ctcctgctat ggttatagat   2160
caatataata ataatgttgc attgagtata actaaccaat ataaagtaga agaattgatg   2220
aaatttcaaa aagacccaca aaaagccgca cggaaaataa aggttccaga agggaatcgt   2280
ttatcgagga acgaaaatta tcctttgtgg cacgattata ttaacattgg agaagctaaa   2340
gctgcattta aggcctctca tattttccaa gaagtgaagg ggaattatgg gaaagattat   2400
tatcataaat tattattaga cagaatgata gaatcgccgt tgctgtggaa acgaggcagc   2460
aaactcgggc tagaaatcgc cgctaccaat cagagaacaa aaatacactt tgttcttgac   2520
aatttaaata tcgagcaggt ggttacgaaa gagggtagcg gcggtcagtc aatcacagct   2580
tcggagctcc gttatattta tcgaaatcgc gaaagattga acgggcgtgt cattttctat   2640
agaaataatg aaaggctaga tcaggctcca tggcaagaaa atccggactt atggagcaaa   2700
tatcaaccgg gtcttagaca aagcagcagt tcaagagtca aagaacgagg gattgggaac   2760
tttttccgcc ggttttcaat gaagagaaag tag                               2793
```

<210> SEQ ID NO 42
<211> LENGTH: 930
<212> TYPE: PRT
<213> ORGANISM: Paenibacillus strain DAS1529

<400> SEQUENCE: 42

```
Met Asn Thr Thr Ser Ile Tyr Arg Gly Thr Pro Thr Ile Ser Val Val
1               5                   10                  15
```

-continued

```
Asp Asn Arg Asn Leu Glu Ile Arg Ile Leu Gln Tyr Asn Arg Ile Ala
            20                  25                  30

Ala Glu Asp Pro Ala Asp Glu Cys Ile Leu Arg Asn Thr Tyr Thr Pro
        35                  40                  45

Leu Ser Tyr Leu Gly Ser Ser Met Asp Pro Arg Leu Phe Ser Gln Tyr
    50                  55                  60

Gln Asp Asp Arg Gly Thr Pro Pro Asn Ile Arg Thr Met Ala Ser Leu
65                  70                  75                  80

Arg Gly Glu Ala Leu Cys Ser Glu Ser Val Asp Ala Gly Arg Lys Ala
                85                  90                  95

Glu Leu Phe Asp Ile Glu Gly Arg Pro Val Trp Leu Ile Asp Ala Asn
            100                 105                 110

Gly Thr Glu Thr Thr Leu Glu Tyr Asp Val Leu Gly Arg Pro Thr Ala
        115                 120                 125

Val Phe Glu Gln Gln Glu Gly Thr Asp Ser Pro Gln Cys Arg Glu Arg
    130                 135                 140

Phe Ile Tyr Gly Glu Lys Glu Ala Asp Ala Gln Ala Asn Asn Leu Arg
145                 150                 155                 160

Gly Gln Leu Val Arg His Tyr Asp Thr Ala Gly Arg Ile Gln Thr Asp
                165                 170                 175

Ser Ile Ser Leu Ala Gly Leu Pro Leu Arg Gln Ser Arg Gln Leu Leu
            180                 185                 190

Lys Asn Trp Asp Glu Pro Gly Asp Trp Ser Met Asp Glu Glu Ser Ala
        195                 200                 205

Trp Ala Ser Leu Leu Ala Ala Glu Ala Tyr Asp Thr Ser Trp Arg Tyr
    210                 215                 220

Asp Ala Gln Asp Arg Val Leu Ala Gln Thr Asp Ala Lys Gly Asn Leu
225                 230                 235                 240

Gln Gln Leu Thr Tyr Asn Asp Ala Gly Gln Pro Gln Ala Val Ser Leu
                245                 250                 255

Lys Leu Gln Gly Gln Ala Glu Gln Arg Ile Trp Asn Arg Ile Glu Tyr
            260                 265                 270

Asn Ala Ala Gly Gln Val Asp Leu Ala Glu Ala Gly Asn Gly Ile Val
        275                 280                 285

Thr Glu Tyr Thr Tyr Glu Glu Ser Thr Gln Arg Leu Ile Arg Lys Lys
    290                 295                 300

Asp Ser Arg Gly Leu Ser Ser Gly Glu Arg Glu Val Leu Gln Asp Tyr
305                 310                 315                 320

Arg Tyr Glu Tyr Asp Pro Val Gly Asn Ile Leu Ser Ile Tyr Asn Glu
                325                 330                 335

Ala Glu Pro Val Arg Tyr Phe Arg Asn Gln Ala Val Ala Pro Lys Arg
            340                 345                 350

Gln Tyr Ala Tyr Asp Ala Leu Tyr Gln Leu Val Ser Ser Ser Gly Arg
        355                 360                 365

Glu Ser Asp Ala Leu Arg Gln Gln Thr Ser Leu Pro Pro Leu Ile Thr
    370                 375                 380

Pro Ile Pro Leu Asp Asp Ser Gln Tyr Val Asn Tyr Ala Glu Lys Tyr
385                 390                 395                 400

Ser Tyr Asp Gln Ala Gly Asn Leu Ile Lys Leu Ser His Asn Gly Ala
                405                 410                 415

Ser Gln Tyr Thr Thr Asn Val Tyr Val Asp Lys Ser Ser Asn Arg Gly
            420                 425                 430

Ile Trp Arg Gln Gly Glu Asp Ile Pro Asp Ile Ala Ala Ser Phe Asp
        435                 440                 445
```

```
Arg Ala Gly Asn Gln Gln Ala Leu Phe Pro Gly Arg Pro Leu Glu Trp
    450                 455                 460

Asp Thr Arg Asn Gln Leu Ser Arg Val His Met Val Val Arg Glu Gly
465                 470                 475                 480

Gly Asp Asn Asp Trp Glu Gly Tyr Leu Tyr Asp Ser Ser Gly Met Arg
                485                 490                 495

Ile Val Lys Arg Ser Thr Arg Lys Thr Gln Thr Thr Thr Gln Thr Asp
            500                 505                 510

Thr Thr Leu Tyr Leu Pro Gly Leu Glu Leu Arg Ile Arg Gln Thr Gly
        515                 520                 525

Asp Arg Val Thr Glu Ala Leu Gln Val Ile Thr Val Asp Glu Gly Ala
    530                 535                 540

Gly Gln Val Arg Val Leu His Trp Glu Asp Gly Thr Glu Pro Gly Gly
545                 550                 555                 560

Ile Ala Asn Asp Gln Tyr Arg Tyr Ser Leu Asn Asp His Leu Thr Ser
                565                 570                 575

Ser Leu Leu Glu Val Asp Gly Gln Gly Gln Ile Ile Ser Lys Glu Glu
            580                 585                 590

Phe Tyr Pro Tyr Gly Gly Thr Ala Leu Trp Thr Ala Arg Ser Glu Val
        595                 600                 605

Glu Ala Ser Tyr Lys Thr Ile Arg Tyr Ser Gly Lys Glu Arg Asp Ala
    610                 615                 620

Thr Gly Leu Tyr Tyr Tyr Gly His Arg Tyr Tyr Met Pro Trp Leu Gly
625                 630                 635                 640

Arg Trp Leu Asn Pro Asp Pro Ala Gly Met Val Asp Gly Leu Asn Leu
                645                 650                 655

Tyr Arg Met Val Arg Asn Asn Pro Ile Gly Leu Met Asp Pro Asn Gly
            660                 665                 670

Asn Ala Pro Ile Asn Val Ala Asp Tyr Ser Phe Val His Gly Asp Leu
        675                 680                 685

Val Tyr Gly Leu Ser Lys Glu Arg Gly Arg Tyr Leu Lys Leu Phe Asn
    690                 695                 700

Pro Asn Phe Asn Met Glu Lys Ser Asp Ser Pro Ala Met Val Ile Asp
705                 710                 715                 720

Gln Tyr Asn Asn Asn Val Ala Leu Ser Ile Thr Asn Gln Tyr Lys Val
                725                 730                 735

Glu Glu Leu Met Lys Phe Gln Lys Asp Pro Gln Lys Ala Ala Arg Lys
            740                 745                 750

Ile Lys Val Pro Glu Gly Asn Arg Leu Ser Arg Asn Glu Asn Tyr Pro
        755                 760                 765

Leu Trp His Asp Tyr Ile Asn Ile Gly Glu Ala Lys Ala Ala Phe Lys
    770                 775                 780

Ala Ser His Ile Phe Gln Glu Val Lys Gly Asn Tyr Gly Lys Asp Tyr
785                 790                 795                 800

Tyr His Lys Leu Leu Leu Asp Arg Met Ile Glu Ser Pro Leu Leu Trp
                805                 810                 815

Lys Arg Gly Ser Lys Leu Gly Leu Glu Ile Ala Ala Thr Asn Gln Arg
            820                 825                 830

Thr Lys Ile His Phe Val Leu Asp Asn Leu Asn Ile Glu Gln Val Val
        835                 840                 845

Thr Lys Glu Gly Ser Gly Gly Gln Ser Ile Thr Ala Ser Glu Leu Arg
    850                 855                 860

Tyr Ile Tyr Arg Asn Arg Glu Arg Leu Asn Gly Arg Val Ile Phe Tyr
```

```
865                 870                 875                 880

Arg Asn Asn Glu Arg Leu Asp Gln Ala Pro Trp Gln Glu Asn Pro Asp
                885                 890                 895

Leu Trp Ser Lys Tyr Gln Pro Gly Leu Arg Gln Ser Ser Ser Ser Arg
            900                 905                 910

Val Lys Glu Arg Gly Ile Gly Asn Phe Phe Arg Arg Phe Ser Met Lys
        915                 920                 925

Arg Lys
    930


<210> SEQ ID NO 43
<211> LENGTH: 953
<212> TYPE: PRT
<213> ORGANISM: Paenibacillus strain DAS1529

<400> SEQUENCE: 43

Met Lys Met Ile Pro Trp Thr His His Tyr Leu Leu His Arg Leu Arg
1               5                   10                  15

Gly Glu Met Glu Val Lys Pro Met Asn Thr Thr Ser Ile Tyr Arg Gly
            20                  25                  30

Thr Pro Thr Ile Ser Val Val Asp Asn Arg Asn Leu Glu Ile Arg Ile
        35                  40                  45

Leu Gln Tyr Asn Arg Ile Ala Ala Glu Asp Pro Ala Asp Glu Cys Ile
    50                  55                  60

Leu Arg Asn Thr Tyr Thr Pro Leu Ser Tyr Leu Gly Ser Ser Met Asp
65                  70                  75                  80

Pro Arg Leu Phe Ser Gln Tyr Gln Asp Asp Arg Gly Thr Pro Pro Asn
                85                  90                  95

Ile Arg Thr Met Ala Ser Leu Arg Gly Glu Ala Leu Cys Ser Glu Ser
            100                 105                 110

Val Asp Ala Gly Arg Lys Ala Glu Leu Phe Asp Ile Glu Gly Arg Pro
        115                 120                 125

Val Trp Leu Ile Asp Ala Asn Gly Thr Glu Thr Thr Leu Glu Tyr Asp
    130                 135                 140

Val Leu Gly Arg Pro Thr Ala Val Phe Glu Gln Gln Glu Gly Thr Asp
145                 150                 155                 160

Ser Pro Gln Cys Arg Glu Arg Phe Ile Tyr Gly Glu Lys Glu Ala Asp
                165                 170                 175

Ala Gln Ala Asn Asn Leu Arg Gly Gln Leu Val Arg His Tyr Asp Thr
            180                 185                 190

Ala Gly Arg Ile Gln Thr Asp Ser Ile Ser Leu Ala Gly Leu Pro Leu
        195                 200                 205

Arg Gln Ser Arg Gln Leu Leu Lys Asn Trp Asp Glu Pro Gly Asp Trp
    210                 215                 220

Ser Met Asp Glu Glu Ser Ala Trp Ala Ser Leu Leu Ala Ala Glu Ala
225                 230                 235                 240

Tyr Asp Thr Ser Trp Arg Tyr Asp Ala Gln Asp Arg Val Leu Ala Gln
                245                 250                 255

Thr Asp Ala Lys Gly Asn Leu Gln Gln Leu Thr Tyr Asn Asp Ala Gly
            260                 265                 270

Gln Pro Gln Ala Val Ser Leu Lys Leu Gln Gly Gln Ala Glu Gln Arg
        275                 280                 285

Ile Trp Asn Arg Ile Glu Tyr Asn Ala Ala Gly Gln Val Asp Leu Ala
    290                 295                 300

Glu Ala Gly Asn Gly Ile Val Thr Glu Tyr Thr Tyr Glu Glu Ser Thr
```

305 310 315 320

Gln Arg Leu Ile Arg Lys Lys Asp Ser Arg Gly Leu Ser Ser Gly Glu
325 330 335

Arg Glu Val Leu Gln Asp Tyr Arg Tyr Glu Tyr Asp Pro Val Gly Asn
340 345 350

Ile Leu Ser Ile Tyr Asn Glu Ala Glu Pro Val Arg Tyr Phe Arg Asn
355 360 365

Gln Ala Val Ala Pro Lys Arg Gln Tyr Ala Tyr Asp Ala Leu Tyr Gln
370 375 380

Leu Val Ser Ser Ser Gly Arg Glu Ser Asp Ala Leu Arg Gln Gln Thr
385 390 395 400

Ser Leu Pro Pro Leu Ile Thr Pro Ile Pro Leu Asp Asp Ser Gln Tyr
405 410 415

Val Asn Tyr Ala Glu Lys Tyr Ser Tyr Asp Gln Ala Gly Asn Leu Ile
420 425 430

Lys Leu Ser His Asn Gly Ala Ser Gln Tyr Thr Thr Asn Val Tyr Val
435 440 445

Asp Lys Ser Ser Asn Arg Gly Ile Trp Arg Gln Gly Glu Asp Ile Pro
450 455 460

Asp Ile Ala Ala Ser Phe Asp Arg Ala Gly Asn Gln Gln Ala Leu Phe
465 470 475 480

Pro Gly Arg Pro Leu Glu Trp Asp Thr Arg Asn Gln Leu Ser Arg Val
485 490 495

His Met Val Val Arg Glu Gly Gly Asp Asn Asp Trp Glu Gly Tyr Leu
500 505 510

Tyr Asp Ser Ser Gly Met Arg Ile Val Lys Arg Ser Thr Arg Lys Thr
515 520 525

Gln Thr Thr Thr Gln Thr Asp Thr Thr Leu Tyr Leu Pro Gly Leu Glu
530 535 540

Leu Arg Ile Arg Gln Thr Gly Asp Arg Val Thr Glu Ala Leu Gln Val
545 550 555 560

Ile Thr Val Asp Glu Gly Ala Gly Gln Val Arg Val Leu His Trp Glu
565 570 575

Asp Gly Thr Glu Pro Gly Gly Ile Ala Asn Asp Gln Tyr Arg Tyr Ser
580 585 590

Leu Asn Asp His Leu Thr Ser Ser Leu Leu Glu Val Asp Gly Gln Gly
595 600 605

Gln Ile Ile Ser Lys Glu Glu Phe Tyr Pro Tyr Gly Gly Thr Ala Leu
610 615 620

Trp Thr Ala Arg Ser Glu Val Glu Ala Ser Tyr Lys Thr Ile Arg Tyr
625 630 635 640

Ser Gly Lys Glu Arg Asp Ala Thr Gly Leu Tyr Tyr Tyr Gly His Arg
645 650 655

Tyr Tyr Met Pro Trp Leu Gly Arg Trp Leu Asn Pro Asp Pro Ala Gly
660 665 670

Met Val Asp Gly Leu Asn Leu Tyr Arg Met Val Arg Asn Asn Pro Ile
675 680 685

Gly Leu Met Asp Pro Asn Gly Asn Ala Pro Ile Asn Val Ala Asp Tyr
690 695 700

Ser Phe Val His Gly Asp Leu Val Tyr Gly Leu Ser Lys Glu Arg Gly
705 710 715 720

Arg Tyr Leu Lys Leu Phe Asn Pro Asn Phe Asn Met Glu Lys Ser Asp
725 730 735

```
Ser Pro Ala Met Val Ile Asp Gln Tyr Asn Asn Asn Val Ala Leu Ser
            740                 745                 750

Ile Thr Asn Gln Tyr Lys Val Glu Glu Leu Met Lys Phe Gln Lys Asp
        755                 760                 765

Pro Gln Lys Ala Ala Arg Lys Ile Lys Val Pro Glu Gly Asn Arg Leu
    770                 775                 780

Ser Arg Asn Glu Asn Tyr Pro Leu Trp His Asp Tyr Ile Asn Ile Gly
785                 790                 795                 800

Glu Ala Lys Ala Ala Phe Lys Ala Ser His Ile Phe Gln Glu Val Lys
                805                 810                 815

Gly Asn Tyr Gly Lys Asp Tyr Tyr His Lys Leu Leu Leu Asp Arg Met
            820                 825                 830

Ile Glu Ser Pro Leu Leu Trp Lys Arg Gly Ser Lys Leu Gly Leu Glu
        835                 840                 845

Ile Ala Ala Thr Asn Gln Arg Thr Lys Ile His Phe Val Leu Asp Asn
    850                 855                 860

Leu Asn Ile Glu Gln Val Val Thr Lys Glu Gly Ser Gly Gly Gln Ser
865                 870                 875                 880

Ile Thr Ala Ser Glu Leu Arg Tyr Ile Tyr Arg Asn Arg Glu Arg Leu
                885                 890                 895

Asn Gly Arg Val Ile Phe Tyr Arg Asn Asn Glu Arg Leu Asp Gln Ala
            900                 905                 910

Pro Trp Gln Glu Asn Pro Asp Leu Trp Ser Lys Tyr Gln Pro Gly Leu
        915                 920                 925

Arg Gln Ser Ser Ser Ser Arg Val Lys Glu Arg Gly Ile Gly Asn Phe
    930                 935                 940

Phe Arg Arg Phe Ser Met Lys Arg Lys
945                 950
```

<210> SEQ ID NO 44
<211> LENGTH: 4425
<212> TYPE: DNA
<213> ORGANISM: Photorhabdus luminescens

<400> SEQUENCE: 44

```
atgcaaaatt cacaagattt tagtattacg gaactgtcac tgcccaaagg ggggggcgct      60

atcacgggaa tgggtgaagc attaaccccc actggaccgg atggtatggc cgcgctatct     120

ctaccattgc ctatttctgc cgggcgcggt tatgctcccg cattcactct gaattacaac     180

agcggcgccg gtaacagtcc atttggtctg ggttgggatt gcaacgttat gactatccgc     240

cgccgcaccc attttggcgt cccccattat gacgaaaccg ataccttttt ggggccagaa     300

ggcgaagtgc tggtggtagc ggatcaacct cgcgacgaat ccacattaca gggtatcaat     360

ttaggcgcca cctttaccgt taccggctac cgttcccgtc tggaaagcca tttcagccga     420

ttggaatatt ggcaacccaa aacaacaggt aaaacagatt tttggttgat atatagccca     480

gatgggcagg tgcatctact gggtaaatca ccgcaagcgc ggatcagcaa cccatcccaa     540

acgacacaaa cagcacaatg gctgctggaa gcctctgtat catcacgtgg cgaacaaatt     600

tattatcaat atcgcgccga agatgacaca ggttgcgaag cagatgaaat tacgcaccat     660

ttacaggcta cagcgcaacg ttatttacac atcgtgtatt acggcaaccg tacagccagc     720

gaaacattac ccggtctgga tggcagcgcc ccatcacaag cagactggtt gttctatctg     780

gtatttgatt acggcgaacg cagtaacaac ctgaaaacgc caccagcatt ttcgactaca     840

ggtagctggc tttgccgtca ggaccgtttt tcccgttatg aatatggctt tgagattcgt     900
```

-continued

```
acccgccgct tatgccgtca ggtattgatg taccatcacc tgcaagcact ggatagtaag    960
ataacagaac acaacggacc aacgctggtt tcacgcctga tactcaatta cgacgaaagc   1020
gcgatagcca gcacgctagt attcgttcgc cgagtgggac acgagcaaga tggtaatgtc   1080
gtcaccctgc cgccattaga attggcatat caggattttt caccgcgaca tcacgctcac   1140
tggcaaccaa tggatgtact ggcaaacttc aatgccattc agcgctggca gctagtcgat   1200
ctaaaaggcg aaggattacc cggcctgtta tatcaggata aaggcgcttg gtggtaccgc   1260
tccgcacagc gtctgggcga aattggctca gatgccgtca cttgggaaaa gatgcaacct   1320
ttatcggtta ttccttcttt gcaaagtaat gcctcgttgg tggatatcaa tggagacggc   1380
caacttgact gggttatcac cggaccggga ttacggggat atcatagtca acgcccggat   1440
ggcagttgga cacgttttac cccactcaac gctctgccgg tggaatacac ccatccacgc   1500
gcgcaactcg cagatttaat gggagccggg ctatccgatt tggtgctgat cggccctaag   1560
agcgtgcgtt tatatgccaa tacccgcgac ggctttgcca aggaaaaaga tgtggtgcaa   1620
tccggtgata tcacactgcc ggtgccgggc gccgatccac gtaagttggt ggcgtttagt   1680
gatgtattgg gttcaggtca agcccatctg gttgaagtaa gcgcgactaa agtcacctgc   1740
tggcctaatc tggggcgcgg acgttttggt caacccatta ccttaccggg attcagccag   1800
ccagcaaccg agtttaaccc ggctcaagtt tatctggccg atctggatgg cagcggtcca   1860
acggatctga tttatgttca tacaaaccgt ctggatatct tcctgaacaa aagtggcaat   1920
ggctttgctg aaccagtgac attacgcttc ccggaaggtc tgcgttttga tcatacctgt   1980
cagttacaaa tggccgatgt acaaggatta ggcgtcgcca gcctgatact gagcgtgccg   2040
catatgtctc cccatcactg gcgctgcgat ctgaccaaca tgaagccgtg gttactcaat   2100
gaaatgaaca acaatatggg ggtccatcac accttgcgtt accgcagttc ctcccaattc   2160
tggctggatg aaaaagccgc ggcgctgact accggacaaa caccggtttg ctatctcccc   2220
ttcccgatcc acaccctatg gcaaacggaa acagaagatg aaatcagcgg caacaaatta   2280
gtcacaacac ttcgttatgc tcgtggcgca tgggacggac gcgagcggga atttcgcgga   2340
tttggttatg tagagcagac agacagccat caactggctc aaggcaacgc gccagaacgt   2400
acgccaccgg cgctgaccaa aaactggtat gccaccggac tgccggtgat agataacgca   2460
ttatcaaccg agtattggcg tgatgatcag gcttttgccg gtttctcacc gcgctttacg   2520
acttggcaag ataacaaaga tgtcccgtta acaccggaag atgataacag tcgttactgg   2580
ttcaaccgcg cgttgaaagg tcaactgcta cgtagtgaac tgtacggatt ggacgatagt   2640
acaaataaac acgttcccta tactgtcact gaatttcgtt cacaggtacg tcgattacag   2700
cataccgaca gccgataccc tgtactttgg tcatctgtag ttgaaagccg caactatcac   2760
tacgaacgta tcgccagcga cccgcaatgc agtcaaaata ttacgctatc cagtgatcga   2820
tttggtcagc cgctaaaaca gctttcggta cagtacccgc gccgccagca gccagcaatc   2880
aatctgtatc ctgatacatt gcctgataag ttgttagcca acagctatga tgaccaacaa   2940
cgccaattac ggctcaccta tcaacaatcc agttggcatc acctgaccaa caataccgtt   3000
cgagtattgg gattaccgga tagtacccgc agtgatatct ttacttatgg cgctgaaaat   3060
gtgcctgctg gtggtttaaa tctggaactt ctgagtgata aaaatagcct gatcgcggac   3120
gataaaccac gtgaatacct cggtcagcaa aaaaccgctt ataccgatgg acaaaataca   3180
acgccgttgc aaacaccaac acggcaagcc ctgattgcct ttaccgaaac aacggtattc   3240
aaccagtcca cattatcagc gtttaacgga agcatcccgt ccgataaatt atcaacgacg   3300
```

```
ctggagcaag ctggatatca gcaaacaaat tatctattcc ctcgcactgg agaagataaa   3360

gtttgggtag cccatcacgg ctataccgat tatggtacag cggcacagtt ctggcgcccg   3420

caaaaacaga gcaacaccca actcaccggt aaaatcaccc tcatctggga tgcaaactat   3480

tgcgttgtgg tacaaacccg ggatgctgct ggactgacaa cctcagccaa atatgactgg   3540

cgttttctga ccccggtgca actcaccgat atcaatgaca atcagcacct tatcacactg   3600

gatgcattgg gccgaccaat cacattgcgc ttttggggaa ctgaaaacgg caagatgaca   3660

ggttattcct caccggaaaa agcatcattt tctccaccat ccgatgttaa tgccgctatt   3720

gagttaaaaa aaccgctccc tgtagcacag tgtcaggtct acgcaccaga aagctggatg   3780

ccagtattaa gtcagaaaac cttcaatcga ctggcagaac aagattggca aaagttatat   3840

aacgcccgaa tcatcaccga agatggacgt atctgcacac tggcttatcg ccgctgggta   3900

caaagccaaa aggcaatccc tcaactcatt agcctgttaa acaacggacc ccgtttacct   3960

cctcacagcc tgacattgac gacggatcgt tatgatcacg atcctgagca acagatccgt   4020

caacaggtgg tattcagtga tggctttggc cgcttgctgc aagccgctgc ccgacatgag   4080

gcaggcatgg cccggcaacg caatgaagac ggctctttga ttataaatgt ccagcatact   4140

gagaaccgtt gggcagtgac tggacgaacg gaatatgaca ataaggggca accgatacgt   4200

acctatcagc cctatttcct caatgactgg cgatacgtca gcaatgatag tgcccggcag   4260

gaaaaagaag cttatgcaga tacccatgtc tatgatccca taggtcgaga aatcaaggtt   4320

atcaccgcaa aaggttggtt ccgtcgaacc ttgttcactc cctggtttac tgtcaatgaa   4380

gatgaaaatg acacagccgc tgaggtgaag aaggtaaaga tgtaa                   4425
```

<210> SEQ ID NO 45
<211> LENGTH: 1474
<212> TYPE: PRT
<213> ORGANISM: Photorhabdus luminescens

<400> SEQUENCE: 45

```
Met Gln Asn Ser Gln Asp Phe Ser Ile Thr Glu Leu Ser Leu Pro Lys
1               5                   10                  15

Gly Gly Gly Ala Ile Thr Gly Met Gly Glu Ala Leu Thr Pro Thr Gly
            20                  25                  30

Pro Asp Gly Met Ala Ala Leu Ser Leu Pro Leu Pro Ile Ser Ala Gly
        35                  40                  45

Arg Gly Tyr Ala Pro Ala Phe Thr Leu Asn Tyr Asn Ser Gly Ala Gly
    50                  55                  60

Asn Ser Pro Phe Gly Leu Gly Trp Asp Cys Asn Val Met Thr Ile Arg
65                  70                  75                  80

Arg Arg Thr His Phe Gly Val Pro His Tyr Asp Glu Thr Asp Thr Phe
                85                  90                  95

Leu Gly Pro Glu Gly Glu Val Leu Val Val Ala Asp Gln Pro Arg Asp
            100                 105                 110

Glu Ser Thr Leu Gln Gly Ile Asn Leu Gly Ala Thr Phe Thr Val Thr
        115                 120                 125

Gly Tyr Arg Ser Arg Leu Glu Ser His Phe Ser Arg Leu Glu Tyr Trp
    130                 135                 140

Gln Pro Lys Thr Thr Gly Lys Thr Asp Phe Trp Leu Ile Tyr Ser Pro
145                 150                 155                 160

Asp Gly Gln Val His Leu Leu Gly Lys Ser Pro Gln Ala Arg Ile Ser
                165                 170                 175

Asn Pro Ser Gln Thr Thr Gln Thr Ala Gln Trp Leu Leu Glu Ala Ser
```

-continued

```
            180                 185                 190

Val Ser Ser Arg Gly Glu Gln Ile Tyr Tyr Gln Tyr Arg Ala Glu Asp
        195                 200                 205

Asp Thr Gly Cys Glu Ala Asp Glu Ile Thr His His Leu Gln Ala Thr
    210                 215                 220

Ala Gln Arg Tyr Leu His Ile Val Tyr Tyr Gly Asn Arg Thr Ala Ser
225                 230                 235                 240

Glu Thr Leu Pro Gly Leu Asp Gly Ser Ala Pro Ser Gln Ala Asp Trp
                245                 250                 255

Leu Phe Tyr Leu Val Phe Asp Tyr Gly Glu Arg Ser Asn Asn Leu Lys
            260                 265                 270

Thr Pro Pro Ala Phe Ser Thr Thr Gly Ser Trp Leu Cys Arg Gln Asp
        275                 280                 285

Arg Phe Ser Arg Tyr Glu Tyr Gly Phe Glu Ile Arg Thr Arg Arg Leu
    290                 295                 300

Cys Arg Gln Val Leu Met Tyr His His Leu Gln Ala Leu Asp Ser Lys
305                 310                 315                 320

Ile Thr Glu His Asn Gly Pro Thr Leu Val Ser Arg Leu Ile Leu Asn
                325                 330                 335

Tyr Asp Glu Ser Ala Ile Ala Ser Thr Leu Val Phe Val Arg Arg Val
            340                 345                 350

Gly His Glu Gln Asp Gly Asn Val Val Thr Leu Pro Pro Leu Glu Leu
        355                 360                 365

Ala Tyr Gln Asp Phe Ser Pro Arg His His Ala His Trp Gln Pro Met
    370                 375                 380

Asp Val Leu Ala Asn Phe Asn Ala Ile Gln Arg Trp Gln Leu Val Asp
385                 390                 395                 400

Leu Lys Gly Glu Gly Leu Pro Gly Leu Leu Tyr Gln Asp Lys Gly Ala
                405                 410                 415

Trp Trp Tyr Arg Ser Ala Gln Arg Leu Gly Glu Ile Gly Ser Asp Ala
            420                 425                 430

Val Thr Trp Glu Lys Met Gln Pro Leu Ser Val Ile Pro Ser Leu Gln
        435                 440                 445

Ser Asn Ala Ser Leu Val Asp Ile Asn Gly Asp Gly Gln Leu Asp Trp
    450                 455                 460

Val Ile Thr Gly Pro Gly Leu Arg Gly Tyr His Ser Gln Arg Pro Asp
465                 470                 475                 480

Gly Ser Trp Thr Arg Phe Thr Pro Leu Asn Ala Leu Pro Val Glu Tyr
                485                 490                 495

Thr His Pro Arg Ala Gln Leu Ala Asp Leu Met Gly Ala Gly Leu Ser
            500                 505                 510

Asp Leu Val Leu Ile Gly Pro Lys Ser Val Arg Leu Tyr Ala Asn Thr
        515                 520                 525

Arg Asp Gly Phe Ala Lys Gly Lys Asp Val Val Gln Ser Gly Asp Ile
    530                 535                 540

Thr Leu Pro Val Pro Gly Ala Asp Pro Arg Lys Leu Val Ala Phe Ser
545                 550                 555                 560

Asp Val Leu Gly Ser Gly Gln Ala His Leu Val Glu Val Ser Ala Thr
                565                 570                 575

Lys Val Thr Cys Trp Pro Asn Leu Gly Arg Gly Arg Phe Gly Gln Pro
            580                 585                 590

Ile Thr Leu Pro Gly Phe Ser Gln Pro Ala Thr Glu Phe Asn Pro Ala
        595                 600                 605
```

-continued

```
Gln Val Tyr Leu Ala Asp Leu Asp Gly Ser Gly Pro Thr Asp Leu Ile
    610                 615                 620

Tyr Val His Thr Asn Arg Leu Asp Ile Phe Leu Asn Lys Ser Gly Asn
625                 630                 635                 640

Gly Phe Ala Glu Pro Val Thr Leu Arg Phe Pro Glu Gly Leu Arg Phe
                645                 650                 655

Asp His Thr Cys Gln Leu Gln Met Ala Asp Val Gln Gly Leu Gly Val
            660                 665                 670

Ala Ser Leu Ile Leu Ser Val Pro His Met Ser Pro His His Trp Arg
        675                 680                 685

Cys Asp Leu Thr Asn Met Lys Pro Trp Leu Leu Asn Glu Met Asn Asn
    690                 695                 700

Asn Met Gly Val His His Thr Leu Arg Tyr Arg Ser Ser Ser Gln Phe
705                 710                 715                 720

Trp Leu Asp Glu Lys Ala Ala Ala Leu Thr Thr Gly Gln Thr Pro Val
                725                 730                 735

Cys Tyr Leu Pro Phe Pro Ile His Thr Leu Trp Gln Thr Glu Thr Glu
            740                 745                 750

Asp Glu Ile Ser Gly Asn Lys Leu Val Thr Thr Leu Arg Tyr Ala Arg
        755                 760                 765

Gly Ala Trp Asp Gly Arg Glu Arg Glu Phe Arg Gly Phe Gly Tyr Val
    770                 775                 780

Glu Gln Thr Asp Ser His Gln Leu Ala Gln Gly Asn Ala Pro Glu Arg
785                 790                 795                 800

Thr Pro Pro Ala Leu Thr Lys Asn Trp Tyr Ala Thr Gly Leu Pro Val
                805                 810                 815

Ile Asp Asn Ala Leu Ser Thr Glu Tyr Trp Arg Asp Asp Gln Ala Phe
            820                 825                 830

Ala Gly Phe Ser Pro Arg Phe Thr Thr Trp Gln Asp Asn Lys Asp Val
        835                 840                 845

Pro Leu Thr Pro Glu Asp Asp Asn Ser Arg Tyr Trp Phe Asn Arg Ala
    850                 855                 860

Leu Lys Gly Gln Leu Leu Arg Ser Glu Leu Tyr Gly Leu Asp Asp Ser
865                 870                 875                 880

Thr Asn Lys His Val Pro Tyr Thr Val Thr Glu Phe Arg Ser Gln Val
                885                 890                 895

Arg Arg Leu Gln His Thr Asp Ser Arg Tyr Pro Val Leu Trp Ser Ser
            900                 905                 910

Val Val Glu Ser Arg Asn Tyr His Tyr Glu Arg Ile Ala Ser Asp Pro
        915                 920                 925

Gln Cys Ser Gln Asn Ile Thr Leu Ser Ser Asp Arg Phe Gly Gln Pro
    930                 935                 940

Leu Lys Gln Leu Ser Val Gln Tyr Pro Arg Arg Gln Gln Pro Ala Ile
945                 950                 955                 960

Asn Leu Tyr Pro Asp Thr Leu Pro Asp Lys Leu Leu Ala Asn Ser Tyr
                965                 970                 975

Asp Asp Gln Gln Arg Gln Leu Arg Leu Thr Tyr Gln Gln Ser Ser Trp
            980                 985                 990

His His Leu Thr Asn Asn Thr Val  Arg Val Leu Gly Leu  Pro Asp Ser
        995                 1000                1005

Thr Arg  Ser Asp Ile Phe Thr  Tyr Gly Ala Glu Asn  Val Pro Ala
    1010                 1015                 1020

Gly Gly  Leu Asn Leu Glu Leu  Leu Ser Asp Lys Asn  Ser Leu Ile
    1025                 1030                 1035
```

```
Ala Asp  Asp Lys Pro Arg Glu  Tyr Leu Gly Gln Gln  Lys Thr Ala
    1040                 1045                 1050

Tyr Thr  Asp Gly Gln Asn Thr  Thr Pro Leu Gln Thr  Pro Thr Arg
    1055                 1060                 1065

Gln Ala  Leu Ile Ala Phe Thr  Glu Thr Thr Val Phe  Asn Gln Ser
    1070                 1075                 1080

Thr Leu  Ser Ala Phe Asn Gly  Ser Ile Pro Ser Asp  Lys Leu Ser
    1085                 1090                 1095

Thr Thr  Leu Glu Gln Ala Gly  Tyr Gln Gln Thr Asn  Tyr Leu Phe
    1100                 1105                 1110

Pro Arg  Thr Gly Glu Asp Lys  Val Trp Val Ala His  His Gly Tyr
    1115                 1120                 1125

Thr Asp  Tyr Gly Thr Ala Ala  Gln Phe Trp Arg Pro  Gln Lys Gln
    1130                 1135                 1140

Ser Asn  Thr Gln Leu Thr Gly  Lys Ile Thr Leu Ile  Trp Asp Ala
    1145                 1150                 1155

Asn Tyr  Cys Val Val Val Gln  Thr Arg Asp Ala Ala  Gly Leu Thr
    1160                 1165                 1170

Thr Ser  Ala Lys Tyr Asp Trp  Arg Phe Leu Thr Pro  Val Gln Leu
    1175                 1180                 1185

Thr Asp  Ile Asn Asp Asn Gln  His Leu Ile Thr Leu  Asp Ala Leu
    1190                 1195                 1200

Gly Arg  Pro Ile Thr Leu Arg  Phe Trp Gly Thr Glu  Asn Gly Lys
    1205                 1210                 1215

Met Thr  Gly Tyr Ser Ser Pro  Glu Lys Ala Ser Phe  Ser Pro Pro
    1220                 1225                 1230

Ser Asp  Val Asn Ala Ala Ile  Glu Leu Lys Lys Pro  Leu Pro Val
    1235                 1240                 1245

Ala Gln  Cys Gln Val Tyr Ala  Pro Glu Ser Trp Met  Pro Val Leu
    1250                 1255                 1260

Ser Gln  Lys Thr Phe Asn Arg  Leu Ala Glu Gln Asp  Trp Gln Lys
    1265                 1270                 1275

Leu Tyr  Asn Ala Arg Ile Ile  Thr Glu Asp Gly Arg  Ile Cys Thr
    1280                 1285                 1290

Leu Ala  Tyr Arg Arg Trp Val  Gln Ser Gln Lys Ala  Ile Pro Gln
    1295                 1300                 1305

Leu Ile  Ser Leu Leu Asn Asn  Gly Pro Arg Leu Pro  Pro His Ser
    1310                 1315                 1320

Leu Thr  Leu Thr Thr Asp Arg  Tyr Asp His Asp Pro  Glu Gln Gln
    1325                 1330                 1335

Ile Arg  Gln Gln Val Val Phe  Ser Asp Gly Phe Gly  Arg Leu Leu
    1340                 1345                 1350

Gln Ala  Ala Ala Arg His Glu  Ala Gly Met Ala Arg  Gln Arg Asn
    1355                 1360                 1365

Glu Asp  Gly Ser Leu Ile Ile  Asn Val Gln His Thr  Glu Asn Arg
    1370                 1375                 1380

Trp Ala  Val Thr Gly Arg Thr  Glu Tyr Asp Asn Lys  Gly Gln Pro
    1385                 1390                 1395

Ile Arg  Thr Tyr Gln Pro Tyr  Phe Leu Asn Asp Trp  Arg Tyr Val
    1400                 1405                 1410

Ser Asn  Asp Ser Ala Arg Gln  Glu Lys Glu Ala Tyr  Ala Asp Thr
    1415                 1420                 1425

His Val  Tyr Asp Pro Ile Gly  Arg Glu Ile Lys Val  Ile Thr Ala
```

```
    1430                1435                1440

Lys Gly  Trp Phe Arg Arg Thr  Leu Phe Thr Pro Trp  Phe Thr Val
    1445                1450                1455

Asn Glu  Asp Glu Asn Asp Thr  Ala Ala Glu Val Lys  Lys Val Lys
    1460                1465                1470

Met


<210> SEQ ID NO 46
<211> LENGTH: 2883
<212> TYPE: DNA
<213> ORGANISM: Photorhabdus luminescens

<400> SEQUENCE: 46

atgaaaaaca ttgatcccaa actttatcaa aaaacccta ctgtcagcgt ttacgataac     60

cgtggtctga taatccgtaa catcgatttt catcgtacta ccgcaaatgg tgatcccgat    120

acccgtatta cccgccatca atacgatatt cacggacacc taaatcaaag catcgatccg    180

cgcctatatg aagccaagca aaccaacaat acgatcaaac ccaattttct ttggcagtat    240

gatttgaccg gtaatcccct atgtacagag agcattgatg caggtcgcac tgtcaccttg    300

aatgatattg aaggccgtcc gctactaacg gtgactgcaa caggggttat acaaactcga    360

caatatgaaa cttcttccct gcccggtcgt ctgttatctg ttgccgaaca aacacccgag    420

gaaaaaacat cccgtatcac cgaacgcctg atttgggctg gcaataccga agcagagaaa    480

gaccataacc ttgccggcca gtgcgtgcgt cactatgaca cggcgggagt tacccggtta    540

gagagtttat cactgaccgg tactgtttta tctcaatcca gccaactatt gatcgacact    600

caagaggcaa actggacagg tgataacgaa accgtctggc aaaacatgct ggctgatgac    660

atctacacaa ccctgagcac cttcgatgcc accggtgctt tactgactca gaccgatgcg    720

aaagggaaca ttcagagact ggcttatgat gtggccgggc agctaaacgg gagctggcta    780

acactcaaag gccagacgga acaagtgatt atcaaatccc tgacctactc cgccgccgga    840

caaaaaattac gtgaggaaca cggcaatgat gttatcaccg aatacagtta tgaaccggaa    900

acccaacggc tgatcggtat caaaacccgc cgtccgtcag acactaaagt gctacaagac    960

ctgcgctatg aatatgaccc ggtaggcaat gtcatcagca tccgtaatga cgcggaagcc   1020

acccgctttt ggcacaatca gaaagtgatg ccggaaaaca cttataccta cgattccctg   1080

tatcagctta tcagcgccac cgggcgcgaa atggcgaata taggtcaaca aagtcaccaa   1140

tttccctcac ccgctctacc ttctgataac aacacctata ccaactatac ccgtacttat   1200

acttatgacc gtggcggcaa tctgaccaaa atccagcaca gttcaccggc gacgcaaaac   1260

aactacacca ccaatatcac ggtttcaaat cgcagcaacc gcgcagtact cagcacattg   1320

accgaagatc cggcgcaagt agatgctttg tttgatgcag gcggacatca gaacaccttg   1380

atatcaggac aaaacctgaa ctggaatact cgtggtgaac tgcaacaagt aacactggtt   1440

aaacgggaca agggcgccaa tgatgatcgg gaatggtatc gttatagcgg tgacggaaga   1500

aggatgttaa aaatcaatga acagcaggcc agcaacaacg ctcaaacaca acgtgtgact   1560

tatttgccga acttagaact tcgtctaaca caaaacagca cggccacaac cgaagatttg   1620

caagttatca ccgtaggcga agcgggccgg gcacaggtac gagtattaca ttgggagagc   1680

ggtaaaccgg aagatatcga caataatcag ttgcgttata gttacgataa tcttatcggt   1740

tccagtcaac ttgaattaga tagcgaagga caaattatca gtgaagaaga atattatccc   1800

tatggtggaa cagcattatg ggccgccagg aatcagacag aagccagtta taaaactatc   1860
```

```
cgttattcag gcaaagagcg ggatgccacc gggctatatt actacggcta tcggtattac   1920

caaccgtgga taggacggtg gttaagctcc gatccggcag gaacaatcga tgggctgaat   1980

ttatatcgga tggtgaggaa taatccagtt accctccttg atcctgatgg attaatgcca   2040

acaattgcag aacgcatagc agcactaaaa aaaaataaag taacagactc agcgccttcg   2100

ccagcaaatg ccacaaacgt agcgataaac atccgcccgc ctgtagcacc aaaacctagc   2160

ttaccgaaag catcaacgag tagccaacca accacacacc ctatcggagc tgcaaacata   2220

aaaccaacga cgtctgggtc atctattgtt gctccattga gtccagtagg aaataaatct   2280

acttctgaaa tctctctgcc agaaagcgct caaagcagtt cttcaagcac tacctcgaca   2340

aatctacaga aaaaatcatt tactttatat agagcagata acagatcctt tgaagaaatg   2400

caaagtaaat tccctgaagg atttaaagcc tggactcctc tagacactaa gatggcaagg   2460

caatttgcta gtatctttat tggtcagaaa gatacatcta atttacctaa agaaacagtc   2520

aagaacataa gcacatgggg agcaaagcca aaactaaaag atctctcaaa ttacataaaa   2580

tataccaagg acaaatctac agtatgggtt tctactgcaa ttaatactga agcaggtgga   2640

caaagctcag ggctccact ccataaaatt gatatggatc tctacgagtt tgccattgat    2700

ggacaaaaac taaatccact accggagggt agaactaaaa acatggtacc ttccctttta   2760

ctcgacaccc cacaaataga gacatcatcc atcattgcac ttaatcatgg accggtaaat   2820

gatgcagaaa tttcatttct gacaacaatt ccgcttaaaa atgtaaaacc tcataagaga   2880

taa                                                                 2883
```

<210> SEQ ID NO 47
<211> LENGTH: 960
<212> TYPE: PRT
<213> ORGANISM: Photorhabdus luminescens

<400> SEQUENCE: 47

```
Met Lys Asn Ile Asp Pro Lys Leu Tyr Gln Lys Thr Pro Thr Val Ser
1               5                   10                  15

Val Tyr Asp Asn Arg Gly Leu Ile Ile Arg Asn Ile Asp Phe His Arg
            20                  25                  30

Thr Thr Ala Asn Gly Asp Pro Asp Thr Arg Ile Thr Arg His Gln Tyr
        35                  40                  45

Asp Ile His Gly His Leu Asn Gln Ser Ile Asp Pro Arg Leu Tyr Glu
    50                  55                  60

Ala Lys Gln Thr Asn Asn Thr Ile Lys Pro Asn Phe Leu Trp Gln Tyr
65                  70                  75                  80

Asp Leu Thr Gly Asn Pro Leu Cys Thr Glu Ser Ile Asp Ala Gly Arg
                85                  90                  95

Thr Val Thr Leu Asn Asp Ile Glu Gly Arg Pro Leu Leu Thr Val Thr
            100                 105                 110

Ala Thr Gly Val Ile Gln Thr Arg Gln Tyr Glu Thr Ser Ser Leu Pro
        115                 120                 125

Gly Arg Leu Leu Ser Val Ala Glu Gln Thr Pro Glu Glu Lys Thr Ser
    130                 135                 140

Arg Ile Thr Glu Arg Leu Ile Trp Ala Gly Asn Thr Glu Ala Glu Lys
145                 150                 155                 160

Asp His Asn Leu Ala Gly Gln Cys Val Arg His Tyr Asp Thr Ala Gly
                165                 170                 175

Val Thr Arg Leu Glu Ser Leu Ser Leu Thr Gly Thr Val Leu Ser Gln
            180                 185                 190
```

```
Ser Ser Gln Leu Leu Ile Asp Thr Gln Glu Ala Asn Trp Thr Gly Asp
        195                 200                 205

Asn Glu Thr Val Trp Gln Asn Met Leu Ala Asp Asp Ile Tyr Thr Thr
    210                 215                 220

Leu Ser Thr Phe Asp Ala Thr Gly Ala Leu Leu Thr Gln Thr Asp Ala
225                 230                 235                 240

Lys Gly Asn Ile Gln Arg Leu Ala Tyr Asp Val Ala Gly Gln Leu Asn
                245                 250                 255

Gly Ser Trp Leu Thr Leu Lys Gly Gln Thr Glu Gln Val Ile Ile Lys
            260                 265                 270

Ser Leu Thr Tyr Ser Ala Ala Gly Gln Lys Leu Arg Glu Glu His Gly
        275                 280                 285

Asn Asp Val Ile Thr Glu Tyr Ser Tyr Glu Pro Glu Thr Gln Arg Leu
    290                 295                 300

Ile Gly Ile Lys Thr Arg Arg Pro Ser Asp Thr Lys Val Leu Gln Asp
305                 310                 315                 320

Leu Arg Tyr Glu Tyr Asp Pro Val Gly Asn Val Ile Ser Ile Arg Asn
                325                 330                 335

Asp Ala Glu Ala Thr Arg Phe Trp His Asn Gln Lys Val Met Pro Glu
            340                 345                 350

Asn Thr Tyr Thr Tyr Asp Ser Leu Tyr Gln Leu Ile Ser Ala Thr Gly
        355                 360                 365

Arg Glu Met Ala Asn Ile Gly Gln Gln Ser His Gln Phe Pro Ser Pro
    370                 375                 380

Ala Leu Pro Ser Asp Asn Asn Thr Tyr Thr Asn Tyr Thr Arg Thr Tyr
385                 390                 395                 400

Thr Tyr Asp Arg Gly Gly Asn Leu Thr Lys Ile Gln His Ser Ser Pro
                405                 410                 415

Ala Thr Gln Asn Asn Tyr Thr Thr Asn Ile Thr Val Ser Asn Arg Ser
            420                 425                 430

Asn Arg Ala Val Leu Ser Thr Leu Thr Glu Asp Pro Ala Gln Val Asp
        435                 440                 445

Ala Leu Phe Asp Ala Gly Gly His Gln Asn Thr Leu Ile Ser Gly Gln
    450                 455                 460

Asn Leu Asn Trp Asn Thr Arg Gly Glu Leu Gln Gln Val Thr Leu Val
465                 470                 475                 480

Lys Arg Asp Lys Gly Ala Asn Asp Asp Arg Glu Trp Tyr Arg Tyr Ser
                485                 490                 495

Gly Asp Gly Arg Arg Met Leu Lys Ile Asn Glu Gln Gln Ala Ser Asn
            500                 505                 510

Asn Ala Gln Thr Gln Arg Val Thr Tyr Leu Pro Asn Leu Glu Leu Arg
        515                 520                 525

Leu Thr Gln Asn Ser Thr Ala Thr Thr Glu Asp Leu Gln Val Ile Thr
    530                 535                 540

Val Gly Glu Ala Gly Arg Ala Gln Val Arg Val Leu His Trp Glu Ser
545                 550                 555                 560

Gly Lys Pro Glu Asp Ile Asp Asn Asn Gln Leu Arg Tyr Ser Tyr Asp
                565                 570                 575

Asn Leu Ile Gly Ser Ser Gln Leu Glu Leu Asp Ser Glu Gly Gln Ile
            580                 585                 590

Ile Ser Glu Glu Glu Tyr Tyr Pro Tyr Gly Gly Thr Ala Leu Trp Ala
        595                 600                 605

Ala Arg Asn Gln Thr Glu Ala Ser Tyr Lys Thr Ile Arg Tyr Ser Gly
    610                 615                 620
```

Lys Glu Arg Asp Ala Thr Gly Leu Tyr Tyr Tyr Gly Tyr Arg Tyr Tyr
625 630 635 640

Gln Pro Trp Ile Gly Arg Trp Leu Ser Ser Asp Pro Ala Gly Thr Ile
645 650 655

Asp Gly Leu Asn Leu Tyr Arg Met Val Arg Asn Asn Pro Val Thr Leu
660 665 670

Leu Asp Pro Asp Gly Leu Met Pro Thr Ile Ala Glu Arg Ile Ala Ala
675 680 685

Leu Lys Lys Asn Lys Val Thr Asp Ser Ala Pro Ser Pro Ala Asn Ala
690 695 700

Thr Asn Val Ala Ile Asn Ile Arg Pro Pro Val Ala Pro Lys Pro Ser
705 710 715 720

Leu Pro Lys Ala Ser Thr Ser Ser Gln Pro Thr Thr His Pro Ile Gly
725 730 735

Ala Ala Asn Ile Lys Pro Thr Thr Ser Gly Ser Ser Ile Val Ala Pro
740 745 750

Leu Ser Pro Val Gly Asn Lys Ser Thr Ser Glu Ile Ser Leu Pro Glu
755 760 765

Ser Ala Gln Ser Ser Ser Ser Ser Thr Thr Ser Thr Asn Leu Gln Lys
770 775 780

Lys Ser Phe Thr Leu Tyr Arg Ala Asp Asn Arg Ser Phe Glu Glu Met
785 790 795 800

Gln Ser Lys Phe Pro Glu Gly Phe Lys Ala Trp Thr Pro Leu Asp Thr
805 810 815

Lys Met Ala Arg Gln Phe Ala Ser Ile Phe Ile Gly Gln Lys Asp Thr
820 825 830

Ser Asn Leu Pro Lys Glu Thr Val Lys Asn Ile Ser Thr Trp Gly Ala
835 840 845

Lys Pro Lys Leu Lys Asp Leu Ser Asn Tyr Ile Lys Tyr Thr Lys Asp
850 855 860

Lys Ser Thr Val Trp Val Ser Thr Ala Ile Asn Thr Glu Ala Gly Gly
865 870 875 880

Gln Ser Ser Gly Ala Pro Leu His Lys Ile Asp Met Asp Leu Tyr Glu
885 890 895

Phe Ala Ile Asp Gly Gln Lys Leu Asn Pro Leu Pro Glu Gly Arg Thr
900 905 910

Lys Asn Met Val Pro Ser Leu Leu Leu Asp Thr Pro Gln Ile Glu Thr
915 920 925

Ser Ser Ile Ile Ala Leu Asn His Gly Pro Val Asn Asp Ala Glu Ile
930 935 940

Ser Phe Leu Thr Thr Ile Pro Leu Lys Asn Val Lys Pro His Lys Arg
945 950 955 960

<210> SEQ ID NO 48
<211> LENGTH: 4521
<212> TYPE: DNA
<213> ORGANISM: Xenorhabdus bovienii

<400> SEQUENCE: 48
atgaaacaag attcacagga catgacagta acacagctgt ccctgcccaa agggggcggt 60
gcgatcagtg gcatgggtga cactatcagc aatgcagggc cggatgggat ggcttcgctt 120
tccgtgcctt tgcctatctc tgccggtcgg gggggcgcac cgaatttatc cctgaactac 180
agtagcggag caggaaacgg gtcatttggt attggctggc aatccagtac catggctatc 240

-continued

```
agccgtcgta ctcaacatgg cgtaccgcaa tatcacggcg aagatacttt tttatgtccg    300
atgggagaag tgatggcggt tgccgtcaat cagagcgggc aacccgatgt gcgtaaaacc    360
gataaactat taggcgggca actgcctgtt acttataccg ttacgcgtca tcagcccaga    420
aatattcagc acttcagcaa acttgaatac tggcagcccc caacggatgt ggaaaccacg    480
cctttttggt taatgtattc acccgatgga caaattcaca ttttcggaaa aactgagcag    540
gctcagatcg ctaacccggc agaggtttca cagattgccc aatggctttt ggaagaaacc    600
gtaacaccag cgggagaaca catttattac cagtatcggg cagaagacga tatcggttgt    660
gatgacagcg aaaaaaatgc ccaccctaat gccagtgctc aacgttattt gactcaggtg    720
aactacggca atattacacc tgaatccagc ctgcttgtgc tgaagaatac gccaccggcg    780
gataacgaat ggctattcca tttggttttt gattatggtg aacgagcgca ggaaataaac    840
acggttcctc ctttcaaagc accttcaaac aactggaaaa tacggccaga ccgtttctcc    900
cgctttgaat atggttttga ggtgcgaacc cgccgcctgt gtcaacaaat tctgatgttc    960
catcgcctga aatcccttgc aggagaacag attgacggag aagaaatccc tgccttggtt   1020
gcccgtctgc ttctcagtta tgacctgaac gacagcgtga caacccttac cgccattcgg   1080
caaatggcgt atgaaactga cgcaacctta atcgctttac cgccactgga gtttgactat   1140
cagccctttg aggcaaaagt cacgcagaaa tggcaggaaa tgcctcaatt ggccggattg   1200
aatgcccaac aaccttacca actcgtcgat ctctatggtg aaggtatctc cggcatcttg   1260
tatcaggaca gacccggagc atggtggtat caggcaccga tccgtcagaa aaacgttgaa   1320
gatattaacg ctgtcaccta tagcccaata aaccccttac ctaagatccc cagccagcag   1380
gacagagcaa cgttgatgga tatcgacggt gatggacatc tggattgggt gatcgctggc   1440
gcaggtattc aggggcggta cagtatgcag ccgaatggag agtggacaca ctttattccc   1500
atttctgcac tgccaacaga atattttcat ccacaggcac aactggcgga tctggtgggg   1560
gccgggttat ctgatttagc gctgattggc cccagaagtg tgcgtttata tgccaacgac   1620
cgaggaaact ggaaagcggg tattaatgtt atgccacctg atggtgtgaa tttgccgata   1680
tttggtggtg atgccagcag tctggtcgca ttttctgaca tgttgggatc gggacagcag   1740
catttggtgg aaattgccgc tcagagcgtc aaatgctggc cgaatctagg acatggccgt   1800
tttggtgcgg ctattttgct gccggggttt agccagccga atggaacatt caatgctaac   1860
caagtttttc tggcagatat cgatggttcc ggcaccgccg acatcatcta tgcacacagt   1920
acgtatctgg atatttacct gaacgaaagc ggcaaccgtt tcagtgcacc cgttcggctt   1980
aatttgccgg aaggggtgat gtttgacaat acctgtcagt tacaggtgtc ggatattcaa   2040
ggattgggcg ctgccagcat tgtactgacc gtacctcata tgacaccgcg ccattggcgt   2100
tatgatttta ctcacaataa accttggctg ctcaatgtca tcaacaacaa tcgtggcgca   2160
gaaaccacgt tgttttaccg tagttctgcc caattctggc tggatgaaaa aagtcagatc   2220
gaagagctgg gaaaatttgc agcgagttat ctgcctttcc ccatacattt gttgtggcgc   2280
aatgaggcgc tggatgaaat tactggtaat cgactgacta aggtcatgaa ttatgcccac   2340
ggtgcatggg atggcagaga gagagaattt tgcggatttg gccgtgtaac gcaaattgat   2400
accgacgaat ttgccaaggg aaccacagag aaagcgccgg atgaaaatat ctatccttcc   2460
cgtagcataa gctggtttgc cacgggttta ccagaagtgg attctcaact tccggcagaa   2520
tactggcgtg gtgacgatca ggcatttgcc ggctttacac cgcgcttcac tcgttatgaa   2580
aaaggtaatg cggggcaaga ggggcaggat accccgatta aagaaccgac cgaaacagaa   2640
```

-continued

```
gcgtattggc ttaaccgcgc catgaaaggc caattactgc gcagtgaagt ctatggtgac   2700

gacaaaacag aaaaagctaa aattccgtac accgtcacag aagctcgctg tcaggtcaga   2760

ttaattccca gcaatgacga agccgcgccg tcgtcttgga cgtcgatcat tgaaaaccgc   2820

agttatcact atgagcgtat cgtcgtcgat ccgagttgca aacaacaggt cgtgctcaag   2880

gcggatgaat atggcttccc actggcaaaa gtagatatcg cctatccacg gcgcaataaa   2940

ccggcacaga acccttatcc ggattcgtta ccggatactc tgttcgccga tagctatgac   3000

gaccagcaaa aacagttata tctgacaaaa cagcagcaga gctattacca cctgacccag   3060

caggatgatt gggttctggg tttgacggat agccgataca gcgaagttta tcattatgcg   3120

caaactgacg ctcaaagtga catccccaag gcagggctga tattggaaga cctgctgaaa   3180

gttgacggcc tgataggtaa agacaagact tttatctatt tagggcagca gcgagtggct   3240

tatgtgggag gagatgcaga aaaaccgaca cgtcaggtgc gggtggctta tacagaaacc   3300

gctgcttttg atgacaatgc gctgcacgcc tttgatggcg tgattgcccc tgatgaactg   3360

acgcaacagt tgctggcggg tggatacctg ctcgtgccgc agatttctga tgtggcaggc   3420

agtagtgaaa aggtatgggt agctcggcag ggatacaccg aatacggcag tgctgctcaa   3480

ttctaccggc cactcatcca gcgcaaaagc ttgctgaccg gaaaatatac ccttagttgg   3540

gatacgcact attgtgtggt ggtaaaaacc gaagatggtg cgggaatgac cacgcaagcg   3600

aagtacgatt accgcttcct gcttccggcg caattgacag atatcaatga caaccagcac   3660

atcgtgacat ttaatgcatt ggggcaggtg acttccagcc gtttctgggg cacagaaaat   3720

ggcaaaataa gcggttactc gacgccggag agtaaaccgt tcacagtacc cgataccgtc   3780

gaaaaagccc ttgccttgca accgacgatc ccggtttcac agtgcaacat ttatgtgccg   3840

gatagttgga tgcggcttct gccccaacag tctctgactg gccagctaaa agagggggaa   3900

actttgtgga acgcattaca ccgggcgggt gtagtaacgg aagacggttt gatctgtgaa   3960

ctggcctatc gtcgttggat caaacgtcag gcaacgtctt caatgatggc cgtgacatta   4020

cagcaaatct tggctcagac tccacgacaa cctccgcatg ccatgacgat cacgacagat   4080

cgttatgaca gcgattctca gcagcaactt cggcagtcga tagtattgag tgatggtttt   4140

ggtcgcgtat tgcaaagcgc ccagcgtcat gaagcaggag aggcatggca gcgtgcagaa   4200

gatggttctt tggttgtcga taataccggt aaacccgttg ttgctaatac cacaacgcgc   4260

tgggcagtat ccggtcgcac agaatacgac ggcaaagggc aggcgatcag agcttacctg   4320

ccttattatc tcaatgattg gcgctatgtc agtgatgaca gcgcccggga tgacctgtac   4380

gccgataccc atttttacga tcctctgggg cgtgaatatc aggtaaaaac cgcgaaagga   4440

ttttggcgtg aaaacatgtt tatgccgtgg tttgtcgtca atgaagatga aaatgacaca   4500

gcagcacgtt taacatctta a                                               4521
```

<210> SEQ ID NO 49
<211> LENGTH: 1506
<212> TYPE: PRT
<213> ORGANISM: Xenorhabdus bovienii

<400> SEQUENCE: 49

```
Met Lys Gln Asp Ser Gln Asp Met Thr Val Thr Gln Leu Ser Leu Pro
1               5                   10                  15

Lys Gly Gly Gly Ala Ile Ser Gly Met Gly Asp Thr Ile Ser Asn Ala
            20                  25                  30

Gly Pro Asp Gly Met Ala Ser Leu Ser Val Pro Leu Pro Ile Ser Ala
        35                  40                  45
```

```
Gly Arg Gly Gly Ala Pro Asn Leu Ser Leu Asn Tyr Ser Ser Gly Ala
    50                  55                  60

Gly Asn Gly Ser Phe Gly Ile Gly Trp Gln Ser Ser Thr Met Ala Ile
65                  70                  75                  80

Ser Arg Arg Thr Gln His Gly Val Pro Gln Tyr His Gly Glu Asp Thr
                85                  90                  95

Phe Leu Cys Pro Met Gly Glu Val Met Ala Val Ala Val Asn Gln Ser
            100                 105                 110

Gly Gln Pro Asp Val Arg Lys Thr Asp Lys Leu Leu Gly Gly Gln Leu
        115                 120                 125

Pro Val Thr Tyr Thr Val Thr Arg His Gln Pro Arg Asn Ile Gln His
    130                 135                 140

Phe Ser Lys Leu Glu Tyr Trp Gln Pro Pro Thr Asp Val Glu Thr Thr
145                 150                 155                 160

Pro Phe Trp Leu Met Tyr Ser Pro Asp Gly Gln Ile His Ile Phe Gly
                165                 170                 175

Lys Thr Glu Gln Ala Gln Ile Ala Asn Pro Ala Glu Val Ser Gln Ile
            180                 185                 190

Ala Gln Trp Leu Leu Glu Glu Thr Val Thr Pro Ala Gly Glu His Ile
        195                 200                 205

Tyr Tyr Gln Tyr Arg Ala Glu Asp Asp Ile Gly Cys Asp Asp Ser Glu
    210                 215                 220

Lys Asn Ala His Pro Asn Ala Ser Ala Gln Arg Tyr Leu Thr Gln Val
225                 230                 235                 240

Asn Tyr Gly Asn Ile Thr Pro Glu Ser Ser Leu Leu Val Leu Lys Asn
                245                 250                 255

Thr Pro Pro Ala Asp Asn Glu Trp Leu Phe His Leu Val Phe Asp Tyr
            260                 265                 270

Gly Glu Arg Ala Gln Glu Ile Asn Thr Val Pro Pro Phe Lys Ala Pro
        275                 280                 285

Ser Asn Asn Trp Lys Ile Arg Pro Asp Arg Phe Ser Arg Phe Glu Tyr
    290                 295                 300

Gly Phe Glu Val Arg Thr Arg Arg Leu Cys Gln Gln Ile Leu Met Phe
305                 310                 315                 320

His Arg Leu Lys Ser Leu Ala Gly Glu Gln Ile Asp Gly Glu Glu Ile
                325                 330                 335

Pro Ala Leu Val Ala Arg Leu Leu Leu Ser Tyr Asp Leu Asn Asp Ser
            340                 345                 350

Val Thr Thr Leu Thr Ala Ile Arg Gln Met Ala Tyr Glu Thr Asp Ala
        355                 360                 365

Thr Leu Ile Ala Leu Pro Pro Leu Glu Phe Asp Tyr Gln Pro Phe Glu
    370                 375                 380

Ala Lys Val Thr Gln Lys Trp Gln Glu Met Pro Gln Leu Ala Gly Leu
385                 390                 395                 400

Asn Ala Gln Gln Pro Tyr Gln Leu Val Asp Leu Tyr Gly Glu Gly Ile
                405                 410                 415

Ser Gly Ile Leu Tyr Gln Asp Arg Pro Gly Ala Trp Trp Tyr Gln Ala
            420                 425                 430

Pro Ile Arg Gln Lys Asn Val Glu Asp Ile Asn Ala Val Thr Tyr Ser
        435                 440                 445

Pro Ile Asn Pro Leu Pro Lys Ile Pro Ser Gln Gln Asp Arg Ala Thr
    450                 455                 460

Leu Met Asp Ile Asp Gly Asp Gly His Leu Asp Trp Val Ile Ala Gly
```

465 470 475 480

Ala Gly Ile Gln Gly Arg Tyr Ser Met Gln Pro Asn Gly Glu Trp Thr
485 490 495

His Phe Ile Pro Ile Ser Ala Leu Pro Thr Glu Tyr Phe His Pro Gln
500 505 510

Ala Gln Leu Ala Asp Leu Val Gly Ala Gly Leu Ser Asp Leu Ala Leu
515 520 525

Ile Gly Pro Arg Ser Val Arg Leu Tyr Ala Asn Asp Arg Gly Asn Trp
530 535 540

Lys Ala Gly Ile Asn Val Met Pro Pro Asp Gly Val Asn Leu Pro Ile
545 550 555 560

Phe Gly Gly Asp Ala Ser Ser Leu Val Ala Phe Ser Asp Met Leu Gly
565 570 575

Ser Gly Gln Gln His Leu Val Glu Ile Ala Ala Gln Ser Val Lys Cys
580 585 590

Trp Pro Asn Leu Gly His Gly Arg Phe Gly Ala Ala Ile Leu Leu Pro
595 600 605

Gly Phe Ser Gln Pro Asn Gly Thr Phe Asn Ala Asn Gln Val Phe Leu
610 615 620

Ala Asp Ile Asp Gly Ser Gly Thr Ala Asp Ile Ile Tyr Ala His Ser
625 630 635 640

Thr Tyr Leu Asp Ile Tyr Leu Asn Glu Ser Gly Asn Arg Phe Ser Ala
645 650 655

Pro Val Arg Leu Asn Leu Pro Glu Gly Val Met Phe Asp Asn Thr Cys
660 665 670

Gln Leu Gln Val Ser Asp Ile Gln Gly Leu Gly Ala Ala Ser Ile Val
675 680 685

Leu Thr Val Pro His Met Thr Pro Arg His Trp Arg Tyr Asp Phe Thr
690 695 700

His Asn Lys Pro Trp Leu Leu Asn Val Ile Asn Asn Asn Arg Gly Ala
705 710 715 720

Glu Thr Thr Leu Phe Tyr Arg Ser Ser Ala Gln Phe Trp Leu Asp Glu
725 730 735

Lys Ser Gln Ile Glu Glu Leu Gly Lys Phe Ala Ala Ser Tyr Leu Pro
740 745 750

Phe Pro Ile His Leu Leu Trp Arg Asn Glu Ala Leu Asp Glu Ile Thr
755 760 765

Gly Asn Arg Leu Thr Lys Val Met Asn Tyr Ala His Gly Ala Trp Asp
770 775 780

Gly Arg Glu Arg Glu Phe Cys Gly Phe Gly Arg Val Thr Gln Ile Asp
785 790 795 800

Thr Asp Glu Phe Ala Lys Gly Thr Thr Glu Lys Ala Pro Asp Glu Asn
805 810 815

Ile Tyr Pro Ser Arg Ser Ile Ser Trp Phe Ala Thr Gly Leu Pro Glu
820 825 830

Val Asp Ser Gln Leu Pro Ala Glu Tyr Trp Arg Gly Asp Asp Gln Ala
835 840 845

Phe Ala Gly Phe Thr Pro Arg Phe Thr Arg Tyr Glu Lys Gly Asn Ala
850 855 860

Gly Gln Glu Gly Gln Asp Thr Pro Ile Lys Glu Pro Thr Glu Thr Glu
865 870 875 880

Ala Tyr Trp Leu Asn Arg Ala Met Lys Gly Gln Leu Leu Arg Ser Glu
885 890 895

```
Val Tyr Gly Asp Asp Lys Thr Glu Lys Ala Lys Ile Pro Tyr Thr Val
            900                 905                 910

Thr Glu Ala Arg Cys Gln Val Arg Leu Ile Pro Ser Asn Asp Glu Ala
        915                 920                 925

Ala Pro Ser Ser Trp Thr Ser Ile Ile Glu Asn Arg Ser Tyr His Tyr
    930                 935                 940

Glu Arg Ile Val Val Asp Pro Ser Cys Lys Gln Gln Val Val Leu Lys
945                 950                 955                 960

Ala Asp Glu Tyr Gly Phe Pro Leu Ala Lys Val Asp Ile Ala Tyr Pro
                965                 970                 975

Arg Arg Asn Lys Pro Ala Gln Asn Pro Tyr Pro Asp Ser Leu Pro Asp
            980                 985                 990

Thr Leu Phe Ala Asp Ser Tyr Asp  Asp Gln Gln Lys Gln  Leu Tyr Leu
        995                 1000                1005

Thr Lys  Gln Gln Gln Ser Tyr  Tyr His Leu Thr Gln  Gln Asp Asp
    1010                 1015                 1020

Trp Val  Leu Gly Leu Thr Asp  Ser Arg Tyr Ser Glu  Val Tyr His
    1025                 1030                 1035

Tyr Ala  Gln Thr Asp Ala Gln  Ser Asp Ile Pro Lys  Ala Gly Leu
    1040                 1045                 1050

Ile Leu  Glu Asp Leu Leu Lys  Val Asp Gly Leu Ile  Gly Lys Asp
    1055                 1060                 1065

Lys Thr  Phe Ile Tyr Leu Gly  Gln Gln Arg Val Ala  Tyr Val Gly
    1070                 1075                 1080

Gly Asp  Ala Glu Lys Pro Thr  Arg Gln Val Arg Val  Ala Tyr Thr
    1085                 1090                 1095

Glu Thr  Ala Ala Phe Asp Asp  Asn Ala Leu His Ala  Phe Asp Gly
    1100                 1105                 1110

Val Ile  Ala Pro Asp Glu Leu  Thr Gln Gln Leu Leu  Ala Gly Gly
    1115                 1120                 1125

Tyr Leu  Leu Val Pro Gln Ile  Ser Asp Val Ala Gly  Ser Ser Glu
    1130                 1135                 1140

Lys Val  Trp Val Ala Arg Gln  Gly Tyr Thr Glu Tyr  Gly Ser Ala
    1145                 1150                 1155

Ala Gln  Phe Tyr Arg Pro Leu  Ile Gln Arg Lys Ser  Leu Leu Thr
    1160                 1165                 1170

Gly Lys  Tyr Thr Leu Ser Trp  Asp Thr His Tyr Cys  Val Val Val
    1175                 1180                 1185

Lys Thr  Glu Asp Gly Ala Gly  Met Thr Thr Gln Ala  Lys Tyr Asp
    1190                 1195                 1200

Tyr Arg  Phe Leu Leu Pro Ala  Gln Leu Thr Asp Ile  Asn Asp Asn
    1205                 1210                 1215

Gln His  Ile Val Thr Phe Asn  Ala Leu Gly Gln Val  Thr Ser Ser
    1220                 1225                 1230

Arg Phe  Trp Gly Thr Glu Asn  Gly Lys Ile Ser Gly  Tyr Ser Thr
    1235                 1240                 1245

Pro Glu  Ser Lys Pro Phe Thr  Val Pro Asp Thr Val  Glu Lys Ala
    1250                 1255                 1260

Leu Ala  Leu Gln Pro Thr Ile  Pro Val Ser Gln Cys  Asn Ile Tyr
    1265                 1270                 1275

Val Pro  Asp Ser Trp Met Arg  Leu Leu Pro Gln Gln  Ser Leu Thr
    1280                 1285                 1290

Gly Gln  Leu Lys Glu Gly Glu  Thr Leu Trp Asn Ala  Leu His Arg
    1295                 1300                 1305
```

```
Ala Gly Val Val Thr Glu Asp Gly Leu Ile Cys Glu Leu Ala Tyr
    1310                1315                1320

Arg Arg Trp Ile Lys Arg Gln Ala Thr Ser Ser Met Met Ala Val
    1325                1330                1335

Thr Leu Gln Gln Ile Leu Ala Gln Thr Pro Arg Gln Pro Pro His
    1340                1345                1350

Ala Met Thr Ile Thr Thr Asp Arg Tyr Asp Ser Asp Ser Gln Gln
    1355                1360                1365

Gln Leu Arg Gln Ser Ile Val Leu Ser Asp Gly Phe Gly Arg Val
    1370                1375                1380

Leu Gln Ser Ala Gln Arg His Glu Ala Gly Glu Ala Trp Gln Arg
    1385                1390                1395

Ala Glu Asp Gly Ser Leu Val Val Asp Asn Thr Gly Lys Pro Val
    1400                1405                1410

Val Ala Asn Thr Thr Thr Arg Trp Ala Val Ser Gly Arg Thr Glu
    1415                1420                1425

Tyr Asp Gly Lys Gly Gln Ala Ile Arg Ala Tyr Leu Pro Tyr Tyr
    1430                1435                1440

Leu Asn Asp Trp Arg Tyr Val Ser Asp Asp Ser Ala Arg Asp Asp
    1445                1450                1455

Leu Tyr Ala Asp Thr His Phe Tyr Asp Pro Leu Gly Arg Glu Tyr
    1460                1465                1470

Gln Val Lys Thr Ala Lys Gly Phe Trp Arg Glu Asn Met Phe Met
    1475                1480                1485

Pro Trp Phe Val Val Asn Glu Asp Glu Asn Asp Thr Ala Ala Arg
    1490                1495                1500

Leu Thr Ser
    1505


<210> SEQ ID NO 50
<211> LENGTH: 2889
<212> TYPE: DNA
<213> ORGANISM: Xenorhabdus bovienii

<400> SEQUENCE: 50

atgaatgttt ttaatccaac tttatatgcc ggtacaccga ctgtcaccgt catggacaat     60

cgagggctgt cagtgcggga tattgcttat caccgtacaa cagcaggaga gcaggctgac    120

actcgcatca cccgccatca atacagtccc cataattttt taatcgagag cattgatcca    180

cgccttttg atttgcaatc tcagagcacc ataaaaccta atttcaccta ctgtcctgcc    240

ttgaagggtg atgtcctacg gacagagagt gtggatgccg gacaaactgt cattttgagt    300

gacatcgaag gtcgtccgtt actgaatatc agtgcgatgg gtgtcgtcaa acactggcaa    360

tatgaagaga gtacattgcc ggggcgcttg ctcgctgtca gtgaacggaa gaatgaggct    420

tcaacacccc aaattattga acggtttatt tggtcgggaa atagcccatc agaaaaagat    480

cacaatttgg cgggaaaata tcttcgtcat tatgataccg ccggattaaa ccagcttaat    540

gctgtgtctc tgaccagcgt ggatctctca caatcccgtc agttattgca ggatgatgtc    600

acagcagatt ggagcggaag tgacgaatcc cagtggaaga cgcgactgag taacgacata    660

ttcacaaccg aaatcaccgc tgatgcggtt ggcaatttct tgactcagaa tgatgccaaa    720

agcaaccagc aacgattgtc ctatgatgtg gcagggcagt taaaggcaag ctggctgacg    780

ataaaaggcc agaatgagca ggtgatagtt aactccctga cttactccgc cgcagggcag    840

aaactgcgtg aagagcaggg taacggcgtt gtcactgaat actcctatga agcacaaacc    900
```

-continued

```
tggcgtttga taggtgtaac ggcttaccgt cagtcagata aaaaaagatt gcaggatctt    960
gtctataact atgatccggt cggtaatctc ctgaatattc gcaataatgc agaggcaacc   1020
cgtttctggc gtaatcagat agtagaacca gagaaccact atgcttatga ctcgctttat   1080
caactcatca gtgctagtgg tcgagaaatc gccagtatcg gtcagcaggg cagccggctg   1140
cctgtaccga ttattcctct tcctgccaat gacgatgttt atactcgcta cacccgcaca   1200
tatcactatg atcgcggtgg aaatctctgc cagatccggc attgcgctcc tgctacagat   1260
aataagtaca ccacaaagat caccgtatcg aatcgtagta atcgtgcagt atgggatacc   1320
ttgaccacag atcccgccaa agtggatacc ctgtttgatc atggagggca tcaacttcaa   1380
ctccagtcag gccagacttt atgttggaac tatcggggtg aactacagca aataacaaag   1440
atacagcgtg acgaaaaacc cgcagataaa gagcggtatc gctatggtgt tggggctgcg   1500
cgggtcgtga aatcagcac acagcaggcg gggggaagca gccatgtgca gcgtgttgtt   1560
tatctgccgg ggttggaact acgcacaact cagcatgatg cgacattaat cgaagactta   1620
caggtgatta tcatgggtga agcaggacgt gctcaggtac gcgtacttca ttgggaaata   1680
ccaccaccgg ataatcttaa caatgactca ctgcgttaca gctacgatag tttgatgggt   1740
tccagtcagc ttgaattgga tggagcaggg cagattatta cgcaggaaga atactacccc   1800
tatggaggta cagcaatatg ggcggcaaga aaccagaccg aagccaatta caaaaccatt   1860
cgctactccg gcaaagagcg tgatgcgacg gggctttatt actacgggca ccgttattat   1920
cagccgtggc tagggcgctg gttgagcgca gatcccgccg gaaccgtgga cggactgaat   1980
ctatatcgaa tggtgaggaa taacccgatt acttaccggg atgcagatgg gcttgcgccg   2040
ataggcgata agatcagcga agggatttat gagcctgagt tgcgagttgg tcttgaacga   2100
gatgacccaa atgtcagaga ttatgaccgg gtttatcctg atacggccaa gacagagatg   2160
atcgaagcaa ctgcgaccac aattgctccc agtcaaatgt tatcggcgca tgcttttgca   2220
tctgtaccta tattgacaga tttgtttaat cctcaaacag caaggctttc tcaaaagaca   2280
acggatattg tattaaacac acaaggtgga ggcgatttaa tctttactgg catgaatatt   2340
aaaggtaagg gaaaagaatt taatgcatta aaaatcgttg atacttatgg cggagaaatg   2400
cctgatagca aaaccgctat ttcagcatat tggcttccgc aaggtgggta tactgatatt   2460
ccgatacatc cgactggaat acaaaagtat ttgtttacgc ctgcgtttag tggttgcact   2520
ctggcagtag ataagcttaa cgaaaataca ttacgggcgt atcacgtcga aggaagtaag   2580
gaagatgctc aatataataa tttagcagtt gcagcgcacg gagagggttt ggtcatggct   2640
atggaatttc ctgactatgg atttcataca gacaaaacag ggcaaagact aaggaacaca   2700
cagggatttg cgtttatgtc ctacaatcaa tcccagaaaa aatgggaaat tcattatcaa   2760
aggcaagcat tgacatcaaa caccggtatc atgaatgtta gtgctaaaaa caagattcga   2820
ttgaatgccc ccagtcatgt aaaaaatagc tcaatcaaag gaactgaaat aatgacgaca   2880
catttttaa                                                           2889
```

```
<210> SEQ ID NO 51
<211> LENGTH: 962
<212> TYPE: PRT
<213> ORGANISM: Xenorhabdus bovienii

<400> SEQUENCE: 51

Met Asn Val Phe Asn Pro Thr Leu Tyr Ala Gly Thr Pro Thr Val Thr
1               5                   10                  15
```

```
Val Met Asp Asn Arg Gly Leu Ser Val Arg Asp Ile Ala Tyr His Arg
            20                  25                  30

Thr Thr Ala Gly Glu Gln Ala Asp Thr Arg Ile Thr Arg His Gln Tyr
        35                  40                  45

Ser Pro His Asn Phe Leu Ile Glu Ser Ile Asp Pro Arg Leu Phe Asp
    50                  55                  60

Leu Gln Ser Gln Ser Thr Ile Lys Pro Asn Phe Thr Tyr Cys Pro Ala
65                  70                  75                  80

Leu Lys Gly Asp Val Leu Arg Thr Glu Ser Val Asp Ala Gly Gln Thr
                85                  90                  95

Val Ile Leu Ser Asp Ile Glu Gly Arg Pro Leu Leu Asn Ile Ser Ala
            100                 105                 110

Met Gly Val Val Lys His Trp Gln Tyr Glu Glu Ser Thr Leu Pro Gly
        115                 120                 125

Arg Leu Leu Ala Val Ser Glu Arg Lys Asn Glu Ala Ser Thr Pro Gln
    130                 135                 140

Ile Ile Glu Arg Phe Ile Trp Ser Gly Asn Ser Pro Ser Glu Lys Asp
145                 150                 155                 160

His Asn Leu Ala Gly Lys Tyr Leu Arg His Tyr Asp Thr Ala Gly Leu
                165                 170                 175

Asn Gln Leu Asn Ala Val Ser Leu Thr Ser Val Asp Leu Ser Gln Ser
            180                 185                 190

Arg Gln Leu Leu Gln Asp Asp Val Thr Ala Asp Trp Ser Gly Ser Asp
        195                 200                 205

Glu Ser Gln Trp Lys Thr Arg Leu Ser Asn Asp Ile Phe Thr Thr Glu
    210                 215                 220

Ile Thr Ala Asp Ala Val Gly Asn Phe Leu Thr Gln Asn Asp Ala Lys
225                 230                 235                 240

Ser Asn Gln Gln Arg Leu Ser Tyr Asp Val Ala Gly Gln Leu Lys Ala
                245                 250                 255

Ser Trp Leu Thr Ile Lys Gly Gln Asn Glu Gln Val Ile Val Asn Ser
            260                 265                 270

Leu Thr Tyr Ser Ala Ala Gly Gln Lys Leu Arg Glu Glu Gln Gly Asn
        275                 280                 285

Gly Val Val Thr Glu Tyr Ser Tyr Glu Ala Gln Thr Trp Arg Leu Ile
    290                 295                 300

Gly Val Thr Ala Tyr Arg Gln Ser Asp Lys Lys Arg Leu Gln Asp Leu
305                 310                 315                 320

Val Tyr Asn Tyr Asp Pro Val Gly Asn Leu Leu Asn Ile Arg Asn Asn
                325                 330                 335

Ala Glu Ala Thr Arg Phe Trp Arg Asn Gln Ile Val Glu Pro Glu Asn
            340                 345                 350

His Tyr Ala Tyr Asp Ser Leu Tyr Gln Leu Ile Ser Ala Ser Gly Arg
        355                 360                 365

Glu Ile Ala Ser Ile Gly Gln Gln Gly Ser Arg Leu Pro Val Pro Ile
    370                 375                 380

Ile Pro Leu Pro Ala Asn Asp Asp Val Tyr Thr Arg Tyr Thr Arg Thr
385                 390                 395                 400

Tyr His Tyr Asp Arg Gly Gly Asn Leu Cys Gln Ile Arg His Cys Ala
                405                 410                 415

Pro Ala Thr Asp Asn Lys Tyr Thr Thr Lys Ile Thr Val Ser Asn Arg
            420                 425                 430

Ser Asn Arg Ala Val Trp Asp Thr Leu Thr Thr Asp Pro Ala Lys Val
        435                 440                 445
```

```
Asp Thr Leu Phe Asp His Gly Gly His Gln Leu Gln Leu Gln Ser Gly
    450                 455                 460

Gln Thr Leu Cys Trp Asn Tyr Arg Gly Glu Leu Gln Gln Ile Thr Lys
465                 470                 475                 480

Ile Gln Arg Asp Glu Lys Pro Ala Asp Lys Glu Arg Tyr Arg Tyr Gly
                485                 490                 495

Val Gly Ala Ala Arg Val Val Lys Ile Ser Thr Gln Gln Ala Gly Gly
            500                 505                 510

Ser Ser His Val Gln Arg Val Val Tyr Leu Pro Gly Leu Glu Leu Arg
        515                 520                 525

Thr Thr Gln His Asp Ala Thr Leu Ile Glu Asp Leu Gln Val Ile Ile
    530                 535                 540

Met Gly Glu Ala Gly Arg Ala Gln Val Arg Val Leu His Trp Glu Ile
545                 550                 555                 560

Pro Pro Pro Asp Asn Leu Asn Asn Asp Ser Leu Arg Tyr Ser Tyr Asp
                565                 570                 575

Ser Leu Met Gly Ser Ser Gln Leu Glu Leu Asp Gly Ala Gly Gln Ile
            580                 585                 590

Ile Thr Gln Glu Glu Tyr Tyr Pro Tyr Gly Gly Thr Ala Ile Trp Ala
        595                 600                 605

Ala Arg Asn Gln Thr Glu Ala Asn Tyr Lys Thr Ile Arg Tyr Ser Gly
    610                 615                 620

Lys Glu Arg Asp Ala Thr Gly Leu Tyr Tyr Tyr Gly His Arg Tyr Tyr
625                 630                 635                 640

Gln Pro Trp Leu Gly Arg Trp Leu Ser Ala Asp Pro Ala Gly Thr Val
                645                 650                 655

Asp Gly Leu Asn Leu Tyr Arg Met Val Arg Asn Asn Pro Ile Thr Tyr
            660                 665                 670

Arg Asp Ala Asp Gly Leu Ala Pro Ile Gly Asp Lys Ile Ser Glu Gly
        675                 680                 685

Ile Tyr Glu Pro Glu Leu Arg Val Gly Leu Glu Arg Asp Asp Pro Asn
    690                 695                 700

Val Arg Asp Tyr Asp Arg Val Tyr Pro Asp Thr Ala Lys Thr Glu Met
705                 710                 715                 720

Ile Glu Ala Thr Ala Thr Thr Ile Ala Pro Ser Gln Met Leu Ser Ala
                725                 730                 735

His Ala Phe Ala Ser Val Pro Ile Leu Thr Asp Leu Phe Asn Pro Gln
            740                 745                 750

Thr Ala Arg Leu Ser Gln Lys Thr Thr Asp Ile Val Leu Asn Thr Gln
        755                 760                 765

Gly Gly Gly Asp Leu Ile Phe Thr Gly Met Asn Ile Lys Gly Lys Gly
    770                 775                 780

Lys Glu Phe Asn Ala Leu Lys Ile Val Asp Thr Tyr Gly Gly Glu Met
785                 790                 795                 800

Pro Asp Ser Lys Thr Ala Ile Ser Ala Tyr Trp Leu Pro Gln Gly Gly
                805                 810                 815

Tyr Thr Asp Ile Pro Ile His Pro Thr Gly Ile Gln Lys Tyr Leu Phe
            820                 825                 830

Thr Pro Ala Phe Ser Gly Cys Thr Leu Ala Val Asp Lys Leu Asn Glu
        835                 840                 845

Asn Thr Leu Arg Ala Tyr His Val Glu Gly Ser Lys Glu Asp Ala Gln
    850                 855                 860

Tyr Asn Asn Leu Ala Val Ala Ala His Gly Glu Gly Leu Val Met Ala
```

865 870 875 880

Met Glu Phe Pro Asp Tyr Gly Phe His Thr Asp Lys Thr Gly Gln Arg
885 890 895

Leu Arg Asn Thr Gln Gly Phe Ala Phe Met Ser Tyr Asn Gln Ser Gln
900 905 910

Lys Lys Trp Glu Ile His Tyr Gln Arg Gln Ala Leu Thr Ser Asn Thr
915 920 925

Gly Ile Met Asn Val Ser Ala Lys Asn Lys Ile Arg Leu Asn Ala Pro
930 935 940

Ser His Val Lys Asn Ser Ser Ile Lys Gly Thr Glu Ile Met Thr Thr
945 950 955 960

His Phe

<210> SEQ ID NO 52
<211> LENGTH: 4595
<212> TYPE: DNA
<213> ORGANISM: Xenorhabdus bovienii

<400> SEQUENCE: 52
tctagaacta gtgtcgacta aagaagaagg agatatacca tgaaacaaga cagccaggac 60
atgacagtaa cacagctgtc cctgcccaaa gggggcggtg cgatcagtgg catgggtgac 120
actatcagca atgcagggcc ggatgggatg gcttcgcttt ccgtgccttt gcctatctct 180
gccggtcggg ggggcgcacc gaatttatcc ctgaactaca gtagcggagc aggaaacggg 240
tcatttggta ttggctggca atccagtacc atggctatca gccgtcgtac tcaacatggc 300
gtaccgcaat atcacggcga agatactttt ttatgtccga tgggagaagt gatggcggtt 360
gccgtcaatc agagcgggca acccgatgtg cgtaaaaccg ataaactatt aggcgggcaa 420
ctgcctgtta cttataccgt tacgcgtcat cagcccagaa atattcagca cttcagcaaa 480
cttgaatact ggcagccccc aacggatgtg gaaaccacgc ctttttggtt aatgtattca 540
cccgatggac aaattcacat tttcggaaaa actgagcagg ctcagatcgc taacccggca 600
gaggtttcac agattgccca atggcttttg gaagaaaccg taacaccagc gggagaacac 660
atttattacc agtatcgggc agaagacgat atcggttgtg atgacagcga aaaaaatgcc 720
caccctaatg ccagtgctca acgttatttg actcaggtga actacggcaa tattacacct 780
gaatccagcc tgcttgtgct gaagaatacg ccaccggcgg ataacgaatg gctattccat 840
ttggtttttg attatggtga acgagcgcag gaaataaaca cggttcctcc tttcaaagca 900
ccttcaaaca actggaaaat acggccagac cgtttctccc gctttgaata tggttttgag 960
gtgcgaaccc gccgcctgtg tcaacaaatt ctgatgttcc atcgcctgaa atcccttgca 1020
ggagaacaga ttgacggaga agaaatccct gccttggttg cccgtctgct tctcagttat 1080
gacctgaacg acagcgtgac aacccttacc gccattcggc aaatggcgta tgaaactgac 1140
gcaaccttaa tcgctttacc gccactggag tttgactatc agccctttga ggcaaaagtc 1200
acgcagaaat ggcaggaaat gcctcaattg gccggattga atgcccaaca accttaccaa 1260
ctcgtcgatc tctatggtga aggtatctcc ggcatcttgt atcaggacag acccggagca 1320
tggtggtatc aggcaccgat ccgtcagaaa aacgttgaag atattaacgc tgtcacctat 1380
agcccaataa accccttacc taagatcccc agccagcagg acagagcaac gttgatggat 1440
atcgacggtg atggacatct ggattgggtg atcgctggcg caggtattca ggggcggtac 1500
agtatgcagc cgaatggaga gtggacacac tttattccca tttctgcact gccaacagaa 1560
tattttcatc cacaggcaca actggcggat ctggtggggg ccgggttatc tgatttagcg 1620

```
ctgattggcc ccagaagtgt gcgtttatat gccaacgacc gaggaaactg gaaagcgggt   1680
attaatgtta tgccacctga tggtgtgaat ttgccgatat ttggtggtga tgccagcagt   1740
ctggtcgcat tttctgacat gttgggatcg ggacagcagc atttggtgga aattgccgct   1800
cagagcgtca aatgctggcc gaatctagga catggccgtt ttggtgcggc tattttgctg   1860
ccggggttta gccagccgaa tggaacattc aatgctaacc aagtttttct ggcagatatc   1920
gatggttccg gcaccgccga catcatctat gcacacagta cgtatctgga tatttacctg   1980
aacgaaagcg gcaaccgttt cagtgcaccc gttcggctta atttgccgga aggggtgatg   2040
tttgacaata cctgtcagtt acaggtgtcg gatattcaag gattgggcgc tgccagcatt   2100
gtactgaccg tacctcatat gacaccgcgc cattggcgtt atgattttac tcacaataaa   2160
ccttggctgc tcaatgtcat caacaacaat cgtggcgcag aaaccacgtt gttttaccgt   2220
agttctgccc aattctggct ggatgaaaaa agtcagatcg aagagctggg aaaatttgca   2280
gcgagttatc tgcctttccc catacatttg ttgtggcgca atgaggcgct ggatgaaatt   2340
actggtaatc gactgactaa ggtcatgaat tatgcccacg gtgcatggga tggcagagag   2400
agagaatttt gcggatttgg ccgtgtaacg caaattgata ccgacgaatt tgccaaggga   2460
accacagaga aagcgccgga tgaaaatatc tatccttccc gtagcataag ctggtttgcc   2520
acgggtttac cagaagtgga ttctcaactt ccggcagaat actggcgtgg tgacgatcag   2580
gcatttgccg gctttacacc gcgcttcact cgttatgaaa aaggtaatgc ggggcaagag   2640
gggcaggata ccccgattaa agaaccgacc gaaacagaag cgtattggct taaccgcgcc   2700
atgaaaggcc aattactgcg cagtgaagtc tatggtgacg acaaaaacaga aaaagctaaa   2760
attccgtaca ccgtcacaga agctcgctgt caggtcagat taattcccag caatgacgaa   2820
gccgcgccgt cgtcttggac gtcgatcatt gaaaaccgca gttatcacta tgagcgtatc   2880
gtcgtcgatc cgagttgcaa acaacaggtc gtgctcaagg cggatgaata tggcttccca   2940
ctggcaaaag tagatatcgc ctatccacgg cgcaataaac cggcacagaa cccttatccg   3000
gattcgttac cggatactct gttcgccgat agctatgacg accagcaaaa acagttatat   3060
ctgacaaaac agcagcagag ctattaccac ctgacccagc aggatgattg ggttctgggt   3120
ttgacggata gccgatacag cgaagtttat cattatgcgc aaactgacgc tcaaagtgac   3180
atccccaagg cagggctgat attggaagac ctgctgaaag ttgacggcct gataggtaaa   3240
gacaagactt ttatctattt agggcagcag cgagtggctt atgtgggagg agatgcagaa   3300
aaaccgacac gtcaggtgcg ggtggcttat acagaaaccg ctgcttttga tgacaatgcg   3360
ctgcacgcct ttgatggcgt gattgcccct gatgaactga cgcaacagtt gctggcgggt   3420
ggatacctgc tcgtgccgca gatttctgat gtggcaggca gtagtgaaaa ggtatgggta   3480
gctcggcagg gatacaccga atacggcagt gctgctcaat tctaccggcc actcatccag   3540
cgcaaaagct tgctgaccgg aaaatatacc cttagttggg atacgcacta ttgtgtggtg   3600
gtaaaaaccg aagatggtgc gggaatgacc acgcaagcga agtacgatta ccgcttcctg   3660
cttccggcgc aattgacaga tatcaatgac aaccagcaca tcgtgacatt taatgcattg   3720
gggcaggtga cttccagccg tttctggggc acagaaaatg gcaaaataag cggttactcg   3780
acgccggaga gtaaaccgtt cacagtaccc gataccgtcg aaaaagccct tgccttgcaa   3840
ccgacgatcc cggtttcaca gtgcaacatt tatgtgccgg atagttggat gcggcttctg   3900
ccccaacagt ctctgactgg ccagctaaaa gagggggaaa ctttgtggaa cgcattacac   3960
cgggcgggtg tagtaacgga agacggtttg atctgtgaac tggcctatcg tcgttggatc   4020
```

aaacgtcagg caacgtcttc aatgatggcc gtgacattac agcaaatctt ggctcagact 4080
ccacgacaac ctccgcatgc catgacgatc acgacagatc gttatgacag cgattctcag 4140
cagcaacttc ggcagtcgat agtattgagt gatggttttg gtcgcgtatt gcaaagcgcc 4200
cagcgtcatg aagcaggaga ggcatggcag cgtgcagaag atggttcttt ggttgtcgat 4260
aataccggta aacccgttgt tgctaatacc acaacgcgct gggcagtatc cggtcgcaca 4320
gaatacgacg gcaaagggca ggcgatcaga gcttacctgc cttattatct caatgattgg 4380
cgctatgtca gtgatgacag cgcccgggat gacctgtacg ccgataccca tttttacgat 4440
cctctggggc gtgaatatca ggtaaaaacc gcgaaaggat tttggcgtga aaacatgttt 4500
atgccgtggt ttgtcgtcaa tgaagatgaa aatgacacag cagcacgttt aacatcttaa 4560
ttaatgcggc cgcaggcctc tgtaagactc tcgag 4595

<210> SEQ ID NO 53
<211> LENGTH: 2947
<212> TYPE: DNA
<213> ORGANISM: Xenorhabdus bovienii

<400> SEQUENCE: 53
tctagaacta gtaggcctta aagaagagag agatatacca tgaatgtttt taatccaact 60
ttatatgccg gtacaccgac tgtcaccgtc atggacaatc gagggctgtc agtgcgggat 120
attgcttatc accgtacaac agcaggagag caggctgaca ctcgcatcac ccgccatcaa 180
tacagtcccc ataatttttt aatcgagagc attgatccac gcctttttga tttgcaatct 240
cagagcacca taaaacctaa tttcacctac tgtcctgcct tgaagggtga tgtcctacgg 300
acagagagtg tggatgccgg acaaactgtc attttgagtg acatcgaagg tcgtccgtta 360
ctgaatatca gtgcgatggg tgtcgtcaaa cactggcaat atgaagagag tacattgccg 420
gggcgcttgc tcgctgtcag tgaacggaag aatgaggctt caacacccca aattattgaa 480
cggtttattt ggtcgggaaa tagcccatca gaaaaagatc acaatttggc gggaaaatat 540
cttcgtcatt atgataccgc cggattaaac cagcttaatg ctgtgtctct gaccagcgtg 600
gatctctcac aatcccgtca gttattgcag gatgatgtca cagcagattg gagcggaagt 660
gacgaatccc agtggaagac gcgactgagt aacgacatat tcacaaccga aatcaccgct 720
gatgcggttg gcaatttctt gactcagaat gatgccaaaa gcaaccagca acgattgtcc 780
tatgatgtgg cagggcagtt aaaggcaagc tggctgacga taaaaggcca gaatgagcag 840
gtgatagtta actccctgac ttactccgcc gcagggcaga aactgcgtga agagcagggt 900
aacggcgttg tcactgaata ctcctatgaa gcacaaacct ggcgtttgat aggtgtaacg 960
gcttaccgtc agtcagataa aaaaagattg caggatcttg tctataacta tgatccggtc 1020
ggtaatctcc tgaatattcg caataatgca gaggcaaccc gtttctggcg taatcagata 1080
gtagaaccag agaaccacta tgcttatgac tcgctttatc aactcatcag tgctagtggt 1140
cgagaaatcg ccagtatcgg tcagcagggc agccggctgc ctgtaccgat tattcctctt 1200
cctgccaatg acgatgttta tactcgctac acccgcacat atcactatga tcgcggtgga 1260
aatctctgcc agatccggca ttgcgctcct gctacagata ataagtacac cacaaagatc 1320
accgtatcga atcgtagtaa tcgtgcagta tgggatacct tgaccacaga tcccgccaaa 1380
gtggataccc tgtttgatca tggagggcat caacttcaac tccagtcagg ccagacttta 1440
tgttggaact atcggggtga actacagcaa ataacaaaga tacagcgtga cgaaaaaccc 1500
gcagataaag agcggtatcg ctatggtgtt ggggctgcgc gggtcgtgaa aatcagcaca 1560

-continued

```
cagcaggcgg ggggaagcag ccatgtgcag cgtgttgttt atctgccggg gttggaacta   1620
cgcacaactc agcatgatgc gacattaatc gaagacttac aggtgattat catgggtgaa   1680
gcaggacgtg ctcaggtacg cgtacttcat tgggaaatac caccaccgga taatcttaac   1740
aatgactcac tgcgttacag ctacgatagt ttgatgggtt ccagtcagct tgaattggat   1800
ggagcagggc agattattac gcaggaagaa tactacccct atggaggtac agcaatatgg   1860
gcggcaagaa accagaccga agccaattac aaaaccattc gctactccgg caaagagcgt   1920
gatgcgacgg ggctttatta ctacgggcac cgttattatc agccgtggct agggcgctgg   1980
ttgagcgcag atcccgccgg aaccgtggac ggactgaatc tatatcgaat ggtgaggaat   2040
aacccgatta cttaccggga tgcagatggg cttgcgccga taggcgataa gatcagcgaa   2100
gggatttatg agcctgagtt gcgagttggt cttgaacgag atgacccaaa tgtcagagat   2160
tatgaccggg tttatcctga tacggccaag acagagatga tcgaagcaac tgcgaccaca   2220
attgctccca gtcaaatgtt atcggcgcat gcttttgcat ctgtacctat attgacagat   2280
ttgtttaatc ctcaaacagc aaggctttct caaaagacaa cggatattgt attaaacaca   2340
caaggtggag gcgatttaat ctttactggc atgaatatta aaggtaaggg aaaagaattt   2400
aatgcattaa aaatcgttga tacttatggc ggagaaatgc ctgatagcaa aaccgctatt   2460
tcagcatatt ggcttccgca aggtgggtat actgatattc cgatacatcc gactggaata   2520
caaaagtatt tgtttacgcc tgcgtttagt ggttgcactc tggcagtaga taagcttaac   2580
gaaaatacat tacgggcgta tcacgtcgaa ggaagtaagg aagatgctca atataataat   2640
ttagcagttg cagcgcacgg agagggtttg gtcatggcta tggaatttcc tgactatgga   2700
tttcatacag acaaaacagg gcaaagacta aggaacacac agggatttgc gtttatgtcc   2760
tacaatcaat cccagaaaaa atgggaaatt cattatcaaa ggcaagcatt gacatcaaac   2820
accggtatca tgaatgttag tgctaaaaac aagattcgat tgaatgcccc cagtcatgta   2880
aaaaatagct caatcaaagg aactgaaata atgacgacac atttttaatt aatgcggccg   2940
cctcgag                                                             2947
```

<210> SEQ ID NO 54
<211> LENGTH: 7508
<212> TYPE: DNA
<213> ORGANISM: Xenorhabdus bovienii

<400> SEQUENCE: 54

```
tctagaacta gtgtcgacta aagaagaagg agatatacca tgaaacaaga cagccaggac     60
atgacagtaa cacagctgtc cctgcccaaa gggggcggtg cgatcagtgg catgggtgac    120
actatcagca atgcagggcc ggatgggatg gcttcgcttt ccgtgccttt gcctatctct    180
gccggtcggg ggggcgcacc gaatttatcc ctgaactaca gtagcggagc aggaaacggg    240
tcatttggta ttggctggca atccagtacc atggctatca gccgtcgtac tcaacatggc    300
gtaccgcaat atcacggcga agatactttt ttatgtccga tgggagaagt gatggcggtt    360
gccgtcaatc agagcgggca acccgatgtg cgtaaaaccg ataaactatt aggcgggcaa    420
ctgcctgtta cttataccgt tacgcgtcat cagcccagaa atattcagca cttcagcaaa    480
cttgaatact ggcagccccc aacggatgtg gaaaccacgc ctttttggtt aatgtattca    540
cccgatggac aaattcacat tttcggaaaa actgagcagg ctcagatcgc taacccggca    600
gaggtttcac agattgccca atggcttttg gaagaaaccg taacaccagc gggagaacac    660
atttattacc agtatcgggc agaagacgat atcggttgtg atgacagcga aaaaaatgcc    720
```

-continued

```
caccctaatg ccagtgctca acgttatttg actcaggtga actacggcaa tattacacct    780
gaatccagcc tgcttgtgct gaagaatacg ccaccggcgg ataacgaatg gctattccat    840
ttggtttttg attatggtga acgagcgcag gaaataaaca cggttcctcc tttcaaagca    900
ccttcaaaca actggaaaat acggccagac cgtttctccc gctttgaata tggttttgag    960
gtgcgaaccc gccgcctgtg tcaacaaatt ctgatgttcc atcgcctgaa atcccttgca   1020
ggagaacaga ttgacggaga agaaatccct gccttggttg cccgtctgct tctcagttat   1080
gacctgaacg acagcgtgac aacccttacc gccattcggc aaatggcgta tgaaactgac   1140
gcaaccttaa tcgctttacc gccactggag tttgactatc agccctttga ggcaaaagtc   1200
acgcagaaat ggcaggaaat gcctcaattg gccggattga atgcccaaca accttaccaa   1260
ctcgtcgatc tctatggtga aggtatctcc ggcatcttgt atcaggacag acccggagca   1320
tggtggtatc aggcaccgat ccgtcagaaa aacgttgaag atattaacgc tgtcacctat   1380
agcccaataa accccttacc taagatcccc agccagcagg acagagcaac gttgatggat   1440
atcgacggtg atggacatct ggattgggtg atcgctggcg caggtattca ggggcggtac   1500
agtatgcagc cgaatggaga gtggacacac tttattccca tttctgcact gccaacagaa   1560
tattttcatc cacaggcaca actggcggat ctggtggggg ccgggttatc tgatttagcg   1620
ctgattggcc ccagaagtgt gcgtttatat gccaacgacc gaggaaactg gaaagcgggt   1680
attaatgtta tgccacctga tggtgtgaat ttgccgatat ttggtggtga tgccagcagt   1740
ctggtcgcat tttctgacat gttgggatcg ggacagcagc atttggtgga aattgccgct   1800
cagagcgtca aatgctggcc gaatctagga catggccgtt ttggtgcggc tattttgctg   1860
ccggggttta gccagccgaa tggaacattc aatgctaacc aagtttttct ggcagatatc   1920
gatggttccg gcaccgccga catcatctat gcacacagta cgtatctgga tatttacctg   1980
aacgaaagcg gcaaccgttt cagtgcaccc gttcggctta atttgccgga aggggtgatg   2040
tttgacaata cctgtcagtt acaggtgtcg gatattcaag gattgggcgc tgccagcatt   2100
gtactgaccg tacctcatat gacaccgcgc cattggcgtt atgattttac tcacaataaa   2160
ccttggctgc tcaatgtcat caacaacaat cgtggcgcag aaaccacgtt gttttaccgt   2220
agttctgccc aattctggct ggatgaaaaa agtcagatcg aagagctggg aaaatttgca   2280
gcgagttatc tgcctttccc catacatttg ttgtggcgca atgaggcgct ggatgaaatt   2340
actggtaatc gactgactaa ggtcatgaat tatgcccacg gtgcatggga tggcagagag   2400
agagaatttt gcggatttgg ccgtgtaacg caaattgata ccgacgaatt tgccaaggga   2460
accacagaga aagcgccgga tgaaaatatc tatccttccc gtagcataag ctggtttgcc   2520
acgggtttac cagaagtgga ttctcaactt ccggcagaat actggcgtgg tgacgatcag   2580
gcatttgccg gctttacacc gcgcttcact cgttatgaaa aaggtaatgc ggggcaagag   2640
gggcaggata ccccgattaa agaaccgacc gaaacagaag cgtattggct taaccgcgcc   2700
atgaaaggcc aattactgcg cagtgaagtc tatggtgacg acaaaaacaga aaaagctaaa   2760
attccgtaca ccgtcacaga agctcgctgt caggtcagat taattcccag caatgacgaa   2820
gccgcgccgt cgtcttggac gtcgatcatt gaaaaccgca gttatcacta tgagcgtatc   2880
gtcgtcgatc cgagttgcaa acaacaggtc gtgctcaagg cggatgaata tggcttccca   2940
ctggcaaaag tagatatcgc ctatccacgg cgcaataaac cggcacagaa cccttatccg   3000
gattcgttac cggatactct gttcgccgat agctatgacg accagcaaaa acagttatat   3060
ctgacaaaac agcagcagag ctattaccac ctgacccagc aggatgattg ggttctgggt   3120
```

-continued

```
ttgacggata gccgatacag cgaagtttat cattatgcgc aaactgacgc tcaaagtgac   3180
atccccaagg cagggctgat attggaagac ctgctgaaag ttgacggcct gataggtaaa   3240
gacaagactt ttatctattt agggcagcag cgagtggctt atgtgggagg agatgcagaa   3300
aaaccgacac gtcaggtgcg ggtggcttat acagaaaccg ctgcttttga tgacaatgcg   3360
ctgcacgcct ttgatggcgt gattgcccct gatgaactga cgcaacagtt gctggcgggt   3420
ggatacctgc tcgtgccgca gatttctgat gtggcaggca gtagtgaaaa ggtatgggta   3480
gctcggcagg gatacaccga atacggcagt gctgctcaat tctaccggcc actcatccag   3540
cgcaaaagct tgctgaccgg aaaatatacc cttagttggg atacgcacta ttgtgtggtg   3600
gtaaaaaccg aagatggtgc gggaatgacc acgcaagcga agtacgatta ccgcttcctg   3660
cttccggcgc aattgacaga tatcaatgac aaccagcaca tcgtgacatt taatgcattg   3720
gggcaggtga cttccagccg tttctggggc acagaaaatg gcaaaataag cggttactcg   3780
acgccggaga gtaaaccgtt cacagtaccc gataccgtcg aaaaagccct tgccttgcaa   3840
ccgacgatcc cggtttcaca gtgcaacatt tatgtgccgg atagttggat gcggcttctg   3900
ccccaacagt ctctgactgg ccagctaaaa gagggggaaa ctttgtggaa cgcattacac   3960
cgggcgggtg tagtaacgga agacggtttg atctgtgaac tggcctatcg tcgttggatc   4020
aaacgtcagg caacgtcttc aatgatggcc gtgacattac agcaaatctt ggctcagact   4080
ccacgacaac ctccgcatgc catgacgatc acgacagatc gttatgacag cgattctcag   4140
cagcaacttc ggcagtcgat agtattgagt gatggttttg gtcgcgtatt gcaaagcgcc   4200
cagcgtcatg aagcaggaga ggcatggcag cgtgcagaag atggttcttt ggttgtcgat   4260
aataccggta aacccgttgt tgctaatacc acaacgcgct gggcagtatc cggtcgcaca   4320
gaatacgacg gcaaagggca ggcgatcaga gcttacctgc cttattatct caatgattgg   4380
cgctatgtca gtgatgacag cgcccgggat gacctgtacg ccgataccca tttttacgat   4440
cctctggggc gtgaatatca ggtaaaaacc gcgaaaggat tttggcgtga aaacatgttt   4500
atgccgtggt ttgtcgtcaa tgaagatgaa aatgacacag cagcacgttt aacatcttaa   4560
ttaatgcggc cgcaggcctt aaagaagaga gagatatacc atgaatgttt ttaatccaac   4620
tttatatgcc ggtacaccga ctgtcaccgt catggacaat cgagggctgt cagtgcggga   4680
tattgcttat caccgtacaa cagcaggaga gcaggctgac actcgcatca cccgccatca   4740
atacagtccc cataattttt taatcgagag cattgatcca cgcctttttg atttgcaatc   4800
tcagagcacc ataaaaccta atttcaccta ctgtcctgcc ttgaagggtg atgtcctacg   4860
gacagagagt gtggatgccg gacaaactgt catttgagt gacatcgaag gtcgtccgtt   4920
actgaatatc agtgcgatgg gtgtcgtcaa acactggcaa tatgaagaga gtacattgcc   4980
ggggcgcttg ctcgctgtca gtgaacggaa gaatgaggct tcaacacccc aaattattga   5040
acggtttatt tggtcgggaa atagcccatc agaaaaagat cacaatttgg cgggaaaata   5100
tcttcgtcat tatgataccg ccggattaaa ccagcttaat gctgtgtctc tgaccagcgt   5160
ggatctctca caatcccgtc agttattgca ggatgatgtc acagcagatt ggagcggaag   5220
tgacgaatcc cagtggaaga cgcgactgag taacgacata ttcacaaccg aaatcaccgc   5280
tgatgcggtt ggcaatttct tgactcagaa tgatgccaaa agcaaccagc aacgattgtc   5340
ctatgatgtg gcagggcagt taaaggcaag ctggctgacg ataaaaggcc agaatgagca   5400
ggtgatagtt aactccctga cttactccgc cgcagggcag aaactgcgtg aagagcaggg   5460
taacggcgtt gtcactgaat actcctatga agcacaaacc tggcgtttga taggtgtaac   5520
```

ggcttaccgt cagtcagata aaaaaagatt gcaggatctt gtctataact atgatccggt 5580
cggtaatctc ctgaatattc gcaataatgc agaggcaacc cgtttctggc gtaatcagat 5640
agtagaacca gagaaccact atgcttatga ctcgctttat caactcatca gtgctagtgg 5700
tcgagaaatc gccagtatcg gtcagcaggg cagccggctg cctgtaccga ttattcctct 5760
tcctgccaat gacgatgttt atactcgcta cacccgcaca tatcactatg atcgcggtgg 5820
aaatctctgc cagatccggc attgcgctcc tgctacagat aataagtaca ccacaaagat 5880
caccgtatcg aatcgtagta atcgtgcagt atgggatacc ttgaccacag atcccgccaa 5940
agtggatacc ctgtttgatc atggagggca tcaacttcaa ctccagtcag gccagacttt 6000
atgttggaac tatcggggtg aactacagca aataacaaag atacagcgtg acgaaaaacc 6060
cgcagataaa gagcggtatc gctatggtgt tggggctgcg cgggtcgtga aaatcagcac 6120
acagcaggcg gggggaagca gccatgtgca gcgtgttgtt tatctgccgg ggttggaact 6180
acgcacaact cagcatgatg cgacattaat cgaagactta caggtgatta tcatgggtga 6240
agcaggacgt gctcaggtac gcgtacttca ttgggaaata ccaccaccgg ataatcttaa 6300
caatgactca ctgcgttaca gctacgatag tttgatgggt tccagtcagc ttgaattgga 6360
tggagcaggg cagattatta cgcaggaaga atactacccc tatggaggta cagcaatatg 6420
ggcggcaaga aaccagaccg aagccaatta caaaaccatt cgctactccg gcaaagagcg 6480
tgatgcgacg ggctttatt actacgggca ccgttattat cagccgtggc tagggcgctg 6540
gttgagcgca gatcccgccg gaaccgtgga cggactgaat ctatatcgaa tggtgaggaa 6600
taacccgatt acttaccggg atgcagatgg gcttgcgccg ataggcgata agatcagcga 6660
agggatttat gagcctgagt tgcgagttgg tcttgaacga gatgacccaa atgtcagaga 6720
ttatgaccgg gtttatcctg atacggccaa gacagagatg atcgaagcaa ctgcgaccac 6780
aattgctccc agtcaaatgt tatcggcgca tgcttttgca tctgtaccta tattgacaga 6840
tttgtttaat cctcaaacag caaggctttc tcaaaagaca acggatattg tattaaacac 6900
acaaggtgga ggcgatttaa tctttactgg catgaatatt aaaggtaagg gaaaagaatt 6960
taatgcatta aaaatcgttg atacttatgg cggagaaatg cctgatagca aaaccgctat 7020
ttcagcatat tggcttccgc aaggtgggta tactgatatt ccgatacatc cgactggaat 7080
acaaaagtat ttgtttacgc ctgcgtttag tggttgcact ctggcagtag ataagcttaa 7140
cgaaaataca ttacgggcgt atcacgtcga aggaagtaag gaagatgctc aatataataa 7200
tttagcagtt gcagcgcacg gagagggttt ggtcatggct atggaatttc ctgactatgg 7260
atttcataca gacaaaacag ggcaaagact aaggaacaca cagggatttg cgtttatgtc 7320
ctacaatcaa tcccagaaaa aatgggaaat tcattatcaa aggcaagcat tgacatcaaa 7380
caccggtatc atgaatgtta gtgctaaaaa caagattcga ttgaatgccc ccagtcatgt 7440
aaaaaatagc tcaatcaaag gaactgaaat aatgacgaca catttttaat taatgcggcc 7500
gcctcgag 7508

<210> SEQ ID NO 55
<211> LENGTH: 2862
<212> TYPE: DNA
<213> ORGANISM: Paenibacillus strain DAS1529

<400> SEQUENCE: 55
atgaaaatga taccgtggac tcaccattat ttgcttcacc gcctgcgcgg tgagatggag 60
gttaaaccta tgaacacaac gtccatatat aggggcacgc ctacgatttc agttgtggat 120

-continued

```
aaccggaact tggagattcg cattcttcag tataaccgta tcgcggctga agatccggca    180
gatgagtgta tcctgcggaa cacgtatacg ccgttaagct atcttggcag cagcatggat    240
ccccgtttgt tctcgcaata tcaggatgat cgcggaacac cgccgaatat acgaaccatg    300
gcttccctga gaggcgaagc gctgtgttcg gaaagtgtgg atgccggccg caaggcggag    360
ctttttgata tcgagggggcg gcccgtctgg cttatcgatg ccaacggcac agagacgact    420
ctcgaatatg atgtcttagg caggccaaca gccgtattcg agcaacagga aggtacggac    480
tccccccagt gcagggagcg gtttatttat ggtgagaagg aggcggatgc ccaggccaac    540
aatttgcgcg gacaactggt tcgccactac gataccgcgg gccggataca gaccgacagc    600
atctccttgg ctggactgcc gttgcgccaa agccgtcaac tgctgaaaaa ttgggatgaa    660
cctggcgact ggagtatgga tgaggaaagc gcctgggcct cgttgctggc tgccgaagct    720
tatgatacga gctggcggta tgacgcgcag gacagggtgc tcgcccaaac cgacgccaaa    780
gggaatctcc agcaactgac ttacaatgac gccggccagc cgcaggcggt cagcctcaag    840
ctgcaaggcc aagcggagca acggatttgg aaccggatcg agtacaacgc ggcgggtcaa    900
gtggatctcg ccgaagccgg gaatggaatc gtaacggaat atacttacga ggaaagcacg    960
cagcggttaa tccgaaaaaa agattcccgc ggactgtcct ccggggaaag agaagtgctg   1020
caggattatc gttatgaata tgatccggta ggcaatatcc tttctattta caatgaagcg   1080
gagccggttc gttatttccg caatcaggcc gttgctccga aaaggcaata tgcctacgat   1140
gccttgtatc agcttgtatc tagttcgggg cgggaatccg acgcgcttcg gcagcagacg   1200
tcgcttcctc ccttgatcac gcctatccct ctggacgata gccaatacgt caattacgct   1260
gaaaaataca gctatgatca ggcgggcaat ttaatcaagc ttagccataa cggggcaagt   1320
caatatacaa cgaatgtgta tgtggacaaa agctcaaacc gggggatttg gcggcaaggg   1380
gaagacatcc cggatatcgc ggcttccttt gacagagcag gcaatcaaca agctttattc   1440
ccggggagac cgttggaatg ggatacacgc aatcaattaa gccgtgtcca tatggtcgtg   1500
cgcgaaggcg gagacaacga ctgggaaggc tatctctatg acagctcggg aatgcgtatc   1560
gtaaaacgat ctacccgcaa aacacagaca acgacgcaaa cggatacgac cctctatttg   1620
ccgggcctgg agctgcgaat ccgccagacc ggggaccggg tcacggaagc attgcaggtc   1680
attaccgtgg atgagggagc gggacaagtg agggtgctgc actgggagga tggaaccgag   1740
ccgggcggca tcgccaatga tcagtaccgg tacagcctga acgatcatct tacctcctct   1800
ttattggaag ttgacgggca aggtcagatc attagtaagg aagaatttta tccctatggc   1860
ggcacagccc tgtggacagc ccggtcagag gtagaggcaa gctacaagac catccgctat   1920
tcaggcaaag agcgggatgc cacaggcctg tattattacg gacaccgcta ctatatgcca   1980
tggttgggtc gctggctgaa tccggacccg gccggaatgg tagatggact aaacctgtac   2040
cgtatggtca ggaacaatcc tataggactg atggatccga atgggaatgc gccaatcaac   2100
gtggcggatt atagcttcgt gcatggtgat ttagtttatg gtcttagtaa ggaaagagga   2160
agatatctaa agctatttaa tccaaacttt aatatggaaa aatcagactc tcctgctatg   2220
gttatagatc aatataataa taatgttgca ttgagtataa ctaaccaata taaagtagaa   2280
gaattgatga aatttcaaaa agacccacaa aaagccgcac ggaaaataaa ggttccagaa   2340
gggaatcgtt tatcgaggaa cgaaaattat cctttgtggc acgattatat taacattgga   2400
gaagctaaag ctgcatttaa ggcctctcat attttccaag aagtgaaggg gaattatggg   2460
aaagattatt atcataaatt attattagac agaatgatag aatcgccgtt gctgtggaaa   2520
```

cgaggcagca aactcgggct agaaatcgcc gctaccaatc agagaacaaa aatacacttt 2580
gttcttgaca atttaaatat cgagcaggtg gttacgaaag agggtagcgg cggtcagtca 2640
atcacagctt cggagctccg ttatatttat cgaaatcgcg aaagattgaa cgggcgtgtc 2700
attttctata gaaataatga aaggctagat caggctccat ggcaagaaaa tccggactta 2760
tggagcaaat atcaaccggg tcttagacaa agcagcagtt caagagtcaa agaacgaggg 2820
attgggaact ttttccgccg gttttcaatg aagagaaagt aa 2862

<210> SEQ ID NO 56
<211> LENGTH: 4458
<212> TYPE: DNA
<213> ORGANISM: Photorhabdus luminescens

<400> SEQUENCE: 56
atgcaggatt caccagaagt atcgattaca acgctgtcac ttcccaaagg tggcggtgct 60
atcaatggca tgggagaagc actgaatgct gccggccctg atggaatggc ctccctatct 120
ctgccattac ccctttcgac cggcagaggg acggctcctg gattatcgct gatttacagc 180
aacagtgcag gtaatgggcc tttcggcatc ggctggcaat gcggtgttat gtccattagc 240
cgacgcaccc aacatggcat tccacaatac ggtaatgacg acacgttcct atccccacaa 300
ggcgaggtca tgaatatcgc cctgaatgac caagggcaac ctgatatccg tcaagacgtt 360
aaaacgctgc aaggcgttac cttgccaatt tcctataccg tgacccgcta tcaagcccgc 420
cagatcctgg atttcagtaa aatcgaatac tggcaacctg cctccggtca agaaggacgc 480
gctttctggc tgatatcgtc accggacggc caactacaca tcttagggaa aaccgcgcag 540
gcttgtctgg caaatccgca aaatgaccaa caaatcgccc agtggttgct ggaagaaact 600
gtgacgccag ccggtgaaca tgtcagctat caatatcgag ccgaagatga agcccattgt 660
gacgacaatg aaaaaaccgc tcatcccaat gttaccgcac agcgctatct ggtacaggtg 720
aactacggca acatcaaacc acaagccagc ctgttcgtac tggataacgc acctcccgca 780
ccggaagagt ggctgtttca tctggtcttt gaccacggtg agcgcgatac ctcacttcat 840
accgtgccaa catgggatgc aggtacagcg caatggtctg tacgcccgga tatcttctct 900
cgctatgaat atggttttga agtgcgtact cgccgcttat gtcaacaagt gctgatgttt 960
caccgcaccg cgctcatggc cggagaagcc agtaccaatg acgccccgga actggttgga 1020
cgcttaatac tggaatatga caaaaacgcc agcgtcacca cgttgattac catccgtcaa 1080
ttaagccatg aatcggacgg cagcccagtc acccagccac cactagaact agcctggcaa 1140
cggtttgatc tggagaaaat gccgacatgg caacgctttg acgcactaga taattttaac 1200
tcgcagcaac gttatcaact ggttgatctg cggggagaag ggttgccagg tatgctgtat 1260
caagatcgag gcgcttggtg gtataaagct ccgcaacgtc aggaagacgg agacagcaat 1320
gccgtcactt acgacaaaat cgccccactg cctaccctac ccaatttgca ggataatgcc 1380
tcattgatgg atatcaacgg agacggccaa ctggattggg ttgttaccgc ctccggtatt 1440
cgcggatacc atagtcagca acccgatgga aagtggacgc actttacgcc aatcaatgcc 1500
ttgcccgtgg aatattttca tccaagcatc cagttcgctg accttaccgg ggcaggctta 1560
tctgatttag tgttgatcgg gccgaaaagc gtgcgtctat atgccaacca gcgaaacggc 1620
tggcgtaaag gagaagatgt cccccaatcc acaggtatca ccctgcctgt cacagggacc 1680
gatgcccgca aactggtggc tttcagtgat atgctcggtt ccggtcaaca acatctggtg 1740
gaaatcaagg ctaatcgcgt cacctgttgg ccgaatctag ggcatggccg tttcggtcaa 1800
ccactaactc tgtcaggatt tagccagccc gaaaatagct tcaatcccga acggctgttt 1860
ctggcggata tcgacggctc cggcaccacc gaccttatct atgcgcaatc cggctctttg 1920
ctcatttatc tcaaccaaag tggtaatcag tttgatgccc cgttgacatt agcgttgcca 1980
gaaggcgtac aatttgacaa cacttgccaa cttcaagtcg ccgatattca gggattaggg 2040
atagccagct tgattctgac tgtgccacat atcgcgccac atcactggcg ttgtgacctg 2100
tcactgacca aaccctggtt gttgaatgta atgaacaata accggggcgc acatcacacg 2160
ctacattatc gtagttccgc gcaattctgg ttggatgaaa aattacagct caccaaagca 2220
ggcaaatctc cggcttgtta tctgccgttt ccaatgcatt tgctatggta taccgaaatt 2280
caggatgaaa tcagcggcaa ccggctcacc agtgaagtca actacagcca cggcgtctgg 2340
gatggtaaag agcgggaatt cagaggattt ggctgcatca aacagacaga taccacaacg 2400
ttttctcacg gcaccgcccc cgaacaggcg gcaccgtcgc tgagtattag ctggtttgcc 2460
accggcatgg atgaagtaga cagccaatta gctacggaat attggcaggc agacacgcaa 2520
gcttatagcg gatttgaaac ccgttatacc gtctgggatc acaccaacca gacagaccaa 2580
gcatttaccc ccaatgagac acaacgtaac tggctgacgc gagcgcttaa aggccaactg 2640
ctacgcactg agctctacgg tctggacgga acagataagc aaacagtgcc ttataccgtc 2700
agtgaatcgc gctatcaggt acgctctatt cccgtaaata aagaaactga attatctgcc 2760
tgggtgactg ctattgaaaa tcgcagctac cactatgaac gtatcatcac tgacccacag 2820
ttcagccaga gtatcaagtt gcaacacgat atctttggtc aatcactgca aagtgtcgat 2880
attgcctggc cgcgccgcga aaaaccagca gtgaatccct acccgcctac cctgccggaa 2940
acgctatttg acagcagcta tgatgatcaa caacaactat tacgtctggt gagacaaaaa 3000
aatagctggc atcacctgac tgatggggaa aactggcgat taggtttacc gaatgcacaa 3060
cgccgtgatg tttatactta tgaccggagc aaaattccaa ccgaagggat ttcccttgaa 3120
atcttgctga aagatgatgg cctgctagca gatgaaaaag cggccgttta tctgggacaa 3180
caacagacgt tttacaccgc cggtcaagcg gaagtcactc tagaaaaacc cacgttacaa 3240
gcactggtcg cgttccaaga aaccgccatg atggacgata cctcattaca ggcgtatgaa 3300
ggcgtgattg aagagcaaga gttgaatacc gcgctgacac aggccggtta tcagcaagtc 3360
gcgcggttgt ttaataccag atcagaaagc ccggtatggg cggcacggca aggttatacc 3420
gattacggtg acgccgcaca gttctggcgg cctcaggctc agcgtaactc gttgctgaca 3480
gggaaaacca cactgacctg ggatacccat cattgtgtaa taatacagac tcaagatgcc 3540
gctggattaa cgacgcaagc ccattacgat tatcgtttcc ttacaccggt acaactgaca 3600
gatattaatg ataatcaaca tattgtgact ctggacgcgc taggtcgcgt aaccaccagc 3660
cggttctggg gcacagaggc aggacaagcc gcaggctatt ccaaccagcc cttcacacca 3720
ccggactccg tagataaagc gctggcatta accggcgcac tccctgttgc ccaatgttta 3780
gtctatgccg ttgatagctg gatgccgtcg ttatctttgt ctcagctttc tcagtcacaa 3840
gaagaggcag aagcgctatg ggcgcaactg cgtgccgctc atatgattac cgaagatggg 3900
aaagtgtgtg cgttaagcgg gaaacgagga acaagccatc agaacctgac gattcaactt 3960
atttcgctat tggcaagtat tccccgttta ccgccacatg tactggggat caccactgat 4020
cgctatgata gcgatccgca acagcagcac caacagacgg tgagctttag tgacggtttt 4080
ggccggttac tccagagttc agctcgtcat gagtcaggtg atgcctggca acgtaaagag 4140
gatggcgggc tggtcgtgga tgcaaatggc gttctggtca gtgcccctac agacacccga 4200
tgggccgttt ccggtcgcac agaatatgac gacaaaggcc aacctgtgcg tacttatcaa 4260
ccctattttc taaatgactg gcgttacgtt agtgatgaca gcgcacgaga tgacctgttt 4320
gccgataccc acctttatga tccattggga cgggaataca aagtcatcac tgctaagaaa 4380
tatttgcgag aaaagctgta caccccgtgg tttattgtca gtgaggatga aaacgataca 4440
gcatcaagaa ccccatag 4458

<210> SEQ ID NO 57
<211> LENGTH: 2817
<212> TYPE: DNA
<213> ORGANISM: Photorhabdus luminescens

<400> SEQUENCE: 57
atggaaaaca ttgacccaaa actttatcac catacgccta ccgtcagtgt tcacgataac 60
cgtggactag ctatccgtaa tattagtttt caccgcacta ccgcagaagc aaataccgat 120
acccgtatta cccgccatca atataatgcc ggcggatatt tgaaccaaag cattgatcct 180
cgcctgtatg acgccaaaca gactaacaac gctgtacaac cgaattttat ctggcgacat 240
aatttgaccg gcaatatcct gcgaacagag agcgtcgatg ccggtcggac gattaccctc 300
aacgatattg aaggccgccc ggtgttgacc atcaatgcag ccggtgtccg gcaaaaccat 360
cgctacgaag ataacaccct gcccggtcgc ctgctcgcta tcagcgaaca aggacaggca 420
gaagagaaaa cgaccgagcg ccttatctgg gccggcaata cgccgcaaga aaaagaccac 480
aaccttgccg gtcagtgcgt ccgccattac gataccgcag gactcactca actcaacagc 540
cttgccctga ccggcgccgt tctatcacaa tctcaacaac tgcttaccga taaccaggat 600
gccgactgga caggtgaaga ccagagcctc tggcaacaaa aactgagtag tgatgtctat 660
atcacccaaa gtaacactga tgccaccggg gctttactga cccagaccga tgccaaaggc 720
aacattcagc ggctggccta tgatgtggcc gggcagctaa aagggagttg gttaacactc 780
aaaggtcagg cggaacaggt gattatcaaa tcgctaacct actccgccgc cgggcaaaaa 840
ttacgtgaag agcacggtaa cgggattgtc actgaataca gctacgaacc ggaaacccaa 900
cggcttatcg gcattaccac tcgccgtcca tcagacgcca aggtgttgca agacctacgc 960
tatcaatatg acccagtagg caatgtcatt agtatccgta atgatgcgga agccactcgc 1020
ttttggcgca atcagaaagt agccccggag aatagctata cctacgattc cctgtatcag 1080
cttatcagcg ccaccgggcg cgagatggcc aatatcggtc agcaaagcaa ccaacttccc 1140
tctccggcgc taccttctga taacaatacc tacaccaact atactcgcac ttatacttat 1200
gaccgtggcg gcaatttgac gaaaattcag catagttcac cagccgcgca aaataactac 1260
acgacggata taacggtttc aaatcgcagc aaccgcgcgg tactcagcac attgaccgca 1320
gatccaactc aagtcgatgc cttatttgat gcgggaggcc atcaaaccag cttgttatcc 1380
ggccaagttc taacttggac accgcgaggc gaattgaaac aagccaacaa tagcgcagga 1440
aatgagtggt atcgctacga tagcaacggc atacgccagc taaaagtgaa tgaacaacaa 1500
actcagaata tcccgcaaca acaaagggta acttatctac cggggctgga aatacgtaca 1560
acccagaaca acgccacaac aacagaagag ttacacgtta tcacactcgg taaagccggc 1620
cgcgcgcaag tccgagtatt gcattgggag agcggtaaac cagaagatat taataacaat 1680
cagcttcgtt acagctacga taatcttatt ggctccagcc aacttcaatt agatagcgac 1740
ggacaaatta tcagtgaaga agaatattat ccatttggtg gtacagcgct gtgggcggca 1800
aggaatcaaa ccgaagccag ctataaaacc attcgttatt ctggtaaaga gcgggatgtt 1860
accgggctgt attattatgg ctaccgttat taccaaccgt gggcgggcag atggttaggt 1920
gcagacccgg caggaaccat tgatggactg aatttatatc gcatggtgag aaataacccg 1980
gtgacgcaat ttgatgttca gggattatca ccggccaaca gaacagaaga agcgataata 2040
aaacagggtt cctttacggg aatggaagaa gctgtttata aaaaaatggc taaacctcaa 2100
actttcaaac gccaaagagc tatcgctgcc caaacagagc aagaagccca tgaatcattg 2160
accaacaacc ctagtgtaga tattagccca attaaaaact acaccacaga tagctcacaa 2220
attaatgccg cgataaggga aaatcgtatt acgccagcag tggaaagttt agacgccaca 2280
ttatcttccc tacaagatag acaaatgagg gtaacttatc gggtgatgac ctatgtagat 2340
aattccacgc catcgccttg gcactcgcca caggaaggaa atagtattaa tgttggtgat 2400
atcgtttcgg ataacgctta tttatcaaca tcggcccatc gtggttttct gaattttgtt 2460
cacaaaaaag aaaccagtga aactcgatac gtcaagatgg catttttaac gaatgcgggt 2520
gtcaatgtcc cagcagcatc tatgtataat aatgctggcg aggagcaagt atttaaaatg 2580
gatttaaacg attcaagaaa aagccttgct gaaaaattaa aactaagagt cagtggacca 2640
caatcgggac aagcggaaat attactacct agggaaacac agttcgaagt tgtttcaatg 2700
aaacatcaag gcagagatac ctatgtatta ttgcaagata ttaaccaatc cgcagccact 2760
catagaaatg tacgtaacac ttacaccggt aatttcaaat catccagtgc aaattaa 2817

<210> SEQ ID NO 58
<211> LENGTH: 915
<212> TYPE: PRT
<213> ORGANISM: Photorhabdus luminescens

<400> SEQUENCE: 58

Met Ser Ser Tyr Asn Ser Ala Ile Asp Gln Lys Thr Pro Ser Ile Lys
1 5 10 15

Val Leu Asp Asn Arg Lys Leu Asn Val Arg Thr Leu Glu Tyr Leu Arg
20 25 30

Thr Gln Ala Asp Glu Asn Ser Asp Glu Leu Ile Thr Phe Tyr Glu Phe
35 40 45

Asn Ile Pro Gly Phe Gln Val Lys Ser Thr Asp Pro Arg Lys Asn Lys
50 55 60

Asn Gln Ser Gly Pro Asn Phe Ile Arg Val Phe Asn Leu Ala Gly Gln
65 70 75 80

Val Leu Arg Glu Glu Ser Val Asp Ala Gly Arg Thr Ile Thr Leu Asn
85 90 95

Asp Ile Glu Ser Arg Pro Val Leu Ile Ile Asn Ala Thr Gly Val Arg
100 105 110

Gln Asn His Arg Tyr Glu Asp Asn Thr Leu Pro Gly Arg Leu Leu Ala
115 120 125

Ile Thr Glu Gln Val Gln Ala Gly Glu Lys Thr Thr Glu Arg Leu Ile
130 135 140

Trp Ala Gly Asn Thr Pro Gln Glu Lys Asp Tyr Asn Leu Ala Gly Gln
145 150 155 160

Cys Val Arg His Tyr Asp Thr Ala Gly Leu Thr Gln Leu Asn Ser Leu
165 170 175

Ser Leu Ala Gly Val Val Leu Ser Gln Ser Gln Gln Leu Leu Val Asp
180 185 190

Asp Lys Asn Ala Asp Trp Thr Gly Glu Asp Gln Ser Leu Trp Gln Gln
195 200 205

-continued

```
Lys Leu Ser Ser Asp Val Tyr Thr Thr Gln Asn Lys Ala Asp Ala Thr
    210                 215                 220

Gly Ala Leu Leu Thr Gln Thr Asp Ala Lys Gly Asn Ile Gln Arg Leu
225                 230                 235                 240

Ala Tyr Asp Val Ala Gly Gln Leu Lys Gly Cys Trp Leu Thr Leu Lys
                245                 250                 255

Gly Gln Ala Glu Gln Val Ile Ile Lys Ser Leu Thr Tyr Ser Ala Ala
            260                 265                 270

Gly Gln Lys Leu Arg Glu Glu His Gly Asn Gly Val Ile Thr Glu Tyr
        275                 280                 285

Ser Tyr Glu Pro Glu Thr Gln Arg Leu Ile Gly Ile Ala Thr Arg Arg
    290                 295                 300

Pro Ser Asp Ala Lys Val Leu Gln Asp Leu Arg Tyr Gln Tyr Asp Pro
305                 310                 315                 320

Val Gly Asn Val Ile Asn Ile Arg Asn Asp Ala Glu Ala Thr Arg Phe
                325                 330                 335

Trp Arg Asn Gln Lys Val Val Pro Glu Asn Ser Tyr Thr Tyr Asp Ser
            340                 345                 350

Leu Tyr Gln Leu Ile Ser Ala Thr Gly Arg Glu Met Ala Asn Ile Gly
        355                 360                 365

Gln Gln Asn Asn Gln Leu Pro Ser Pro Ala Leu Pro Ser Asp Asn Asn
    370                 375                 380

Thr Tyr Thr Asn Tyr Thr Arg Ser Tyr Ser Tyr Asp His Ser Gly Asn
385                 390                 395                 400

Leu Thr Gln Ile Arg His Ser Ser Pro Ala Thr Gln Asn Asn Tyr Thr
                405                 410                 415

Val Ala Ile Thr Leu Ser Asn Arg Ser Asn Arg Gly Val Leu Ser Thr
            420                 425                 430

Leu Thr Thr Asp Pro Asn Gln Val Asp Thr Leu Phe Asp Ala Gly Gly
        435                 440                 445

His Gln Thr Ser Leu Leu Pro Gly Gln Thr Leu Ile Trp Thr Pro Arg
    450                 455                 460

Gly Glu Leu Lys Gln Val Asn Asn Gly Pro Gly Asn Glu Trp Tyr Arg
465                 470                 475                 480

Tyr Asp Ser Asn Gly Met Arg Gln Leu Lys Val Ser Glu Gln Pro Thr
                485                 490                 495

Gln Asn Thr Thr Gln Gln Gln Arg Val Ile Tyr Leu Pro Gly Leu Glu
            500                 505                 510

Leu Arg Thr Thr Gln Ser Asn Ala Thr Thr Thr Glu Glu Leu His Val
        515                 520                 525

Ile Thr Leu Gly Glu Ala Gly Arg Ala Gln Val Arg Val Leu His Trp
    530                 535                 540

Glu Ser Gly Lys Pro Glu Asp Val Asn Asn Asn Gln Leu Arg Tyr Ser
545                 550                 555                 560

Tyr Asp Asn Leu Ile Gly Ser Ser Gln Leu Glu Leu Asp Asn Gln Gly
                565                 570                 575

Gln Ile Ile Ser Glu Glu Glu Tyr Tyr Pro Phe Gly Gly Thr Ala Leu
            580                 585                 590

Trp Ala Ala Asn Ser Gln Thr Glu Ala Ser Tyr Lys Thr Ile Arg Tyr
        595                 600                 605

Ser Gly Lys Glu Arg Asp Ala Thr Gly Leu Tyr Tyr Tyr Gly Tyr Arg
    610                 615                 620

Tyr Tyr Gln Pro Trp Ala Gly Arg Trp Leu Ser Ala Asp Pro Ala Gly
625                 630                 635                 640
```

Thr Ile Asp Gly Leu Asn Leu Tyr Arg Met Val Arg Asn Asn Pro Val
645 650 655

Ser Leu Gln Asp Glu Asn Gly Leu Ala Pro Glu Lys Gly Lys Tyr Thr
660 665 670

Lys Glu Val Asn Phe Phe Asp Glu Leu Lys Phe Lys Leu Ala Ala Lys
675 680 685

Ser Ser His Val Val Lys Trp Asn Glu Lys Glu Ser Ser Tyr Thr Lys
690 695 700

Asn Lys Ser Leu Lys Val Val Arg Val Gly Asp Ser Asp Pro Ser Gly
705 710 715 720

Tyr Leu Leu Ser His Glu Glu Leu Leu Lys Gly Ile Glu Lys Ser Gln
725 730 735

Ile Ile Tyr Ser Arg Leu Glu Glu Asn Ser Ser Leu Ser Glu Lys Ser
740 745 750

Lys Thr Asn Leu Ser Leu Gly Ser Glu Ile Ser Gly Tyr Met Ala Arg
755 760 765

Thr Ile Gln Asp Thr Ile Ser Glu Tyr Ala Glu Glu His Lys Tyr Arg
770 775 780

Ser Asn His Pro Asp Phe Tyr Ser Glu Thr Asp Phe Phe Ala Leu Met
785 790 795 800

Asp Lys Ser Glu Lys Asn Asp Tyr Ser Gly Glu Arg Lys Ile Tyr Ala
805 810 815

Ala Met Glu Val Lys Val Tyr His Asp Leu Lys Asn Lys Gln Ser Glu
820 825 830

Leu His Val Asn Tyr Ala Leu Ala His Pro Tyr Thr Gln Leu Ser Asn
835 840 845

Glu Glu Arg Ala Leu Leu Gln Glu Thr Glu Pro Ala Ile Ala Ile Asp
850 855 860

Arg Glu Tyr Asn Phe Lys Gly Val Gly Lys Phe Leu Thr Met Lys Ala
865 870 875 880

Ile Lys Lys Ser Leu Lys Gly His Lys Ile Asn Arg Ile Ser Thr Glu
885 890 895

Ala Ile Asn Ile Arg Ser Ala Ala Ile Ala Glu Asn Leu Gly Met Arg
900 905 910

Arg Thr Ser
915

<210> SEQ ID NO 59
<211> LENGTH: 2504
<212> TYPE: PRT
<213> ORGANISM: Photorhabdus luminescens

<400> SEQUENCE: 59

Met Gln Asn Ser Leu Ser Ser Thr Ile Asp Thr Ile Cys Gln Lys Leu
1 5 10 15

Gln Leu Thr Cys Pro Ala Glu Ile Ala Leu Tyr Pro Phe Asp Thr Phe
20 25 30

Arg Glu Lys Thr Arg Gly Met Val Asn Trp Gly Glu Ala Lys Arg Ile
35 40 45

Tyr Glu Ile Ala Gln Ala Glu Gln Asp Arg Asn Leu Leu His Glu Lys
50 55 60

Arg Ile Phe Ala Tyr Ala Asn Pro Leu Leu Lys Asn Ala Val Arg Leu
65 70 75 80

Gly Thr Arg Gln Met Leu Gly Phe Ile Gln Gly Tyr Ser Asp Leu Phe
85 90 95

```
Gly Asn Arg Ala Asp Asn Tyr Ala Ala Pro Gly Ser Val Ala Ser Met
            100                 105                 110

Phe Ser Pro Ala Ala Tyr Leu Thr Glu Leu Tyr Arg Glu Ala Lys Asn
        115                 120                 125

Leu His Asp Ser Ser Ser Ile Tyr Tyr Leu Asp Lys Arg Arg Pro Asp
    130                 135                 140

Leu Ala Ser Leu Met Leu Ser Gln Lys Asn Met Asp Glu Glu Ile Ser
145                 150                 155                 160

Thr Leu Ala Leu Ser Asn Glu Leu Cys Leu Ala Gly Ile Glu Thr Lys
                165                 170                 175

Thr Gly Lys Ser Gln Asp Glu Val Met Asp Met Leu Ser Thr Tyr Arg
            180                 185                 190

Leu Ser Gly Glu Thr Pro Tyr His His Ala Tyr Glu Thr Val Arg Glu
        195                 200                 205

Ile Val His Glu Arg Asp Pro Gly Phe Arg His Leu Ser Gln Ala Pro
    210                 215                 220

Ile Val Ala Ala Lys Leu Asp Pro Val Thr Leu Leu Gly Ile Ser Ser
225                 230                 235                 240

His Ile Ser Pro Glu Leu Tyr Asn Leu Leu Ile Glu Glu Ile Pro Glu
                245                 250                 255

Lys Asp Glu Ala Ala Leu Asp Thr Leu Tyr Lys Thr Asn Phe Gly Asp
            260                 265                 270

Ile Thr Thr Ala Gln Leu Met Ser Pro Ser Tyr Leu Ala Arg Tyr Tyr
        275                 280                 285

Gly Val Ser Pro Glu Asp Ile Ala Tyr Val Thr Thr Ser Leu Ser His
    290                 295                 300

Val Gly Tyr Ser Ser Asp Ile Leu Val Ile Pro Leu Val Asp Gly Val
305                 310                 315                 320

Gly Lys Met Glu Val Val Arg Val Thr Arg Thr Pro Ser Asp Asn Tyr
                325                 330                 335

Thr Ser Gln Thr Asn Tyr Ile Glu Leu Tyr Pro Gln Gly Gly Asp Asn
            340                 345                 350

Tyr Leu Ile Lys Tyr Asn Leu Ser Asn Ser Phe Gly Leu Asp Asp Phe
        355                 360                 365

Tyr Leu Gln Tyr Lys Asp Gly Ser Ala Asp Trp Thr Glu Ile Ala His
    370                 375                 380

Asn Pro Tyr Pro Asp Met Val Ile Asn Gln Lys Tyr Glu Ser Gln Ala
385                 390                 395                 400

Thr Ile Lys Arg Ser Asp Ser Asp Asn Ile Leu Ser Ile Gly Leu Gln
                405                 410                 415

Arg Trp His Ser Gly Ser Tyr Asn Phe Ala Ala Ala Asn Phe Lys Ile
            420                 425                 430

Asp Gln Tyr Ser Pro Lys Ala Phe Leu Leu Lys Met Asn Lys Ala Ile
        435                 440                 445

Arg Leu Leu Lys Ala Thr Gly Leu Ser Phe Ala Thr Leu Glu Arg Ile
    450                 455                 460

Val Asp Ser Val Asn Ser Thr Lys Ser Ile Thr Val Glu Val Leu Asn
465                 470                 475                 480

Lys Val Tyr Arg Val Lys Phe Tyr Ile Asp Arg Tyr Gly Ile Ser Glu
                485                 490                 495

Glu Thr Ala Ala Ile Leu Ala Asn Ile Asn Ile Ser Gln Gln Ala Val
            500                 505                 510

Gly Asn Gln Leu Ser Gln Phe Glu Gln Leu Phe Asn His Pro Pro Leu
```

```
        515                 520                 525

Asn Gly Ile Arg Tyr Glu Ile Ser Glu Asp Asn Ser Lys His Leu Pro
    530                 535                 540

Asn Pro Asp Leu Asn Leu Lys Pro Asp Ser Thr Gly Asp Asp Gln Arg
545                 550                 555                 560

Lys Ala Val Leu Lys Arg Ala Phe Gln Val Asn Ala Ser Glu Leu Tyr
                565                 570                 575

Gln Met Leu Leu Ile Thr Asp Arg Lys Glu Asp Gly Val Ile Lys Asn
            580                 585                 590

Asn Leu Glu Asn Leu Ser Asp Leu Tyr Leu Val Ser Leu Leu Ala Gln
        595                 600                 605

Ile His Asn Leu Thr Ile Ala Glu Leu Asn Ile Leu Leu Val Ile Cys
    610                 615                 620

Gly Tyr Gly Asp Thr Asn Ile Tyr Gln Ile Thr Asp Asp Asn Leu Ala
625                 630                 635                 640

Lys Ile Val Glu Thr Leu Leu Trp Ile Thr Gln Trp Leu Lys Thr Gln
                645                 650                 655

Lys Trp Thr Val Thr Asp Leu Phe Leu Met Thr Thr Ala Thr Tyr Ser
            660                 665                 670

Thr Thr Leu Thr Pro Glu Ile Ser Asn Leu Thr Ala Thr Leu Ser Ser
        675                 680                 685

Thr Leu His Gly Lys Glu Ser Leu Ile Gly Glu Asp Leu Lys Arg Ala
    690                 695                 700

Met Ala Pro Cys Phe Thr Ser Ala Leu His Leu Thr Ser Gln Glu Val
705                 710                 715                 720

Ala Tyr Asp Leu Leu Leu Trp Ile Asp Gln Ile Gln Pro Ala Gln Ile
                725                 730                 735

Thr Val Asp Gly Phe Trp Glu Glu Val Gln Thr Thr Pro Thr Ser Leu
            740                 745                 750

Lys Val Ile Thr Phe Ala Gln Val Leu Ala Gln Leu Ser Leu Ile Tyr
        755                 760                 765

Arg Arg Ile Gly Leu Ser Glu Thr Glu Leu Ser Leu Ile Val Thr Gln
    770                 775                 780

Ser Ser Leu Leu Val Ala Gly Lys Ser Ile Leu Asp His Gly Leu Leu
785                 790                 795                 800

Thr Leu Met Ala Leu Glu Gly Phe His Thr Trp Val Asn Gly Leu Gly
                805                 810                 815

Gln His Ala Ser Leu Ile Leu Ala Ala Leu Lys Asp Gly Ala Leu Thr
            820                 825                 830

Val Thr Asp Val Ala Gln Ala Met Asn Lys Glu Glu Ser Leu Leu Gln
        835                 840                 845

Met Ala Ala Asn Gln Val Glu Lys Asp Leu Thr Lys Leu Thr Ser Trp
    850                 855                 860

Thr Gln Ile Asp Ala Ile Leu Gln Trp Leu Gln Met Ser Ser Ala Leu
865                 870                 875                 880

Ala Val Ser Pro Leu Asp Leu Ala Gly Met Met Ala Leu Lys Tyr Gly
                885                 890                 895

Ile Asp His Asn Tyr Ala Ala Trp Gln Ala Ala Ala Ala Ala Leu Met
            900                 905                 910

Ala Asp His Ala Asn Gln Ala Gln Lys Lys Leu Asp Glu Thr Phe Ser
        915                 920                 925

Lys Ala Leu Cys Asn Tyr Tyr Ile Asn Ala Val Val Asp Ser Ala Ala
    930                 935                 940
```

```
Gly Val Arg Asp Arg Asn Gly Leu Tyr Thr Tyr Leu Leu Ile Asp Asn
945                 950                 955                 960

Gln Val Ser Ala Asp Val Ile Thr Ser Arg Ile Ala Glu Ala Ile Ala
                965                 970                 975

Gly Ile Gln Leu Tyr Val Asn Arg Ala Leu Asn Arg Asp Glu Gly Gln
            980                 985                 990

Leu Ala Ser Asp Val Ser Thr Arg  Gln Phe Phe Thr Asp  Trp Glu Arg
        995                 1000                 1005

Tyr Asn  Lys Arg Tyr Ser Thr  Trp Ala Gly Val Ser  Glu Leu Val
    1010                 1015                 1020

Tyr Tyr  Pro Glu Asn Tyr Val  Asp Pro Thr Gln Arg  Ile Gly Gln
    1025                 1030                 1035

Thr Lys  Met Met Asp Ala Leu  Leu Gln Ser Ile Asn  Gln Ser Gln
    1040                 1045                 1050

Leu Asn  Ala Asp Thr Val Glu  Asp Ala Phe Lys Thr  Tyr Leu Thr
    1055                 1060                 1065

Ser Phe  Glu Gln Val Ala Asn  Leu Lys Val Ile Ser  Ala Tyr His
    1070                 1075                 1080

Asp Asn  Val Asn Val Asp Gln  Gly Leu Thr Tyr Phe  Ile Gly Ile
    1085                 1090                 1095

Asp Gln  Ala Ala Pro Gly Thr  Tyr Tyr Trp Arg Ser  Val Asp His
    1100                 1105                 1110

Ser Lys  Cys Glu Asn Gly Lys  Phe Ala Ala Asn Ala  Trp Gly Glu
    1115                 1120                 1125

Trp Asn  Lys Ile Thr Cys Ala  Val Asn Pro Trp Lys  Asn Ile Ile
    1130                 1135                 1140

Arg Pro  Val Val Tyr Met Ser  Arg Leu Tyr Leu Leu  Trp Leu Glu
    1145                 1150                 1155

Gln Gln  Ser Lys Lys Ser Asp  Asp Gly Lys Thr Thr  Ile Tyr Gln
    1160                 1165                 1170

Tyr Asn  Leu Lys Leu Ala His  Ile Arg Tyr Asp Gly  Ser Trp Asn
    1175                 1180                 1185

Thr Pro  Phe Thr Phe Asp Val  Thr Glu Lys Val Lys  Asn Tyr Thr
    1190                 1195                 1200

Ser Ser  Thr Asp Ala Ala Glu  Ser Leu Gly Leu Tyr  Cys Thr Gly
    1205                 1210                 1215

Tyr Gln  Gly Glu Asp Thr Leu  Leu Val Met Phe Tyr  Ser Met Gln
    1220                 1225                 1230

Ser Ser  Tyr Ser Ser Tyr Thr  Asp Asn Asn Ala Pro  Val Thr Gly
    1235                 1240                 1245

Leu Tyr  Ile Phe Ala Asp Met  Ser Ser Asp Asn Met  Thr Asn Ala
    1250                 1255                 1260

Gln Ala  Thr Asn Tyr Trp Asn  Asn Ser Tyr Pro Gln  Phe Asp Thr
    1265                 1270                 1275

Val Met  Ala Asp Pro Asp Ser  Asp Asn Lys Lys Val  Ile Thr Arg
    1280                 1285                 1290

Arg Val  Asn Asn Arg Tyr Ala  Glu Asp Tyr Glu Ile  Pro Ser Ser
    1295                 1300                 1305

Val Thr  Ser Asn Ser Asn Tyr  Ser Trp Gly Asp His  Ser Leu Thr
    1310                 1315                 1320

Met Leu  Tyr Gly Gly Ser Val  Pro Asn Ile Thr Phe  Glu Ser Ala
    1325                 1330                 1335

Ala Glu  Asp Leu Arg Leu Ser  Thr Asn Met Ala Leu  Ser Ile Ile
    1340                 1345                 1350
```

-continued

```
His Asn  Gly Tyr Ala Gly Thr  Arg Arg Ile Gln Cys  Asn Leu Met
    1355                 1360                 1365

Lys Gln  Tyr Ala Ser Leu Gly  Asp Lys Phe Ile Ile  Tyr Asp Ser
    1370                 1375                 1380

Ser Phe  Asp Asp Ala Asn Arg  Phe Asn Leu Val Pro  Leu Phe Lys
    1385                 1390                 1395

Phe Gly  Lys Asp Glu Asn Ser  Asp Asp Ser Ile Cys  Ile Tyr Asn
    1400                 1405                 1410

Glu Asn  Pro Ser Ser Glu Asp  Lys Lys Trp Tyr Phe  Ser Ser Lys
    1415                 1420                 1425

Asp Asp  Asn Lys Thr Ala Asp  Tyr Asn Gly Gly Thr  Gln Cys Ile
    1430                 1435                 1440

Asp Ala  Gly Thr Ser Asn Lys  Asp Phe Tyr Tyr Asn  Leu Gln Glu
    1445                 1450                 1455

Ile Glu  Val Ile Ser Val Thr  Gly Gly Tyr Trp Ser  Ser Tyr Lys
    1460                 1465                 1470

Ile Ser  Asn Pro Ile Asn Ile  Asn Thr Gly Ile Asp  Ser Ala Lys
    1475                 1480                 1485

Val Lys  Val Thr Val Lys Ala  Gly Gly Asp Asp Gln  Ile Phe Thr
    1490                 1495                 1500

Ala Asp  Asn Ser Thr Tyr Val  Pro Gln Gln Pro Ala  Pro Ser Phe
    1505                 1510                 1515

Glu Glu  Met Ile Tyr Gln Phe  Asn Asn Leu Thr Ile  Asp Cys Lys
    1520                 1525                 1530

Asn Leu  Asn Phe Ile Asp Asn  Gln Ala His Ile Glu  Ile Asp Phe
    1535                 1540                 1545

Thr Ala  Thr Ala Gln Asp Gly  Arg Phe Leu Gly Ala  Glu Thr Phe
    1550                 1555                 1560

Ile Ile  Pro Val Thr Lys Lys  Val Leu Gly Thr Glu  Asn Val Ile
    1565                 1570                 1575

Ala Leu  Tyr Ser Glu Asn Asn  Gly Val Gln Tyr Met  Gln Ile Gly
    1580                 1585                 1590

Ala Tyr  Arg Thr Arg Leu Asn  Thr Leu Phe Ala Gln  Gln Leu Val
    1595                 1600                 1605

Ser Arg  Ala Asn Arg Gly Ile  Asp Ala Val Leu Ser  Met Glu Thr
    1610                 1615                 1620

Gln Asn  Ile Gln Glu Pro Gln  Leu Gly Ala Gly Thr  Tyr Val Gln
    1625                 1630                 1635

Leu Val  Leu Asp Lys Tyr Asp  Glu Ser Ile His Gly  Thr Asn Lys
    1640                 1645                 1650

Ser Phe  Ala Ile Glu Tyr Val  Asp Ile Phe Lys Glu  Asn Asp Ser
    1655                 1660                 1665

Phe Val  Ile Tyr Gln Gly Glu  Leu Ser Glu Thr Ser  Gln Thr Val
    1670                 1675                 1680

Val Lys  Val Phe Leu Ser Tyr  Phe Ile Glu Ala Thr  Gly Asn Lys
    1685                 1690                 1695

Asn His  Leu Trp Val Arg Ala  Lys Tyr Gln Lys Glu  Thr Thr Asp
    1700                 1705                 1710

Lys Ile  Leu Phe Asp Arg Thr  Asp Glu Lys Asp Pro  His Gly Trp
    1715                 1720                 1725

Phe Leu  Ser Asp Asp His Lys  Thr Phe Ser Gly Leu  Ser Ser Ala
    1730                 1735                 1740

Gln Ala  Leu Lys Asn Asp Ser  Glu Pro Met Asp Phe  Ser Gly Ala
```

```
    1745                1750                1755

Asn Ala  Leu Tyr Phe Trp Glu  Leu Phe Tyr Tyr Thr  Pro Met Met
    1760                1765                1770

Met Ala  His Arg Leu Leu Gln  Glu Gln Asn Phe Asp  Ala Ala Asn
    1775                1780                1785

His Trp  Phe Arg Tyr Val Trp  Ser Pro Ser Gly Tyr  Ile Val Asp
    1790                1795                1800

Gly Lys  Ile Ala Ile Tyr His  Trp Asn Val Arg Pro  Leu Glu Glu
    1805                1810                1815

Asp Thr  Ser Trp Asn Ala Gln  Gln Leu Asp Ser Thr  Asp Pro Asp
    1820                1825                1830

Ala Val  Ala Gln Asp Asp Pro  Met His Tyr Lys Val  Ala Thr Phe
    1835                1840                1845

Met Ala  Thr Leu Asp Leu Leu  Met Ala Arg Gly Asp  Ala Ala Tyr
    1850                1855                1860

Arg Gln  Leu Glu Arg Asp Thr  Leu Ala Glu Ala Lys  Met Trp Tyr
    1865                1870                1875

Thr Gln  Ala Leu Asn Leu Leu  Gly Asp Glu Pro Gln  Val Met Leu
    1880                1885                1890

Ser Thr  Thr Trp Ala Asn Pro  Thr Leu Gly Asn Ala  Ala Ser Lys
    1895                1900                1905

Thr Thr  Gln Gln Val Arg Gln  Gln Val Leu Thr Gln  Leu Arg Leu
    1910                1915                1920

Asn Ser  Arg Val Lys Thr Pro  Leu Leu Gly Thr Ala  Asn Ser Leu
    1925                1930                1935

Thr Ala  Leu Phe Leu Pro Gln  Glu Asn Ser Lys Leu  Lys Gly Tyr
    1940                1945                1950

Trp Arg  Thr Leu Ala Gln Arg  Met Phe Asn Leu Arg  His Asn Leu
    1955                1960                1965

Ser Ile  Asp Gly Gln Pro Leu  Ser Leu Pro Leu Tyr  Ala Lys Pro
    1970                1975                1980

Ala Asp  Pro Lys Ala Leu Leu  Ser Ala Ala Val Ser  Ala Ser Gln
    1985                1990                1995

Gly Gly  Ala Asp Leu Pro Lys  Ala Pro Leu Thr Ile  His Arg Phe
    2000                2005                2010

Pro Gln  Met Leu Glu Gly Ala  Arg Gly Leu Val Asn  Gln Leu Ile
    2015                2020                2025

Gln Phe  Gly Ser Ser Leu Leu  Gly Tyr Ser Glu Arg  Gln Asp Ala
    2030                2035                2040

Glu Ala  Met Ser Gln Leu Leu  Gln Thr Gln Ala Ser  Glu Leu Ile
    2045                2050                2055

Leu Thr  Ser Ile Arg Met Gln  Asp Asn Gln Leu Ala  Glu Leu Asp
    2060                2065                2070

Ser Glu  Lys Thr Ala Leu Gln  Val Ser Leu Ala Gly  Val Gln Gln
    2075                2080                2085

Arg Phe  Asp Ser Tyr Ser Gln  Leu Tyr Glu Glu Asn  Ile Asn Ala
    2090                2095                2100

Gly Glu  Gln Arg Ala Leu Ala  Leu Arg Ser Glu Ser  Ala Ile Glu
    2105                2110                2115

Ser Gln  Gly Ala Gln Ile Ser  Arg Met Ala Gly Ala  Gly Val Asp
    2120                2125                2130

Met Ala  Pro Asn Ile Phe Gly  Leu Ala Asp Gly Gly  Met His Tyr
    2135                2140                2145
```

```
Gly Ala  Ile Ala Tyr Ala Ile  Ala Asp Gly Ile Glu  Leu Ser Ala
    2150                 2155                 2160

Ser Ala  Lys Met Val Asp Ala  Glu Lys Val Ala Gln  Ser Glu Ile
    2165                 2170                 2175

Tyr Arg  Arg Arg Arg Gln Glu  Trp Lys Ile Gln Arg  Asp Asn Ala
    2180                 2185                 2190

Gln Ala  Glu Ile Asn Gln Leu  Asn Ala Gln Leu Glu  Ser Leu Ser
    2195                 2200                 2205

Ile Arg  Arg Glu Ala Ala Glu  Met Gln Lys Glu Tyr  Leu Lys Thr
    2210                 2215                 2220

Gln Gln  Ala Gln Ala Gln Ala  Gln Leu Thr Phe Leu  Arg Ser Lys
    2225                 2230                 2235

Phe Ser  Asn Gln Ala Leu Tyr  Ser Trp Leu Arg Gly  Arg Leu Ser
    2240                 2245                 2250

Gly Ile  Tyr Phe Gln Phe Tyr  Asp Leu Ala Val Ser  Arg Cys Leu
    2255                 2260                 2265

Met Ala  Glu Gln Ser Tyr Gln  Trp Glu Ala Asn Asp  Asn Ser Ile
    2270                 2275                 2280

Ser Phe  Val Lys Pro Gly Ala  Trp Gln Gly Thr Tyr  Ala Gly Leu
    2285                 2290                 2295

Leu Cys  Gly Glu Ala Leu Ile  Gln Asn Leu Ala Gln  Met Glu Glu
    2300                 2305                 2310

Ala Tyr  Leu Lys Trp Glu Ser  Arg Ala Leu Glu Val  Glu Arg Thr
    2315                 2320                 2325

Val Ser  Leu Ala Val Val Tyr  Asp Ser Leu Glu Gly  Asn Asp Arg
    2330                 2335                 2340

Phe Asn  Leu Ala Glu Gln Ile  Pro Ala Leu Leu Asp  Lys Gly Glu
    2345                 2350                 2355

Gly Thr  Ala Gly Thr Lys Glu  Asn Gly Leu Ser Leu  Ala Asn Ala
    2360                 2365                 2370

Ile Leu  Ser Ala Ser Val Lys  Leu Ser Asp Leu Lys  Leu Gly Thr
    2375                 2380                 2385

Asp Tyr  Pro Asp Ser Ile Val  Gly Ser Asn Lys Val  Arg Arg Ile
    2390                 2395                 2400

Lys Gln  Ile Ser Val Ser Leu  Pro Ala Leu Val Gly  Pro Tyr Gln
    2405                 2410                 2415

Asp Val  Gln Ala Met Leu Ser  Tyr Gly Gly Ser Thr  Gln Leu Pro
    2420                 2425                 2430

Lys Gly  Cys Ser Ala Leu Ala  Val Ser His Gly Thr  Asn Asp Ser
    2435                 2440                 2445

Gly Gln  Phe Gln Leu Asp Phe  Asn Asp Gly Lys Tyr  Leu Pro Phe
    2450                 2455                 2460

Glu Gly  Ile Ala Leu Asp Asp  Gln Gly Thr Leu Asn  Leu Gln Phe
    2465                 2470                 2475

Pro Asn  Ala Thr Asp Lys Gln  Lys Ala Ile Leu Gln  Thr Met Ser
    2480                 2485                 2490

Asp Ile  Ile Leu His Ile Arg  Tyr Thr Ile Arg
    2495                 2500
```

<210> SEQ ID NO 60
<211> LENGTH: 1428
<212> TYPE: PRT
<213> ORGANISM: Serratia entomophila

<400> SEQUENCE: 60

-continued

```
Met Gln Asn His Gln Asp Met Ala Ile Thr Ala Pro Thr Leu Pro Ser
1               5                   10                  15

Gly Gly Gly Ala Val Thr Gly Leu Lys Gly Asp Ile Ala Ala Ala Gly
            20                  25                  30

Pro Asp Gly Ala Ala Thr Leu Ser Ile Pro Leu Pro Val Ser Pro Gly
        35                  40                  45

Arg Gly Tyr Ala Pro Thr Gly Ala Leu Asn Tyr His Ser Arg Ser Gly
    50                  55                  60

Asn Gly Pro Phe Gly Ile Gly Trp Gly Ile Gly Gly Ala Ala Val Gln
65                  70                  75                  80

Arg Arg Thr Arg Asn Gly Ala Pro Thr Tyr Asp Asp Thr Asp Glu Phe
                85                  90                  95

Thr Gly Pro Asp Gly Glu Val Leu Val Pro Ala Leu Thr Ala Ala Gly
            100                 105                 110

Thr Gln Glu Ala Arg Gln Ala Thr Ser Leu Leu Gly Ile Asn Pro Gly
        115                 120                 125

Gly Ser Phe Asn Val Gln Val Tyr Arg Ser Arg Thr Glu Gly Ser Leu
    130                 135                 140

Ser Arg Leu Glu Arg Trp Leu Pro Ala Asp Glu Thr Glu Thr Glu Phe
145                 150                 155                 160

Trp Val Leu Tyr Thr Pro Asp Gly Gln Val Ala Leu Leu Gly Arg Asn
                165                 170                 175

Ala Gln Ala Arg Ile Ser Asn Pro Thr Ala Pro Thr Gln Thr Ala Val
            180                 185                 190

Trp Leu Met Glu Ser Ser Val Ser Leu Thr Gly Glu Gln Met Tyr Tyr
        195                 200                 205

Gln Tyr Arg Ala Glu Asp Asp Asp Gly Cys Asp Glu Ala Glu Arg Asp
    210                 215                 220

Ala His Pro Gln Ala Gly Ala Gln Arg Tyr Pro Val Ala Val Trp Tyr
225                 230                 235                 240

Gly Asn Arg Gln Ala Ala Arg Thr Leu Pro Ala Leu Val Ser Thr Pro
                245                 250                 255

Ser Met Asp Ser Trp Leu Phe Ile Leu Val Phe Asp Tyr Gly Glu Arg
            260                 265                 270

Ser Ser Val Leu Ser Glu Ala Pro Ala Trp Gln Thr Pro Gly Ser Gly
        275                 280                 285

Glu Trp Leu Cys Arg Gln Asp Cys Phe Ser Gly Tyr Glu Phe Gly Phe
    290                 295                 300

Asn Leu Arg Thr Arg Arg Leu Cys Arg Gln Val Leu Met Phe His Tyr
305                 310                 315                 320

Leu Gly Val Leu Ala Gly Ser Ser Gly Ala Asn Asp Ala Pro Ala Leu
                325                 330                 335

Ile Ser Arg Leu Leu Leu Asp Tyr Arg Glu Ser Pro Ser Leu Ser Leu
            340                 345                 350

Leu Glu Asn Val His Gln Val Ala Tyr Glu Ser Asp Gly Thr Ser Cys
        355                 360                 365

Ala Leu Pro Ala Leu Ala Leu Gly Trp Gln Thr Phe Thr Pro Pro Thr
    370                 375                 380

Leu Ser Ala Trp Gln Thr Arg Asp Asp Met Gly Lys Leu Ser Leu Leu
385                 390                 395                 400

Gln Pro Tyr Gln Leu Val Asp Leu Asn Gly Glu Gly Val Val Gly Ile
                405                 410                 415

Leu Tyr Gln Asp Ser Gly Ala Trp Trp Tyr Arg Glu Pro Val Arg Gln
            420                 425                 430
```

```
Ser Gly Asp Asp Pro Asp Ala Val Thr Trp Gly Ala Ala Ala Ala Leu
        435                 440                 445

Pro Thr Met Pro Ala Leu His Asn Ser Gly Ile Leu Ala Asp Leu Asn
    450                 455                 460

Gly Asp Gly Arg Leu Glu Trp Val Val Thr Ala Pro Gly Val Ala Gly
465                 470                 475                 480

Met Tyr Asp Arg Thr Pro Gly Arg Asp Trp Leu His Phe Thr Pro Leu
                485                 490                 495

Ser Ala Leu Pro Val Glu Tyr Ala His Pro Lys Ala Val Leu Ala Asp
            500                 505                 510

Ile Leu Gly Ala Gly Leu Thr Asp Met Val Leu Ile Gly Pro Arg Ser
        515                 520                 525

Val Arg Leu Tyr Ser Gly Lys Asn Asp Gly Trp Asn Lys Gly Glu Thr
    530                 535                 540

Val Gln Gln Thr Glu Arg Leu Thr Leu Pro Val Pro Gly Val Asp Pro
545                 550                 555                 560

Arg Thr Leu Val Ala Phe Ser Asp Met Ala Gly Ser Gly Gln Gln His
                565                 570                 575

Leu Thr Glu Val Arg Ala Asn Gly Val Arg Tyr Trp Pro Asn Leu Gly
            580                 585                 590

His Gly Arg Phe Gly Gln Pro Val Asn Ile Pro Gly Phe Ser Gln Ser
        595                 600                 605

Val Thr Thr Phe Asn Pro Asp Gln Ile Leu Leu Ala Asp Thr Asp Gly
    610                 615                 620

Ser Gly Thr Thr Asp Leu Ile Tyr Ala Met Ser Asp Arg Leu Val Ile
625                 630                 635                 640

Tyr Phe Asn Gln Ser Gly Asn Tyr Phe Ala Glu Pro His Thr Leu Leu
                645                 650                 655

Leu Pro Lys Gly Val Arg Tyr Asp Arg Thr Cys Ser Leu Gln Val Ala
            660                 665                 670

Asp Ile Gln Gly Leu Gly Val Pro Ser Leu Leu Leu Thr Val Pro His
        675                 680                 685

Val Ala Pro His His Trp Val Cys His Leu Ser Ala Asp Lys Pro Trp
    690                 695                 700

Leu Leu Asn Gly Met Asn Asn Asn Met Gly Ala Arg His Ala Leu His
705                 710                 715                 720

Tyr Arg Ser Ser Val Gln Phe Trp Leu Asp Glu Lys Ala Glu Ala Leu
                725                 730                 735

Ala Ala Gly Ser Ser Pro Ala Cys Tyr Leu Pro Phe Thr Leu His Thr
            740                 745                 750

Leu Trp Arg Ser Val Val Gln Asp Glu Ile Thr Gly Asn Arg Leu Val
        755                 760                 765

Ser Asp Val Leu Tyr Arg His Gly Val Trp Asp Gly Gln Glu Arg Glu
    770                 775                 780

Phe Arg Gly Phe Gly Phe Val Glu Ile Arg Asp Thr Asp Thr Leu Ala
785                 790                 795                 800

Ser Gln Gly Thr Ala Thr Glu Leu Ser Met Pro Ser Val Ser Arg Asn
                805                 810                 815

Trp Tyr Ala Thr Gly Val Pro Ala Val Asp Glu Arg Leu Pro Glu Thr
            820                 825                 830

Tyr Trp Gln Asn Asp Ala Ala Ala Phe Ala Asp Phe Ala Thr Arg Phe
        835                 840                 845

Thr Val Gly Ser Gly Glu Asp Glu Gln Thr Tyr Thr Pro Asp Asp Ser
```

```
    850                 855                 860

Lys Thr Phe Trp Leu Gln Arg Ala Leu Lys Gly Ile Leu Leu Arg Ser
865                 870                 875                 880

Glu Leu Tyr Gly Ala Asp Gly Ser Ser Gln Ala Asp Ile Pro Tyr Ser
                885                 890                 895

Val Thr Glu Ser Arg Pro Gln Val Arg Leu Val Glu Ala Asn Gly Asp
            900                 905                 910

Tyr Pro Val Val Trp Pro Met Gly Ala Glu Ser Arg Thr Ser Val Tyr
        915                 920                 925

Glu Arg Tyr His Asn Asp Pro Gln Cys Gln Gln Gln Ala Val Leu Leu
    930                 935                 940

Ser Asp Glu Tyr Gly Phe Pro Leu Arg Gln Val Ser Val Asn Tyr Pro
945                 950                 955                 960

Arg Arg Pro Pro Ser Ala Asp Asn Pro Tyr Pro Ala Ser Leu Pro Ala
                965                 970                 975

Thr Leu Phe Ala Asn Ser Tyr Asp Glu Gln Gln Gln Ile Leu Arg Leu
            980                 985                 990

Gly Leu Gln Gln Ser Ser Ala His  His Leu Val Ser Leu  Ser Glu Gly
        995                 1000                1005

His Trp  Leu Leu Gly Leu Ala  Glu Ala Ser Arg Asp  Asp Val Phe
    1010                 1015                 1020

Thr Tyr  Ser Ala Asp Asn Val  Pro Glu Gly Gly Leu  Thr Leu Glu
    1025                 1030                 1035

His Leu  Leu Ala Pro Glu Ser  Leu Val Ser Asp Ser  Gln Val Gly
    1040                 1045                 1050

Thr Leu  Ala Gly Gln Gln Gln  Val Trp Tyr Leu Asp  Ser Gln Asp
    1055                 1060                 1065

Val Ala  Thr Val Ala Ala Pro  Pro Leu Pro Pro Lys  Val Ala Phe
    1070                 1075                 1080

Ile Glu  Thr Ala Val Leu Asp  Glu Gly Met Val Ser  Ser Leu Ala
    1085                 1090                 1095

Ala Tyr  Ile Val Asp Glu His  Leu Glu Gln Ala Gly  Tyr Arg Gln
    1100                 1105                 1110

Ser Gly  Tyr Leu Phe Pro Arg  Gly Arg Glu Ala Glu  Gln Ala Leu
    1115                 1120                 1125

Trp Thr  Gln Cys Gln Gly Tyr  Val Thr Tyr Ala Gly  Ala Glu His
    1130                 1135                 1140

Phe Trp  Leu Pro Leu Ser Phe  Arg Asp Ser Met Leu  Thr Gly Pro
    1145                 1150                 1155

Val Thr  Val Thr Arg Asp Ala  Tyr Asp Cys Val Ile  Thr Gln Trp
    1160                 1165                 1170

Gln Asp  Ala Ala Gly Ile Val  Thr Thr Ala Asp Tyr  Asp Trp Arg
    1175                 1180                 1185

Phe Leu  Thr Pro Val Arg Val  Thr Asp Pro Asn Asp  Asn Leu Gln
    1190                 1195                 1200

Ser Val  Thr Leu Asp Ala Leu  Gly Arg Val Thr Thr  Leu Arg Phe
    1205                 1210                 1215

Trp Gly  Thr Glu Asn Gly Ile  Ala Thr Gly Tyr Ser  Asp Ala Thr
    1220                 1225                 1230

Leu Ser  Val Pro Asp Gly Ala  Ala Ala Ala Leu Ala  Leu Thr Ala
    1235                 1240                 1245

Pro Leu  Pro Val Ala Gln Cys  Leu Val Tyr Val Thr  Asp Ser Trp
    1250                 1255                 1260
```

```
Gly Asp  Asp Asp Asn Glu Lys  Met Pro Pro His Val  Val Val Leu
    1265                 1270                 1275

Ala Thr  Asp Arg Tyr Asp Ser  Asp Thr Gly Gln Gln  Val Arg Gln
    1280                 1285                 1290

Gln Val  Thr Phe Ser Asp Gly  Phe Gly Arg Glu Leu  Gln Ser Ala
    1295                 1300                 1305

Thr Arg  Gln Ala Glu Gly Asn  Ala Trp Gln Arg Gly  Arg Asp Gly
    1310                 1315                 1320

Lys Leu  Val Thr Ala Ser Asp  Gly Leu Pro Val Thr  Val Ala Thr
    1325                 1330                 1335

Asn Phe  Arg Trp Ala Val Thr  Gly Arg Ala Glu Tyr  Asp Asn Lys
    1340                 1345                 1350

Gly Leu  Pro Val Arg Val Tyr  Gln Pro Tyr Phe Leu  Asp Ser Trp
    1355                 1360                 1365

Gln Tyr  Val Ser Asp Asp Ser  Ala Arg Gln Asp Leu  Tyr Ala Asp
    1370                 1375                 1380

Thr His  Phe Tyr Asp Pro Thr  Ala Arg Glu Trp Gln  Val Ile Thr
    1385                 1390                 1395

Ala Lys  Gly Glu Arg Arg Gln  Val Leu Tyr Thr Pro  Trp Phe Val
    1400                 1405                 1410

Val Ser  Glu Asp Glu Asn Asp  Thr Val Gly Leu Asn  Asp Ala Ser
    1415                 1420                 1425


<210> SEQ ID NO 61
<211> LENGTH: 973
<212> TYPE: PRT
<213> ORGANISM: Serratia entomophila

<400> SEQUENCE: 61

Met Ser Thr Ser Leu Phe Ser Ser Thr Pro Ser Val Ala Val Leu Asp
1               5                   10                  15

Asn Arg Gly Leu Leu Val Arg Glu Leu Gln Tyr Tyr Arg His Pro Asp
            20                  25                  30

Thr Pro Glu Glu Thr Asp Glu Arg Ile Thr Cys His Gln His Asp Glu
        35                  40                  45

Arg Gly Ser Leu Ser Gln Ser Ala Asp Pro Arg Leu His Ala Ala Gly
    50                  55                  60

Leu Thr Asn Phe Thr Tyr Leu Asn Ser Leu Thr Gly Thr Val Leu Gln
65                  70                  75                  80

Ser Val Ser Ala Asp Ala Gly Thr Ser Leu Glu Leu Ser Asp Ala Ala
                85                  90                  95

Gly Arg Ala Phe Leu Ala Val Thr Gly Ala Gly Thr Glu Asp Ala Val
            100                 105                 110

Thr Arg Thr Trp Gln Tyr Glu Asp Asp Thr Leu Pro Gly Arg Pro Leu
        115                 120                 125

Ser Ile Thr Glu Gln Val Thr Gly Glu Ala Ala Gln Ile Thr Glu Arg
    130                 135                 140

Phe Val Tyr Ala Gly Asn Thr Asp Ala Glu Lys Ile Leu Asn Leu Ala
145                 150                 155                 160

Gly Gln Cys Val Ser His Tyr Asp Thr Ala Gly Leu Val Gln Thr Asp
                165                 170                 175

Ser Ile Ala Leu Ser Gly Val Pro Leu Ala Val Thr Arg Gln Leu Leu
            180                 185                 190

Pro Asp Ala Ala Gly Ala Asn Trp Met Gly Glu Asp Ala Ser Ala Trp
        195                 200                 205
```

-continued

```
Asn Asp Leu Leu Asp Gly Glu Thr Phe Phe Thr Gln Thr His Ala Asp
    210                 215                 220

Ala Thr Gly Ala Val Leu Ser Ile Thr Asp Ala Lys Gly Asn Leu Gln
225                 230                 235                 240

Arg Val Ala Tyr Asp Val Ala Gly Leu Leu Ser Gly Ser Trp Leu Thr
                245                 250                 255

Leu Lys Asp Gly Thr Glu Gln Val Ile Val Ala Ser Leu Thr Tyr Ser
            260                 265                 270

Ala Ala Gly Lys Lys Leu Arg Glu Glu His Gly Asn Gly Val Val Thr
        275                 280                 285

Ser Tyr Ile Tyr Glu Pro Glu Thr Gln Arg Leu Thr Gly Ile Lys Thr
    290                 295                 300

Glu Arg Pro Ser Gly His Val Ala Gly Ala Lys Val Leu Gln Asp Leu
305                 310                 315                 320

Arg Tyr Thr Tyr Asp Pro Val Gly Asn Val Leu Ser Val Asn Asn Asp
                325                 330                 335

Ala Glu Glu Thr Arg Phe Trp Arg Asn Gln Lys Val Val Pro Glu Asn
            340                 345                 350

Thr Tyr Ile Tyr Asp Ser Leu Tyr Gln Leu Val Ser Ala Thr Gly Arg
        355                 360                 365

Glu Met Ala Asn Ala Gly Gln Gln Gly Asn Asp Leu Pro Ser Ala Thr
    370                 375                 380

Ala Pro Leu Pro Thr Asp Ser Ser Ala Tyr Thr Asn Tyr Thr Arg Thr
385                 390                 395                 400

Tyr Arg Tyr Asp Arg Gly Gly Asn Leu Thr Gln Met Arg His Ser Ala
                405                 410                 415

Pro Ala Thr Asn Asn Asn Tyr Thr Thr Asp Ile Thr Val Ser Asp Arg
            420                 425                 430

Ser Asn Arg Ala Val Leu Ser Thr Leu Ala Glu Val Pro Ser Asp Val
        435                 440                 445

Asp Met Leu Phe Ser Ala Gly Gly His Gln Lys His Leu Gln Pro Gly
    450                 455                 460

Gln Ala Leu Val Trp Thr Pro Arg Gly Glu Leu Gln Lys Val Thr Pro
465                 470                 475                 480

Val Val Arg Asp Gly Gly Ala Asp Asp Ser Glu Ser Tyr Arg Tyr Asp
                485                 490                 495

Ala Gly Ser Gln Arg Ile Ile Lys Thr Gly Thr Arg Gln Thr Gly Asn
            500                 505                 510

Asn Val Gln Thr Gln Arg Val Val Tyr Leu Pro Gly Leu Glu Leu Arg
        515                 520                 525

Ile Met Ala Asn Gly Val Thr Glu Lys Glu Ser Leu Gln Val Ile Thr
    530                 535                 540

Val Gly Glu Ala Gly Arg Ala Gln Val Arg Val Leu His Trp Glu Ile
545                 550                 555                 560

Gly Lys Pro Asp Asp Leu Asp Glu Asp Ser Val Arg Tyr Ser Tyr Asp
                565                 570                 575

Asn Leu Val Gly Ser Ser Gln Leu Glu Leu Asp Arg Glu Gly Tyr Leu
            580                 585                 590

Ile Ser Glu Glu Glu Phe Tyr Pro Tyr Gly Gly Thr Ala Val Leu Thr
        595                 600                 605

Ala Arg Ser Glu Val Glu Ala Asp Tyr Lys Thr Ile Arg Tyr Ser Gly
    610                 615                 620

Lys Glu Arg Asp Ala Thr Gly Leu Asp Tyr Tyr Gly Tyr Arg Tyr Tyr
625                 630                 635                 640
```

```
Gln Pro Trp Ala Gly Arg Trp Leu Ser Thr Asp Pro Ala Gly Thr Val
                645                 650                 655

Asp Gly Leu Asn Leu Phe Arg Met Val Arg Asn Asn Pro Val Thr Leu
            660                 665                 670

Phe Asp Ser Asn Gly Arg Ile Ser Thr Gly Gln Glu Ala Arg Arg Leu
        675                 680                 685

Val Gly Glu Ala Phe Val His Pro Leu His Met Pro Val Phe Glu Arg
    690                 695                 700

Ile Ser Val Glu Arg Lys Ile Ser Met Ser Val Arg Glu Ala Gly Ile
705                 710                 715                 720

Tyr Thr Ile Ser Ala Leu Gly Glu Gly Ala Ala Ala Lys Gly His Asn
                725                 730                 735

Ile Leu Glu Lys Thr Ile Lys Pro Gly Ser Leu Lys Ala Ile Tyr Gly
            740                 745                 750

Asp Lys Ala Glu Ser Ile Leu Gly Leu Ala Lys Arg Ser Gly Leu Val
        755                 760                 765

Gly Arg Val Gly Gln Trp Asp Ala Ser Gly Val Arg Gly Ile Tyr Ala
    770                 775                 780

His Asn Arg Pro Gly Gly Glu Asp Leu Val Tyr Pro Val Ser Leu Gln
785                 790                 795                 800

Asn Thr Ser Ala Asn Glu Ile Val Asn Ala Trp Ile Lys Phe Lys Ile
                805                 810                 815

Ile Thr Pro Tyr Thr Gly Asp Tyr Asp Met His Asp Ile Ile Lys Phe
            820                 825                 830

Ser Asp Gly Lys Gly His Val Pro Thr Ala Glu Ser Ser Glu Glu Arg
        835                 840                 845

Gly Val Lys Asp Leu Ile Asn Lys Gly Val Ala Glu Val Asp Pro Ser
    850                 855                 860

Arg Pro Phe Glu Tyr Thr Ala Met Asn Val Ile Arg His Gly Pro Gln
865                 870                 875                 880

Val Asn Phe Val Pro Tyr Met Trp Glu His Glu His Asp Lys Val Val
                885                 890                 895

Asn Asp Asn Gly Tyr Leu Gly Val Val Ala Ser Pro Gly Pro Phe Pro
            900                 905                 910

Val Ala Met Val His Gln Gly Glu Trp Thr Val Phe Asp Asn Ser Glu
        915                 920                 925

Glu Leu Phe Asn Phe Tyr Lys Ser Thr Asn Thr Pro Leu Pro Glu His
    930                 935                 940

Trp Ser Gln Asp Phe Met Asp Arg Gly Lys Gly Ile Val Ala Thr Pro
945                 950                 955                 960

Arg His Ala Glu Leu Leu Asp Lys Arg Arg Val Met Tyr
                965                 970


<210> SEQ ID NO 62
<211> LENGTH: 2499
<212> TYPE: PRT
<213> ORGANISM: Photorhabdus luminescens

<400> SEQUENCE: 62

Met Asn Thr Leu Lys Ser Glu Tyr Gln Gln Ala Leu Gly Ala Gly Phe
1               5                   10                  15

Asn Asn Leu Thr Asp Ile Cys His Leu Ser Phe Asp Glu Leu Arg Lys
            20                  25                  30

Lys Val Lys Asp Lys Leu Ser Trp Ser Gln Thr Gln Ser Leu Tyr Leu
        35                  40                  45
```

```
Glu Ala Gln Gln Val Gln Lys Asp Asn Leu Leu His Glu Ala Arg Ile
    50                  55                  60

Leu Lys Arg Ala Asn Pro His Leu Gln Ser Ala Val His Leu Ala Leu
65                  70                  75                  80

Thr Ala Pro His Ala Asp Gln Gln Gly Tyr Asn Ser Arg Phe Gly Asn
                85                  90                  95

Arg Ala Ser Lys Tyr Ala Ala Pro Gly Ala Ile Ser Ser Met Phe Ser
            100                 105                 110

Leu Ala Ala Tyr Leu Thr Glu Leu Tyr Arg Gln Ala Arg Asn Leu His
        115                 120                 125

Ala Glu Gly Ser Ile Tyr His Leu Asp Thr Arg Arg Pro Asp Leu Lys
    130                 135                 140

Ser Leu Val Leu Ser Gln Lys Asn Met Asn Thr Glu Ile Ser Thr Leu
145                 150                 155                 160

Ser Leu Ser Asn Asn Met Leu Leu Asn Ser Ile Lys Thr Gln Pro Asn
                165                 170                 175

Leu Asn Ser His Ala Lys Val Met Glu Lys Leu Ser Thr Phe Arg Thr
            180                 185                 190

Ser Gly Ser Met Pro Tyr His Asp Ala Tyr Glu Ser Val Arg Lys Ile
        195                 200                 205

Ile Gln Leu Gln Ala Pro Val Phe Glu Gln Ser Ser Thr Leu Thr Asp
    210                 215                 220

Thr Pro Ile Thr Lys Leu Met Tyr Gln Ile Ser Leu Leu Gly Ile Asn
225                 230                 235                 240

Ala Ser Val Ser Pro Glu Leu Phe Thr Ile Leu Thr Gln Lys Ile Lys
                245                 250                 255

Pro Ala Thr Asn Ala Asp Asn Thr Asn Glu Leu Lys Lys Leu Tyr Lys
            260                 265                 270

Lys Asn Phe Gly Glu Ile Lys Ser Ile Gln Met Ala Arg Ala Glu Tyr
        275                 280                 285

Leu Lys Ser Tyr Tyr Asn Leu Thr Asp Lys Glu Leu Asn Gln Phe Ser
    290                 295                 300

Lys Lys Ile Lys Gln Ile Asp Ser Leu Trp Asn Ile Gly Asp Glu Ile
305                 310                 315                 320

Thr Gln Tyr His Leu Leu Lys Phe Asn Lys Ala Ile Asn Leu Ser Arg
                325                 330                 335

Ser Thr Glu Leu Ser Pro Ile Ile Leu Asn Ser Ile Ala Ile Asp Ile
            340                 345                 350

Leu Lys Lys Thr Pro Pro Glu Asp Asp Ser Asp Asn Pro Phe Arg Asp
        355                 360                 365

Asp Pro Asp Tyr Leu Glu Ser Phe Gln Asp Leu Asp Leu Ser Asp Glu
    370                 375                 380

Pro Asp Ile Asp Glu Asp Val Leu Arg Glu Ala Leu Arg Val Lys Asp
385                 390                 395                 400

Tyr Met Gln Arg Tyr Gly Ile Asp Ala Glu Thr Ala Leu Ile Leu Cys
                405                 410                 415

Lys Ala Pro Ile Ser Glu Asn Pro Ser His Pro Asp Leu Ser Lys Leu
            420                 425                 430

Leu Ala Asp Ile His Gln Leu Thr Ile Asp Glu Leu Gly Val Leu Leu
        435                 440                 445

Val Ala Ile Asp Glu Gly Lys Thr Asp Leu Ser Gln Ile Thr His Asp
    450                 455                 460

Asn Leu Ala Val Leu Ile Ser Lys Leu Tyr Ser Val Thr Asn Trp Leu
```

```
465                 470                 475                 480

Arg Thr Arg Lys Trp Ser Val Tyr Gln Leu Phe Val Met Thr Thr Asp
                485                 490                 495

Lys Tyr Asn Lys Thr Leu Thr Pro Glu Ile Asn Asn Leu Leu Asp Thr
            500                 505                 510

Val Tyr Asn Gly Leu Gln Asn Phe Tyr Lys Asp Asn Leu Leu Lys Ile
        515                 520                 525

Lys Asp Asn Leu Leu Lys Ala Lys Glu Ser Leu Pro Glu Asp Lys Asp
    530                 535                 540

Asn Leu Pro Lys Ala Glu Gln Tyr Leu Leu Glu Ala Glu Lys Tyr Leu
545                 550                 555                 560

Leu Ala Ala Glu Lys Tyr Leu Leu Ala Ala Glu Lys Tyr Leu Leu Glu
                565                 570                 575

Ala Asn Lys Asn Pro Leu Glu Ala Lys Lys Ala Leu Lys Glu Tyr Glu
            580                 585                 590

Lys Asn Gln Glu Ala Tyr Glu Lys Asn Leu Lys Glu His Glu Lys Tyr
        595                 600                 605

Leu Leu Lys Ala Gly Glu Asn Leu Pro Ala Ile Lys Glu Asn Leu Leu
    610                 615                 620

Lys Ile Lys Glu Asn Leu Pro Lys Ala Ile Ser Pro Tyr Ile Ala Ala
625                 630                 635                 640

Ala Leu Gln Leu Pro Ser Glu Asn Val Ala Leu Ser Val Leu Ala Trp
                645                 650                 655

Ala Asp Lys Leu Asn Ser Gly Lys Glu Asn Lys Met Thr Ala Asp Ser
            660                 665                 670

Phe Trp Asn Trp Leu Arg Lys Lys Pro Ile Glu Thr Gln Ser Lys Thr
        675                 680                 685

Thr Glu Ala Thr Glu Ala Thr Glu Ala Thr Glu Ala Thr Glu Ala Thr
    690                 695                 700

Glu Ala Thr Glu Lys Thr Thr Leu Ile Gln Gln Ala Val Gln Tyr Cys
705                 710                 715                 720

Gln Cys Leu Ala Gln Leu Ala Leu Ile Tyr Arg Ser Thr Gly Leu Ser
                725                 730                 735

Glu Ser Thr Leu Arg Leu Phe Val Thr Asn Pro Gln Ile Phe Gly Leu
            740                 745                 750

Thr Ala Lys Thr Thr Ser Thr His Asn Val Leu Ser Leu Ile Met Leu
        755                 760                 765

Thr Arg Phe Thr Asp Trp Val Asn Ser Leu Gly Glu Asn Ala Ser Ser
    770                 775                 780

Val Leu Thr Glu Phe Glu Lys Gly Thr Leu Thr Ala Glu Leu Leu Ala
785                 790                 795                 800

Asn Ala Met Asn Leu Asp Lys Asn Leu Leu Glu Gln Ala Ser Thr Gln
                805                 810                 815

Ala Gln Ala Asp Phe Ser Asn Trp Pro Ser Ile Asp Asn Leu Leu Gln
            820                 825                 830

Trp Ile Asn Ile Ser Arg Gln Leu Asn Ile Ser Pro Gln Gly Val Ser
        835                 840                 845

Glu Leu Ala Lys Ile Leu Asp Ile Glu Ser Ser Thr Asn Tyr Ala Gln
    850                 855                 860

Trp Glu Asn Val Ala Ser Ile Leu Thr Ala Gly Leu Asp Thr Gln Lys
865                 870                 875                 880

Ala Asn Thr Leu His Ala Phe Leu Gly Glu Ser Arg Ser Thr Ala Leu
                885                 890                 895
```

```
Ser Thr Tyr Tyr Ile Tyr Ser His Asn Gln Lys Asp Arg Glu Glu Arg
            900                 905                 910

Lys His Thr Val Ile Lys Asp Arg Asp Asp Leu Tyr Gln Tyr Leu Leu
        915                 920                 925

Ile Asp Asn Gln Val Ser Ala Ala Ile Lys Thr Thr Glu Ile Ala Glu
    930                 935                 940

Ala Ile Ala Ser Ile Gln Leu Tyr Ile Asn Arg Ala Leu Lys Asn Met
945                 950                 955                 960

Glu Gly Asp Thr Asp Thr Ser Val Thr Ser Arg Leu Phe Phe Thr Asn
                965                 970                 975

Trp Asp Lys Tyr Asn Lys Arg Tyr Ser Thr Trp Ala Gly Ile Thr Lys
            980                 985                 990

Leu Leu Tyr Tyr Pro Glu Asn Tyr  Ile Asp Pro Thr Leu  Arg Ile Gly
        995                 1000                 1005

Gln Thr  Lys Met Met Asp Thr  Leu Leu Gln Ser Ile  Ser Gln Ser
    1010                 1015                 1020

Gln Leu  Asn Thr Asp Thr Val  Glu Asp Ala Phe Lys  Ser Tyr Leu
    1025                 1030                 1035

Thr Ser  Phe Glu Gln Val Ala  Asn Leu Glu Val Ile  Ser Ala Tyr
    1040                 1045                 1050

His Asp  Asn Ile Asn Asn Asp  Gln Gly Leu Thr Tyr  Phe Ile Gly
    1055                 1060                 1065

Arg Ser  Lys Thr Glu Val Asn  Gln Tyr Tyr Trp Arg  Ser Val Asp
    1070                 1075                 1080

His Asn  Lys Phe Ser Glu Gly  Lys Phe Pro Ala Asn  Ala Trp Ser
    1085                 1090                 1095

Glu Trp  His Lys Ile Asp Cys  Pro Ile Asn Pro Tyr  Glu Asp Thr
    1100                 1105                 1110

Ile Arg  Pro Val Val Tyr Gln  Ser Arg Leu Tyr Ile  Ile Trp Leu
    1115                 1120                 1125

Glu Gln  Lys Lys Val Thr Asn  Arg Ala Glu Gly Glu  Ala Ile Lys
    1130                 1135                 1140

Gln Gly  Ser Lys Thr Thr Thr  Ser Tyr His Tyr Glu  Leu Lys Leu
    1145                 1150                 1155

Ala His  Ile Arg Tyr Asp Gly  Thr Trp Asn Thr Pro  Ile Thr Phe
    1160                 1165                 1170

Asp Val  Asp Glu Lys Ile Ser  Gly Leu Asn Leu Glu  Leu Asn Lys
    1175                 1180                 1185

Ala Leu  Gly Leu Tyr Cys Ala  Ser Tyr Gln Gly Lys  Asp Lys Leu
    1190                 1195                 1200

Leu Val  Met Phe Tyr Lys Lys  Gln Glu Gln Leu Asn  Asn Tyr Thr
    1205                 1210                 1215

Glu Lys  Thr Gly Asn Thr Tyr  Thr Ala Pro Ile Lys  Gly Leu Tyr
    1220                 1225                 1230

Ile Thr  Ser Asn Met Ser Pro  Glu Glu Met Thr Pro  Glu Ser Tyr
    1235                 1240                 1245

Arg Leu  Asn Ala His Lys Gln  Phe Asp Thr Asn Asn  Val Val Arg
    1250                 1255                 1260

Val Asn  Asn Arg Tyr Ala Glu  Ser Tyr Glu Ile Pro  Ser Ser Val
    1265                 1270                 1275

Asn Ser  Asn Asn Gly Tyr Asp  Trp Gly Glu Gly Tyr  Leu Ser Met
    1280                 1285                 1290

Val Tyr  Gly Gly Ser Ile Leu  Ile Thr Arg Asp Pro  Ser Asp Asn
    1295                 1300                 1305
```

```
Ser Lys  Ile Gln Ile Ser Pro  Lys Leu Arg Ile Ile  His Asn Gly
    1310                 1315                 1320

Tyr Glu  Gly Arg Gln Arg Asn  Gln Cys Asn Leu Met  Lys Lys Tyr
    1325                 1330                 1335

Gly Lys  Leu Gly Asp Lys Phe  Ile Ile Tyr Thr Thr  Leu Gly Ile
    1340                 1345                 1350

Asn Pro  Asn Asn Leu Ser Asn  Lys Lys Leu Ile Tyr  Pro Val Tyr
    1355                 1360                 1365

Gln Tyr  Glu Gly Asn Glu Ser  Lys Leu Ser Gln Gly  Arg Leu Leu
    1370                 1375                 1380

Phe Tyr  Arg Asp Ser Thr Thr  Asn Phe Thr Arg Ala  Trp Phe Pro
    1385                 1390                 1395

Asn Leu  Ser Ser Asp Ser Lys  Glu Met Ser Ile Thr  Thr Gly Gly
    1400                 1405                 1410

Asn Ile  Ser Gly Asn Tyr Gly  Tyr Ile Asp Asn Lys  His Ser Asp
    1415                 1420                 1425

Asn Lys  Pro Phe Glu Glu Tyr  Phe Tyr Met Asp Asp  His Gly Gly
    1430                 1435                 1440

Ile Asp  Thr Asp Val Ser Glu  Pro Ile Phe Ile Asn  Thr Lys Ile
    1445                 1450                 1455

Gln Pro  Ser Asn Val Lys Ile  Ile Val Lys Thr Val  Lys Asp Asp
    1460                 1465                 1470

Gly Lys  Leu Asp Ser Lys Pro  Tyr Ile Ala Glu Asp  Lys Val Ser
    1475                 1480                 1485

Val Lys  Pro Thr Pro Asn Phe  Glu Glu Met Cys Tyr  Gln Phe Asn
    1490                 1495                 1500

Asn Leu  Asp Gln Ile Asp Val  Ser Thr Leu Val Phe  Lys Asn Asn
    1505                 1510                 1515

Glu Ala  Ser Ile Asp Ile Thr  Phe Thr Ala Ser Ala  Asp Ala Phe
    1520                 1525                 1530

Glu Ser  Gly Lys Glu Gln Arg  Asn Leu Gly Glu Glu  His Phe Ser
    1535                 1540                 1545

Ile Arg  Ile Ile Lys Lys Ala  Asn Val Asn Asp Val  Leu Thr Leu
    1550                 1555                 1560

His His  Asp Pro Ser Gly Ala  Gln Tyr Met Gln Trp  Gly Ala Tyr
    1565                 1570                 1575

Arg Thr  Arg Leu Asn Thr Leu  Phe Ala Arg Lys Leu  Ile Ser Arg
    1580                 1585                 1590

Ala Asn  Ala Gly Ile Asp Thr  Ile Leu Ser Met Glu  Thr Gln Asn
    1595                 1600                 1605

Ile Gln  Glu Pro Gln Leu Gly  Lys Gly Phe Tyr Val  Asn Phe Thr
    1610                 1615                 1620

Leu Pro  Lys Tyr Asp Gln Asn  Thr His Gly Asn Glu  Arg Gln Phe
    1625                 1630                 1635

Lys Ile  His Ile Gly Asn Ile  Ala Gly Asp Asn Thr  Met Arg Pro
    1640                 1645                 1650

Tyr Tyr  Gln Gly Ile Leu Ala  Asp Thr Glu Thr Ser  Val Val Leu
    1655                 1660                 1665

Phe Val  Pro Tyr Glu Lys Gln  Ser Tyr Thr Asn Glu  Gly Val Arg
    1670                 1675                 1680

Leu Gly  Val Glu Tyr Lys Lys  Val Ser Tyr Leu Gly  Val Trp Glu
    1685                 1690                 1695

Pro Ala  Phe Phe Tyr Phe Asn  Glu Ile Gln Gln Lys  Phe Ile Leu
```

1700 1705 1710

Ile Asn Asp Ala Asp His Asn Ser Ala Met Thr Gln Ser Gly Glu
1715 1720 1725

Lys Thr Gly Ile Lys Lys Tyr Lys Gly Phe Leu Asp Val Ser Ile
1730 1735 1740

Leu Ile Asp His Gln His Thr Glu Pro Met Asp Phe Asn Gly Ala
1745 1750 1755

Asn Ser Leu Tyr Phe Trp Glu Leu Phe Tyr Tyr Thr Pro Met Leu
1760 1765 1770

Ile Ala Gln Arg Leu Leu His Glu Gln Asn Phe Asp Glu Ala Asn
1775 1780 1785

Arg Trp Leu Lys Tyr Val Trp Asn Pro Ser Gly His Ile Ala Asn
1790 1795 1800

Gly Gln Lys Gln His Pro His Asn Trp Asn Val Arg Pro Leu Gln
1805 1810 1815

Glu Asp Thr Ser Trp Asn Asp Asp Pro Leu Asp Thr Phe Asp Pro
1820 1825 1830

Asp Ala Ile Ala Gln His Asp Pro Met His Tyr Lys Val Ala Thr
1835 1840 1845

Phe Met Cys Ala Leu Asp Leu Leu Ile Glu Gln Gly Asp Tyr Ala
1850 1855 1860

Tyr Arg Gln Leu Glu Arg Asp Thr Leu Ala Glu Ala Lys Met Trp
1865 1870 1875

Tyr Met Gln Ala Leu His Leu Leu Gly Asp Lys Pro His Leu Leu
1880 1885 1890

Leu Ser Ser Thr Trp Ser Asp Pro Glu Leu Lys Glu Ala Ala Asp
1895 1900 1905

Leu Glu Lys Gln Gln Ala His Ala Lys Ala Ile Ala Asp Leu Arg
1910 1915 1920

Gln Gly Gln Pro Lys Asp Gly Ser Asn Thr Asp Leu Phe Leu Pro
1925 1930 1935

Gln Val Asn Glu Val Met Leu Ser Tyr Trp Gln Lys Leu Glu Gln
1940 1945 1950

Arg Leu Tyr Asn Leu Arg His Asn Leu Ser Ile Asp Gly Gln Pro
1955 1960 1965

Leu His Leu Pro Ile Phe Ala Thr Pro Ala Asp Pro Lys Ala Leu
1970 1975 1980

Leu Ser Ala Ala Val Ala Ser Ser Gln Gly Gly Ser Asn Leu Pro
1985 1990 1995

Ser Glu Phe Ile Ser Val Trp Arg Phe Pro His Met Leu Glu Asn
2000 2005 2010

Ala Arg Ser Met Val Ser Gln Leu Thr Gln Phe Gly Ser Thr Leu
2015 2020 2025

Gln Asn Ile Ile Glu Arg Gln Asp Ala Glu Ala Leu Asn Thr Leu
2030 2035 2040

Leu Gln Asn Gln Ala Ala Glu Leu Ile Leu Thr Asn Leu Ser Ile
2045 2050 2055

Gln Asp Lys Thr Ile Glu Glu Leu Asp Val Glu Lys Thr Val Leu
2060 2065 2070

Glu Lys Thr Arg Ala Gly Ala Lys Ser Arg Phe Asp Ser Tyr Ser
2075 2080 2085

Lys Phe Tyr Asp Glu Asp Ile Asn Ala Gly Glu Lys Gln Ala Met
2090 2095 2100

-continued

```
Ala Leu  Arg Ala Ser Val Ala  Gly Ile Ser Thr Ala  Leu Gln Ala
    2105                 2110                 2115

Ser His  Leu Ala Gly Ala Ala  Leu Asp Leu Ala Pro  Asn Ile Phe
    2120                 2125                 2130

Gly Phe  Ala Asp Gly Gly Ser  His Trp Gly Ala Ile  Ala Gln Ala
    2135                 2140                 2145

Thr Ser  Asn Val Met Glu Phe  Ser Ala Ser Val Met  Ser Thr Glu
    2150                 2155                 2160

Ala Asp  Lys Ile Ser Gln Ser  Glu Ala Tyr Arg Arg  Arg Arg Gln
    2165                 2170                 2175

Glu Trp  Lys Ile Gln Arg Asn  Asn Ala Asp Ala Glu  Leu Lys Gln
    2180                 2185                 2190

Ile Asp  Ala Gln Leu Gln Ser  Leu Val Val Arg Arg  Glu Ala Ala
    2195                 2200                 2205

Val Leu  Gln Lys Thr Ser Leu  Lys Thr Gln Gln Glu  Gln Thr His
    2210                 2215                 2220

Ala Gln  Leu Thr Phe Leu Gln  His Lys Phe Ser Asn  Gln Ala Leu
    2225                 2230                 2235

Tyr Asn  Trp Leu Arg Gly Arg  Leu Ser Ala Ile Tyr  Phe Gln Phe
    2240                 2245                 2250

Tyr Asp  Leu Ala Val Ala Arg  Cys Leu Met Ala Glu  Met Ala Tyr
    2255                 2260                 2265

Arg Trp  Glu Thr Asn Asp Ala  Ala Ala Arg Phe Ile  Lys Pro Gly
    2270                 2275                 2280

Ala Trp  Gln Gly Thr His Ala  Gly Leu Leu Ala Gly  Glu Thr Leu
    2285                 2290                 2295

Met Leu  Asn Leu Ala Gln Met  Glu Asp Ala His Leu  Lys Gln Glu
    2300                 2305                 2310

Gln Arg  Val Leu Glu Val Glu  Arg Thr Val Ser Leu  Ala Glu Val
    2315                 2320                 2325

Tyr Lys  Glu Lys Gly Gln Phe  Ser Leu Thr Lys Lys  Ile Ala Glu
    2330                 2335                 2340

Leu Val  Asn Lys Lys Pro Asp  Thr Thr Ser Ser Arg  Asn Asn Thr
    2345                 2350                 2355

Leu Asn  Phe Gly Glu Gly Asn  Ala Lys Thr Ser Leu  Gln Ala Ser
    2360                 2365                 2370

Ile Ser  Leu Ala Asp Leu Gln  Ile Arg His Asp Tyr  Pro Glu Asn
    2375                 2380                 2385

Ser Gly  Ala Gly Asn Val Arg  Arg Ile Lys Gln Ile  Ser Val Thr
    2390                 2395                 2400

Leu Pro  Ala Leu Leu Gly Pro  Tyr Gln Asp Val Gln  Ala Ile Leu
    2405                 2410                 2415

Ser Tyr  Gly Gly Asp Ala Thr  Gly Leu Ala Lys Gly  Cys Lys Ala
    2420                 2425                 2430

Leu Ala  Val Ser His Gly Met  Asn Asp Ser Gly Gln  Phe Gln Leu
    2435                 2440                 2445

Asp Phe  Asn Asp Gly Lys Phe  Leu Pro Phe Glu Gly  Ile Glu Ile
    2450                 2455                 2460

Asp Lys  Gly Thr Leu Thr Leu  Ser Phe Pro Asn Ala  Thr Glu Lys
    2465                 2470                 2475

Gln Lys  Thr Met Leu Glu Ser  Ile Ser Asp Ile Ile  Leu His Ile
    2480                 2485                 2490

Arg Tyr  Thr Ile Arg Gln
    2495
```

<210> SEQ ID NO 63
<211> LENGTH: 2381
<212> TYPE: PRT
<213> ORGANISM: Photorhabdus luminescens

<400> SEQUENCE: 63

Met Asn Ser Tyr Val Lys Glu Ile Pro Asp Val Leu Gln Ser Gln Tyr
1 5 10 15

Gly Ile Asn Cys Leu Thr Asp Ile Cys His Tyr Ser Phe Asn Glu Phe
20 25 30

Arg Gln Gln Val Ser Asp His Leu Ser Trp Ser Glu Thr Asn Arg Leu
35 40 45

Tyr Arg Asp Ala Gln Gln Glu Gln Lys Glu Asn Gln Leu Tyr Glu Ala
50 55 60

Arg Ile Leu Lys Arg Ala Asn Pro Gln Leu Gln Asn Ala Val His Leu
65 70 75 80

Gly Ile Thr Leu Pro His Ala Glu Leu Arg Gly Tyr Asn Ser Glu Phe
85 90 95

Gly Gly Arg Ala Ser Gln Tyr Val Ala Pro Gly Ser Val Ser Ser Met
100 105 110

Phe Ser Pro Ala Ala Tyr Leu Thr Glu Leu Tyr Arg Glu Ala Arg Asn
115 120 125

Leu His Ala Ser Asp Ser Val Tyr His Leu Asp Glu Arg Arg Pro Asp
130 135 140

Leu Gln Ser Met Thr Leu Ser Gln Gln Asn Met Asp Thr Glu Leu Ser
145 150 155 160

Thr Leu Ser Leu Ser Asn Glu Ile Leu Leu Lys Gly Ile Lys Ala Asn
165 170 175

Gln Ser Asn Leu Asp Ser Asp Thr Lys Val Met Glu Met Leu Ser Thr
180 185 190

Phe Arg Pro Ser Gly Thr Ile Pro Tyr His Asp Ala Tyr Glu Asn Val
195 200 205

Arg Lys Ala Ile Gln Leu Gln Asp Pro Lys Leu Glu Gln Phe Gln Lys
210 215 220

Ser Pro Ala Val Ala Gly Leu Met His Gln Ala Ser Leu Leu Gly Ile
225 230 235 240

Asn Asn Ser Ile Ser Pro Glu Leu Phe Asn Ile Leu Thr Glu Glu Ile
245 250 255

Thr Glu Ala Asn Ala Glu Ala Ile Tyr Lys Gln Asn Phe Gly Asp Ile
260 265 270

Asp Pro Ala Cys Leu Ala Met Pro Glu Tyr Leu Lys Ser Tyr Tyr Asn
275 280 285

Phe Ser Asp Glu Glu Leu Ser Gln Phe Ile Arg Lys Tyr Pro Asp Asn
290 295 300

Glu Leu Asn Thr Gln Lys Ile His Leu Leu Lys Ile Asn Lys Ile Ile
305 310 315 320

Leu Leu Ser Gln Ala Val Asn Leu Pro Phe Leu Lys Leu Asp Glu Ile
325 330 335

Ile Pro Glu Gln Asn Ile Thr Pro Thr Val Leu Gly Lys Ile Phe Leu
340 345 350

Val Lys Tyr Tyr Met Gln Lys Tyr Asn Ile Gly Thr Glu Thr Ala Leu
355 360 365

Ile Leu Cys Asn Asp Ser Ile Ser Gln Tyr Ser Tyr Ser Asn Gln Pro
370 375 380

-continued

```
Ser Gln Phe Asp Arg Leu Phe Asn Thr Ser Pro Leu Asn Gly Gln Tyr
385                 390                 395                 400

Phe Val Ile Glu Asp Thr Asn Ile Asp Leu Ser Leu Asn Ser Thr Asp
                405                 410                 415

Asn Trp His Lys Ala Val Leu Lys Arg Ala Phe Asn Val Asp Asp Ile
            420                 425                 430

Ser Leu Tyr Arg Leu Leu His Ile Ala Asn His Asn Asn Thr Asp Gly
        435                 440                 445

Lys Ile Ala Asn Asn Ile Lys Asn Leu Ser Asn Leu Tyr Met Thr Lys
    450                 455                 460

Leu Leu Ala Asp Ile His Gln Leu Thr Ile Asp Glu Leu Tyr Leu Leu
465                 470                 475                 480

Leu Ile Thr Ile Gly Glu Asp Lys Ile Asn Leu Tyr Asp Ile Asp Asp
                485                 490                 495

Lys Glu Leu Glu Lys Leu Ile Asn Arg Leu Asp Thr Leu Ser Asn Trp
            500                 505                 510

Leu His Thr Gln Lys Trp Ser Ile Tyr Gln Leu Phe Leu Met Thr Thr
        515                 520                 525

Thr Asn Tyr Asp Lys Thr Leu Thr Pro Glu Ile Gln Asn Leu Leu Asp
    530                 535                 540

Thr Val Tyr Asn Gly Leu Gln Asn Phe Asp Lys Asn Lys Thr Lys Leu
545                 550                 555                 560

Leu Ala Ala Ile Ala Pro Tyr Ile Ala Ala Thr Leu Gln Leu Pro Ser
                565                 570                 575

Glu Asn Val Ala His Ser Ile Leu Leu Trp Ala Asp Lys Ile Lys Pro
            580                 585                 590

Ser Glu Asn Lys Ile Thr Ala Glu Lys Phe Trp Ile Trp Leu Gln Asn
        595                 600                 605

Arg Asp Thr Thr Glu Leu Ser Lys Pro Pro Glu Met Gln Glu Gln Ile
    610                 615                 620

Ile Gln Tyr Cys His Cys Leu Ala Gln Leu Thr Met Ile Tyr Arg Ser
625                 630                 635                 640

Ser Gly Ile Asn Glu Asn Ala Phe Arg Leu Phe Ile Glu Lys Pro Thr
                645                 650                 655

Ile Phe Gly Ile Pro Asp Glu Pro Asn Lys Ala Thr Pro Ala His Asn
            660                 665                 670

Ala Pro Thr Leu Ile Ile Leu Thr Arg Phe Ala Asn Trp Val Asn Ser
        675                 680                 685

Leu Gly Glu Lys Ala Ser Pro Ile Leu Thr Ala Phe Glu Asn Lys Thr
    690                 695                 700

Leu Thr Ala Glu Lys Leu Ala Asn Ala Met Asn Leu Asp Ala Asn Leu
705                 710                 715                 720

Leu Glu Gln Ala Ser Ile Gln Ala Gln Asn Tyr Lys Gln Val Thr Lys
                725                 730                 735

Glu Asn Thr Phe Ser Asn Trp Gln Ser Ile Asp Ile Ile Leu Gln Trp
            740                 745                 750

Thr Asn Ile Ala Ser Asn Leu Asn Ile Ser Pro Gln Gly Ile Ser Pro
        755                 760                 765

Leu Ile Ala Leu Asp Tyr Ile Lys Pro Ala Gln Lys Thr Pro Thr Tyr
    770                 775                 780

Ala Gln Trp Glu Asn Ala Ala Ile Ala Leu Thr Ala Gly Leu Asp Thr
785                 790                 795                 800

Gln Gln Thr His Thr Leu His Val Phe Leu Asp Glu Ser Arg Ser Thr
```

```
                805                 810                 815

Ala Leu Ser Asn Tyr Tyr Ile Gly Lys Val Ala Asn Arg Ala Ala Ser
            820                 825                 830

Ile Lys Ser Arg Asp Asp Leu Tyr Gln Tyr Leu Leu Ile Asp Asn Gln
        835                 840                 845

Val Ser Ala Glu Ile Lys Thr Thr Arg Ile Ala Glu Ala Ile Ala Ser
    850                 855                 860

Ile Gln Leu Tyr Val Asn Arg Ala Leu Glu Asn Ile Glu Ile His Ala
865                 870                 875                 880

Val Ser Asp Val Ile Thr Arg Gln Phe Phe Ile Asp Trp Asp Lys Tyr
                885                 890                 895

Asn Lys Arg Tyr Ser Thr Trp Ala Gly Val Ser Gln Leu Val Tyr Tyr
            900                 905                 910

Pro Glu Asn Tyr Ile Asp Pro Thr Met Arg Ile Gly Gln Thr Lys Met
        915                 920                 925

Met Asp Thr Leu Leu Gln Ser Val Ser Gln Ser Gln Leu Asn Ala Asp
    930                 935                 940

Thr Val Glu Asp Ala Phe Lys Ser Tyr Leu Thr Ser Phe Glu Gln Val
945                 950                 955                 960

Ala Asn Leu Glu Val Ile Ser Ala Tyr His Asp Asn Val Asn Asn Asp
                965                 970                 975

Gln Gly Leu Thr Tyr Phe Ile Gly Asn Ser Lys Thr Glu Val Asn Gln
            980                 985                 990

Tyr Tyr Trp Arg Ser Val Asp His  Ser Lys Phe Asn Asp  Gly Lys Phe
        995                 1000                1005

Ala Ala  Asn Ala Trp Ser Glu  Trp His Lys Ile Asp  Cys Ala Ile
    1010                 1015                 1020

Asn Pro  Tyr Gln Ser Thr Ile  Arg Pro Val Ile Tyr  Lys Ser Arg
    1025                 1030                 1035

Leu Tyr  Leu Ile Trp Leu Glu  Gln Lys Glu Thr Ala  Lys Gln Lys
    1040                 1045                 1050

Glu Asp  Asn Lys Val Thr Thr  Asp Tyr His Tyr Glu  Leu Lys Leu
    1055                 1060                 1065

Ala His  Ile Arg Tyr Asp Gly  Thr Trp Asn Val Pro  Ile Thr Phe
    1070                 1075                 1080

Asp Val  Asp Glu Lys Ile Leu  Ala Leu Glu Leu Thr  Lys Ser Gln
    1085                 1090                 1095

Ala Pro  Gly Leu Tyr Cys Ala  Gly Tyr Gln Gly Glu  Asp Thr Leu
    1100                 1105                 1110

Leu Ile  Met Phe Tyr Arg Lys  Lys Glu Lys Leu Asp  Asp Tyr Lys
    1115                 1120                 1125

Thr Ala  Pro Met Gln Gly Phe  Tyr Ile Phe Ser Asp  Met Ser Ser
    1130                 1135                 1140

Lys Asp  Met Thr Asn Glu Gln  Cys Asn Ser Tyr Arg  Asp Asn Gly
    1145                 1150                 1155

Tyr Thr  His Phe Asp Thr Asn  Ser Asp Thr Asn Ser  Val Ile Arg
    1160                 1165                 1170

Ile Asn  Asn Arg Tyr Ala Glu  Asp Tyr Glu Ile Pro  Ser Leu Ile
    1175                 1180                 1185

Asn His  Ser Asn Ser His Asp  Trp Gly Glu Tyr Asn  Leu Ser Gln
    1190                 1195                 1200

Val Tyr  Gly Gly Asn Ile Val  Ile Asn Tyr Lys Val  Thr Ser Asn
    1205                 1210                 1215
```

```
Asp Leu  Lys Ile Tyr Ile Ser  Pro Lys Leu Arg Ile  Ile His Asp
    1220                 1225                 1230

Gly Lys  Glu Gly Arg Glu Arg  Ile Gln Ser Asn Leu  Ile Lys Lys
    1235                 1240                 1245

Tyr Gly  Lys Leu Gly Asp Lys  Phe Ile Ile Tyr Thr  Ser Leu Gly
    1250                 1255                 1260

Ile Asn  Pro Asn Asn Ser Ser  Asn Arg Phe Met Phe  Tyr Pro Val
    1265                 1270                 1275

Tyr Gln  Tyr Asn Gly Asn Thr  Ser Gly Leu Ala Gln  Gly Arg Leu
    1280                 1285                 1290

Leu Phe  His Arg Asp Thr Ser  Tyr Ser Ser Lys Val  Ala Ala Trp
    1295                 1300                 1305

Ile Pro  Gly Ala Gly Arg Ser  Leu Ile Asn Glu Asn  Ala Asn Ile
    1310                 1315                 1320

Gly Asp  Asp Cys Ala Glu Asp  Ser Val Asn Lys Pro  Asp Asp Leu
    1325                 1330                 1335

Lys Gln  Tyr Ile Tyr Met Thr  Asp Ser Lys Gly Thr  Ala Thr Asp
    1340                 1345                 1350

Val Ser  Gly Pro Val Asp Ile  Asn Thr Ala Ile Ser  Ser Glu Lys
    1355                 1360                 1365

Val Gln  Ile Thr Ile Lys Ala  Gly Lys Glu Tyr Ser  Leu Thr Ala
    1370                 1375                 1380

Asn Lys  Asp Val Ser Val Gln  Pro Ser Pro Ser Phe  Glu Glu Met
    1385                 1390                 1395

Cys Tyr  Gln Phe Asn Ala Leu  Glu Ile Asp Gly Ser  Asn Leu Asn
    1400                 1405                 1410

Phe Thr  Asn Asn Ser Ala Ser  Ile Asp Val Thr Phe  Thr Ala Leu
    1415                 1420                 1425

Ala Asp  Asp Gly Arg Lys Leu  Gly Tyr Glu Ile Phe  Asn Ile Pro
    1430                 1435                 1440

Val Ile  Gln Lys Val Lys Thr  Asp Asn Ala Leu Thr  Leu Phe His
    1445                 1450                 1455

Asp Glu  Asn Gly Ala Gln Tyr  Met Gln Trp Gly Ala  Tyr Arg Ile
    1460                 1465                 1470

Arg Leu  Asn Thr Leu Phe Ala  Arg Gln Leu Val Glu  Arg Ala Asn
    1475                 1480                 1485

Thr Gly  Ile Asp Thr Ile Leu  Ser Met Glu Thr Gln  Asn Ile Gln
    1490                 1495                 1500

Glu Pro  Met Met Gly Ile Gly  Ala Tyr Ile Glu Leu  Ile Leu Asp
    1505                 1510                 1515

Lys Tyr  Asn Pro Asp Ile His  Gly Thr Asn Lys Ser  Phe Lys Ile
    1520                 1525                 1530

Ile Tyr  Gly Asp Ile Phe Lys  Ala Gly Asp His Phe  Pro Ile Tyr
    1535                 1540                 1545

Gln Gly  Ala Leu Ser Asp Ile  Thr Gln Thr Thr Val  Lys Leu Phe
    1550                 1555                 1560

Leu Pro  Arg Val Asp Asn Ala  Tyr Gly Asn Lys Asn  Asn Leu Tyr
    1565                 1570                 1575

Val Tyr  Ala Ala Tyr Gln Lys  Val Glu Thr Asn Phe  Ile Arg Phe
    1580                 1585                 1590

Val Lys  Glu Asp Asn Asn Lys  Pro Ala Thr Phe Asp  Thr Thr Tyr
    1595                 1600                 1605

Lys Asn  Gly Thr Phe Pro Gly  Leu Ala Ser Ala Arg  Val Ile Gln
    1610                 1615                 1620
```

-continued

```
Thr Val  Ser Glu Pro Met Asp  Phe Ser Gly Ala Asn  Ser Leu Tyr
    1625                 1630                 1635

Phe Trp  Glu Leu Phe Tyr Tyr  Thr Pro Met Met Val  Ala Gln Arg
    1640                 1645                 1650

Leu Leu  His Glu Gln Asn Phe  Asp Glu Ala Asn Arg  Trp Leu Lys
    1655                 1660                 1665

Tyr Val  Trp Ser Pro Ser Gly  Tyr Ile Val Arg Gly  Gln Ile Lys
    1670                 1675                 1680

Asn Tyr  His Trp Asn Val Arg  Pro Leu Leu Glu Asn  Thr Ser Trp
    1685                 1690                 1695

Asn Ser  Asp Pro Leu Asp Ser  Val Asp Pro Asp Ala  Val Ala Gln
    1700                 1705                 1710

His Asp  Pro Met His Tyr Lys  Val Ala Thr Phe Met  Arg Thr Leu
    1715                 1720                 1725

Asp Leu  Leu Met Ala Arg Gly  Asp His Ala Tyr Arg  Gln Leu Glu
    1730                 1735                 1740

Arg Asp  Thr Leu Asn Glu Ala  Lys Met Trp Tyr Met  Gln Ala Leu
    1745                 1750                 1755

His Leu  Leu Gly Asn Lys Pro  Tyr Leu Pro Leu Ser  Ser Val Trp
    1760                 1765                 1770

Asn Asp  Pro Arg Leu Asp Asn  Ala Ala Ala Thr Thr  Thr Gln Lys
    1775                 1780                 1785

Ala His  Ala Tyr Ala Ile Thr  Ser Leu Arg Gln Gly  Thr Gln Thr
    1790                 1795                 1800

Pro Ala  Leu Leu Leu Arg Ser  Ala Asn Thr Leu Thr  Asp Leu Phe
    1805                 1810                 1815

Leu Pro  Gln Ile Asn Asp Val  Met Leu Ser Tyr Trp  Asn Lys Leu
    1820                 1825                 1830

Glu Leu  Arg Leu Tyr Asn Leu  Arg His Asn Leu Ser  Ile Asp Gly
    1835                 1840                 1845

Gln Pro  Leu His Leu Pro Ile  Tyr Ala Thr Pro Ala  Asp Pro Lys
    1850                 1855                 1860

Ala Leu  Leu Ser Ala Ala Val  Ala Thr Ser Gln Gly  Gly Gly Lys
    1865                 1870                 1875

Leu Pro  Glu Ser Phe Ile Ser  Leu Trp Arg Phe Pro  His Met Leu
    1880                 1885                 1890

Glu Asn  Ala Arg Ser Met Val  Thr Gln Leu Ile Gln  Phe Gly Ser
    1895                 1900                 1905

Thr Leu  Gln Asn Ile Ile Glu  Arg Gln Asp Ala Glu  Ser Leu Asn
    1910                 1915                 1920

Ala Leu  Leu Gln Asn Gln Ala  Lys Glu Leu Ile Leu  Thr Thr Leu
    1925                 1930                 1935

Ser Ile  Gln Asp Lys Thr Ile  Glu Glu Ile Asp Ala  Glu Lys Thr
    1940                 1945                 1950

Val Leu  Glu Lys Ser Lys Ala  Gly Ala Lys Ser Arg  Phe Asp Asn
    1955                 1960                 1965

Tyr Ser  Lys Leu Tyr Asp Glu  Asp Val Asn Ala Gly  Glu Arg Gln
    1970                 1975                 1980

Ala Leu  Asp Met Arg Ile Ala  Ser Gln Ser Ile Thr  Ser Gly Leu
    1985                 1990                 1995

Lys Gly  Leu His Met Ala Ala  Ala Ala Leu Glu Met  Val Pro Asn
    2000                 2005                 2010

Ile Tyr  Gly Phe Ala Val Gly  Gly Thr Arg Tyr Gly  Ala Ile Ala
```

```
    2015                2020                2025

Asn Ala  Ile Ala Ile Gly Gly  Gly Ile Ala Ala Glu  Gly Leu Leu
    2030                2035                2040

Ile Glu  Ala Glu Lys Val Ser  Gln Ser Glu Ile Trp  Arg Arg Arg
    2045                2050                2055

Arg Gln  Glu Trp Glu Ile Gln  Arg Asn Asn Ala Glu  Ala Glu Met
    2060                2065                2070

Lys Gln  Ile Asp Ala Gln Leu  Lys Ser Leu Thr Val  Arg Arg Glu
    2075                2080                2085

Ala Ala  Val Leu Gln Lys Thr  Gly Leu Lys Thr Gln  Gln Glu Gln
    2090                2095                2100

Thr Gln  Ala Gln Leu Ala Phe  Leu Gln Arg Lys Phe  Ser Asn Gln
    2105                2110                2115

Ala Leu  Tyr Asn Trp Leu Arg  Gly Arg Leu Ala Ala  Ile Tyr Phe
    2120                2125                2130

Gln Phe  Tyr Asp Leu Val Val  Ala Arg Cys Leu Met  Ala Glu Gln
    2135                2140                2145

Ala Tyr  Arg Trp Glu Thr Asn  Asp Ser Ser Ala Arg  Phe Ile Lys
    2150                2155                2160

Pro Gly  Ala Trp Gln Gly Thr  Tyr Ala Gly Leu Leu  Ala Gly Glu
    2165                2170                2175

Thr Leu  Met Leu Asn Leu Ala  Gln Met Glu Asp Ala  His Leu Lys
    2180                2185                2190

Gln Glu  Gln Arg Ala Leu Glu  Val Glu Arg Thr Val  Ser Leu Ala
    2195                2200                2205

Gln Val  Tyr Gln Ser Leu Gly  Glu Lys Ser Phe Ala  Leu Lys Asp
    2210                2215                2220

Lys Ile  Glu Ala Leu Leu Gln  Gly Asp Lys Glu Thr  Ser Ala Gly
    2225                2230                2235

Asn Asp  Gly Asn Gln Leu Lys  Leu Thr Asn Asn Thr  Leu Ser Ala
    2240                2245                2250

Thr Leu  Thr Leu Gln Asp Leu  Lys Leu Lys Asp Asp  Tyr Pro Glu
    2255                2260                2265

Glu Met  Gln Leu Gly Lys Thr  Arg Arg Ile Lys Gln  Ile Ser Val
    2270                2275                2280

Ser Leu  Pro Ala Leu Leu Gly  Pro Tyr Gln Asp Val  Gln Ala Val
    2285                2290                2295

Leu Ser  Tyr Gly Gly Asp Ala  Thr Gly Leu Ala Lys  Gly Cys Lys
    2300                2305                2310

Ala Leu  Ala Val Ser His Gly  Leu Asn Asp Asn Gly  Gln Phe Gln
    2315                2320                2325

Leu Asp  Phe Asn Asp Gly Lys  Phe Leu Pro Phe Glu  Gly Ile Asp
    2330                2335                2340

Ile Asn  Asp Lys Gly Thr Phe  Thr Leu Ser Phe Pro  Asn Ala Ala
    2345                2350                2355

Ser Lys  Gln Lys Asn Ile Leu  Gln Met Leu Thr Asp  Ile Ile Leu
    2360                2365                2370

His Ile  Arg Tyr Thr Ile Leu  Glu
    2375                2380
```

<210> SEQ ID NO 64
<211> LENGTH: 949
<212> TYPE: PRT
<213> ORGANISM: Photorhabdus luminescens

<400> SEQUENCE: 64

Met Lys Asn Ile Asp Pro Lys Leu Tyr Gln His Thr Pro Thr Val Asn
1               5                   10                  15

Val Tyr Asp Asn Arg Gly Leu Thr Ile Arg Asn Ile Asp Phe His Arg
            20                  25                  30

Asp Val Ala Gly Gly Asp Thr Asp Thr Arg Ile Thr Arg His Gln Tyr
        35                  40                  45

Asp Thr Arg Gly His Leu Ser Gln Ser Ile Asp Pro Arg Leu Tyr Asp
    50                  55                  60

Ala Lys Gln Thr Asn Asn Ser Thr Asn Pro Asn Phe Leu Trp Gln Tyr
65                  70                  75                  80

Asn Leu Thr Gly Asp Thr Leu Arg Thr Glu Ser Val Asp Ala Gly Arg
                85                  90                  95

Thr Val Ala Leu Asn Asp Ile Glu Gly Arg Gln Val Leu Ile Val Thr
            100                 105                 110

Ala Thr Gly Ala Ile Gln Thr Arg Gln Tyr Glu Ala Asn Thr Leu Pro
        115                 120                 125

Gly Arg Leu Leu Ser Val Ser Glu Gln Ala Pro Gly Glu Gln Thr Pro
    130                 135                 140

Arg Val Thr Glu His Phe Ile Trp Ala Gly Asn Thr Gln Ala Glu Lys
145                 150                 155                 160

Asp His Asn Leu Ala Gly Gln Tyr Val Arg His Tyr Asp Thr Ala Gly
                165                 170                 175

Val Thr Gln Leu Glu Ser Leu Ser Leu Thr Glu Asn Ile Leu Ser Gln
            180                 185                 190

Ser Arg Gln Leu Leu Ala Asp Gly Gln Glu Ala Asp Trp Thr Gly Asn
        195                 200                 205

Asp Glu Thr Leu Trp Gln Thr Lys Leu Asn Ser Glu Thr Tyr Thr Thr
    210                 215                 220

Gln Ser Thr Phe Asp Ala Thr Gly Ala Leu Leu Thr Gln Thr Asp Ala
225                 230                 235                 240

Lys Gly Asn Met Gln Arg Leu Ala Tyr Asn Val Ala Gly Gln Leu Gln
                245                 250                 255

Gly Ser Trp Leu Thr Leu Lys Asn Gln Ser Glu Gln Val Ile Val Lys
            260                 265                 270

Ser Leu Thr Tyr Ser Ala Ala Gly Gln Lys Leu Arg Glu Glu His Gly
        275                 280                 285

Asn Gly Val Ile Thr Glu Tyr Ser Tyr Glu Pro Glu Thr Leu Arg Leu
    290                 295                 300

Ile Gly Thr Thr Thr Arg Arg Gln Ser Asp Ser Lys Val Leu Gln Asp
305                 310                 315                 320

Leu Arg Tyr Glu His Asp Pro Val Gly Asn Ile Ile Ser Val Arg Asn
                325                 330                 335

Asp Ala Glu Ala Thr Arg Phe Trp Arg Asn Gln Lys Ile Val Pro Glu
            340                 345                 350

Asn Thr Tyr Thr Tyr Asp Ser Leu Tyr Gln Leu Ile Ser Ala Thr Gly
        355                 360                 365

Arg Glu Met Ala Asn Ile Gly Gln Gln Ser Asn Gln Leu Pro Ser Pro
    370                 375                 380

Ile Ile Pro Leu Pro Thr Asp Glu Asn Ser Tyr Thr Asn Tyr Thr Arg
385                 390                 395                 400

Ser Tyr Asn Tyr Asp Arg Gly Gly Asn Leu Val Gln Ile Arg His Ser
                405                 410                 415

-continued

```
Ser Pro Ala Ala Gln Asn Asn Tyr Thr Thr Asp Ile Thr Val Ser Asn
            420                 425                 430

Arg Ser Asn Arg Ala Val Leu Ser Ser Leu Thr Ser Asp Pro Thr Gln
        435                 440                 445

Val Glu Ala Leu Phe Asp Ala Gly Gly His Gln Thr Lys Leu Leu Pro
    450                 455                 460

Gly Gln Glu Leu Ser Trp Asn Thr Arg Gly Glu Leu Lys Gln Val Thr
465                 470                 475                 480

Pro Val Ser Arg Glu Ser Ala Ser Asp Arg Glu Trp Tyr Arg Tyr Gly
                485                 490                 495

Asn Asp Gly Met Arg Arg Leu Lys Val Ser Glu Gln Gln Thr Gly Asn
            500                 505                 510

Ser Thr Gln Gln Gln Arg Val Thr Tyr Leu Pro Asp Leu Glu Leu Arg
        515                 520                 525

Thr Thr Gln Asn Gly Thr Thr Thr Ser Glu Asp Leu His Ala Ile Thr
    530                 535                 540

Val Gly Ala Ala Gly His Ala Gln Val Arg Val Leu His Trp Glu Thr
545                 550                 555                 560

Thr Pro Pro Ala Gly Ile Asn Asn Asn Gln Leu Arg Tyr Ser Tyr Asp
                565                 570                 575

Asn Leu Ile Gly Ser Ser Gln Leu Glu Leu Asp Asn Ala Gly Gln Ile
            580                 585                 590

Ile Ser Gln Glu Glu Tyr Tyr Pro Phe Gly Gly Thr Ala Leu Trp Ala
        595                 600                 605

Ala Arg Asn Gln Ile Glu Ala Ser Tyr Lys Ile Leu Arg Tyr Ser Gly
    610                 615                 620

Lys Glu Arg Asp Ala Thr Gly Leu Tyr Tyr Tyr Gly Tyr Arg Tyr Tyr
625                 630                 635                 640

Gln Pro Trp Val Gly Arg Trp Leu Ser Ala Asp Pro Ala Gly Thr Ile
                645                 650                 655

Asp Gly Leu Asn Leu Tyr Arg Met Val Arg Asn Asn Pro Ser Thr Leu
            660                 665                 670

Val Asp Ile Ser Gly Leu Ala Pro Thr Lys Tyr Asn Ile Pro Gly Phe
        675                 680                 685

Asp Phe Asp Val Glu Ile Asp Glu Gln Lys Arg Ser Lys Leu Lys Pro
    690                 695                 700

Thr Leu Ile Arg Ile Lys Asp Glu Phe Leu His Tyr Gly Pro Val Asp
705                 710                 715                 720

Lys Leu Leu Glu Glu Lys Lys Pro Gly Leu Asn Val Pro Glu Glu Leu
                725                 730                 735

Phe Asp Arg Gly Pro Ser Glu Asn Gly Val Ser Thr Leu Thr Phe Lys
            740                 745                 750

Lys Asp Leu Pro Ile Ser Cys Ile Ser Asn Thr Glu Tyr Thr Leu Asp
        755                 760                 765

Ile Leu Tyr Asn Lys His Glu Thr Lys Pro Phe Pro Tyr Glu Asn Glu
    770                 775                 780

Ala Thr Val Gly Ala Asp Leu Gly Val Ile Met Ser Val Glu Phe Gly
785                 790                 795                 800

Asn Lys Ser Ile Gly Asn Ala Ser Asp Glu Asp Leu Lys Glu Glu His
                805                 810                 815

Leu Pro Leu Gly Lys Ser Thr Met Asp Lys Thr Asp Leu Pro Asp Leu
            820                 825                 830

Lys Gln Gly Leu Met Ile Ala Glu Lys Ile Lys Ser Gly Lys Gly Ala
        835                 840                 845
```

Tyr Pro Phe His Phe Gly Ala Ala Ile Ala Val Val Tyr Gly Glu Asp
850 855 860

Lys Lys Val Ala Ala Ser Ile Leu Thr Asp Leu Ser Glu Pro Lys Arg
865 870 875 880

Asp Glu Gly Glu Tyr Leu Gln Ser Thr Arg Lys Val Ser Ala Met Phe
885 890 895

Ile Thr Asn Val Asn Glu Phe Arg Gly His Asp Tyr Pro Lys Ser Lys
900 905 910

Tyr Ser Ile Gly Leu Val Thr Ala Glu Lys Arg Gln Pro Val Ile Ser
915 920 925

Lys Lys Arg Ala Asn Pro Glu Glu Ala Pro Ser Ser Ser Arg Asn Lys
930 935 940

Lys Leu His Val His
945

<210> SEQ ID NO 65
<211> LENGTH: 2516
<212> TYPE: PRT
<213> ORGANISM: Photorhabdus luminescens

<400> SEQUENCE: 65

Met Asn Glu Ser Val Lys Glu Ile Pro Asp Val Leu Lys Ser Gln Cys
1 5 10 15

Gly Phe Asn Cys Leu Thr Asp Ile Ser His Ser Ser Phe Asn Glu Phe
20 25 30

Arg Gln Gln Val Ser Glu His Leu Ser Trp Ser Glu Thr His Asp Leu
35 40 45

Tyr His Asp Ala Gln Gln Ala Gln Lys Asp Asn Arg Leu Tyr Glu Ala
50 55 60

Arg Ile Leu Lys Arg Ala Asn Pro Gln Leu Gln Asn Ala Val His Leu
65 70 75 80

Ala Ile Leu Ala Pro Asn Ala Glu Leu Ile Gly Tyr Asn Asn Gln Phe
85 90 95

Ser Gly Arg Ala Ser Gln Tyr Val Ala Pro Gly Thr Val Ser Ser Met
100 105 110

Phe Ser Pro Ala Ala Tyr Leu Thr Glu Leu Tyr Arg Glu Ala Arg Asn
115 120 125

Leu His Ala Ser Asp Ser Val Tyr Tyr Leu Asp Thr Arg Arg Pro Asp
130 135 140

Leu Lys Ser Met Ala Leu Ser Gln Gln Asn Met Asp Ile Glu Leu Ser
145 150 155 160

Thr Leu Ser Leu Ser Asn Glu Leu Leu Leu Glu Ser Ile Lys Thr Glu
165 170 175

Ser Lys Leu Glu Asn Tyr Thr Lys Val Met Glu Met Leu Ser Thr Phe
180 185 190

Arg Pro Ser Gly Ala Thr Pro Tyr His Asp Ala Tyr Glu Asn Val Arg
195 200 205

Glu Val Ile Gln Leu Gln Asp Pro Gly Leu Glu Gln Leu Asn Ala Ser
210 215 220

Pro Ala Ile Ala Gly Leu Met His Gln Ala Ser Leu Leu Gly Ile Asn
225 230 235 240

Ala Ser Ile Ser Pro Glu Leu Phe Asn Ile Leu Thr Glu Glu Ile Thr
245 250 255

Glu Gly Asn Ala Glu Glu Leu Tyr Lys Lys Asn Phe Gly Asn Ile Glu
260 265 270

```
Pro Ala Ser Leu Ala Met Pro Glu Tyr Leu Lys Arg Tyr Tyr Asn Leu
        275                 280                 285

Ser Asp Glu Glu Leu Ser Gln Phe Ile Gly Lys Ala Ser Asn Phe Gly
    290                 295                 300

Gln Gln Glu Tyr Ser Asn Asn Gln Leu Ile Thr Pro Val Val Asn Ser
305                 310                 315                 320

Ser Asp Gly Thr Val Lys Val Tyr Arg Ile Thr Arg Glu Tyr Thr Thr
                325                 330                 335

Asn Ala Tyr Gln Met Asp Val Glu Leu Phe Pro Phe Gly Gly Glu Asn
            340                 345                 350

Tyr Arg Leu Asp Tyr Lys Phe Lys Asn Phe Tyr Asn Ala Ser Tyr Leu
        355                 360                 365

Ser Ile Lys Leu Asn Asp Lys Arg Glu Leu Val Arg Thr Glu Gly Ala
    370                 375                 380

Pro Gln Val Asn Ile Glu Tyr Ser Ala Asn Ile Thr Leu Asn Thr Ala
385                 390                 395                 400

Asp Ile Ser Gln Pro Phe Glu Ile Gly Leu Thr Arg Val Leu Pro Ser
                405                 410                 415

Gly Ser Trp Ala Tyr Ala Ala Ala Lys Phe Thr Val Glu Glu Tyr Asn
            420                 425                 430

Gln Tyr Ser Phe Leu Leu Lys Leu Asn Lys Ala Ile Arg Leu Ser Arg
        435                 440                 445

Ala Thr Glu Leu Ser Pro Thr Ile Leu Glu Gly Ile Val Arg Ser Val
    450                 455                 460

Asn Leu Gln Leu Asp Ile Asn Thr Asp Val Leu Gly Lys Val Phe Leu
465                 470                 475                 480

Thr Lys Tyr Tyr Met Gln Arg Tyr Ala Ile His Ala Glu Thr Ala Leu
                485                 490                 495

Ile Leu Cys Asn Ala Pro Ile Ser Gln Arg Ser Tyr Asp Asn Gln Pro
            500                 505                 510

Ser Gln Phe Asp Arg Leu Phe Asn Thr Pro Leu Leu Asn Gly Gln Tyr
        515                 520                 525

Phe Ser Thr Gly Asp Glu Glu Ile Asp Leu Asn Ser Gly Ser Thr Gly
    530                 535                 540

Asp Trp Arg Lys Thr Ile Leu Lys Arg Ala Phe Asn Ile Asp Asp Val
545                 550                 555                 560

Ser Leu Phe Arg Leu Leu Lys Ile Thr Asp His Asp Asn Lys Asp Gly
                565                 570                 575

Lys Ile Lys Asn Asn Leu Lys Asn Leu Ser Asn Leu Tyr Ile Gly Lys
            580                 585                 590

Leu Leu Ala Asp Ile His Gln Leu Thr Ile Asp Glu Leu Asp Leu Leu
        595                 600                 605

Leu Ile Ala Val Gly Glu Gly Lys Thr Asn Leu Ser Ala Ile Ser Asp
    610                 615                 620

Lys Gln Leu Ala Thr Leu Ile Arg Lys Leu Asn Thr Ile Thr Ser Trp
625                 630                 635                 640

Leu His Thr Gln Lys Trp Ser Val Phe Gln Leu Phe Ile Met Thr Ser
                645                 650                 655

Thr Ser Tyr Asn Lys Thr Leu Thr Pro Glu Ile Lys Asn Leu Leu Asp
            660                 665                 670

Thr Val Tyr His Gly Leu Gln Gly Phe Asp Lys Asp Lys Ala Asp Leu
        675                 680                 685

Leu His Val Met Ala Pro Tyr Ile Ala Ala Thr Leu Gln Leu Ser Ser
```

-continued

```
    690                 695                 700

Glu Asn Val Ala His Ser Val Leu Leu Trp Ala Asp Lys Leu Gln Pro
705                 710                 715                 720

Gly Asp Gly Ala Met Thr Ala Glu Lys Phe Trp Asp Trp Leu Asn Thr
                725                 730                 735

Lys Tyr Thr Pro Gly Ser Ser Glu Ala Val Glu Thr Gln Glu His Ile
            740                 745                 750

Val Gln Tyr Cys Gln Ala Leu Ala Gln Leu Glu Met Val Tyr His Ser
        755                 760                 765

Thr Gly Ile Asn Glu Asn Ala Phe Arg Leu Phe Val Thr Lys Pro Glu
    770                 775                 780

Met Phe Gly Ala Ala Thr Gly Ala Ala Pro Ala His Asp Ala Leu Ser
785                 790                 795                 800

Leu Ile Met Leu Thr Arg Phe Ala Asp Trp Val Asn Ala Leu Gly Glu
                805                 810                 815

Lys Ala Ser Ser Val Leu Ala Ala Phe Glu Ala Asn Ser Leu Thr Ala
            820                 825                 830

Glu Gln Leu Ala Asp Ala Met Asn Leu Asp Ala Asn Leu Leu Leu Gln
        835                 840                 845

Ala Ser Ile Gln Ala Gln Asn His Gln His Leu Pro Pro Val Thr Pro
    850                 855                 860

Glu Asn Ala Phe Ser Cys Trp Thr Ser Ile Asn Thr Ile Leu Gln Trp
865                 870                 875                 880

Val Asn Val Ala Gln Gln Leu Asn Val Ala Pro Gln Gly Val Ser Ala
                885                 890                 895

Leu Val Gly Leu Asp Tyr Ile Gln Ser Met Lys Glu Thr Pro Thr Tyr
            900                 905                 910

Ala Gln Trp Glu Asn Ala Ala Gly Val Leu Thr Ala Gly Leu Asn Ser
        915                 920                 925

Gln Gln Ala Asn Thr Leu His Ala Phe Leu Asp Glu Ser Arg Ser Ala
    930                 935                 940

Ala Leu Ser Thr Tyr Tyr Ile Arg Gln Val Ala Lys Ala Ala Ala Ala
945                 950                 955                 960

Ile Lys Ser Arg Asp Asp Leu Tyr Gln Tyr Leu Leu Ile Asp Asn Gln
                965                 970                 975

Val Ser Ala Ala Ile Lys Thr Thr Arg Ile Ala Glu Ala Ile Ala Ser
            980                 985                 990

Ile Gln Leu Tyr Val Asn Arg Ala  Leu Glu Asn Val Glu  Glu Asn Ala
        995                 1000                1005

Asn Ser  Gly Val Ile Ser Arg  Gln Phe Phe Ile Asp  Trp Asp Lys
    1010                1015                1020

Tyr Asn  Lys Arg Tyr Ser Thr  Trp Ala Gly Val Ser  Gln Leu Val
    1025                1030                1035

Tyr Tyr  Pro Glu Asn Tyr Ile  Asp Pro Thr Met Arg  Ile Gly Gln
    1040                1045                1050

Thr Lys  Met Met Asp Ala Leu  Leu Gln Ser Val Ser  Gln Ser Gln
    1055                1060                1065

Leu Asn  Ala Asp Thr Val Glu  Asp Ala Phe Met Ser  Tyr Leu Thr
    1070                1075                1080

Ser Phe  Glu Gln Val Ala Asn  Leu Lys Val Ile Ser  Ala Tyr His
    1085                1090                1095

Asp Asn  Ile Asn Asn Asp Gln  Gly Leu Thr Tyr Phe  Ile Gly Leu
    1100                1105                1110
```

-continued

```
Ser Glu  Thr Asp Ala Gly Glu  Tyr Tyr Trp Arg Ser  Val Asp His
    1115                 1120                 1125

Ser Lys  Phe Asn Asp Gly Lys  Phe Ala Ala Asn Ala  Trp Ser Glu
    1130                 1135                 1140

Trp His  Lys Ile Asp Cys Pro  Ile Asn Pro Tyr Lys  Ser Thr Ile
    1145                 1150                 1155

Arg Pro  Val Ile Tyr Lys Ser  Arg Leu Tyr Leu Leu  Trp Leu Glu
    1160                 1165                 1170

Gln Lys  Glu Ile Thr Lys Gln  Thr Gly Asn Ser Lys  Asp Gly Tyr
    1175                 1180                 1185

Gln Thr  Glu Thr Asp Tyr Arg  Tyr Glu Leu Lys Leu  Ala His Ile
    1190                 1195                 1200

Arg Tyr  Asp Gly Thr Trp Asn  Thr Pro Ile Thr Phe  Asp Val Asn
    1205                 1210                 1215

Lys Lys  Ile Ser Glu Leu Lys  Leu Glu Lys Asn Arg  Ala Pro Gly
    1220                 1225                 1230

Leu Tyr  Cys Ala Gly Tyr Gln  Gly Glu Asp Thr Leu  Leu Val Met
    1235                 1240                 1245

Phe Tyr  Asn Gln Gln Asp Thr  Leu Asp Ser Tyr Lys  Asn Ala Ser
    1250                 1255                 1260

Met Gln  Gly Leu Tyr Ile Phe  Ala Asp Met Ala Ser  Lys Asp Met
    1265                 1270                 1275

Thr Pro  Glu Gln Ser Asn Val  Tyr Arg Asp Asn Ser  Tyr Gln Gln
    1280                 1285                 1290

Phe Asp  Thr Asn Asn Val Arg  Arg Val Asn Asn Arg  Tyr Ala Glu
    1295                 1300                 1305

Asp Tyr  Glu Ile Pro Ser Ser  Val Ser Ser Arg Lys  Asp Tyr Gly
    1310                 1315                 1320

Trp Gly  Asp Tyr Tyr Leu Ser  Met Val Tyr Asn Gly  Asp Ile Pro
    1325                 1330                 1335

Thr Ile  Asn Tyr Lys Ala Ala  Ser Ser Asp Leu Lys  Ile Tyr Ile
    1340                 1345                 1350

Ser Pro  Lys Leu Arg Ile Ile  His Asn Gly Tyr Glu  Gly Gln Lys
    1355                 1360                 1365

Arg Asn  Gln Cys Asn Leu Met  Asn Lys Tyr Gly Lys  Leu Gly Asp
    1370                 1375                 1380

Lys Phe  Ile Val Tyr Thr Ser  Leu Gly Val Asn Pro  Asn Asn Ser
    1385                 1390                 1395

Ser Asn  Lys Leu Met Phe Tyr  Pro Val Tyr Gln Tyr  Ser Gly Asn
    1400                 1405                 1410

Thr Ser  Gly Leu Asn Gln Gly  Arg Leu Leu Phe His  Arg Asp Thr
    1415                 1420                 1425

Thr Tyr  Pro Ser Lys Val Glu  Ala Trp Ile Pro Gly  Ala Lys Arg
    1430                 1435                 1440

Ser Leu  Thr Asn Gln Asn Ala  Ala Ile Gly Asp Asp  Tyr Ala Thr
    1445                 1450                 1455

Asp Ser  Leu Asn Lys Pro Asp  Asp Leu Lys Gln Tyr  Ile Phe Met
    1460                 1465                 1470

Thr Asp  Ser Lys Gly Thr Ala  Thr Asp Val Ser Gly  Pro Val Glu
    1475                 1480                 1485

Ile Asn  Thr Ala Ile Ser Pro  Ala Lys Val Gln Ile  Ile Val Lys
    1490                 1495                 1500

Ala Gly  Gly Lys Glu Gln Thr  Phe Thr Ala Asp Lys  Asp Val Ser
    1505                 1510                 1515
```

Ile Gln Pro Ser Pro Ser Phe Asp Glu Met Asn Tyr Gln Phe Asn
1520 1525 1530

Ala Leu Glu Ile Asp Gly Ser Gly Leu Asn Phe Ile Asn Asn Ser
1535 1540 1545

Ala Ser Ile Asp Val Thr Phe Thr Ala Phe Ala Glu Asp Gly Arg
1550 1555 1560

Lys Leu Gly Tyr Glu Ser Phe Ser Ile Pro Val Thr Leu Lys Val
1565 1570 1575

Ser Thr Asp Asn Ala Leu Thr Leu His His Asn Glu Asn Gly Ala
1580 1585 1590

Gln Tyr Met Gln Trp Gln Ser Tyr Arg Thr Arg Leu Asn Thr Leu
1595 1600 1605

Phe Ala Arg Gln Leu Val Ala Arg Ala Thr Thr Gly Ile Asp Thr
1610 1615 1620

Ile Leu Ser Met Glu Thr Gln Asn Ile Gln Glu Pro Gln Leu Gly
1625 1630 1635

Lys Gly Phe Tyr Ala Thr Phe Val Ile Pro Pro Tyr Asn Leu Ser
1640 1645 1650

Thr His Gly Asp Glu Arg Trp Phe Lys Leu Tyr Ile Lys His Val
1655 1660 1665

Val Asp Asn Asn Ser His Ile Ile Tyr Ser Gly Gln Leu Thr Asp
1670 1675 1680

Thr Asn Ile Asn Ile Thr Leu Phe Ile Pro Leu Asp Asp Val Pro
1685 1690 1695

Leu Asn Gln Asp Tyr His Ala Lys Val Tyr Met Thr Phe Lys Lys
1700 1705 1710

Ser Pro Ser Asp Gly Thr Trp Trp Gly Pro His Phe Val Arg Asp
1715 1720 1725

Asp Lys Gly Ile Val Thr Ile Asn Pro Lys Ser Ile Leu Thr His
1730 1735 1740

Phe Glu Ser Val Asn Val Leu Asn Asn Ile Ser Ser Glu Pro Met
1745 1750 1755

Asp Phe Ser Gly Ala Asn Ser Leu Tyr Phe Trp Glu Leu Phe Tyr
1760 1765 1770

Tyr Thr Pro Met Leu Val Ala Gln Arg Leu Leu His Glu Gln Asn
1775 1780 1785

Phe Asp Glu Ala Asn Arg Trp Leu Lys Tyr Val Trp Ser Pro Ser
1790 1795 1800

Gly Tyr Ile Val His Gly Gln Ile Gln Asn Tyr Gln Trp Asn Val
1805 1810 1815

Arg Pro Leu Leu Glu Asp Thr Ser Trp Asn Ser Asp Pro Leu Asp
1820 1825 1830

Ser Val Asp Pro Asp Ala Val Ala Gln His Asp Pro Met His Tyr
1835 1840 1845

Lys Val Ser Thr Phe Met Arg Thr Leu Asp Leu Leu Ile Ala Arg
1850 1855 1860

Gly Asp His Ala Tyr Arg Gln Leu Glu Arg Asp Thr Leu Asn Glu
1865 1870 1875

Ala Lys Met Trp Tyr Met Gln Ala Leu His Leu Leu Gly Asp Lys
1880 1885 1890

Pro Tyr Leu Pro Leu Ser Thr Thr Trp Ser Asp Pro Arg Leu Asp
1895 1900 1905

Arg Ala Ala Asp Ile Thr Thr Gln Asn Ala His Asp Ser Ala Ile

```
    1910                1915                1920

Val Ala  Leu Arg Gln Asn Ile  Pro Thr Pro Ala Pro  Leu Ser Leu
    1925                1930                1935

Arg Ser  Ala Asn Thr Leu Thr  Asp Leu Phe Leu Pro  Gln Ile Asn
    1940                1945                1950

Glu Val  Met Met Asn Tyr Trp  Gln Thr Leu Ala Gln  Arg Val Tyr
    1955                1960                1965

Asn Leu  Arg His Asn Leu Ser  Ile Asp Gly Gln Pro  Leu Tyr Leu
    1970                1975                1980

Pro Ile  Tyr Ala Thr Pro Ala  Asp Pro Lys Ala Leu  Leu Ser Ala
    1985                1990                1995

Ala Val  Ala Thr Ser Gln Gly  Gly Gly Lys Leu Pro  Glu Ser Phe
    2000                2005                2010

Met Ser  Leu Trp Arg Phe Pro  His Met Leu Glu Asn  Ala Arg Gly
    2015                2020                2025

Met Val  Ser Gln Leu Thr Gln  Phe Gly Ser Thr Leu  Gln Asn Ile
    2030                2035                2040

Ile Glu  Arg Gln Asp Ala Glu  Ala Leu Asn Ala Leu  Leu Gln Asn
    2045                2050                2055

Gln Ala  Ala Glu Leu Ile Leu  Thr Asn Leu Ser Ile  Gln Asp Lys
    2060                2065                2070

Thr Ile  Glu Glu Leu Asp Ala  Glu Lys Thr Val Leu  Glu Lys Ser
    2075                2080                2085

Lys Ala  Gly Ala Gln Ser Arg  Phe Asp Ser Tyr Gly  Lys Leu Tyr
    2090                2095                2100

Asp Glu  Asn Ile Asn Ala Gly  Glu Asn Gln Ala Met  Thr Leu Arg
    2105                2110                2115

Ala Ser  Ala Ala Gly Leu Thr  Thr Ala Val Gln Ala  Ser Arg Leu
    2120                2125                2130

Ala Gly  Ala Ala Ala Asp Leu  Val Pro Asn Ile Phe  Gly Phe Ala
    2135                2140                2145

Gly Gly  Gly Ser Arg Trp Gly  Ala Ile Ala Glu Ala  Thr Gly Tyr
    2150                2155                2160

Val Met  Glu Phe Ser Ala Asn  Val Met Asn Thr Glu  Ala Asp Lys
    2165                2170                2175

Ile Ser  Gln Ser Glu Thr Tyr  Arg Arg Arg Arg Gln  Glu Trp Glu
    2180                2185                2190

Ile Gln  Arg Asn Asn Ala Glu  Ala Glu Leu Lys Gln  Ile Asp Ala
    2195                2200                2205

Gln Leu  Lys Ser Leu Ala Val  Arg Arg Glu Ala Ala  Val Leu Gln
    2210                2215                2220

Lys Thr  Ser Leu Lys Thr Gln  Gln Glu Gln Thr Gln  Ser Gln Leu
    2225                2230                2235

Ala Phe  Leu Gln Arg Lys Phe  Ser Asn Gln Ala Leu  Tyr Asn Trp
    2240                2245                2250

Leu Arg  Gly Arg Leu Ala Ala  Ile Tyr Phe Gln Phe  Tyr Asp Leu
    2255                2260                2265

Ala Val  Ala Arg Cys Leu Met  Ala Glu Gln Ala Tyr  Arg Trp Glu
    2270                2275                2280

Leu Asn  Asp Asp Ser Ala Arg  Phe Ile Lys Pro Gly  Ala Trp Gln
    2285                2290                2295

Gly Thr  Tyr Ala Gly Leu Leu  Ala Gly Glu Thr Leu  Met Leu Ser
    2300                2305                2310
```

```
Leu Ala  Gln Met Glu Asp Ala  His Leu Lys Arg Asp  Lys Arg Ala
    2315                 2320                 2325

Leu Glu  Val Glu Arg Thr Val  Ser Leu Ala Glu Val  Tyr Ala Gly
    2330                 2335                 2340

Leu Pro  Lys Asp Asn Gly Pro  Phe Ser Leu Ala Gln  Glu Ile Asp
    2345                 2350                 2355

Lys Leu  Val Ser Gln Gly Ser  Gly Ser Ala Gly Ser  Gly Asn Asn
    2360                 2365                 2370

Asn Leu  Ala Phe Gly Ala Gly  Thr Asp Thr Lys Thr  Ser Leu Gln
    2375                 2380                 2385

Ala Ser  Val Ser Phe Ala Asp  Leu Lys Ile Arg Glu  Asp Tyr Pro
    2390                 2395                 2400

Ala Ser  Leu Gly Lys Ile Arg  Arg Ile Lys Gln Ile  Ser Val Thr
    2405                 2410                 2415

Leu Pro  Ala Leu Leu Gly Pro  Tyr Gln Asp Val Gln  Ala Ile Leu
    2420                 2425                 2430

Ser Tyr  Gly Asp Lys Ala Gly  Leu Ala Asn Gly Cys  Glu Ala Leu
    2435                 2440                 2445

Ala Val  Ser His Gly Met Asn  Asp Ser Gly Gln Phe  Gln Leu Asp
    2450                 2455                 2460

Phe Asn  Asp Gly Lys Phe Leu  Pro Phe Glu Gly Ile  Ala Ile Asp
    2465                 2470                 2475

Gln Gly  Thr Leu Thr Leu Ser  Phe Pro Asn Ala Ser  Met Pro Glu
    2480                 2485                 2490

Lys Gly  Lys Gln Ala Thr Met  Leu Lys Thr Leu Asn  Asp Ile Ile
    2495                 2500                 2505

Leu His  Ile Arg Tyr Thr Ile  Lys
    2510                 2515


<210> SEQ ID NO 66
<211> LENGTH: 938
<212> TYPE: PRT
<213> ORGANISM: Photorhabdus luminescens strain W14

<400> SEQUENCE: 66

Met Glu Asn Ile Asp Pro Lys Leu Tyr His His Thr Pro Thr Val Ser
1               5                   10                  15

Val His Asp Asn Arg Gly Leu Ala Ile Arg Asn Ile Ser Phe His Arg
            20                  25                  30

Thr Thr Ala Glu Ala Asn Thr Asp Thr Arg Ile Thr Arg His Gln Tyr
        35                  40                  45

Asn Ala Gly Gly Tyr Leu Asn Gln Ser Ile Asp Pro Arg Leu Tyr Asp
    50                  55                  60

Ala Lys Gln Thr Asn Asn Ala Val Gln Pro Asn Phe Ile Trp Arg His
65                  70                  75                  80

Asn Leu Thr Gly Asn Ile Leu Arg Thr Glu Ser Val Asp Ala Gly Arg
                85                  90                  95

Thr Ile Thr Leu Asn Asp Ile Glu Gly Arg Pro Val Leu Thr Ile Asn
            100                 105                 110

Ala Ala Gly Val Arg Gln Asn His Arg Tyr Glu Asp Asn Thr Leu Pro
        115                 120                 125

Gly Arg Leu Leu Ala Ile Ser Glu Gln Gly Gln Ala Glu Glu Lys Thr
    130                 135                 140

Thr Glu Arg Leu Ile Trp Ala Gly Asn Thr Pro Gln Glu Lys Asp His
145                 150                 155                 160
```

-continued

```
Asn Leu Ala Gly Gln Cys Val Arg His Tyr Asp Thr Ala Gly Leu Thr
                165                 170                 175

Gln Leu Asn Ser Leu Ala Leu Thr Gly Ala Val Leu Ser Gln Ser Gln
            180                 185                 190

Gln Leu Leu Thr Asp Asn Gln Asp Ala Asp Trp Thr Gly Glu Asp Gln
        195                 200                 205

Ser Leu Trp Gln Gln Lys Leu Ser Ser Asp Val Tyr Ile Thr Gln Ser
    210                 215                 220

Asn Thr Asp Ala Thr Gly Ala Leu Leu Thr Gln Thr Asp Ala Lys Gly
225                 230                 235                 240

Asn Ile Gln Arg Leu Ala Tyr Asp Val Ala Gly Gln Leu Lys Gly Ser
                245                 250                 255

Trp Leu Thr Leu Lys Gly Gln Ala Glu Gln Val Ile Ile Lys Ser Leu
            260                 265                 270

Thr Tyr Ser Ala Ala Gly Gln Lys Leu Arg Glu Glu His Gly Asn Gly
        275                 280                 285

Ile Val Thr Glu Tyr Ser Tyr Glu Pro Glu Thr Gln Arg Leu Ile Gly
    290                 295                 300

Ile Thr Thr Arg Arg Pro Ser Asp Ala Lys Val Leu Gln Asp Leu Arg
305                 310                 315                 320

Tyr Gln Tyr Asp Pro Val Gly Asn Val Ile Ser Ile Arg Asn Asp Ala
                325                 330                 335

Glu Ala Thr Arg Phe Trp Arg Asn Gln Lys Val Ala Pro Glu Asn Ser
            340                 345                 350

Tyr Thr Tyr Asp Ser Leu Tyr Gln Leu Ile Ser Ala Thr Gly Arg Glu
        355                 360                 365

Met Ala Asn Ile Gly Gln Gln Ser Asn Gln Leu Pro Ser Pro Ala Leu
    370                 375                 380

Pro Ser Asp Asn Asn Thr Tyr Thr Asn Tyr Thr Arg Thr Tyr Thr Tyr
385                 390                 395                 400

Asp Arg Gly Gly Asn Leu Thr Lys Ile Gln His Ser Ser Pro Ala Ala
                405                 410                 415

Gln Asn Asn Tyr Thr Thr Asp Ile Thr Val Ser Asn Arg Ser Asn Arg
            420                 425                 430

Ala Val Leu Ser Thr Leu Thr Ala Asp Pro Thr Gln Val Asp Ala Leu
        435                 440                 445

Phe Asp Ala Gly Gly His Gln Thr Ser Leu Leu Ser Gly Gln Val Leu
    450                 455                 460

Thr Trp Thr Pro Arg Gly Glu Leu Lys Gln Ala Asn Asn Ser Ala Gly
465                 470                 475                 480

Asn Glu Trp Tyr Arg Tyr Asp Ser Asn Gly Ile Arg Gln Leu Lys Val
                485                 490                 495

Asn Glu Gln Gln Thr Gln Asn Ile Pro Gln Gln Gln Arg Val Thr Tyr
            500                 505                 510

Leu Pro Gly Leu Glu Ile Arg Thr Thr Gln Asn Asn Ala Thr Thr Thr
        515                 520                 525

Glu Glu Leu His Val Ile Thr Leu Gly Lys Ala Gly Arg Ala Gln Val
    530                 535                 540

Arg Val Leu His Trp Glu Ser Gly Lys Pro Glu Asp Ile Asn Asn Asn
545                 550                 555                 560

Gln Leu Arg Tyr Ser Tyr Asp Asn Leu Ile Gly Ser Ser Gln Leu Gln
                565                 570                 575

Leu Asp Ser Asp Gly Gln Ile Ile Ser Glu Glu Glu Tyr Tyr Pro Phe
            580                 585                 590
```

```
Gly Gly Thr Ala Leu Trp Ala Ala Arg Asn Gln Thr Glu Ala Ser Tyr
        595                 600                 605

Lys Thr Ile Arg Tyr Ser Gly Lys Glu Arg Asp Val Thr Gly Leu Tyr
    610                 615                 620

Tyr Tyr Gly Tyr Arg Tyr Tyr Gln Pro Trp Ala Gly Arg Trp Leu Gly
625                 630                 635                 640

Ala Asp Pro Ala Gly Thr Ile Asp Gly Leu Asn Leu Tyr Arg Met Val
                645                 650                 655

Arg Asn Asn Pro Val Thr Gln Phe Asp Val Gln Gly Leu Ser Pro Ala
            660                 665                 670

Asn Arg Thr Glu Glu Ala Ile Ile Lys Gln Gly Ser Phe Thr Gly Met
        675                 680                 685

Glu Glu Ala Val Tyr Lys Lys Met Ala Lys Pro Gln Thr Phe Lys Arg
    690                 695                 700

Gln Arg Ala Ile Ala Ala Gln Thr Glu Gln Glu Ala His Glu Ser Leu
705                 710                 715                 720

Thr Asn Asn Pro Ser Val Asp Ile Ser Pro Ile Lys Asn Tyr Thr Thr
                725                 730                 735

Asp Ser Ser Gln Ile Asn Ala Ala Ile Arg Glu Asn Arg Ile Thr Pro
            740                 745                 750

Ala Val Glu Ser Leu Asp Ala Thr Leu Ser Ser Leu Gln Asp Arg Gln
        755                 760                 765

Met Arg Val Thr Tyr Arg Val Met Thr Tyr Val Asp Asn Ser Thr Pro
    770                 775                 780

Ser Pro Trp His Ser Pro Gln Glu Gly Asn Ser Ile Asn Val Gly Asp
785                 790                 795                 800

Ile Val Ser Asp Asn Ala Tyr Leu Ser Thr Ser Ala His Arg Gly Phe
                805                 810                 815

Leu Asn Phe Val His Lys Lys Glu Thr Ser Glu Thr Arg Tyr Val Lys
            820                 825                 830

Met Ala Phe Leu Thr Asn Ala Gly Val Asn Val Pro Ala Ala Ser Met
        835                 840                 845

Tyr Asn Asn Ala Gly Glu Glu Gln Val Phe Lys Met Asp Leu Asn Asp
    850                 855                 860

Ser Arg Lys Ser Leu Ala Glu Lys Leu Lys Leu Arg Val Ser Gly Pro
865                 870                 875                 880

Gln Ser Gly Gln Ala Glu Ile Leu Leu Pro Arg Glu Thr Gln Phe Glu
                885                 890                 895

Val Val Ser Met Lys His Gln Gly Arg Asp Thr Tyr Val Leu Leu Gln
            900                 905                 910

Asp Ile Asn Gln Ser Ala Ala Thr His Arg Asn Val Arg Asn Thr Tyr
        915                 920                 925

Thr Gly Asn Phe Lys Ser Ser Ser Ala Asn
    930                 935
```

<210> SEQ ID NO 67
<211> LENGTH: 1476
<212> TYPE: PRT
<213> ORGANISM: Photorhabdus luminescens

<400> SEQUENCE: 67

```
Met Gln Asn Ser Gln Thr Phe Ser Val Thr Glu Leu Ser Leu Pro Lys
1               5                   10                  15

Gly Gly Gly Ala Ile Thr Gly Met Gly Glu Ala Leu Thr Pro Ala Gly
            20                  25                  30
```

Pro Asp Gly Met Ala Ala Leu Ser Leu Pro Leu Pro Ile Ser Ala Gly
35 40 45

Arg Gly Tyr Ala Pro Ser Leu Thr Leu Asn Tyr Asn Ser Gly Thr Gly
50 55 60

Asn Ser Pro Phe Gly Leu Gly Trp Asp Cys Gly Val Met Ala Ile Arg
65 70 75 80

Arg Arg Thr Ser Thr Gly Val Pro Asn Tyr Asp Glu Thr Asp Thr Phe
85 90 95

Leu Gly Pro Glu Gly Glu Val Leu Val Val Ala Leu Asn Glu Ala Gly
100 105 110

Gln Ala Asp Ile Arg Ser Glu Ser Ser Leu Gln Gly Ile Asn Leu Gly
115 120 125

Ala Thr Phe Thr Val Thr Cys Tyr Arg Ser Arg Leu Glu Ser His Phe
130 135 140

Asn Arg Leu Glu Tyr Trp Gln Pro Gln Thr Thr Gly Ala Thr Asp Phe
145 150 155 160

Trp Leu Ile Tyr Ser Pro Asp Gly Gln Val His Leu Leu Gly Lys Asn
165 170 175

Pro Gln Ala Arg Ile Ser Asn Pro Leu Asn Val Asn Gln Thr Ala Gln
180 185 190

Trp Leu Leu Glu Ala Ser Ile Ser Ser His Ser Glu Gln Ile Tyr Tyr
195 200 205

Gln Tyr Arg Ala Glu Asp Glu Ala Gly Cys Glu Thr Asp Glu Leu Ala
210 215 220

Ala His Pro Ser Ala Thr Val Gln Arg Tyr Leu Gln Thr Val His Tyr
225 230 235 240

Gly Asn Leu Thr Ala Ser Asp Val Phe Pro Thr Leu Asn Gly Asp Asp
245 250 255

Pro Leu Lys Ser Gly Trp Met Phe Cys Leu Val Phe Asp Tyr Gly Glu
260 265 270

Arg Lys Asn Ser Leu Ser Glu Met Pro Leu Phe Lys Ala Thr Gly Asn
275 280 285

Trp Leu Cys Arg Lys Asp Arg Phe Ser Arg Tyr Glu Tyr Gly Phe Glu
290 295 300

Leu Arg Thr Arg Arg Leu Cys Arg Gln Ile Leu Met Phe His Arg Leu
305 310 315 320

Gln Thr Leu Ser Gly Gln Ala Lys Gly Asp Asp Glu Pro Ala Leu Val
325 330 335

Ser Arg Leu Ile Leu Asp Tyr Asp Glu Asn Ala Met Val Ser Thr Leu
340 345 350

Val Ser Val Arg Arg Val Gly His Glu Asp Asn Asn Thr Val Thr Ala
355 360 365

Leu Pro Pro Leu Glu Leu Ala Tyr Gln Pro Phe Glu Pro Glu Gln Thr
370 375 380

Ala Leu Trp Gln Ser Met Asp Val Leu Ala Asn Phe Asn Thr Ile Gln
385 390 395 400

Arg Trp Gln Leu Leu Asp Leu Lys Gly Glu Gly Val Pro Gly Ile Leu
405 410 415

Tyr Gln Asp Arg Asn Gly Trp Trp Tyr Arg Ser Ala Gln Arg Gln Ala
420 425 430

Gly Glu Glu Met Asn Ala Val Thr Trp Gly Lys Met Gln Leu Leu Pro
435 440 445

Ile Thr Pro Ala Val Gln Asp Asn Ala Ser Leu Met Asp Ile Asn Gly

-continued

```
    450                 455                 460

Asp Gly Gln Leu Asp Trp Val Ile Thr Gly Pro Gly Leu Arg Gly Tyr
465                 470                 475                 480

His Ser Gln His Pro Asp Gly Ser Trp Thr Arg Phe Thr Pro Leu His
                485                 490                 495

Ala Leu Pro Ile Glu Tyr Ser His Pro Arg Ala Gln Leu Ala Asp Leu
            500                 505                 510

Met Gly Ala Gly Leu Ser Asp Leu Val Leu Ile Gly Pro Lys Ser Val
        515                 520                 525

Arg Leu Tyr Val Asn Asn Arg Asp Gly Phe Thr Glu Gly Arg Asp Val
    530                 535                 540

Val Gln Ser Gly Asp Ile Thr Leu Pro Leu Pro Gly Ala Asp Ala Arg
545                 550                 555                 560

Lys Leu Val Ala Phe Ser Asp Val Leu Gly Ser Gly Gln Ala His Leu
                565                 570                 575

Val Glu Val Ser Ala Thr Gln Val Thr Cys Trp Pro Asn Leu Gly His
            580                 585                 590

Gly Arg Phe Gly Gln Pro Ile Val Leu Pro Gly Phe Ser Gln Ser Ala
        595                 600                 605

Ala Ser Phe Asn Pro Asp Arg Val His Leu Ala Asp Leu Asp Gly Ser
    610                 615                 620

Gly Pro Ala Asp Leu Ile Tyr Val His Ala Asp Arg Leu Asp Ile Phe
625                 630                 635                 640

Ser Asn Glu Ser Gly Asn Gly Phe Ala Lys Pro Phe Thr Leu Ser Phe
                645                 650                 655

Pro Asp Gly Leu Arg Phe Asp Asp Thr Cys Gln Leu Gln Val Ala Asp
            660                 665                 670

Val Gln Gly Leu Gly Val Val Ser Leu Ile Leu Ser Val Pro His Met
        675                 680                 685

Ala Pro His His Trp Arg Cys Asp Leu Thr Asn Ala Lys Pro Trp Leu
    690                 695                 700

Leu Ser Glu Thr Asn Asn Asn Met Gly Ala Asn His Thr Leu His Tyr
705                 710                 715                 720

Arg Ser Ser Val Gln Phe Trp Leu Asp Glu Lys Ala Ala Ala Leu Ala
                725                 730                 735

Thr Gly Gln Thr Pro Val Cys Tyr Leu Pro Phe Pro Val His Thr Leu
            740                 745                 750

Trp Gln Thr Glu Thr Glu Asp Glu Ile Ser Gly Asn Lys Leu Val Thr
        755                 760                 765

Thr Leu Arg Tyr Ala His Gly Ala Trp Asp Gly Arg Glu Arg Glu Phe
    770                 775                 780

Arg Gly Phe Gly Tyr Val Glu Gln Thr Asp Ser His Gln Leu Ala Gln
785                 790                 795                 800

Gly Asn Ala Pro Glu Arg Thr Pro Pro Ala Leu Thr Lys Ser Trp Tyr
                805                 810                 815

Ala Thr Gly Leu Pro Ala Val Asp Asn Ala Leu Ser Ala Gly Tyr Trp
            820                 825                 830

Arg Gly Asp Lys Gln Ala Phe Ala Gly Phe Thr Pro Arg Phe Thr Leu
        835                 840                 845

Trp Lys Glu Gly Lys Asp Val Pro Leu Thr Pro Glu Asp Asp His Asn
    850                 855                 860

Leu Tyr Trp Leu Asn Arg Ala Leu Lys Gly Gln Pro Leu Arg Ser Glu
865                 870                 875                 880
```

```
Leu Tyr Gly Leu Asp Gly Ser Ala Gln Gln Gln Ile Pro Tyr Thr Val
                885                 890                 895

Thr Glu Ser Arg Pro Gln Val Arg Gln Leu Gln Asp Gly Ala Thr Val
            900                 905                 910

Ser Pro Val Leu Trp Ala Ser Val Val Glu Ser Arg Ser Tyr His Tyr
        915                 920                 925

Glu Arg Ile Ile Ser Asp Pro Gln Cys Asn Gln Asp Ile Thr Leu Ser
    930                 935                 940

Ser Asp Leu Phe Gly Gln Pro Leu Lys Gln Val Ser Val Gln Tyr Pro
945                 950                 955                 960

Arg Arg Asn Lys Pro Thr Thr Asn Pro Tyr Pro Asp Thr Leu Pro Asp
                965                 970                 975

Thr Leu Phe Ala Ser Ser Tyr Asp Asp Gln Gln Gln Leu Leu Arg Leu
            980                 985                 990

Thr Cys Arg Gln Ser Ser Trp His  His Leu Ile Gly Asn  Glu Leu Arg
        995                 1000                1005

Val Leu  Gly Leu Pro Asp Gly  Thr Arg Ser Asp Ala  Phe Thr Tyr
    1010                 1015                 1020

Asp Ala  Lys Gln Val Pro Val  Asp Gly Leu Asn Leu  Glu Thr Leu
    1025                 1030                 1035

Cys Ala  Glu Asn Ser Leu Ile  Ala Asp Asp Lys Pro  Arg Glu Tyr
    1040                 1045                 1050

Leu Asn  Gln Gln Arg Thr Phe  Tyr Thr Asp Gly Lys  Asn Gln Thr
    1055                 1060                 1065

Pro Leu  Lys Thr Pro Thr Arg  Gln Ala Leu Ile Ala  Phe Thr Glu
    1070                 1075                 1080

Thr Ala  Val Leu Thr Glu Ser  Leu Leu Ser Ala Phe  Asp Gly Gly
    1085                 1090                 1095

Ile Thr  Pro Asp Glu Leu Pro  Gly Ile Leu Thr Gln  Ala Gly Tyr
    1100                 1105                 1110

Gln Gln  Glu Pro Tyr Leu Phe  Pro Arg Thr Gly Glu  Asn Lys Val
    1115                 1120                 1125

Trp Val  Ala Arg Gln Gly Tyr  Thr Asp Tyr Gly Thr  Glu Ala Gln
    1130                 1135                 1140

Phe Trp  Arg Pro Val Ala Gln  Arg Asn Ser Leu Leu  Thr Gly Lys
    1145                 1150                 1155

Met Thr  Leu Lys Trp Asp Thr  His Tyr Cys Val Ile  Thr Gln Thr
    1160                 1165                 1170

Gln Asp  Ala Ala Gly Leu Thr  Val Ser Ala Asn Tyr  Asp Trp Arg
    1175                 1180                 1185

Phe Leu  Thr Pro Thr Gln Leu  Thr Asp Ile Asn Asp  Asn Val His
    1190                 1195                 1200

Leu Ile  Thr Leu Asp Ala Leu  Gly Arg Pro Val Thr  Gln Arg Phe
    1205                 1210                 1215

Trp Gly  Ile Glu Ser Gly Val  Ala Thr Gly Tyr Ser  Ser Ser Glu
    1220                 1225                 1230

Glu Lys  Pro Phe Ser Pro Pro  Asn Asp Ile Asp Thr  Ala Ile Asn
    1235                 1240                 1245

Leu Thr  Gly Pro Leu Pro Val  Ala Gln Cys Leu Val  Tyr Ala Pro
    1250                 1255                 1260

Asp Ser  Trp Met Pro Leu Phe  Ser Gln Glu Thr Phe  Asn Thr Leu
    1265                 1270                 1275

Thr Gln  Glu Glu Gln Glu Thr  Leu Arg Asp Ser Arg  Ile Ile Thr
    1280                 1285                 1290
```

```
Glu Asp  Trp Arg Ile Cys Ala  Leu Thr Arg Arg Arg  Trp Leu Gln
    1295                 1300                 1305

Ser Gln  Lys Ile Ser Thr Pro  Leu Val Lys Leu Leu  Thr Asn Ser
    1310                 1315                 1320

Ile Gly  Leu Pro Pro His Asn  Leu Thr Leu Thr Thr  Asp Arg Tyr
    1325                 1330                 1335

Asp Arg  Asp Ser Glu Gln Gln  Ile Arg Gln Gln Val  Ala Phe Ser
    1340                 1345                 1350

Asp Gly  Phe Gly Arg Leu Leu  Gln Ala Ser Val Arg  His Glu Ala
    1355                 1360                 1365

Gly Glu  Ala Trp Gln Arg Asn  Gln Asp Gly Ser Leu  Val Thr Lys
    1370                 1375                 1380

Val Glu  Asn Thr Lys Thr Arg  Trp Ala Val Thr Gly  Arg Thr Glu
    1385                 1390                 1395

Tyr Asp  Asn Lys Gly Gln Thr  Ile Arg Thr Tyr Gln  Pro Tyr Phe
    1400                 1405                 1410

Leu Asn  Asp Trp Arg Tyr Val  Ser Asp Asp Ser Ala  Arg Lys Glu
    1415                 1420                 1425

Ala Tyr  Ala Asp Thr His Ile  Tyr Asp Pro Ile Gly  Arg Glu Ile
    1430                 1435                 1440

Arg Val  Ile Thr Ala Lys Gly  Trp Leu Arg Gln Ser  Gln Tyr Phe
    1445                 1450                 1455

Pro Trp  Phe Thr Val Ser Glu  Asp Glu Asn Asp Thr  Ala Ala Asp
    1460                 1465                 1470

Ala Leu  Val
    1475
```

<210> SEQ ID NO 68
<211> LENGTH: 1043
<212> TYPE: PRT
<213> ORGANISM: Photorhabdus luminescens

<400> SEQUENCE: 68

```
Met Ser Pro Ser Glu Thr Thr Leu Tyr Thr Gln Thr Pro Thr Val Ser
1               5                   10                  15

Val Leu Asp Asn Arg Gly Leu Ser Ile Arg Asp Ile Gly Phe His Arg
            20                  25                  30

Ile Val Ile Gly Gly Asp Thr Asp Thr Arg Val Thr Arg His Gln Tyr
        35                  40                  45

Asp Ala Arg Gly His Leu Asn Tyr Ser Ile Asp Pro Arg Leu Tyr Asp
    50                  55                  60

Ala Lys Gln Ala Asp Asn Ser Val Lys Pro Asn Phe Val Trp Gln His
65                  70                  75                  80

Asp Leu Ala Gly His Ala Leu Arg Thr Glu Ser Val Asp Ala Gly Arg
                85                  90                  95

Thr Val Ala Leu Asn Asp Ile Glu Gly Arg Ser Val Met Thr Met Asn
            100                 105                 110

Ala Thr Gly Val Arg Gln Thr Arg Arg Tyr Glu Gly Asn Thr Leu Pro
        115                 120                 125

Gly Arg Leu Leu Ser Val Ser Glu Gln Val Phe Asn Gln Glu Ser Ala
    130                 135                 140

Lys Val Thr Glu Arg Phe Ile Trp Ala Gly Asn Thr Thr Ser Glu Lys
145                 150                 155                 160

Glu Tyr Asn Leu Ser Gly Leu Cys Ile Arg His Tyr Asp Thr Ala Gly
                165                 170                 175
```

```
Val Thr Arg Leu Met Ser Gln Ser Leu Ala Gly Ala Met Leu Ser Gln
            180                 185                 190

Ser His Gln Leu Leu Ala Glu Gly Gln Glu Ala Asn Trp Ser Gly Asp
        195                 200                 205

Asp Glu Thr Val Trp Gln Gly Met Leu Ala Ser Glu Val Tyr Thr Thr
    210                 215                 220

Gln Ser Thr Thr Asn Ala Ile Gly Ala Leu Leu Thr Gln Thr Asp Ala
225                 230                 235                 240

Lys Gly Asn Ile Gln Arg Leu Ala Tyr Asp Ile Ala Gly Gln Leu Lys
                245                 250                 255

Gly Ser Trp Leu Thr Val Lys Gly Gln Ser Glu Gln Val Ile Val Lys
            260                 265                 270

Ser Leu Ser Trp Ser Ala Ala Gly His Lys Leu Arg Glu Glu His Gly
        275                 280                 285

Asn Gly Val Val Thr Glu Tyr Ser Tyr Glu Pro Glu Thr Gln Arg Leu
    290                 295                 300

Ile Gly Ile Thr Thr Arg Arg Ala Glu Gly Ser Gln Ser Gly Ala Arg
305                 310                 315                 320

Val Leu Gln Asp Leu Arg Tyr Lys Tyr Asp Pro Val Gly Asn Val Ile
                325                 330                 335

Ser Ile His Asn Asp Ala Glu Ala Thr Arg Phe Trp Arg Asn Gln Lys
            340                 345                 350

Val Glu Pro Glu Asn Arg Tyr Val Tyr Asp Ser Leu Tyr Gln Leu Met
        355                 360                 365

Ser Ala Thr Gly Arg Glu Met Ala Asn Ile Gly Gln Gln Ser Asn Gln
    370                 375                 380

Leu Pro Ser Pro Val Ile Pro Val Pro Thr Asp Asp Ser Thr Tyr Thr
385                 390                 395                 400

Asn Tyr Leu Arg Thr Tyr Thr Tyr Asp Arg Gly Gly Asn Leu Val Gln
                405                 410                 415

Ile Arg His Ser Ser Pro Ala Thr Gln Asn Ser Tyr Thr Thr Asp Ile
            420                 425                 430

Thr Val Ser Ser Arg Ser Asn Arg Ala Val Leu Ser Thr Leu Thr Thr
        435                 440                 445

Asp Pro Thr Arg Val Asp Ala Leu Phe Asp Ser Gly Gly His Gln Lys
    450                 455                 460

Met Leu Ile Pro Gly Gln Asn Leu Asp Trp Asn Ile Arg Gly Glu Leu
465                 470                 475                 480

Gln Arg Val Thr Pro Val Ser Arg Glu Asn Ser Ser Asp Ser Glu Trp
                485                 490                 495

Tyr Arg Tyr Ser Ser Asp Gly Met Arg Leu Leu Lys Val Ser Glu Gln
            500                 505                 510

Gln Thr Gly Asn Ser Thr Gln Val Gln Arg Val Thr Tyr Leu Pro Gly
        515                 520                 525

Leu Glu Leu Arg Thr Thr Gly Val Ala Asp Lys Thr Thr Glu Asp Leu
    530                 535                 540

Gln Val Ile Thr Val Gly Glu Ala Gly Arg Ala Gln Val Arg Val Leu
545                 550                 555                 560

His Trp Glu Ser Gly Lys Pro Thr Asp Ile Asp Asn Asn Gln Val Arg
                565                 570                 575

Tyr Ser Tyr Asp Asn Leu Leu Gly Ser Ser Gln Leu Glu Leu Asp Ser
            580                 585                 590

Glu Gly Gln Ile Leu Ser Gln Glu Glu Tyr Tyr Pro Tyr Gly Gly Thr
```

-continued

```
        595                 600                 605

Ala Ile Trp Ala Ala Arg Asn Gln Thr Glu Ala Ser Tyr Lys Phe Ile
    610                 615                 620

Arg Tyr Ser Gly Lys Glu Arg Asp Ala Thr Gly Leu Tyr Tyr Tyr Gly
625                 630                 635                 640

Tyr Arg Tyr Tyr Gln Pro Trp Val Gly Arg Trp Leu Ser Ala Asp Pro
                645                 650                 655

Ala Gly Thr Val Asp Gly Leu Asn Leu Tyr Arg Met Val Arg Asn Asn
            660                 665                 670

Pro Ile Thr Leu Thr Asp His Asp Gly Leu Ala Pro Ser Pro Asn Arg
        675                 680                 685

Asn Arg Asn Thr Phe Trp Phe Ala Ser Phe Leu Phe Arg Lys Pro Asp
    690                 695                 700

Glu Gly Met Ser Ala Ser Met Arg Arg Gly Gln Lys Ile Gly Arg Ala
705                 710                 715                 720

Ile Ala Gly Gly Ile Ala Ile Gly Gly Leu Ala Ala Thr Ile Ala Ala
                725                 730                 735

Thr Ala Gly Ala Ala Ile Pro Val Ile Leu Gly Val Ala Ala Val Gly
            740                 745                 750

Ala Gly Ile Gly Ala Leu Met Gly Tyr Asn Val Gly Ser Leu Leu Glu
        755                 760                 765

Lys Gly Gly Ala Leu Leu Ala Arg Leu Val Gln Gly Lys Ser Thr Leu
    770                 775                 780

Val Gln Ser Ala Ala Gly Ala Ala Ala Gly Ala Ser Ser Ala Ala Ala
785                 790                 795                 800

Tyr Gly Ala Arg Ala Gln Gly Val Gly Val Ala Ser Ala Ala Gly Ala
                805                 810                 815

Val Thr Gly Ala Val Gly Ser Trp Ile Asn Asn Ala Asp Arg Gly Ile
            820                 825                 830

Gly Gly Ala Ile Gly Ala Gly Ser Ala Val Gly Thr Ile Asp Thr Met
        835                 840                 845

Leu Gly Thr Ala Ser Thr Leu Thr His Glu Val Gly Ala Ala Ala Gly
    850                 855                 860

Gly Ala Ala Gly Gly Met Ile Thr Gly Thr Gln Gly Ser Thr Arg Ala
865                 870                 875                 880

Gly Ile His Ala Gly Ile Gly Thr Tyr Tyr Gly Ser Trp Ile Gly Phe
                885                 890                 895

Gly Leu Asp Val Ala Ser Asn Pro Ala Gly His Leu Ala Asn Tyr Ala
            900                 905                 910

Val Gly Tyr Ala Ala Gly Leu Gly Ala Glu Met Ala Val Asn Arg Ile
        915                 920                 925

Met Gly Gly Gly Phe Leu Ser Arg Leu Leu Gly Arg Val Val Ser Pro
    930                 935                 940

Tyr Ala Ala Gly Leu Ala Arg Gln Leu Val His Phe Ser Val Ala Arg
945                 950                 955                 960

Pro Val Phe Glu Pro Ile Phe Ser Val Leu Gly Gly Leu Val Gly Gly
                965                 970                 975

Ile Gly Thr Gly Leu His Arg Val Met Gly Arg Glu Ser Trp Ile Ser
            980                 985                 990

Arg Ala Leu Ser Ala Ala Gly Ser  Gly Ile Asp His Val  Ala Gly Met
        995                 1000                1005

Ile Gly  Asn Gln Ile Arg Gly  Arg Val Leu Thr Thr  Thr Gly Ile
    1010                1015                1020
```

```
Ala Asn  Ala Ile Asp Tyr Gly  Thr Ser Ala Val Gly  Ala Ala Arg
    1025                1030                1035

Arg Val  Phe Ser Leu
    1040


<210> SEQ ID NO 69
<211> LENGTH: 1485
<212> TYPE: PRT
<213> ORGANISM: Photorhabdus luminescens

<400> SEQUENCE: 69

Met Gln Asp Ser Pro Glu Val Ser Ile Thr Thr Leu Ser Leu Pro Lys
1               5                   10                  15

Gly Gly Gly Ala Ile Asn Gly Met Gly Glu Ala Leu Asn Ala Ala Gly
            20                  25                  30

Pro Asp Gly Met Ala Ser Leu Ser Leu Pro Leu Pro Leu Ser Thr Gly
        35                  40                  45

Arg Gly Thr Ala Pro Gly Leu Ser Leu Ile Tyr Ser Asn Ser Ala Gly
    50                  55                  60

Asn Gly Pro Phe Gly Ile Gly Trp Gln Cys Gly Val Met Ser Ile Ser
65                  70                  75                  80

Arg Arg Thr Gln His Gly Ile Pro Gln Tyr Gly Asn Asp Asp Thr Phe
                85                  90                  95

Leu Ser Pro Gln Gly Glu Val Met Asn Ile Ala Leu Asn Asp Gln Gly
            100                 105                 110

Gln Pro Asp Ile Arg Gln Asp Val Lys Thr Leu Gln Gly Val Thr Leu
        115                 120                 125

Pro Ile Ser Tyr Thr Val Thr Arg Tyr Gln Ala Arg Gln Ile Leu Asp
    130                 135                 140

Phe Ser Lys Ile Glu Tyr Trp Gln Pro Ala Ser Gly Gln Glu Gly Arg
145                 150                 155                 160

Ala Phe Trp Leu Ile Ser Ser Pro Asp Gly Gln Leu His Ile Leu Gly
                165                 170                 175

Lys Thr Ala Gln Ala Cys Leu Ala Asn Pro Gln Asn Asp Gln Gln Ile
            180                 185                 190

Ala Gln Trp Leu Leu Glu Glu Thr Val Thr Pro Ala Gly Glu His Val
        195                 200                 205

Ser Tyr Gln Tyr Arg Ala Glu Asp Glu Ala His Cys Asp Asp Asn Glu
    210                 215                 220

Lys Thr Ala His Pro Asn Val Thr Ala Gln Arg Tyr Leu Val Gln Val
225                 230                 235                 240

Asn Tyr Gly Asn Ile Lys Pro Gln Ala Ser Leu Phe Val Leu Asp Asn
                245                 250                 255

Ala Pro Pro Ala Pro Glu Glu Trp Leu Phe His Leu Val Phe Asp His
            260                 265                 270

Gly Glu Arg Asp Thr Ser Leu His Thr Val Pro Thr Trp Asp Ala Gly
        275                 280                 285

Thr Ala Gln Trp Ser Val Arg Pro Asp Ile Phe Ser Arg Tyr Glu Tyr
    290                 295                 300

Gly Phe Glu Val Arg Thr Arg Arg Leu Cys Gln Gln Val Leu Met Phe
305                 310                 315                 320

His Arg Thr Ala Leu Met Ala Gly Glu Ala Ser Thr Asn Asp Ala Pro
                325                 330                 335

Glu Leu Val Gly Arg Leu Ile Leu Glu Tyr Asp Lys Asn Ala Ser Val
            340                 345                 350
```

```
Thr Thr Leu Ile Thr Ile Arg Gln Leu Ser His Glu Ser Asp Gly Ser
        355                 360                 365

Pro Val Thr Gln Pro Pro Leu Glu Leu Ala Trp Gln Arg Phe Asp Leu
    370                 375                 380

Glu Lys Met Pro Thr Trp Gln Arg Phe Asp Ala Leu Asp Asn Phe Asn
385                 390                 395                 400

Ser Gln Gln Arg Tyr Gln Leu Val Asp Leu Arg Gly Glu Gly Leu Pro
                405                 410                 415

Gly Met Leu Tyr Gln Asp Arg Gly Ala Trp Trp Tyr Lys Ala Pro Gln
            420                 425                 430

Arg Gln Glu Asp Gly Asp Ser Asn Ala Val Thr Tyr Asp Lys Ile Ala
        435                 440                 445

Pro Leu Pro Thr Leu Pro Asn Leu Gln Asp Asn Ala Ser Leu Met Asp
    450                 455                 460

Ile Asn Gly Asp Gly Gln Leu Asp Trp Val Val Thr Ala Ser Gly Ile
465                 470                 475                 480

Arg Gly Tyr His Ser Gln Gln Pro Asp Gly Lys Trp Thr His Phe Thr
                485                 490                 495

Pro Ile Asn Ala Leu Pro Val Glu Tyr Phe His Pro Ser Ile Gln Phe
            500                 505                 510

Ala Asp Leu Thr Gly Ala Gly Leu Ser Asp Leu Val Leu Ile Gly Pro
        515                 520                 525

Lys Ser Val Arg Leu Tyr Ala Asn Gln Arg Asn Gly Trp Arg Lys Gly
    530                 535                 540

Glu Asp Val Pro Gln Ser Thr Gly Ile Thr Leu Pro Val Thr Gly Thr
545                 550                 555                 560

Asp Ala Arg Lys Leu Val Ala Phe Ser Asp Met Leu Gly Ser Gly Gln
                565                 570                 575

Gln His Leu Val Glu Ile Lys Ala Asn Arg Val Thr Cys Trp Pro Asn
            580                 585                 590

Leu Gly His Gly Arg Phe Gly Gln Pro Leu Thr Leu Ser Gly Phe Ser
        595                 600                 605

Gln Pro Glu Asn Ser Phe Asn Pro Glu Arg Leu Phe Leu Ala Asp Ile
    610                 615                 620

Asp Gly Ser Gly Thr Thr Asp Leu Ile Tyr Ala Gln Ser Gly Ser Leu
625                 630                 635                 640

Leu Ile Tyr Leu Asn Gln Ser Gly Asn Gln Phe Asp Ala Pro Leu Thr
                645                 650                 655

Leu Ala Leu Pro Glu Gly Val Gln Phe Asp Asn Thr Cys Gln Leu Gln
            660                 665                 670

Val Ala Asp Ile Gln Gly Leu Gly Ile Ala Ser Leu Ile Leu Thr Val
        675                 680                 685

Pro His Ile Ala Pro His His Trp Arg Cys Asp Leu Ser Leu Thr Lys
    690                 695                 700

Pro Trp Leu Leu Asn Val Met Asn Asn Asn Arg Gly Ala His His Thr
705                 710                 715                 720

Leu His Tyr Arg Ser Ser Ala Gln Phe Trp Leu Asp Glu Lys Leu Gln
                725                 730                 735

Leu Thr Lys Ala Gly Lys Ser Pro Ala Cys Tyr Leu Pro Phe Pro Met
            740                 745                 750

His Leu Leu Trp Tyr Thr Glu Ile Gln Asp Glu Ile Ser Gly Asn Arg
        755                 760                 765

Leu Thr Ser Glu Val Asn Tyr Ser His Gly Val Trp Asp Gly Lys Glu
    770                 775                 780
```

```
Arg Glu Phe Arg Gly Phe Gly Cys Ile Lys Gln Thr Asp Thr Thr Thr
785                 790                 795                 800

Phe Ser His Gly Thr Ala Pro Glu Gln Ala Ala Pro Ser Leu Ser Ile
                805                 810                 815

Ser Trp Phe Ala Thr Gly Met Asp Glu Val Asp Ser Gln Leu Ala Thr
            820                 825                 830

Glu Tyr Trp Gln Ala Asp Thr Gln Ala Tyr Ser Gly Phe Glu Thr Arg
        835                 840                 845

Tyr Thr Val Trp Asp His Thr Asn Gln Thr Asp Gln Ala Phe Thr Pro
    850                 855                 860

Asn Glu Thr Gln Arg Asn Trp Leu Thr Arg Ala Leu Lys Gly Gln Leu
865                 870                 875                 880

Leu Arg Thr Glu Leu Tyr Gly Leu Asp Gly Thr Asp Lys Gln Thr Val
                885                 890                 895

Pro Tyr Thr Val Ser Glu Ser Arg Tyr Gln Val Arg Ser Ile Pro Val
            900                 905                 910

Asn Lys Glu Thr Glu Leu Ser Ala Trp Val Thr Ala Ile Glu Asn Arg
        915                 920                 925

Ser Tyr His Tyr Glu Arg Ile Ile Thr Asp Pro Gln Phe Ser Gln Ser
    930                 935                 940

Ile Lys Leu Gln His Asp Ile Phe Gly Gln Ser Leu Gln Ser Val Asp
945                 950                 955                 960

Ile Ala Trp Pro Arg Arg Glu Lys Pro Ala Val Asn Pro Tyr Pro Pro
                965                 970                 975

Thr Leu Pro Glu Thr Leu Phe Asp Ser Ser Tyr Asp Asp Gln Gln Gln
            980                 985                 990

Leu Leu Arg Leu Val Arg Gln Lys  Asn Ser Trp His His  Leu Thr Asp
        995                 1000                1005

Gly Glu  Asn Trp Arg Leu Gly  Leu Pro Asn Ala Gln  Arg Arg Asp
    1010                1015                1020

Val Tyr  Thr Tyr Asp Arg Ser  Lys Ile Pro Thr Glu  Gly Ile Ser
    1025                1030                1035

Leu Glu  Ile Leu Leu Lys Asp  Asp Gly Leu Leu Ala  Asp Glu Lys
    1040                1045                1050

Ala Ala  Val Tyr Leu Gly Gln  Gln Gln Thr Phe Tyr  Thr Ala Gly
    1055                1060                1065

Gln Ala  Glu Val Thr Leu Glu  Lys Pro Thr Leu Gln  Ala Leu Val
    1070                1075                1080

Ala Phe  Gln Glu Thr Ala Met  Met Asp Asp Thr Ser  Leu Gln Ala
    1085                1090                1095

Tyr Glu  Gly Val Ile Glu Glu  Gln Glu Leu Asn Thr  Ala Leu Thr
    1100                1105                1110

Gln Ala  Gly Tyr Gln Gln Val  Ala Arg Leu Phe Asn  Thr Arg Ser
    1115                1120                1125

Glu Ser  Pro Val Trp Ala Ala  Arg Gln Gly Tyr Thr  Asp Tyr Gly
    1130                1135                1140

Asp Ala  Ala Gln Phe Trp Arg  Pro Gln Ala Gln Arg  Asn Ser Leu
    1145                1150                1155

Leu Thr  Gly Lys Thr Thr Leu  Thr Trp Asp Thr His  His Cys Val
    1160                1165                1170

Ile Ile  Gln Thr Gln Asp Ala  Ala Gly Leu Thr Thr  Gln Ala His
    1175                1180                1185

Tyr Asp  Tyr Arg Phe Leu Thr  Pro Val Gln Leu Thr  Asp Ile Asn
```

-continued

```
    1190                1195                1200

Asp Asn  Gln His Ile Val Thr  Leu Asp Ala Leu Gly  Arg Val Thr
    1205                1210                1215

Thr Ser  Arg Phe Trp Gly Thr  Glu Ala Gly Gln Ala  Ala Gly Tyr
    1220                1225                1230

Ser Asn  Gln Pro Phe Thr Pro  Pro Asp Ser Val Asp  Lys Ala Leu
    1235                1240                1245

Ala Leu  Thr Gly Ala Leu Pro  Val Ala Gln Cys Leu  Val Tyr Ala
    1250                1255                1260

Val Asp  Ser Trp Met Pro Ser  Leu Ser Leu Ser Gln  Leu Ser Gln
    1265                1270                1275

Ser Gln  Glu Glu Ala Glu Ala  Leu Trp Ala Gln Leu  Arg Ala Ala
    1280                1285                1290

His Met  Ile Thr Glu Asp Gly  Lys Val Cys Ala Leu  Ser Gly Lys
    1295                1300                1305

Arg Gly  Thr Ser His Gln Asn  Leu Thr Ile Gln Leu  Ile Ser Leu
    1310                1315                1320

Leu Ala  Ser Ile Pro Arg Leu  Pro Pro His Val Leu  Gly Ile Thr
    1325                1330                1335

Thr Asp  Arg Tyr Asp Ser Asp  Pro Gln Gln Gln His  Gln Gln Thr
    1340                1345                1350

Val Ser  Phe Ser Asp Gly Phe  Gly Arg Leu Leu Gln  Ser Ser Ala
    1355                1360                1365

Arg His  Glu Ser Gly Asp Ala  Trp Gln Arg Lys Glu  Asp Gly Gly
    1370                1375                1380

Leu Val  Val Asp Ala Asn Gly  Val Leu Val Ser Ala  Pro Thr Asp
    1385                1390                1395

Thr Arg  Trp Ala Val Ser Gly  Arg Thr Glu Tyr Asp  Asp Lys Gly
    1400                1405                1410

Gln Pro  Val Arg Thr Tyr Gln  Pro Tyr Phe Leu Asn  Asp Trp Arg
    1415                1420                1425

Tyr Val  Ser Asp Asp Ser Ala  Arg Asp Asp Leu Phe  Ala Asp Thr
    1430                1435                1440

His Leu  Tyr Asp Pro Leu Gly  Arg Glu Tyr Lys Val  Ile Thr Ala
    1445                1450                1455

Lys Lys  Tyr Leu Arg Glu Lys  Leu Tyr Thr Pro Trp  Phe Ile Val
    1460                1465                1470

Ser Glu  Asp Glu Asn Asp Thr  Ala Ser Arg Thr Pro
    1475                1480                1485
```